(12) United States Patent
Cook et al.

(10) Patent No.: US 8,278,434 B2
(45) Date of Patent: Oct. 2, 2012

(54) PROMOTER, PROMOTER CONTROL ELEMENTS, AND COMBINATIONS, AND USES THEREOF

(75) Inventors: Zhihong Cook, Laguna Hills, CA (US); Yiwen Fang, Los Angeles, CA (US); Ken Feldmann, Newbury Park, CA (US); Edward A Kiegle, Chester, VT (US); Shing Kwok, Woodland Hills, CA (US); Yu-Ping Lu, Camarillo, CA (US); Leonard Medrano, Azusa, CA (US); Roger Pennell, Malibu, CA (US); Richard Schneeberger, Carlsbad, CA (US); Chuan-Yin Wu, Newbury Park, CA (US)

(73) Assignee: Ceres, Inc., Thousand Oaks, CA (US)

( * ) Notice: Subject to any disclaimer, the term of this patent is extended or adjusted under 35 U.S.C. 154(b) by 0 days.

(21) Appl. No.: 12/504,863

(22) Filed: Jul. 17, 2009

(65) Prior Publication Data
US 2010/0037344 A1 Feb. 11, 2010

Related U.S. Application Data

(60) Continuation of application No. 11/598,118, filed on Nov. 10, 2006, now abandoned, which is a division of application No. 10/950,321, filed on Sep. 23, 2004, now Pat. No. 7,173,121.

(60) Provisional application No. 60/505,689, filed on Sep. 23, 2003, provisional application No. 60/511,460, filed on Oct. 14, 2003, provisional application No. 60/518,075, filed on Nov. 6, 2003, provisional application No. 60/527,611, filed on Dec. 4, 2003, provisional application No. 60/529,352, filed on Dec. 12, 2003, provisional application No. 60/544,771, filed on Feb. 13, 2004.

(51) Int. Cl.
*C07H 21/04* (2006.01)
*C12N 15/11* (2006.01)
*C12N 15/63* (2006.01)
(52) U.S. Cl. ............ 536/24.1; 536/23.1; 435/320.1
(58) Field of Classification Search ................ None
See application file for complete search history.

(56) References Cited

U.S. PATENT DOCUMENTS
2007/0006348 A1 1/2007 Shinozaki

FOREIGN PATENT DOCUMENTS
EP 1209228 5/2002

OTHER PUBLICATIONS
Genbank accession No. AC074226, 2000.*

* cited by examiner

*Primary Examiner* — Michele K Joike
(74) *Attorney, Agent, or Firm* — Birch, Stewart, Kolasch & Birch, LLP

(57) ABSTRACT

The present invention is directed to promoter sequences and promoter control elements, polynucleotide constructs comprising the promoters and control elements, and methods of identifying the promoters, control elements, or fragments thereof. The invention further relates to the use of the present promoters or promoter control elements to modulate transcript levels.

12 Claims, 1 Drawing Sheet

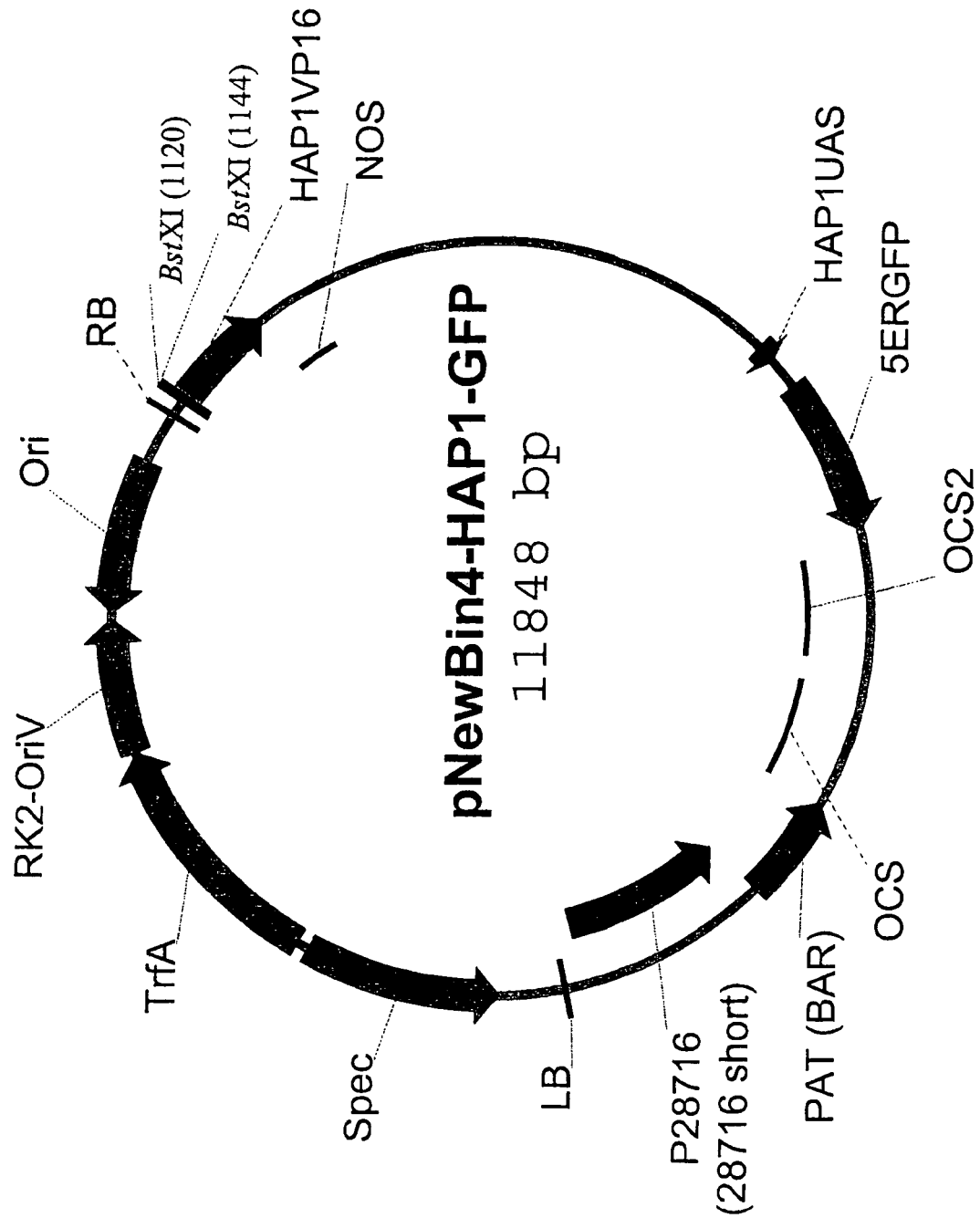

SEQUENCE LISTING

<160> NUMBER OF SEQ ID NOS: 64

<210> SEQ ID NO 1
<211> LENGTH: 19
<212> TYPE: DNA
<213> ORGANISM: Artificial Sequence
<220> FEATURE:
<223> OTHER INFORMATION: Synthetic oligo(dT)18 primer

<400> SEQUENCE: 1
tttttttttt tttttttv                                              19

<210> SEQ ID NO 2
<211> LENGTH: 19
<212> TYPE: DNA
<213> ORGANISM: Artificial Sequence
<220> FEATURE:
<223> OTHER INFORMATION: Synthetic oligo dTV primer
<220> FEATURE:
<221> NAME/KEY: misc_feature
<222> LOCATION: (19)..(19)
<223> OTHER INFORMATION: n is a, c, or g

<400> SEQUENCE: 2
tttttttttt tttttttn                                              19

<210> SEQ ID NO 3
<211> LENGTH: 930
<212> TYPE: DNA
<213> ORGANISM: Arabidopsis thaliana

<400> SEQUENCE: 3
ctaagtaaaa taagataaaa catgttattt gaatttgaat atcgtgggat gcgtatttcg    60
gtatttgatt aaaggtctgg aaaccggagc tcctataacc cgaataaaaa tgcataacat   120
gttcttcccc aacgaggcga gcgggtcagg gcactagggt cattgcaggc agctcataaa   180
gtcatgatca tctaggagat caaattgtat gtcggccttc tcaaaattac ctctaagaat   240
ctcaaaccca atcatagaac ctctaaaaag acaaagtcgt cgctttagaa tgggttcggt   300
ttttggaacc atatttcacg tcaatttaat gtttagtata atttctgaac aacagaattt   360
tggatttatt tgcacgtata caaatatcta attaataagg acgactcgtg actatcctta   420
cattaagttt cactgtcgaa ataacatagt acaatacttg tcgttaattt ccacgtctca   480
agtctatacc gtcatttacg gagaaagaac atctctgttt ttcatccaaa ctactattct   540
cactttgtct atatatttaa aattaagtaa aaaagactca atagtccaat aaaatgatga   600
ccaaatgaga agatggtttt gtgccagatt ttaggaaaag tgagtcaagg tttcacatct   660

```
caaatttgac tgcataatct tcgccattaa caacggcatt atatatgtca agccaatttt    720
ccatgttgcg tacttttcta ttgaggtgaa atatgggtt tgttgattaa tcaaagagtt     780
tgcctaacta atataactac gactttttca gtgaccattc catgtaaact ctgcttagtg    840
tttcatttgt caacaatatt gtcgttactc attaaatcaa ggaaaaatat acaattgtat    900
aattttctta tattttaaaa ttaattttga                                     930

<210> SEQ ID NO 4
<211> LENGTH: 86
<212> TYPE: DNA
<213> ORGANISM: Arabidopsis thaliana

<400> SEQUENCE: 4
ccaaaagaac atctttcctt cgaattttct ttcattaaca tttcttttac ttgtctcctt    60
gtgtcttcac ttcacatcac aacatg                                         86

<210> SEQ ID NO 5
<211> LENGTH: 949
<212> TYPE: DNA
<213> ORGANISM: Arabidopsis thaliana

<400> SEQUENCE: 5
actacaccca aagaacatc tttccttcga attttcttc aattaacatt tcttttactt      60
gtctccttgt gtcttcactt cacatcacaa catggctttg aagacagttt tcgtagcttt    120
tatgattctc cttgccatct attcgcaaac gacgtttggg gacgatgtga agtgcgagaa    180
tctggatgaa aacacgtgtg ccttcgcggt ctcgtccact ggaaaacgtt gcgttttgga    240
gaagagcatg aagaggagcg ggatcgaggt gtacacatgt cgatcatcgg agatagaagc    300
taacaaggtc acaaacatta ttgaatcgga cgagtgcatt aaagcgtgtg gtctagaccg    360
gaaagcttta ggtatatctt cggacgcatt gttggaatct cagttcacac ataaactctg    420
ctcggttaaa tgcttaaacc aatgtcctaa cgtagtcgat ctctacttca accttgctgc    480
tggtgaagga gtgtatttac caaagctatg tgaatcacaa gagggaagt caagaagagc    540 aatgtcggaa attaggagct cgggaattgc aatggacact cttgcaccgg ttggaccagt    600
catgttgggc gagatagcac ctgagccggc tacttcaatg acaacatgc cttacgtgcc      660 ggcaccttca ccgtattaat taaggcaagg gaaaatggag aggacacgta tgatatcatg    720
agttttcgac gagaataatt aagagattta tgtttagttc gacggttta gtattacatc     780 gtttattgcg tccttatata tatgtacttc ataaaaacac accacgacac attaagagat    840
ggtgaaagta ggctgcgttc tggtgtaact tttacacaag taacgtctta taatatatat    900
gattcgaata aaatgttgag ttttggtgaa aatatataat atgtttctg                949

<210> SEQ ID NO 6
<211> LENGTH: 195
<212> TYPE: PRT
<213> ORGANISM: Arabidopsis thaliana

<400> SEQUENCE: 6

Met Ala Leu Lys Thr Val Phe Val Ala Phe Met Ile Leu Leu Ala Ile
1               5                   10                  15

Tyr Ser Gln Thr Thr Phe Gly Asp Asp Val Lys Cys Glu Asn Leu Asp
            20                  25                  30

Glu Asn Thr Cys Ala Phe Ala Val Ser Ser Thr Gly Lys Arg Cys Val
        35                  40                  45
```

```
Leu Glu Lys Ser Met Lys Arg Ser Gly Ile Glu Val Tyr Thr Cys Arg
 50                  55                  60

Ser Ser Glu Ile Glu Ala Asn Lys Val Thr Asn Ile Ile Glu Ser Asp
 65                  70                  75                  80

Glu Cys Ile Lys Ala Cys Gly Leu Asp Arg Lys Ala Leu Gly Ile Ser
                 85                  90                  95

Ser Asp Ala Leu Leu Glu Ser Gln Phe Thr His Lys Leu Cys Ser Val
                100                 105                 110

Lys Cys Leu Asn Gln Cys Pro Asn Val Val Asp Leu Tyr Phe Asn Leu
            115                 120                 125

Ala Ala Gly Glu Gly Val Tyr Leu Pro Lys Leu Cys Glu Ser Gln Glu
        130                 135                 140

Gly Lys Ser Arg Arg Ala Met Ser Glu Ile Arg Ser Ser Gly Ile Ala
145                 150                 155                 160

Met Asp Thr Leu Ala Pro Val Gly Pro Val Met Leu Gly Glu Ile Ala
                165                 170                 175

Pro Glu Pro Ala Thr Ser Met Asp Asn Met Pro Tyr Val Pro Ala Pro
            180                 185                 190

Ser Pro Tyr
        195

<210> SEQ ID NO 7
<211> LENGTH: 963
<212> TYPE: DNA
<213> ORGANISM: Arabidopsis thaliana

<400> SEQUENCE: 7
tatttgtagt gacatattct acaattatca cattttttctc ttatgtttcg tagtcgcaga    60
tggtcaattt tttctataat aatttgtcct tgaacacacc aaactttaga aacgatgata   120
tataccgtat tgtcacgctc acaatgaaac aaacgcgatg aatcgtcatc accagctaaa   180
agcctaaaac accatcttag ttttcactca gataaaaaga ttatttgttt ccaacctttc   240
tattgaattg attagcagtg atgacgtaat tagtgatagt ttatagtaaa acaaatggaa   300
gtggtaataa atttacacaa caaaatatgg taagaatcta taaaataaga ggttaagaga   360
tctcatgtta tattaaatga ttgaaagaaa aacaaactat tggttgattt ccatatgtaa   420
tagtaagttg tgatgaaagt gatgacgtaa ttagttgtat ttatagtaaa acaaattaaa   480
atggtaaggt aaatttccac aacaaaactt ggtaaaaatc ttaaaaaaaa aaaagaggt    540 ttagagatcg catgcgtgtc atcaaaggtt ctttttcact ttaggtctga gtagtgttag   600
actttgattg gtgcacgtaa gtgtttcgta tcgcgattta ggagaagtac gttttacacg   660
tggacacaat caacggtcaa gatttcgtcg tccagataga ggagcgatac gtcacgccat   720
tcaacaatct cctcttcttc attccttcat tttgattttg agttttgatc tgcccgttca   780
aaagtctcgg tcatctgccc gtaaatataa agatgattat atttatttat atcttctggt   840
gaaagaagct aatataaagc ttccatggct aatcttgttt aagcttctct tcttcttctc   900
tctcctgtgt ctcgttcact agttttttttt cggggagag tgatggagtg tgtttgttga   960
ata                                                                  963

<210> SEQ ID NO 8
<211> LENGTH: 1627
<212> TYPE: DNA
<213> ORGANISM: Arabidopsis thaliana

<400> SEQUENCE: 8
```

```
aaagcttcca tggctaatct tgtttaagct tctcttcttc ttctctctcc tgtgtctcgt    60
tcactagttt tttttcgggg gagagtgatg gagtgtgttt gttgaatagt tttgacgatc   120
acatggctga gatttgttac gagaacgaga ctatgatgat tgaaacgacg gcgacggtgg   180
tgaagaaggc aacgacgaca acgaggagac gagaacggag ctcgtctcaa gcagcgagaa   240
gaaggagaat ggagatccgg aggtttaagt ttgtttccgg cgaacaagaa cctgtcttcg   300
tcgacggtga cttacagagg cggaggagaa gagaatccac cgtcgcagcc tccacctcca   360
ccgtgtttta cgaaacggcg aaggaagttg tcgtcctatg cgagtctctt agttcaacgg   420
ttgtggcatt gcctgatcct gaagcttatc ctaaatacgg cgtcgcttca gtctgtggaa   480
gaagacgtga atggaagac gccgtcgctg tgcatccgtt tttttcccgt catcagacgg   540
aatattcatc caccggattt cactattgcg gcgtttacga tggccatggc tgttcccatg   600
tagcgatgaa atgtagagaa agactacacg agctagtccg tgaagagttt gaagctgatg   660
ctgactggga aaagtcaatg gcgcgtagct tcacgcgcat ggacatggag gttgttgcgt   720
tgaacgccga tggtgcggca aaatgccggt gcgagcttca gaggccggac tgcgacgcgg   780
tgggatccac tgccggttgtg tctgtcctta cgccggagaa aatcatcgtg gcgaattgcg   840
gtgactcacg tgccgttctc tgtcgtaacg gcaaagccat tgctttatcc tccgatcata   900
agccagaccg tccggacgag ctagaccgga ttcaagcagc gggtggtcgt gttatctact   960
gggatggccc acgtgtcctt ggagtacttg caatgtcacg agccattgga gataattact  1020
tgaagccgta tgtaatcagc agaccggagg taaccgtgac ggaccgggcc aacggagacg  1080
atttttcttat tctcgcaagt gacggtcttt gggacgttgt ttcaaacgaa actgcatgta  1140
gcgtcgttcg aatgtgtttg agaggaaaag tcaatggtca agtatcatca tcaccggaaa  1200
gggaaatgac aggtgtcggc gccgggaatg tggtggttgg aggaggagat ttgccagata  1260
aagcgtgtga ggaggcgtcg ctgttgctga cgaggcttgc gttggctaga caaagttcgg  1320
acaacgtaag tgttgtggtg gttgatctac gacgagacac gtagttgtat ttgtctctct  1380
cgtaatgttt gttgtttttt gtcctgagtc atcgactttt gggcttttc ttttaacctt   1440
ttttgctctt cggtgtaaga caacgaaggg ttttttaattt agcttgacta tgggttatgt  1500
cagtcactgt gttgaatcgc ggtttagatc tacaaagatt ttcaccagta gtgaaaatgg  1560
taaaaagccg tgaaatgtga aagacttgag ttcaatttaa ttttaaattt aatagaatca  1620
gttgatc                                                            1627
```

<210> SEQ ID NO 9
<211> LENGTH: 413
<212> TYPE: PRT
<213> ORGANISM: Arabidopsis thaliana

<400> SEQUENCE: 9

```
Met Ala Glu Ile Cys Tyr Glu Asn Glu Thr Met Met Ile Glu Thr Thr
 1               5                  10                  15

Ala Thr Val Val Lys Lys Ala Thr Thr Thr Arg Arg Arg Glu Arg
                20                  25                  30

Ser Ser Ser Gln Ala Ala Arg Arg Arg Arg Met Glu Ile Arg Arg Phe
            35                  40                  45

Lys Phe Val Ser Gly Glu Gln Glu Pro Val Phe Val Asp Gly Asp Leu
        50                  55                  60

Gln Arg Arg Arg Arg Arg Glu Ser Thr Val Ala Ala Ser Thr Ser Thr
65                  70                  75                  80

Val Phe Tyr Glu Thr Ala Lys Glu Val Val Val Leu Cys Glu Ser Leu
```

|  |  |  |  |  |  |  |  |  |  |  |  |
|--|--|--|--|--|--|--|--|--|--|--|--|
|  |  |  | 85 |  |  |  | 90 |  |  |  | 95 |

Ser Ser Thr Val Val Ala Leu Pro Asp Pro Glu Ala Tyr Pro Lys Tyr
                    100                 105                 110

Gly Val Ala Ser Val Cys Gly Arg Arg Glu Met Glu Asp Ala Val
            115                 120                 125

Ala Val His Pro Phe Phe Ser Arg His Gln Thr Glu Tyr Ser Ser Thr
        130                 135                 140

Gly Phe His Tyr Cys Gly Val Tyr Asp Gly His Gly Cys Ser His Val
145                 150                 155                 160

Ala Met Lys Cys Arg Glu Arg Leu His Glu Leu Val Arg Glu Phe
                165                 170                 175

Glu Ala Asp Ala Asp Trp Glu Lys Ser Met Ala Arg Ser Phe Thr Arg
                180                 185                 190

Met Asp Met Glu Val Val Ala Leu Asn Ala Asp Gly Ala Ala Lys Cys
            195                 200                 205

Arg Cys Glu Leu Gln Arg Pro Asp Cys Asp Ala Val Gly Ser Thr Ala
        210                 215                 220

Val Val Ser Val Leu Thr Pro Glu Lys Ile Ile Val Ala Asn Cys Gly
225                 230                 235                 240

Asp Ser Arg Ala Val Leu Cys Arg Asn Gly Lys Ala Ile Ala Leu Ser
                245                 250                 255

Ser Asp His Lys Pro Asp Arg Pro Asp Glu Leu Asp Arg Ile Gln Ala
            260                 265                 270

Ala Gly Gly Arg Val Ile Tyr Trp Asp Gly Pro Arg Val Leu Gly Val
        275                 280                 285

Leu Ala Met Ser Arg Ala Ile Gly Asp Asn Tyr Leu Lys Pro Tyr Val
290                 295                 300

Ile Ser Arg Pro Glu Val Thr Val Thr Asp Arg Ala Asn Gly Asp Asp
305                 310                 315                 320

Phe Leu Ile Leu Ala Ser Asp Gly Leu Trp Asp Val Val Ser Asn Glu
                325                 330                 335

Thr Ala Cys Ser Val Val Arg Met Cys Leu Arg Gly Lys Val Asn Gly
            340                 345                 350

Gln Val Ser Ser Ser Pro Glu Arg Glu Met Thr Gly Val Gly Ala Gly
        355                 360                 365

Asn Val Val Gly Gly Gly Asp Leu Pro Asp Lys Ala Cys Glu Glu
370                 375                 380

Ala Ser Leu Leu Leu Thr Arg Leu Ala Leu Ala Arg Gln Ser Ser Asp
385                 390                 395                 400

Asn Val Ser Val Val Val Asp Leu Arg Arg Asp Thr
                405                 410

<210> SEQ ID NO 10
<211> LENGTH: 950
<212> TYPE: DNA
<213> ORGANISM: Arabidopsis thaliana

<400> SEQUENCE: 10
aaaattccaa ttattgtgtt actctattct tctaaatttg aacactaata gactatgaca     60
tatgagtata taatgtgaag tcttaagata ttttcatgtg ggagatgaat aggccaagtt    120
ggagtctgca aacaagaagc tcttgagcca cgacataagc caagttgatg accgtaatta    180
atgaaactaa atgtgtgtgg ttatatatta gggacccatg gccatataca caattttttgt   240 ttctgtcgat agcatgcgtt tatatatatt tctaaaaaaa ctaacatatt tactggatt     300

```
gagttcgaat attgacacta atataaacta cgtaccaaac tacatatgtt tatctatatt      360
tgattgatcg aagaattctg aactgtttta gaaaatttca atacacttaa cttcatctta      420
caacggtaaa agaaatcacc actagacaaa caatgcctca taatgtctcg aaccctcaaa      480
ctcaagagta tacattttac tagattagag aatttgatat cctcaagttg ccaaagaatt      540
ggaagctttt gttaccaaac ttagaaacag aagaagccac aaaaaaagac aaagggagtt      600
aaagattgaa gtgatgcatt tgtctaagtg tgaaaggtct caagtctcaa ctttgaacca      660
taataacatt actcacactc cctttttttt tcttttttt tcccaaagta cccttttaa        720 ttccctctat aacccactca ctccattccc tctttctgtc actgattcaa cacgtggcca      780
cactgatggg atccacccttt cctcttaccc acctcccggt ttatataaac ccttcacaac     840
acttcatcgc tctcaaacca actctctctt ctctcttctc tcctctcttc tacaagaaga      900
aaaaaaacag agcctttaca catctcaaaa tcgaacttac tttaaccacc                 950
```

<210> SEQ ID NO 11
<211> LENGTH: 2310
<212> TYPE: DNA
<213> ORGANISM: Arabidopsis thaliana

<400> SEQUENCE: 11

```
aaaccaactc tctcttctct cttctctcct ctcttctaca agaagaaaaa aaacagagcc       60
tttacacatc tcaaaatcga acttacttta accaccaaat actgattgaa cacacttgaa      120
aaatggcttc tttcacggca acggctgcgg tttctgggag atggcttggt ggcaatcata      180
ctcagccgcc attatcgtct tctcaaagct ccgacttgag ttattgtagc tccttaccta      240
tggccagtcg tgtcacacgt aagctcaatg tttcatctgc gcttcacact cctccagctc      300
ttcatttccc taagcaatca tcaaactctc ccgccattgt tgttaagccc aaagccaaag      360
aatccaacac taaacagatg aatttgttcc agagagcggc ggcggcagcg ttggacgcgg      420
cggagggttt ccttgtcagc cacgagaagc tacacccgct tcctaaaacg gctgatccta      480
gtgttcagat cgccggaaat tttgctccgg tgaatgaaca gcccgtccgg cgtaatcttc      540
cggtggtcgg aaaacttccc gattccatca aaggagtgta tgtgcgcaac ggagctaacc      600
cacttcacga gccggtgaca ggtcaccact tcttcgacgg agacggtatg gttcacgccg      660
tcaaattcga acacgttca gctagctacg cttgccggtt tactcagact aaccggtttg       720
ttcaggaacg tcaattgggt cgaccggttt tccccaaagc catcggtgag cttcacggcc      780
acaccggtat tgcccgactc atgctattct acgccagagc tgcagccggt atagtcgacc      840
cggcacacgg aacggtgta gctaacgccg gtttggtcta tttcaatggc cggttattgg       900
ctatgtcgga ggatgattta ccttaccaag ttcagatcac tcccaatgga gatttaaaaa      960
ccgttggtcg gttcgatttt gatggacaat tagaatccac aatgattgcc cacccgaaag     1020
tcgacccgga atccgtgaa ctcttcgctt aagctacga cgtcgtttca aagccttacc       1080
taaaatactt ccgattctca ccggacggaa ctaaatcacc ggacgtcgag attcagcttg     1140
atcagccaac gatgatgcac gatttcgcga ttacagagaa cttcgtcgtc gtacctgacc     1200
agcaagtcgt tttcaagctg ccggagatga tccgcggtgg gtctccggtg gtttacgaca     1260
agaacaaggt cgcaagattc gggatttttag acaaatacgc cgaagattca tcgaacatta     1320
agtggattga tgctccagat tgcttctgct tccatctctg gaacgcttgg gaagagccag     1380
aaacagatga agtcgtcgtg atagggtcct gtatgactcc accagactca attttcaacg     1440
agtctgacga gaatctcaag agtgtcctgt ctgaaatccg cctgaatctc aaaaccggtg     1500
```

-continued

```
aatcaactcg ccgtccgatc atctccaacg aagatcaaca agtcaacctc gaagcaggga   1560
tggtcaacag aaacatgctc ggccgtaaaa ccaaattcgc ttacttggct ttagccgagc   1620
cgtggcctaa agtctcagga ttcgctaaag ttgatctcac tactggagaa gttaagaaac   1680
atctttacgg cgataaccgt tacggaggag agcctctgtt tctccccgga gaaggaggag   1740
aggaagacga aggatacatc ctctgtttcg ttcacgacga aaagacatgg aaatcggagt   1800
tacagatagt taacgccgtt agcttagagg ttgaagcaac ggttaaactt ccgtcaaggg   1860
ttccgtacgg atttcacggt acattcatcg gagccgatga tttggcgaag caggtcgtgt   1920
gagttcttat gtgtaaatac gcacaaaata catatacgtg atgaagaagc ttctagaagg   1980
aaaagagaga gcgagattta ccagtgggat gctctgcata tacgtccccg gaatctgctc   2040
ctctgttttt ttttttttgc tctgtttctt gtttgttgtt tcttttgggg tgcggtttgc   2100
tagttccctt tttttgggg tcaatctaga aatctgaaag attttgaggg accagcttgt   2160
agcttttggg ctgtagggta gcctagccgt tcgagctcag ctggtttctg ttattctttc   2220
acttattgtt catcgtaatg agaagtatat aaaatattaa acaacaaaga tatgtttgta   2280
tatgtgcatg aattaaggaa catttttttt                                    2310
```

<210> SEQ ID NO 12
<211> LENGTH: 599
<212> TYPE: PRT
<213> ORGANISM: Arabidopsis thaliana

<400> SEQUENCE: 12

```
Met Ala Ser Phe Thr Ala Thr Ala Ala Val Ser Gly Arg Trp Leu Gly
1               5                   10                  15

Gly Asn His Thr Gln Pro Pro Leu Ser Ser Ser Gln Ser Ser Asp Leu
            20                  25                  30

Ser Tyr Cys Ser Ser Leu Pro Met Ala Ser Arg Val Thr Arg Lys Leu
        35                  40                  45

Asn Val Ser Ser Ala Leu His Thr Pro Pro Ala Leu His Phe Pro Lys
    50                  55                  60

Gln Ser Ser Asn Ser Pro Ala Ile Val Val Lys Pro Lys Ala Lys Glu
65                  70                  75                  80

Ser Asn Thr Lys Gln Met Asn Leu Phe Gln Arg Ala Ala Ala Ala
                85                  90                  95

Leu Asp Ala Ala Glu Gly Phe Leu Val Ser His Glu Lys Leu His Pro
            100                 105                 110

Leu Pro Lys Thr Ala Asp Pro Ser Val Gln Ile Ala Gly Asn Phe Ala
        115                 120                 125

Pro Val Asn Glu Gln Pro Val Arg Arg Asn Leu Pro Val Val Gly Lys
    130                 135                 140

Leu Pro Asp Ser Ile Lys Gly Val Tyr Val Arg Asn Gly Ala Asn Pro
145                 150                 155                 160

Leu His Glu Pro Val Thr Gly His His Phe Asp Gly Asp Gly Met
                165                 170                 175

Val His Ala Val Lys Phe Glu His Gly Ser Ala Ser Tyr Ala Cys Arg
            180                 185                 190

Phe Thr Gln Thr Asn Arg Phe Val Gln Glu Arg Gln Leu Gly Arg Pro
        195                 200                 205

Val Phe Pro Lys Ala Ile Gly Glu Leu His Gly His Thr Gly Ile Ala
    210                 215                 220

Arg Leu Met Leu Phe Tyr Ala Arg Ala Ala Ala Gly Ile Val Asp Pro
225                 230                 235                 240
```

```
Ala His Gly Thr Gly Val Ala Asn Ala Gly Leu Val Tyr Phe Asn Gly
                245                 250                 255

Arg Leu Leu Ala Met Ser Glu Asp Leu Pro Tyr Gln Val Gln Ile
            260                 265                 270

Thr Pro Asn Gly Asp Leu Lys Thr Val Gly Arg Phe Asp Phe Asp Gly
            275                 280                 285

Gln Leu Glu Ser Thr Met Ile Ala His Pro Lys Val Asp Pro Glu Ser
            290                 295                 300

Gly Glu Leu Phe Ala Leu Ser Tyr Asp Val Val Ser Lys Pro Tyr Leu
305                 310                 315                 320

Lys Tyr Phe Arg Phe Ser Pro Asp Gly Thr Lys Ser Pro Asp Val Glu
                325                 330                 335

Ile Gln Leu Asp Gln Pro Thr Met Met His Asp Phe Ala Ile Thr Glu
                340                 345                 350

Asn Phe Val Val Pro Asp Gln Gln Val Phe Lys Leu Pro Glu
                355                 360                 365

Met Ile Arg Gly Gly Ser Pro Val Tyr Asp Lys Asn Lys Val Ala
370                 375                 380

Arg Phe Gly Ile Leu Asp Lys Tyr Ala Glu Asp Ser Ser Asn Ile Lys
385                 390                 395                 400

Trp Ile Asp Ala Pro Asp Cys Phe Cys Phe His Leu Trp Asn Ala Trp
                405                 410                 415

Glu Glu Pro Glu Thr Asp Glu Val Val Ile Gly Ser Cys Met Thr
                420                 425                 430

Pro Pro Asp Ser Ile Phe Asn Glu Ser Asp Glu Asn Leu Lys Ser Val
                435                 440                 445

Leu Ser Glu Ile Arg Leu Asn Leu Lys Thr Gly Glu Ser Thr Arg Arg
                450                 455                 460

Pro Ile Ile Ser Asn Glu Asp Gln Gln Val Asn Leu Glu Ala Gly Met
465                 470                 475                 480

Val Asn Arg Asn Met Leu Gly Arg Lys Thr Lys Phe Ala Tyr Leu Ala
                485                 490                 495

Leu Ala Glu Pro Trp Pro Lys Val Ser Gly Phe Ala Lys Val Asp Leu
                500                 505                 510

Thr Thr Gly Glu Val Lys Lys His Leu Tyr Gly Asp Asn Arg Tyr Gly
                515                 520                 525

Gly Glu Pro Leu Phe Leu Pro Gly Glu Gly Glu Glu Asp Glu Gly
            530                 535                 540

Tyr Ile Leu Cys Phe Val His Asp Glu Lys Thr Trp Lys Ser Glu Leu
545                 550                 555                 560

Gln Ile Val Asn Ala Val Ser Leu Glu Val Glu Ala Thr Val Lys Leu
                565                 570                 575

Pro Ser Arg Val Pro Tyr Gly Phe His Gly Thr Phe Ile Gly Ala Asp
                580                 585                 590

Asp Leu Ala Lys Gln Val Val
            595
```

<210> SEQ ID NO 13
<211> LENGTH: 950
<212> TYPE: DNA
<213> ORGANISM: Arabidopsis thaliana

<400> SEQUENCE: 13
ataaaaattc acatttgcaa attttattca gtcggaatat atatttgaaa caagttttga    60

```
aatccattgg acgattaaaa ttcattgttg agaggataaa tatggatttg ttcatctgaa    120
ccatgtcgtt gattagtgat tgactaccat gaaaaatatg ttatgaaaag tataacaact    180
tttgataaat cacatttatt aacaataaat caagacaaaa tatgtcaaca ataatagtag    240
tagaagatat taattcaaat tcatccgtaa caacaaaaaa tcataccaca attaagtgta    300
cagaaaaacc ttttggatat atttattgtc gcttttcaat gattttcgtg aaaaggatat    360
atttgtgtaa aataagaagg atcttgacgg gtgtaaaaac atgcacaatt cttaatttag    420
accaatcaga agacaacacg aacacttctt tattataagc tattaaacaa atcttgcct     480
attttgctta gaataatatg aagagtgact catcagggag tggaaaatat ctcaggattt    540
gcttttagct ctaacatgtc aaactatcta gatgccaaca acacaaagtg caaattcttt    600
taatatgaaa acaacaataa tatttctaat agaaaattaa aaagggaaat aaaatatttt    660
tttaaaatat acaaagaag aaggaatcca tcatcaaagt tttataaaat tgtaatataa     720
tacaaacttg tttgcttcct tgtctctccc tctgtctctc tcatctctcc tatcttctcc    780
atatatactt catcttcaca cccaaaactc cacacaaaat atctctccct ctatctgcaa    840
attttccaaa gttgcatcct ttcaatttcc actcctctct aatataattc acattttccc    900
actattgctg attcattttt ttttgtgaat tatttcaaac ccacataaaa                950

<210> SEQ ID NO 14
<211> LENGTH: 1538
<212> TYPE: DNA
<213> ORGANISM: Arabidopsis thaliana

<400> SEQUENCE: 14
acaaaatatc tctccctcta tctgcaaatt ttccaaagtt gcatcctttc aatttccact     60
cctctctaat ataattcaca ttttcccact attgctgatt catttttttt tgtgaattat    120
ttcaaaccca cataaaaaaa tctttgttta aatttaaaac catggatcct tcatttaggt    180
tcattaaaga ggagtttcct gctggattca gtgattctcc atcaccacca tcttcttctt    240
cataccttta ttcatcttcc atggctgaag cagccataaa tgatccaaca acattgagct    300
atccacaacc attagaaggt ctccatgaat cagggccacc tccattttg acaaagacat    360
atgacttggt ggaagattca agaaccaatc atgtcgtgtc ttggagcaaa tccaataaca    420
gcttcattgt ctgggatcca caggcctttt ctgtaactct ccttcccaga ttcttcaagc    480
acaataactt ctccagtttt gtccgccagc tcaacacata tggtttcaga aaggtgaatc    540
cggatcggtg ggagtttgca acgaaggggt ttcttagagg gcaaaagcat ctcctcaaga    600
acataaggag aagaaaaaca agtaataata gtaatcaaat gcaacaacct caaagttctg    660
aacaacaatc tctagacaat ttttgcatag aagtgggtag gtacggtcta gatggagaga    720
tggacagcct aaggcgagac aagcaagtgt tgatgatgga gctagtgaga ctaagacagc    780
aacaacaaag caccaaaatg tatctcacat tgattgaaga gaagctcaag aagaccgagt    840
caaaacaaaa acaaatgatg agcttccttg cccgcgcaat gcagaatcca gatttttattc   900
agcagctagt agagcagaag gaaaagagga aagagatcga gaggcgatc agcaagaaga    960
gacaaagacc gatcgatcaa ggaaaaagaa atgtggaaga ttatggtgat gaaagtggtt   1020
atgggaatga tgttgcagcc tcatcctcag cattgattgg tatgagtcag gaatatacat   1080
atggaaacat gtctgaattc gagatgtcgg agttggacaa acttgctatg cacattcaag   1140
gacttggaga taattccagt gctagggaag aagtcttgaa tgtggaaaaa ggaaatgatg   1200
aggaagaagt agaagatcaa caacaagggt accataagga gaacaatgag atttatggtg   1260
```

```
aaggttttg  ggaagatttg  ttaaatgaag  gtcaaaattt  tgattttgaa  ggagatcaag   1320
aaaatgttga  tgtgttaatt  cagcaacttg  gttatttggg  ttctagttca  cacactaatt   1380
aagaagaaat  tgaaatgatg  actactttaa  gcatttgaat  caacttgttt  cctattagta   1440
atttggcttt  gttcaatca   agtgagtcgt  ggactaactt  attgaatttg  ggggttaaat   1500
ccgtttctta  tttttggaaa  taaaattgct  ttttgttt                             1538
```

<210> SEQ ID NO 15
<211> LENGTH: 406
<212> TYPE: PRT
<213> ORGANISM: Arabidopsis thaliana

<400> SEQUENCE: 15

```
Met Asp Pro Ser Phe Arg Phe Ile Lys Glu Glu Phe Pro Ala Gly Phe
1               5                   10                  15

Ser Asp Ser Pro Ser Pro Ser Ser Ser Ser Tyr Leu Tyr Ser Ser
            20                  25                  30

Ser Met Ala Glu Ala Ala Ile Asn Asp Pro Thr Thr Leu Ser Tyr Pro
        35                  40                  45

Gln Pro Leu Glu Gly Leu His Glu Ser Gly Pro Pro Phe Leu Thr
    50                  55                  60

Lys Thr Tyr Asp Leu Val Glu Asp Ser Arg Thr Asn His Val Val Ser
65                  70                  75                  80

Trp Ser Lys Ser Asn Asn Ser Phe Ile Val Trp Asp Pro Gln Ala Phe
                85                  90                  95

Ser Val Thr Leu Leu Pro Arg Phe Phe Lys His Asn Asn Phe Ser Ser
            100                 105                 110

Phe Val Arg Gln Leu Asn Thr Tyr Gly Phe Arg Lys Val Asn Pro Asp
        115                 120                 125

Arg Trp Glu Phe Ala Asn Glu Gly Phe Leu Arg Gly Gln Lys His Leu
    130                 135                 140

Leu Lys Asn Ile Arg Arg Lys Thr Ser Asn Asn Ser Asn Gln Met
145                 150                 155                 160

Gln Gln Pro Gln Ser Ser Glu Gln Gln Ser Leu Asp Asn Phe Cys Ile
                165                 170                 175

Glu Val Gly Arg Tyr Gly Leu Asp Gly Glu Met Asp Ser Leu Arg Arg
            180                 185                 190

Asp Lys Gln Val Leu Met Met Glu Leu Val Arg Leu Arg Gln Gln Gln
        195                 200                 205

Gln Ser Thr Lys Met Tyr Leu Thr Leu Ile Glu Glu Lys Leu Lys Lys
    210                 215                 220

Thr Glu Ser Lys Gln Lys Gln Met Met Ser Phe Leu Ala Arg Ala Met
225                 230                 235                 240

Gln Asn Pro Asp Phe Ile Gln Gln Leu Val Glu Gln Lys Glu Lys Arg
                245                 250                 255

Lys Glu Ile Glu Glu Ala Ile Ser Lys Lys Arg Gln Arg Pro Ile Asp
            260                 265                 270

Gln Gly Lys Arg Asn Val Glu Asp Tyr Gly Asp Glu Ser Gly Tyr Gly
        275                 280                 285

Asn Asp Val Ala Ala Ser Ser Ser Ala Leu Ile Gly Met Ser Gln Glu
    290                 295                 300

Tyr Thr Tyr Gly Asn Met Ser Glu Phe Glu Met Ser Glu Leu Asp Lys
305                 310                 315                 320

Leu Ala Met His Ile Gln Gly Leu Gly Asp Asn Ser Ser Ala Arg Glu
                325                 330                 335
```

```
Glu Val Leu Asn Val Glu Lys Gly Asn Asp Glu Glu Val Glu Asp
            340                 345                 350

Gln Gln Gln Gly Tyr His Lys Glu Asn Asn Glu Ile Tyr Gly Glu Gly
            355                 360                 365

Phe Trp Glu Asp Leu Leu Asn Glu Gly Gln Asn Phe Asp Phe Glu Gly
    370                 375                 380

Asp Gln Glu Asn Val Asp Val Leu Ile Gln Gln Leu Gly Tyr Leu Gly
385                 390                 395                 400

Ser Ser Ser His Thr Asn
            405

<210> SEQ ID NO 16
<211> LENGTH: 950
<212> TYPE: DNA
<213> ORGANISM: Arabidopsis thaliana

<400> SEQUENCE: 16 tttttaaaa ttcgttggaa cttggaaggg attttaaata ttattttgtt ttccttcatt     60
tttataggtt aataattgtc aaagatacaa ctcgatggac caaataaaa taataaaatt    120 cgtcgaattt ggtaaagcaa acggtcgag  atagctaat atttatgcga aacccgttgt    180
caaagcagat gttcagcgtc acgcacatgc gcaaaaaga atatcatca acctcttttg    240 aacttcacgc cgttttttag gcccacaata atgctacgtc gtcttctggg ttcaccctcg    300 ttttttttt  aaacttctaa ccgataaaat aaatggtcca ctatttcttt tcttctctgt    360
gtattgtcgt cagagatggt ttaaaagttg aaccgaacta taacgattct cttaaaatct    420
gaaaaccaaa ctgaccgatt tcttaactg  aaaaaaaaa  aaaaaaaac tgaatttagg     480 ccaacttgtt gtaatatcac aaagaaaatt ctacaattta attcatttaa aaataaagaa    540
aaatttaggt aacaatttaa ctaagtggtc tatctaaatc ttgcaaattc tttgactttg    600
accaaacaca acttaagttg acagccgtct cctctctgtt gtttccgtgt tattaccgaa    660
atatcagagg aaagtccact aaaccccaaa tattaaaaat agaaacatta ctttctttac    720
aaaaggaatc taaattgatc cctttcattc gtttcactcg tttcatatag ttgtatgtat    780
atatgcgtat gcatcaaaaa gtctctttat atcctcagag tcacccaatc ttatctctct    840
ctccttcgtc ctcaagaaaa gtaattctct gtttgtgtag ttttctttac cggtgaattt    900
tctcttcgtt ttgtgcttca aacgtcaccc aaatcaccaa gatcgatcaa               950

<210> SEQ ID NO 17
<211> LENGTH: 1720
<212> TYPE: DNA
<213> ORGANISM: Arabidopsis thaliana

<400> SEQUENCE: 17
agagtcaccc aatcttatct ctctctcctt cgtcctcaag aaaagtaatt ctctgtttgt     60
gtagttttct ttaccggtga attttctctt cgttttgtgc ttcaaacgtc acccaaatca    120 ccagatcga  tcaaaatcga aacttaacgt tcagaagat  ggtgcagtac cagagattaa    180
tcatccacca tggaagaaaa gaagataagt ttagagtttc ttcagcagag gaaagtggtg    240
gaggtggttg ttgctactcc aagagagcta aacaaaagtt tcgttgtctt ctcttctctc    300 tatcctctc  ttgctgtttc gtcttgtctc cttattacct cttcggcttc tctactctct    360
ccctcctaga ttcgtttcgc agagaaatcg aaggtcttag ctcttatgag ccagttatta    420
cccctctgtg ctcagaaatc tccaatggaa ccatttgttg tgacagaacc ggtttgagat    480
```

```
ctgatatttg tgtaatgaaa ggtgatgttc aacaaactc tgcttcttcc tcaatcttcc    540
tcttcacctc ctccaccaat aacaacacaa accggaaaa gatcaaacct acactagaa    600
aatgggagac tagtgtgatg acaccgttc aagaactcaa cctcatcacc aaagattcca   660
acaaatcttc agatcgtgta tgcgatgtgt accatgatgt tcctgctgtg ttcttctcca   720
ctggtggata caccggtaac gtataccacg agtttaacga cgggattatc cctttgttta   780
taacttcaca gcattacaac aaaaaagttg tgtttgtgat cgtcgagtat catgactggt   840
gggagatgaa gtatggagat gtcgtttcgc agctctcgga ttatcctctg gttgatttca   900
atggagatac gagaacacat tgtttcaaag aagcaaccgt tggattacgt attcacgacg   960
agttaactgt gaattcttct ttggtcattg ggaatcaaac cattgttgac ttcagaaacg  1020
tttggatag gggttactcg catcgtatcc aaagcttgac tcaggaggaa acagaggcga  1080
acgtgaccgc actcgatttc aagaagaagc caaaactggt gattctttca agaaacgggt  1140
catcaagggc gatattaaac gagaatcttc tcgtggagct agcagagaaa acagggttca  1200
atgtggaggt tctaagacca caaaagacaa cggaaatggc caagatttat cgttcgttga  1260
acacgagcga tgtaatgatc ggtgtacatg gagcagcaat gactcatttc cttttcttga  1320
aaccgaaaac cgttttcatt cagatcatcc cattagggac ggactgggcg gcagagacat  1380
attatggaga accggcgaag aagctaggat tgaagtacgt tggttacaag attgcgccga  1440
aagagagctc tttgtatgaa gaatatggga agatgaccc tgtaatccga gatccggata  1500
gtctaaacga caaaggatgg gaatatacga agaaaatcta tctacaagga cagaacgtga  1560
agcttgactt gagaagattc agagaaacgt taactcgttc gtatgatttc tccattagaa  1620
ggagatttag agaagattac ttgttacata gagaagatta agaatcgtgt gatatttttt  1680
ttgtaaagtt ttgaatgaca attaaattta tttattttat                        1720

<210> SEQ ID NO 18
<211> LENGTH: 500
<212> TYPE: PRT
<213> ORGANISM: Arabidopsis thaliana

<400> SEQUENCE: 18

Met Val Gln Tyr Gln Arg Leu Ile Ile His His Gly Arg Lys Glu Asp
1               5                   10                  15

Lys Phe Arg Val Ser Ser Ala Glu Ser Gly Gly Gly Gly Cys Cys
            20                  25                  30

Tyr Ser Lys Arg Ala Lys Gln Lys Phe Arg Cys Leu Leu Phe Leu Ser
        35                  40                  45

Ile Leu Ser Cys Cys Phe Val Leu Ser Pro Tyr Tyr Leu Gly Phe
    50                  55                  60

Ser Thr Leu Ser Leu Leu Asp Ser Phe Arg Arg Glu Ile Glu Gly Leu
65                  70                  75                  80

Ser Ser Tyr Glu Pro Val Ile Thr Pro Leu Cys Ser Glu Ile Ser Asn
                85                  90                  95

Gly Thr Ile Cys Cys Asp Arg Thr Gly Leu Arg Ser Asp Ile Cys Val
            100                 105                 110

Met Lys Gly Asp Val Arg Thr Asn Ser Ala Ser Ser Ile Phe Leu
        115                 120                 125

Phe Thr Ser Ser Thr Asn Asn Asn Thr Lys Pro Glu Lys Ile Lys Pro
    130                 135                 140

Tyr Thr Arg Lys Trp Glu Thr Ser Val Met Asp Thr Val Gln Glu Leu
145                 150                 155                 160
```

```
Asn Leu Ile Thr Lys Asp Ser Asn Lys Ser Ser Asp Arg Val Cys Asp
            165                 170                 175

Val Tyr His Asp Val Pro Ala Val Phe Phe Ser Thr Gly Gly Tyr Thr
        180                 185                 190

Gly Asn Val Tyr His Glu Phe Asn Asp Gly Ile Ile Pro Leu Phe Ile
    195                 200                 205

Thr Ser Gln His Tyr Asn Lys Lys Val Val Phe Val Ile Val Glu Tyr
210                 215                 220

His Asp Trp Trp Glu Met Lys Tyr Gly Asp Val Val Ser Gln Leu Ser
225                 230                 235                 240

Asp Tyr Pro Leu Val Asp Phe Asn Gly Asp Thr Arg Thr His Cys Phe
                245                 250                 255

Lys Glu Ala Thr Val Gly Leu Arg Ile His Asp Glu Leu Thr Val Asn
                260                 265                 270

Ser Ser Leu Val Ile Gly Asn Gln Thr Ile Val Asp Phe Arg Asn Val
            275                 280                 285

Leu Asp Arg Gly Tyr Ser His Arg Ile Gln Ser Leu Thr Gln Glu Glu
    290                 295                 300

Thr Glu Ala Asn Val Thr Ala Leu Asp Phe Lys Lys Pro Lys Leu
305                 310                 315                 320

Val Ile Leu Ser Arg Asn Gly Ser Ser Arg Ala Ile Leu Asn Glu Asn
                325                 330                 335

Leu Leu Val Glu Leu Ala Glu Lys Thr Gly Phe Asn Val Glu Val Leu
            340                 345                 350

Arg Pro Gln Lys Thr Thr Glu Met Ala Lys Ile Tyr Arg Ser Leu Asn
    355                 360                 365

Thr Ser Asp Val Met Ile Gly Val His Gly Ala Ala Met Thr His Phe
370                 375                 380

Leu Phe Leu Lys Pro Lys Thr Val Phe Ile Gln Ile Pro Leu Gly
385                 390                 395                 400

Thr Asp Trp Ala Ala Glu Thr Tyr Tyr Gly Glu Pro Ala Lys Lys Leu
                405                 410                 415

Gly Leu Lys Tyr Val Gly Tyr Lys Ile Ala Pro Lys Glu Ser Ser Leu
            420                 425                 430

Tyr Glu Glu Tyr Gly Lys Asp Asp Pro Val Ile Arg Asp Pro Asp Ser
    435                 440                 445

Leu Asn Asp Lys Gly Trp Glu Tyr Thr Lys Lys Ile Tyr Leu Gln Gly
    450                 455                 460

Gln Asn Val Lys Leu Asp Leu Arg Arg Phe Arg Glu Thr Leu Thr Arg
465                 470                 475                 480

Ser Tyr Asp Phe Ser Ile Arg Arg Arg Phe Arg Glu Asp Tyr Leu Leu
                485                 490                 495

His Arg Glu Asp
            500

<210> SEQ ID NO 19
<211> LENGTH: 950
<212> TYPE: DNA
<213> ORGANISM: Arabidopsis thaliana

<400> SEQUENCE: 19
tcattacatt gaaaagaaa attaattgtc tttactcatg tttattctat acaaataaaa      60
atattaacca accatcgcac taacaaaata gaaatcttat tctaatcact taattgttga    120
caattaaatc attgaaaaat acacttaaat gtcaaatatt cgttttgcat acttttcaat    180
```

-continued

```
ttaaatacat ttaaagttcg acaagttgcg tttactatca tagaaaacta aatctcctac    240
caaagcgaaa tgaaactact aaagcgacag gcaggttaca taacctaaca aatctccacg    300
tgtcaattac caagagaaaa aagagaaga taagcggaac acgtggtagc acaaaaaga     360 taatgtgatt taaattaaaa aacaaaaaca aagacacgtg acgacctgac gctgcaacat    420
cccaccttac aacgtaataa ccactgaaca taagacacgt gtacgatctt gtctttgttt    480
tctcgatgaa aaccacgtgg gtgctcaaag tccttgggtc agagtcttcc atgattccac    540
gtgtcgttaa tgcaccaaac aagggtactt tcggtatttt ggcttccgca aattagacaa    600
aacagctttt tgtttgattg attttctct tctctttttc catctaaatt ctctttgggc     660
tcttaatttc tttttgagtg ttcgttcgag atttgtcgga gattttttcg gtaaatgttg    720
aaattttgtg ggattttttt ttatttcttt attaaacttt tttttattga atttataaaa    780
agggaaggtc gtcattaatc gaagaaatgg aatcttccaa aatttgatat tttgctgttt    840
tcttgggatt tgaattgctc tttatcatca agaatctgtt aaaatttcta atctaaaatc    900
taagttgaga aaaagagaga tctctaattt aaccggaatt aatattctcc              950
```

```
<210> SEQ ID NO 20
<211> LENGTH: 1193
<212> TYPE: DNA
<213> ORGANISM: Arabidopsis thaliana

<400> SEQUENCE: 20
aaattctctt tgggctctta atttcttttt gagtgttcgt tcgagatttg tcggagattt     60
tttcggtaaa tgttgaaatt tgtgggatt tttttttatt tctttattaa acttttttt     120 attgaattta taaaaggga aggtcgtcat taatcgaaga aatggaatct tccaaaattt    180
gatattttgc tgttttcttg ggatttgaat tgctctttat catcaagaat ctgttaaaat    240
ttctaatcta aaatctaagt tgagaaaaag agagatctct aatttaaccg gaattaatat    300
tctccgaccg aagttattat gttgcaggct catgtcgaag aaacagagat tgtctgaaga    360
agatggagag gtagagattg agttagactt aggtctatct ctaaatggaa gatttggtgt    420
tgacccactt gcgaaaacaa ggcttatgag gtctacgtcg gttcttgatt tggtggtcaa    480
cgataggtca gggctgagta ggacttgttc gttacccgtg gagacggagg aagagtggag    540
gaagaggaag gagttgcaga gtttgaggag gcttgaggct aagagaaaga gatcagagaa    600
gcagaggaaa cataaagctt gtggtggtga agagaaggtt gtggaagaag gatctattgg    660
ttcttctggt agtggttcct ctggtttgtc tgaagttgat actcttcttc ctcctgttca    720
agcaacaacg aacaagtccg tggaaacaag cccttcaagt gcccaatctc agcccgagaa    780
tttgggcaaa gaagcgagcc aaaacattat agaggacatg ccattcgtgt caacaacagg    840
cgatggaccg aacgggaaaa agattaatgg gttctgtat cggtaccgca aaggtgagga    900
ggtgaggatt gtctgtgtgt gtcatggaag cttcctctca ccggcagaat tcgttaagca    960
tgctggtggt ggtgacgttg cacatccctt aaagcacatc gttgtaaatc catctccctt   1020
cttgtgaccc tttgggtctc ttttgagggg tttgttgtat cggaaccatg ttacaaatcc   1080
tcattatctc cgaggtgtat aaacataaat ttatcgaact cgcaattttc agattttgta   1140
cttaaaagaa tggtttcatt cgttgagatt aatttttagac ctttttcttg tac          1193
```

```
<210> SEQ ID NO 21
<211> LENGTH: 231
<212> TYPE: PRT
<213> ORGANISM: Arabidopsis thaliana
```

<400> SEQUENCE: 21

```
Met Ser Lys Lys Gln Arg Leu Ser Glu Glu Asp Gly Glu Val Glu Ile
1               5                   10                  15
Glu Leu Asp Leu Gly Leu Ser Leu Asn Gly Arg Phe Gly Val Asp Pro
            20                  25                  30
Leu Ala Lys Thr Arg Leu Met Arg Ser Thr Ser Val Leu Asp Leu Val
        35                  40                  45
Val Asn Asp Arg Ser Gly Leu Ser Arg Thr Cys Ser Leu Pro Val Glu
    50                  55                  60
Thr Glu Glu Trp Arg Lys Arg Lys Glu Leu Gln Ser Leu Arg Arg
65                  70                  75                  80
Leu Glu Ala Lys Arg Lys Arg Ser Glu Lys Gln Arg Lys His Lys Ala
                85                  90                  95
Cys Gly Gly Glu Glu Lys Val Val Glu Glu Gly Ser Ile Gly Ser Ser
            100                 105                 110
Gly Ser Gly Ser Ser Gly Leu Ser Glu Val Asp Thr Leu Leu Pro Pro
            115                 120                 125
Val Gln Ala Thr Thr Asn Lys Ser Val Glu Thr Ser Pro Ser Ser Ala
    130                 135                 140
Gln Ser Gln Pro Glu Asn Leu Gly Lys Glu Ala Ser Gln Asn Ile Ile
145                 150                 155                 160
Glu Asp Met Pro Phe Val Ser Thr Thr Gly Asp Gly Pro Asn Gly Lys
                165                 170                 175
Lys Ile Asn Gly Phe Leu Tyr Arg Tyr Arg Lys Gly Glu Glu Val Arg
            180                 185                 190
Ile Val Cys Val Cys His Gly Ser Phe Leu Ser Pro Ala Glu Phe Val
        195                 200                 205
Lys His Ala Gly Gly Gly Asp Val Ala His Pro Leu Lys His Ile Val
    210                 215                 220
Val Asn Pro Ser Pro Phe Leu
225                 230
```

<210> SEQ ID NO 22
<211> LENGTH: 950
<212> TYPE: DNA
<213> ORGANISM: Arabidopsis thaliana

<400> SEQUENCE: 22

```
tttcaatgta tacaatcatc atgtgataaa aaaaaaaatg taaccaatca acacactgag    60
atacggccaa aaaatggtaa tacataaatg tttgtaggtt ttgtaattta aatactttag   120
ttaagttatg attttattat ttttgcttat cacttatacg aaatcatcaa tctattggta   180
tctcttaatc ccgcttttta atttccaccg cacacgcaaa tcagcaaatg gttccagcca   240
cgtgcatgtg accacatatt gtggtcacag tactcgtcct ttttttttct tttgtaatca   300
ataaatttca atcctaaaac ttcacacatt gagcacgtcg gcaacgttag ctcctaaatc   360
ataacgagca aaaagttcaa attagggta tatgatcaat tgatcatcac tacatgtcta   420
cataattaat atgtattcaa ccggtcggtt tgttgatact catagttaag tatatatgtg   480
ctaattagaa ttaggatgaa tcagttcttg caaacaacta cggtttcata taatatggga   540
gtgttatgta caaaatgaaa gaggatggat cattctgaga tgttatgggc tcccagtcaa   600
tcatgttttg ctcgcatatg ctatcttttg agtctcttcc taaactcata gaataagcac   660
gttggttttt tccaccgtcc tcctcgtgaa caaaagtaca attacatttt agcaaattga   720
aaataaccac gtggatggac catattatat gtgatcatat tgcttgtcgt cttcgttttc   780
```

```
tttttaaatgt ttacaccact acttcctgac acgtgtccct attcacatca tccttgttat    840
atcgttttac ttataaagga tcacgaacac caaaacatca atgtgtacgt cttttgcata    900
agaagaaaca gagagcatta tcaattatta acaattacac aagacagcga               950
```

<210> SEQ ID NO 23
<211> LENGTH: 995
<212> TYPE: DNA
<213> ORGANISM: Arabidopsis thaliana

<400> SEQUENCE: 23

```
aatgtgtacg tcttttgcat aagaagaaac agagagcatt atcaattatt aacaattaca     60
caagacagcg agattgtaaa agagtaagag agagagaatg gcaggagagg cagaggcttt    120
ggccacgacg gcaccgttag ctccggtcac cagtcagcga aaagtacgga acgatttgga    180
ggaaacatta ccaaaaccat acatggcaag agcattagca gctccagata cagagcatcc    240
gaatggaaca gaaggtcacg atagcaaagg aatgagtgtt atgcaacaac atgttgcttt    300
cttcgaccaa aacgacgatg gaatcgtcta tccttgggag acttataagg gatttcgtga    360
ccttggtttc aacccaattt cctctatctt ttggacctta ctcataaact tagcgttcag    420
ctacgttaca cttccgagtt gggtgccatc accattattg ccggtttata tcgacaacat    480
acacaaagcc aagcatggga gtgattcgag cacctatgac accgaaggaa ggtatgtccc    540
agttaacctc gagaacatat ttagcaaata cgcgctaacg gttaaagata agttatcatt    600
taaagaggtt tggaatgtaa ccgagggaaa tcgaatggca atcgatcctt ttggatggct    660
ttcaaacaaa gttgaatgga tactactcta tattcttgct aaggacgaag atggtttcct    720
atctaaagaa gctgtgagag gttgctttga tggaagttta tttgaacaaa ttgccaaaga    780
gagggccaat tctcgcaaac aagactaaga atgtgtgtgt ttggttagcg aataaagctt    840
tttgaagaaa agcattgtgt aatttagctt ctttcgtctt gttattcagt ttggggattt    900
gtataattaa tgtgtttgta aactatgttt caaagttata taaataagag aagatgttac    960
aaaaaaaaaa aaaagactaa taagaagaat ttggt                              995
```

<210> SEQ ID NO 24
<211> LENGTH: 236
<212> TYPE: PRT
<213> ORGANISM: Arabidopsis thaliana

<400> SEQUENCE: 24

```
Met Ala Gly Glu Ala Glu Ala Leu Ala Thr Thr Ala Pro Leu Ala Pro
 1               5                  10                  15

Val Thr Ser Gln Arg Lys Val Arg Asn Asp Leu Glu Glu Thr Leu Pro
            20                  25                  30

Lys Pro Tyr Met Ala Arg Ala Leu Ala Ala Pro Asp Thr Glu His Pro
        35                  40                  45

Asn Gly Thr Glu Gly His Asp Ser Lys Gly Met Ser Val Met Gln Gln
    50                  55                  60

His Val Ala Phe Phe Asp Gln Asn Asp Asp Gly Ile Val Tyr Pro Trp
65                  70                  75                  80

Glu Thr Tyr Lys Gly Phe Arg Asp Leu Gly Phe Asn Pro Ile Ser Ser
                85                  90                  95

Ile Phe Trp Thr Leu Leu Ile Asn Leu Ala Phe Ser Tyr Val Thr Leu
            100                 105                 110

Pro Ser Trp Val Pro Ser Pro Leu Leu Pro Val Tyr Ile Asp Asn Ile
        115                 120                 125
```

```
His Lys Ala Lys His Gly Ser Asp Ser Ser Thr Tyr Asp Thr Glu Gly
    130                 135                 140

Arg Tyr Val Pro Val Asn Leu Glu Asn Ile Phe Ser Lys Tyr Ala Leu
145                 150                 155                 160

Thr Val Lys Asp Lys Leu Ser Phe Lys Glu Val Trp Asn Val Thr Glu
                165                 170                 175

Gly Asn Arg Met Ala Ile Asp Pro Phe Gly Trp Leu Ser Asn Lys Val
            180                 185                 190

Glu Trp Ile Leu Leu Tyr Ile Leu Ala Lys Asp Glu Asp Gly Phe Leu
        195                 200                 205

Ser Lys Glu Ala Val Arg Gly Cys Phe Asp Gly Ser Leu Phe Glu Gln
    210                 215                 220

Ile Ala Lys Glu Arg Ala Asn Ser Arg Lys Gln Asp
225                 230                 235

<210> SEQ ID NO 25
<211> LENGTH: 950
<212> TYPE: DNA
<213> ORGANISM: Arabidopsis thaliana

<400> SEQUENCE: 25
agaagaaact agaaacgtta aacgcatcaa atcaagaaat taaattgaag gtaattttta      60
acgccgcctt tcaaatattc ttcctaggag aggctacaag acgcgtattt ctttcgaatt     120
ctccaaacca ttaccatttt gatatataat accgacatgc cgttgataaa gtttgtatgc     180
aaatcgttca ttgggtatga gcaaatgcca tccattggtt cttgtaatta aatggtccaa     240
aaatagtttg ttcccactac tagttactaa tttgtatcac tctgcaaaat aatcatgata     300
taaacgtatg tgctatttct aattaaaact caaaagtaat caatgtacaa tgcagagatg     360
accataaaag aacattaaaa cactacttcc actaaatcta tggggtgcct tggcaaggca     420
attgaataag gagaatgcat caagatgata tagaaaatgc tattcagttt ataacattaa     480
tgttttggcg gaaaattttc tatatattag acctttctgt aaaaaaaaaa aaatgatgta     540
gaaaatgcta ttatgtttca aaaatttcgc actagtataa tacggaacat gtagtttac      600 actgctcatt accatgaaaa ccaaggcagt ataccaac attaataaac taaatcgcga      660
tttctagcac ccccattaat taattttact attatacatt ctctttgctt ctcgaaataa     720
taaacttctc tatatcattc tacataataa ataagaaaga aatcgacaag atctaaattt     780
agatctattc agcttttctcg cctgagaagc caaaattgtg aatagaagaa agcagtcgtc     840
atcttcccac gtttggacga ataaaacat aacaataata aaataataaa tcaaatatat      900
aaatccctaa tttgtcttta ttactccaca attttctatg tgtatatata                 950

<210> SEQ ID NO 26
<211> LENGTH: 124
<212> TYPE: DNA
<213> ORGANISM: Arabidopsis thaliana

<400> SEQUENCE: 26
tgtatgtttt tgttccctat tatatcttct agcttctttc ttcctcttct tccttaaaaa      60
ttcatcctcc aaaacattct atcatcaacg aaacatttca tattaaatta ataataatc      120 gatg                                                                  124

<210> SEQ ID NO 27
<211> LENGTH: 1685
<212> TYPE: DNA
```

<213> ORGANISM: Arabidopsis thaliana

<400> SEQUENCE: 27

```
gtatgttttt gttccctatt atatcttcta gcttctttct tcctcttctt ccttaaaaat      60
tcatcctcca aaacattcta tcatcaacga aacatttcat attaaattaa ataataatcg     120
atggctgaaa tttggttctt ggttgtacca atcctcatct tatgcttgct tttggtaaga     180
gtgattgttt caagaagaaa aagaacagt agaggtaagc ttcctcctgg ttccatggga     240
tggccttact taggagagac tctacaactc tattcacaaa accccaatgt tttcttcacc     300
tccaagcaaa agagatatgg agagatattc aaaacccgaa tcctcggcta tccatgcgtg     360
atgttggcta gccctgaggc tgcgaggttt gtacttgtga ctcatgccca tatgttcaaa     420
ccaacttatc cgagaagcaa agagaagctg ataggaccct ctgcactctt tttccaccaa     480
ggagattatc attcccatat aaggaaactt gttcaatcct ctttctaccc tgaaaccatc     540
cgtaaactca tccctgatat cgagcacatt gccctttctt ccttacaatc ttgggccaat     600
atgccgattg tctccaccta ccaggagatg aagaagttcg cctttgatgt gggtattcta     660
gccatatttg gacatttgga gagttcttac aaagagatct tgaaacataa ctacaatatt     720
gtggacaaag gctacaactc tttccccatg agtctccccg gaacatctta tcacaaagct     780
ctcatggcga aaagcagct aaagacgata gtaagcgaga ttatatgcga agaagagag     840
aaaagggcct tgcaaacgga ctttcttggt catctactca acttcaagaa cgaaaaaggt     900
cgtgtgctaa cccaagaaca gattgcagac aacatcatcg gagtcctttt cgccgcacag     960
gacacgacag ctagttgctt aacttggatt cttaagtact tacatgatga tcagaaactt    1020
ctagaagctg ttaaggctga gcaaaaggct atatatgaag aaaacagtag agagaagaaa    1080
cctttaacat ggagacaaac gaggaatatg ccactgacac ataaggttat agttgaaagc    1140
ttgaggatgg caagcatcat atccttcaca ttcagaagag cagtggttga tgttgaatat    1200
aagggatatt tgatacctaa gggatggaaa gtgatgccac tgtttcggaa tattcatcac    1260
aatccgaaat atttttcaaa ccctgaggtt ttcgacccat ctagattcga ggtaaatccg    1320
aagccgaata cattcatgcc ttttggaagt ggagttcatg cttgtcccgg aacgaactc    1380
gccaagttac aaattcttat atttctccac catttagttt ccaatttccg atgggaagtg    1440
aagggaggag agaaaggaat acagtacagt ccatttccaa tacctcaaaa cggtcttccc    1500
gctacatttc gtcgacattc tctttagttc cttaaacctt tgtagtaatc tttgttgtag    1560
ttagccaaat ctaatccaaa ttcgatataa aaatcccct ttctatttt ttttaaaatc     1620
attgttgtag tcttgagggg gtttaacatg taacaactat gatgaagtaa aatgtcgatt    1680
ccggt                                                                 1685
```

<210> SEQ ID NO 28
<211> LENGTH: 468
<212> TYPE: PRT
<213> ORGANISM: Arabidopsis thaliana

<400> SEQUENCE: 28

```
Met Ala Glu Ile Trp Phe Leu Val Val Pro Ile Leu Ile Leu Cys Leu
 1               5                  10                  15

Leu Leu Val Arg Val Ile Val Ser Lys Lys Lys Asn Ser Arg Gly
            20                  25                  30

Lys Leu Pro Pro Gly Ser Met Gly Trp Pro Tyr Leu Gly Glu Thr Leu
        35                  40                  45

Gln Leu Tyr Ser Gln Asn Pro Asn Val Phe Phe Thr Ser Lys Gln Lys
```

```
             50                  55                  60
Arg Tyr Gly Glu Ile Phe Lys Thr Arg Ile Leu Gly Tyr Pro Cys Val
65                  70                  75                  80

Met Leu Ala Ser Pro Glu Ala Ala Arg Phe Val Leu Val Thr His Ala
                85                  90                  95

His Met Phe Lys Pro Thr Tyr Pro Arg Ser Lys Glu Lys Leu Ile Gly
                100                 105                 110

Pro Ser Ala Leu Phe Phe His Gln Gly Asp Tyr His Ser His Ile Arg
                115                 120                 125

Lys Leu Val Gln Ser Ser Phe Tyr Pro Glu Thr Ile Arg Lys Leu Ile
                130                 135                 140

Pro Asp Ile Glu His Ile Ala Leu Ser Ser Leu Gln Ser Trp Ala Asn
145                 150                 155                 160

Met Pro Ile Val Ser Thr Tyr Gln Glu Met Lys Lys Phe Ala Phe Asp
                165                 170                 175

Val Gly Ile Leu Ala Ile Phe Gly His Leu Glu Ser Ser Tyr Lys Glu
                180                 185                 190

Ile Leu Lys His Asn Tyr Asn Ile Val Asp Lys Gly Tyr Asn Ser Phe
                195                 200                 205

Pro Met Ser Leu Pro Gly Thr Ser Tyr His Lys Ala Leu Met Ala Arg
210                 215                 220

Lys Gln Leu Lys Thr Ile Val Ser Glu Ile Ile Cys Glu Arg Arg Glu
225                 230                 235                 240

Lys Arg Ala Leu Gln Thr Asp Phe Leu Gly His Leu Leu Asn Phe Lys
                245                 250                 255

Asn Glu Lys Gly Arg Val Leu Thr Gln Glu Gln Ile Ala Asp Asn Ile
                260                 265                 270

Ile Gly Val Leu Phe Ala Ala Gln Asp Thr Thr Ala Ser Cys Leu Thr
                275                 280                 285

Trp Ile Leu Lys Tyr Leu His Asp Asp Gln Lys Leu Leu Glu Ala Val
                290                 295                 300

Lys Ala Glu Gln Lys Ala Ile Tyr Glu Glu Asn Ser Arg Glu Lys Lys
305                 310                 315                 320

Pro Leu Thr Trp Arg Gln Thr Arg Asn Met Pro Leu Thr His Lys Val
                325                 330                 335

Ile Val Glu Ser Leu Arg Met Ala Ser Ile Ile Ser Phe Thr Phe Arg
                340                 345                 350

Glu Ala Val Val Asp Val Glu Tyr Lys Gly Tyr Leu Ile Pro Lys Gly
                355                 360                 365

Trp Lys Val Met Pro Leu Phe Arg Asn Ile His His Asn Pro Lys Tyr
                370                 375                 380

Phe Ser Asn Pro Glu Val Phe Asp Pro Ser Arg Phe Glu Val Asn Pro
385                 390                 395                 400

Lys Pro Asn Thr Phe Met Pro Phe Gly Ser Gly Val His Ala Cys Pro
                405                 410                 415

Gly Asn Glu Leu Ala Lys Leu Gln Ile Leu Ile Phe Leu His His Leu
                420                 425                 430

Val Ser Asn Phe Arg Trp Glu Val Lys Gly Gly Glu Lys Gly Ile Gln
                435                 440                 445

Tyr Ser Pro Phe Pro Ile Pro Gln Asn Gly Leu Pro Ala Thr Phe Arg
                450                 455                 460

Arg His Ser Leu
465
```

```
<210> SEQ ID NO 29
<211> LENGTH: 950
<212> TYPE: DNA
<213> ORGANISM: Arabidopsis thaliana

<400> SEQUENCE: 29
gattctgcga agacaggaga agccatacct ttcaatctaa gccgtcaact tgttccctta      60
cgtgggatcc tattatacaa tccaacggtt ctaaatgagc cacgccttcc agatctaaca     120
cagtcatgct ttctacagtc tgcacccctt tttttttag tgttttatct acatttttc      180 ctttgtgttt aattttgtgc caacatctat aacttacccc tataaaaata ttcaattatc     240
acagaatacc cacaatcgaa acaaaattt accggaataa tttaattaaa gctggactat      300
aatgacaatt ccgaaactat caaggaataa attaaagaaa ctaaaaaact aaagggcatt     360
agagtaaaga agcggcaaca tcagaattaa aaaactgccg aaaaccaac ctagtagccg      420 tttatatgac aacacgtacg caaagtctcg gtaatgactc atcagtttc atgtgcaaac      480 atattcccc catgaaataa aaaagcagag aagcgatcaa aaaaatcttc attaaaagaa      540
ccctaaatct ctcatatccg ccgccgtctt tgcctcattt tcaacaccgg tgatgacgtg     600
taaatagatc tggttttcac ggttctcact actctctgtg atttttcaga ctattgaatc     660
gttaggacca aaacaagtac aaagaaactg cagaagaaaa gatttgagag agatatctta     720
cgaaacaagg tatatatttc tcttgttaaa tctttgaaaa tactttcaaa gtttcggttg     780
gattctcgaa taagttaggt taaatagtca atatagaatt atagataaat cgatacctttt     840 tgtttgttat cattcaattt ttattgttgt tacgattagt aacaacgttt tagatcttga     900
tctatatatt aataatacta atactttgtt ttttttgtt ttttttaa                  950

<210> SEQ ID NO 30
<211> LENGTH: 2828
<212> TYPE: DNA
<213> ORGANISM: Arabidopsis thaliana

<400> SEQUENCE: 30
agcgatcaaa aaaatcttca ttaaaagaac cctaaatctc tcatatccgc cgccgtcttt      60
gcctcatttt caacaccggt gatgacgtgt aaatagatct ggttttcacg gttctcacta     120
ctctctgtga ttttttcagac tattgaatcg ttaggaccaa aacaagtaca aagaaactgc     180
agaagaaaag atttgagaga gatatcttac gaaacaagca acagatgtt gttgtcggcg      240 cttggcgtcg gagttggagt aggtgtgggt ttaggcttgg cttctggtca agccgtcgga     300
aaatgggccg gcgggaactc gtcgtcaaat aacgccgtca cggcggataa gatggagaag     360
gagatactcc gtcaagttgt tgacggcaga gagagtaaaa ttactttcga tgagtttcct     420
tattatctca gtgaacaaac acgagtgctt ctaacaagtg cagcttatgt ccatttgaag     480
cacttcgatg cttcaaaata tacgagaaac ttgtctccag ctagccgagc cattctcttg     540
tccggccctg ccgagcttta ccaacaaatg ctagccaaag ccctagctca tttcttcgat     600
gccaagttac ttcttctaga cgtcaacgat tttgcactca agatacagag caaatacggc     660
agtggaaata cagaatcatc gtcattcaag agatctccct cagaatctgc tttagagcaa     720
ctatcaggac tgtttagttc cttctccatc cttcctcaga gagaagagtc aaaagctggt     780
ggtaccttga ggaggcaaag cagtggtgtg gatatcaaat caagctcaat ggaaggctct     840
agtaatcctc caaagcttcg tcgaaactct tcagcagcag ctaatattag caaccttgca     900
tcttcctcaa atcaagtttc agcgcctttg aaacgaagta gcagttggtc attcgatgaa     960
```

```
aagcttctcg tccaatcttt atataaggtc ttggcctatg tctccaaggc gaatccgatt    1020
gtgttatatc ttcgagacgt cgagaacttt ctgttccgct cacagagaac ttacaacttg    1080
ttccagaagc ttctccagaa actcagtgga ccggtcctca ttctcggttc aagaattgtg    1140
gacttgtcaa gcgaagacgc tcaagaaatt gatgagaagc tctctgctgt tttcccttat    1200
aatatcgaca taagacctcc tgaggatgag actcatctag tgagctggaa atcgcagctt    1260
gaacgcgaca tgaacatgat ccaaactcag gacaatagga accatatcat ggaagttttg    1320
tcggagaatg atcttatatg cgatgacctt gaatccatct cttttgagga cacgaaggtt    1380
ttaagcaatt acattgaaga gatcgttgtc tctgctcttt cctatcatct gatgaacaac    1440
aaagatcctg agtacagaaa cggaaaactg gtgatatctt ctataagttt gtcgcatgga    1500
ttcagtctct tcagagaagg caaagctggc ggtcgtgaga agctgaagca aaaaactaag    1560
gaggaatcat ccaaggaagt aaaagctgaa tcaatcaagc cggagacaaa aacagagagt    1620
gtcaccaccg taagcagcaa ggaagaacca gagaaagaag ctaaagctga aaagttacc     1680 ccaaaagctc cggaagttgc accggataac gagtttgaga acggataag accggaagta    1740 atcccagcag aagaaattaa cgtcacattc aaagacattg gtgcacttga cgagataaaa    1800
gagtcactac aagaacttgt aatgcttcct ctccgtaggc cagacctctt cacaggaggt    1860
ctcttgaagc cctgcagagg aatcttactc ttcggtccac cgggtacagg taaacaatg     1920 ctagctaaag ccattgccaa agaggcagga gcgagtttca taacgtttc gatgtcaaca    1980 ataacttcga aatggtttgg agaagacgag aagaatgtta gggctttgtt tactctagct    2040
tcgaaggtgt caccaaccat aatatttgtg gatgaagttg atagtatgtt gggacagaga    2100
acaagagttg gagaacatga agctatgaga aagatcaaga atgagtttat gagtcattgg    2160
gatgggttaa tgactaaacc tggtgaacgt atcttagtcc ttgctgctac taatcggcct    2220
ttcgatcttg atgaagccat tatcagacga ttcgaacgaa ggatcatggt gggactaccg    2280
gctgtagaga acagagaaaa gattctaaga acattgttgg cgaaggagaa agtagatgaa    2340
aacttggatt acaaggaact agcaatgatg acagaaggat acacaggaag tgatcttaag    2400
aatctgtgca caaccgctgc gtataggccg gtgagagaac ttatacagca agagaggatc    2460
aaagacacag agaagaagaa gcagagagag cctacaaaag caggtgaaga agatgaagga    2520
aaagaagaga gagttataac acttcgtccg ttgaacagaa aagactttaa agaagccaag    2580
aatcaggtgg cggcgagttt tgcggctgag ggagcgggaa tgggagagtt gaagcagtgg    2640
aatgaattgt atggagaagg aggatcgagg aagaaagaac aactcactta cttcttgtaa    2700
tgatgatgat gaatcatgat gctggtaatg gattatgaaa tttggtaatg taatagtatg    2760
gtgaattttt gtttccatgg ttaataagag aataagaata tgatgatatt gctaaaagtt    2820
tgacccgt                                                            2828
```

<210> SEQ ID NO 31
<211> LENGTH: 824
<212> TYPE: PRT
<213> ORGANISM: Arabidopsis thaliana

<400> SEQUENCE: 31

Met Leu Leu Ser Ala Leu Gly Val Gly Val Gly Val Gly Val Gly Leu
1               5                   10                  15

Gly Leu Ala Ser Gly Gln Ala Val Gly Lys Trp Ala Gly Gly Asn Ser
            20                  25                  30

Ser Ser Asn Asn Ala Val Thr Ala Asp Lys Met Glu Lys Glu Ile Leu
        35                  40                  45

```
Arg Gln Val Val Asp Gly Arg Glu Ser Lys Ile Thr Phe Asp Glu Phe
     50                  55                  60

Pro Tyr Tyr Leu Ser Glu Gln Thr Arg Val Leu Leu Thr Ser Ala Ala
65                   70                  75                  80

Tyr Val His Leu Lys His Phe Asp Ala Ser Lys Tyr Thr Arg Asn Leu
                 85                  90                  95

Ser Pro Ala Ser Arg Ala Ile Leu Leu Ser Gly Pro Ala Glu Leu Tyr
                100                 105                 110

Gln Gln Met Leu Ala Lys Ala Leu Ala His Phe Phe Asp Ala Lys Leu
            115                 120                 125

Leu Leu Leu Asp Val Asn Asp Phe Ala Leu Lys Ile Gln Ser Lys Tyr
            130                 135                 140

Gly Ser Gly Asn Thr Glu Ser Ser Phe Lys Arg Ser Pro Ser Glu
145                 150                 155                 160

Ser Ala Leu Glu Gln Leu Ser Gly Leu Phe Ser Ser Phe Ser Ile Leu
                165                 170                 175

Pro Gln Arg Glu Glu Ser Lys Ala Gly Gly Thr Leu Arg Arg Gln Ser
            180                 185                 190

Ser Gly Val Asp Ile Lys Ser Ser Met Glu Gly Ser Ser Asn Pro
            195                 200                 205

Pro Lys Leu Arg Arg Asn Ser Ser Ala Ala Asn Ile Ser Asn Leu
210                 215                 220

Ala Ser Ser Ser Asn Gln Val Ser Ala Pro Leu Lys Arg Ser Ser Ser
225                 230                 235                 240

Trp Ser Phe Asp Glu Lys Leu Leu Val Gln Ser Leu Tyr Lys Val Leu
            245                 250                 255

Ala Tyr Val Ser Lys Ala Asn Pro Ile Val Leu Tyr Leu Arg Asp Val
            260                 265                 270

Glu Asn Phe Leu Phe Arg Ser Gln Arg Thr Tyr Asn Leu Phe Gln Lys
            275                 280                 285

Leu Leu Gln Lys Leu Ser Gly Pro Val Leu Ile Leu Gly Ser Arg Ile
            290                 295                 300

Val Asp Leu Ser Ser Glu Asp Ala Gln Glu Ile Asp Glu Lys Leu Ser
305                 310                 315                 320

Ala Val Phe Pro Tyr Asn Ile Asp Ile Arg Pro Pro Glu Asp Glu Thr
            325                 330                 335

His Leu Val Ser Trp Lys Ser Gln Leu Glu Arg Asp Met Asn Met Ile
            340                 345                 350

Gln Thr Gln Asp Asn Arg Asn His Ile Met Glu Val Leu Ser Glu Asn
            355                 360                 365

Asp Leu Ile Cys Asp Asp Leu Glu Ser Ile Ser Phe Glu Asp Thr Lys
            370                 375                 380

Val Leu Ser Asn Tyr Ile Glu Glu Ile Val Ser Ala Leu Ser Tyr
385                 390                 395                 400

His Leu Met Asn Asn Lys Asp Pro Glu Tyr Arg Asn Gly Lys Leu Val
            405                 410                 415

Ile Ser Ser Ile Ser Leu Ser His Gly Phe Ser Leu Phe Arg Glu Gly
            420                 425                 430

Lys Ala Gly Gly Arg Glu Lys Leu Lys Gln Lys Thr Lys Glu Glu Ser
            435                 440                 445

Ser Lys Glu Val Lys Ala Glu Ser Ile Lys Pro Glu Thr Lys Thr Glu
            450                 455                 460

Ser Val Thr Thr Val Ser Ser Lys Glu Glu Pro Glu Lys Glu Ala Lys
```

```
                465                 470                 475                 480
Ala Glu Lys Val Thr Pro Lys Ala Pro Glu Val Ala Pro Asp Asn Glu
                    485                 490                 495

Phe Glu Lys Arg Ile Arg Pro Glu Val Ile Pro Ala Glu Glu Ile Asn
                500                 505                 510

Val Thr Phe Lys Asp Ile Gly Ala Leu Asp Glu Ile Lys Glu Ser Leu
            515                 520                 525

Gln Glu Leu Val Met Leu Pro Leu Arg Arg Pro Asp Leu Phe Thr Gly
        530                 535                 540

Gly Leu Lys Pro Cys Arg Gly Ile Leu Leu Phe Gly Pro Pro Gly
545                 550                 555                 560

Thr Gly Lys Thr Met Leu Ala Lys Ala Ile Ala Lys Glu Ala Gly Ala
                565                 570                 575

Ser Phe Ile Asn Val Ser Met Ser Thr Ile Thr Ser Lys Trp Phe Gly
                580                 585                 590

Glu Asp Glu Lys Asn Val Arg Ala Leu Phe Thr Leu Ala Ser Lys Val
            595                 600                 605

Ser Pro Thr Ile Ile Phe Val Asp Glu Val Asp Ser Met Leu Gly Gln
        610                 615                 620

Arg Thr Arg Val Gly Glu His Glu Ala Met Arg Lys Ile Lys Asn Glu
625                 630                 635                 640

Phe Met Ser His Trp Asp Gly Leu Met Thr Lys Pro Gly Glu Arg Ile
                645                 650                 655

Leu Val Leu Ala Ala Thr Asn Arg Pro Phe Asp Leu Asp Glu Ala Ile
                660                 665                 670

Ile Arg Arg Phe Glu Arg Arg Ile Met Val Gly Leu Pro Ala Val Glu
            675                 680                 685

Asn Arg Glu Lys Ile Leu Arg Thr Leu Leu Ala Lys Glu Lys Val Asp
        690                 695                 700

Glu Asn Leu Asp Tyr Lys Glu Leu Ala Met Met Thr Glu Gly Tyr Thr
705                 710                 715                 720

Gly Ser Asp Leu Lys Asn Leu Cys Thr Thr Ala Ala Tyr Arg Pro Val
                725                 730                 735

Arg Glu Leu Ile Gln Gln Glu Arg Ile Lys Asp Thr Glu Lys Lys Lys
                740                 745                 750

Gln Arg Glu Pro Thr Lys Ala Gly Glu Glu Asp Glu Lys Glu Glu
            755                 760                 765

Arg Val Ile Thr Leu Arg Pro Leu Asn Arg Gln Asp Phe Lys Glu Ala
        770                 775                 780

Lys Asn Gln Val Ala Ala Ser Phe Ala Ala Glu Gly Ala Gly Met Gly
785                 790                 795                 800

Glu Leu Lys Gln Trp Asn Glu Leu Tyr Gly Glu Gly Gly Ser Arg Lys
                805                 810                 815

Lys Glu Gln Leu Thr Tyr Phe Leu
            820

<210> SEQ ID NO 32
<211> LENGTH: 950
<212> TYPE: DNA
<213> ORGANISM: Arabidopsis thaliana

<400> SEQUENCE: 32
tacttgcaac cactttgtag gaccattaac tgcaaaataa gaattctcta agcttcacaa      60
ggggttcgtt tggtgctata aaaacattgt tttaagaact ggtttactgg ttctataaat     120
```

```
ctataaatcc aaatatgaag tatggcaata ataataacat gttagcacaa aaaatactca     180
ttaaattcct acccaaaaaa aatcttata tgaaactaaa acttatatac acaataatag      240
tgatacaaag taggtcttga tattcaacta ttcgggattt tctggtttcg agtaattcgt     300
ataaaaggtt taagatctat tatgttcact gaaatcttaa ctttgttttg tttccagttt     360
taactagtag aaattgaaag ttttaaaaat tgttacttac aataaaattt gaatcaatat     420
ccttaatcaa aggatcttaa gactagcaca attaaaacat ataacgtaga atatctgaaa     480
taactcgaaa atatctgaac taagttagta gttttaaaat ataatcccgg tttggaccgg     540
gcagtatgta cttcaatact tgtgggtttt gacgattttg gatcggattg ggcgggccag     600
ccagattgat ctattacaaa tttcacctgt caacgctaac tccgaactta atcaaagatt     660
ttgagctaag gaaaactaat cagtgatcac ccaaagaaaa cattcgtgaa taattgtttg     720 cttttccatgg cagcaaaaca aataggaccc aaataggaat gtcaaaaaaa agaaagacac    780
gaaacgaagt agtataacgt aacacacaaa aataaactag agatattaaa aacacatgtc     840
cacacatgga tacaagagca tttaaggagc agaaggcacg tagtggttag aaggtatgtg     900
atataattaa tcggcccaaa tagattggta agtagtagcc gtctatatca                950

<210> SEQ ID NO 33
<211> LENGTH: 104
<212> TYPE: DNA
<213> ORGANISM: Arabidopsis thaliana

<400> SEQUENCE: 33
cagctccttt ctactaaaac cctttactaa taaattctac gtacacgtac cacttcttct     60
cctcaaattc atcaaaccca tttctattcc aactcccaaa aatg                      104

<210> SEQ ID NO 34
<211> LENGTH: 1521
<212> TYPE: DNA
<213> ORGANISM: Arabidopsis thaliana

<400> SEQUENCE: 34
agctcctttc tactaaaacc cttttactat aaattctacg tacacgtacc acttcttctc     60
ctcaaattca tcaaacccat ttctattcca actcccaaaa atggcgattc gtcttcctct    120
gatctgtctt cttggttcat tcatggtagt ggcgattgcg gctgatttaa caccggagcg    180
ttattggagc actgctttac caaacactcc cattcccaac tctctccata atcttttgac    240
tttcgatttt accgacgaga aaagtaccaa cgtccaagta ggtaaaggcg gagtaaacgt    300
taacacccat aaaggtaaaa ccggtagcgg aaccgccgtg aacgttggaa agggaggtgt    360
acgcgtggac acaggcaagg gcaagcccgg aggagggaca cacgtgagcg ttggcagcgg    420
aaaaggtcac ggaggtggcg tcgcagtcca cacgggtaaa cccggtaaaa gaaccgacgt    480
aggagtcggt aaaggcggtg tgacggtgca cacgcgccac aagggaagac cgatttacgt    540
tggtgtgaaa ccaggagcaa acccttcgt gtataactat gcagcgaagg agactcagct    600
ccacgacgat cctaacgcgg ctctcttctt cttggagaag gacttggttc gcgggaaaga    660
aatgaatgtc cggtttaacg ctgaggatgg ttacggaggc aaaactgcgt tcttgccacg    720
tggagaggct gaaacggtgc cttttggatc ggagaagttt tcgagacgt tgaaacgttt     780 ctcggtggaa gctggttcgg aagaagcgga gatgatgaag aagaccattg aggagtgtga    840
agccagaaaa gttagtggag aggagaagta ttgtgcgacg tctttggagt cgatggtcga    900
ctttagtgtt tcgaaacttg gtaaatatca cgtcagggct gttccactg aggtggctaa      960
```

```
gaagaacgca ccgatgcaga agtacaaaat cgcggcggct ggggtaaaga agttgtctga    1020
cgataaatct gtggtgtgtc acaaacagaa gtacccattc gcggtgttct actgccacaa    1080
ggcgatgatg acgaccgtct acgcggttcc gctcgaggga gagaacggga tgcgagctaa    1140
agcagttgcg gtatgccaca agaacacctc agcttggaac ccaaaccact tggccttcaa    1200
agtcttaaag gtgaagccag ggaccgttcc ggtctgccac ttcctcccgg agactcatgt    1260
tgtgtggttc agctactaga tagatctgtt ttctatctta ttgtgggtta tgtataatta    1320
cgtttcagat aatctatctt ttgggatgtt ttggttatga atatacatac atatacatat    1380
agtaatgcgt ggtttccata taagagtgaa ggcatctata tgttttttttt tttattaacc    1440 tacgtagctg tcttttgtgg tctgtatctt gtggttttgc aaaaacctat aataaaatta    1500
gagctgaaat gttaccattt c                                              1521
```

<210> SEQ ID NO 35
<211> LENGTH: 392
<212> TYPE: PRT
<213> ORGANISM: Arabidopsis thaliana

<400> SEQUENCE: 35

```
Met Ala Ile Arg Leu Pro Leu Ile Cys Leu Leu Gly Ser Phe Met Val
1               5                   10                  15

Val Ala Ile Ala Ala Asp Leu Thr Pro Glu Arg Tyr Trp Ser Thr Ala
            20                  25                  30

Leu Pro Asn Thr Pro Ile Pro Asn Ser Leu His Asn Leu Leu Thr Phe
        35                  40                  45

Asp Phe Thr Asp Glu Lys Ser Thr Asn Val Gln Val Gly Lys Gly Gly
    50                  55                  60

Val Asn Val Asn Thr His Lys Gly Lys Thr Gly Ser Gly Thr Ala Val
65                  70                  75                  80

Asn Val Gly Lys Gly Gly Val Arg Val Asp Thr Gly Lys Gly Lys Pro
                85                  90                  95

Gly Gly Gly Thr His Val Ser Val Gly Ser Gly Lys Gly His Gly Gly
            100                 105                 110

Gly Val Ala Val His Thr Gly Lys Pro Gly Lys Arg Thr Asp Val Gly
        115                 120                 125

Val Gly Lys Gly Gly Val Thr Val His Thr Arg His Lys Gly Arg Pro
    130                 135                 140

Ile Tyr Val Gly Val Lys Pro Gly Ala Asn Pro Phe Val Tyr Asn Tyr
145                 150                 155                 160

Ala Ala Lys Glu Thr Gln Leu His Asp Asp Pro Asn Ala Ala Leu Phe
                165                 170                 175

Phe Leu Glu Lys Asp Leu Val Arg Gly Lys Glu Met Asn Val Arg Phe
            180                 185                 190

Asn Ala Glu Asp Gly Tyr Gly Gly Lys Thr Ala Phe Leu Pro Arg Gly
        195                 200                 205

Glu Ala Glu Thr Val Pro Phe Gly Ser Glu Lys Phe Ser Glu Thr Leu
    210                 215                 220

Lys Arg Phe Ser Val Glu Ala Gly Ser Glu Glu Ala Glu Met Met Lys
225                 230                 235                 240

Lys Thr Ile Glu Glu Cys Glu Ala Arg Lys Val Ser Gly Glu Glu Lys
                245                 250                 255

Tyr Cys Ala Thr Ser Leu Glu Ser Met Val Asp Phe Ser Val Ser Lys
            260                 265                 270

Leu Gly Lys Tyr His Val Arg Ala Val Ser Thr Glu Val Ala Lys Lys
```

```
                    275                 280                 285
Asn Ala Pro Met Gln Lys Tyr Lys Ile Ala Ala Gly Val Lys Lys
            290                 295                 300

Leu Ser Asp Asp Lys Ser Val Val Cys His Lys Gln Lys Tyr Pro Phe
305                 310                 315                 320

Ala Val Phe Tyr Cys His Lys Ala Met Met Thr Val Tyr Ala Val
                325                 330                 335

Pro Leu Glu Gly Glu Asn Gly Met Arg Ala Lys Ala Val Ala Val Cys
                340                 345                 350

His Lys Asn Thr Ser Ala Trp Asn Pro Asn His Leu Ala Phe Lys Val
                355                 360                 365

Leu Lys Val Lys Pro Gly Thr Val Pro Val Cys His Phe Leu Pro Glu
            370                 375                 380

Thr His Val Val Trp Phe Ser Tyr
385                 390

<210> SEQ ID NO 36
<211> LENGTH: 950
<212> TYPE: DNA
<213> ORGANISM: Arabidopsis thaliana

<400> SEQUENCE: 36
acttattagt ttaggtttcc atcacctatt taattcgtaa ttcttataca tgcatataat     60
agagatacat atatacaaat ttatgatcat ttttgcacaa catgtgatct cattcattag    120
tatgcattat gcgaaaacct cgacgcgcaa aagacacgta atagctaata atgttactca    180
tttataatga ttgaagcaag acgaaaacaa caacatatat atcaaattgt aaactagata    240
tttcttaaaa gtgaaaaaaa acaaagaaat ataaaggaca atttttgagtc agtctcttaa    300 tattaaaaca tatatacata aataagcaca aacgtggtta cctgtcttca tgcaatgtgg    360
actttagttt atctaatcaa aatcaaaata aaaggtgtaa tagttctcgt cattttttcaa    420 atttttaaaaa tcagaaccaa gtgatttttg tttgagtatt gatccattgt ttaaacaatt    480
taacacagta tatacgtctc ttgagatgtt gacatgatga taaaatacga gatcgtctct    540
tggttttcga attttgaact ttaatagttt ttttttttttag ggaaacttta atagttgttt    600
atcataagat tagtcaccta atggttacgt tgcagtaccg aaccaatttt ttaccctttt    660
ttctaaatgt ggtcgtggca taatttccaa aagagatcca aaacccggtt tgctcaactg    720
ataagccggt cggttctggt ttgaaaaaca agaaataatc tgaaagtgtg aaacagcaac    780
gtgtctcggt gtttcatgag ccacctgcca cctcattcac gtcggtcatt ttgtcgtttc    840
acggttcacg ctctagacac gtgctctgtc cccaccatga ctttcgctgc cgactcgctt    900
cgctttgcaa actcaaacat gtgtgtatat gtaagtttca tcctaataag    950

<210> SEQ ID NO 37
<211> LENGTH: 700
<212> TYPE: DNA
<213> ORGANISM: Arabidopsis thaliana

<400> SEQUENCE: 37
accacattaa tttaaaacaa agaaaacatc aaaatggctg aaaaagtaaa gtctggtcaa     60 gttttttaacc tattatgcat attctcgatc tttttcttcc tctttgtgtt atcagtgaat    120
gtttcggctg atgtcgattc tgagagagcg gtgccatctg aagataaaac gacgactgtt    180
tggctaacta aaatcaaacg gtccggtaaa aattattggg ctaaagttag agagactttg    240
gatcgtggac agtcccactt ctttcctccg aacacatatt ttaccggaaa gaatgatgcg    300
```

```
ccgatgggag ccggtgaaaa tatgaaagag gcggcgacga ggagctttga gcatagcaaa    360
gcgacggtgg aggaagctgc tagatcagcg gcagaagtgg tgagtgatac ggcggaagct    420
gtgaaagaaa aggtgaagag gagcgtttcc ggtggagtga cgcagccgtc ggagggatct    480
gaggagctat aaatacgcag ttgttctaag cttatgggtt ttaattattt aaataattag    540
tgtgtgtttg agatcaaaat gacacagttt tgggggagta tatctccaca tcatatgttg    600
tttgcatcac atggtttctc tgtatacaac gaccagatcc acatcactca ttctcgtcct    660 tcttttttgtc atgaatacag aataatattt tagattctac                         700
```

<210> SEQ ID NO 38
<211> LENGTH: 152
<212> TYPE: PRT
<213> ORGANISM: Arabidopsis thaliana

<400> SEQUENCE: 38

```
Met Ala Glu Lys Val Lys Ser Gly Gln Val Phe Asn Leu Leu Cys Ile
1               5                   10                  15

Phe Ser Ile Phe Phe Phe Leu Phe Val Leu Ser Val Asn Val Ser Ala
            20                  25                  30

Asp Val Asp Ser Glu Arg Ala Val Pro Ser Glu Asp Lys Thr Thr Thr
        35                  40                  45

Val Trp Leu Thr Lys Ile Lys Arg Ser Gly Lys Asn Tyr Trp Ala Lys
    50                  55                  60

Val Arg Glu Thr Leu Asp Arg Gly Gln Ser His Phe Phe Pro Pro Asn
65                  70                  75                  80

Thr Tyr Phe Thr Gly Lys Asn Asp Ala Pro Met Gly Ala Gly Glu Asn
                85                  90                  95

Met Lys Glu Ala Ala Thr Arg Ser Phe Glu His Ser Lys Ala Thr Val
            100                 105                 110

Glu Glu Ala Ala Arg Ser Ala Ala Glu Val Val Ser Asp Thr Ala Glu
        115                 120                 125

Ala Val Lys Glu Lys Val Lys Arg Ser Val Ser Gly Gly Val Thr Gln
    130                 135                 140

Pro Ser Glu Gly Ser Glu Glu Leu
145                 150
```

<210> SEQ ID NO 39
<211> LENGTH: 947
<212> TYPE: DNA
<213> ORGANISM: Arabidopsis thaliana

<400> SEQUENCE: 39

```
caaacaatta ctgctcaatg tatttgcgta tagagcatgt ccaataccat gcctcatgat     60
gtgagattgc gaggcggagt cagagaacga gttaaagtga cgacgttttt ttgttttttt    120
ttgggcatag tgtaaagtga tattaaaatt tcatggttgg caggtgactg aaaataaaaa    180
tgtgtatagg atgtgtttat atgctgacgg aaaaatagtt actcaactaa tacagatctt    240
tataaagagt atataagtct atggttaatc atgaatggca atatataaga gtagatgaga    300
tttatgttta tattgaaaca agggaaagat atgtgtaatt gaaacaatgg caaaatataa    360
gtcaaatcaa actggtttct gataatatat gtgttgaatc aatgtatatc ttggtattca    420
aaaccaaaac aactacacca atttctttaa aaaccagtt gatctaataa ctacatttta     480
atactagtag ctattagctg aatttcataa tcaatttctt gcattaaaat ttaaagtggg    540
ttttgcattt aaacttactc ggtttgtatt aatagacttt caaagattaa aagaaaacta    600
```

```
ctgcattcag agaataaagc tatcttacta aacactactt ttaaagtttc ttttttcact    660
tattaatctt cttttacaaa tggatctgtc tctctgcatg gcaaaatatc ttacactaat    720
tttattttct ttgtttgata acaaatttat cggctaagca tcacttaaat ttaatacacg    780
ttatgaagac ttaaaccacg tcacactata agaaccttac aggctgtcaa acacccttcc    840
ctacccactc acatctctcc acgtggcaat ctttgatatt dacaccttag ccactacagc    900
tgtcacactc ctctctcggt ttcaaaacaa catctctggt ataaata                  947

<210> SEQ ID NO 40
<211> LENGTH: 53
<212> TYPE: DNA
<213> ORGANISM: Arabidopsis thaliana

<400> SEQUENCE: 40
aatcaaaacc tctcctatat ctcttcaatc tgatataact acccttctca atg           53

<210> SEQ ID NO 41
<211> LENGTH: 1218
<212> TYPE: DNA
<213> ORGANISM: Arabidopsis thaliana

<400> SEQUENCE: 41
aaatcaaaac ctctcctata tctcttcaat ctgatataac tacccttctc aatggcttct    60
aattaccgtt ttgccatctt cctcactctc ttttttcgcca ccgctggttt ctccgccgcc   120
gcgttggtcg aggagcagcc gcttgttatg aaataccaca acggagttct gttgaaaggt    180
aacatcacag tcaatctcgt atggtacggg aaattcacac cgatccaacg gtccgtaatc   240
gtcgatttca tccactcgct aaactccaaa gacgttgcat cttccgccgc agttccttcc    300
gttgcttcgt ggtggaagac gacggagaaa tacaaaggtg gctcttcaac actcgtcgtc    360
gggaaacagc ttctactcga gaactatcct tcggaaaaat ctctcaaaaa tccttacctc    420
cgtgctttat ccaccaaact taacggcggt ctccgttcca taaccgtcgt tctaacggcg    480
aaagatgtta ccgtcgaaag attctgtatg agccggtgcg ggactcacgg atcctccggt    540
tcgaatcccc gtcgcgcagc taacggcgcg gcttacgtat gggtcgggaa ctccgagacg    600
cagtgccctg gatattgcgc gtggccgttt caccagccga tttacggacc acaaacgccg    660
ccgttagtag cgcctaacgg tgacgttgga gttgacggaa tgattataaa ccttgccaca    720
cttctagcta acaccgtgac gaatccgttt aataacggat attaccaagg cccaccaact    780
gcaccgcttg aagctgtgtc tgcttgtcct ggtatattcg ggtcaggttc ttatccgggt    840
tacgcgggtc gggtacttgt tgacaaaaca accgggtcta gttacaacgc tcgtggactc    900
gccggtagga atatctatt gccggcgatg tgggatccgc agagttcgac gtgcaagact    960
ctggtttgat ccaagggatg tgagtaagac acgtggcata gtagtgagag cgatgacgag   1020
atctagacgg catgtgtagt caaaatcaag ttgcacgcga gcgtgtgtat aaaaaaatct   1080
ttcgggtttg ggtctcgggt ttggattgtg gatagggctc tctctttgct ttttgtcgtt   1140
ttgtaatgac gtgtaaaaac tgtactcgga aatgtgaaga atgcatataa aataataaaa   1200
aatcattttg tttctact                                                 1218

<210> SEQ ID NO 42
<211> LENGTH: 305
<212> TYPE: PRT
<213> ORGANISM: Arabidopsis thaliana

<400> SEQUENCE: 42
```

Met Ala Ser Asn Tyr Arg Phe Ala Ile Phe Leu Thr Leu Phe Phe Ala
1               5                   10                  15

Thr Ala Gly Phe Ser Ala Ala Ala Leu Val Glu Glu Gln Pro Leu Val
            20                  25                  30

Met Lys Tyr His Asn Gly Val Leu Leu Lys Gly Asn Ile Thr Val Asn
            35                  40                  45

Leu Val Trp Tyr Gly Lys Phe Thr Pro Ile Gln Arg Ser Val Ile Val
50                  55                  60

Asp Phe Ile His Ser Leu Asn Ser Lys Asp Val Ala Ser Ser Ala Ala
65                  70                  75                  80

Val Pro Ser Val Ala Ser Trp Trp Lys Thr Thr Glu Lys Tyr Lys Gly
                85                  90                  95

Gly Ser Ser Thr Leu Val Val Gly Lys Gln Leu Leu Leu Glu Asn Tyr
            100                 105                 110

Pro Leu Gly Lys Ser Leu Lys Asn Pro Tyr Leu Arg Ala Leu Ser Thr
            115                 120                 125

Lys Leu Asn Gly Gly Leu Arg Ser Ile Thr Val Val Leu Thr Ala Lys
130                 135                 140

Asp Val Thr Val Glu Arg Phe Cys Met Ser Arg Cys Gly Thr His Gly
145                 150                 155                 160

Ser Ser Gly Ser Asn Pro Arg Arg Ala Ala Asn Gly Ala Ala Tyr Val
                165                 170                 175

Trp Val Gly Asn Ser Glu Thr Gln Cys Pro Gly Tyr Cys Ala Trp Pro
            180                 185                 190

Phe His Gln Pro Ile Tyr Gly Pro Gln Thr Pro Leu Val Ala Pro
            195                 200                 205

Asn Gly Asp Val Gly Val Asp Gly Met Ile Ile Asn Leu Ala Thr Leu
210                 215                 220

Leu Ala Asn Thr Val Thr Asn Pro Phe Asn Asn Gly Tyr Tyr Gln Gly
225                 230                 235                 240

Pro Pro Thr Ala Pro Leu Glu Ala Val Ser Ala Cys Pro Gly Ile Phe
            245                 250                 255

Gly Ser Gly Ser Tyr Pro Gly Tyr Ala Gly Arg Val Leu Val Asp Lys
            260                 265                 270

Thr Thr Gly Ser Ser Tyr Asn Ala Arg Gly Leu Ala Gly Arg Lys Tyr
            275                 280                 285

Leu Leu Pro Ala Met Trp Asp Pro Gln Ser Ser Thr Cys Lys Thr Leu
290                 295                 300

Val
305

<210> SEQ ID NO 43
<211> LENGTH: 950
<212> TYPE: DNA
<213> ORGANISM: Arabidopsis thaliana

<400> SEQUENCE: 43
atcatcgaaa ggtatgtgat gcatattccc attgaaccag atttccatat attttatttg      60
taaagtgata atgaatcaca agatgattca atattaaaaa tgggtaactc actttgacgt     120
gtagtacgtg gaagaatagt tagctatcac gcatatatat atctatgatt aagtgtgtat     180
gacataagaa actaaaatat ttacctaaag tccagttact catactgatt ttatgcatat     240
atgtattatt tatttatttt taataaagaa gcgattggtg ttttcataga aatcatgata     300
gattgatagg tatttcagtt ccacaaatct agatctgtgt gctatacatg catgtattaa     360

```
tttttttcccc ttaaatcatt tcagttgata atattgctct ttgttccaac tttagaaaag    420
gtatgaacca acctgacgat taacaagtaa acattaatta atctttatat atatgagata    480
aaaccgagga tatatatgat tgtgttgctg tctattgatg atgtgtcgat attatgcttg    540
ttgtaccaat gctcgagccg agcgtgatcg atgccttgac aaactatata tgtttcccga    600
attaattaag ttttgtatct taattagaat aacattttta tacaatgtaa tttctcaagc    660
agacaagata tgtatcctat attaattact atatatgaat tgccgggcac ctaccaggat    720
gtttcaaata cgagagccca ttagtttcca cgtaaatcac aatgacgcga caaaatctag    780
aatcgtgtca aaactctatc aatacaataa tatatatttc aagggcaatt tcgacttctc    840
ctcaactcaa tgattcaacg ccatgaatct ctatataaag gctacaacac cacaaaggat    900
catcagtcat cacaaccaca ttaactcttc accactatct ctcaatctct              950

<210> SEQ ID NO 44
<211> LENGTH: 837
<212> TYPE: DNA
<213> ORGANISM: Arabidopsis thaliana

<400> SEQUENCE: 44
atgacagaaa tgccctcgta catgatcgag aacccaaagt tcgagccaaa gaaacgacgt     60
tattactctt cttcgatgct taccatcttc ttaccgatct tcacatacat tatgatcttt    120
cacgttttcg aagtatcact atcttcggtc tttaaagaca caaaggtctt gttcttcatc    180
tccaatactc tcatcctcat aatagccgcc gattatggtt ccttctctga taaagagagt    240
caagactttt acggtgaata cactgtcgca gcggcaacga tgcgaaaccg agctgataac    300
tactctccga ttcccgtctt gacataccga gaaaacacta agatggaga atcaagaac     360 cctaaagatg tcgaattcag gaaccctgaa gaagaagacg aaccgatggt gaaagatatc    420
atttgcgttt ctcctcccga gaaaatagta cgagtggtga gtgagaagaa acagagagat    480
gatgtagcta tggaagaata caaaccagtt acagaacaaa ctcttgctag cgaagaagct    540
tgcaacacaa gaaaccatgt gaaccctaat aaaccgtacg ggcgaagtaa atcagataag    600
ccacggagaa agaggctcag cgtagataca gagacgacca aacgtaaaag ttatggtcga    660
aagaaatcag attgctcgag atggatggtt attccggaga agtgggaata tgttaaagaa    720
gaatctgaag agttttcaaa gttgtccaac gaggagttga acaaacgagt cgaagaattc    780
atccaacggt tcaatagaca gatcagatca caatcaccgc gagtttcgtc tacttga      837

<210> SEQ ID NO 45
<211> LENGTH: 278
<212> TYPE: PRT
<213> ORGANISM: Arabidopsis thaliana

<400> SEQUENCE: 45

Met Thr Glu Met Pro Ser Tyr Met Ile Glu Asn Pro Lys Phe Glu Pro
1               5                   10                  15

Lys Lys Arg Arg Tyr Tyr Ser Ser Ser Met Leu Thr Ile Phe Leu Pro
            20                  25                  30

Ile Phe Thr Tyr Ile Met Ile Phe His Val Phe Glu Val Ser Leu Ser
        35                  40                  45

Ser Val Phe Lys Asp Thr Lys Val Leu Phe Phe Ile Ser Asn Thr Leu
    50                  55                  60

Ile Leu Ile Ile Ala Ala Asp Tyr Gly Ser Phe Ser Asp Lys Glu Ser
65                  70                  75                  80
```

```
Gln Asp Phe Tyr Gly Glu Tyr Thr Val Ala Ala Thr Met Arg Asn
             85                  90                  95

Arg Ala Asp Asn Tyr Ser Pro Ile Pro Val Leu Thr Tyr Arg Glu Asn
        100                 105                 110

Thr Lys Asp Gly Glu Ile Lys Asn Pro Lys Asp Val Glu Phe Arg Asn
    115                 120                 125

Pro Glu Glu Asp Glu Pro Met Val Lys Asp Ile Ile Cys Val Ser
130                 135                 140

Pro Pro Glu Lys Ile Val Arg Val Ser Glu Lys Lys Gln Arg Asp
145                 150                 155                 160

Asp Val Ala Met Glu Glu Tyr Lys Pro Val Thr Glu Gln Thr Leu Ala
            165                 170                 175

Ser Glu Glu Ala Cys Asn Thr Arg Asn His Val Asn Pro Asn Lys Pro
        180                 185                 190

Tyr Gly Arg Ser Lys Ser Asp Lys Pro Arg Arg Lys Arg Leu Ser Val
    195                 200                 205

Asp Thr Glu Thr Thr Lys Arg Lys Ser Tyr Gly Arg Lys Ser Asp
210                 215                 220

Cys Ser Arg Trp Met Val Ile Pro Glu Lys Trp Glu Tyr Val Lys Glu
225                 230                 235                 240

Glu Ser Glu Glu Phe Ser Lys Leu Ser Asn Glu Glu Leu Asn Lys Arg
            245                 250                 255

Val Glu Glu Phe Ile Gln Arg Phe Asn Arg Gln Ile Arg Ser Gln Ser
            260                 265                 270

Pro Arg Val Ser Ser Thr
        275
```

<210> SEQ ID NO 46
<211> LENGTH: 950
<212> TYPE: DNA
<213> ORGANISM: Arabidopsis thaliana

<400> SEQUENCE: 46

```
gcgtatgctt tacttttta aatgggccta tgctataatt gaatgacaag gattaaacaa      60
ctaataaaag tgtagatggg ttaagatgac ttattttttt acttaccaat ttataaatgg     120
gcttcgatgt actgaaatat atcgcgccta ttaacgaggc cattcaacga atgttttaag    180
ggccctattt cgacatttta agaacacct aggtcatcat tccagaaatg gatattatag     240
gatttagata atttcccacg tttggtttat ttatctattt tttgacgttg accaacataa    300
tcgtgcccaa ccgtttcacg caacgaattt atatacgaaa tatatatatt tttcaaatta    360
agataccaca atcaaaacag ctgttgatta acaaagagat ttttttttt tggttttgag     420
ttacaataac gttagaggat aaggtttctt gcaacgatta ggaaatcgta taaaataaaa    480
tatgttataa ttaagtgttt tatttttaaa tgagtattaa tataaataaa acctgcaaaa    540
ggatagggat attgaataat aaagagaaac gaaagagcaa ttttacttct ttataattga    600
aattatgtga atgttatgtt tacaatgaat gattcatcgt tctatatatt gaagtaaaga    660
atgagtttat tgtgcttgca taatgacgtt aacttcacat atacacttat tacataacat    720
ttatcacatg tgcgtctttt ttttttttta ctttgtaaaa tttcctcact ttaaagactt    780
ttataacaat tactagtaaa ataaagttgc ttggggctac acccttttctc cctccaacaa    840
ctctatttat agataacatt atatcaaaat caaacatag tccctttctt ctataaaggt     900
ttttcacaa ccaaatttcc attataaatc aaaaaataaa aacttaatta                950
```

<210> SEQ ID NO 47
<211> LENGTH: 1747
<212> TYPE: DNA
<213> ORGANISM: Arabidopsis thaliana

<400> SEQUENCE: 47

| | | | | | |
|---|---|---|---|---|---|
| ataaaaactt | aattagtttt | tacagaagaa | agaaaacaa | tgagaggtaa | atttctaagt | 60 |
| ttactgttgc | tcattacttt | ggcctgcatt | ggagtttccg | ccaagaagca | ttccacaagg | 120 |
| cctagattaa | gaagaaatga | tttcccacaa | gatttcgttt | ttggatctgc | tacttctgct | 180 |
| tatcagtgtg | aaggagctgc | acatgaagat | ggtagaggtc | caagtatctg | ggactccttc | 240 |
| tctgaaaaat | tcccagaaaa | gataatggat | ggtagtaatg | ggtccattgc | agatgattct | 300 |
| tacaatcttt | acaaggaaga | tgtgaatttg | ctgcatcaaa | ttggcttcga | tgcttaccga | 360 |
| ttttcgatct | catggtcacg | gattttgcct | cgtgggactc | taaagggagg | aatcaaccag | 420 |
| gctggaattg | aatattataa | caacttgatt | aatcaactta | tatctaaagg | agtgaagcca | 480 |
| tttgtcacac | tctttcactg | ggacttacca | gatgcactcg | aaaatgctta | cggtggcctc | 540 |
| cttggagatg | aatttgtgaa | cgatttccga | gactatgcag | aactttgttt | ccagaagttt | 600 |
| ggagatagag | tgaagcagtg | gacgacacta | aacgagccat | atacaatggt | acatgaaggt | 660 |
| tatataacag | gtcaaaaggc | acctggaaga | tgttccaatt | tctataaacc | tgattgctta | 720 |
| ggtggcgatg | cagccacgga | gccttacatc | gtcggccata | acctcctcct | tgctcatgga | 780 |
| gttgccgtaa | agtatatag | agaaaagtac | caggcaactc | agaaaggtga | aattggtatt | 840 |
| gccttaaaca | cagcatggca | ctacccttat | tcagattcat | atgctgaccg | gttagctgcg | 900 |
| actcgagcga | ctgccttcac | cttcgactac | ttcatggagc | caatcgtgta | cggtagatat | 960 |
| ccaattgaaa | tggtcagcca | cgttaaagac | ggtcgtcttc | ctaccttcac | accagaagag | 1020 |
| tccgaaatgc | tcaaaggatc | atatgatttc | ataggcgtta | actattactc | atctctttac | 1080 |
| gcaaaagacg | tgccgtgtgc | aactgaaaac | atcaccatga | ccaccgattc | ttgcgtcagc | 1140 |
| ctcgtaggtg | aacgaaatgg | agtgcctatc | ggtccagcgg | ctggatcgga | ttggcttttg | 1200 |
| atatatccca | agggtattcg | tgatctccta | ctacatgcaa | aattcagata | caatgatccc | 1260 |
| gtcttgtaca | ttacagagaa | tggagtggat | gaagcaaata | ttggcaaaat | atttcttaac | 1320 |
| gacgatttga | gaattgatta | ctatgctcat | caccctcaaga | tggttagcga | tgctatctcg | 1380 |
| atcggggtga | atgtgaaggg | atatttcgcg | tggtcattga | tggataattt | cgagtggtcg | 1440 |
| gaaggataca | cggtccggtt | cgggctagtg | tttgtggact | ttgaagatgg | acgtaagagg | 1500 |
| tatctgaaga | aatcagctaa | gtggtttagg | agattgttga | agggagcgca | tggtgggacg | 1560 |
| aatgagcagg | tggctgttat | ttaataaacc | acgagtcatt | ggtcaattta | gtctactgtt | 1620 |
| tcttttgctc | tatgtacaga | aagaaaataa | actttccaaa | ataagaggtg | gctttgtttg | 1680 |
| gactttggat | gttactatat | atattggtaa | ttcttggcgt | tgttagtttt | ccaaaccaaa | 1740 |
| cattaat | | | | | | 1747 |

<210> SEQ ID NO 48
<211> LENGTH: 514
<212> TYPE: PRT
<213> ORGANISM: Arabidopsis thaliana

<400> SEQUENCE: 48

Met Arg Gly Lys Phe Leu Ser Leu Leu Leu Ile Thr Leu Ala Cys
1               5                   10                  15

Ile Gly Val Ser Ala Lys Lys His Ser Thr Arg Pro Arg Leu Arg Arg
            20                  25                  30

```
Asn Asp Phe Pro Gln Asp Phe Val Phe Gly Ser Ala Thr Ser Ala Tyr
         35                  40                  45
Gln Cys Glu Gly Ala Ala His Glu Asp Gly Arg Gly Pro Ser Ile Trp
 50                  55                  60
Asp Ser Phe Ser Glu Lys Phe Pro Glu Lys Ile Met Asp Gly Ser Asn
 65                  70                  75                  80
Gly Ser Ile Ala Asp Asp Ser Tyr Asn Leu Tyr Lys Glu Asp Val Asn
                 85                  90                  95
Leu Leu His Gln Ile Gly Phe Asp Ala Tyr Arg Phe Ser Ile Ser Trp
            100                 105                 110
Ser Arg Ile Leu Pro Arg Gly Thr Leu Lys Gly Ile Asn Gln Ala
            115                 120                 125
Gly Ile Glu Tyr Tyr Asn Asn Leu Ile Asn Gln Leu Ile Ser Lys Gly
        130                 135                 140
Val Lys Pro Phe Val Thr Leu Phe His Trp Asp Leu Pro Asp Ala Leu
145                 150                 155                 160
Glu Asn Ala Tyr Gly Gly Leu Leu Gly Asp Glu Phe Val Asn Asp Phe
                165                 170                 175
Arg Asp Tyr Ala Glu Leu Cys Phe Gln Lys Phe Gly Asp Arg Val Lys
            180                 185                 190
Gln Trp Thr Thr Leu Asn Glu Pro Tyr Thr Met Val His Glu Gly Tyr
            195                 200                 205
Ile Thr Gly Gln Lys Ala Pro Gly Arg Cys Ser Asn Phe Tyr Lys Pro
        210                 215                 220
Asp Cys Leu Gly Gly Asp Ala Ala Thr Glu Pro Tyr Ile Val Gly His
225                 230                 235                 240
Asn Leu Leu Leu Ala His Gly Val Ala Val Lys Val Tyr Arg Glu Lys
                245                 250                 255
Tyr Gln Ala Thr Gln Lys Gly Glu Ile Gly Ile Ala Leu Asn Thr Ala
            260                 265                 270
Trp His Tyr Pro Tyr Ser Asp Ser Tyr Ala Asp Arg Leu Ala Ala Thr
            275                 280                 285
Arg Ala Thr Ala Phe Thr Phe Asp Tyr Phe Met Glu Pro Ile Val Tyr
        290                 295                 300
Gly Arg Tyr Pro Ile Glu Met Val Ser His Val Lys Asp Gly Arg Leu
305                 310                 315                 320
Pro Thr Phe Thr Pro Glu Glu Ser Glu Met Leu Lys Gly Ser Tyr Asp
                325                 330                 335
Phe Ile Gly Val Asn Tyr Tyr Ser Ser Leu Tyr Ala Lys Asp Val Pro
            340                 345                 350
Cys Ala Thr Glu Asn Ile Thr Met Thr Thr Asp Ser Cys Val Ser Leu
            355                 360                 365
Val Gly Glu Arg Asn Gly Val Pro Ile Gly Pro Ala Ala Gly Ser Asp
        370                 375                 380
Trp Leu Leu Ile Tyr Pro Lys Gly Ile Arg Asp Leu Leu His Ala
385                 390                 395                 400
Lys Phe Arg Tyr Asn Asp Pro Val Leu Tyr Ile Thr Glu Asn Gly Val
                405                 410                 415
Asp Glu Ala Asn Ile Gly Lys Ile Phe Leu Asn Asp Leu Arg Ile
            420                 425                 430
Asp Tyr Tyr Ala His His Leu Lys Met Val Ser Asp Ala Ile Ser Ile
            435                 440                 445
Gly Val Asn Val Lys Gly Tyr Phe Ala Trp Ser Leu Met Asp Asn Phe
```

```
                450             455             460
Glu Trp Ser Glu Gly Tyr Thr Val Arg Phe Gly Leu Val Phe Val Asp
465                 470                 475                 480

Phe Glu Asp Gly Arg Lys Arg Tyr Leu Lys Lys Ser Ala Lys Trp Phe
                485                 490                 495

Arg Arg Leu Leu Lys Gly Ala His Gly Gly Thr Asn Glu Gln Val Ala
            500                 505                 510

Val Ile

<210> SEQ ID NO 49
<211> LENGTH: 950
<212> TYPE: DNA
<213> ORGANISM: Arabidopsis thaliana

<400> SEQUENCE: 49
aaagtcttat tgtgaaatt ttacaaatgt tggaaaaaag cattttatgg tgctatattt      60
gtcaatttcc cttgattata tatccttttg aaaagtaatg ttttttttat gtgtgtgtat    120
tcatgaacct tggaaaaact acaaatcaga tcatggtttg ttttaggtga aaaatttaga    180
acacagttac gcaagaaaga tatcggtaaa tttttgtttc tttgaatcga aattaatcaa    240
aaagtatttt ccattatata acaacaacta atctctgttt tttttttttt ttttaacaa    300
ctaatctctt atcaaaatga cactacagaa tcacgattgt aaatctttaa aaggcagtct    360
gaaaaatatt catgaggatg agattttatt cattcatggt tgtaagtaat cattatgtaa    420
agtttaggat aaggacgttc aaaatcatat aaaaaaactc tacgaataaa gtttatagtc    480
tatcatattg attcatattt catagaaagt tactggaaaa cattacacaa gtattctcga    540
tttttacgag tttgtttagt agtcgcaaaa ttttatttta cttttgagta tacgaaccca    600
taagctgatt ttcttttccaa gttccaataa tgatatcata gtgtactctt catgaatgtt    660
tcaagcatat aattataacg ttcataagta atattctact gcatgtttgt tattataaat    720
taactaataa tcgaacgtat gagttttgat tgagattgtt gtgctcacga aatgaaggac    780
tcggtcaatt ctaaagctta aaataagaag ctcagatctt aaaactcgct ttcgtcttcg    840
tcctccattt aagtttgcga ttcttttgct cttctttctc tctcacattt ttgtcccaaa    900
acaataaaaa gaaacaataa tagaaagtgt tacagaaaaa gaaagaaaac                950

<210> SEQ ID NO 50
<211> LENGTH: 3048
<212> TYPE: DNA
<213> ORGANISM: Arabidopsis thaliana

<400> SEQUENCE: 50
atggagagtt acctcaactc gaatttcgac gttaaggcga agcattcgtc ggaggaagtg      60
ctagaaaaat ggcggaatct ttgcagtgtc gtcaagaacc cgaaacgtcg gtttcgattc    120
actgccaatc tctccaaacg ttacgaagct gctgccatgc gccgcaccaa ccaggagaaa    180
ttaaggattg cagttctcgt gtcaaaagcc gcatttcaat ttatctctgg tgtttctcca    240
agtgactaca aggtgcctga ggaagttaaa gcagcaggct tgacatttg tgcagacgag    300
ttaggatcaa tagtggaagg tcatgatgtg aagaagctca gttccatgg tggtgttgat    360
ggtctttcag gtaagctcaa ggcatgtccc aatgctggtc tctcaacagg tgaacctgag    420
cagttaagca aacgacaaga gcttttcgga atcaataagt ttgcagagag tgaattacga    480
agtttctggg tgtttgtttg ggaagcactt caagatatga ctcttatgat tcttggtgtt    540
tgtgctttcg tctctttgat tgttgggatt gcaactgaag gatggcctca aggatcgcat    600
```

```
gatggtcttg gcattgttgc tagtattctt ttagttgtgt ttgtgacagc aactagtgac   660
tatagacaat ctttgcagtt ccgggatttg gataaagaga agaagaagat cacggttcaa   720
gttacgcgaa acgggtttag acaaaagatg tctatatatg atttgctccc tggagatgtt   780
gttcatcttg ctatcggaga tcaagtccct gcagatggtc ttttcctctc gggattctct   840
gttgttatcg atgaatcgag tttaactgga gagagtgagc ctgtgatggt gactgcacag   900
aaccctttcc ttctctctgg aaccaaagtt caagatgggt catgtaagat gttggttaca   960
acagttggga tgagaactca atggggaaag ttaatggcaa cacttagtga aggaggagat  1020
gacgaaactc cgttgcaggt gaaacttaat ggagttgcaa ccatcattgg gaaaattggt  1080 cttccttcg ctattgttac ctttgcggtt ttggtacaag gaatgtttat gaggaagctt  1140
tcattaggcc ctcattggtg gtggtccgga gatgatgcat tagagctttt ggagtatttt  1200
gctattgctg tcacaattgt tgttgttgcg gttcctgaag gtttaccatt agctgtcaca  1260
cttagtctcg cgtttgcgat gaagaagatg atgaacgata aagcgcttgt tcgccattta  1320
gcagcttgtg agacaatggg atctgcaact accatttgta gtgacaagac tggtacatta  1380
acaacaaatc acatgactgt tgtgaaatct tgcatttgta tgaatgttca agatgtagct  1440
agcaaaagtt ctagtttaca atctgatatc cctgaagctg ccttgaaact acttctccag  1500
ttgattttta ataataccgg tggagaagtt gttgtgaacg aacgtggcaa gactgagata  1560
ttggggacac caacagagac tgctatattg gagttaggac tatctcttgg aggtaagttt  1620
caagaagaga gacaatctaa caaagttatt aaagttgagc cttttaactc aacaaagaaa  1680
agaatgggag tagtcattga gctgcctgaa ggaggacgca ttcgcgctca cacgaaagga  1740
gcttcagaga tagttttagc ggcttgtgat aaagtcatca actcaagtgg tgaagttgtt  1800
ccgcttgatg atgaatccat caagttcttg aatgttacaa tcgatgagtt tgcaaatgaa  1860
gctcttcgta ctctttgcct tgcttatatg gatatcgaaa gcgggttttc ggctgatgaa  1920
ggtattccgg aaaaagggtt tacatgcata gggattgttg gtatcaaaga ccctgttcgt  1980
cctggagttc gggagtccgt ggaactttgt cgccgtgcgg gtattatggt gagaatggtt  2040
acaggagata acattaacac cgcaaaggct attgctagag aatgtggaat tctcactgat  2100
gatggtatag caattgaagg tcctgtgttt agagagaaga accaagaaga gatgcttgaa  2160
ctcattccca agattcaggt catggctcgt tcttccccaa tggacaagca tacactggtg  2220
aagcagttga ggactacttt tgatgaagtt gttgctgtga ctggcgacgg gacaaacgat  2280
gcaccagcgc tccacgaggc tgacatagga ttagcaatgg gcattgccgg gactgaagta  2340
gcgaaagaga ttgcggatgt catcattctc gacgataact tcagcacaat cgtcaccgta  2400
gcgaaatggg gacgttctgt ttacattaac attcagaaat tgtgcagtt tcaactaaca  2460 gtcaatgttg ttgcccttat tgttaacttc tcttcagctt gcttgactgg aagtgctcct  2520
ctaactgctg ttcaactgct ttgggttaac atgatcatgg acacacttgg agctcttgct  2580
ctagctacag aacctccgaa caacgagctg atgaaacgta tgcctgttgg aagaagaggg  2640
aatttcatta ccaatgcgat gtggagaaac atcttaggac aagctgtgta tcaatttatt  2700
atcatatgga ttctacaggc caaagggaag tccatgtttg gtcttgttgg ttctgactct  2760
actctcgtat tgaacacact tatcttcaac tgctttgtat tctgccaggt tttcaatgaa  2820
gtaagctcgc gggagatgga agagatcgat gttttcaaag gcatactcga caactatgtt  2880
ttcgtggttg ttattggtgc aacagttttc tttcagatca taatcattga gttcttgggc  2940
acatttgcaa gcaccacacc tcttacaata gttcaatggt tcttcagcat tttcgttggc  3000
```
ttcttgggta tgccgatcgc tgctggcttg aagaaaatac ccgtgtga        3048

<210> SEQ ID NO 51
<211> LENGTH: 1015
<212> TYPE: PRT
<213> ORGANISM: Arabidopsis thaliana

<400> SEQUENCE: 51

Met Glu Ser Tyr Leu Asn Ser Asn Phe Asp Val Lys Ala Lys His Ser
1               5                   10                  15

Ser Glu Glu Val Leu Glu Lys Trp Arg Asn Leu Cys Ser Val Val Lys
                20                  25                  30

Asn Pro Lys Arg Arg Phe Arg Phe Thr Ala Asn Leu Ser Lys Arg Tyr
            35                  40                  45

Glu Ala Ala Ala Met Arg Arg Thr Asn Gln Glu Lys Leu Arg Ile Ala
        50                  55                  60

Val Leu Val Ser Lys Ala Ala Phe Gln Phe Ile Ser Gly Val Ser Pro
65                  70                  75                  80

Ser Asp Tyr Lys Val Pro Glu Glu Val Lys Ala Ala Gly Phe Asp Ile
                85                  90                  95

Cys Ala Asp Glu Leu Gly Ser Ile Val Glu Gly His Asp Val Lys Lys
            100                 105                 110

Leu Lys Phe His Gly Gly Val Asp Gly Leu Ser Gly Lys Leu Lys Ala
        115                 120                 125

Cys Pro Asn Ala Gly Leu Ser Thr Gly Glu Pro Glu Gln Leu Ser Lys
    130                 135                 140

Arg Gln Glu Leu Phe Gly Ile Asn Lys Phe Ala Glu Ser Glu Leu Arg
145                 150                 155                 160

Ser Phe Trp Val Phe Val Trp Glu Ala Leu Gln Asp Met Thr Leu Met
                165                 170                 175

Ile Leu Gly Val Cys Ala Phe Val Ser Leu Ile Val Gly Ile Ala Thr
            180                 185                 190

Glu Gly Trp Pro Gln Gly Ser His Asp Gly Leu Gly Ile Val Ala Ser
        195                 200                 205

Ile Leu Leu Val Val Phe Val Thr Ala Thr Ser Asp Tyr Arg Gln Ser
    210                 215                 220

Leu Gln Phe Arg Asp Leu Asp Lys Glu Lys Lys Lys Ile Thr Val Gln
225                 230                 235                 240

Val Thr Arg Asn Gly Phe Arg Gln Lys Met Ser Ile Tyr Asp Leu Leu
                245                 250                 255

Pro Gly Asp Val Val His Leu Ala Ile Gly Asp Gln Val Pro Ala Asp
            260                 265                 270

Gly Leu Phe Leu Ser Gly Phe Ser Val Val Ile Asp Glu Ser Ser Leu
        275                 280                 285

Thr Gly Glu Ser Glu Pro Val Met Val Thr Ala Gln Asn Pro Phe Leu
    290                 295                 300

Leu Ser Gly Thr Lys Val Gln Asp Gly Ser Cys Lys Met Leu Val Thr
305                 310                 315                 320

Thr Val Gly Met Arg Thr Gln Trp Gly Lys Leu Met Ala Thr Leu Ser
                325                 330                 335

Glu Gly Gly Asp Asp Glu Thr Pro Leu Gln Val Lys Leu Asn Gly Val
            340                 345                 350

Ala Thr Ile Ile Gly Lys Ile Gly Leu Ser Phe Ala Ile Val Thr Phe
        355                 360                 365

```
Ala Val Leu Val Gln Gly Met Phe Met Arg Lys Leu Ser Leu Gly Pro
        370                 375                 380

His Trp Trp Trp Ser Gly Asp Asp Ala Leu Glu Leu Leu Glu Tyr Phe
385                 390                 395                 400

Ala Ile Ala Val Thr Ile Val Val Ala Val Pro Glu Gly Leu Pro
                405                 410                 415

Leu Ala Val Thr Leu Ser Leu Ala Phe Ala Met Lys Lys Met Met Asn
            420                 425                 430

Asp Lys Ala Leu Val Arg His Leu Ala Ala Cys Glu Thr Met Gly Ser
        435                 440                 445

Ala Thr Thr Ile Cys Ser Asp Lys Thr Gly Thr Leu Thr Asn His
        450                 455                 460

Met Thr Val Val Lys Ser Cys Ile Cys Met Asn Val Gln Asp Val Ala
465                 470                 475                 480

Ser Lys Ser Ser Ser Leu Gln Ser Asp Ile Pro Glu Ala Ala Leu Lys
                485                 490                 495

Leu Leu Leu Gln Leu Ile Phe Asn Asn Thr Gly Gly Glu Val Val
            500                 505                 510

Asn Glu Arg Gly Lys Thr Glu Ile Leu Gly Thr Pro Thr Glu Thr Ala
        515                 520                 525

Ile Leu Glu Leu Gly Leu Ser Leu Gly Gly Lys Phe Gln Glu Arg
        530                 535                 540

Gln Ser Asn Lys Val Ile Lys Val Glu Pro Phe Asn Ser Thr Lys Lys
545                 550                 555                 560

Arg Met Gly Val Val Ile Glu Leu Pro Glu Gly Gly Arg Ile Arg Ala
                565                 570                 575

His Thr Lys Gly Ala Ser Glu Ile Val Leu Ala Ala Cys Asp Lys Val
            580                 585                 590

Ile Asn Ser Ser Gly Glu Val Val Pro Leu Asp Asp Glu Ser Ile Lys
        595                 600                 605

Phe Leu Asn Val Thr Ile Asp Glu Phe Ala Asn Glu Ala Leu Arg Thr
610                 615                 620

Leu Cys Leu Ala Tyr Met Asp Ile Glu Ser Gly Phe Ser Ala Asp Glu
625                 630                 635                 640

Gly Ile Pro Glu Lys Gly Phe Thr Cys Ile Gly Ile Val Gly Ile Lys
                645                 650                 655

Asp Pro Val Arg Pro Gly Val Arg Glu Ser Val Glu Leu Cys Arg Arg
            660                 665                 670

Ala Gly Ile Met Val Arg Met Val Thr Gly Asp Asn Ile Asn Thr Ala
        675                 680                 685

Lys Ala Ile Ala Arg Glu Cys Gly Ile Leu Thr Asp Asp Gly Ile Ala
        690                 695                 700

Ile Glu Gly Pro Val Phe Arg Glu Lys Asn Gln Glu Glu Met Leu Glu
705                 710                 715                 720

Leu Ile Pro Lys Ile Gln Val Met Ala Arg Ser Ser Pro Met Asp Lys
                725                 730                 735

His Thr Leu Val Lys Gln Leu Arg Thr Thr Phe Asp Glu Val Val Ala
            740                 745                 750

Val Thr Gly Asp Gly Thr Asn Asp Ala Pro Ala Leu His Glu Ala Asp
        755                 760                 765

Ile Gly Leu Ala Met Gly Ile Ala Gly Thr Glu Val Ala Lys Glu Ile
        770                 775                 780

Ala Asp Val Ile Ile Leu Asp Asp Asn Phe Ser Thr Ile Val Thr Val
785                 790                 795                 800
```

Ala Lys Trp Gly Arg Ser Val Tyr Ile Asn Ile Gln Lys Phe Val Gln
                805                 810                 815

Phe Gln Leu Thr Val Asn Val Val Ala Leu Ile Val Asn Phe Ser Ser
            820                 825                 830

Ala Cys Leu Thr Gly Ser Ala Pro Leu Thr Ala Val Gln Leu Leu Trp
        835                 840                 845

Val Asn Met Ile Met Asp Thr Leu Gly Ala Leu Ala Leu Ala Thr Glu
    850                 855                 860

Pro Pro Asn Asn Glu Leu Met Lys Arg Met Pro Val Gly Arg Arg Gly
865                 870                 875                 880

Asn Phe Ile Thr Asn Ala Met Trp Arg Asn Ile Leu Gly Gln Ala Val
                885                 890                 895

Tyr Gln Phe Ile Ile Ile Trp Ile Leu Gln Ala Lys Gly Lys Ser Met
            900                 905                 910

Phe Gly Leu Val Gly Ser Asp Ser Thr Leu Val Leu Asn Thr Leu Ile
        915                 920                 925

Phe Asn Cys Phe Val Phe Cys Gln Val Phe Asn Glu Val Ser Ser Arg
    930                 935                 940

Glu Met Glu Glu Ile Asp Val Phe Lys Gly Ile Leu Asp Asn Tyr Val
945                 950                 955                 960

Phe Val Val Val Ile Gly Ala Thr Val Phe Phe Gln Ile Ile Ile Ile
                965                 970                 975

Glu Phe Leu Gly Thr Phe Ala Ser Thr Thr Pro Leu Thr Ile Val Gln
            980                 985                 990

Trp Phe Phe Ser Ile Phe Val Gly  Phe Leu Gly Met Pro  Ile Ala Ala
        995                 1000                1005

Gly Leu  Lys Lys Ile Pro Val
    1010                1015

<210> SEQ ID NO 52
<211> LENGTH: 960
<212> TYPE: DNA
<213> ORGANISM: Arabidopsis thaliana

<400> SEQUENCE: 52
tcaaaagtgt aatttccaca aaccaattgc gcctgcaaaa gttttcaaag gatcatcaaa      60
cataatgatg aatatctcat caccacgatt ttataataat gcatcttttc ccaccatttt     120
ttttcccctca ctttcttttα taatcttgtt cgacaacaat catggtctaa ggaaaaagtt     180
gaaaatatat attatcttag ttattagaaa agaaagataa tcaaatggtc aatatgcaaa     240
tggcatatga ccataaacga gtttgctagt ataagaatg atggccaacc tgttaaagag     300
agactaaaat taggtctaaa atctaggagc aatgtaacca atacatagta tatgaaatat     360
aaaagttaat ttagattttt tgattagccc aaattaaaga aaaatggtat ttaaaacaga     420
gactcttcat cctaaaggct aaagcaatac aattttttggt taagaaaaga aaaaaaccac     480
aagcggaaaa gaaaacaaaa aagaactata ttatgatgca acagcaacac aaagcaaaac     540
cttgcacaca cacatacaac tgtaaacaag tttcttggga ctctctattt tctcttgctg     600
cttgaaccaa acacaacaac gatatcccaa cgagagcaca acaggtttga ttatgtcgga     660
agacaagttt tgagagaaaa caaacaatat tttataacaa aggagaagac ttttggttag     720
aaaaaattgg tatggccatt acaagacata tgggtcccaa ttctcatcac tctctccacc     780
accaaaatcc tcctctctct ctctctcttt tactctgttt tcatcatctc tttctctcgt     840
ctctctcaaa ccctaaatac actctttctc ttcttgttgt ctccattctc tctgtgtcat     900
caagcttctt ttttgtgtgg gttatttgaa agacactttc tctgctggta tcattggagt    960

<210> SEQ ID NO 53
<211> LENGTH: 1194
<212> TYPE: DNA
<213> ORGANISM: Arabidopsis thaliana

<400> SEQUENCE: 53
actctgtttt catcatctct ttctctcgtc tctctcaaac cctaaataca ctctttctct     60
tcttgttgtc tccattctct ctgtgtcatc aagcttcttt tttgtgtggg ttatttgaaa    120
gacactttct ctgctggtat cattggagtc tagggttttg ttattgacat gcgtggtgtg    180
tcagaattgg aggtggggaa gagtaatctt ccggcggaga gtgagctgga attgggatta    240
gggctcagcc tcggtggtgg cgcgtggaaa gagcgtggga ggattcttac tgctaaggat    300
tttccttccg ttgggtctaa acgctctgct gaatcttcct ctcaccaagg agcttctcct    360
cctcgttcaa gtcaagtggt aggatggcca ccaattgggt tacacaggat gaacagtttg    420
gttaataacc aagctatgaa ggcagcaaga gcggaagaag gagacgggga agaaaagtt    480 gtgaagaatg atgagctcaa agatgtgtca atgaaggtga atccgaaagt tcagggctta    540
gggtttgtta aggtgaatat ggatggagtt ggtataggca gaaaagtgga tatgagagct    600
cattcgtctt acgaaaactt ggctcagacg cttgaggaaa tgttctttgg aatgacaggt    660
actacttgtc gagaaaaggt taaaccttta aggcttttag atggatcatc agactttgta    720
ctcacttatg aagataagga aggggattgg atgcttgttg gagatgttcc atggagaatg    780
tttatcaact cggtgaaaag gcttcggatc atgggaacct cagaagctag tggactagct    840
ccaagacgtc aagagcagaa ggatagacaa agaaacaacc ctgtttagct tcccttccaa    900
agctggcatt gtttatgtat tgtttgaggt ttgcaattta ctcgatactt tttgaagaaa    960
gtattttgga gaatatggat aaaagcatgc agaagcttag atatgatttg aatccggttt   1020
tcggatatgg ttttgcttag gtcattcaat tcgtagtttt ccagtttgtt tcttctttgg   1080
ctgtgtacca attatctatg ttctgtgaga gaaagctctt gtttatttgt tctctcagat   1140
tgtaaatagt tgaagttatc taattaatgt gataagagtt atgtttatga ttcc         1194

<210> SEQ ID NO 54
<211> LENGTH: 239
<212> TYPE: PRT
<213> ORGANISM: Arabidopsis thaliana

<400> SEQUENCE: 54

Met Arg Gly Val Ser Glu Leu Glu Val Gly Lys Ser Asn Leu Pro Ala
1               5                   10                  15

Glu Ser Glu Leu Glu Leu Gly Leu Gly Leu Ser Leu Gly Gly Gly Ala
            20                  25                  30

Trp Lys Glu Arg Gly Arg Ile Leu Thr Ala Lys Asp Phe Pro Ser Val
        35                  40                  45

Gly Ser Lys Arg Ser Ala Glu Ser Ser His Gln Gly Ala Ser Pro
    50                  55                  60

Pro Arg Ser Ser Gln Val Val Gly Trp Pro Pro Ile Gly Leu His Arg
65                  70                  75                  80

Met Asn Ser Leu Val Asn Asn Gln Ala Met Lys Ala Ala Arg Ala Glu
                85                  90                  95

Glu Gly Asp Gly Glu Lys Lys Val Val Lys Asn Asp Glu Leu Lys Asp
            100                 105                 110

```
Val Ser Met Lys Val Asn Pro Lys Val Gln Gly Leu Gly Phe Val Lys
        115                 120                 125

Val Asn Met Asp Gly Val Gly Ile Gly Arg Lys Val Asp Met Arg Ala
        130                 135                 140

His Ser Ser Tyr Glu Asn Leu Ala Gln Thr Leu Glu Glu Met Phe Phe
145                 150                 155                 160

Gly Met Thr Gly Thr Thr Cys Arg Glu Lys Val Lys Pro Leu Arg Leu
                165                 170                 175

Leu Asp Gly Ser Ser Asp Phe Val Leu Thr Tyr Glu Asp Lys Glu Gly
                180                 185                 190

Asp Trp Met Leu Val Gly Asp Val Pro Trp Arg Met Phe Ile Asn Ser
        195                 200                 205

Val Lys Arg Leu Arg Ile Met Gly Thr Ser Glu Ala Ser Gly Leu Ala
        210                 215                 220

Pro Arg Arg Gln Glu Gln Lys Asp Arg Gln Asn Asn Pro Val
225                 230                 235
```

```
<210> SEQ ID NO 55
<211> LENGTH: 950
<212> TYPE: DNA
<213> ORGANISM: Arabidopsis thaliana

<400> SEQUENCE: 55
```

| | | | | | |
|---|---|---|---|---|---|
| gacgggtcat | cacagattct | tcgtttttt | atagatagaa | aaggaataac | gttaaaagta | 60 |
| tacaaattat | atgcaagagt | cattcgaaag | aattaaataa | agagatgaac | tcaaagtga | 120 |
| ttttaaattt | taatgataag | aatatacatc | tcacagaaat | cttttatttg | acatgtaaaa | 180 |
| tcttgttttc | acctatcttt | tgttagtaaa | caagaatatt | taatttgagc | ctcacttgga | 240 |
| acgtgataat | aatatacatc | ttatcataat | tgcatatttt | gcggatagtt | tttgcatggg | 300 |
| gagattaaag | gcttaataaa | gccttgaatt | tccgagggga | ggaatcatgt | tttatacttg | 360 |
| caaactatac | aaccatctgc | atcgataatt | ggtgttaata | catgcaagga | ttatacacta | 420 |
| aaacaaatca | tttatttcct | tacaaaaaga | gagtcgactg | tgagtcacat | tctgtgacaa | 480 |
| ggaaaggtca | agaaccatcg | cttttatcat | cattctcttt | gctaacaact | tacaaccaca | 540 |
| caaacgcaag | agttccattc | tcatggagaa | gaacatatta | tgcaaaataa | tgtatgtcga | 600 |
| tcgatagaga | aaaggatcca | caattattgc | tccatctcaa | aagcttcttt | agtacacgat | 660 |
| acatgtatca | tgtaaataga | aatatgaaag | atacaataca | cgacccattc | tcataaagat | 720 |
| agcaacattt | catgttatgt | aaagagtctt | cctaggaca | catgcattaa | aactaaggat | 780 |
| taccaaccca | cttactcctc | actccaacca | aatatcaatc | atctattttg | ggtccttcac | 840 |
| tcataagtca | actctcatgc | cttcctctat | aaataccgta | ccctacgcat | cccttagttc | 900 |
| tacatcacat | aaaaacaatc | atagcaaaaa | catatatcct | caaattaatt | | 950 |

```
<210> SEQ ID NO 56
<211> LENGTH: 918
<212> TYPE: DNA
<213> ORGANISM: Arabidopsis thaliana

<400> SEQUENCE: 56
```

| | | | | | |
|---|---|---|---|---|---|
| atggatcatg | aggaaattcc | atccacgccc | tcaacgccgg | cgacaacccc | ggggactcca | 60 |
| ggagcgccgc | tctttggagg | attcgaaggg | aagaggaatg | gacacaatgg | tagatacaca | 120 |
| ccaaagtcac | ttctcaaaag | ctgcaaatgt | ttcagtgttg | acaatgaatg | ggctcttgaa | 180 |
| gatggaagac | tccctccggt | cacttgctct | ctcccctcccc | ctaacgtttc | cctctaccgc | 240 |

```
aagttgggag cagagtttgt tgggacattg atcctgatat tcgccggaac agcgacggcg    300
atcgtgaacc agaagacaga tggagctgag acgcttattg gttgcgccgc ctcggctggt    360
ttggcggtta tgatcgttat attatcgacc ggtcacatct ccggggcaca tctcaatccg    420
gctgtaacca ttgcctttgc tgctctcaaa cacttcccct tggaaacacgt gccggtgtat    480
atcggagctc aggtgatggc ctccgtgagt gcggcgtttg cactgaaagc agtgtttgaa    540
ccaacgatga gcggtggcgt gacggtgccg acggtgggtc tcagccaagc tttcgccttg    600
gaattcatta tcagcttcaa cctcatgttc gttgtcacag ccgtagccac cgacacgaga    660
gctgtgggag agttggcggg aattgccgta ggagcaacgg tcatgcttaa catacttata    720
gctggacctg caacttctgc ttcgatgaac cctgtaagaa cactgggtcc agccattgca    780
gcaaacaatt acagagctat ttgggtttac ctcactgccc ccattcttgg agcgttaatc    840
ggagcaggta catacacaat tgtcaagttg ccagaggaag atgaagcacc caagagagg    900
aggagcttca gaagatga                                                   918
```

<210> SEQ ID NO 57
<211> LENGTH: 305
<212> TYPE: PRT
<213> ORGANISM: Arabidopsis thaliana
<400> SEQUENCE: 57

```
Met Asp His Glu Glu Ile Pro Ser Thr Pro Ser Thr Pro Ala Thr Thr
1               5                   10                  15

Pro Gly Thr Pro Gly Ala Pro Leu Phe Gly Gly Phe Glu Gly Lys Arg
            20                  25                  30

Asn Gly His Asn Gly Arg Tyr Thr Pro Lys Ser Leu Leu Lys Ser Cys
        35                  40                  45

Lys Cys Phe Ser Val Asp Asn Glu Trp Ala Leu Glu Asp Gly Arg Leu
    50                  55                  60

Pro Pro Val Thr Cys Ser Leu Pro Pro Asn Val Ser Leu Tyr Arg
65                  70                  75                  80

Lys Leu Gly Ala Glu Phe Val Gly Thr Leu Ile Leu Ile Phe Ala Gly
                85                  90                  95

Thr Ala Thr Ala Ile Val Asn Gln Lys Thr Asp Gly Ala Glu Thr Leu
            100                 105                 110

Ile Gly Cys Ala Ala Ser Ala Gly Leu Ala Val Met Ile Val Ile Leu
        115                 120                 125

Ser Thr Gly His Ile Ser Gly Ala His Leu Asn Pro Ala Val Thr Ile
    130                 135                 140

Ala Phe Ala Ala Leu Lys His Phe Pro Trp Lys His Val Pro Val Tyr
145                 150                 155                 160

Ile Gly Ala Gln Val Met Ala Ser Val Ser Ala Phe Ala Leu Lys
                165                 170                 175

Ala Val Phe Glu Pro Thr Met Ser Gly Gly Val Thr Val Pro Thr Val
            180                 185                 190

Gly Leu Ser Gln Ala Phe Ala Leu Glu Phe Ile Ile Ser Phe Asn Leu
        195                 200                 205

Met Phe Val Val Thr Ala Val Ala Thr Asp Thr Arg Ala Val Gly Glu
210                 215                 220

Leu Ala Gly Ile Ala Val Gly Ala Thr Val Met Leu Asn Ile Leu Ile
225                 230                 235                 240

Ala Gly Pro Ala Thr Ser Ala Ser Met Asn Pro Val Arg Thr Leu Gly
                245                 250                 255
```

```
Pro Ala Ile Ala Ala Asn Asn Tyr Arg Ala Ile Trp Val Tyr Leu Thr
        260                 265                 270
Ala Pro Ile Leu Gly Ala Leu Ile Gly Ala Gly Thr Tyr Thr Ile Val
            275                 280                 285
Lys Leu Pro Glu Glu Asp Glu Ala Pro Lys Gly Arg Arg Ser Phe Arg
        290                 295                 300

Arg
305

<210> SEQ ID NO 58
<211> LENGTH: 950
<212> TYPE: DNA
<213> ORGANISM: Arabidopsis thaliana

<400> SEQUENCE: 58
cgctccagac cactgtttgc tttcctctga ttaaccaatc tcaattaaac tactaattta      60
taattcaaga taattagata accaatctta aaatttggaa tcttcttccc tcacttgata     120
ttacaaaaaa aaaactgatt tatcatacgg ttaattcaag aaaacagcaa aaaaattgca     180
ctataatgca aacatcaat taattacatt cgattaaaaa atcatcattg aatctaaaat      240
ggcctcaaat ctattgagca tttgtcatgt gcctaaaatg gttcaggagt tttacatcta     300
atcacataaa aagcaaacaa taaccaaaaa aattgcattt tagcaaatca atacttata     360 tatatacgta tgattaagcg tcatgacttt aaaacctctg taaaattttg atttatttt     420 cgatgctttt atttttaac caatagtaat aaagtccaaa tcttaaatac gaaaaaatgt     480
ttctttctaa gcgaccaaca aaatggtcca atcacagaa atgttccat aatccaggcc     540 cattaagcta atcaccaagt aatacattac acgtcaccaa ttaatacatt acacgtacgg     600
ccttctctct tcacgagtaa tatgcaaaca aacgtacatt agctgtaatg tactcactca     660
tgcaacgtct taacctgcca cgtattacgt aattacacca ctccttgttc ctaacctacg     720
catttcactt tagcgcatgt tagtcaaaaa acacaaacat aaaactacaa taaaaaaact     780
caaaacaaaa cccaatgaac gaacggacca gccccgtctc gattgatgga acagtgacaa     840
cagtcccgtt ttctcgggca taacggaaac ggtaaccgtc tctctgtttc atttgcaaca     900
acaccatttt tataaataaa aacacattta ataaaaaat tattaaaacc                 950

<210> SEQ ID NO 59
<211> LENGTH: 153
<212> TYPE: DNA
<213> ORGANISM: Arabidopsis thaliana

<400> SEQUENCE: 59
tatatccaaa caaatgaatg tgttaaacct tcactcttct ctccacacaa aattcaaaaa      60
cctcacattt cacttctctc ttctcgcttc ttctagatct caccggttta tctagctccg     120
gtttgattca tctccggtta tggggagaga atg                                   153

<210> SEQ ID NO 60
<211> LENGTH: 2017
<212> TYPE: DNA
<213> ORGANISM: Arabidopsis thaliana

<400> SEQUENCE: 60
atatatccaa acaaatgaat gtgttaaacc ttcactcttc tctccacaca aaattcaaaa      60
acctcacatt tcacttctct cttctcgctt cttctagatc tcaccggttt atctagctcc     120
ggtttgattc atctccggtt atggggagag aatgaggagt taccgtttta gtgattatct     180
```

```
acacatgtct gtttcattct ctaacgatat ggatttgttt tgtggagaag actccggtgt    240
gttttccggt gagtcaacgg ttgatttctc gtcttccgag gttgattcat ggcctggtga    300
ttctatcgct tgttttatcg aagacgagcg tcacttcgtt cctggacatg attatctctc    360
tagatttcaa actcgatctc tcgatgcttc cgctagagaa gattccgtcg catggattct    420
caaggtacaa gcgtattata actttcagcc tttaacggcg tacctcgccg ttaactatat    480
ggatcggttt ctttacgctc gtcgattacc ggaaacgagt ggttggccaa tgcaactttt    540
agcagtggca tgcttgtctt tagctgcaaa gatggaggaa attctcgttc cttctctttt    600
tgattttcag gttgcaggag tgaagtattt atttgaagca aaaactataa aaagaatgga    660
acttcttgtt ctaagtgtgt tagattggag actaagatcg gttacaccgt ttgatttcat    720
tagcttcttt gcttacaaga tcgatccttc gggtaccttt ctcgggttct ttatctccca    780
tgctacagag attatactct ccaacataaa agaagcgagc tttcttgagt actggccatc    840
gagtatagct gcagccgcga ttctctgtgt agcgaacgag ttaccttctc tatcctctgt    900
tgtcaatccc cacgagagcc ctgagacttg gtgtgacgga ttgagcaaag agaagatagt    960
gagatgctat agactgatga aagcgatggc catcgagaat aaccggttaa atacaccaaa   1020
agtgatagca aagcttcgag tgagtgtaag ggcatcatcg acgttaacaa ggccaagtga   1080
tgaatcctct ttctcatcct cttctccttg taaaaggaga aaattaagtg gctattcatg   1140
ggtaggtgat gaaacatcta cctctaatta aaatttgggg agtgaaagta gaggaccaag   1200
gaaacaaaac ctagaagaaa aaaaaccctc ttctgtttaa gtagagtata tttttttaaca  1260
agtacatagt aataagggag tgatgaagaa aagtaaaagt gtttattggc tgagttaaag   1320
taattaagag ttttccaacc aaggggaagg aataagagtt ttggttacaa tttctttttat  1380
ggaaagggta aaaattgggt tttggggttg gttggttggt tgggagagac gaagctcatc   1440
attaatggct ttgcagattc ccaagaaagc aaaatgagta agtgagtgta acacacacgt   1500
gttagagaaa agatatgatc atgtgagtgt gtgtgtgtga gagagagaga gaaagagtatt  1560
tgcattagag tcctcatcac acaggtactg atggataaga caggggagcg tttgcaaaag   1620
atttgtgagt ggagattttt ctgagctctt tgtcttaatg gatcgcagca gttcatggga   1680
cccttcctca gcttcatcat caaacaaaaa aaaaatcaag ttgcgaagta tatataattt   1740
gttttttttgt ttggattttt aagatttttg attccttgtg tgtgacttca cgtgacggag   1800
gcgtgtgtct cacgtgtttg ttttctcttc aaatctttta ttttggcggg aaattttgtg   1860
ttttttgattt ctacgtattc gtggactcca aatgagtttt gtcacggtgc gttttagtag   1920
cgtttgcatg cgtgtaaggt gtcacgtatg tgtatatata tgattttttt ttggtttctt   1980
gaaaggttga attttataaa taaaacgttt ctattat                             2017
```

<210> SEQ ID NO 61
<211> LENGTH: 339
<212> TYPE: PRT
<213> ORGANISM: Arabidopsis thaliana

<400> SEQUENCE: 61

```
Met Arg Ser Tyr Arg Phe Ser Asp Tyr Leu His Met Ser Val Ser Phe
1               5                   10                  15

Ser Asn Asp Met Asp Leu Phe Cys Gly Glu Ser Gly Val Phe Ser
            20                  25                  30

Gly Glu Ser Thr Val Asp Phe Ser Ser Glu Val Asp Ser Trp Pro
        35                  40                  45

Gly Asp Ser Ile Ala Cys Phe Ile Glu Asp Glu Arg His Phe Val Pro
```

```
              50                  55                  60
Gly His Asp Tyr Leu Ser Arg Phe Gln Thr Arg Ser Leu Asp Ala Ser
 65                  70                  75                  80

Ala Arg Glu Asp Ser Val Ala Trp Ile Leu Lys Val Gln Ala Tyr Tyr
                 85                  90                  95

Asn Phe Gln Pro Leu Thr Ala Tyr Leu Ala Val Asn Tyr Met Asp Arg
            100                 105                 110

Phe Leu Tyr Ala Arg Arg Leu Pro Glu Thr Ser Gly Trp Pro Met Gln
        115                 120                 125

Leu Leu Ala Val Ala Cys Leu Ser Leu Ala Ala Lys Met Glu Glu Ile
130                 135                 140

Leu Val Pro Ser Leu Phe Asp Phe Gln Val Ala Gly Val Lys Tyr Leu
145                 150                 155                 160

Phe Glu Ala Lys Thr Ile Lys Arg Met Glu Leu Val Leu Ser Val
                165                 170                 175

Leu Asp Trp Arg Leu Arg Ser Val Thr Pro Phe Asp Phe Ile Ser Phe
            180                 185                 190

Phe Ala Tyr Lys Ile Asp Pro Ser Gly Thr Phe Leu Gly Phe Phe Ile
        195                 200                 205

Ser His Ala Thr Glu Ile Ile Leu Ser Asn Ile Lys Glu Ala Ser Phe
210                 215                 220

Leu Glu Tyr Trp Pro Ser Ser Ile Ala Ala Ala Ile Leu Cys Val
225                 230                 235                 240

Ala Asn Glu Leu Pro Ser Leu Ser Ser Val Val Asn Pro His Glu Ser
                245                 250                 255

Pro Glu Thr Trp Cys Asp Gly Leu Ser Lys Glu Lys Ile Val Arg Cys
            260                 265                 270

Tyr Arg Leu Met Lys Ala Met Ala Ile Glu Asn Asn Arg Leu Asn Thr
        275                 280                 285

Pro Lys Val Ile Ala Lys Leu Arg Val Ser Val Arg Ala Ser Ser Thr
290                 295                 300

Leu Thr Arg Pro Ser Asp Glu Ser Ser Phe Ser Ser Ser Ser Pro Cys
305                 310                 315                 320

Lys Arg Arg Lys Leu Ser Gly Tyr Ser Trp Val Gly Asp Glu Thr Ser
                325                 330                 335

Thr Ser Asn

<210> SEQ ID NO 62
<211> LENGTH: 950
<212> TYPE: DNA
<213> ORGANISM: Arabidopsis thaliana

<400> SEQUENCE: 62
tttaaacata acaatgaatt gcttggattt caaactttat taaatttgga ttttaaattt      60
taatttgatt gaattatacc cccttaattg gataaattca aatatgtcaa ctttttttt     120 ttgtaagatt ttttatgga aaaaaaaatt gattattcac taaaaagatg acaggttact     180
tataatttaa tatatgtaaa ccctaaaaag aagaaaatag tttctgtttt cactttaggt     240
cttattatct aaacttcttt aagaaaatcg caataaattg gtttgagttc taactttaaa     300
cacattaata tttgtgtgct atttaaaaaa taatttacaa aaaaaaaaac aaattgacag     360
aaaatatcag gttttgtaat aagatatttc ctgataaata tttagggaat ataacatatc     420 aaagattca aattctgaaa atcaagaatg gtagacatgt gaaagttgtc atcaatatgg     480 tccactttc tttgctctat aacccaaaat tgaccctgac agtcaacttg tacacgcggc     540
```

```
caaacctttt tataatcatg ctatttattt ccttcatttt tattctattt gctatctaac    600 tgattttttca ttaacatgat accagaaatg aatttagatg gattaattct tttccatcca   660
cgacatctgg aaacacttat ctcctaatta accttacttt tttttttagtt tgtgtgctcc   720 ttcataaaat ctatattgtt taaaacaaag gtcaataaat ataaatatgg ataagtataa    780
taaatcttta ttggatattt cttttttttaa aaagaaata aatctttttt ggatattttc    840
gtggcagcat cataatgaga gactacgtcg aaactgctgg caaccacttt tgccgcgttt    900
aatttctttc tgaggcttat ataaatagat caaaggggaa agtgagatat               950
```

```
<210> SEQ ID NO 63
<211> LENGTH: 703
<212> TYPE: DNA
<213> ORGANISM: Arabidopsis thaliana

<400> SEQUENCE: 63
aaagaaaatg ggtttgagaa gaacatggtt ggttttgtac attctcttca tctttcatct     60
tcagcacaat cttccttccg tgagctcacg accttcctca gtcgatacaa accacgagac    120 tctcccttttt agtgtttcaa agccagacgt tgttgtgttt gaaggaaagg ctcgggaatt   180
agctgtcgtt atcaaaaaag gaggaggtgg aggaggtgga ggacgcggag cggtggagc    240 acgaagcggc ggtaggagca ggggaggagg aggtggcagc agtagtagcc gcagccgtga    300
ctggaaacgc ggcggagggg tggttccgat tcatacgggt ggtggtaatg gcagtctggg    360
tggtggatcg gcaggatcac atagatcaag cggcagcatg aatcttcgag gaacaatgtg    420
tgcggtctgt tggttggctt tatcggtttt agccggttta gtcttggttc agtagggttc    480
agagtaatta ttggccattt atttattggt tttgtaacgt ttatgtttgt ggtccggtct    540
gatatttatt tgggcaaacg gtacattaag gtgtagactg ttaatattat atgtagaaag    600
agattcttag caggattcta ctggtagtat taagagtgag ttatctttag tatgccattt    660
gtaaatggaa atttaatgaa ataagaaatt gtgaaattta aac                      703
```

```
<210> SEQ ID NO 64
<211> LENGTH: 157
<212> TYPE: PRT
<213> ORGANISM: Arabidopsis thaliana

<400> SEQUENCE: 64

Lys Lys Met Gly Leu Arg Arg Thr Trp Leu Val Leu Tyr Ile Leu Phe
1               5                   10                  15

Ile Phe His Leu Gln His Asn Leu Pro Ser Val Ser Arg Pro Ser
            20                  25                  30

Ser Val Asp Thr Asn His Glu Thr Leu Pro Phe Ser Val Ser Lys Pro
        35                  40                  45

Asp Val Val Phe Glu Gly Lys Ala Arg Glu Leu Ala Val Ile
    50                  55                  60

Lys Lys Gly Gly Gly Gly Gly Gly Arg Gly Gly Gly Ala
65                  70                  75                  80

Arg Ser Gly Gly Arg Ser Gly Gly Gly Ser Ser Ser
                85                  90                  95

Arg Ser Arg Asp Trp Lys Arg Gly Gly Val Pro Ile His Thr
            100                 105                 110

Gly Gly Gly Asn Gly Ser Leu Gly Gly Gly Ser Ala Gly Ser His Arg
        115                 120                 125

Ser Ser Gly Ser Met Asn Leu Arg Gly Thr Met Cys Ala Val Cys Trp
```

-continued

```
            130                 135                 140
Leu Ala Leu Ser Val Leu Ala Gly Leu Val Leu Val Gln
145                 150                 155
```

PROMOTER, PROMOTER CONTROL ELEMENTS, AND COMBINATIONS, AND USES THEREOF

CROSS REFERENCES TO RELATED APPLICATIONS

This application is a Continuation of co-pending application Ser. No. 11/598,118, filed on Nov. 10, 2009 the entire contents of which are hereby incorporated by reference and for which priority is claimed under 35 U.S.C. §120.

The nonprovisional application Ser. No. 11/598,118, filed on Nov. 10, 2006, claims priority under 35 U.S.C. §119(e) on U.S. application Ser. No. 10/950,321, filed Sep. 23, 2004, and Provisional Application No. 60/505,689 filed on Sep. 23, 2003; Application No. 60/511,460 filed on Oct. 14, 2003; Application No. 60/518,075 filed on Nov. 6, 2003; Application No. 60/527,611 filed on Dec. 4, 2003; Application No. 60,529,352 filed on Dec. 12, 2003; and Application No. 60/544,771 filed on Feb. 13, 2004, the entire contents of each of which are herein incorporated by reference.

FIELD OF THE INVENTION

The present invention relates to promoters and promoter control elements that are useful for modulating transcription of a desired polynucleotide. Such promoters and promoter control elements can be included in polynucleotide constructs, expression cassettes, vectors, or inserted into the chromosome or as an exogenous element, to modulate in vivo and in vitro transcription of a polynucleotide. Host cells, including plant cells, and organisms, such as regenerated plants therefrom, with desired traits or characteristics using polynucleotides comprising the promoters and promoter control elements of the present invention are also a part of the invention.

BACKGROUND OF THE INVENTION

This invention relates to the field of biotechnology and, in particular, to specific promoter sequences and promoter control element sequences which are useful for the transcription of polynucleotides in a host cell or transformed host organism.

One of the primary goals of biotechnology is to obtain organisms, such as plants, mammals, yeast, and prokaryotes having particular desired characteristics or traits. Examples of these characteristic or traits abound and may include, for example, in plants, virus resistance, insect resistance, herbicide resistance, enhanced stability or additional nutritional value. Recent advances in genetic engineering have enabled researchers in the field to incorporate polynucleotide sequences into host cells to obtain the desired qualities in the organism of choice. This technology permits one or more polynucleotides from a source different than the organism of choice to be transcribed by the organism of choice. If desired, the transcription and/or translation of these new polynucleotides can be modulated in the organism to exhibit a desired characteristic or trait. Alternatively, new patterns of transcription and/or translation of polynucleotides endogenous to the organism can be produced. Both approaches can be used at the same time.

SUMMARY OF THE INVENTION

The present invention is directed to isolated polynucleotide sequences that comprise promoters and promoter control elements from plants, especially *Arabidopsis thaliana*, *Glycine max*, *Oryza sativa*, and *Zea mays*, and other promoters and promoter control elements functional in plants.

It is an object of the present invention to provide isolated polynucleotides that are promoter sequences. These promoter sequences comprise, for example,
  (1) a polynucleotide having a nucleotide sequence as set forth in Table 1, in the section entitled "The predicted promoter sequence" or fragment thereof;
  (2) a polynucleotide having a nucleotide sequence having at least 80% sequence identity to a sequence as set forth in Table 1, in the section entitled "The predicted promoter sequence" or fragment thereof; and
  (3) a polynucleotide having a nucleotide sequence which hybridizes to a sequence as set forth in Table 1, in the section entitled "The predicted promoter sequence" under a condition establishing a Tm−20° C.

It is another object of the present invention to provide isolated polynucleotides that are promoter control element sequences. These promoter control element sequences comprise, for example,
  (1) a polynucleotide having a nucleotide sequence as set forth in Table 1, in the section entitled "The predicted promoter sequence" or fragment thereof;
  (2) a polynucleotide having a nucleotide sequence having at least 80% sequence identity to a sequence as set forth in Table 1, in the section entitled "The predicted promoter sequence" or fragment thereof; and
  (3) a polynucleotide having a nucleotide sequence which hybridizes to a sequence as set forth in Table 1, in the section entitled "The predicted promoter sequence" under a condition establishing a Tm−20° C.

Promoter or promoter control element sequences of the present invention are capable of modulating preferential transcription.

In another embodiment, the present promoter control elements are capable of serving as or fulfilling the function, for example, as a core promoter, a TATA box, a polymerase binding site, an initiator site, a transcription binding site, an enhancer, an inverted repeat, a locus control region, or a scaffold/matrix attachment region.

It is yet another object of the present invention to provide a polynucleotide that includes at least a first and a second promoter control element. The first promoter control element is a promoter control element sequence as discussed above, and the second promoter control element is heterologous to the first control element. Moreover, the first and second control elements are operably linked. Such promoters may modulate transcript levels preferentially in a tissue or under particular conditions.

In another embodiment, the present isolated polynucleotide comprises a promoter or a promoter control element as described above, wherein the promoter or promoter control element is operably linked to a polynucleotide to be transcribed.

In another embodiment of the present vector, the promoter and promoter control elements of the instant invention are operably linked to a heterologous polynucleotide that is a regulatory sequence.

It is another object of the present invention to provide a host cell comprising an isolated polynucleotide or vector as described above or fragment thereof. Host cells include, for instance, bacterial, yeast, insect, mammalian, and plant. The host cell can comprise a promoter or promoter control element exogenous to the genome. Such a promoter can modulate transcription in cis- and in trans-.

In yet another embodiment, the present host cell is a plant cell capable of regenerating into a plant.

It is yet another embodiment of the present invention to provide a plant comprising an isolated polynucleotide or vector described above.

It is another object of the present invention to provide a method of modulating transcription in a sample that contains either a cell-free system of transcription or host cell. This method comprises providing a polynucleotide or vector according to the present invention as described above, and contacting the sample of the polynucleotide or vector with conditions that permit transcription.

In another embodiment of the present method, the polynucleotide or vector preferentially modulates (a) constitutive transcription,
(b) stress induced transcription,
(c) light induced transcription,
(d) dark induced transcription,
(e) leaf transcription,
(f) root transcription,
(g) stem or shoot transcription,
(h) silique transcription,
(i) callus transcription,
(j) flower transcription,
(k) immature bud and inflorescence specific transcription, or
(l) senescing induced transcription
(m) germination transcription.

Other and further objects of the present invention will be made clear or become apparent from the following description.

BRIEF DESCRIPTION OF THE TABLES AND FIGURES

Table 1

Table 1 consists of the Expression Reports for each promoter of the invention providing the nucleotide sequence for each promoter and details for expression driven by each of the nucleic acid promoter sequences as observed in transgenic plants. The results are presented as summaries of the spatial expression, which provides information as to gross and/or specific expression in various plant organs and tissues. The observed expression pattern is also presented, which gives details of expression during different generations or different developmental stages within a generation. Additional information is provided regarding the associated gene, the GenBank reference, the source organism of the promoter, and the vector and marker genes used for the construct. The following symbols are used consistently throughout the Table:

T1: First generation transformant

T2: Second generation transformant

T3: Third generation transformant (L): low expression level (M): medium expression level (H): high expression level Each row of the table begins with heading of the data to be found in the section. The following provides a description of the data to be found in each section:

| Heading in Table 1 | Description |
|---|---|
| Promoter | Identifies the particular promoter by its construct ID. |
| Modulates the gene: | This row states the name of the gene modulated by the promoter |
| The GenBank description of the gene: | This field gives the Locus Number of the gene as well as the accession number. |
| The predicted promoter sequence: | Identifies the nucleic acid promoter sequence in question. |
| The promoter was cloned from the organism: | Identifies the source of the DNA template used to clone the promoter. |
| The experimental promoter sequence: | Identifies the nucleic acid sequence in planta driving expression of the reporter gene. |
| The promoter was cloned in the vector: | Identifies the vector used into which a promoter was cloned. |
| When cloned into the vector the promoter was operably linked to a marker, which was the type: | Identifies the type of marker linked to the promoter. The marker is used to determine patterns of gene expression in plant tissue. |
| Promoter-marker vector was tested in: | Identifies the organism in which the promoter-marker vector was tested. |
| Generation screened: T1 Mature T2 Seedling T2 Mature T3 Seedling | Identifies the plant generation(s) used in the screening process. T1 plants are those plants subjected to the transformation event while the T2 generation plants are from the seeds collected from the T1 plants and T3 plants are from the seeds of T2 plants. |
| The spatial expression of the promoter-marker vector was found observed in and would be useful in expression in any or all of the following: | Identifies the specific parts of the plant where various levels of GFP expression are observed. Expression levels are noted as either low (L), medium (M), or high (H). |
| Observed expression pattern of the promoter-marker vector was in:<br>T1 mature:<br>T2 seedling: | Identifies a general explanation of where GFP expression in different generations of plants was observed. |
| The promoter can be of use in the following trait and sub-trait areas: (search for the trait and sub-trait table) | Identifies which traits and subtraits the promoter cDNA can modulate |
| The promoter has utility in: | Identifies a specific function or functions that can be modulated using the promoter cDNA. |

| Heading in Table 1 | Description |
| --- | --- |
| Misc. promoter information:<br>Bidirectionality:<br>Exons:<br>Repeats: | "Bidirectionality" is determined by the number of base pairs between the promoter and the start codon of a neighboring gene. A promoter is considered bidirectional if it is closer than 200 bp to a start codon of a gene 5' or 3' to the promoter. "Exons" (or any coding sequence) identifies if the promoter has overlapped with either the modulating gene's or other neighboring gene's coding sequence. A "fail" for exons means that this overlap has occurred. "Repeats" identifies the presence of normally occurring sequence repeats that randomly exist throughout the genome. A "pass" for repeats indicates a lack of repeats in the promoter. |
| An overlap in an exon with the endogenous coding sequence to the promoter occurs at base pairs: | Identifies the specific nucleotides overlapping the UTR region or exon of a neighboring gene. The orientation relative to the promoter is designated with a 5' or 3'. |
| The Ceres cDNA ID of the endogenous coding sequence to the promoter: | Identifies the number associated with the Ceres cDNA that corresponds to the endogenous cDNA sequence of the promoter. |
| cDNA nucleotide sequence: | The nucleic acid sequence of the Ceres cDNA matching the endogenous cDNA region of the promoter. |
| Coding sequence: | A translated protein sequence of the gene modulated by a protein encoded by a cDNA |
| Microarray Data shows that the coding sequence was expressed in the following experiments, which shows that the promoter would useful to modulate expression in situations similar to the following: | Microarray data is identified along with the corresponding experiments along with the corresponding gene expression. Gene expression is identified by a "+" or a "−" in the "SIGN(LOG_RATIO)" column. A "+" notation indicates the cDNA is upregulated while a "−" indicates that the cDNA is downregulated. The "SHORT_NAME" field describes the experimental conditions. |
| The parameters for the microarray experiments listed above by EXPT_REP_ID and Short_Name are as follow below: | Parameters for microarray experiments include age, organism, specific tissues, age, treatments and other distinguishing characteristics or features. |

Table 2

Table 1 provides the results of differential expression experiments indicating if the expression levels were increased ("+") or decreased ("−"). Such increase or decrease expression levels indicates the utility of the corresponding promoter. The following Table 2 correlates the various differential expression experiments with the utility for the promoter that would be understood from an increased or decreased expression. Table 2 includes three columns, the first column ("EXPT_REP_ID") lists the microarray experiments by their experimental prep ID number and correspond to the same number listings in Table 1 in the "Microarray data" section. The second column lists the Short_Name of the experiment that corresponds to the EXPT_REP_if D. When a cDNA is differentially expressed in an experiment, identified by its EXPT_REP_ID, the cDNA and its endogenous promoter can be used to modulate the traits and subtraits listed in the third column.

FIG. 1

FIG. 1 is a schematic representation of the vector pNew-Bin4-HAP1-GFP. The definitions of the abbreviations used in the vector map are as follows:
Ori—the origin of replication used by an *E. coli* host
RB—sequence for the right border of the T-DNA from pMOG800
BstXI—restriction enzyme cleavage site used for cloning
HAP1VP16—coding sequence for a fusion protein of the HAP1 and VP16 activation domains
NOS—terminator region from the nopaline synthase gene
HAP1UAS—the upstream activating sequence for HAP1
5ERGFP—the green fluorescent protein gene that has been optimized for localization to the endoplasmic reticulum
OCS2—the terminator sequence from the octopine synthase 2 gene
OCS—the terminator sequence from the octopine synthase gene
p28716 (a.k.a 28716 short)—promoter used to drive expression of the PAT (BAR) gene
PAT (BAR)—a marker gene conferring herbicide resistance
LB—sequence for the left border of the T-DNA from pMOG800
Spec—a marker gene conferring spectinomycin resistance
TrfA—transcription repression factor gene
RK2-OriV—origin of replication for *Agrobacterium*

DETAILED DESCRIPTION OF THE INVENTION

1. Definitions

Chimeric: The term "chimeric" is used to describe polynucleotides or genes, as defined supra, or constructs wherein at least two of the elements of the polynucleotide or gene or construct, such as the promoter and the polynucleotide to be transcribed and/or other regulatory sequences and/or filler sequences and/or complements thereof, are heterologous to each other.

Constitutive Promoter: Promoters referred to herein as "constitutive promoters" actively promote transcription under most, but not necessarily all, environmental conditions and states of development or cell differentiation. Examples of constitutive promoters include the cauliflower mosaic virus (CaMV) 35S transcript initiation region and the 1' or 2' promoter derived from T-DNA of *Agrobacterium tumefaciens*, and other transcription initiation regions from various plant genes, such as the maize ubiquitin-1 promoter, known to those of skill.

Core Promoter: This is the minimal stretch of contiguous DNA sequence that is sufficient to direct accurate initiation of transcription by the RNA polymerase II machinery (for review see: Struhl, 1987, *Cell* 49: 295-297; Smale, 1994, In *Transcription: Mechanisms and Regulation* (eds R. C. Conaway and J. W. Conaway), pp 63-81/Raven Press, Ltd., New York; Smale, 1997, *Biochim. Biophys. Acta* 1351: 73-88; Smale et al., 1998, *Cold Spring Harb. Symp. Quant. Biol.* 58: 21-31; Smale, 2001, *Genes & Dev.* 15: 2503-2508; Weis and Reinberg, 1992, *FASEB J.* 6: 3300-3309; Burke et al., 1998, *Cold Spring Harb. Symp. Quant. Biol* 63: 75-82). There are several sequence motifs, including the TATA box, initiator (Inr), TFIIB recognition element (BRE) and downstream core promoter element (DPE), that are commonly found in core promoters, however not all of these elements occur in all promoters and there are no universal core promoter elements (Butler and Kadonaga, 2002, Genes & Dev. 16: 2583-2592).

Domain: Domains are fingerprints or signatures that can be used to characterize protein families and/or parts of proteins. Such fingerprints or signatures can comprise conserved (1) primary sequence, (2) secondary structure, and/or (3) three-dimensional conformation. A similar analysis can be applied to polynucleotides. Generally, each domain has been associated with either a conserved primary sequence or a sequence motif. Generally these conserved primary sequence motifs have been correlated with specific in vitro and/or in vivo activities. A domain can be any length, including the entirety of the polynucleotide to be transcribed. Examples of domains include, without limitation, AP2, helicase, homeobox, zinc finger, etc.

Endogenous: The term "endogenous," within the context of the current invention refers to any polynucleotide, polypeptide or protein sequence which is a natural part of a cell or organisms regenerated from said cell. In the context of promoter, the term "endogenous coding region" or "endogenous cDNA" refers to the coding region that is naturally operably linked to the promoter.

Enhancer/Suppressor: An "enhancer" is a DNA regulatory element that can increase the steady state level of a transcript, usually by increasing the rate of transcription initiation. Enhancers usually exert their effect regardless of the distance, upstream or downstream location, or orientation of the enhancer relative to the start site of transcription. In contrast, a "suppressor" is a corresponding DNA regulatory element that decreases the steady state level of a transcript, again usually by affecting the rate of transcription initiation. The essential activity of enhancer and suppressor elements is to bind a protein factor(s). Such binding can be assayed, for example, by methods described below. The binding is typically in a manner that influences the steady state level of a transcript in a cell or in an in vitro transcription extract.

Exogenous: As referred to within, "exogenous" is any polynucleotide, polypeptide or protein sequence, whether chimeric or not, that is introduced into the genome of a host cell or organism regenerated from said host cell by any means other than by a sexual cross. Examples of means by which this can be accomplished are described below, and include *Agrobacterium*-mediated transformation (of dicots—e.g. Salomon et al. EMBO J. 3:141 (1984); Herrera-Estrella et al. EMBO J. 2:987 (1983); of monocots, representative papers are those by Escudero et al., Plant J. 10:355 (1996), Ishida et al., Nature Biotechnology 14:745 (1996), May et al., Bio/Technology 13:486 (1995)), biolistic methods (Armaleo et al., Current Genetics 17:97 1990)), electroporation, in planta techniques, and the like. Such a plant containing the exogenous nucleic acid is referred to here as a $T_0$ for the primary transgenic plant and $T_1$ for the first generation. The term "exogenous" as used herein is also intended to encompass inserting a naturally found element into a non-naturally found location.

Gene: The term "gene," as used in the context of the current invention, encompasses all regulatory and coding sequence contiguously associated with a single hereditary unit with a genetic function. Genes can include non-coding sequences that modulate the genetic function that include, but are not limited to, those that specify polyadenylation, transcriptional regulation, DNA conformation, chromatin conformation, extent and position of base methylation and binding sites of proteins that control all of these. Genes encoding proteins are comprised of "exons" (coding sequences), which may be interrupted by "introns" (non-coding sequences). In some instances complexes of a plurality of protein or nucleic acids or other molecules, or of any two of the above, may be required for a gene's function. On the other hand a gene's genetic function may require only RNA expression or protein production, or may only require binding of proteins and/or nucleic acids without associated expression. In certain cases, genes adjacent to one another may share sequence in such a way that one gene will overlap the other. A gene can be found within the genome of an organism, in an artificial chromosome, in a plasmid, in any other sort of vector, or as a separate isolated entity.

Heterologous sequences: "Heterologous sequences" are those that are not operatively linked or are not contiguous to each other in nature. For example, a promoter from corn is considered heterologous to an *Arabidopsis* coding region sequence. Also, a promoter from a gene encoding a growth factor from corn is considered heterologous to a sequence encoding the corn receptor for the growth factor. Regulatory element sequences, such as UTRs or 3' end termination sequences that do not originate in nature from the same gene as the coding sequence originates from, are considered heterologous to said coding sequence. Elements operatively linked in nature and contiguous to each other are not heterologous to each other.

Homologous: In the current invention, a "homologous" gene or polynucleotide or polypeptide refers to a gene or polynucleotide or polypeptide that shares sequence similarity with the gene or polynucleotide or polypeptide of interest. This similarity may be in only a fragment of the sequence and often represents a functional domain such as, examples including without limitation a DNA binding domain or a domain with tyrosine kinase activity. The functional activities of homologous polynucleotide are not necessarily the same.

Inducible Promoter: An "inducible promoter" in the context of the current invention refers to a promoter, the activity of which is influenced by certain conditions, such as light, temperature, chemical concentration, protein concentration, conditions in an organism, cell, or organelle, etc. A typical example of an inducible promoter, which can be utilized with the polynucleotides of the present invention, is PARSK1, the promoter from an *Arabidopsis* gene encoding a serine-threonine kinase enzyme, and which promoter is induced by dehydration, abscissic acid and sodium chloride (Wang and Goodman, Plant J. 8:37 (1995)). Examples of environmental conditions that may affect transcription by inducible promoters include anaerobic conditions, elevated temperature, the presence or absence of a nutrient or other chemical compound or the presence of light.

Modulate Transcription Level: As used herein, the phrase "modulate transcription" describes the biological activity of a promoter sequence or promoter control element. Such modulation includes, without limitation, includes up- and down-regulation of initiation of transcription, rate of transcription, and/or transcription levels.

Mutant: In the current invention, "mutant" refers to a heritable change in nucleotide sequence at a specific location. Mutant genes of the current invention may or may not have an associated identifiable phenotype.

Operable Linkage: An "operable linkage" is a linkage in which a promoter sequence or promoter control element is connected to a polynucleotide sequence (or sequences) in such a way as to place transcription of the polynucleotide sequence under the influence or control of the promoter or promoter control element. Two DNA sequences (such as a polynucleotide to be transcribed and a promoter sequence linked to the 5' end of the polynucleotide to be transcribed) are said to be operably linked if induction of promoter function results in the transcription of mRNA encoding the polynucleotide and if the nature of the linkage between the two DNA sequences does not (1) result in the introduction of a frame-shift mutation, (2) interfere with the ability of the promoter sequence to direct the expression of the protein, antisense RNA or ribozyme, or (3) interfere with the ability of the DNA template to be transcribed. Thus, a promoter sequence would be operably linked to a polynucleotide sequence if the promoter was capable of effecting transcription of that polynucleotide sequence.

Optional Promoter Fragments: The phrase "optional promoter fragments" is used to refer to any sub-sequence of the promoter that is not required for driving transcription of an operationally linked coding region. These fragments comprise the 5' UTR and any exon(s) of the endogenous coding region. The optional promoter fragments may also comprise any exon(s) and the 3' or 5' UTR of the gene residing upstream of the promoter (that is, 5' to the promoter). Optional promoter fragments also include any intervening sequences that are introns or sequence that occurs between exons or an exon and the UTR.

Orthologous: "Orthologous" is a term used herein to describe a relationship between two or more polynucleotides or proteins. Two polynucleotides or proteins are "orthologous" to one another if they serve a similar function in different organisms. In general, orthologous polynucleotides or proteins will have similar catalytic functions (when they encode enzymes) or will serve similar structural functions (when they encode proteins or RNA that form part of the ultrastructure of a cell).

Percentage of sequence identity: "Percentage of sequence identity," as used herein, is determined by comparing two optimally aligned sequences over a comparison window, where the fragment of the polynucleotide or amino acid sequence in the comparison window may comprise additions or deletions (e.g., gaps or overhangs) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity. Optimal alignment of sequences for comparison may be conducted by the local homology algorithm of Smith and Waterman Add. APL. Math. 2:482 (1981), by the homology alignment algorithm of Needleman and Wunsch J. Mol. Biol. 48:443 (1970), by the search for similarity method of Pearson and Lipman Proc. Natl. Acad. Sci. (USA) 85: 2444 (1988), by computerized implementations of these algorithms (GAP, BESTFIT, BLAST, PASTA, and TFASTA in the Wisconsin Genetics Software Package, Genetics Computer Group (GCG), 575 Science Dr., Madison, Wis.), or by inspection. Given that two sequences have been identified for comparison, GAP and BESTFIT are preferably employed to determine their optimal alignment. Typically, the default values of 5.00 for gap weight and 0.30 for gap weight length are used.

Plant Promoter: A "plant promoter" is a promoter capable of initiating transcription in plant cells and can modulate transcription of a polynucleotide. Such promoters need not be of plant origin. For example, promoters derived from plant viruses, such as the CaMV35S promoter or from *Agrobacterium tumefaciens* such as the T-DNA promoters, can be plant promoters. A typical example of a plant promoter of plant origin is the maize ubiquitin-1 (ubi-1) promoter known to those of skill.

Plant Tissue: The term "plant tissue" includes differentiated and undifferentiated tissues or plants, including but not limited to roots, stems, shoots, cotyledons, epicotyl, hypocotyl, leaves, pollen, seeds, tumor tissue and various forms of cells in culture such as single cells, protoplast, embryos, and callus tissue. The plant tissue may be in plants or in organ, tissue or cell culture.

Preferential Transcription: "Preferential transcription" is defined as transcription that occurs in a particular pattern of cell types or developmental times or in response to specific stimuli or combination thereof. Non-limitive examples of preferential transcription include: high transcript levels of a desired sequence in root tissues; detectable transcript levels of a desired sequence in certain cell types during embryogenesis; and low transcript levels of a desired sequence under drought conditions. Such preferential transcription can be determined by measuring initiation, rate, and/or levels of transcription.

Promoter: A "promoter" is a DNA sequence that directs the transcription of a polynucleotide. Typically a promoter is located in the 5' region of a polynucleotide to be transcribed, proximal to the transcriptional start site of such polynucleotide. More typically, promoters are defined as the region upstream of the first exon; more typically, as a region upstream of the first of multiple transcription start sites; more typically, as the region downstream of the preceding gene and upstream of the first of multiple transcription start sites; more typically, the region downstream of the polyA signal and upstream of the first of multiple transcription start sites; even more typically, about 3,000 nucleotides upstream of the ATG of the first exon; even more typically, 2,000 nucleotides upstream of the first of multiple transcription start sites. The promoters of the invention comprise at least a core promoter as defined above. Frequently promoters are capable of directing transcription of genes located on each of the complementary DNA strands that are 3' to the promoter. Stated differently, many promoters exhibit bidirectionality and can direct transcription of a downstream gene when present in either orientation (i.e. 5' to 3' or 3' to 5' relative to the coding region of the gene). Additionally, the promoter may also include at least one control element such as an upstream element. Such elements include UARs and optionally, other DNA sequences that affect transcription of a polynucleotide such as a synthetic upstream element.

Promoter Control Element: The term "promoter control element" as used herein describes elements that influence the activity of the promoter. Promoter control elements include transcriptional regulatory sequence determinants such as, but not limited to, enhancers, scaffold/matrix attachment regions, TATA boxes, transcription start locus control regions, UARs, URRs, other transcription factor binding sites and inverted repeats.

Public sequence: The term "public sequence," as used in the context of the instant application, refers to any sequence that has been deposited in a publicly accessible database prior to the filing date of the present application. This term encompasses both amino acid and nucleotide sequences. Such sequences are publicly accessible, for example, on the BLAST databases on the NCBI FTP web site (accessible at ncbi.nlm.nih.gov/ftp). The database at the NCBI FTP site utilizes "gi" numbers assigned by NCBI as a unique identifier for each sequence in the databases, thereby providing a non-redundant database for sequence from various databases, including GenBank, EMBL, DBBJ, (DNA Database of Japan) and PDB (Brookhaven Protein Data Bank).

Regulatory Sequence The term "regulatory sequence," as used in the current invention, refers to any nucleotide sequence that influences transcription or translation initiation and rate, or stability and/or mobility of a transcript or polypeptide product. Regulatory sequences include, but are not limited to, promoters, promoter control elements, protein binding sequences, 5' and 3' UTRs, transcriptional start sites, termination sequences, polyadenylation sequences, introns, certain sequences within amino acid coding sequences such as secretory signals, protease cleavage sites, etc.

Related Sequences: "Related sequences" refer to either a polypeptide or a nucleotide sequence that exhibits some degree of sequence similarity with a reference sequence.

Specific Promoters: In the context of the current invention, "specific promoters" refers to a subset of promoters that have a high preference for modulating transcript levels in a specific tissue or organ or cell and/or at a specific time during development of an organism. By "high preference" is meant at least 3-fold, preferably 5-fold, more preferably at least 10-fold still more preferably at least 20-fold, 50-fold or 100-fold increase in transcript levels under the specific condition over the transcription under any other reference condition considered. Typical examples of temporal and/or tissue or organ specific promoters of plant origin that can be used with the polynucleotides of the present invention, are: PTA29, a promoter which is capable of driving gene transcription specifically in tapetum and only during another development (Koltonow et al., Plant Cell 2:1201 (1990); RCc2 and RCc3, promoters that direct root-specific gene transcription in rice (Xu et al., Plant Mol. Biol. 27:237 (1995); TobRB27, a root-specific promoter from tobacco (Yamamoto et al., Plant Cell 3:371 (1991)). Examples of tissue-specific promoters under developmental control include promoters that initiate transcription only in certain tissues or organs, such as root, ovule, fruit, seeds, or flowers. Other specific promoters include those from genes encoding seed storage proteins or the lipid body membrane protein, oleosin. A few root-specific promoters are noted above. See also "Preferential transcription".

Stringency: "Stringency" as used herein is a function of probe length, probe composition (G+C content), and salt concentration, organic solvent concentration, and temperature of hybridization or wash conditions. Stringency is typically compared by the parameter $T_m$, which is the temperature at which 50% of the complementary molecules in the hybridization are hybridized, in terms of a temperature differential from $T_m$. High stringency conditions are those providing a condition of $T_m$–5° C. to $T_m$–10° C. Medium or moderate stringency conditions are those providing $T_m$–20° C. to $T_m$–29° C. Low stringency conditions are those providing a condition of $T_m$–40° C. to $T_m$–48° C. The relationship of hybridization conditions to $T_m$ (in ° C.) is expressed in the mathematical equation $$T_m = 81.5 - 16.6(\log_{10}[Na^+]) + 0.41(\% \, G+C) - (600/N) \quad (1)$$

where N is the length of the probe. This equation works well for probes 14 to 70 nucleotides in length that are identical to the target sequence. The equation below for $T_m$ of DNA-DNA hybrids is useful for probes in the range of 50 to greater than 500 nucleotides, and for conditions that include an organic solvent (formamide).

$$T_m = 81.5 + 16.6 \log\{[Na^+]/(1+0.7[Na^+])\} + 0.41(\% \, G+C) - 500/L \, 0.63(\% \, \text{formamide}) \quad (2)$$

where L is the length of the probe in the hybrid. (P. Tijessen, "Hybridization with Nucleic Acid Probes" in *Laboratory Techniques in Biochemistry and Molecular Biology*, P. C. vand der Vliet, ed., c. 1993 by Elsevier, Amsterdam.) The $T_m$ of equation (2) is affected by the nature of the hybrid; for DNA-RNA hybrids $T_m$ is 10-15° C. higher than calculated, for RNA-RNA hybrids $T_m$ is 20-25° C. higher. Because the $T_m$ decreases about 1° C. for each 1% decrease in homology when a long probe is used (Bonner et al., J. Mol. Biol. 81:123 (1973)), stringency conditions can be adjusted to favor detection of identical genes or related family members.

Equation (2) is derived assuming equilibrium and therefore, hybridizations according to the present invention are most preferably performed under conditions of probe excess and for sufficient time to achieve equilibrium. The time required to reach equilibrium can be shortened by inclusion of a hybridization accelerator such as dextran sulfate or another high volume polymer in the hybridization buffer.

Stringency can be controlled during the hybridization reaction or after hybridization has occurred by altering the salt and temperature conditions of the wash solutions used. The formulas shown above are equally valid when used to compute the stringency of a wash solution. Preferred wash solution stringencies lie within the ranges stated above; high stringency is 5-8° C. below $T_m$, medium or moderate stringency is 26-29° C. below $T_m$ and low stringency is 45-48° C. below $T_m$.

Substantially free of: A composition containing A is "substantially free of" B when at least 85% by weight of the total A+B in the composition is A. Preferably, A comprises at least about 90% by weight of the total of A+B in the composition, more preferably at least about 95% or even 99% by weight. For example, a plant gene can be substantially free of other plant genes. Other examples include, but are not limited to, ligands substantially free of receptors (and vice versa), a growth factor substantially free of other growth factors and a transcription binding factor substantially free of nucleic acids.

Suppressor: See "Enhancer/Suppressor"

TATA to start: "TATA to start" shall mean the distance, in number of nucleotides, between the primary TATA motif and the start of transcription.

Transgenic plant: A "transgenic plant" is a plant having one or more plant cells that contain at least one exogenous polynucleotide introduced by recombinant nucleic acid methods.

Translational start site: In the context of the present invention, a "translational start site" is usually an ATG or AUG in a transcript, often the first ATG or AUG. A single protein encoding transcript, however, may have multiple translational start sites.

Transcription start site: "Transcription start site" is used in the current invention to describe the point at which transcription is initiated. This point is typically located about 25 nucleotides downstream from a TFIID binding site, such as a TATA box. Transcription can initiate at one or more sites within the gene, and a single polynucleotide to be transcribed may have multiple transcriptional start sites, some of which may be specific for transcription in a particular cell-type or tissue or organ. "+1" is stated relative to the transcription start site and indicates the first nucleotide in a transcript.

Upstream Activating Region (UAR): An "Upstream Activating Region" or "UAR" is a position or orientation dependent nucleic acid element that primarily directs tissue, organ, cell type, or environmental regulation of transcript level, usually by affecting the rate of transcription initiation. Corresponding DNA elements that have a transcription inhibitory effect are called herein "Upstream Repressor Regions" or "URR"s. The essential activity of these elements is to bind a protein factor. Such binding can be assayed by methods described below. The binding is typically in a manner that influences the steady state level of a transcript in a cell or in vitro transcription extract.

Untranslated region (UTR): A "UTR" is any contiguous series of nucleotide bases that is transcribed, but is not translated. A 5' UTR lies between the start site of the transcript and the translation initiation codon and includes the +1 nucleotide. A 3' UTR lies between the translation termination codon and the end of the transcript. UTRs can have particular functions such as increasing mRNA message stability or translation attenuation. Examples of 3' UTRs include, but are not limited to polyadenylation signals and transcription termination sequences.

Variant: The term "variant" is used herein to denote a polypeptide or protein or polynucleotide molecule that differs from others of its kind in some way. For example, polypeptide and protein variants can consist of changes in amino acid sequence and/or charge and/or post-translational modifications (such as glycosylation, etc). Likewise, polynucleotide variants can consist of changes that add or delete a specific UTR or exon sequence. It will be understood that there may be sequence variations within sequence or fragments used or disclosed in this application. Preferably, variants will be such that the sequences have at least 80%, preferably at least 90%, 95, 97, 98, or 99% sequence identity. Variants preferably measure the primary biological function of the native polypeptide or protein or polynucleotide.

2. Introduction

The polynucleotides of the invention comprise promoters and promoter control elements that are capable of modulating transcription.

Such promoters and promoter control elements can be used in combination with native or heterologous promoter fragments, control elements or other regulatory sequences to modulate transcription and/or translation.

Specifically, promoters and control elements of the invention can be used to modulate transcription of a desired polynucleotide, which includes without limitation:
(a) antisense;
(b) ribozymes;
(c) coding sequences; or
(d) fragments thereof.
The promoter also can modulate transcription in a host genome in cis- or in trans-.

In an organism, such as a plant, the promoters and promoter control elements of the instant invention are useful to produce preferential transcription which results in a desired pattern of transcript levels in a particular cells, tissues, or organs, or under particular conditions.

3. Table of Contents

The following description of the present invention is outlined in the following table of contents.
A. Identifying and Isolating Promoter Sequences of the Invention
  (1) Cloning Methods
  (2) Chemical Synthesis
B. Generating a "core" promoter sequence
C. Isolating Related Promoter Sequences
  (1) Relatives Based on Nucleotide Sequence Identity
  (2) Relatives Based on Coding Sequence Identity
  (3) Relatives based on Common Function
D. Identifying Control Elements
  (1) Types of Transcription Control Elements
  (2) Those Described by the Examples
  (3) Those Identifiable by Bioinformatics
  (4) Those Identifiable by In Vitro and In Vivo Assays
  (5) Non-Natural Control Elements
E. Constructing Promoters and Control Elements
  (1) Combining Promoters and Promoter Control Elements
  (2) Number of Promoter Control Elements
  (3) Spacing Between Control Elements
F. Vectors
  (1) Modification of Transcription by Promoters and Promoter Control Elements
  (2) Polynucleotide to be Transcribed
  (3) Other Regulatory Elements
  (4) Other Components of Vectors
G. Insertion of Polynucleotides and Vectors into a Host Cell
  (1) Autonomous of the Host Genome
  (2) Integrated into the Host Genome
H. Utility A. Identifying and Isolating Promoter Sequences of the Invention The promoters and promoter control elements of the present invention are presented in Table 1 in the section entitled "The predicted promoter" sequence and were identified from *Arabidopsis thaliana* or *Oryza sativa*. Additional promoter sequences encompassed by the invention can be identified as described below.

(1) Cloning Methods

Isolation from genomic libraries of polynucleotides comprising the sequences of the promoters and promoter control elements of the present invention is possible using known techniques.

For example, polymerase chain reaction (PCR) can amplify the desired polynucleotides utilizing primers designed from sequences in the row titled "The spatial expression of the promoter-marker-vector". Polynucleotide libraries comprising genomic sequences can be constructed according to Sambrook et al., *Molecular Cloning: A Laboratory Manual*, $2^{nd}$ Ed. (1989) Cold Spring Harbor Press, Cold Spring Harbor, N.Y.), for example.

Other procedures for isolating polynucleotides comprising the promoter sequences of the invention include, without limitation, tail-PCR, and 5' rapid amplification of cDNA ends (RACE). See, for tail-PCR, for example, Liu et al., *Plant J* 8(3): 457-463 (September, 1995); Liu et al., *Genomics* 25: 674-681 (1995); Liu et al., *Nucl. Acids Res.* 21(14): 3333-3334 (1993); and Zoe et al., *BioTechniques* 27(2): 240-248

(1999); for RACE, see, for example, *PCR Protocols: A Guide to Methods and Applications*, (1990) Academic Press, Inc.

(2) Chemical Synthesis

In addition, the promoters and promoter control elements described in Table 1 in the section entitled "The predicted promoter" sequence can be chemically synthesized according to techniques in common use. See, for example, Beaucage et al., *Tet. Lett.* (1981) 22: 1859 and U.S. Pat. No. 4,668,777.

Such chemical oligonucleotide synthesis can be carried out using commercially available devices, such as, Biosearch 4600 or 8600 DNA synthesizer, by Applied Biosystems, a division of Perkin-Elmer Corp., Foster City, Calif., USA; and Expedite by Perceptive Biosystems, Framingham, Mass., USA.

Synthetic RNA, including natural and/or analog building blocks, can be synthesized on the Biosearch 8600 machines, see above.

Oligonucleotides can be synthesized and then ligated together to construct the desired polynucleotide.

B. Generating Reduced and "Core" Promoter Sequences

Included in the present invention are reduced and "core" promoter sequences. The reduced promoters can be isolated from the promoters of the invention by deleting at least one 5' UTR, exon or 3' UTR sequence present in the promoter sequence that is associated with a gene or coding region located 5' to the promoter sequence or in the promoter's endogenous coding region.

Similarly, the "core" promoter sequences can be generated by deleting all 5' UTRs, exons and 3' UTRs present in the promoter sequence and the associated intervening sequences that are related to the gene or coding region 5' to the promoter region and the promoter's endogenous coding region.

This data is presented in the row titled "Optional Promoter Fragments".

C. Isolating Related Promoter Sequences

Included in the present invention are promoter and promoter control elements that are related to those described in Table 1 in the section entitled "The predicted promoter sequence". Such related sequence can be isolated utilizing
(a) nucleotide sequence identity;
(b) coding sequence identity; or
(c) common function or gene products.

Relatives can include both naturally occurring promoters and non-natural related promoter sequences. Non-natural related promoters include nucleotide substitutions, insertions or deletions of naturally-occurring promoter sequences that do not substantially affect transcription modulation activity. For example, the binding of relevant DNA binding proteins can still occur with the non-natural promoter sequences and promoter control elements of the present invention.

According to current knowledge, promoter sequences and promoter control elements exist as functionally important regions, such as protein binding sites, and spacer regions. These spacer regions are apparently required for proper positioning of the protein binding sites. Thus, nucleotide substitutions, insertions and deletions can be tolerated in these spacer regions to a certain degree without loss of function.

In contrast, less variation is permissible in the functionally important regions, since changes in the sequence can interfere with protein binding. Nonetheless, some variation in the functionally important regions is permissible so long as function is conserved.

The effects of substitutions, insertions and deletions to the promoter sequences or promoter control elements may be to increase or decrease the binding of relevant DNA binding proteins to modulate transcript levels of a polynucleotide to be transcribed. Effects may include tissue-specific or condition-specific modulation of transcript levels of the polypeptide to be transcribed. Polynucleotides representing changes to the nucleotide sequence of the DNA-protein contact region by insertion of additional nucleotides, changes to identity of relevant nucleotides, including use of chemically-modified bases, or deletion of one or more nucleotides are considered encompassed by the present invention.

(1) Relatives Based on Nucleotide Sequence Identity

Included in the present invention are promoters exhibiting nucleotide sequence identity to those described in Table 1 in the section entitled "The predicted promoter sequence".

Definition

Typically, such related promoters exhibit at least 80% sequence identity, preferably at least 85%, more preferably at least 90%, and most preferably at least 95%, even more preferably, at least 96%, 97%, 98% or 99% sequence identity compared to those shown in Table 1 in the section entitled "The predicted promoter" sequence. Such sequence identity can be calculated by the algorithms and computers programs described above.

Usually, such sequence identity is exhibited in an alignment region that is at least 75% of the length of a sequence shown in Table 1 in the section entitled "The predicted promoter" sequence or corresponding full-length sequence; more usually at least 80%; more usually, at least 85%, more usually at least 90%, and most usually at least 95%, even more usually, at least 96%, 97%, 98% or 99% of the length of a sequence shown in Table 1 in the section entitled "The predicted promoter sequence".

The percentage of the alignment length is calculated by counting the number of residues of the sequence in region of strongest alignment, e.g., a continuous region of the sequence that contains the greatest number of residues that are identical to the residues between two sequences that are being aligned. The number of residues in the region of strongest alignment is divided by the total residue length of a sequence in Table 1 in the section entitled "The predicted promoter sequence".

These related promoters may exhibit similar preferential transcription as those promoters described in Table 1 in the section entitled "The predicted promoter sequence".

Construction of Polynucleotides

Naturally occurring promoters that exhibit nucleotide sequence identity to those shown in Table 1 in the section entitled "The predicted promoter sequence" can be isolated using the techniques as described above. More specifically, such related promoters can be identified by varying stringencies, as defined above, in typical hybridization procedures such as Southern blots or probing of polynucleotide libraries, for example.

Non-natural promoter variants of those shown in Table 1 can be constructed using cloning methods that incorporate the desired nucleotide variation. See, for example, Ho, S. N., et al. Gene 77:51-59 1989, describing a procedure site directed mutagenesis using PCR.

Any related promoter showing sequence identity to those shown in Table can be chemically synthesized as described above.

Also, the present invention includes non-natural promoters that exhibit the above-sequence identity to those in Table 1.

The promoters and promoter control elements of the present invention may also be synthesized with 5' or 3' extensions, to facilitate additional manipulation, for instance.

The present invention also includes reduced promoter sequences. These sequences have at least one of the optional promoter fragments deleted.

Core promoter sequences are another embodiment of the present invention. The core promoter sequences have all of the optional promoter fragments deleted.

Testing of Polynucleotides

Polynucleotides of the invention were tested for activity by cloning the sequence into an appropriate vector, transforming plants with the construct and assaying for marker gene expression. Recombinant DNA constructs were prepared which comprise the polynucleotide sequences of the invention inserted into a vector suitable for transformation of plant cells. The construct can be made using standard recombinant DNA techniques (Sambrook et al. 1989) and can be introduced to the species of interest by *Agrobacterium*-mediated transformation or by other means of transformation as referenced below.

The vector backbone can be any of those typical in the art such as plasmids, viruses, artificial chromosomes, BACs, YACs and PACs and vectors of the sort described by (a) BAC: Shizuya et al., Proc. Natl. Acad. Sci. USA 89: 8794-8797 (1992); Hamilton et al., Proc. Natl. Acad. Sci. USA 93: 9975-9979 (1996);

(b) YAC: Burke et al., Science 236:806-812 (1987);

(c) PAC: Sternberg N. et al., Proc Natl Acad Sci USA. January; 87(1):103-7 (1990);

(d) Bacteria-Yeast Shuttle Vectors: Bradshaw et al., Nucl Acids Res 23: 4850-4856 (1995);

(e) Lambda Phage Vectors: Replacement Vector, e.g., Frischauf et al., J. Mol Biol 170: 827-842 (1983); or Insertion vector, e.g., Huynh et al., In: Glover N M (ed) DNA Cloning: A practical Approach, Vol. 1 Oxford: IRL Press (1985); T-DNA gene fusion vectors: Walden et al., Mol Cell Biol 1: 175-194 (1990); and (g) Plasmid vectors: Sambrook et al., infra.

Typically, the construct comprises a vector containing a sequence of the present invention operationally linked to any marker gene. The polynucleotide was identified as a promoter by the expression of the marker gene. Although many marker genes can be used, Green Fluorescent Protein (GFP) is preferred. The vector may also comprise a marker gene that confers a selectable phenotype on plant cells. The marker may encode biocide resistance, particularly antibiotic resistance, such as resistance to kanamycin, G418, bleomycin, hygromycin, or herbicide resistance, such as resistance to chlorosulfuron or phosphinotricin. Vectors can also include origins of replication, scaffold attachment regions (SARs), markers, homologous sequences, introns, etc.

Promoter Control Elements of the Invention

The promoter control elements of the present invention include those that comprise a sequence shown in Table 1 in the section entitled "The predicted promoter sequence" and fragments thereof. The size of the fragments of the row titled "The predicted promoter sequence" can range from 5 bases to 10 kilobases (kb). Typically, the fragment size is no smaller than 8 bases; more typically, no smaller than 12; more typically, no smaller than 15 bases; more typically, no smaller than 20 bases; more typically, no smaller than 25 bases; even more typically, no more than 30, 35, 40 or 50 bases.

Usually, the fragment size in no larger than 5 kb bases; more usually, no larger than 2 kb; more usually, no larger than 1 kb; more usually, no larger than 800 bases; more usually, no larger than 500 bases; even more usually, no more than 250, 200, 150 or 100 bases.

Relatives Based on Nucleotide Sequence Identity

Included in the present invention are promoter control elements exhibiting nucleotide sequence identity to those described in Table 1 in the section entitled "The predicted promoter sequence" of fragments thereof.

Typically, such related promoters exhibit at least 80% sequence identity, preferably at least 85%, more preferably at least 90%, and most preferably at least 95%, even more preferably, at least 96%, 97%, 98% or 99% sequence identity compared to those shown in Table 1 in the section entitled "The predicted promoter sequence". Such sequence identity can be calculated by the algorithms and computers programs described above.

Promoter Control Element Configuration

A common configuration of the promoter control elements in RNA polymerase II promoters is shown below:

For more description, see, for example, "Models for prediction and recognition of eukaryotic promoters", T. Werner, Mammalian Genome, 10, 168-175 (1999).

Promoters are generally modular in nature. Promoters can consist of a basal promoter which functions as a site for assembly of a transcription complex comprising an RNA polymerase, for example RNA polymerase II. A typical transcription complex will include additional factors such as $TF_{II}B$, $TF_{II}D$, and $TF_{II}E$. Of these, $TF_{II}D$ appears to be the only one to bind DNA directly. The promoter might also contain one or more promoter control elements such as the elements discussed above. These additional control elements may function as binding sites for additional transcription factors that have the function of modulating the level of transcription with respect to tissue specificity and of transcriptional responses to particular environmental or nutritional factors, and the like.

One type of promoter control element is a polynucleotide sequence representing a binding site for proteins. Typically, within a particular functional module, protein binding sites constitute regions of 5 to 60, preferably 10 to 30, more preferably 10 to 20 nucleotides. Within such binding sites, there are typically 2 to 6 nucleotides which specifically contact amino acids of the nucleic acid binding protein.

The protein binding sites are usually separated from each other by 10 to several hundred nucleotides, typically by 15 to 150 nucleotides, often by 20 to 50 nucleotides.

Further, protein binding sites in promoter control elements often display dyad symmetry in their sequence. Such elements can bind several different proteins, and/or a plurality of sites can bind the same protein. Both types of elements may be combined in a region of 50 to 1,000 base pairs.

Binding sites for any specific factor have been known to occur almost anywhere in a promoter. For example, functional AP-1 binding sites can be located far upstream, as in the rat bone sialoprotein gene, where an AP-1 site located about 900 nucleotides upstream of the transcription start site suppresses expression. Yamauchi et al., Matrix Biol., 15, 119-130 (1996). Alternatively, an AP-1 site located close to the transcription start site plays an important role in the expression of Moloney murine leukemia virus. Sap et al., Nature, 340, 242-244, (1989).

(2) Those Identifiable by Bioinformatics

Promoter control elements from the promoters of the instant invention can be identified utilizing bioinformatic or computer driven techniques.

One method uses a computer program AlignACE to identify regulatory motifs in genes that exhibit common preferential transcription across a number of time points. The program identifies common sequence motifs in such genes. See, Roth et al., Nature Biotechnol. 16: 949-945 (1998); Tavazoie et al., Nat Genet. 1999 July; 22(3):281-5;

Genomatix, also makes available a GEMS Launcher program and other programs to identify promoter control elements and configuration of such elements. Genomatix is located in Munich, Germany.

Other references also describe detection of promoter modules by models independent of overall nucleotide sequence similarity. See, for instance, Klingenhoff et al., Bioinformatics 15, 180-186 (1999).

Protein binding sites of promoters can be identified as reported in "Computer-assisted prediction, classification, and delimination of protein binding sites in nucleic acids", Frech, et al., Nucleic Acids Research, Vol. 21, No. 7, 1655-1664, 1993.

Other programs used to identify protein binding sites include, for example, Signal Scan, Prestridge et al., Comput. Appl, Biosci. 12: 157-160 (1996); Matrix Search, Chen et al., Comput. Appl. Biosci. 11: 563-566 (1995), available as part of Signal Scan 4.0; MatInspector, Ghosh et al., Nucl, Acid Res, 21: 3117-3118 (1993) available on the internet; ConsInspector, Frech et al., Nucl, Acids Res, 21: 1655-1664 (1993), available at ftp://ariane.gsf.de/pub/dos; TFSearch; and TESS.

Frech et al., "Software for the analysis of DNA sequence elements of transcription", Bioinformatics & Sequence Analysis, Vol. 13, no. 1, 89-97 (1997) is a review of different software for analysis of promoter control elements. This paper also reports the usefulness of matrix-based approaches to yield more specific results.

For other procedures, see, Fickett et al., Curr. Op. Biotechnol. 11: 19-24 (2000); and Quandt et al., Nucleic Acids Res., 23, 4878-4884 (1995).

(3) Those Identifiable by In-Vitro and In-Vivo Assays

Promoter control elements also can be identified with in-vitro assays, such as transcription detection methods; and with in-vivo assays, such as enhancer trapping protocols.

In-Vitro Assays

Examples of in-vitro assays include detection of binding of protein factors that bind promoter control elements. Fragments of the instant promoters can be used to identify the location of promoter control elements. Another option for obtaining a promoter control element with desired properties is to modify known promoter sequences. This is based on the fact that the function of a promoter is dependent on the interplay of regulatory proteins that bind to specific, discrete nucleotide sequences in the promoter, termed motifs. Such interplay subsequently affects the general transcription machinery and regulates transcription efficiency. These proteins are positive regulators or negative regulators (repressors), and one protein can have a dual role depending on the context (Johnson, P. F. and McKnight, S. L. Annu. Rev. Biochem. 58:799-839 (1989)).

One type of in-vitro assay utilizes a known DNA binding factor to isolate DNA fragments that bind. If a fragment or promoter variant does not bind, then a promoter control element has been removed or disrupted. For specific assays, see, for instance, B. Luo et al., J. Mol. Biol. 266:470 (1997), S. Chusacultanachai et al., J. Biol. Chem. 274:23591 (1999), D. Fabbro et al., Biochem. Biophys. Res. Comm. 213:781 (1995)).

Alternatively, a fragment of DNA suspected of conferring a particular pattern of specificity can be examined for activity in binding transcription factors involved in that specificity by methods such as DNA footprinting (e.g. D. J. Cousins et al., Immunology 99:101 (2000); V. Kolla et al., Biochem. Biophys. Res. Comm. 266:5 (1999)) or "mobility-shift" assays (E. D. Fabiani et al., J. Biochem. 347:147 (2000); N. Sugiura et al., J. Biochem 347:155 (2000)) or fluorescence polarization (e.g. Royer et al., U.S. Pat. No. 5,445,935). Both mobility shift and DNA footprinting assays can also be used to identify portions of large DNA fragments that are bound by proteins in unpurified transcription extracts prepared from tissues or organs of interest.

Cell-free transcription extracts can be prepared and used to directly assay in a reconstitutable system (Narayan et al., Biochemistry 39:818 (2000)).

In-Vivo Assays

Promoter control elements can be identified with reporter genes in in-vivo assays with the use of fragments of the instant promoters or variants of the instant promoter polynucleotides.

For example, various fragments can be inserted into a vector, comprising a basal or "core" promoter, for example, operably linked to a reporter sequence, which, when transcribed, can produce a detectable label. Examples of reporter genes include those encoding luciferase, green fluorescent protein, GUS, neo, cat and bar. Alternatively, reporter sequence can be detected utilizing AFLP and microarray techniques.

In promoter probe vector systems, genomic DNA fragments are inserted upstream of the coding sequence of a reporter gene that is expressed only when the cloned fragment contains DNA having transcription modulation activity (Neve, R. L. et al., Nature 277:324-325 (1979)). Control elements are disrupted when fragments or variants lacking any transcription modulation activity. Probe vectors have been designed for assaying transcription modulation in E. coli (An, G. et al., J. Bact. 140:400-407 (1979)) and other bacterial hosts (Band, L. et al., Gene 26:313-315 (1983); Achen, M. G., Gene 45:45-49 (1986)), yeast (Goodey, A. R. et al., Mol. Gen. Genet. 204:505-511 (1986)) and mammalian cells (Pater, M. M. et al., J. Mol. App. Gen. 2:363-371 (1984)).

A different design of a promoter/control element trap includes packaging into retroviruses for more efficient delivery into cells. One type of retroviral enhancer trap was described by von Melchner et al. (Genes Dev. 1992; U.S. Pat. No. 5,364,783). The basic design of this vector includes a reporter protein coding sequence engineered into the U3 portion of the 3' LTR. No splice acceptor consensus sequences are included, limiting its utility to work as an enhancer trap only. A different approach to a gene trap using retroviral vectors was pursued by Friedrich and Soriano (Genes Dev. 1991), who engineered a lacZ-neo fusion protein linked to a splicing acceptor. LacZ-neo fusion protein expression from trapped loci allows not only for drug selection, but also for visualization of β-galatactosidase expression using the chromogenic substrate, X-gal.

A general review of tools for identifying transcriptional regulatory regions of genomic DNA is provided by J. W. Fickett et al. (Curr. Opn. Biotechnol. 11:19 (2000).

(4) Non-Natural Control Elements

Non-natural control elements can be constructed by inserting, deleting or substituting nucleotides into the promoter control elements described above. Such control elements are capable of transcription modulation that can be determined using any of the assays described above.

D. Constructing Promoters with Control Elements (1) Combining Promoters and Promoter Control Elements The promoter polynucleotides and promoter control elements of the present invention, both naturally occurring and synthetic, can be combined with each other to produce the desired preferential transcription. Also, the polynucleotides of the invention can be combined with other known sequences to obtain other useful promoters to modulate, for example, tissue transcription specific or transcription specific to certain conditions. Such preferential transcription can be determined using the techniques or assays described above.

Fragments, variants, as well as full-length sequences those shown in Table 1 in the section entitled "The predicted promoter sequence" and relatives are useful alone or in combination.

The location and relation of promoter control elements within a promoter can affect the ability of the promoter to modulate transcription. The order and spacing of control elements is a factor when constructing promoters.

(2) Number of Promoter Control Elements

Promoters can contain any number of control elements. For example, a promoter can contain multiple transcription binding sites or other control elements. One element may confer tissue or organ specificity; another element may limit transcription to specific time periods, etc. Typically, promoters will contain at least a basal or core promoter as described above. Any additional element can be included as desired. For example, a fragment comprising a basal or "core" promoter can be fused with another fragment with any number of additional control elements.

(3) Spacing Between Control Elements

Spacing between control elements or the configuration or control elements can be determined or optimized to permit the desired protein-polynucleotide or polynucleotide interactions to occur.

For example, if two transcription factors bind to a promoter simultaneously or relatively close in time, the binding sites are spaced to allow each factor to bind without steric hinderance. The spacing between two such hybridizing control elements can be as small as a profile of a protein bound to a control element. In some cases, two protein binding sites can be adjacent to each other when the proteins bind at different times during the transcription process.

Further, when two control elements hybridize the spacing between such elements will be sufficient to allow the promoter polynucleotide to hairpin or loop to permit the two elements to bind. The spacing between two such hybridizing control elements can be as small as a t-RNA loop, to as large as 10 kb.

Typically, the spacing is no smaller than 5 bases; more typically, no smaller than 8; more typically, no smaller than 15 bases; more typically, no smaller than 20 bases; more typically, no smaller than 25 bases; even more typically, no more than 30, 35, 40 or 50 bases.

Usually, the fragment size in no larger than 5 kb bases; more usually, no larger than 2 kb; more usually, no larger than 1 kb; more usually, no larger than 800 bases; more usually, no larger than 500 bases; even more usually, no more than 250, 200, 150 or 100 bases.

Such spacing between promoter control elements can be determined using the techniques and assays described above.

(4) Other Promoters

The following are promoters that are induced under stress conditions and can be combined with those of the present invention: ldh1 (oxygen stress; tomato; see Germain and Ricard. 1997. Plant Mol Biol 35:949-54), GPx and CAT (oxygen stress; mouse; see Franco et al. 1999. Free Radic Biol Med 27:1122-32), ci7 (cold stress; potato; see Kirch et al. 1997. Plant Mol. Biol. 33:897-909), Bz2 (heavy metals; maize; see Marrs and Walbot. 1997. Plant Physiol 113:93-102), HSP32 (hyperthermia; rat; see Raju and Maines. 1994. Biochim Biophys Acta 1217:273-80); MAPKAPK-2 (heat shock; Drosophila; see Larochelle and Suter. 1995. Gene 163:209-14).

In addition, the following examples of promoters are induced by the presence or absence of light can be used in combination with those of the present invention: Topoisomerase II (pea; see Reddy et al. 1999. Plant Mol Biol 41:125-37), chalcone synthase (soybean; see Wingender et al. 1989. Mol Gen Genet 218:315-22) mdm2 gene (human tumor; see Saucedo et al. 1998. Cell Growth Differ 9:119-30), Clock and BMAL1 (rat; see Namihira et al. 1999. Neurosci Lett 271:1-4, PHYA (Arabidopsis; see Canton and Quail 1999. Plant Physiol 121:1207-16), PRB-1b (tobacco; see Sessa et al. 1995. Plant Mol Biol 28:537-47) and Ypr10 (common bean; see Walter et al. 1996. Eur J Biochem 239: 281-93).

The promoters and control elements of the following genes can be used in combination with the present invention to confer tissue specificity: MipB (iceplant; Yamada et al. 1995. Plant Cell 7:1129-42) and SUCS (root nodules; broadbean; Kuster et al. 1993. Mol Plant Microbe Interact 6:507-14) for roots, OsSUT1 (rice; Hirose et al. 1997. Plant Cell Physiol 38:1389-96) for leaves, Msg (soybean; Stomvik et al. 1999. Plant Mol Biol 41:217-31) for siliques, cell (Arabidopsis; Shani et al. 1997. Plant Mol Biol 34(6):837-42) and ACT11 (Arabidopsis; Huang et al. 1997. Plant Mol Biol 33:125-39) for inflorescence.

Still other promoters are affected by hormones or participate in specific physiological processes, which can be used in combination with those of present invention. Some examples are the ACC synthase gene that is induced differently by ethylene and brassinosteroids (mung bean; Yi et al. 1999. Plant Mol Biol 41:443-54), the TAPG1 gene that is active during abscission (tomato; Kalaitzis et al. 1995. Plant Mol Biol 28:647-56), and the 1-aminocyclopropane-1-carboxylate synthase gene (carnation; Jones et al. 19951 Plant Mol Biol 28:505-12) and the CP-2/cathepsin L gene (rat; Kim and Wright. 1997. Biol Reprod 57:1467-77), both active during senescence.

E. Vectors

Vectors are a useful component of the present invention. In particular, the present promoters and/or promoter control elements may be delivered to a system such as a cell by way of a vector. For the purposes of this invention, such delivery may range from simply introducing the promoter or promoter control element by itself randomly into a cell to integration of a cloning vector containing the present promoter or promoter control element. Thus, a vector need not be limited to a DNA molecule such as a plasmid, cosmid or bacterial phage that has the capability of replicating autonomously in a host cell. All other manner of delivery of the promoters and promoter control elements of the invention are envisioned. The various T-DNA vector types are a preferred vector for use with the present invention. Many useful vectors are commercially available.

It may also be useful to attach a marker sequence to the present promoter and promoter control element in order to determine activity of such sequences. Marker sequences typically include genes that provide antibiotic resistance, such as tetracycline resistance, hygromycin resistance or ampicillin resistance, or provide herbicide resistance. Specific selectable marker genes may be used to confer resistance to herbicides such as glyphosate, glufosinate or broxynil (Comai et al., Nature 317: 741-744 (1985); Gordon-Kamm et al., Plant Cell 2: 603-618 (1990); and Stalker et al., Science 242: 419-423 (1988)). Other marker genes exist which provide hormone responsiveness.

(1) Modification of Transcription by Promoters and Promoter Control Elements

The promoter or promoter control element of the present invention may be operably linked to a polynucleotide to be transcribed. In this manner, the promoter or promoter control element may modify transcription by modulate transcript levels of that polynucleotide when inserted into a genome.

However, prior to insertion into a genome, the promoter or promoter control element need not be linked, operably or otherwise, to a polynucleotide to be transcribed. For example, the promoter or promoter control element may be inserted alone into the genome in front of a polynucleotide already present in the genome. In this manner, the promoter or promoter control element may modulate the transcription of a polynucleotide that was already present in the genome. This polynucleotide may be native to the genome or inserted at an earlier time.

Alternatively, the promoter or promoter control element may be inserted into a genome alone to modulate transcription. See, for example, Vaucheret, H et al. (1998) *Plant J* 16: 651-659. Rather, the promoter or promoter control element may be simply inserted into a genome or maintained extrachromosomally as a way to divert transcription resources of the system to itself. This approach may be used to downregulate the transcript levels of a group of polynucleotide(s).

(2) Polynucleotide to be Transcribed

The nature of the polynucleotide to be transcribed is not limited. Specifically, the polynucleotide may include sequences that will have activity as RNA as well as sequences that result in a polypeptide product. These sequences may include, but are not limited to antisense sequences, ribozyme sequences, spliceosomes, amino acid coding sequences, and fragments thereof.

Specific coding sequences may include, but are not limited to endogenous proteins or fragments thereof, or heterologous proteins including marker genes or fragments thereof.

Promoters and control elements of the present invention are useful for modulating metabolic or catabolic processes. Such processes include, but are not limited to, secondary product metabolism, amino acid synthesis, seed protein storage, oil development, pest defense and nitrogen usage. Some examples of genes, transcripts and peptides or polypeptides participating in these processes, which can be modulated by the present invention: are tryptophan decarboxylase (tdc) and strictosidine synthase (str1), dihydrodipicolinate synthase (DHDPS) and aspartate kinase (AK), 2S albumin and alpha-, beta-, and gamma-zeins, ricinoleate and 3-ketoacyl-ACP synthase (KAS), *Bacillus thuringiensis* (Bt) insecticidal protein, cowpea trypsin inhibitor (CpTI), asparagine synthetase and nitrite reductase. Alternatively, expression constructs can be used to inhibit expression of these peptides and polypeptides by incorporating the promoters in constructs for antisense use, co-suppression use or for the production of dominant negative mutations.

(3) Other Regulatory Elements

As explained above, several types of regulatory elements exist concerning transcription regulation. Each of these regulatory elements may be combined with the present vector if desired.

(4) Other Components of Vectors

Translation of eukaryotic mRNA is often initiated at the codon that encodes the first methionine. Thus, when constructing a recombinant polynucleotide according to the present invention for expressing a protein product, it is preferable to ensure that the linkage between the 3' portion, preferably including the TATA box, of the promoter and the polynucleotide to be transcribed, or a functional derivative thereof, does not contain any intervening codons which are capable of encoding a methionine.

The vector of the present invention may contain additional components. For example, an origin of replication allows for replication of the vector in a host cell. Additionally, homologous sequences flanking a specific sequence allows for specific recombination of the specific sequence at a desired location in the target genome. T-DNA sequences also allow for insertion of a specific sequence randomly into a target genome.

The vector may also be provided with a plurality of restriction sites for insertion of a polynucleotide to be transcribed as well as the promoter and/or promoter control elements of the present invention. The vector may additionally contain selectable marker genes. The vector may also contain a transcriptional and translational initiation region, and a transcriptional and translational termination region functional in the host cell. The termination region may be native with the transcriptional initiation region, may be native with the polynucleotide to be transcribed, or may be derived from another source. Convenient termination regions are available from the Ti-plasmid of *A. tumefaciens*, such as the octopine synthase and nopaline synthase termination regions. See also, Guerineau et al., (1991) Mol. Gen. Genet. 262:141-144; Proudfoot (1991) Cell 64:671-674; Sanfacon et al. (1991) Genes Dev. 5:141-149; Mogen et al. (1990) Plant Cell 2:1261-1272; Munroe et al. (1990) Gene 91:151-158; Ballas et al. 1989) Nucleic Acids Res. 17:7891-7903; Joshi et al. (1987) Nucleic Acid Res. 15:9627-9639.

Where appropriate, the polynucleotide to be transcribed may be optimized for increased expression in a certain host cell. For example, the polynucleotide can be synthesized using preferred codons for improved transcription and translation. See U.S. Pat. Nos. 5,380,831, 5,436,391; see also and Murray et al., (1989) Nucleic Acids Res. 17:477-498.

Additional sequence modifications include elimination of sequences encoding spurious polyadenylation signals, exon intron splice site signals, transposon-like repeats, and other such sequences well characterized as deleterious to expression. The G-C content of the polynucleotide may be adjusted to levels average for a given cellular host, as calculated by reference to known genes expressed in the host cell. The polynucleotide sequence may be modified to avoid hairpin secondary mRNA structures.

A general description of expression vectors and reporter genes can be found in Gruber, et al., "Vectors for Plant Transformation, in Methods in Plant Molecular Biology & Biotechnology" in Glich et al., (Eds. pp. 89-119, CRC Press, 1993). Moreover GUS expression vectors and GUS gene cassettes are available from Clonetech Laboratories, Inc., Palo Alto, Calif. while luciferase expression vectors and luciferase gene cassettes are available from Promega Corp. (Madison, Wis.). GFP vectors are available from Aurora Biosciences.

F. Polynucleotide Insertion into a Host Cell

The polynucleotides according to the present invention can be inserted into a host cell. A host cell includes but is not limited to a plant, mammalian, insect, yeast, and prokaryotic cell, preferably a plant cell.

The method of insertion into the host cell genome is chosen based on convenience. For example, the insertion into the host cell genome may either be accomplished by vectors that integrate into the host cell genome or by vectors which exist independent of the host cell genome.

(1) Polynucleotides Autonomous of the Host Genome

The polynucleotides of the present invention can exist autonomously or independent of the host cell genome. Vectors of these types are known in the art and include, for example, certain type of non-integrating viral vectors, autonomously replicating plasmids, artificial chromosomes, and the like.

Additionally, in some cases transient expression of a polynucleotide may be desired.

(2) Polynucleotides Integrated into the Host Genome

The promoter sequences, promoter control elements or vectors of the present invention may be transformed into host cells. These transformations may be into protoplasts or intact tissues or isolated cells. Preferably expression vectors are introduced into intact tissue. General methods of culturing plant tissues are provided for example by Maki et al. "Procedures for Introducing Foreign DNA into Plants" in Methods in Plant Molecular Biology & Biotechnology, Glich et al. (Eds. pp. 67-88 CRC Press, 1993); and by Phillips et al. "Cell-Tissue Culture and In-Vitro Manipulation" in Corn & Corn Improvement, 3rd Edition 10Sprague et al. (Eds. pp. 345-387) American Society of Agronomy Inc. et al. 1988.

Methods of introducing polynucleotides into plant tissue include the direct infection or co-cultivation of plant cell with *Agrobacterium tumefaciens*, Horsch et al., Science, 227:1229 (1985). Descriptions of *Agrobacterium* vector systems and methods for *Agrobacterium*-mediated gene transfer provided by Gruber et al. supra.

Alternatively, polynucleotides are introduced into plant cells or other plant tissues using a direct gene transfer method such as microprojectile-mediated delivery, DNA injection, electroporation and the like. More preferably polynucleotides are introduced into plant tissues using the microprojectile media delivery with the biolistic device. See, for example, Tomes et al., "Direct DNA transfer into intact plant cells via microprojectile bombardment" In: Gamborg and Phillips (Eds.) Plant Cell, Tissue and Organ Culture: Fundamental Methods, Springer Verlag, Berlin (1995).

In another embodiment of the current invention, expression constructs can be used for gene expression in callus culture for the purpose of expressing marker genes encoding peptides or polypeptides that allow identification of transformed plants. Here, a promoter that is operatively linked to a polynucleotide to be transcribed is transformed into plant cells and the transformed tissue is then placed on callus-inducing media. If the transformation is conducted with leaf discs, for example, callus will initiate along the cut edges. Once callus growth has initiated, callus cells can be transferred to callus shoot-inducing or callus root-inducing media. Gene expression will occur in the callus cells developing on the appropriate media: callus root-inducing promoters will be activated on callus root-inducing media, etc. Examples of such peptides or polypeptides useful as transformation markers include, but are not limited to barstar, glyphosate, chloramphenicol acetyltransferase (CAT), kanamycin, spectinomycin, streptomycin or other antibiotic resistance enzymes, green fluorescent protein (GFP), and β-glucuronidase (GUS), etc. Some of the exemplary promoters of the row titled "The predicted promoter sequence" will also be capable of sustaining expression in some tissues or organs after the initiation or completion of regeneration. Examples of these tissues or organs are somatic embryos, cotyledon, hypocotyl, epicotyl, leaf, stems, roots, flowers and seed.

Integration into the host cell genome also can be accomplished by methods known in the art, for example, by the homologous sequences or T-DNA discussed above or using the cre-lox system (A. C. Vergunst et al., *Plant Mol. Biol.* 38:393 (1998)).

G. Utility

Common Uses

In yet another embodiment, the promoters of the present invention can be used to further understand developmental mechanisms. For example, promoters that are specifically induced during callus formation, somatic embryo formation, shoot formation or root formation can be used to explore the effects of overexpression, repression or ectopic expression of target genes, or for isolation of trans-acting factors.

The vectors of the invention can be used not only for expression of coding regions but may also be used in exon-trap cloning, or promoter trap procedures to detect differential gene expression in various tissues, K. Lindsey et al., 1993 "Tagging Genomic Sequences That Direct Transgene Expression by Activation of a Promoter Trap in Plants", Transgenic Research 2:3347. D. Auch & Reth, et al., "Exon Trap Cloning: Using PCR to Rapidly Detect and Clone Exons from Genomic DNA Fragments", Nucleic Acids Research, Vol. 18, No. 22, p. 674.

Entrapment vectors, first described for use in bacteria (Casadaban and Cohen, 1979, Proc. Nat. Aca. Sci. U.S.A., 76: 4530; Casadaban et al., 1980, J. Bacteriol., 143: 971) permit selection of insertional events that lie within coding sequences. Entrapment vectors can be introduced into pluripotent ES cells in culture and then passed into the germline via chimeras (Gossler et al., 1989, Science, 244: 463; Skarnes, 1990, Biotechnology, 8: 827). Promoter or gene trap vectors often contain a reporter gene, e.g., lacZ, lacking its own promoter and/or splice acceptor sequence upstream. That is, promoter gene traps contain a reporter gene with a splice site but no promoter. If the vector lands in a gene and is spliced into the gene product, then the reporter gene is expressed.

Recently, the isolation of preferentially-induced genes has been made possible with the use of sophisticated promoter traps (e.g. IVET) that are based on conditional auxotrophy complementation or drug resistance. In one IVET approach, various bacterial genome fragments are placed in front of a necessary metabolic gene coupled to a reporter gene. The DNA constructs are inserted into a bacterial strain otherwise lacking the metabolic gene, and the resulting bacteria are used to infect the host organism. Only bacteria expressing the metabolic gene survive in the host organism; consequently, inactive constructs can be eliminated by harvesting only bacteria that survive for some minimum period in the host. At the same time, constitutively active constructs can be eliminated by screening only bacteria that do not express the reporter gene under laboratory conditions. The bacteria selected by such a method contain constructs that are selectively induced only during infection of the host. The IVET approach can be modified for use in plants to identify genes induced in either the bacteria or the plant cells upon pathogen infection or root colonization. For information on IVET see the articles by Mahan et al. in Science 259:686-688 (1993), Mahan et al. in PNAS USA 92:669-673 (1995), Heithoff et al. in PNAS USA 94:934-939 (1997), and Wang et al. in PNAS USA. 93:10434 (1996).

Constitutive Transcription

Use of promoters and control elements providing constitutive transcription is desired for modulation of transcription in most cells of an organism under most environmental conditions. In a plant, for example, constitutive transcription is useful for modulating genes involved in defense, pest resistance, herbicide resistance, etc.

Constitutive up-regulation and transcription down-regulation is useful for these applications. For instance, genes, transcripts, and/or polypeptides that increase defense, pest and herbicide resistance may require constitutive up-regulation of transcription. In contrast, constitutive transcriptional down-regulation may be desired to inhibit those genes, transcripts, and/or polypeptides that lower defense, pest and herbicide resistance.

Typically, promoter or control elements that provide constitutive transcription produce transcription levels that are statistically similar in many tissues and environmental conditions observed.

Calculation of P-value from the different observed transcript levels is one means of determining whether a promoter or control element is providing constitutive up-regulation. P-value is the probability that the difference of transcript levels is not statistically significant. The higher the P-value, the more likely the difference of transcript levels is not significant. One formula used to calculate P-value is as follows:

$\int \phi(x)dx$, integrated from $a$ to $\infty$, where $\phi(x)$ is a normal distribution;

where $a = \dfrac{|Sx - \mu|}{\sigma(\text{all Samples except } Sx)}$;

where $Sx$ = the intensity of the sample of interest where $\mu$ = is the average of the intensities of all samples except Sx, $= \dfrac{(\Sigma S1 \ldots Sn) - Sx}{n - 1}$ where $\sigma(S1 \ldots S11$, not including $Sx$)=the standard deviation of all sample intensities except Sx.
The P-value from the formula ranges from 1.0 to 0.0.

Usually, each P-value of the transcript levels observed in a majority of cells, tissues, or organs under various environmental conditions produced by the promoter or control element is greater than $10^{-8}$; more usually, greater than $10^{-7}$; even more usually, greater than $10^{-6}$; even more usually, greater than $10^{-5}$ or $10^{-4}$.

For up-regulation of transcription, promoter and control elements produce transcript levels that are above background of the assay.

Stress Induced Preferential Transcription

Promoters and control elements providing modulation of transcription under oxidative, drought, oxygen, wound, and methyl jasmonate stress are particularly useful for producing host cells or organisms that are more resistant to biotic and abiotic stresses. In a plant, for example, modulation of genes, transcripts, and/or polypeptides in response to oxidative stress can protect cells against damage caused by oxidative agents, such as hydrogen peroxide and other free radicals.

Drought induction of genes, transcripts, and/or polypeptides are useful to increase the viability of a plant, for example, when water is a limiting factor. In contrast, genes, transcripts, and/or polypeptides induced during oxygen stress can help the flood tolerance of a plant.

The promoters and control elements of the present invention can modulate stresses similar to those described in, for example, stress conditions are VuPLD1 (drought stress; Cowpea; see Pham-Thi et al. 1999. Plant molecular Biology. 1257-65), pyruvate decarboxylase (oxygen stress; rice; see Rivosal et al. 1997. Plant Physiol. 114(3): 1021-29), chromoplast specific carotenoid gene (oxidative stress; *capsicum*; see Bouvier et al. 1998. Journal of Biological Chemistry 273: 30651-59).

Promoters and control elements providing preferential transcription during wounding or induced by methyl jasmonate can produce a defense response in host cells or organisms. In a plant, for example, preferential modulation of genes, transcripts, and/or polypeptides under such conditions is useful to induce a defense response to mechanical wounding, pest or pathogen attack or treatment with certain chemicals.

Promoters and control elements of the present invention also can trigger a response similar to those described for cf9 (viral pathogen; tomato; see O'Donnell et al. 1998. The Plant journal: for cell and molecular biology 14(1): 137-42), hepatocyte growth factor activator inhibitor type 1 (HAI-1), which enhances tissue regeneration (tissue injury; human; Koono et al. 1999. Journal of Histochemistry and Cytochemistry 47: 673-82), copper amine oxidase (CuAO), induced during ontogenesis and wound healing (wounding; chick-pea; Rea et al. 1998. FEBS Letters 437: 177-82), proteinase inhibitor II (wounding; potato; see Pena-Cortes et al. 1988. Planta 174: 84-89), protease inhibitor II (methyl jasmonate; tomato; see Farmer and Ryan. 1990. Proc Natl Acad Sci USA 87: 7713-7716), two vegetative storage protein genes VspA and VspB (wounding, jasmonic acid, and water deficit; soybean; see Mason and Mullet. 1990. Plant Cell 2: 569-579).

Up-regulation and transcription down-regulation are useful for these applications. For instance, genes, transcripts, and/or polypeptides that increase oxidative, flood, or drought tolerance may require up-regulation of transcription. In contrast, transcriptional down-regulation may be desired to inhibit those genes, transcripts, and/or polypeptides that lower such tolerance.

Typically, promoter or control elements, which provide preferential transcription in wounding or under methyl jasmonate induction, produce transcript levels that are statistically significant as compared to cell types, organs or tissues under other conditions.

For preferential up-regulation of transcription, promoter and control elements produce transcript levels that are above background of the assay.

Light Induced Preferential Transcription

Promoters and control elements providing preferential transcription when induced by light exposure can be utilized to modulate growth, metabolism, and development; to increase drought tolerance; and decrease damage from light stress for host cells or organisms. In a plant, for example, modulation of genes, transcripts, and/or polypeptides in response to light is useful
(1) to increase the photosynthetic rate;
(2) to increase storage of certain molecules in leaves or green parts only, e.g., silage with high protein or starch content;
(3) to modulate production of exogenous compositions in green tissue, e.g., certain feed enzymes;
(4) to induce growth or development, such as fruit development and maturity, during extended exposure to light;
(5) to modulate guard cells to control the size of stomata in leaves to prevent water loss, or
(6) to induce accumulation of beta-carotene to help plants cope with light induced stress.

The promoters and control elements of the present invention also can trigger responses similar to those described in: abscisic acid insensitive3 (ABI3) (dark-grown *Arabidopsis* seedlings, see Rohde et al. 2000. The Plant Cell 12: 35-52), asparagine synthetase (pea root nodules, see Tsai, F. Y.; Coruzzi, G. M. 1990. EMBO J 9: 323-32), mdm2 gene (human tumor; see Saucedo et al. 1998. Cell Growth Differ 9: 119-30).

Up-regulation and transcription down-regulation are useful for these applications. For instance, genes, transcripts, and/or polypeptides that increase drought or light tolerance may require up-regulation of transcription. In contrast, transcriptional down-regulation may be desired to inhibit those genes, transcripts, and/or polypeptides that lower such tolerance.

Typically, promoter or control elements, which provide preferential transcription in cells, tissues or organs exposed to light, produce transcript levels that are statistically significant as compared to cells, tissues, or organs under decreased light exposure (intensity or length of time).

For preferential up-regulation of transcription, promoter and control elements produce transcript levels that are above background of the assay.

Dark Induced Preferential Transcription

Promoters and control elements providing preferential transcription when induced by dark or decreased light intensity or decreased light exposure time can be utilized to time growth, metabolism, and development, to modulate photosynthesis capabilities for host cells or organisms. In a plant, for example, modulation of genes, transcripts, and/or polypeptides in response to dark is useful, for example,
  (1) to induce growth or development, such as fruit development and maturity, despite lack of light;
  (2) to modulate genes, transcripts, and/or polypeptide active at night or on cloudy days; or
  (3) to preserve the plastid ultra structure present at the onset of darkness.

The present promoters and control elements can also trigger response similar to those described in the section above.

Up-regulation and transcription down-regulation is useful for these applications. For instance, genes, transcripts, and/or polypeptides that increase growth and development may require up-regulation of transcription. In contrast, transcriptional down-regulation may be desired to inhibit those genes, transcripts, and/or polypeptides that modulate photosynthesis capabilities.

Typically, promoter or control elements, which provide preferential transcription under exposure to dark or decrease light intensity or decrease exposure time, produce transcript levels that are statistically significant.

For preferential up-regulation of transcription, promoter and control elements produce transcript levels that are above background of the assay.

Leaf Preferential Transcription

Promoters and control elements providing preferential transcription in a leaf can modulate growth, metabolism, and development or modulate energy and nutrient utilization in host cells or organisms. In a plant, for example, preferential modulation of genes, transcripts, and/or polypeptide in a leaf, is useful, for example,
  (1) to modulate leaf size, shape, and development;
  (2) to modulate the number of leaves; or
  (3) to modulate energy or nutrient usage in relation to other organs and tissues Up-regulation and transcription down-regulation is useful for these applications. For instance, genes, transcripts, and/or polypeptides that increase growth, for example, may require up-regulation of transcription. In contrast, transcriptional down-regulation may be desired to inhibit energy usage in a leaf to be directed to the fruit instead, for instance.

Typically, promoter or control elements, which provide preferential transcription in the cells, tissues, or organs of a leaf, produce transcript levels that are statistically significant as compared to other cells, organs or tissues.

For preferential up-regulation of transcription, promoter and control elements produce transcript levels that are above background of the assay.

Root Preferential Transcription

Promoters and control elements providing preferential transcription in a root can modulate growth, metabolism, development, nutrient uptake, nitrogen fixation, or modulate energy and nutrient utilization in host cells or organisms. In a plant, for example, preferential modulation of genes, transcripts, and/or in a leaf, is useful
  (1) to modulate root size, shape, and development;
  (2) to modulate the number of roots, or root hairs;
  (3) to modulate mineral, fertilizer, or water uptake;
  (4) to modulate transport of nutrients; or
  (4) to modulate energy or nutrient usage in relation to other organs and tissues.

Up-regulation and transcription down-regulation is useful for these applications. For instance, genes, transcripts, and/or polypeptides that increase growth, for example, may require up-regulation of transcription. In contrast, transcriptional down-regulation may be desired to inhibit nutrient usage in a root to be directed to the leaf instead, for instance.

Typically, promoter or control elements, which provide preferential transcription in cells, tissues, or organs of a root, produce transcript levels that are statistically significant as compared to other cells, organs or tissues.

For preferential up-regulation of transcription, promoter and control elements produce transcript levels that are above background of the assay.

Stem/Shoot Preferential Transcription

Promoters and control elements providing preferential transcription in a stem or shoot can modulate growth, metabolism, and development or modulate energy and nutrient utilization in host cells or organisms. In a plant, for example, preferential modulation of genes, transcripts, and/or polypeptide in a stem or shoot, is useful, for example,
  (1) to modulate stem/shoot size, shape, and development; or
  (2) to modulate energy or nutrient usage in relation to other organs and tissues Up-regulation and transcription down-regulation is useful for these applications. For instance, genes, transcripts, and/or polypeptides that increase growth, for example, may require up-regulation of transcription. In contrast, transcriptional down-regulation may be desired to inhibit energy usage in a stem/shoot to be directed to the fruit instead, for instance.

Typically, promoter or control elements, which provide preferential transcription in the cells, tissues, or organs of a stem or shoot, produce transcript levels that are statistically significant as compared to other cells, organs or tissues.

For preferential up-regulation of transcription, promoter and control elements produce transcript levels that are above background of the assay.

Fruit and Seed Preferential Transcription

Promoters and control elements providing preferential transcription in a silique or fruit can time growth, development, or maturity; or modulate fertility; or modulate energy and nutrient utilization in host cells or organisms. In a plant, for example, preferential modulation of genes, transcripts, and/or polypeptides in a fruit, is useful
  (1) to modulate fruit size, shape, development, and maturity;
  (2) to modulate the number of fruit or seeds;
  (3) to modulate seed shattering;
  (4) to modulate components of seeds, such as, storage molecules, starch, protein, oil, vitamins, anti-nutritional components, such as phytic acid;
  (5) to modulate seed and/or seedling vigor or viability;
  (6) to incorporate exogenous compositions into a seed, such as lysine rich proteins;
  (7) to permit similar fruit maturity timing for early and late blooming flowers; or
  (8) to modulate energy or nutrient usage in relation to other organs and tissues.

Up-regulation and transcription down-regulation is useful for these applications. For instance, genes, transcripts, and/or polypeptides that increase growth, for example, may require up-regulation of transcription. In contrast, transcriptional down-regulation may be desired to inhibit late fruit maturity, for instance.

Typically, promoter or control elements, which provide preferential transcription in the cells, tissues, or organs of siliques or fruits, produce transcript levels that are statistically significant as compared to other cells, organs or tissues.

For preferential up-regulation of transcription, promoter and control elements produce transcript levels that are above background of the assay.

Callus Preferential Transcription

Promoters and control elements providing preferential transcription in a callus can be useful to modulating transcription in dedifferentiated host cells. In a plant transformation, for example, preferential modulation of genes, transcripts, in callus is useful to modulate transcription of a marker gene, which can facilitate selection of cells that are transformed with exogenous polynucleotides.

Up-regulation and transcription down-regulation is useful for these applications. For instance, genes, transcripts, and/or polypeptides that increase marker gene detectability, for example, may require up-regulation of transcription. In contrast, transcriptional down-regulation may be desired to increase the ability of the calluses to later differentiate, for instance.

Typically, promoter or control elements, which provide preferential transcription in callus, produce transcript levels that are statistically significant as compared to other cell types, tissues, or organs. Calculation of P-value from the different observed transcript levels is one means of determining whether a promoter or control element is providing such preferential transcription.

Usually, each P-value of the transcript levels observed in callus as compared to, at least one other cell type, tissue or organ, is less than $10^{-4}$; more usually, less than $10^{-5}$; even more usually, less than $10^{-6}$; even more usually, less than $10^{-7}$ or $10^{-8}$.

For preferential up-regulation of transcription, promoter and control elements produce transcript levels that are above background of the assay.

Flower Specific Transcription

Promoters and control elements providing preferential transcription in flowers can modulate pigmentation; or modulate fertility in host cells or organisms. In a plant, for example, preferential modulation of genes, transcripts, and/or polypeptides in a flower, is useful, (1) to modulate petal color; or (2) to modulate the fertility of pistil and/or stamen.

Up-regulation and transcription down-regulation is useful for these applications. For instance, genes, transcripts, and/or polypeptides that increase pigmentation, for example, may require up-regulation of transcription. In contrast, transcriptional down-regulation may be desired to inhibit fertility, for instance.

Typically, promoter or control elements, which provide preferential transcription in flowers, produce transcript levels that are statistically significant as compared to other cells, organs or tissues.

For preferential up-regulation of transcription, promoter and control elements produce transcript levels that are above background of the assay.

Immature Bud and Inflorescence Preferential Transcription

Promoters and control elements providing preferential transcription in a immature bud or inflorescence can time growth, development, or maturity; or modulate fertility or viability in host cells or organisms. In a plant, for example, preferential modulation of genes, transcripts, and/or polypeptide in a fruit, is useful, (1) to modulate embryo development, size, and maturity;

(2) to modulate endosperm development, size, and composition;

(3) to modulate the number of seeds and fruits; or (4) to modulate seed development and viability.

Up-regulation and transcription down-regulation is useful for these applications. For instance, genes, transcripts, and/or polypeptides that increase growth, for example, may require up-regulation of transcription. In contrast, transcriptional down-regulation may be desired to decrease endosperm size, for instance.

Typically, promoter or control elements, which provide preferential transcription in immature buds and inflorescences, produce transcript levels that are statistically significant as compared to other cell types, organs or tissues.

For preferential up-regulation of transcription, promoter and control elements produce transcript levels that are above background of the assay.

Senescence Preferential Transcription

Promoters and control elements providing preferential transcription during senescence can be used to modulate cell degeneration, nutrient mobilization, and scavenging of free radicals in host cells or organisms. Other types of responses that can be modulated include, for example, senescence associated genes (SAG) that encode enzymes thought to be involved in cell degeneration and nutrient mobilization (*Arabidopsis*; see Hensel et al. 1993. Plant Cell 5: 553-64), and the CP-2/cathepsin L gene (rat; Kim and Wright. 1997. Biol Reprod 57: 1467-77), both induced during senescence.

In a plant, for example, preferential modulation of genes, transcripts, and/or polypeptides during senescencing is useful to modulate fruit ripening.

Up-regulation and transcription down-regulation is useful for these applications. For instance, genes, transcripts, and/or polypeptides that increase scavenging of free radicals, for example, may require up-regulation of transcription. In contrast, transcriptional down-regulation may be desired to inhibit cell degeneration, for instance.

Typically, promoter or control elements, which provide preferential transcription in cells, tissues, or organs during senescence, produce transcript levels that are statistically significant as compared to other conditions.

For preferential up-regulation of transcription, promoter and control elements produce transcript levels that are above background of the assay.

Germination Preferential Transcription

Promoters and control elements providing preferential transcription in a germinating seed can time growth, development, or maturity; or modulate viability in host cells or organisms. In a plant, for example, preferential modulation of genes, transcripts, and/or polypeptide in a germinating seed, is useful, (1) to modulate the emergence of they hypocotyls, cotyledons and radical; or (2) to modulate shoot and primary root growth and development;

Up-regulation and transcription down-regulation is useful for these applications. For instance, genes, transcripts, and/or polypeptides that increase growth, for example, may require up-regulation of transcription. In contrast, transcriptional down-regulation may be desired to decrease endosperm size, for instance.

Typically, promoter or control elements, which provide preferential transcription in a germinating seed, produce transcript levels that are statistically significant as compared to other cell types, organs or tissues.

For preferential up-regulation of transcription, promoter and control elements produce transcript levels that are above background of the assay.

Microarray Analysis

A major way that a cell controls its response to internal or external stimuli is by regulating the rate of transcription of specific genes. For example, the differentiation of cells during organogenesis into forms characteristic of the organ is associated with the selective activation and repression of large numbers of genes. Thus, specific organs, tissues and cells are functionally distinct due to the different populations of mRNAs and protein products they possess. Internal signals program the selective activation and repression programs. For example, internally synthesized hormones produce such signals. The level of hormone can be raised by increasing the level of transcription of genes encoding proteins concerned with hormone synthesis.

To measure how a cell reacts to internal and/or external stimuli, individual mRNA levels can be measured and used as an indicator for the extent of transcription of the gene. Cells can be exposed to a stimulus, and mRNA can be isolated and assayed at different time points after stimulation. The mRNA from the stimulated cells can be compared to control cells that were not stimulated. The mRNA levels that are higher in the stimulated cell versus the control indicate a stimulus-specific response of the cell. The same is true of mRNA levels that are lower in stimulated cells versus the control condition.

Similar studies can be performed with cells taken from an organism with a defined mutation in their genome as compared with cells without the mutation. Altered mRNA levels in the mutated cells indicate how the mutation causes transcriptional changes. These transcriptional changes are associated with the phenotype that the mutated cells exhibit that is different from the phenotype exhibited by the control cells.

Applicants have utilized microarray techniques to measure the levels of mRNAs in cells from plants transformed with a construct containing the promoter or control elements of the present invention together with their endogenous cDNA sequences. In general, transformants with the constructs were grown to an appropriate stage, and tissue samples were prepared for the microarray differential expression analysis. In this manner it is possible to determine the differential expression for the cDNAs under the control of the endogenous promoter under various conditions.

Microarray Experimental Procedures and Results

Procedures

1. Sample Tissue Preparation

Tissue samples for each of the expression analysis experiments were prepared as follows:

(a) Roots

Seeds of *Arabidopsis thaliana* (Ws) were sterilized in full strength bleach for less than 5 min., washed more than 3 times in sterile distilled deionized water and plated on MS agar plates. The plates were placed at 4° C. for 3 nights and then placed vertically into a growth chamber having 16 hr light/8 hr dark cycles, 23° C., 70% relative humidity and ~11,000 LUX. After 2 weeks, the roots were cut from the agar, flash frozen in liquid nitrogen and stored at −80° C.

(b) Rosette Leaves, Stems, and Siliques

*Arabidopsis thaliana* (Ws) seed was vernalized at 4° C. for 3 days before sowing in Metro-mix soil type 350. Flats were placed in a growth chamber having 16 hr light/8 hr dark, 80% relative humidity, 23° C. and 13,000 LUX for germination and growth. After 3 weeks, rosette leaves, stems, and siliques were harvested, flash frozen in liquid nitrogen and stored at −80° C. until use. After 4 weeks, siliques (<5 mm, 5-10 mm and >10 mm) were harvested, flash frozen in liquid nitrogen and stored at −80° C. until use. 5 week old whole plants (used as controls) were harvested, flash frozen in liquid nitrogen and kept at −80° C. until RNA was isolated.

(c) Germination

*Arabidopsis thaliana* seeds (ecotype Ws) were sterilized in bleach and rinsed with sterile water. The seeds were placed in 100 mm petri plates containing soaked autoclaved filter paper. Plates were foil-wrapped and left at 4° C. for 3 nights to vernalize. After cold treatment, the foil was removed and plates were placed into a growth chamber having 16 hr light/8 hr dark cycles, 23° C., 70% relative humidity and ~11,000 lux. Seeds were collected 1 d, 2 d, 3 d and 4 d later, flash frozen in liquid nitrogen and stored at −80° C. until RNA was isolated.

(d) Abscissic Acid (ABA)

Seeds of *Arabidopsis thaliana* (ecotype Wassilewskija) were sown in trays and left at 4° C. for 4 days to vernalize. They were then transferred to a growth chamber having grown 16 hr light/8 hr dark, 13,000 LUX, 70% humidity, and 20° C. and watered twice a week with 1 L of 1× Hoagland's solution. Approximately 1,000 14 day old plants were spayed with 200-250 mls of 100 µM ABA in a 0.02% solution of the detergent Silwet L-77. Whole seedlings, including roots, were harvested within a 15 to 20 minute time period at 1 hr and 6 hr after treatment, flash-frozen in liquid nitrogen and stored at −80° C.

Seeds of maize hybrid 35A (Pioneer) were sown in water-moistened sand in flats (10 rows, 5-6 seed/row) and covered with clear, plastic lids before being placed in a growth chamber having 16 hr light (25° C.)/8 hr dark (20° C.), 75% relative humidity and 13,000-14,000 LUX. Covered flats were watered every three days for 7 days. Seedlings were carefully removed from the sand and placed in 1-liter beakers with 100 µM ABA for treatment. Control plants were treated with water. After 6 hr and 24 hr, aerial and root tissues were separated and flash frozen in liquid nitrogen prior to storage at −80° C.

(e) Brassinosteroid Responsive

Two separate experiments were performed, one with epi-brassinolide and one with the brassinosteroid biosynthetic inhibitor brassinazole. In the epi-brassinolide experiments, seeds of wild-type *Arabidopsis thaliana* (ecotype Wassilewskija) and the brassinosteroid biosynthetic mutant dwf4-1 were sown in trays and left at 4° C. for 4 days to vernalize. They were then transferred to a growth chamber having 16 hr light/8 hr dark, 11,000 LUX, 70% humidity and 22° C. temperature. Four week old plants were spayed with a 1 µM solution of epi-brassinolide and shoot parts (unopened floral primordia and shoot apical meristems) harvested three hours later. Tissue was flash-frozen in liquid nitrogen and stored at −80° C. In the brassinazole experiments, seeds of wild-type *Arabidopsis thaliana* (ecotype Wassilewskija) were grown as described above. Four week old plants were spayed with a 1 µM solution of brassinazole and shoot parts (unopened floral primordia and shoot apical meristems) harvested three hours later. Tissue was flash-frozen in liquid nitrogen and stored at −80° C.

In addition to the spray experiments, tissue was prepared from two different mutants; (1) a dwf4-1 knock out mutant and (2) a mutant overexpressing the dwf4-1 gene.

Seeds of wild-type *Arabidopsis thaliana* (ecotype Wassilewskija) and of the dwf4-1 knock out and overexpressor mutants were sown in trays and left at 4° C. for 4 days to vernalize. They were then transferred to a growth chamber having 16 hr light/8 hr dark, 11,000 LUX, 70% humidity and 22° C. temperature. Tissue from shoot parts (unopened floral primordia and shoot apical meristems) was flash-frozen in liquid nitrogen and stored at −80° C.

Another experiment was completed with seeds of *Arabidopsis thaliana* (ecotype Wassilewskija) were sown in trays and left at 4° C. for 4 days to vernalize. They were then transferred to a growth chamber. Plants were grown under long-day (16 hr light: 8 hr. dark) conditions, 13,000 LUX light intensity, 70% humidity, 20° C. temperature and watered twice a week with 1 L 1× Hoagland's solution (recipe recited in Feldmann et al., (1987) Mol. Gen. Genet. 208: 1-9 and described as complete nutrient solution). Approximately 1,000 14 day old plants were spayed with 200-250 mls of 0.1 µM Epi-Brassinolite in 0.02% solution of the detergent Silwet L-77. At 1 hr. and 6 hrs. after treatment aerial tissues were harvested within a 15 to 20 minute time period and flash-frozen in liquid nitrogen.

Seeds of maize hybrid 35A (Pioneer) were sown in water-moistened sand in flats (10 rows, 5-6 seed/row) and covered with clear, plastic lids before being placed in a growth chamber having 16 hr light (25° C.)/8 hr dark (20° C.), 75% relative humidity and 13,000-14,000 LUX. Covered flats were watered every three days for 7 days. Seedlings were carefully removed from the sand and placed in 1-liter beakers with 0.1 µM epi-brassinolide for treatment. Control plants were treated with distilled deionized water. After 24 hr, aerial and root tissues were separated and flash frozen in liquid nitrogen prior to storage at −80° C.

(f) Nitrogen: High to Low

Wild type *Arabidopsis thaliana* seeds (ecotpye Ws) were surface sterilized with 30% Clorox, 0.1% Triton X-100 for 5 minutes. Seeds were then rinsed with 4-5 exchanges of sterile double distilled deionized water. Seeds were vernalized at 4° C. for 2-4 days in darkness. After cold treatment, seeds were plated on modified 1×MS media (without $NH_4NO_3$ or $KNO_3$), 0.5% sucrose, 0.5 g/L MES pH5.7, 1% phytagar and supplemented with $KNO_3$ to a final concentration of 60 mM (high nitrate modified 1×MS media). Plates were then grown for 7 days in a Percival growth chamber at 22° C. with 16 hr. light/8 hr dark.

Germinated seedlings were then transferred to a sterile flask containing 50 mL of high nitrate modified 1×MS liquid media. Seedlings were grown with mild shaking for 3 additional days at 22° C. in 16 hr. light/8 hr dark (in a Percival growth chamber) on the high nitrate modified 1×MS liquid media.

After three days of growth on high nitrate modified 1×MS liquid media, seedlings were transferred either to a new sterile flask containing 50 mL of high nitrate modified 1×MS liquid media or to low nitrate modified 1×MS liquid media (containing 20 □M $KNO_3$). Seedlings were grown in these media conditions with mild shaking at 22° C. in 16 hr light/8 hr dark for the appropriate time points and whole seedlings harvested for total RNA isolation via the Trizol method (LifeTech.). The time points used for the microarray experiments were 10 min. and 1 hour time points for both the high and low nitrate modified 1×MS media.

Alternatively, seeds that were surface sterilized in 30% bleach containing 0.1% Triton X-100 and further rinsed in sterile water, were planted on MS agar, (0.5% sucrose) plates containing 50 mM $KNO_3$ (potassium nitrate). The seedlings were grown under constant light (3500 LUX) at 22° C. After 12 days, seedlings were transferred to MS agar plates containing either 1 mM $KNO_3$ or 50 mM $KNO_3$. Seedlings transferred to agar plates containing 50 mM $KNO_3$ were treated as controls in the experiment. Seedlings transferred to plates with 1 mM $KNO_3$ were rinsed thoroughly with sterile MS solution containing 1 mM $KNO_3$. There were ten plates per transfer. Root tissue was collected and frozen in 15 mL Falcon tubes at various time points which included 1 hour, 2 hours, 3 hours, 4 hours, 6 hours, 9 hours, 12 hours, 16 hours, and 24 hours.

Maize 35A19 Pioneer hybrid seeds were sown on flats containing sand and grown in a Conviron growth chamber at 25° C., 16 hr light/8 hr dark, ~13,000 LUX and 80% relative humidity. Plants were watered every three days with double distilled deionized water. Germinated seedlings are allowed to grow for 10 days and were watered with high nitrate modified 1×MS liquid media (see above). On day 11, young corn seedlings were removed from the sand (with their roots intact) and rinsed briefly in high nitrate modified 1×MS liquid media. The equivalent of half a flat of seedlings were then submerged (up to their roots) in a beaker containing either 500 mL of high or low nitrate modified 1×MS liquid media (see above for details).

At appropriate time points, seedlings were removed from their respective liquid media, the roots separated from the shoots and each tissue type flash frozen in liquid nitrogen and stored at −80° C. This was repeated for each time point. Total RNA was isolated using the Trizol method (see above) with root tissues only.

Corn root tissues isolated at the 4 hr and 16 hr time points were used for the microarray experiments. Both the high and low nitrate modified 1×MS media were used.

(g) Nitrogen: Low to High

*Arabidopsis thaliana* ecotype Ws seeds were sown on flats containing 4 L of a 1:2 mixture of Grace Zonolite vermiculite and soil. Flats were watered with 3 L of water and vernalized at 4° C. for five days. Flats were placed in a Conviron growth chamber having 16 hr light/8 hr dark at 20° C., 80% humidity and 17.450 LUX. Flats were watered with approximately 1.5 L of water every four days. Mature, bolting plants (24 days after germination) were bottom treated with 2 L of either a control (100 mM mannitol pH 5.5) or an experimental (50 mM ammonium nitrate, pH 5.5) solution. Roots, leaves and siliques were harvested separately 30, 120 and 240 minutes after treatment, flash frozen in liquid nitrogen and stored at −80° C.

Hybrid maize seed (Pioneer hybrid 35A19) were aerated overnight in deionized water. Thirty seeds were plated in each flat, which contained 4 liters of Grace zonolite vermiculite. Two liters of water were bottom fed and flats were kept in a Conviron growth chamber with 16 hr light/8 hr dark at 20° C. and 80% humidity. Flats were watered with 1 L of tap water every three days. Five day old seedlings were treated as described above with 2 L of either a control (100 mM mannitol pH 6.5) solution or 1 L of an experimental (50 mM ammonium nitrate, pH 6.8) solution. Fifteen shoots per time point per treatment were harvested 10, 90 and 180 minutes after treatment, flash frozen in liquid nitrogen and stored at −80° C.

Alternatively, seeds of *Arabidopsis thaliana* (ecotype Wassilewskija) were left at 4° C. for 3 days to vernalize. They were then sown on vermiculite in a growth chamber having 16 hours light/8 hours dark, 12,000-14,000 LUX, 70% humidity, and 20° C. They were bottom-watered with tap water, twice weekly. Twenty-four days old plants were sprayed with either water (control) or 0.6% ammonium nitrate at 4 µL/cm$^2$ of tray surface. Total shoots and some primary roots were cleaned of vermiculite, flash-frozen in liquid nitrogen and stored at −80° C.

(h) Methyl Jasmonate

Seeds of *Arabidopsis thaliana* (ecotype Wassilewskija) were sown in trays and left at 4° C. for 4 days to vernalize before being transferred to a growth chamber having 16 hr light/8 hr. dark, 13,000 LUX, 70% humidity, 20° C. temperature and watered twice a week with 1 L of a 1× Hoagland's solution. Approximately 1,000 14 day old plants were spayed with 200-250 mls of 0.001% methyl jasmonate in a 0.02% solution of the detergent Silwet L-77. At 1 hr and 6 hrs after treatment, whole seedlings, including roots, were harvested within a 15 to 20 minute time period, flash-frozen in liquid nitrogen and stored at −80° C.

Seeds of maize hybrid 35A (Pioneer) were sown in water-moistened sand in flats (10 rows, 5-6 seed/row) and covered with clear, plastic lids before being placed in a growth chamber having 16 hr light (25° C.)/8 hr dark (20° C.), 75% relative humidity and 13,000-14,000 LUX. Covered flats were watered every three days for 7 days. Seedlings were carefully removed from the sand and placed in 1-liter beakers with 0.001% methyl jasmonate for treatment. Control plants were treated with water. After 24 hr, aerial and root tissues were separated and flash frozen in liquid nitrogen prior to storage at −80° C.

(i) Salicylic Acid

Seeds of *Arabidopsis thaliana* (ecotype Wassilewskija) were sown in trays and left at 4° C. for 4 days to vernalize before being transferred to a growth chamber having 16 hr light/8 hr. dark, 13,000 LUX, 70% humidity, 20° C. temperature and watered twice a week with 1 L of a 1× Hoagland's solution. Approximately 1,000 14 day old plants were spayed with 200-250 mls of 5 mM salicylic acid (solubilized in 70% ethanol) in a 0.02% solution of the detergent Silwet L-77. At 1 hr and 6 hrs after treatment, whole seedlings, including roots, were harvested within a 15 to 20 minute time period flash-frozen in liquid nitrogen and stored at −80° C.

Alternatively, seeds of wild-type *Arabidopsis thaliana* (ecotype Columbia) and mutant CS3726 were sown in soil type 200 mixed with osmocote fertilizer and Marathon insecticide and left at 4° C. for 3 days to vernalize. Flats were incubated at room temperature with continuous light. Sixteen days post germination plants were sprayed with 2 mM SA, 0.02% SilwettL-77 or control solution (0.02% SilwettL-77. Aerial parts or flowers were harvested 1 hr, 4 hr, 6 hr, 24 hr and 3 weeks post-treatment flash frozen and stored at −80° C.

Seeds of maize hybrid 35A (Pioneer) were sown in water-moistened sand in flats (10 rows, 5-6 seed/row) and covered with clear, plastic lids before being placed in a growth chamber having 16 hr light (25° C.)/8 hr dark (20° C.), 75% relative humidity and 13,000-14,000 LUX. Covered flats were watered every three days for 7 days. Seedlings were carefully removed from the sand and placed in 1-liter beakers with 2 mM SA for treatment. Control plants were treated with water. After 12 hr and 24 hr, aerial and root tissues were separated and flash frozen in liquid nitrogen prior to storage at −80° C.

(j) Drought Stress

Seeds of *Arabidopsis thaliana* (Wassilewskija) were sown in pots and left at 4° C. for three days to vernalize before being transferred to a growth chamber having 16 hr light/8 hr dark, 150,000-160,000 LUX, 20° C. and 70% humidity. After 14 days, aerial tissues were cut and left to dry on 3 MM Whatman paper in a Petri-plate for 1 hour and 6 hours. Aerial tissues exposed for 1 hour and 6 hours to 3 MM Whatman paper wetted with 1× Hoagland's solution served as controls. Tissues were harvested, flash-frozen in liquid nitrogen and stored at −80° C.

Alternatively, *Arabidopsis thaliana* (Ws) seed was vernalized at 4° C. for 3 days before sowing in Metromix soil type 350. Flats were placed in a growth chamber with 23° C., 16 hr light/8 hr. dark, 80% relative humidity, ~13,000 LUX for germination and growth. Plants were watered with 1-1.5 L of water every four days. Watering was stopped 16 days after germination for the treated samples, but continued for the control samples. Rosette leaves and stems, flowers and siliques were harvested 2 d, 3 d, 4 d, 5 d, 6 d and 7 d after watering was stopped. Tissue was flash frozen in liquid nitrogen and kept at −80° C. until RNA was isolated. Flowers and siliques were also harvested on day 8 from plants that had undergone a 7 d drought treatment followed by 1 day of watering. Control plants (whole plants) were harvested after 5 weeks, flash frozen in liquid nitrogen and stored as above.

Seeds of maize hybrid 35A (Pioneer) were sown in water-moistened sand in flats (10 rows, 5-6 seed/row) and covered with clear, plastic lids before being placed in a growth chamber having 16 hr light (25° C.)/8 hr dark (20° C.), 75% relative humidity and 13,000-14,000 LUX. Covered flats were watered every three days for 7 days. Seedlings were carefully removed from the sand and placed in empty 1-liter beakers at room temperature for treatment. Control plants were placed in water. After 1 hr, 6 hr, 12 hr and 24 hr aerial and root tissues were separated and flash frozen in liquid nitrogen prior to storage at −80° C.

(k) Osmotic Stress

Seeds of *Arabidopsis thaliana* (Wassilewskija) were sown in trays and left at 4° C. for three days to vernalize before being transferred to a growth chamber having 16 hr light/8 hr dark, 12,000-14,000 LUX, 20° C., and 70% humidity. After 14 days, the aerial tissues were cut and placed on 3 MM Whatman paper in a petri-plate wetted with 20% PEG (polyethylene glycol-$M_r$ 8,000) in 1× Hoagland's solution. Aerial tissues on 3 MM Whatman paper containing 1× Hoagland's solution alone served as the control. Aerial tissues were harvested at 1 hour and 6 hours after treatment, flash-frozen in liquid nitrogen and stored at −80° C.

Seeds of maize hybrid 35A (Pioneer) were sown in water-moistened sand in flats (10 rows, 5-6 seed/row) and covered with clear, plastic lids before being placed in a growth chamber having 16 hr light (25° C.)/8 hr dark (20° C.), 75% relative humidity and 13,000-14,000 LUX. Covered flats were watered every three days for 7 days. Seedlings were carefully removed from the sand and placed in 1-liter beakers with 10% PEG (polyethylene glycol-$M_r$ 8,000) for treatment. Control plants were treated with water. After 1 hr and 6 hr aerial and root tissues were separated and flash frozen in liquid nitrogen prior to storage at −80° C.

Seeds of maize hybrid 35A (Pioneer) were sown in water-moistened sand in flats (10 rows, 5-6 seed/row) and covered with clear, plastic lids before being placed in a growth chamber having 16 hr light (25° C.)/8 hr dark (20° C.), 75% relative humidity and 13,000-14,000 LUX. Covered flats were watered every three days for 7 days. Seedlings were carefully removed from the sand and placed in 1-liter beakers with 150 mM NaCl for treatment. Control plants were treated with water. After 1 hr, 6 hr, and 24 hr aerial and root tissues were separated and flash frozen in liquid nitrogen prior to storage at −80° C.

(l) Heat Shock Treatment

Seeds of *Arabidopsis Thaliana* (Wassilewskija) were sown in trays and left at 4° C. for three days to vernalize before being transferred to a growth chamber with 16 hr light/8 hr dark, 12,000-14,000 Lux, 70% humidity and 20° C., fourteen day old plants were transferred to a 42° C. growth chamber and aerial tissues were harvested 1 hr and 6 hr after transfer. Control plants were left at 20° C. and aerial tissues were harvested. Tissues were flash-frozen in liquid nitrogen and stored at −80° C.

Seeds of maize hybrid 35A (Pioneer) were sown in water-moistened sand in flats (10 rows, 5-6 seed/row) and covered with clear, plastic lids before being placed in a growth chamber having 16 hr light (25° C.)/8 hr dark (20° C.), 75% relative humidity and 13,000-14,000 LUX. Covered flats were watered every three days for 7 days. Seedlings were carefully removed from the sand and placed in 1-liter beakers containing 42° C. water for treatment. Control plants were treated with water at 25° C. After 1 hr and 6 hr aerial and root tissues were separated and flash frozen in liquid nitrogen prior to storage at −80° C.

(m) Cold Shock Treatment

Seeds of *Arabidopsis thaliana* (Wassilewskija) were sown in trays and left at 4° C. for three days to vernalize before being transferred to a growth chamber having 16 hr light/8 hr dark, 12,000-14,000 LUX, 20° C. and 70% humidity. Fourteen day old plants were transferred to a 4° C. dark growth chamber and aerial tissues were harvested 1 hour and 6 hours later. Control plants were maintained at 20° C. and covered with foil to avoid exposure to light. Tissues were flash-frozen in liquid nitrogen and stored at −80° C.

Seeds of maize hybrid 35A (Pioneer) were sown in water-moistened sand in flats (10 rows, 5-6 seed/row) and covered with clear, plastic lids before being placed in a growth chamber having 16 hr light (25° C.)/8 hr dark (20° C.), 75% relative humidity and 13,000-14,000 LUX. Covered flats were watered every three days for 7 days. Seedlings were carefully removed from the sand and placed in 1-liter beakers containing 4° C. water for treatment. Control plants were treated with water at 25° C. After 1 hr and 6 hr aerial and root tissues were separated and flash frozen in liquid nitrogen prior to storage at −80° C.

(n) *Arabidopsis* Seeds

Fruits (Pod+Seed) 0-5 mm

Seeds of *Arabidopsis thaliana* (ecotype Wassilewskija) were sown in pots and left at 4° C. for two to three days to vernalize. They were then transferred to a growth chamber. Plants were grown under long-day (16 hr light: 8 hr dark) conditions, 7000-8000 LUX light intensity, 70% humidity, and 22° C. temperature. 3-4 siliques (fruits) bearing developing seeds were selected from at least 3 plants and were hand-dissected to determine what developmental stage(s) were represented by the enclosed embryos. Description of the stages of *Arabidopsis* embryogenesis used in this determination were summarized by Bowman (1994). Silique lengths were then determined and used as an approximate determinant for embryonic stage. Siliques 0-5 mm in length containing post fertilization through pre-heart stage [0-72 hours after fertilization (HAF)] embryos were harvested and flash frozen in liquid nitrogen.

Fruits (Pod+Seed) 5-10 mm

Seeds of *Arabidopsis thaliana* (ecotype Wassilewskija) were sown in pots and left at 4° C. for two to three days to vernalize. They were then transferred to a growth chamber. Plants were grown under long-day (16 hr light: 8 hr dark) conditions, 7000-8000 LUX light intensity, 70% humidity, and 22° C. temperature. 3-4 siliques (fruits) bearing developing seeds were selected from at least 3 plants and were hand-dissected to determine what developmental stage(s) were represented by the enclosed embryos. Description of the stages of *Arabidopsis* embryogenesis used in this determination were summarized by Bowman (1994). Silique lengths were then determined and used as an approximate determinant for embryonic stage. Siliques 5-10 mm in length containing heart—through early upturned-U-stage [72-120 hours after fertilization (HAF)] embryos were harvested and flash frozen in liquid nitrogen.

Fruits (Pod+Seed)>10 mm

Seeds of *Arabidopsis thaliana* (ecotype Wassilewskija) were sown in pots and left at 4° C. for two to three days to vernalize. They were then transferred to a growth chamber. Plants were grown under long-day (16 hr light: 8 hr dark) conditions, 7000-8000 LUX light intensity, 70% humidity, and 22° C. temperature. 3-4 siliques (fruits) bearing developing seeds were selected from at least 3 plants and were hand-dissected to determine what developmental stage(s) were represented by the enclosed embryos. Description of the stages of *Arabidopsis* embryogenesis used in this determination were summarized by Bowman (1994). Silique lengths were then determined and used as an approximate determinant for embryonic stage. Siliques >10 mm in length containing green, late upturned-U-stage [>120 hours after fertilization (HAF)-9 days after flowering (DAF)] embryos were harvested and flash frozen in liquid nitrogen.

Green Pods 5-10 mm (Control Tissue for Samples 72-74)

Seeds of *Arabidopsis thaliana* (ecotype Wassilewskija) were sown in pots and left at 4° C. for two to three days to vernalize. They were then transferred to a growth chamber. Plants were grown under long-day (16 hr light: 8 hr dark) conditions, 7000-8000 LUX light intensity, 70% humidity, and 22° C. temperature. 3-4 siliques (fruits) bearing developing seeds were selected from at least 3 plants and were hand-dissected to determine what developmental stage(s) were represented by the enclosed embryos. Description of the stages of *Arabidopsis* embryogenesis used in this determination were summarized by Bowman (1994). Silique lengths were then determined and used as an approximate determinant for embryonic stage. Green siliques 5-10 mm in length containing developing seeds 72-120 hours after fertilization (HAF)] were opened and the seeds removed. The remaining tissues (green pods minus seed) were harvested and flash frozen in liquid nitrogen.

Green Seeds from Fruits >10 mm

Seeds of *Arabidopsis thaliana* (ecotype Wassilewskija) were sown in pots and left at 4° C. for two to three days to vernalize. They were then transferred to a growth chamber. Plants were grown under long-day (16 hr light: 8 hr dark) conditions, 7000-8000 LUX light intensity, 70% humidity, and 22° C. temperature. 3-4 siliques (fruits) bearing developing seeds were selected from at least 3 plants and were hand-dissected to determine what developmental stage(s) were represented by the enclosed embryos. Description of the stages of *Arabidopsis* embryogenesis used in this determination were summarized by Bowman (1994). Silique lengths were then determined and used as an approximate determinant for embryonic stage. Green siliques >10 mm in length containing developing seeds up to 9 days after flowering (DAF)] were opened and the seeds removed and harvested and flash frozen in liquid nitrogen.

Brown Seeds from Fruits >10 mm

Seeds of *Arabidopsis thaliana* (ecotype Wassilewskija) were sown in pots and left at 4° C. for two to three days to vernalize. They were then transferred to a growth chamber. Plants were grown under long-day (16 hr light: 8 hr dark) conditions, 7000-8000 LUX light intensity, 70% humidity, and 22° C. temperature. 3-4 siliques (fruits) bearing developing seeds were selected from at least 3 plants and were hand-dissected to determine what developmental stage(s) were represented by the enclosed embryos. Description of the stages of *Arabidopsis* embryogenesis used in this determination were summarized by Bowman (1994). Silique lengths were then determined and used as an approximate determinant for embryonic stage. Yellowing siliques >10 mm in length containing brown, desiccating seeds >11 days after flowering (DAF)] were opened and the seeds removed and harvested and flash frozen in liquid nitrogen.

Green/Brown Seeds from Fruits >10 mm

Seeds of *Arabidopsis thaliana* (ecotype Wassilewskija) were sown in pots and left at 4° C. for two to three days to vernalize. They were then transferred to a growth chamber. Plants were grown under long-day (16 hr light: 8 hr dark) conditions, 7000-8000 LUX light intensity, 70% humidity, and 22° C. temperature. 3-4 siliques (fruits) bearing developing seeds were selected from at least 3 plants and were hand-dissected to determine what developmental stage(s) were represented by the enclosed embryos. Description of the stages of *Arabidopsis* embryogenesis used in this determination were summarized by Bowman (1994). Silique lengths were then determined and used as an approximate determinant for embryonic stage. Green siliques >10 mm in length containing both green and brown seeds >9 days after flowering (DAF)] were opened and the seeds removed and harvested and flash frozen in liquid nitrogen.

Mature Seeds (24 Hours after Imbibition)

Mature dry seeds of *Arabidopsis thaliana* (ecotype Wassilewskija) were sown onto moistened filter paper and left at 4° C. for two to three days to vernalize. Imbibed seeds were then transferred to a growth chamber [16 hr light: 8 hr dark conditions, 7000-8000 LUX light intensity, 70% humidity, and 22° C. temperature], the emerging seedlings harvested after 48 hours and flash frozen in liquid nitrogen.

Mature Seeds (Dry)

Seeds of *Arabidopsis thaliana* (ecotype Wassilewskija) were sown in pots and left at 4° C. for two to three days to vernalize. They were then transferred to a growth chamber. Plants were grown under long-day (16 hr light: 8 hr dark) conditions, 7000-8000 LUX light intensity, 70% humidity, and 22° C. temperature and taken to maturity. Mature dry seeds are collected, dried for one week at 28° C., and vernalized for one week at 4° C. before used as a source of RNA.

(o) Herbicide Treatment

*Arabidopsis thaliana* (Ws) seeds were sterilized for 5 min. with 30% bleach, 50 µl Triton in a total volume of 50 ml. Seeds were vernalized at 4° C. for 3 days before being plated onto GM agar plates at a density of about 144 seeds per plate. Plates were incubated in a Percival growth chamber having 16 hr light/8 hr dark, 80% relative humidity, 22° C. and 11,000 LUX for 14 days.

Plates were sprayed (~0.5 mls/plate) with water, Finale (1.128 g/L), Glean (1.88 g/L), RoundUp (0.01 g/L) or Trimec (0.08 g/L). Tissue was collected and flash frozen in liquid nitrogen at the following time points: 0, 1, 2, 4, 8, 12 and 24 hours. Frozen tissue was stored at −80° C. prior to RNA isolation.

(p) Root Tips

Seeds of *Arabidopsis thaliana* (ecotype Ws) were placed on MS plates and vernalized at 4° C. for 3 days before being placed in a 25° C. growth chamber having 16 hr light/8 hr dark, 70% relative humidity and about 3 W/m². After 6 days, young seedlings were transferred to flasks containing B5 liquid medium, 1% sucrose and 0.05 mg/l indole-3-butyric acid. Flasks were incubated at room temperature with 100 rpm agitation. Media was replaced weekly. After three weeks, roots were harvested and incubated for 1 hr with 2% pectinase, 0.2% cellulase, pH 7 before straining through a #80 (Sigma) sieve. The root body material remaining on the sieve (used as the control) was flash frozen and stored at −80° C. until use. The material that passed through the #80 sieve was strained through a #200 (Sigma) sieve and the material remaining on the sieve (root tips) was flash frozen and stored at −80° C. until use. Approximately 10 mg of root tips were collected from one flask of root culture.

Seeds of maize hybrid 35A (Pioneer) were sown in water-moistened sand in flats (10 rows, 5-6 seed/row) and covered with clear, plastic lids before being placed in a growth chamber having 16 hr light (25° C.)/8 hr dark (20° C.), 75% relative humidity and 13,000-14,000 LUX. Covered flats were watered every three days for 8 days. Seedlings were carefully removed from the sand and the root tips (~2 mm long) were removed and flash frozen in liquid nitrogen prior to storage at −80° C. The tissues above the root tips (~1 cm long) were cut, treated as above and used as control tissue.

(q) Imbibed Seed

Seeds of maize hybrid 35A (Pioneer) were sown in water-moistened sand in covered flats (10 rows, 5-6 seed/row) and covered with clear, plastic lids before being placed in a growth chamber having 16 hr light (25° C.)/8 hr dark (20° C.), 75% relative humidity and 13,000-14,000 LUX. One day after sowing, whole seeds were flash frozen in liquid nitrogen prior to storage at −80° C. Two days after sowing, embryos and endosperm were isolated and flash frozen in liquid nitrogen prior to storage at −80° C. On days 3-6, aerial tissues, roots and endosperm were isolated and flash frozen in liquid nitrogen prior to storage at −80° C.

(r) Flowers (Green, White or Buds)

Approximately 10 µl of *Arabidopsis thaliana* seeds (ecotype Ws) were sown on 350 soil (containing 0.03% marathon) and vernalized at 4 C for 3 days. Plants were then grown at room temperature under fluorescent lighting until flowering. Flowers were harvested after 28 days in three different categories. Buds that had not opened at all and were completely green were categorized as "flower buds" (also referred to as green buds by the investigator). Buds that had started to open, with white petals emerging slightly were categorized as "green flowers" (also referred to as white buds by the investigator). Flowers that had opened mostly (with no silique elongation) with white petals completely visible were categorized as "white flowers" (also referred to as open flowers by the investigator). Buds and flowers were harvested with forceps, flash frozen in liquid nitrogen and stored at −80 C until RNA was isolated.

s) Ovules

Seeds of *Arabidopsis thaliana* heterozygous for pistillata (pi) [ecotype Landsberg erecta (Ler)] were sown in pots and left at 4° C. for two to three days to vernalize. They were then transferred to a growth chamber. Plants were grown under long-day (16 hr light: 8 hr dark) conditions, 7000-8000 LUX light intensity, 76% humidity, and 24° C. temperature. Inflorescences were harvested from seedlings about 40 days old. The inflorescences were cut into small pieces and incubated in the following enzyme solution (pH 5) at room temperature for 0.5-1 hr.: 0.2% pectolyase Y-23, 0.04% pectinase, 5 mM MES, 3% Sucrose and MS salts (1900 mg/l $KNO_3$, 1650 mg/l $NH_4NO_3$, 370 mg/l $MgSO_4.7H_2O$, 170 mg/l $KH_2PO_4$, 440 mg/l $CaCl_2.2H_2O$, 6.2 mg/l $H_3BO_3$, 15.6 mg/l $MnSO_4.4H_2O$, 8.6 mg/l $ZnSO_4.7H_2O$, 0.25 mg/l $NaMoO_4.2H_2O$, 0.025 mg/l $CuCO_4.5H_2O$, 0.025 mg/l $CoCl_2.6H_2O$, 0.83 mg/l KI, 27.8 mg/l $FeSO_4.7H_2O$, 37.3 mg/l Disodium EDTA, pH 5.8). At the end of the incubation the mixture of inflorescence material and enzyme solution was passed through a size 60 sieve and then through a sieve with a pore size of 125 µm. Ovules greater than 125 µm in diameter were collected, rinsed twice in B5 liquid medium (2500 mg/l $KNO_3$, 250 mg/l $MgSO_4.7H_2O$, 150 mg/l $NaH2PO4.H_2O$, 150 mg/l $CaCl_2.2H_2O$, 134 mg/l (NH4)2 $CaCl_2.SO_4$, 3 mg/l $H_3BO_3$, 10 mg/l $MnSO_4.4H_2O$, 2 $ZnSO_4.7H_2O$, 0.25 mg/l $NaMoO_4.2H_2O$, 0.025 mg/l $CuCO_4.5H_2O$, 0.025 mg/l $CoCl_2.6H_2O$, 0.75 mg/l KI, 40 mg/l EDTA sodium ferric salt, 20 g/l sucrose, 10 mg/l Thiamine hydrochloride, 1 mg/l Pyridoxine hydrochloride, 1 mg/l Nicotinic acid, 100 mg/l myo-inositol, pH 5.5)), rinsed once in deionized water and flash frozen in liquid nitrogen. The supernatant from the 125 µm sieving was passed through subsequent sieves of 50 µm and 32 µm. The tissue retained in the 32 µm sieve was collected and mRNA prepared for use as a control.

t) Wounding

Seeds of *Arabidopsis thaliana* (Wassilewskija) were sown in trays and left at 4° C. for three days to vernalize before being transferred to a growth chamber having 16 hr light/8 hr dark, 12,000-14,000 LUX, 70% humidity and 20° C. After 14 days, the leaves were wounded with forceps. Aerial tissues were harvested 1 hour and 6 hours after wounding. Aerial tissues from unwounded plants served as controls. Tissues were flash-frozen in liquid nitrogen and stored at −80° C.

Seeds of maize hybrid 35A (Pioneer) were sown in water-moistened sand in flats (10 rows, 5-6 seed/row) and covered with clear, plastic lids before being placed in a growth chamber having 16 hr light (25° C.)/8 hr dark (20° C.), 75% relative humidity and 13,000-14,000 LUX. Covered flats were watered every three days for 7 days. Seedlings were wounded (one leaf nicked by scissors) and placed in 1-liter beakers of water for treatment. Control plants were treated not wounded. After 1 hr and 6 hr aerial and root tissues were separated and flash frozen in liquid nitrogen prior to storage at −80° C.

u) Nitric Oxide Treatment

Seeds of *Arabidopsis thaliana* (Wassilewskija) were sown in trays and left at 4° C. for three days to vernalize before being transferred to a growth chamber having 16 hr light/8 hr dark, 12,000-14,000 LUX, 20° C. and 70% humidity. Fourteen day old plants were sprayed with 5 mM sodium nitroprusside in a 0.02% Silwett L-77 solution. Control plants were sprayed with a 0.02% Silwett L-77 solution. Aerial tissues were harvested 1 hour and 6 hours after spraying, flash-frozen in liquid nitrogen and stored at −80° C.

Seeds of maize hybrid 35A (Pioneer) were sown in water-moistened sand in flats (10 rows, 5-6 seed/row) and covered with clear, plastic lids before being placed in a growth chamber having 16 hr light (25° C.)/8 hr dark (20° C.), 75% relative humidity and 13,000-14,000 LUX. Covered flats were watered every three days for 7 days. Seedlings were carefully removed from the sand and placed in 1-liter beakers with 5 mM nitroprusside for treatment. Control plants were treated with water. After 1 hr, 6 hr and 12 hr, aerial and root tissues were separated and flash frozen in liquid nitrogen prior to storage at −80° C.

v) Root Hairless mutants

Plants mutant at the rhl gene locus lack root hairs. This mutation is maintained as a heterozygote.

Seeds of *Arabidopsis thaliana* (Landsberg erecta) mutated at the rhl gene locus were sterilized using 30% bleach with 1 ul/ml 20% Triton-X 100 and then vernalized at 4° C. for 3 days before being plated onto GM agar plates. Plates were placed in growth chamber with 16 hr light/8 hr. dark, 23° C., 14,500-15,900 LUX, and 70% relative humidity for germination and growth.

After 7 days, seedlings were inspected for root hairs using a dissecting microscope. Mutants were harvested and the cotyledons removed so that only root tissue remained. Tissue was then flash frozen in liquid nitrogen and stored at −80 C.

*Arabidopsis thaliana* (Landsberg erecta) seedlings grown and prepared as above were used as controls.

Alternatively, seeds of *Arabidopsis thaliana* (Landsberg erecta), heterozygous for the rhl1 (root hairless) mutation, were surface-sterilized in 30% bleach containing 0.1% Triton X-100 and further rinsed in sterile water. They were then vernalized at 4° C. for 4 days before being plated onto MS agar plates. The plates were maintained in a growth chamber at 24° C. with 16 hr light/8 hr dark for germination and growth. After 10 days, seedling roots that expressed the phenotype (i.e. lacking root hairs) were cut below the hypocotyl junction, frozen in liquid nitrogen and stored at −80° C. Those seedlings with the normal root phenotype (heterozygous or wt) were collected as described for the mutant and used as controls.

w) Ap2

Seeds of *Arabidopsis thaliana* (ecotype Landesberg erecta) and floral mutant apetala2 (Jofuku et al., 1994, Plant Cell 6:1211-1225) were sown in pots and left at 4° C. for two to three days to vernalize. They were then transferred to a growth chamber. Plants were grown under long-day (16 hr light, 8 hr dark) conditions 7000-8000 LUX light intensity, 70% humidity and 22° C. temperature. Inflorescences containing immature floral buds (stages 1-7; Bowman, 1994) as well as the inflorescence meristem were harvested and flash-frozen. Polysomal polyA+ RNA was isolated from tissue according to Cox and Goldberg, 1988).

x) Salt

*Arabidopsis thaliana* ecotype Ws seeds were vernalized at 4° C. for 3 days before sowing in flats containing vermiculite soil. Flats were placed at 20° C. in a Conviron growth chamber having 16 hr light/8 hr dark. Whole plants (used as controls) received water. Other plants were treated with 100 mM NaCl. After 6 hr and 72 hr, aerial and root tissues were harvested and flash frozen in liquid nitrogen prior to storage at −80° C.

y) Petals

*Arabidopsis thaliana* ecotype Ws seeds were vernalized at 4° C. for 3 days before sowing in flats containing vermiculite soil. Flats were watered placed at 20° C. in a Conviron growth chamber having 16 hr light/8 hr dark. Whole plants (used as the control) and petals from inflorescences 23-25 days after germination were harvested, flash frozen in liquid nitrogen and stored at −80° C.

z) Pollen

*Arabidopsis thaliana* ecotype Ws seeds were vernalized at 4° C. for 3 days before sowing in flats containing vermiculite soil. Flats were watered and placed at 20° C. in a Conviron growth chamber having 16 hr light/8 hr dark. Whole plants (used as controls) and pollen from plants 38 dap was harvested, flash frozen in liquid nitrogen and stored at −80° C.

aa) Interploidy Crosses

Interploidy crosses involving a 6× parent are lethal. Crosses involving a 4× parent are complete and analyzed. The imbalance in the maternal/paternal ratio produced from the cross can lead to big seeds. *Arabidopsis thaliana* ecotype Ws seeds were vernalized at 4° C. for 3 days before sowing. Small siliques were harvested at 5 days after pollination, flash frozen in liquid nitrogen and stored at −80° C.

bb) Line Comparisons

Alkaloid 35S over-expressing lines were used to monitor the expression levels of terpenoid/alkaloid biosynthetic and P450 genes to identify the transcriptional regulatory points I the biosynthesis pathway and the related P450 genes. *Arabidopsis thaliana* ecotype Ws seeds were vernalized at 4° C. for 3 days before sowing in vermiculite soil (Zonolite) supplemented by Hoagland solution. Flats were placed in Conviron growth chambers under long day conditions (16 hr light, 23° C./8 hr dark, 20° C.) Basta spray and selection of the overexpressing lines was conducted about 2 weeks after germination. Approximately 2-3 weeks after bolting (approximately 5-6 weeks after germination), stem and siliques from the over-expressing lines and from wild-type plants were harvested, flash frozen in liquid nitrogen and stored at −80° C.

cc) DMT-II

Demeter (dmt) is a mutant of a methyl transferase gene and is similar to fie. *Arabidopsis thaliana* ecotype Ws seeds were vernalized at 4° C. for 3 days before sowing. Cauline leaves and closed flowers were isolated from 35S::DMT and dmt −/− plant lines, flash frozen in liquid nitrogen and stored at −80° C.

dd) CS6630 Roots and Shoots

*Arabidopsis thaliana* ecotype Ws seeds were vernalized at 4° C. for 3 days before sowing on MS media (1%) sucrose on bactor-agar. Roots and shoots were separated 14 days after germination, flash frozen in liquid nitrogen and stored at −80° C.

ee) CS237

CS237 is an ethylene triple response mutant that is insensitive to ethylene and which has an etr1-1 phenotype. *Arabidopsis thaliana* CS237 seeds were vernalized at 4° C. for 3 days before sowing. Aerial tissue was collected from mutants and wild-type Columbia ecotype plants, flash frozen in liquid nitrogen and stored at −80° C.

ff) Guard Cells

*Arabidopsis thaliana* ecotype Ws seeds were vernalized at 4° C. for 3 days before sowing. Leaves were harvested, homogenized and centrifuged to isolate the guard cell containing fraction. Homogenate from leaves served as the control. Samples were flash frozen in liquid nitrogen and stored at −80° C. Identical experiments using leaf tissue from canola were performed.

gg) 3642-1

3642-1 is a T-DNA mutant that affects leaf development. This mutant segregates 3:1, wild-type:mutant. *Arabidopsis thaliana* 3642-1 mutant seeds were vernalized at 4° C. for 3 days before sowing in flats of MetroMix 200. Flats were placed in the greenhouse, watered and grown to the 8 leaf, pre-flower stage. Stems and rosette leaves were harvested from the mutants and the wild-type segregants, flash frozen and stored at −80° C.

hh) Caf

Carp1e factory (Caf) is a double-stranded RNAse protein that is hypothesized to process small RNAs in *Arabidopsis*. The protein is closely related to a *Drosophila* protein named DICER that functions in the RNA degradation steps of RNA interference. *Arabidopsis thaliana* Caf mutant seeds were vernalized at 4° C. for 3 days before sowing in flats of Metro-Mix 200. Flats were placed in the greenhouse, watered and grown to the 8 leaf, pre-flower stage. Stems and rosette leaves were harvested from the mutants and the wild-type segregants, flash frozen and stored at −80° C.

2. Microarray Hybridization Procedures

Microarray technology provides the ability to monitor mRNA transcript levels of thousands of genes in a single experiment. These experiments simultaneously hybridize two differentially labeled fluorescent cDNA pools to glass slides that have been previously spotted with cDNA clones of the same species. Each arrayed cDNA spot will have a corresponding ratio of fluorescence that represents the level of disparity between the respective mRNA species in the two sample pools. Thousands of polynucleotides can be spotted on one slide, and each experiment generates a global expression pattern.

Coating Slides

The microarray consists of a chemically coated microscope slide, referred herein as a "chip" with numerous polynucleotide samples arrayed at a high density. The poly-L-lysine coating allows for this spotting at high density by providing a hydrophobic surface, reducing the spreading of spots of DNA solution arrayed on the slides. Glass microscope slides (Gold Seal #3010 manufactured by Gold Seal Products, Portsmouth, N.H., USA) were coated with a 0.1% W/V solution of Poly-L-lysine (Sigma, St. Louis, Mo.) using the following protocol:

1. Slides were placed in slide racks (Shandon Lipshaw #121). The racks were then put in chambers (Shandon Lipshaw #121).
2. Cleaning solution was prepared:
   70 g NaOH was dissolved in 280 mL ddH$_2$O.
   420 mL 95% ethanol was added. The total volume was 700 mL (=2×350 mL); it was stirred until completely mixed. If the solution remained cloudy, ddH$_2$O was added until clear.
3. The solution was poured into chambers with slides; the chambers were covered with glass lids. The solution was mixed on an orbital shaker for 2 hr.
4. The racks were quickly transferred to fresh chambers filled with ddH$_2$O. They were rinsed vigorously by plunging racks up and down. Rinses were repeated 4× with fresh ddH$_2$O each time, to remove all traces of NaOH-ethanol.
5. Polylysine solution was prepared:
   0 mL poly-L-lysine+70 mL tissue culture PBS in 560 mL water, using plastic graduated cylinder and beaker.
6. Slides were transferred to polylysine solution and shaken for 1 hr.
7. The rack was transferred to a fresh chambers filled with ddH$_2$O. It was plunged up and down 5× to rinse.
8. The slides were centrifuged on microtiter plate carriers (paper towels were placed below the rack to absorb liquid) for 5 min. @ 500 rpm. The slide racks were transferred to empty chambers with covers.
9. Slide racks were dried in a 45 C oven for 10 min.
10. The slides were stored in a closed plastic slide box.
11. Normally, the surface of lysine coated slides was not very hydrophobic immediately after this process, but became increasingly hydrophobic with storage. A hydrophobic surface helped ensure that spots didn't run together while printing at high densities. After they aged for 10 days to a month the slides were ready to use. However, coated slides that have been sitting around for long periods of time were usually too old to be used. This was because they developed opaque patches, visible when held to the light, and these resulted in high background hybridization from the fluorescent probe. Alternatively, pre-coated glass slides were purchased from TeleChem International, Inc. (Sunnyvale, Calif., 94089; catalog number SMM-25, Superamine substrates).

PCR Amplification of cDNA Clone Inserts

Polynucleotides were amplified from *Arabidopsis* cDNA clones using insert specific probes. The resulting 100 uL PCR reactions were purified with Qiaquick 96 PCR purification columns (Qiagen, Valencia, Calif., USA) and eluted in 30 uL of 5 mM Tris. 8.5 uL of the elution were mixed with 1.5 uL of 20×SSC to give a final spotting solution of DNA in 3×SSC. The concentrations of DNA generated from each clone varied between 10-100 ng/ul, but were usually about 50 ng/ul.

Arraying of PCR Products on Glass Slides

PCR products from cDNA clones were spotted onto the poly-L-Lysine coated glass slides using an arrangement of quill-tip pins (ChipMaker 3 spotting pins; Telechem, International, Inc., Sunnyvale, Calif., USA) and a robotic arrayer (PixSys 3500, Cartesian Technologies, Irvine, Calif., USA). Around 0.5 nl of a prepared PCR product was spotted at each location to produce spots with approximately 100 um diameters. Spot center-to-center spacing was from 180 um to 210 um depending on the array. Printing was conducted in a chamber with relative humidity set at 50%.

Slides containing maize sequences were purchased from Agilent Technology (Palo Alto, Calif. 94304).

Post-Processing of Slides

After arraying, slides were processed through a series of steps—rehydration, UV cross-linking, blocking and denaturation—required prior to hybridization. Slides were rehydrated by placing them over a beaker of warm water (DNA face down), for 2-3 sec, to distribute the DNA more evenly within the spots, and then snap dried on a hot plate (DNA side, face up). The DNA was then cross-linked to the slides by UV irradiation (60-65 mJ; 2400 Stratalinker, Stratagene, La Jolla, Calif., USA).

Following this a blocking step was performed to modify remaining free lysine groups, and hence minimize their ability to bind labeled probe DNA. To achieve this the arrays were placed in a slide rack. An empty slide chamber was left ready on an orbital shaker. The rack was bent slightly inwards in the middle, to ensure the slides would not run into each other while shaking. The blocking solution was prepared as follows:

3×350-ml glass chambers (with metal tops) were set to one side, and a large round Pyrex dish with $dH_2O$ was placed ready in the microwave. At this time, 15 ml sodium borate was prepared in a 50 ml conical tube.

6-g succinic anhydride was dissolved in approx. 325-350 mL 1-methyl-2-pyrrolidinone. Rapid addition of reagent was crucial.

a. Immediately after the last flake of the succinic anhydride dissolved, the 15-mL sodium borate was added.

b. Immediately after the sodium borate solution mixed in, the solution was poured into an empty slide chamber.

c. The slide rack was plunged rapidly and evenly in the solution. It was vigorously shaken up and down for a few seconds, making sure slides never left the solution.

d. It was mixed on an orbital shaker for 15-20 min. Meanwhile, the water in the Pyrex dish (enough to cover slide rack) was heated to boiling.

Following this, the slide rack was gently plunge in the 95 C water (just stopped boiling) for 2 min. Then the slide rack was plunged 5× in 95% ethanol. The slides and rack were centrifuged for 5 min. @ 500 rpm. The slides were loaded quickly and evenly onto the carriers to avoid streaking. The arrays were used immediately or store in slide box.

The Hybridization process began with the isolation of mRNA from the two tissues (see "Isolation of total RNA" and "Isolation of mRNA", below) in question followed by their conversion to single stranded cDNA (see "Generation of probes for hybridization", below). The cDNA from each tissue was independently labeled with a different fluorescent dye and then both samples were pooled together. This final differentially labeled cDNA pool was then placed on a processed microarray and allowed to hybridize (see "Hybridization and wash conditions", below).

Isolation of Total RNA

Approximately 1 g of plant tissue was ground in liquid nitrogen to a fine powder and transferred into a 50-ml centrifuge tube containing 10 ml of Trizol reagent. The tube was vigorously vortexed for 1 min and then incubated at room temperature for 10-20 min. on an orbital shaker at 220 rpm. Two ml of chloroform was added to the tube and the solution vortexed vigorously for at least 30-sec before again incubating at room temperature with shaking. The sample was then centrifuged at 12,000×g (10,000 rpm) for 15-20 min at 4° C. The aqueous layer was removed and mixed by inversion with 2.5 ml of 1.2 M NaCl/0.8 M Sodium Citrate and 2.5 ml of isopropyl alcohol added. After a 10 min. incubation at room temperature, the sample was centrifuged at 12,000×g (10,000 rpm) for 15 min at 4° C. The pellet was washed with 70% ethanol, re-centrifuged at 8,000 rpm for 5 min and then air dried at room temperature for 10 min. The resulting total RNA was dissolved in either TE (10 mM Tris-HCl, 1 mM EDTA, pH 8.0) or DEPC (diethylpyrocarbonate) treated deionized water (RNAse-free water). For subsequent isolation of mRNA using the Qiagen kit, the total RNA pellet was dissolved in RNAse-free water.

Isolation of mRNA mRNA was isolated using the Qiagen Oligotex mRNA Spin-Column protocol (Qiagen, Valencia, Calif.). Briefly, 500 μl OBB buffer (20 mM Tris-Cl, pH 7.5, 1 M NaCl, 2 mM EDTA, 0.2% SDS) was added to 500 μl of total RNA (0.5-0.75 mg) and mixed thoroughly. The sample was first incubated at 70° C. for 3 min, then at room temperature for 10 minutes and finally centrifuged for 2 min at 14,000-18,000×g. The pellet was resuspended in 400 μl OW2 buffer (10 mM Tris-Cl, pH 7.5, 150 mM NaCl, 1 mM EDTA) by vortexing, the resulting solution placed on a small spin column in a 1.5 ml RNase-free microcentrifuge tube and centrifuged for 1 min at 14,000-18,000×g. The spin column was transferred to a new 1.5 ml RNase-free microcentrifuge tube and washed with 400 μl of OW2 buffer. To release the isolated mRNA from the resin, the spin column was again transferred to a new RNase-free 1.5 ml microcentrifuge tube, 20-100 μl 70° C. OEB buffer (5 mM Tris-Cl, pH 7.5) added and the resin resuspended in the resulting solution via pipetting. The mRNA solution was collected after centrifuging for 1 min at 14,000-18,000×g.

Alternatively, mRNA was isolated using the Stratagene Poly(A) Quik mRNA Isolation Kit (Startagene, La Jolla, Calif.). Here, up to 0.5 mg of total RNA (maximum volume of 1 ml) was incubated at 65° C. for 5 minutes, snap cooled on ice and 0.1× volumes of 10× sample buffer (10 mM Tris-HCl (pH 7.5), 1 mM EDTA (pH 8.0) 5 M NaCl) added. The RNA sample was applied to a prepared push column and passed through the column at a rate of ~1 drop every 2 sec. The solution collected was reapplied to the column and collected as above. 200 μl of high salt buffer (10 mM Tris-HCl (pH 7.5), 1 mM EDTA, 0.5 NaCl) was applied to the column and passed through the column at a rate of ~1 drop every 2 sec. This step was repeated and followed by three low salt buffer (10 mM Tris-HCl (pH 7.5), 1 mM EDTA, 0.1 M NaCl) washes preformed in a similar manner. mRNA was eluted by applying to the column four separate 200 μl aliquots of elution buffer (10 mM Tris-HCl (pH 7.5), 1 mM EDTA) preheated to 65° C. Here, the elution buffer was passed through the column at a rate of 1 drop/sec. The resulting mRNA solution was precipitated by adding 0.1× volumes of 10× sample buffer, 2.5 volumes of ice-cold 100% ethanol, incubating overnight at −20° C. and centrifuging at 14,000-18,000×g for 20-30 min at 4° C. The pellet was washed with 70% ethanol and air dried for 10 min. at room temperature before resuspension in RNase-free deionized water.

Preparation of Yeast Controls

Plasmid DNA was isolated from the following yeast clones using Qiagen filtered maxiprep kits (Qiagen, Valencia, Calif.): YAL022c(Fun26), YAL031c(Fun21), YBR032w, YDL131w, YDL182w, YDL194w, YDL196w, YDR050c and YDR116c. Plasmid DNA was linearized with either BsrBI (YAL022c(Fun26), YAL031c(Fun21), YDL131w, YDL182w, YDL194w, YDL196w, YDR050c) or AflIII (YBR032w, YDR116c) and isolated.

In Vitro Transcription of Yeast Clones

The following solution was incubated at 37° C. for 2 hours: 17 μl of isolated yeast insert DNA (1 μg), 20 μl 5× buffer, 10 μl 100 mM DTT, 2.5 μl (100 U) RNasin, 20 μl 2.5 mM (ea.)

rNTPs, 2.7 µl (40 U) SP6 polymerase and 27.8 µl RNase-free deionized water. 2 µl (2 U) Ampli DNase I was added and the incubation continued for another 15 min. 10 µl 5M NH$_4$OAC and 100 µl phenol:chloroform:isoamyl alcohol (25:24:1) were added, the solution vortexed and then centrifuged to separate the phases. To precipitate the RNA, 250 µl ethanol was added and the solution incubated at −20° C. for at least one hour. The sample was then centrifuged for 20 min at 4° C. at 14,000-18,000×g, the pellet washed with 500 µl of 70% ethanol, air dried at room temperature for 10 min and resuspended in 100 µl of RNase-free deionized water. The precipitation procedure was then repeated.

Alternatively, after the two-hour incubation, the solution was extracted with phenol/chloroform once before adding 0.1 volume 3M sodium acetate and 2.5 volumes of 100% ethanol. The solution was centrifuged at 15,000 rpm, 4° C. for 20 minutes and the pellet resuspended in RNase-free deionized water. The DNase I treatment was carried out at 37° C. for 30 minutes using 2 U of Ampli DNase I in the following reaction condition: 50 mM Tris-HCl (pH 7.5), 10 mM MgCl$_2$. The DNase I reaction was then stopped with the addition of NH$_4$OAC and phenol:chloroform:isoamyl alcohol (25:24:1), and RNA isolated as described above.

0.15-2.5 ng of the in vitro transcript RNA from each yeast clone were added to each plant mRNA sample prior to labeling to serve as positive (internal) probe controls.

Generation of Probes for Hybridization
Generation of Labeled Probes for Hybridization from First-Strand cDNA Hybridization probes were generated from isolated mRNA using an Atlas™ Glass Fluorescent Labeling Kit (Clontech Laboratories, Inc., Palo Alto, Calif., USA). This entails a two step labeling procedure that first incorporates primary aliphatic amino groups during cDNA synthesis and then couples fluorescent dye to the cDNA by reaction with the amino functional groups. Briefly, 5 µg of oligo(dT)$_{18}$ primer d(TTTTTTTTTTTTTTTTTTV) was mixed with Poly A+ mRNA (1.5-2 µg mRNA isolated using the Qiagen Oligotex mRNA Spin-Column protocol or the Stratagene Poly(A) Quik mRNA Isolation protocol (Stratagene, La Jolla, Calif., USA)) in a total volume of 25 µl. The sample was incubated in a thermocycler at 70° C. for 5 min, cooled to 48° C. and 10 µl of 5× cDNA Synthesis Buffer (kit supplied), 5 µl 10× dNTP mix (dATP, dCTP, dGTP, dTTP and aminoallyl-dUTP; kit supplied), 7.5 µl deionized water and 2.5 µl MMLV Reverse Transcriptase (500 U) added. The reaction was then incubated at 48° C. for 30 minutes, followed by 1 hr incubation at 42° C. At the end of the incubation the reaction was heated to 70° C. for 10 min, cooled to 37° C. and 0.5 µl (5 U) RNase H added, before incubating for 15 min at 37° C. The solution was vortexed for 1 min after the addition of 0.5 µl 0.5 M EDTA and 5 µl of QuickClean Resin (kit supplied) then centrifuged at 14,000-18,000×g for 1 min. After removing the supernatant to a 0.45 µm spin filter (kit supplied), the sample was again centrifuged at 14,000-18,000×g for 1 min, and 5.5 µl 3 M sodium acetate and 137.5 µl of 100% ethanol added to the sample before incubating at −20° C. for at least 1 hr. The sample was then centrifuged at 14,000-18,000×g at 4° C. for 20 min, the resulting pellet washed with 500 µl 70% ethanol, air-dried at room temperature for 10 min and resuspended in 10 µl of 2× fluorescent labeling buffer (kit provided). 10 µl each of the fluorescent dyes Cy3 and Cy5 (Amersham Pharmacia (Piscataway, N.J., USA); prepared according to Atlas™ kit directions of Clontech) were added and the sample incubated in the dark at room temperature for 30 min.

The fluorescently labeled first strand cDNA was precipitated by adding 2 µl 3M sodium acetate and 50 µl 100% ethanol, incubated at −20° C. for at least 2 hrs, centrifuged at 14,000-18,000×g for 20 min, washed with 70% ethanol, air-dried for 10 min and dissolved in 100 µl of water.

Alternatively, 3-4 µg mRNA, 2.5 (~8.9 ng of in vitro translated mRNA) µl yeast control and 3 µg oligo dTV (TTTTTTTTTTTTTTTTTTT(A/C/G) were mixed in a total volume of 24.7 µl. The sample was incubated in a thermocycler at 70° C. for 10 min. before chilling on ice. To this, 8 µl of 5× first strand buffer (SuperScript II RNase H—Reverse Transcriptase kit from Invitrogen (Carlsbad, Calif. 92008); cat no. 18064022), 0.8° C. of aa-dUTP/dNTP mix (50×; 25 mM dATP, 25 mM dGTP, 25 mM dCTP, 15 mM dTTP, 10 mM aminoallyl-dUTP), 4 µl of 0.1 M DTT and 2.5 µl (500 units) of Superscript R.T.II enzyme (Stratagene) were added. The sample was incubated at 42° C. for 2 hours before a mixture of 10° C. of 1M NaOH and 10° C. of 0.5 M EDTA were added. After a 15 minute incubation at 65° C., 25 µl of 1 M Tris pH 7.4 was added. This was mixed with 450 µl of water in a Microcon 30 column before centrifugation at 11,000×g for 12 min. The column was washed twice with 450 µl (centrifugation at 11,000 g, 12 min.) before eluting the sample by inverting the Microcon column and centrifuging at 11,000×g for 20 seconds. Sample was dehydrated by centrifugation under vacuum and stored at −20° C.

Each reaction pellet was dissolved in 9 µl of 0.1 M carbonate buffer (0.1M sodium carbonate and sodium bicarbonate, pH=8.5-9) and 4.5 µl of this placed in two microfuge tubes. 4.5 µl of each dye (in DMSO) were added and the mixture incubated in the dark for 1 hour. 4.5 µl of 4 M hydroxylamine was added and again incubated in the dark for 15 minutes.

Regardless of the method used for probe generation, the probe was purified using a Qiagen PCR cleanup kit (Qiagen, Valencia, Calif., USA), and eluted with 100 ul EB (kit provided). The sample was loaded on a Microcon YM-30 (Millipore, Bedford, Mass., USA) spin column and concentrated to 4-5 ul in volume. Probes for the maize microarrays were generated using the Fluorescent Linear Amplification Kit (cat. No. G2556A) from Agilent Technologies (Palo Alto, Calif.).

Hybridization and Wash Conditions
The following Hybridization and Washing Condition were developed:
Hybridization Conditions:

Labeled probe was heated at 95° C. for 3 min and chilled on ice. Then 25 □L of the hybridization buffer which was warmed at 42 C was added to the probe, mixing by pipetting, to give a final concentration of:

50% formamide
4×SSC
0.03% SDS
5×Denhardt's solution
0.1 µg/ml single-stranded salmon sperm DNA The probe was kept at 42 C. Prior to the hybridization, the probe was heated for 1 more min., added to the array, and then covered with a glass cover slip. Slides were placed in hybridization chambers (Telechem, Sunnyvale, Calif.) and incubated at 42° C. overnight.

Washing Conditions:
A. Slides were washed in 1×SSC+0.03% SDS solution at room temperature for 5 minutes,
B. Slides were washed in 0.2×SSC at room temperature for 5 minutes,
C. Slides were washed in 0.05×SSC at room temperature for 5 minutes.

After A, B, and C, slides were spun at 800×g for 2 min. to dry. They were then scanned.

Maize microarrays were hybridized according to the instructions included Fluorescent Linear Amplification Kit (cat. No. G2556A) from Agilent Technologies (Palo Alto, Calif.).

Scanning of Slides

The chips were scanned using a ScanArray 3000 or 5000 (General Scanning, Watertown, Mass., USA). The chips were scanned at 543 and 633 nm, at 10 um resolution to measure the intensity of the two fluorescent dyes incorporated into the samples hybridized to the chips.

Data Extraction and Analysis

The images generated by scanning slides consisted of two 16-bit TIFF images representing the fluorescent emissions of the two samples at each arrayed spot. These images were then quantified and processed for expression analysis using the data extraction software Imagene™ (Biodiscovery, Los Angeles, Calif., USA). Imagene output was subsequently analyzed using the analysis program Genespring™ (Silicon Genetics, San Carlos, Calif., USA). In Genespring, the data was imported using median pixel intensity measurements derived from Imagene output. Background subtraction, ratio calculation and normalization were all conducted in Genespring. Normalization was achieved by breaking the data in to 32 groups, each of which represented one of the 32 pin printing regions on the microarray. Groups consist of 360 to 550 spots. Each group was independently normalized by setting the median of ratios to one and multiplying ratios by the appropriate factor.

Results

The results of the microarray experiments are set forth in Table 1 in the section entitled "Microarray Data" which shows the results of the differential expression experiments for the mRNAs, as reported by their corresponding cDNA ID number, that were differentially transcribed under a particular set of conditions as compared to a control sample. The cDNA ID numbers correspond to those utilized. Increases in mRNA abundance levels in experimental plants versus the controls are denoted with the plus sign (+). Likewise, reductions in mRNA abundance levels in the experimental plants are denoted with the minus (−) sign.

The Table 1 section entitled "Microarray Data" is organized according to the clone number with each set of experimental conditions being denoted by the term "Expt Rep ID:" followed by a "short name". The row titled "Microarray Experiment Parameters" links each "short name" with a short description of the experiment and the parameters.

The sequences showing differential expression in a particular experiment (denoted by either a "+" or "−" in the column in Table 1 entitled "SIGNCLOG_RATIO") thereby show utility for a function in a plant, and these functions/utilities are described in detail below, where the title of each section (i.e. a "utility section") is correlated with the particular differential expression experiment in the section of Table 1 entitled "Microarray Experiment Parameters".

Organ-Affecting Genes, Gene Components, Products (Including Differentiation and Function)

Root Genes

The economic values of roots arise not only from harvested adventitious roots or tubers, but also from the ability of roots to funnel nutrients to support growth of all plants and increase their vegetative material, seeds, fruits, etc. Roots have four main functions. First, they anchor the plant in the soil. Second, they facilitate and regulate the molecular signals and molecular traffic between the plant, soil, and soil fauna. Third, the root provides a plant with nutrients gained from the soil or growth medium. Fourth, they condition local soil chemical and physical properties.

Root genes are active or potentially active to a greater extent in roots than in most other organs of the plant. These genes and gene products can regulate many plant traits from yield to stress tolerance. Root genes can be used to modulate root growth and development.

Differential Expression of the Sequences in Roots

The relative levels of mRNA product in the root versus the aerial portion of the plant was measured. Specifically, mRNA was isolated from roots and root tips of *Arabidopsis* plants and compared to mRNA isolated from the aerial portion of the plants utilizing microarray procedures.

Root Hair Genes, Gene Components and Products

Root hairs are specialized outgrowths of single epidermal cells termed trichoblasts. In many and perhaps all species of plants, the trichoblasts are regularly arranged around the perimeter of the root. In *Arabidopsis*, for example, trichoblasts tend to alternate with non-hair cells or atrichoblasts. This spatial patterning of the root epidermis is under genetic control, and a variety of mutants have been isolated in which this spacing is altered or in which root hairs are completely absent.

The root hair development genes of the instant invention are useful to modulate one or more processes of root hair structure and/or function including (1) development; (2) interaction with the soil and soil contents; (3) uptake and transport in the plant; and (4) interaction with microorganisms.

1.) Development

The surface cells of roots can develop into single epidermal cells termed trichoblasts or root hairs. Some of the root hairs will persist for the life of the plant; others will gradually die back; some may cease to function due to external influences. These genes and gene products can be used to modulate root hair density or root hair growth; including rate, timing, direction, and size, for example. These genes and gene products can also be used to modulate cell properties such as cell size, cell division, rate and direction and number, cell elongation, cell differentiation, lignified cell walls, epidermal cells (including trichoblasts) and root apical meristem cells (growth and initiation); and root hair architecture such as leaf cells under the trichome, cells forming the base of the trichome, trichome cells, and root hair responses. In addition these genes and gene products can be used to modulate one or more of the growth and development processes in response to internal plant programs or environmental stimuli in, for example, the seminal system, nodal system, hormone responses, Auxin, root cap abscission, root senescence, gravitropism, coordination of root growth and development with that of other organs (including leaves, flowers, seeds, fruits, and stems), and changes in soil environment (including water, minerals, Ph, and microfauna and flora).

2.) Interaction with Soil and Soil Contents

Root hairs are sites of intense chemical and biological activity and as a result can strongly modify the soil they contact. Roots hairs can be coated with surfactants and mucilage to facilitate these activities. Specifically, roots hairs are responsible for nutrient uptake by mobilizing and assimilating water, reluctant ions, organic and inorganic compounds and chemicals. In addition, they attract and interact with beneficial microfauna and flora. Root hairs also help to mitigate the effects of toxic ions, pathogens and stress. Thus, root hair genes and gene products can be used to modulate traits such as root hair surfactant and mucilage (including composition and secretion rate and time); nutrient uptake (including water, nitrate and other sources of nitrogen, phosphate, potassium, and micronutrients (e.g. iron, copper, etc.); microbe and nematode associations (such as bacteria including nitrogen-fixing bacteria, mycorrhizae, nodule-forming and other nematodes, and nitrogen fixation); oxygen transpiration; detoxification effects of iron, aluminum, cadium, mercury, salt, and other soil constituents; pathogens (including chemical repellents) glucosinolates (GSL1), which release pathogen-controlling isothiocyanates; and changes in soil (such as Ph, mineral excess and depletion), and rhizosheath.

3.) Transport of Materials in Plants

Uptake of the nutrients by the root and root hairs contributes a source-sink effect in a plant. The greater source of nutrients, the more sinks, such as stems, leaves, flowers, seeds, fruits, etc. can draw sustenance to grow. Thus, root hair development genes and gene products can be used to modulate the vigor and yield of the overall plant as well as distinct cells, organs, or tissues of a plant. The genes and gene products, therefore, can modulate plant nutrition, growth rate (such as whole plant, including height, flowering time, etc., seedling, coleoptile elongation, young leaves, stems, flowers, seeds and fruit) and yield, including biomass (fresh and dry weight during any time in plant life, including maturation and senescence), number of flowers, number of seeds, seed yield, number, size, weight and harvest index (content and composition, e.g. amino acid, jasmonate, oil, protein and starch) and fruit yield (number, size, weight, harvest index, and post harvest quality).

Reproduction Genes, Gene Components and Products

Reproduction genes are defined as genes or components of genes capable of modulating any aspect of sexual reproduction from flowering time and inflorescence development to fertilization and finally seed and fruit development. These genes are of great economic interest as well as biological importance. The fruit and vegeTable industry grosses over $1 billion USD a year. The seed market, valued at approximately $15 billion USD annually, is even more lucrative.

Inflorescence and Floral Development Genes, Gene Components and Products

During reproductive growth the plant enters a program of floral development that culminates in fertilization, followed by the production of seeds. Senescence may or may not follow. The flower formation is a precondition for the sexual propagation of plants and is therefore essential for the propagation of plants that cannot be propagated vegetatively as well as for the formation of seeds and fruits. The point of time at which the merely vegetative growth of plants changes into flower formation is of vital importance for example in agriculture, horticulture and plant breeding. Also the number of flowers is often of economic importance, for example in the case of various useful plants (tomato, cucumber, zucchini, cotton etc.) with which an increased number of flowers may lead to an increased yield, or in the case of growing ornamental plants and cut flowers.

Flowering plants exhibit one of two types of inflorescence architecture: indeterminate, in which the inflorescence grows indefinitely, or determinate, in which a terminal flower is produced. Adult organs of flowering plants develop from groups of stem cells called meristems. The identity of a meristem is inferred from structures it produces: vegetative meristems give rise to roots and leaves, inflorescence meristems give rise to flower meristems, and flower meristems give rise to floral organs such as sepals and petals. Not only are meristems capable of generating new meristems of different identity, but their own identity can change during development. For example, a vegetative shoot meristem can be transformed into an inflorescence meristem upon floral induction, and in some species, the inflorescence meristem itself will eventually become a flower meristem. Despite the importance of meristem transitions in plant development, little is known about the underlying mechanisms.

Following germination, the shoot meristem produces a series of leaf meristems on its flanks. However, once floral induction has occurred, the shoot meristem switches to the production of flower meristems. Flower meristems produce floral organ primordia, which develop individually into sepals, petals, stamens or carpels. Thus, flower formation can be thought of as a series of distinct developmental steps, i.e. floral induction, the formation of flower primordia and the production of flower organs. Mutations disrupting each of the steps have been isolated in a variety of species, suggesting that a genetic hierarchy directs the flowering process (see for review, Weigel and Meyerowitz, In Molecular Basis of Morphogenesis (ed. M. Bernfield). 51st Annual Symposium of the Society for Developmental Biology, pp. 93-107, New York, 1993).

Expression of many reproduction genes and gene products is orchestrated by internal programs or the surrounding environment of a plant. These genes can be used to modulate traits such as fruit and seed yield Seed and Fruit Development Genes, Gene Components and Products The ovule is the primary female sexual reproductive organ of flowering plants. At maturity it contains the egg cell and one large central cell containing two polar nuclei encased by two integuments that, after fertilization, develops into the embryo, endosperm, and seed coat of the mature seed, respectively. As the ovule develops into the seed, the ovary matures into the fruit or silique. As such, seed and fruit development requires the orchestrated transcription of numerous polynucleotides, some of which are ubiquitous, others that are embryo-specific and still others that are expressed only in the endosperm, seed coat, or fruit. Such genes are termed fruit development responsive genes and can be used to modulate seed and fruit growth and development such as seed size, seed yield, seed composition and seed dormancy.

Differential Expression of the Sequences in Siliques, Inflorescences and Flowers The relative levels of mRNA product in the siliques relative to the plant as a whole was measured.

Differential Expression of the Sequences in Hybrid Seed Development

The levels of mRNA product in the seeds relative to those in a leaf and floral stems was measured.

Development Genes, Gene Components And Products

Imbibition And Germination Responsive Genes, Gene Components And Products

Seeds are a vital component of the world's diet. Cereal grains alone, which comprise ~90% of all cultivated seeds, contribute up to half of the global per capita energy intake. The primary organ system for seed production in flowering plants is the ovule. At maturity, the ovule consists of a haploid female gametophyte or embryo sac surrounded by several layers of maternal tissue including the nucleus and the integuments. The embryo sac typically contains seven cells including the egg cell, two synergids, a large central cell containing two polar nuclei, and three antipodal cells. That pollination results in the fertilization of both egg and central cell. The fertilized egg develops into the embryo. The fertilized central cell develops into the endosperm. And the integuments mature into the seed coat. As the ovule develops into the seed, the ovary matures into the fruit or silique. Late in development, the developing seed ends a period of extensive biosynthetic and cellular activity and begins to desiccate to complete its development and enter a dormant, metabolically quiescent state. Seed dormancy is generally an undesirable characteristic in agricultural crops, where rapid germination and growth are required. However, some degree of dormancy is advantageous, at least during seed development. This is particularly true for cereal crops because it prevents germination of grains while still on the ear of the parent plant (preharvest sprouting), a phenomenon that results in major losses to the agricultural industry. Extensive domestication and breeding of crop species have ostensibly reduced the level of dormancy mechanisms present in the seeds of their wild ancestors, although under some adverse environmental conditions, dormancy may reappear. By contrast, weed seeds frequently mature with inherent dormancy mechanisms that allow some seeds to persist in the soil for many years before completing germination.

Germination commences with imbibition, the uptake of water by the dry seed, and the activation of the quiescent embryo and endosperm. The result is a burst of intense metabolic activity. At the cellular level, the genome is transformed from an inactive state to one of intense transcriptional activity. Stored lipids, carbohydrates and proteins are catabolized fueling seedling growth and development. DNA and organelles are repaired, replicated and begin functioning. Cell expansion and cell division are triggered. The shoot and root apical meristem are activated and begin growth and organogenesis. Schematic 4 summarizes some of the metabolic and cellular processes that occur during imbibition. Germination is complete when a part of the embryo, the radicle, extends to penetrate the structures that surround it. In *Arabidopsis*, seed germination takes place within twenty-four (24) hours after imbibition. As such, germination requires the rapid and orchestrated transcription of numerous polynucleotides. Germination is followed by expansion of the hypocotyl and opening of the cotyledons. Meristem development continues to promote root growth and shoot growth, which is followed by early leaf formation.

Imbibition and Germination Genes

Imbibition and germination includes those events that commence with the uptake of water by the quiescent dry seed and terminate with the expansion and elongation of the shoots and roots. The germination period exists from imbibition to when part of the embryo, usually the radicle, extends to penetrate the seed coat that surrounds it. Imbibition and germination genes are defined as genes, gene components and products capable of modulating one or more processes of imbibition and germination described above. They are useful to modulate many plant traits from early vigor to yield to stress tolerance.

Differential Expression of the Sequences in Germinating Seeds and Imbibed Embryos The levels of mRNA product in the seeds versus the plant as a whole was measured.

Hormone Responsive Genes, Gene Components and Products

Abscissic Acid Responsive Genes, Gene Components and Products

Plant hormones are naturally occurring substances, effective in very small amounts, which act as signals to stimulate or inhibit growth or regulate developmental processes in plants. Abscisic acid (ABA) is a ubiquitous hormone in vascular plants that has been detected in every major organ or living tissue from the root to the apical bud. The major physiological responses affected by ABA are dormancy, stress stomatal closure, water uptake, abscission and senescence. In contrast to Auxins, cytokinins and gibberellins, which are principally growth promoters, ABA primarily acts as an inhibitor of growth and metabolic processes.

Changes in ABA concentration internally or in the surrounding environment in contact with a plant results in modulation of many genes and gene products. These genes and/or products are responsible for effects on traits such as plant vigor and seed yield. While ABA responsive polynucleotides and gene products can act alone, combinations of these polynucleotides also affect growth and development. Useful combinations include different ABA responsive polynucleotides and/or gene products that have similar transcription profiles or similar biological activities, and members of the same or similar biochemical pathways. Whole pathways or segments of pathways are controlled by transcription factor proteins and proteins controlling the activity of signal transduction pathways. Therefore, manipulation of such protein levels is especially useful for altering phenotypes and biochemical activities of plants. In addition, the combination of an ABA responsive polynucleotide and/or gene product with another environmentally responsive polynucleotide is also useful because of the interactions that exist between hormone-regulated pathways, stress and defense induced pathways, nutritional pathways and development.

Differential Expression of the Sequences in ABA Treated Plants

The relative levels of mRNA product in plants treated with ABA versus controls treated with water were measured.

Brassinosteroid Responsive Genes, Gene Components and Products

Plant hormones are naturally occurring substances, effective in very small amounts, which act as signals to stimulate or inhibit growth or regulate developmental processes in plants. Brassinosteroids (BRs) are the most recently discovered, and least studied, class of plant hormones. The major physiological response affected by BRs is the longitudinal growth of young tissue via cell elongation and possibly cell division. Consequently, disruptions in BR metabolism, perception and activity frequently result in a dwarf phenotype. In addition, because BRs are derived from the sterol metabolic pathway, any perturbations to the sterol pathway can affect the BR pathway. In the same way, perturbations in the BR pathway can have effects on the later part of the sterol pathway and thus the sterol composition of membranes.

Changes in BR concentration in the surrounding environment or in contact with a plant result in modulation of many genes and gene products. These genes and/or products are responsible for effects on traits such as plant biomass and seed yield. These genes were discovered and characterized from a much larger set of genes by experiments designed to find genes whose mRNA abundance changed in response to application of BRs to plants.

While BR responsive polynucleotides and gene products can act alone, combinations of these polynucleotides also affect growth and development. Useful combinations include different BR responsive polynucleotides and/or gene products that have similar transcription profiles or similar biological activities, and members of the same or functionally related biochemical pathways. Whole pathways or segments of pathways are controlled by transcription factors and proteins controlling the activity of signal transduction pathways. Therefore, manipulation of such protein levels is especially useful for altering phenotypes and biochemical activities of plants. In addition, the combination of a BR responsive polynucleotide and/or gene product with another environmentally responsive polynucleotide is useful because of the interactions that exist between hormone-regulated pathways, stress pathways, nutritional pathways and development. Here, in addition to polynucleotides having similar transcription profiles and/or biological activities, useful combinations include polynucleotides that may have different transcription profiles but which participate in common or overlapping pathways.

Differential Expression of the Sequences in Epi-Brassinolide or Brassinozole Plants The relative levels of mRNA product in plants treated with either epi-brassinolide or brassinozole were measured.

Metabolism Affecting Genes, Gene Components and Products

Nitrogen Responsive Genes, Gene Components and Products

Nitrogen is often the rate-limiting element in plant growth, and all field crops have a fundamental dependence on exogenous nitrogen sources. Nitrogenous fertilizer, which is usually supplied as ammonium nitrate, potassium nitrate, or urea, typically accounts for 40% of the costs associated with crops, such as corn and wheat in intensive agriculture. Increased efficiency of nitrogen use by plants should enable the production of higher yields with existing fertilizer inputs and/or enable existing yields of crops to be obtained with lower fertilizer input, or better yields on soils of poorer quality. Also, higher amounts of proteins in the crops could also be produced more cost-effectively. "Nitrogen responsive" genes and gene products can be used to alter or modulate plant growth and development.

Differential Expression of the Sequences in Whole Seedlings, Shoots and Roots

The relative levels of mRNA product in whole seedlings, shoots and roots treated with either high or low nitrogen media were compared to controls.

Viability Genes, Gene Components and Products

Plants contain many proteins and pathways that when blocked or induced lead to cell, organ or whole plant death. Gene variants that influence these pathways can have profound effects on plant survival, vigor and performance. The critical pathways include those concerned with metabolism and development or protection against stresses, diseases and pests. They also include those involved in apoptosis and necrosis. Viability genes can be modulated to affect cell or plant death.

Herbicides are, by definition, chemicals that cause death of tissues, organs and whole plants. The genes and pathways that are activated or inactivated by herbicides include those that cause cell death as well as those that function to provide protection.

Differential Expression of the Sequences in Herbicide Treated Plants and Herbicide Resistant Mutants The relative levels of mRNA product in plants treated with herbicide and mutants resistant to herbicides were compared to control plants.

Stress Responsive Genes, Gene Components and Products

Wounding Responsive Genes, Gene Components and Products

Plants are continuously subjected to various forms of wounding from physical attacks including the damage created by pathogens and pests, wind, and contact with other objects. Therefore, survival and agricultural yields depend on constraining the damage created by the wounding process and inducing defense mechanisms against future damage.

Plants have evolved complex systems to minimize and/or repair local damage and to minimize subsequent attacks by pathogens or pests or their effects. These involve stimulation of cell division and cell elongation to repair tissues, induction of programmed cell death to isolate the damage caused mechanically and by invading pests and pathogens, and induction of long-range signaling systems to induce protecting molecules, in case of future attack. The genetic and biochemical systems associated with responses to wounding are connected with those associated with other stresses such as pathogen attack and drought.

Wounding responsive genes and gene products can be used to alter or modulate traits such as growth rate; whole plant height, width, or flowering time; organ development (such as coleoptile elongation, young leaves, roots, lateral roots, tuber formation, flowers, fruit, and seeds); biomass; fresh and dry weight during any time in plant life, such as at maturation; number of flowers; number of seeds; seed yield, number, size, weight, harvest index (such as content and composition, e.g., amino acid, nitrogen, oil, protein, and carbohydrate); fruit yield, number, size, weight, harvest index, post harvest quality, content and composition (e.g., amino acid, carotenoid, jasmonate, protein, and starch); seed and fruit development; germination of dormant and non-dormant seeds; seed viability, seed reserve mobilization, fruit ripening, initiation of the reproductive cycle from a vegetative state, flower development time, insect attraction for fertilization, time to fruit maturity, senescence; fruits, fruit drop; leaves; stress and disease responses; drought; heat and cold; wounding by any source, including wind, objects, pests and pathogens; uv and high light damage (insect, fungus, virus, worm, nematode damage).

Cold Responsive Genes, Gene Components and Products

The ability to endure low temperatures and freezing is a major determinant of the geographical distribution and productivity of agricultural crops. Even in areas considered suiTable for the cultivation of a given species or cultivar, can give rise to yield decreases and crop failures as a result of aberrant, freezing temperatures. Even modest increases (1-2° C.) in the freezing tolerance of certain crop species would have a dramatic impact on agricultural productivity in some areas. The development of genotypes with increased freezing tolerance would provide a more reliable means to minimize crop losses and diminish the use of energy-costly practices to modify the microclimate.

Sudden cold temperatures result in modulation of many genes and gene products, including promoters. These genes and/or products are responsible for effects on traits such as plant vigor and seed yield.

Manipulation of one or more cold responsive gene activities is useful to modulate growth and development.

Differential Expression of the Sequences in Cold Treated Plants

The relative levels of mRNA product in cold treated plants were compared to control plants.

Heat Responsive Genes, Gene Components and Products

The ability to endure high temperatures is a major determinant of the geographical distribution and productivity of agricultural crops. Decreases in yield and crop failure frequently occur as a result of aberrant, hot conditions even in areas considered suiTable for the cultivation of a given species or cultivar. Only modest increases in the heat tolerance of crop species would have a dramatic impact on agricultural productivity. The development of genotypes with increased heat tolerance would provide a more reliable means to minimize crop losses and diminish the use of energy-costly practices to modify the microclimate.

Changes in temperature in the surrounding environment or in a plant microclimate results in modulation of many genes and gene products.

Differential Expression of the Sequences in Heat Treated Plants

The relative levels of mRNA product in heat treated plants were compared to control plants.

Drought Responsive Genes, Gene Components and Products

The ability to endure drought conditions is a major determinant of the geographical distribution and productivity of agricultural crops. Decreases in yield and crop failure frequently occur as a result of aberrant, drought conditions even in areas considered suiTable for the cultivation of a given species or cultivar. Only modest increases in the drought tolerance of crop species would have a dramatic impact on agricultural productivity. The development of genotypes with increased drought tolerance would provide a more reliable means to minimize crop losses and diminish the use of energy-costly practices to modify the microclimate.

Drought conditions in the surrounding environment or within a plant, results in modulation of many genes and gene products.

Differential Expression of the Sequences in Drought Treated Plants and Drought Mutants The relative levels of mRNA product in drought treated plants and drought mutants were compared to control plants.
Methyl Jasmonate (Jasmonate) Responsive Genes, Gene Components and Products Jasmonic acid and its derivatives, collectively referred to as jasmonates, are naturally occurring derivatives of plant lipids. These substances are synthesized from linolenic acid in a lipoxygenase-dependent biosynthetic pathway. Jasmonates are signalling molecules which have been shown to be growth regulators as well as regulators of defense and stress responses. As such, jasmonates represent a separate class of plant hormones. Jasmonate responsive genes can be used to modulate plant growth and development.
Differential Expression of the Sequences in Methyl Jasmonate Treated Plants The relative levels of mRNA product in methyl jasmonate treated plants were compared to control plants.
Salicylic Acid Responsive Genes, Gene Components and Products Plant defense responses can be divided into two groups: constitutive and induced. Salicylic acid (SA) is a signaling molecule necessary for activation of the plant induced defense system known as systemic acquired resistance or SAR. This response, which is triggered by prior exposure to avirulent pathogens, is long lasting and provides protection against a broad spectrum of pathogens. Another induced defense system is the hypersensitive response (HR). HR is far more rapid, occurs at the sites of pathogen (avirulent pathogens) entry and precedes SAR. SA is also the key signaling molecule for this defense pathway.

Differential Expression of the Sequences in Salicylic Acid Treated Plants

The relative levels of mRNA product in salicylic acid treated plants were compared to control plants.
Osmotic Stress Responsive Genes, Gene Components and Products The ability to endure and recover from osmotic and salt related stress is a major determinant of the geographical distribution and productivity of agricultural crops. Osmotic stress is a major component of stress imposed by saline soil and water deficit. Decreases in yield and crop failure frequently occur as a result of aberrant or transient environmental stress conditions even in areas considered suitable for the cultivation of a given species or cultivar. Only modest increases in the osmotic and salt tolerance of a crop species would have a dramatic impact on agricultural productivity. The development of genotypes with increased osmotic tolerance would provide a more reliable means to minimize crop losses and diminish the use of energy-costly practices to modify the soil environment. Thus, osmotic stress responsive genes can be used to modulate plant growth and development.

Differential Expression of the Sequences in Peg Treated Plants

The relative levels of mRNA product in PEG treated plants were compared to control plants.
Shade Responsive Genes, Gene Components and Products Plants sense the ratio of Red (R):Far Red (FR) light in their environment and respond differently to particular ratios. A low R:FR ratio, for example, enhances cell elongation and favors flowering over leaf production. The changes in R:FR ratios mimic and cause the shading response effects in plants. The response of a plant to shade in the canopy structures of agricultural crop fields influences crop yields significantly. Therefore manipulation of genes regulating the shade avoidance responses can improve crop yields. While phytochromes mediate the shade avoidance response, the down-stream factors participating in this pathway are largely unknown. One potential downstream participant, ATHB-2, is a member of the HD-Zip class of transcription factors and shows a strong and rapid response to changes in the R:FR ratio. ATHB-2 overexpressors have a thinner root mass, smaller and fewer leaves and longer hypocotyls and petioles. This elongation arises from longer epidermal and cortical cells, and a decrease in secondary vascular tissues, paralleling the changes observed in wild-type seedlings grown under conditions simulating canopy shade. On the other hand, plants with reduced ATHB-2 expression have a thick root mass and many larger leaves and shorter hypocotyls and petioles. Here, the changes in the hypocotyl result from shorter epidermal and cortical cells and increased proliferation of vascular tissue. Interestingly, application of Auxin is able to reverse the root phenotypic consequences of high ATHB-2 levels, restoring the wild-type phenotype. Consequently, given that ATHB-2 is tightly regulated by phytochrome, these data suggest that ATHB-2 may link the Auxin and phytochrome pathways in the shade avoidance response pathway.

Shade responsive genes can be used to modulate plant growth and development.

Differential Expression of the Sequences in Far-Red Light Treated Plants

The relative levels of mRNA product in far-red light treated plants were compared to control plants.
Viability Genes, Gene Components and Products Plants contain many proteins and pathways that when blocked or induced lead to cell, organ or whole plant death. Gene variants that influence these pathways can have profound effects on plant survival, vigor and performance. The critical pathways include those concerned with metabolism and development or protection against stresses, diseases and pests. They also include those involved in apoptosis and necrosis. The applicants have elucidated many such genes and pathways by discovering genes that when inactivated lead to cell or plant death.

Herbicides are, by definition, chemicals that cause death of tissues, organs and whole plants. The genes and pathways that are activated or inactivated by herbicides include those that cause cell death as well as those that function to provide protection. The applicants have elucidated these genes.

The genes defined in this section have many uses including manipulating which cells, tissues and organs are selectively killed, which are protected, making plants resistant to herbicides, discovering new herbicides and making plants resistant to various stresses.

Viability genes were also identified from a much larger set of genes by experiments designed to find genes whose mRNA products changed in concentration in response to applications of different herbicides to plants. Viability genes are characteristically differentially transcribed in response to fluctuating herbicide levels or concentrations, whether internal or external to an organism or cell. The MA_diff Table reports the changes in transcript levels of various viability genes.

Early Seedling-Phase Specific Responsive Genes, Gene Components and Products

One of the more active stages of the plant life cycle is a few days after germination is complete, also referred to as the early seedling phase. During this period the plant begins development and growth of the first leaves, roots, and other organs not found in the embryo. Generally this stage begins when germination ends. The first sign that germination has been completed is usually that there is an increase in length and fresh weight of the radicle. Such genes and gene products can regulate a number of plant traits to modulate yield. For example, these genes are active or potentially active to a greater extent in developing and rapidly growing cells, tissues and organs, as exemplified by development and growth of a seedling 3 or 4 days after planting a seed.

Rapid, efficient establishment of a seedling is very important in commercial agriculture and horticulture. It is also vital that resources are approximately partitioned between shoot and root to facilitate adaptive growth. Phototropism and geotropism need to be established. All these require post-germination process to be sustained to ensure that vigorous seedlings are produced. Early seedling phase genes, gene components and products are useful to manipulate these and other processes.

Guard Cell Genes, Gene Components and Products

Scattered throughout the epidermis of the shoot are minute pores called stomata. Each stomal pore is surrounded by two guard cells. The guard cells control the size of the stomal pore, which is critical since the stomata control the exchange of carbon dioxide, oxygen, and water vapor between the interior of the plant and the outside atmosphere. Stomata open and close through turgor changes driven by ion fluxes, which occur mainly through the guard cell plasma membrane and tonoplast. Guard cells are known to respond to a number of external stimuli such as changes in light intensity, carbon dioxide and water vapor, for example. Guard cells can also sense and rapidly respond to internal stimuli including changes in ABA, auxin and calcium ion flux.

Thus, genes, gene products, and fragments thereof differentially transcribed and/or translated in guard cells can be useful to modulate ABA responses, drought tolerance, respiration, water potential, and water management as examples. All of which can in turn affect plant yield including seed yield, harvest index, fruit yield, etc.

To identify such guard cell genes, gene products, and fragments thereof, Applicants have performed a microarray experiment comparing the transcript levels of genes in guard cells versus leaves. Experimental data is shown below.

Nitric Oxide Responsive Genes, Gene Components and Products

The rate-limiting element in plant growth and yield is often its ability to tolerate suboptimal or stress conditions, including pathogen attack conditions, wounding and the presence of various other factors. To combat such conditions, plant cells deploy a battery of inducible defense responses, including synergistic interactions between nitric oxide (NO), reactive oxygen intermediates (ROS), and salicylic acid (SA). NO has been shown to play a critical role in the activation of innate immune and inflammatory responses in animals. At least part of this mammalian signaling pathway is present in plants, where NO is known to potentiate the hypersensitive response (HR). In addition, NO is a stimulator molecule in plant photomorphogenesis.

Changes in nitric oxide concentration in the internal or surrounding environment, or in contact with a plant, results in modulation of many genes and gene products.

In addition, the combination of a nitric oxide responsive polynucleotide and/or gene product with other environmentally responsive polynucleotides is also useful because of the interactions that exist between hormone regulated pathways, stress pathways, pathogen stimulated pathways, nutritional pathways and development.

Nitric oxide responsive genes and gene products can function either to increase or dampen the above phenotypes or activities either in response to changes in nitric oxide concentration or in the absence of nitric oxide fluctuations. More specifically, these genes and gene products can modulate stress responses in an organism. In plants, these genes and gene products are useful for modulating yield under stress conditions. Measurements of yield include seed yield, seed size, fruit yield, fruit size, etc.

Shoot-Apical Meristem Genes, Gene Components and Products

New organs, stems, leaves, branches and inflorescences develop from the stem apical meristem (SAM). The growth structure and architecture of the plant therefore depends on the behavior of SAMs. Shoot apical meristems (SAMs) are comprised of a number of morphologically undifferentiated, dividing cells located at the tips of shoots. SAM genes elucidated here are capable of modifying the activity of SAMs and thereby many traits of economic interest from ornamental leaf shape to organ number to responses to plant density.

In addition, a key attribute of the SAM is its capacity for self-renewal. Thus, SAM genes of the instant invention are useful for modulating one or more processes of SAM structure and/or function including (I) cell size and division; (II) cell differentiation and organ primordia. The genes and gene components of this invention are useful for modulating any one or all of these cell division processes generally, as in timing and rate, for example. In addition, the polynucleotides and polypeptides of the invention can control the response of these processes to the internal plant programs associated with embryogenesis, and hormone responses, for example.

Because SAMs determine the architecture of the plant, modified plants will be useful in many agricultural, horticultural, forestry and other industrial sectors. Plants with a different shape, numbers of flowers and seed and fruits will have altered yields of plant parts. For example, plants with more branches can produce more flowers, seed or fruits. Trees without lateral branches will produce long lengths of clean timber. Plants with greater yields of specific plant parts will be useful sources of constituent chemicals.

GFP Experimental Procedures and Results

Procedures

The polynucleotide sequences of the present invention were tested for promoter activity using Green Fluorescent Protein (GFP) assays in the following manner.

Approximately 1-2 kb of genomic sequence occurring immediately upstream of the ATG translational start site of the gene of interest was isolated using appropriate primers tailed with BstXI restriction sites. Standard PCR reactions using these primers and genomic DNA were conducted. The resulting product was isolated, cleaved with BstXI and cloned into the BstXI site of an appropriate vector, such as pNewBin4-HAP1-GFP (see FIG. 1).

Transformation

The following procedure was used for transformation of plants

1. Stratification of WS-2 Seed.
    Add 0.5 ml WS-2 (CS2360) seed to 50 ml of 0.2% Phytagar in a 50 ml Corning tube and vortex until seeds and Phytagar form a homogenous mixture.
    Cover tube with foil and stratify at 4° C. for 3 days.
2. Preparation of Seed Mixture.
    Obtain stratified seed from cooler.
    Add seed mixture to a 1000 ml beaker.
    Add an additional 950 ml of 0.2% Phytagar and mix to homogenize.
3. Preparation of Soil Mixture.
    Mix 24 L SunshineMix #5 soil with 16 L Therm-O-Rock vermiculite in cement mixer to make a 60:40 soil mixture.
    Amend soil mixture by adding 2 Tbsp Marathon and 3 Tbsp Osmocote and mix contents thoroughly.
    Add 1 Tbsp Peters fertilizer to 3 gallons of water and add to soil mixture and mix thoroughly.
    Fill 4-inch pots with soil mixture and round the surface to create a slight dome.
    Cover pots with 8-inch squares of nylon netting and fasten using rubber bands.
    Place 14 4-inch pots into each no-hole utility flat.
4. Planting.
    Using a 60 ml syringe, aspirate 35 ml of the seed mixture.
    Exude 25 drops of the seed mixture onto each pot.
    Repeat until all pots have been seeded.
    Place flats on greenhouse bench, cover flat with clear propagation domes, place 55% shade cloth on top of flats and subirrigate by adding 1 inch of water to bottom of each flat.
5. Plant Maintenance.
    3 to 4 days after planting, remove clear lids and shade cloth.
    Subirrigate flats with water as needed.
    After 7-10 days, thin pots to 20 plants per pot using forceps.
    After 2 weeks, subirrigate all plants with Peters fertilizer at a rate of 1 Tsp per gallon water.
    When bolts are about 5-10 cm long, clip them between the first node and the base of stem to induce secondary bolts.
    6 to 7 days after clipping, perform dipping infiltration.
6. Preparation of *Agrobacterium*.
    Add 150 ml fresh YEB to 250 ml centrifuge bottles and cap each with a foam plug (Identi-Plug).
    Autoclave for 40 min at 121° C.
    After cooling to room temperature, uncap and add 0.1 ml each of carbenicillin, spectinomycin and rifampicin stock solutions to each culture vessel.
    Obtain *Agrobacterium* starter block (96-well block with *Agrobacterium* cultures grown to an $OD_{600}$ of approximately 1.0) and inoculate one culture vessel per construct by transferring 1 ml from appropriate well in the starter block.
    Cap culture vessels and place on Lab-Line incubator shaker set at 27° C. and 250 RPM.
    Remove after *Agrobacterium* cultures reach an $OD_{600}$ of approximately 1.0 (about 24 hours), cap culture vessels with plastic caps, place in Sorvall SLA 1500 rotor and centrifuge at 8000 RPM for 8 min at 4° C.
    Pour out supernatant and put bottles on ice until ready to use.
    Add 200 ml Infiltration Media (IM) to each bottle, resuspend *Agrobacterium* pellets and store on ice.
7. Dipping Infiltration.
    Pour resuspended *Agrobacterium* into 16 oz polypropylene containers.
    Invert 4-inch pots and submerge the aerial portion of the plants into the *Agrobacterium* suspension and let stand for 5 min.
    Pour out *Agrobacterium* suspension into waste bucket while keeping polypropylene container in place and return the plants to the upright position.
    Place 10 covered pots per flat.
    Fill each flat with 1-inch of water and cover with shade cloth.
    Keep covered for 24 hr and then remove shade cloth and polypropylene containers.
    Resume normal plant maintenance.
    When plants have finished flowering cover each pot with a ciber plant sleeve.
    After plants are completely dry, collect seed and place into 2.0 ml micro tubes and store in 100-place cryogenic boxes.

Recipes:

0.2% Phytagar
    2 g Phytagar
    1 L nanopure water
    Shake until Phytagar suspended
    Autoclave 20 min YEB (for 1 L)
    5 g extract of meat
    5 g Bacto peptone
    1 g yeast extract
    5 g sucrose
    0.24 g magnesium sulfate
    While stirring, add ingredients, in order, to 900 ml nanopure water
    When dissolved, adjust pH to 7.2
    Fill to 1 L with nanopure water
    Autoclave 35 min Infiltration Medium (IM) (for 1 L)
    2.2 g MS salts
    50 g sucrose
    5 ul BAP solution (stock is 2 mg/ml)
    While stirring, add ingredients in order listed to 900 ml nanopure water
    When dissolved, adjust pH to 5.8.
    Volume up to 1 L with nanopure water.
    Add 0.02% Silwet L-77 just prior to resuspending *Agrobacterium*

High Throughput Screening—T1 Generation

1. Soil Preparation. Wear gloves at all times.
    In a large container, mix 60% autoclaved SunshineMix #5 with 40% vermiculite.
    Add 2.5 Tbsp of Osmocote, and 2.5 Tbsp of 1% granular Marathon per 25 L of soil.
    Mix thoroughly.
2. Fill Com-Packs With Soil.
    Loosely fill D601 Com-Packs level to the rim with the prepared soil.
    Place filled pot into utility flat with holes, within a no-hole utility flat.
    Repeat as necessary for planting. One flat set should contain 6 pots.
3. Saturate Soil.
    Evenly water all pots until the soil is saturated and water is collecting in the bottom of the flats.
    After the soil is completely saturated, dump out the excess water.
4. Plant the Seed.
5. Stratify the Seeds.
    After sowing the seed for all the flats, place them into a dark 4° C. cooler.

Keep the flats in the cooler for 2 nights for WS seed. Other ecotypes may take longer. This cold treatment will help promote uniform germination of the seed.

6. Remove Flats From Cooler and Cover With Shade Cloth. (Shade cloth is only needed in the greenhouse)

After the appropriate time, remove the flats from the cooler and place onto growth racks or benches.

Cover the entire set of flats with 55% shade cloth. The cloth is necessary to cut down the light intensity during the delicate germination period.

The cloth and domes should remain on the flats until the cotyledons have fully expanded. This usually takes about 4-5 days under standard greenhouse conditions.

7. Remove 55% Shade Cloth and Propagation Domes.

After the cotyledons have fully expanded, remove both the 55% shade cloth and propagation domes.

8. Spray Plants With Finale Mixture. Wear gloves and protective clothing at all times.

Prepare working Finale mixture by mixing 3 ml concentrated Finale in 48 oz of water in the Poly-TEK sprayer.

Completely and evenly spray plants with a fine mist of the Finale mixture.

Repeat Finale spraying every 3-4 days until only transformants remain. (Approximately 3 applications are necessary.)

When satisfied that only transformants remain, discontinue Finale spraying.

9. Weed Out Excess Transformants.

Weed out excess transformants such that a maximum number of five plants per pot exist evenly spaced throughout the pot.

GFP Assay

Tissues are dissected by eye or under magnification using INOX 5 grade forceps and placed on a slide with water and coversliped. An attempt is made to record images of observed expression patterns at earliest and latest stages of development of tissues listed below. Specific tissues will be preceded with High (H), Medium (M), Low (L) designations.

T2 Seedling: Progeny are collected from the T1 plants giving the same expression pattern and the progeny (T2) are sterilized and plated on agar-solidified medium containing M&S salts. In the event that there was no expression in the T1 plants, T2 seeds are planted from all lines. The seedlings are grown in Percival incubators under continuous light at 22° C. for 10-12 days. Cotyledons, roots, hypocotyls, petioles, leaves, and the shoot meristem region of individual seedlings were screened until two seedlings were observed to have the same pattern. Generally found the same expression pattern was found in the first two seedlings. However, up to 6 seedlings were screened before "no expression pattern" was recorded. All constructs are screened as T2 seedlings even if they did not have an expression pattern in the T1 generation.

T2 Mature: The T2 mature plants were screened in a similar manner to the T1 plants. The T2 seeds were planted in the greenhouse, exposed to selection and at least one plant screened to confirm the T1 expression pattern. In instances where there were any subtle changes in expression, multiple plants were examined and the changes noted in the tables.

T3 Seedling: This was done similar to the T2 seedlings except that only the plants for which we are trying to confirm the pattern are planted.

Image Data:

Images are collected by scanning laser confocal microscopy. Scanned images are taken as 2-D optical sections or 3-D images generated by stacking the 2-D optical sections collected in series. All scanned images are saved as TIFF files by imaging software, edited in Adobe Photoshop, and labeled in Powerpoint specifying organ and specific expressing tissues.

Instrumentation:

Microscope

Inverted Leica DM IRB

Fluorescence filter blocks:

Blue excitation BP 450-490; long pass emission LP 515.

Green excitation BP 515-560; long pass emission LP 590

Objectives

| | |
|---|---|
| Flower | pedicel receptacle nectary sepal petal filament anther pollen carpel style papillae vascular epidermis stomata trichome |
| Silique | stigma style carpel septum placentae transmitting tissue vascular epidermis stomata abscission zone ovule |
| Ovule | Pre-fertilization: inner integument outer integument embryo sac funiculus chalaza micropyle gametophyte<br>Post-fertilization: zygote inner integument outer integument seed coat primordia chalaza micropyle early endosperm mature endosperm embryo |
| Embryo | suspensor preglobular globular heart torpedo late mature provascular hypophysis radicle cotyledons hypocotyl |
| Stem | epidermis cortex vascular xylem phloem pith stomata trichome |
| Leaf | petiole mesophyll vascular epidermis trichome primordia stomata stipule margin |

T1 Mature: These are the T1 plants resulting from independent transformation events. These are screened between stage 6.50-6.90 (means the plant is flowering and that 50-90% of the flowers that the plant will make have developed) which is 4-6 weeks of age. At this stage the mature plant possesses flowers, siliques at all stages of development, and fully expanded leaves. We do not generally differentiate between 6.50 and 6.90 in the report but rather just indicate 6.50. The plants are initially imaged under UV with a Leica Confocal microscope. This allows examination of the plants on a global level. If expression is present, they are imaged using scanning laser confocal microscopy.

HC PL FLUOTAR 5×/0.5
HCPL APO 10×/0.4 IMM water/glycerol/oil
HCPL APO 20×/0.7 IMM water/glycerol/oil
HCXL APO 63×/1.2 IMM water/glycerol/oil
Leica TCS SP2 Confocal Scanner
Spectral range of detector optics 400-850 nm.
Variable computer controlled pinhole diameter.
Optical zoom 1-32×.
Four simultaneous detectors:
Three channels for collection of fluorescence or reflected light.
One channel for transmitted light detector.

Laser sources:
Blue Ar 458/5 mW, 476 nm/5 mW, 488 nm/20 mW, 514 nm/20 mW.
Green HeNe 543 nm/1.2 mW
Red HeNe 633 nm/10 mW
Results The section in Table 1 entitled "The spatial expression of the promoter-marker-vector" presents the results of the GFP assays as reported by their corresponding cDNA ID number, construct number and line number. Unlike the microarray results, which measure the difference in expression of the endogenous cDNA under various conditions, the GFP data gives the location of expression that is visible under the imaging parameters. Table 3 summarizes the results of the spatial expression results for each promoter.

Explanation of Table 1

Table 1 includes various information about each promoter or promoter control element of the invention including the nucleotide sequence, the spatial expression promoted by each promoter, and the corresponding results from different expression experiments.

TABLE 1

Promoter Sequences and Related Information

Promoter YP0396

Modulates the gene: PAR-related protein
The GenBank description of the gene:: NM_124618 Arabidopsis thaliana photoassimilate-responsive protein PAR-related protein (At5g52390) mRNA, complete cds gi|30696178|ref|NM_124618.2|[30696178]
The promoter sequence:
5'ctaagtaaaataagataaaacatgttatttgaatttgaatatcgtgggatgcgtatttcggtatttgat taaaggtctggaaaccggagctcctataacccgaataaaaatgcataacatgttcttccccaacgaggcga gcgggtcagggcactagggtcattgcaggcagctcataaagtcatgatcatctaggagatcaaattgtatg tcggccttctcaaaattacctctaagaatctcaaacccaatcatagaacctctaaaaagacaaagtcgtcg ctttagaatgggttcggttttttggaaccatatttcacgtcaatttaatgtttagtataatttctgaacaac agaattttggatttatttgcacgtatacaaatatctaattaataaggacgactcgtgactatccttacatt aagtttcactgtcgaaataacatagtacaatacttgtcgttaatttccacgtctcaagtctataccgtcat ttacggagaaagaacatctctgtttttcatccaaactactattctcactttgtctatatatttaaaattaa gtaaaaaagactcaatagtccaataaaatgatgaccaaatgagaagatggttttgtgccagattttaggaa aagtgagtcaaggtttcacatctcaaatttgactgcataatcttcgccattaacaacggcattatatatgt caagccaattttccatgttgcgtacttttctattgaggtgaaaatatgggtttgttgattaatcaaagagt ttgcctaactaatataactacgacttttttcagtgaccattccatgtaaactctgcttagtgtttcatttgt caacaatattgtcgttactcattaaatcaaggaaaaatatacaattgtataattttcttatattttaaaat taattttga 3' ccaaaagaacatctttccttcgaattttctttcattaacatttcttttacttgtctccttgtgtcttcact tcacatcacaacATG
The promoter was cloned from the organism: Arabidopsis thaliana, Columbia ecotype

| Alternative nucleotides: | | |
|---|---|---|
| Predicted Position (bp) | Mismatch | Predicted/Experimental |
| 1-1000 | None | Identities = 1000/1000 (100%) |

The promoter was cloned in the vector: pNewbin4-HAP1-GFP
When cloned into the vector the promoter was operably linked to a marker, which was the type: GFP-ER
Promoter-marker vector was tested in: Arabidopsis thaliana, WS ecotype
Generation screened: XT1 Mature  XT2 Seedling  T2 Mature  T3 Seedling The spatial expression of the promoter-marker vector was found observed in and would be useful in expression in any or all of the following:

Flower                          H sepal H petal H anther H style
Silique                         H style H ovule
Ovule                           H outer integument H outer integument L seed coat
Leaf                            H vascular
Primary Root                    H epidermis
Observed expression pattern:
T1 mature: High GFP expression in the style, sepals, petals, and anthers in flowers.
Expressed in outer integuments of ovule primordia through developing seed stages and in remnants of aborted ovules. High vasculature expression in leaf
T2 seedling: Medium to low root epidermal expression at root transition zone decreasing TABLE 1-continued Promoter Sequences and Related Information toward root tip. Specific to epidermal cells flanking lateral roots.
Misc. promoter information:   Bidirectionality: Pass   Exons: Pass   Repeats: No
The Ceres cDNA ID of the endogenous coding sequence to the promoter: 12646726
cDNA nucleotide sequence:
ACTACACCCAAAAGAACATCTTTCCTTCGAATTTTCTTTCAATTAACATTTCTTTTACTTGTCTC

CTTGTGTCTTCACTTCACATCACAACATGGCTTTGAAGACAGTTTTCGTAGCTTTTATGATTCT

CCTTGCCATCTATTCGCAAACGACGTTTGGGGACGATGTGAAGTGCGAGAATCTGGATGAAAA

CACGTGTGCCTTCGCGGTCTCGTCCACTGGAAAACGTTGCGTTTTGGAGAAGAGCATGAAGAG

GAGCGGGATCGAGGTGTACACATGTCGATCATCGGAGATAGAAGCTAACAAGGTCACAAACA

TTATTGAATCGGACGAGTGCATTAAAGCGTGTGGTCTAGACCGGAAAGCTTTAGGTATATCTT

CGGACGCATTGTTGGAATCTCAGTTCACACATAAACTCTGCTCGGTTAAATGCTTAAACCAAT

GTCCTAACGTAGTCGATCTCTACTTCAACCTTGCTGCTGGTGAAGGAGTGTATTTACCAAAGCT

ATGTGAATCACAAGAAGGGAAGTCAAGAAGAGCAATGTCGGAATTAGGAGCTCGGGAATTG

CAATGGACACTCTTGCACCGGTTGGACCAGTCATGTTGGGCGAGATAGCACCTGAGCCGGCTA

CTTCAATGGACAACATGCCTTACGTGCCGGCACCTTCACCGTATTAATTAAGGCAAGGGAAAA

TGGAGAGGACACGTATGATATCATGAGTTTTCGACGAGAATAATTAAGAGATTTATGTTTAGT

TCGACGGTTTTAGTATTACATCGTTTATTGCGTCCTTATATATATGTACTTCATAAAAACACAC

CACGACACATTAAGAGATGGTGAAAGTAGGCTGCGTTCTGGTGTAACTTTTACACAAGTAACG

TCTTATAATATATATGATTCGAATAAAATGTTGAGTTTTGGTGAAAATATATAATATGTTTCTG

Coding sequence:
MALKTVFVAFMILLAIYSQTTFGDDVKCENLDENTCAFAVSSTGKRCVLEKSMKRSGIEVYTCRSS

EIEANKVTNIIESDECIKACGLDRKALGISSDALLESQFTHKLCSVKCLNQCPNVVDLYFNLAAGEG

VYLPKLCESQEGKSRRAMSEIRSSGIAMDTLAPVGPVMLGEIAPEPATSMDNMPYVPAPSPY*

Microarray data shows that the coding sequence was expressed in the
following experiments, which shows that the promoter would be useful to
modulate expression in situations similar to the following:

| CDNA_ID | SHORT_NAME | EXPT_REP_ID | IS_UP |
| --- | --- | --- | --- |
| 12646726 | At_Root_Tips | 108434 | − |
| 12646726 | At_Drought_Flowers | 108473 | + |
| 12646726 | At_Drought_Flowers | 108474 | + |
| 12646726 | At_Shoot_Apices | 108479 | + |
| 12646726 | At_Shoot_Apices | 108480 | − |
| 12646726 | At_15mM_NH4NO3_L-to-H_Rosette | 108489 | + |
| 12646726 | At_ap2_floral_buds | 108501 | − |
| 12646726 | At_Ler-rhl_Root | 108594 | − |
| 12646726 | At_Ler-pi_Ovule | 108595 | + |
| 12646726 | At_100uM_ABA | 108609 | + |
| 12646726 | At_100uM_ABA_Mutants | 20000069 | + |
| 12646726 | At_100uM_ABA_Mutants | 20000070 | + |
| 12646726 | At_100uM_ABA_Mutants | 20000071 | + |
| 12646726 | At_100uM_ABA_Mutants | 20000072 | + |
| 12646726 | At_100uM_ABA_Mutants | 20000117 | + |
| 12646726 | At_42deg_Heat | 20000173 | − |
| 12646726 | At_Shoots | 20000184 | − |
| 12646726 | At_Roots | 20000185 | − |
| 12646726 | At_Root-Tips-vs-Tops | 20000227 | − |
| 12646726 | At_Siliques | 20000234 | + |
| 12646726 | At_Open_Flower | 20000265 | + |
| 12646726 | At_Drought | 20000267 | + |
| 12646726 | At_100mM_NaCl | 20000268 | + |
| 12646726 | At_100mM_NaCl | 20000308 | + |
| 12646726 | At_Drought | 20000436 | + |
| 12646726 | At_Drought | 20000437 | + |
| 12646726 | At_Shoots | 20000438 | − |
| 12646726 | At_1uM_BR-BRZ | 20000441 | − |
| 12646726 | At_1uM_BR-BRZ | 20000443 | − |
| 12646726 | At_100uM_ABA | 20000453 | + |
| 12646726 | At_42deg_Heat | 20000457 | + |

TABLE 1-continued

Promoter Sequences and Related Information

| | | | |
|---|---|---|---|
| 12646726 | At_42deg_Heat | 20000458 | − |
| 12646726 | At_Guard_Cells | 20000495 | − |
| 12646726 | At_10percent_PEG | 20000527 | − |
| 12646726 | At_100uM_ABA_Mutants | 20000573 | − |
| 12646726 | At_100uM_ABA_Mutants | 20000574 | − |
| 12646726 | At_15mM_NH4NO3_L-to-H | 20000709 | − |
| 12646726 | At_Line_Comparisons | 20001151 | + |
| 12646726 | At_Line_Comparisons | 20001300 | + |
| 12646726 | At_Line_Comparisons | 20001307 | + |
| 12646726 | At_Line_Comparisons | 20001309 | − |
| 12646726 | At_Line_Comparisons | 20001310 | − |
| 12646726 | At_Interploidy_Crosses | 20001316 | − |
| 12646726 | At_Line_Comparisons | 20001448 | + |
| 12646726 | At_Drought_Soil_Dry | 20001554 | + |
| 12646726 | At_Drought_Soil_Dry | 20001555 | + |
| 12646726 | At_Drought_Soil_Dry | 20001556 | + |
| 12646726 | At_Interploidy_Crosses | 20001654 | + |
| 12646726 | At_Interploidy_Crosses | 20001704 | + |
| 12646726 | At_Interploidy_Crosses | 20001853 | + |
| 12646726 | At_Drought_Reproduction | 20001905 | + |
| 12646726 | At_Drought_Reproduction | 20001906 | + |
| 12646726 | At_Drought_Reproduction | 20001910 | + |
| 12646726 | At_Drought_Reproduction | 20001911 | + |
| 12646726 | At_8deg_Cold | 20002108 | − |
| 12646726 | At_8deg_Cold | 20002109 | − |

The parameters for the microarray experiments listed above by Expt_Rep_ID and Short_Name are as follow below:

| CDNA_ID | SHORT_NAME | EXPT_REP_ID | PARAM_NAME | VALUE |
|---|---|---|---|---|
| 12646726 | At_Root_Tips | 108434 | Tissue | Root Tips |
| 12646726 | At_Drought_Flowers | 108473 | Timepoint (hr) | 7 d |
| 12646726 | At_Drought_Flowers | 108473 | Treatment | Drought vs. No Drought |
| 12646726 | At_Drought_Flowers | 108473 | Tissue | Flower |
| 12646726 | At_Drought_Flowers | 108474 | Timepoint (hr) | 8 d (1 d-post_re-watering) |
| 12646726 | At_Drought_Flowers | 108474 | Treatment | Drought vs. No Drought |
| 12646726 | At_Drought_Flowers | 108474 | Tissue | Flower |
| 12646726 | At_Shoot_Apices | 108479 | Plant Line | AOD4-4 |
| 12646726 | At_Shoot_Apices | 108479 | Treatment | None |
| 12646726 | At_Shoot_Apices | 108480 | Treatment | 1uM BR vs. No Treatment |
| 12646726 | At_Shoot_Apices | 108480 | Plant Line | Ws-2 |
| 12646726 | At_15mM_NH4NO3_L-to-H_Rosette | 108489 | Timepoint (hr) | 4 |
| 12646726 | At_15mM_NH4NO3_L-to-H_Rosette | 108489 | Treatment | 15 mM NH4NO3 vs. 30 mM Mannitol |
| 12646726 | At_15mM_NH4NO3_L-to-H_Rosette | 108489 | Tissue | Rosette |
| 12646726 | At_ap2_floral_buds | 108501 | Plant Line | ap2 (Ler.) |
| 12646726 | At_ap2_floral_buds | 108501 | Tissue | Closed Flower |
| 12646726 | At_Ler-rhl_Root | 108594 | Plant Line | Ler_rhl |
| 12646726 | At_Ler-rhl_Root | 108594 | Tissue | Roots |
| 12646726 | At_Ler-pi_Ovule | 108595 | Plant Line | Ler_pi |
| 12646726 | At_Ler-pi_Ovule | 108595 | Tissue | Ovules |
| 12646726 | At_100uM_ABA | 108609 | Timepoint (hr) | 24 |
| 12646726 | At_100uM_ABA | 108609 | Treatment | 100 uM ABA vs. No Treatment |
| 12646726 | At_100uM_ABA | 108609 | Tissue | Aerial |
| 12646726 | At_100uM_ABA_Mutants | 20000069 | Timepoint (hr) | 6 |
| 12646726 | At_100uM_ABA_Mutants | 20000069 | Treatment | 100 uM ABA vs. No Treatment |
| 12646726 | At_100uM_ABA_Mutants | 20000069 | Tissue | Aerial |
| 12646726 | At_100uM_ABA_Mutants | 20000069 | Plant Line | CS23 |
| 12646726 | At_100uM_ABA_Mutants | 20000070 | Timepoint (hr) | 6 |
| 12646726 | At_100uM_ABA_Mutants | 20000070 | Treatment | 100 uM ABA vs. No Treatment |
| 12646726 | At_100uM_ABA_Mutants | 20000070 | Tissue | Aerial |
| 12646726 | At_100uM_ABA_Mutants | 20000070 | Plant Line | CS24 |
| 12646726 | At_100uM_ABA_Mutants | 20000071 | Timepoint (hr) | 6 |
| 12646726 | At_100uM_ABA_Mutants | 20000071 | Treatment | 100 uM ABA vs. No Treatment |
| 12646726 | At_100uM_ABA_Mutants | 20000071 | Tissue | Aerial |
| 12646726 | At_100uM_ABA_Mutants | 20000071 | Plant Line | CS8104 |
| 12646726 | At_100uM_ABA_Mutants | 20000072 | Timepoint (hr) | 6 |
| 12646726 | At_100uM_ABA_Mutants | 20000072 | Treatment | 100 uM ABA vs. No Treatment |
| 12646726 | At_100uM_ABA_Mutants | 20000072 | Tissue | Aerial |
| 12646726 | At_100uM_ABA_Mutants | 20000072 | Plant Line | CS8105 |

TABLE 1-continued

Promoter Sequences and Related Information

| | | | | |
|---|---|---|---|---|
| 12646726 | At_100uM_ABA_Mutants | 20000117 | Timepoint (hr) | 6 |
| 12646726 | At_100uM_ABA_Mutants | 20000117 | Treatment | 100 uM ABA vs. No Treatment |
| 12646726 | At_100uM_ABA_Mutants | 20000117 | Tissue | Aerial |
| 12646726 | At_100uM_ABA_Mutants | 20000117 | Plant Line | Columbia |
| 12646726 | At_42deg_Heat | 20000173 | Timepoint (hr) | 6 |
| 12646726 | At_42deg_Heat | 20000173 | Age (day) | 14 |
| 12646726 | At_42deg_Heat | 20000173 | Temperature (deg C.) | 42 vs. 22 |
| 12646726 | At_42deg_Heat | 20000173 | Organism | *A. thaliana* |
| 12646726 | At_42deg_Heat | 20000173 | Tissue | Aerial |
| 12646726 | At_42deg_Heat | 20000173 | Plant Line | WS |
| 12646726 | At_Shoots | 20000184 | Age (day) | 7 vs. 21 |
| 12646726 | At_Shoots | 20000184 | Organism | *A. thaliana* |
| 12646726 | At_Shoots | 20000184 | Tissue | Shoots vs. Whole Plant |
| 12646726 | At_Shoots | 20000184 | Plant Line | WS |
| 12646726 | At_Roots | 20000185 | Age (day) | 7 vs. 21 |
| 12646726 | At_Roots | 20000185 | Organism | *A. thaliana* |
| 12646726 | At_Roots | 20000185 | Tissue | Roots vs. Whole Plant |
| 12646726 | At_Roots | 20000185 | Plant Line | WS |
| 12646726 | At_Root-Tips-vs-Tops | 20000227 | Age (day) | 7, 10, 14 |
| 12646726 | At_Root-Tips-vs-Tops | 20000227 | Organism | *A. thaliana* |
| 12646726 | At_Root-Tips-vs-Tops | 20000227 | Tissue | Root Tips vs. Root Tops |
| 12646726 | At_Root-Tips-vs-Tops | 20000227 | Plant Line | WS |
| 12646726 | At_Siliques | 20000234 | Age (day) | 21 |
| 12646726 | At_Siliques | 20000234 | Tissue | <5 mm Siliques vs. Whole Plant |
| 12646726 | At_Siliques | 20000234 | Organism | *A. thaliana* |
| 12646726 | At_Siliques | 20000234 | Plant Line | WS |
| 12646726 | At_Open_Flower | 20000265 | Age (day) | 21 |
| 12646726 | At_Open_Flower | 20000265 | Organism | *A. thaliana* |
| 12646726 | At_Open_Flower | 20000265 | Tissue | Closed Flower vs. Whole Plant |
| 12646726 | At_Open_Flower | 20000265 | Plant Line | WS |
| 12646726 | At_Drought | 20000267 | Timepoint (hr) | 6 |
| 12646726 | At_Drought | 20000267 | Age (day) | 7 |
| 12646726 | At_Drought | 20000267 | Organism | *A. thaliana* |
| 12646726 | At_Drought | 20000267 | Treatment | Drought vs. No Drought |
| 12646726 | At_Drought | 20000267 | Tissue | Whole Plant |
| 12646726 | At_Drought | 20000267 | Plant Line | WS |
| 12646726 | At_100mM_NaCl | 20000268 | Timepoint (hr) | 6 |
| 12646726 | At_100mM_NaCl | 20000268 | Age (day) | 14 |
| 12646726 | At_100mM_NaCl | 20000268 | Treatment | 100 mM NaCl vs. No Treatment |
| 12646726 | At_100mM_NaCl | 20000268 | Organism | *A. thaliana* |
| 12646726 | At_100mM_NaCl | 20000268 | Tissue | Whole Plant |
| 12646726 | At_100mM_NaCl | 20000268 | Plant Line | WS |
| 12646726 | At_100mM_NaCl | 20000308 | Age (day) | 17 |
| 12646726 | At_100mM_NaCl | 20000308 | Timepoint (hr) | 72 |
| 12646726 | At_100mM_NaCl | 20000308 | Treatment | 100 mM NaCl vs. No Treatment |
| 12646726 | At_100mM_NaCl | 20000308 | Organism | *A. thaliana* |
| 12646726 | At_100mM_NaCl | 20000308 | Tissue | Whole Plant |
| 12646726 | At_100mM_NaCl | 20000308 | Plant Line | WS |
| 12646726 | At_Drought | 20000436 | Age (day) | 7 |
| 12646726 | At_Drought | 20000436 | Timepoint (hr) | 12 |
| 12646726 | At_Drought | 20000436 | Organism | *A. thaliana* |
| 12646726 | At_Drought | 20000436 | Treatment | Drought vs. No Drought |
| 12646726 | At_Drought | 20000436 | Tissue | Whole Plant |
| 12646726 | At_Drought | 20000436 | Plant Line | WS |
| 12646726 | At_Drought | 20000437 | Age (day) | 8 |
| 12646726 | At_Drought | 20000437 | Timepoint (hr) | 24 |
| 12646726 | At_Drought | 20000437 | Organism | *A. thaliana* |
| 12646726 | At_Drought | 20000437 | Treatment | Drought vs. No Drought |
| 12646726 | At_Drought | 20000437 | Tissue | Whole Plant |
| 12646726 | At_Drought | 20000437 | Plant Line | WS |
| 12646726 | At_Shoots | 20000438 | Age (day) | 14 vs. 21 |
| 12646726 | At_Shoots | 20000438 | Organism | *A. thaliana* |
| 12646726 | At_Shoots | 20000438 | Tissue | Shoots vs. Whole Plant |
| 12646726 | At_Shoots | 20000438 | Plant Line | WS |
| 12646726 | At_1uM_BR-BRZ | 20000441 | Treatment | 1uM BR vs. No Treatment |
| 12646726 | At_1uM_BR-BRZ | 20000441 | Tissue | Shoot Apices |
| 12646726 | At_1uM_BR-BRZ | 20000443 | Treatment | 1 uM BRZ vs. No Treatment |
| 12646726 | At_1uM_BR-BRZ | 20000443 | Tissue | Shoot Apices |
| 12646726 | At_100uM_ABA | 20000453 | Age (day) | 15 |
| 12646726 | At_100uM_ABA | 20000453 | Timepoint (hr) | 24 |
| 12646726 | At_100uM_ABA | 20000453 | Treatment | 100 uM ABA vs. No Treatment |

TABLE 1-continued

Promoter Sequences and Related Information

| 12646726 | At_100uM_ABA | 20000453 | Organism | A. thaliana |
| 12646726 | At_100uM_ABA | 20000453 | Tissue | Aerial |
| 12646726 | At_100uM_ABA | 20000453 | Plant Line | WS |
| 12646726 | At_42deg_Heat | 20000457 | Timepoint (hr) | 0.166 |
| 12646726 | At_42deg_Heat | 20000457 | Age (day) | 14 |
| 12646726 | At_42deg_Heat | 20000457 | Temperature (deg C.) | 42 vs. 22 |
| 12646726 | At_42deg_Heat | 20000457 | Organism | A. thaliana |
| 12646726 | At_42deg_Heat | 20000457 | Tissue | Aerial |
| 12646726 | At_42deg_Heat | 20000457 | Plant Line | WS |
| 12646726 | At_42deg_Heat | 20000458 | Timepoint (hr) | 8 |
| 12646726 | At_42deg_Heat | 20000458 | Age (day) | 14 |
| 12646726 | At_42deg_Heat | 20000458 | Temperature (deg C.) | 42 vs. 22 |
| 12646726 | At_42deg_Heat | 20000458 | Organism | A. thaliana |
| 12646726 | At_42deg_Heat | 20000458 | Tissue | Aerial |
| 12646726 | At_42deg_Heat | 20000458 | Plant Line | WS |
| 12646726 | At_Guard_Cells | 20000495 | Harvest Date | 08 Feb. 2002 |
| 12646726 | At_Guard_Cells | 20000495 | Organism | A. thaliana |
| 12646726 | At_Guard_Cells | 20000495 | Tissue | Guard Cells vs. Leaves |
| 12646726 | At_10percent_PEG | 20000527 | Age (day) | 20 |
| 12646726 | At_10percent_PEG | 20000527 | Timepoint (day) | 20 |
| 12646726 | At_10percent_PEG | 20000527 | Treatment | 10 percent PEG vs. No Treatment |
| 12646726 | At_10percent_PEG | 20000527 | Organism | A. thaliana |
| 12646726 | At_10percent_PEG | 20000527 | Tissue | Whole Plant |
| 12646726 | At_10percent_PEG | 20000527 | Plant Line | WS |
| 12646726 | At_100uM_ABA_Mutants | 20000573 | Organism | A. thaliana |
| 12646726 | At_100uM_ABA_Mutants | 20000573 | Plant Line | CS22 vs. Ler wt |
| 12646726 | At_100uM_ABA_Mutants | 20000573 | Timepoint (hr) | N/A |
| 12646726 | At_100uM_ABA_Mutants | 20000573 | Treatment | None |
| 12646726 | At_100uM_ABA_Mutants | 20000573 | Tissue | Whole Plant |
| 12646726 | At_100uM_ABA_Mutants | 20000574 | Organism | A. thaliana |
| 12646726 | At_100uM_ABA_Mutants | 20000574 | Plant Line | CS23 vs. Ler wt |
| 12646726 | At_100uM_ABA_Mutants | 20000574 | Timepoint (hr) | N/A |
| 12646726 | At_100uM_ABA_Mutants | 20000574 | Treatment | None |
| 12646726 | At_100uM_ABA_Mutants | 20000574 | Tissue | Whole Plant |
| 12646726 | At_15mM_NH4NO3_L-to-H | 20000709 | Timepoint (hr) | 4 |
| 12646726 | At_15mM_NH4NO3_L-to-H | 20000709 | Age (hr) | 14 |
| 12646726 | At_15mM_NH4NO3_L-to-H | 20000709 | Treatment | 15 mM NH4NO3 vs. 30 mM Mannitol |
| 12646726 | At_15mM_NH4NO3_L-to-H | 20000709 | Organism | A. thaliana |
| 12646726 | At_15mM_NH4NO3_L-to-H | 20000709 | Tissue | Aerial |
| 12646726 | At_15mM_NH4NO3_L-to-H | 20000709 | Plant Line | WS |
| 12646726 | At_Line_Comparisons | 20001151 | Plant Line | ME01339-01 vs. WS |
| 12646726 | At_Line_Comparisons | 20001300 | Plant Line | ME01338-05 vs. WS |
| 12646726 | At_Line_Comparisons | 20001307 | Plant Line | WBin4-WX2-A vs. WS |
| 12646726 | At_Line_Comparisons | 20001309 | Plant Line | WBin4-WX49R-A vs. WS |
| 12646726 | At_Line_Comparisons | 20001310 | Plant Line | WBin4-WX17-A vs. WS |
| 12646726 | At_Interploidy_Crosses | 20001316 | Age (day) | 5 |
| 12646726 | At_Interploidy_Crosses | 20001316 | Organism | A. thaliana |
| 12646726 | At_Interploidy_Crosses | 20001316 | Plant Line | Columbia |
| 12646726 | At_Interploidy_Crosses | 20001316 | Cross | hemi x 2X vs. 2X x 2X |
| 12646726 | At_Interploidy_Crosses | 20001316 | Tissue | Siliques |
| 12646726 | At_Line_Comparisons | 20001448 | Plant Line | ME01323-01 vs. WS |
| 12646726 | At_Drought_Soil_Dry | 20001554 | Timepoint (day) | 7 |
| 12646726 | At_Drought_Soil_Dry | 20001554 | Age (day) | 21 |
| 12646726 | At_Drought_Soil_Dry | 20001554 | Organism | A. thaliana |
| 12646726 | At_Drought_Soil_Dry | 20001554 | Treatment | Drought vs. No Drought |
| 12646726 | At_Drought_Soil_Dry | 20001554 | Post Timepoint (hr) | None |
| 12646726 | At_Drought_Soil_Dry | 20001554 | Post-Treatment | None |
| 12646726 | At_Drought_Soil_Dry | 20001554 | Plant Line | WS |
| 12646726 | At_Drought_Soil_Dry | 20001555 | Timepoint (day) | 10 |
| 12646726 | At_Drought_Soil_Dry | 20001555 | Age (day) | 24 |
| 12646726 | At_Drought_Soil_Dry | 20001555 | Organism | A. thaliana |
| 12646726 | At_Drought_Soil_Dry | 20001555 | Treatment | Drought vs. No Drought |
| 12646726 | At_Drought_Soil_Dry | 20001555 | Post Timepoint (hr) | None |
| 12646726 | At_Drought_Soil_Dry | 20001555 | Post-Treatment | None |
| 12646726 | At_Drought_Soil_Dry | 20001555 | Plant Line | WS |
| 12646726 | At_Drought_Soil_Dry | 20001556 | Timepoint (day) | 12 |
| 12646726 | At_Drought_Soil_Dry | 20001556 | Age (day) | 26 |
| 12646726 | At_Drought_Soil_Dry | 20001556 | Organism | A. thaliana |
| 12646726 | At_Drought_Soil_Dry | 20001556 | Treatment | Drought vs. No Drought |
| 12646726 | At_Drought_Soil_Dry | 20001556 | Post Timepoint (hr) | None |
| 12646726 | At_Drought_Soil_Dry | 20001556 | Post-Treatment | None |
| 12646726 | At_Drought_Soil_Dry | 20001556 | Plant Line | WS |
| 12646726 | At_Interploidy_Crosses | 20001654 | Age (day) | 5 |
| 12646726 | At_Interploidy_Crosses | 20001654 | Cross | 6X x 2X vs. 2X x 2X |

TABLE 1-continued

Promoter Sequences and Related Information

| | | | | |
|---|---|---|---|---|
| 12646726 | At_Interploidy_Crosses | 20001654 | Organism | A. thaliana |
| 12646726 | At_Interploidy_Crosses | 20001654 | Plant Line | Columbia |
| 12646726 | At_Interploidy_Crosses | 20001654 | Tissue | Siliques |
| 12646726 | At_Interploidy_Crosses | 20001704 | Age (day) | 5 |
| 12646726 | At_Interploidy_Crosses | 20001704 | Cross | 4X × 2X vs. 2X × 2X |
| 12646726 | At_Interploidy_Crosses | 20001704 | Organism | A. thaliana |
| 12646726 | At_Interploidy_Crosses | 20001704 | Plant Line | Columbia |
| 12646726 | At_Interploidy_Crosses | 20001704 | Tissue | Siliques |
| 12646726 | At_Interploidy_Crosses | 20001853 | Age (day) | 5 |
| 12646726 | At_Interploidy_Crosses | 20001853 | Organism | A. thaliana |
| 12646726 | At_Interploidy_Crosses | 20001853 | Plant Line | Columbia |
| 12646726 | At_Interploidy_Crosses | 20001853 | Cross | Fis1 vs. 2X × 2X |
| 12646726 | At_Interploidy_Crosses | 20001853 | Tissue | Siliques |
| 12646726 | At_Drought_Reproduction | 20001905 | Timepoint (day) | 10 |
| 12646726 | At_Drought_Reproduction | 20001905 | Age (day) | 40 |
| 12646726 | At_Drought_Reproduction | 20001905 | Organism | A. thaliana |
| 12646726 | At_Drought_Reproduction | 20001905 | Treatment | Drought vs. No Drought |
| 12646726 | At_Drought_Reproduction | 20001905 | Tissue | Rosettes |
| 12646726 | At_Drought_Reproduction | 20001905 | Plant Line | WS |
| 12646726 | At_Drought_Reproduction | 20001906 | Timepoint (day) | 5 |
| 12646726 | At_Drought_Reproduction | 20001906 | Age (day) | 35 |
| 12646726 | At_Drought_Reproduction | 20001906 | Organism | A. thaliana |
| 12646726 | At_Drought_Reproduction | 20001906 | Treatment | Drought vs. No Drought |
| 12646726 | At_Drought_Reproduction | 20001906 | Tissue | Siliques |
| 12646726 | At_Drought_Reproduction | 20001906 | Plant Line | WS |
| 12646726 | At_Drought_Reproduction | 20001910 | Timepoint (day) | 7 |
| 12646726 | At_Drought_Reproduction | 20001910 | Age (day) | 37 |
| 12646726 | At_Drought_Reproduction | 20001910 | Organism | A. thaliana |
| 12646726 | At_Drought_Reproduction | 20001910 | Treatment | Drought vs. No Drought |
| 12646726 | At_Drought_Reproduction | 20001910 | Tissue | Flowers |
| 12646726 | At_Drought_Reproduction | 20001910 | Plant Line | WS |
| 12646726 | At_Drought_Reproduction | 20001911 | Timepoint (day) | 10 |
| 12646726 | At_Drought_Reproduction | 20001911 | Age (day) | 40 |
| 12646726 | At_Drought_Reproduction | 20001911 | Organism | A. thaliana |
| 12646726 | At_Drought_Reproduction | 20001911 | Treatment | Drought vs. No Drought |
| 12646726 | At_Drought_Reproduction | 20001911 | Tissue | Flowers |
| 12646726 | At_Drought_Reproduction | 20001911 | Plant Line | WS |
| 12646726 | At_8deg_Cold | 20002108 | Age (day) | 14 |
| 12646726 | At_8deg_Cold | 20002108 | Timepoint (hr) | 168 |
| 12646726 | At_8deg_Cold | 20002108 | Temperature (deg C.) | 8 vs. 22 |
| 12646726 | At_8deg_Cold | 20002108 | Organism | A. thaliana |
| 12646726 | At_8deg_Cold | 20002108 | Tissue | Whole Plant |
| 12646726 | At_8deg_Cold | 20002108 | Plant Line | WS |
| 12646726 | At_8deg_Cold | 20002109 | Age (day) | 16 |
| 12646726 | At_8deg_Cold | 20002109 | Timepoint (hr) | 216 |
| 12646726 | At_8deg_Cold | 20002109 | Temperature (deg C.) | 8 vs. 22 |
| 12646726 | At_8deg_Cold | 20002109 | Organism | A. thaliana |
| 12646726 | At_8deg_Cold | 20002109 | Tissue | Whole Plant |
| 12646726 | At_8deg_Cold | 20002109 | Plant Line | WS |

Promoter YP0388

Modulates the gene: protein phosphatase 2C (PP2C), putative
The GenBank description of the gene: NM_125312 *Arabidopsis thaliana* protein phosphatase 2C (PP2C), putative (At5g59220) mRNA, complete cds gi|30697191|ref|NM_125312.2|[30697191]
The promoter sequence:
5'tatttgtagtgacatattctacaattatcacattttttctcttatgtttcgtagtcgcagatggtca atttttttctataataatttgtccttgaacacaccaaactttagaaacgatgatatataccgtattgtc acgctcacaatgaaacaaacgcgatgaatcgtcatcaccagctaaaagcctaaaacaccatcttagtt ttcactcagataaaaagattatttgtttccaacctttctattgaattgattagcagtgatgacgtaat tagtgatagtttatagtaaaacaaatggaagtggtaataaatttacacaacaaaatatggtaagaatc tataaaataagaggttaagagatctcatgttatattaaatgattgaaagaaaaacaaactattggttg atttccatatgtaatagtaagttgtgatgaaagtgatgacgtaattagttgtatttatagtaaaacaa attaaaatggtaaggtaaatttccacaacaaaacttggtaaaaatcttaaaaaaaaaaaaagaggttt agagatcgcatgcgtgtcatcaaaggttcttttttcacttttaggtctgagtagtgttagactttgattg gtgcacgtaagtgtttcgtatcgcgatttaggagaagtacgttttacacgtggacacaatcaacggtc TABLE 1-continued Promoter Sequences and Related Information aagatttcgtcgtccagatagaggagcgatacgtcacgccattcaacaatctcctcttcttcattcct tcatttgattttgagttttgatctgcccgttcaaaagtctcggtcatctgcccgtaaatataaagat gattatatttatttatatcttctggtgaaagaagctaaTATAaagcttccatggctaatcttgtttaa gcttctcttcttcttctctctcctgtgtctcgttcactagttttttttcgggggagagtgatggagtg tgtttgttgaata 3' cATG
The promoter was cloned from the organism: *Arabidopsis thaliana*, Columbia ecotype Alternative nucleotides:

| Predicted Position (bp) | Mismatch | Predicted/Experimental |
| --- | --- | --- |
| 1-1000 | None | Identities = 1000/1000 (100%) |

The promoter was cloned in the vector: pNewbin4-HAP1-GFP
When cloned into the vector the promoter was operably linked to a marker,
which was the type: GFP-ER
Promoter-marker vector was tested in: *Arabidopsis thaliana*, WS ecotype
Generation screened: XT1 Mature   XT2 Seedling   T2 Mature   T3 Seedling The spatial expression of the promoter-marker vector was found observed in and would be useful in expression in any or all of the following:

Flower              H filament H anther H stomata
Silique             H ovule
Ovule               Post-fertilization: H outer H seed coat H chalaza
Leaf                L vascular H stomata
Primary Root        H epidermis
Observed expression pattern:
T1 mature: Very high GFP expression levels in stamens of developing flowers. Low expression in
vasculature of leaves and guard cells throughout plant. High expression in outer integument
of ovules and in seed coats. High incidence of aborted ovules.
T2 seedling: Low expression in root epidermal cells.
Misc. promoter information: Bidirectionality: Pass   Exons: Pass   Repeats: No
Optional Promoter Fragments: 5' UTR region at base pairs 880-987.
The Ceres cDNA ID of the endogenous coding sequence to the promoter: 13593066
cDNA nucleotide sequence:
AAAGCTTCCATGGCTAATCTTGTTTAAGCTTCTCTTCTTCTTCTCTCTCCTGTGTCTCGTTCACT

AGTTTTTTTCGGGGGAGAGTGATGGAGTGTGTTTGTTGAATAGTTTTGACGATCACATGGCT

GAGATTTGTTACGAGAACGAGACTATGATGATTGAAACGACGGCGACGGTGGTGAAGAAGGC

AACGACGACAACGAGGAGACGAGAACGGAGCTCGTCTCAAGCAGCGAGAAGAAGGAGAATG

GAGATCCGGAGGTTTAAGTTTGTTTCCGGCGAACAAGAACCTGTCTTCGTCGACGGTGACTTA

CAGAGGCGGAGGAGAAGAGAATCCACCGTCGCAGCCTCCACCTCCACCGTGTTTTACGAAACG

GCGAAGGAAGTTGTCGTCCTATGCGAGTCTCTTAGTTCAACGGTTGTGGCATTGCCTGATCCT

GAAGCTTATCCTAAATACGGCGTCGCTTCAGTCTGTGGAAGAAGACGTGAAATGAAGACGCC

GTCGCTGTGCATCCGTTTTTTTCCCGTCATCAGACGGAATATTCATCCACCGGATTTCACTATT

GCGGCGTTTACGATGGCCATGGCTGTTCCCATGTAGCGATGAAATGTAGAGAAAGACTACACG

AGCTAGTCCGTGAAGAGTTTGAAGCTGATGCTGACTGGGAAAAGTCAATGGCGCGTAGCTTCA

CGCGCATGGACATGGAGGTTGTTGCGTTGAACGCCGATGGTGCGGCAAAATGCCGGTGCGAG

CTTCAGAGGCCGGACTGCGACGCGGTGGGATCCACTGCGGTTGTGTCTGTCCTTACGCCGGAG

AAAATCATCGTGGCGAATTGCGGTGACTCACGTGCCGTTCTCTGTCGTAACGGCAAAGCCATT

GCTTTATCCTCCGATCATAAGCCAGACCGTCCGGACGAGCTAGACCGGATTCAAGCAGCGGGT

GGTCGTGTTATCTACTGGGATGGCCCACGTGTCCTTGGAGTACTTGCAATGTCACGAGCCATT

GGAGATAATTACTTGAAGCCGTATGTAATCAGCAGACCGGAGGTAACCGTGACGGACCGGGC

CAACGGAGACGATTTTCTTATTCTCGCAAGTGACGGTCTTTGGGACGTTGTTTCAAACGAAAC

TGCATGTAGCGTCGTTCGAATGTGTTTGAGAGGAAAAGTCAATGGTCAAGTATCATCATCACC

TABLE 1-continued

Promoter Sequences and Related Information

GGAAAGGGAAATGACAGGTGTCGGCGCCGGGAATGTGGTGGTTGGAGGAGGAGATTTGCCAG

ATAAAGCGTGTGAGGAGGCGTCGCTGTTGCTGACGAGGCTTGCGTTGGCTAGACAAAGTTCGG

ACAACGTAAGTGTTGTGGTGGTTGATCTACGACGAGACACGTAGTTGTATTTGTCTCTCTCGT

AATGTTTGTTGTTTTTTGTCCTGAGTCATCGACTTTTGGGCTTTTTCTTTTAACCTTTTTTGCTC

TTCGGTGTAAGACAACGAAGGGTTTTTAATTTAGCTTGACTATGGGTTATGTCAGTCACTGTGT

TGAATCGCGGTTTAGATCTACAAAGATTTTCACCAGTAGTGAAAATGGTAAAAAGCCGTGAAA

TGTGAAAGACTTGAGTTCAATTTAATTTTAAATTTAATAGAATCAGTTGATC

Coding sequence:
MAEICYENETMMIETTATVVKKATTTTRRRERSSSQAARRRRMEIRRFKFVSGEQEPVFVDGDLQ

RRRRRESTVAASTSTVFYETAKEVVVLCESLSSTVVALPDPEAYPKYGVASVCGRRREMEDAVAV

HPFFSRHQTEYSSTGFHYCGVYDGHGCSHVAMKCRERLHELVREEFEADADWEKSMARSFTRMD

MEVVALNADGAAKCRCELQRPDCDAVGSTAVVSVLTPEKIIVANCGDSRAVLCRNGKAIALSSDH

KPDRPDELDRIQAAGGRVIYWDGPRVLGVLAMSRAIGDNYLKPYVISRPEVTVTDRANGDDFLILA

SDGLWDVVSNETACSVVRMCLRGKVNGQVSSSPEREMTGVGAGNVVVGGGDLPDKACEEASLL

LTRLALARQSSDNVSVVVVDLRRDT*

Microarray data shows that the coding sequence was expressed in the following experiments, which shows that the promoter would be useful to modulate expression in situations similar to the following:

| CDNA_ID | SHORT_NAME | EXPT_REP_ID | IS_UP |
|---|---|---|---|
| 13593066 | At_100uM_ABA | 20000166 | + |
| 13593066 | At_100uM_ABA | 20000169 | + |
| 13593066 | At_2mM_SA | 20000182 | + |
| 13593066 | At_20%_PEG | 20000233 | + |
| 13593066 | At_Open_Flower | 20000264 | − |
| 13593066 | At_Drought | 20000267 | + |
| 13593066 | At_100mM_NaCl | 20000268 | + |
| 13593066 | At_Pollen | 20000326 | − |
| 13593066 | At_Drought | 20000436 | + |
| 13593066 | At_Drought | 20000437 | + |
| 13593066 | At_Shoots | 20000438 | − |
| 13593066 | At_100uM_ABA | 20000453 | + |
| 13593066 | At_100uM_ABA | 20000455 | + |
| 13593066 | At_100uM_ABA_Mutants | 20000576 | + |
| 13593066 | At_Herbicide_Mutants | 20000642 | − |
| 13593066 | At_Line_Comparisons | 20001151 | + |
| 13593066 | At_Line_Comparisons | 20001184 | + |
| 13593066 | At_Line_Comparisons | 20001307 | + |
| 13593066 | At_Line_Comparisons | 20001309 | − |
| 13593066 | At_Line_Comparisons | 20001310 | − |
| 13593066 | At_Far-red-induction | 20001451 | + |
| 13593066 | At_Drought_Soil_Dry | 20001554 | + |
| 13593066 | At_Drought_Soil_Dry | 20001555 | + |
| 13593066 | At_Drought_Soil_Dry | 20001556 | + |
| 13593066 | At_Drought_Soil_Dry | 20001557 | + |
| 13593066 | At_Drought_Soil_Dry | 20001559 | + |
| 13593066 | At_Drought_Soil_Dry | 20001560 | + |
| 13593066 | At_50mM_NH4NO3_L-to-H | 20001757 | − |
| 13593066 | At_Far-red-enriched-adult | 20001771 | + |
| 13593066 | At_Drought_Reproduction | 20001904 | + |
| 13593066 | At_Drought_Reproduction | 20001905 | + |
| 13593066 | At_Drought_Reproduction | 20001906 | + |
| 13593066 | At_Drought_Reproduction | 20001907 | + |
| 13593066 | At_Drought_Reproduction | 20001908 | + |
| 13593066 | At_Drought_Reproduction | 20001911 | + |
| 13593066 | At_8deg_Cold | 20002107 | − |
| 13593066 | At_8deg_Cold | 20002108 | − |
| 13593066 | At_8deg_Cold | 20002109 | − |
| 13593066 | At_Drought-Air-Dry | 20002256 | + |

TABLE 1-continued

Promoter Sequences and Related Information

The parameters for the microarray experiments listed above by Expt_Rep_ID and Short_Name are as follow below:

| CDNA_ID | SHORT_NAME | EXPT_REP_ID | PARAM_NAME | VALUE |
|---|---|---|---|---|
| 13593066 | At_100uM_ABA | 20000166 | Timepoint (hr) | 1 |
| 13593066 | At_100uM_ABA | 20000166 | Age (day) | 14 |
| 13593066 | At_100uM_ABA | 20000166 | Treatment | 100 uM ABA vs. No Treatment |
| 13593066 | At_100uM_ABA | 20000166 | Organism | A. thaliana |
| 13593066 | At_100uM_ABA | 20000166 | Tissue | Aerial |
| 13593066 | At_100uM_ABA | 20000166 | Plant Line | WS |
| 13593066 | At_100uM_ABA | 20000169 | Timepoint (hr) | 6 |
| 13593066 | At_100uM_ABA | 20000169 | Age (day) | 14 |
| 13593066 | At_100uM_ABA | 20000169 | Treatment | 100 uM ABA vs. No Treatment |
| 13593066 | At_100uM_ABA | 20000169 | Organism | A. thaliana |
| 13593066 | At_100uM_ABA | 20000169 | Tissue | Aerial |
| 13593066 | At_100uM_ABA | 20000169 | Plant Line | WS |
| 13593066 | At_2mM_SA | 20000182 | Timepoint (hr) | 6 |
| 13593066 | At_2mM_SA | 20000182 | Age (day) | 14 |
| 13593066 | At_2mM_SA | 20000182 | Treatment | 2 mM SA vs. No Treatment |
| 13593066 | At_2mM_SA | 20000182 | Organism | A. thaliana |
| 13593066 | At_2mM_SA | 20000182 | Tissue | Aerial |
| 13593066 | At_2mM_SA | 20000182 | Plant Line | WS |
| 13593066 | At_20%_PEG | 20000233 | Timepoint (hr) | 6 |
| 13593066 | At_20%_PEG | 20000233 | Treatment | 20% PEG vs. No Treatment |
| 13593066 | At_20%_PEG | 20000233 | Tissue | Aerial |
| 13593066 | At_Open_Flower | 20000264 | Age (day) | 21 |
| 13593066 | At_Open_Flower | 20000264 | Organism | A. thaliana |
| 13593066 | At_Open_Flower | 20000264 | Tissue | Open Flower vs. Whole Plant |
| 13593066 | At_Open_Flower | 20000264 | Plant Line | WS |
| 13593066 | At_Drought | 20000267 | Timepoint (hr) | 6 |
| 13593066 | At_Drought | 20000267 | Age (day) | 7 |
| 13593066 | At_Drought | 20000267 | Organism | A. thaliana |
| 13593066 | At_Drought | 20000267 | Treatment | Drought vs. No Drought |
| 13593066 | At_Drought | 20000267 | Tissue | Whole Plant |
| 13593066 | At_Drought | 20000267 | Plant Line | WS |
| 13593066 | At_100mM_NaCl | 20000268 | Timepoint (hr) | 6 |
| 13593066 | At_100mM_NaCl | 20000268 | Age (day) | 14 |
| 13593066 | At_100mM_NaCl | 20000268 | Treatment | 100 mM NaCl vs. No Treatment |
| 13593066 | At_100mM_NaCl | 20000268 | Organism | A. thaliana |
| 13593066 | At_100mM_NaCl | 20000268 | Tissue | Whole Plant |
| 13593066 | At_100mM_NaCl | 20000268 | Plant Line | WS |
| 13593066 | At_Pollen | 20000326 | Age (day) | 0 vs. 21 |
| 13593066 | At_Pollen | 20000326 | Organism | A. thaliana |
| 13593066 | At_Pollen | 20000326 | Tissue | Pollen vs. Whole Plant |
| 13593066 | At_Pollen | 20000326 | Plant Line | WS |
| 13593066 | At_Drought | 20000436 | Age (day) | 7 |
| 13593066 | At_Drought | 20000436 | Timepoint (hr) | 12 |
| 13593066 | At_Drought | 20000436 | Organism | A. thaliana |
| 13593066 | At_Drought | 20000436 | Treatment | Drought vs. No Drought |
| 13593066 | At_Drought | 20000436 | Tissue | Whole Plant |
| 13593066 | At_Drought | 20000436 | Plant Line | WS |
| 13593066 | At_Drought | 20000437 | Age (day) | 8 |
| 13593066 | At_Drought | 20000437 | Timepoint (hr) | 24 |
| 13593066 | At_Drought | 20000437 | Organism | A. thaliana |
| 13593066 | At_Drought | 20000437 | Treatment | Drought vs. No Drought |
| 13593066 | At_Drought | 20000437 | Tissue | Whole Plant |
| 13593066 | At_Drought | 20000437 | Plant Line | WS |
| 13593066 | At_Shoots | 20000438 | Age (day) | 14 vs. 21 |
| 13593066 | At_Shoots | 20000438 | Organism | A. thaliana |
| 13593066 | At_Shoots | 20000438 | Tissue | Shoots vs. Whole Plant |
| 13593066 | At_Shoots | 20000438 | Plant Line | WS |
| 13593066 | At_100uM_ABA | 20000453 | Age (day) | 15 |
| 13593066 | At_100uM_ABA | 20000453 | Timepoint (hr) | 24 |
| 13593066 | At_100uM_ABA | 20000453 | Treatment | 100 uM ABA vs. No Treatment |
| 13593066 | At_100uM_ABA | 20000453 | Organism | A. thaliana |
| 13593066 | At_100uM_ABA | 20000453 | Tissue | Aerial |
| 13593066 | At_100uM_ABA | 20000453 | Plant Line | WS |
| 13593066 | At_100uM_ABA | 20000455 | Age (day) | 16 |
| 13593066 | At_100uM_ABA | 20000455 | Timepoint (hr) | 48 |
| 13593066 | At_100uM_ABA | 20000455 | Treatment | 100 uM ABA vs. No Treatment |
| 13593066 | At_100uM_ABA | 20000455 | Organism | A. thaliana |
| 13593066 | At_100uM_ABA | 20000455 | Tissue | Aerial |
| 13593066 | At_100uM_ABA | 20000455 | Plant Line | WS |
| 13593066 | At_100uM_ABA_Mutants | 20000576 | Timepoint (hr) | 6 |
| 13593066 | At_100uM_ABA_Mutants | 20000576 | Treatment | 1uM ABA vs. No Treatment |
| 13593066 | At_100uM_ABA_Mutants | 20000576 | Organism | A. thaliana |
| 13593066 | At_100uM_ABA_Mutants | 20000576 | Plant Line | CS23 |

TABLE 1-continued

Promoter Sequences and Related Information

| | | | | |
|---|---|---|---|---|
| 13593066 | At_100uM_ABA_Mutants | 20000576 | Tissue | Whole Plant |
| 13593066 | At_Herbicide_Mutants | 20000642 | Timepoint (hr) | 12 |
| 13593066 | At_Herbicide_Mutants | 20000642 | Plant Line | 3950BR/PCJE10000 |
| 13593066 | At_Herbicide_Mutants | 20000642 | Treatment | Finale vs. No Treatment |
| 13593066 | At_Herbicide_Mutants | 20000642 | Tissue | Seedlings |
| 13593066 | At_Line_Comparisons | 20001151 | Plant Line | ME01339-01 vs. WS |
| 13593066 | At_Line_Comparisons | 20001184 | Plant Line | ME01848-01 vs. WS |
| 13593066 | At_Line_Comparisons | 20001307 | Plant Line | WBin4-WX2-A vs. WS |
| 13593066 | At_Line_Comparisons | 20001309 | Plant Line | WBin4-WX49R-A vs. WS |
| 13593066 | At_Line_Comparisons | 20001310 | Plant Line | WBin4-WX17-A vs. WS |
| 13593066 | At_Far-red-induction | 20001451 | Age (day) | 8 |
| 13593066 | At_Far-red-induction | 20001451 | Timepoint (hr) | 24 |
| 13593066 | At_Far-red-induction | 20001451 | Organism | A. thaliana |
| 13593066 | At_Far-red-induction | 20001451 | Plant Line | Columbia |
| 13593066 | At_Far-red-induction | 20001451 | Light | Far-red vs. White |
| 13593066 | At_Far-red-induction | 20001451 | Tissue | Whole Plant |
| 13593066 | At_Drought_Soil_Dry | 20001554 | Timepoint (day) | 7 |
| 13593066 | At_Drought_Soil_Dry | 20001554 | Age (day) | 21 |
| 13593066 | At_Drought_Soil_Dry | 20001554 | Organism | A. thaliana |
| 13593066 | At_Drought_Soil_Dry | 20001554 | Treatment | Drought vs. No Drought |
| 13593066 | At_Drought_Soil_Dry | 20001554 | Post Timepoint (hr) | None |
| 13593066 | At_Drought_Soil_Dry | 20001554 | Post-Treatment | None |
| 13593066 | At_Drought_Soil_Dry | 20001554 | Plant Line | WS |
| 13593066 | At_Drought_Soil_Dry | 20001555 | Timepoint (day) | 10 |
| 13593066 | At_Drought_Soil_Dry | 20001555 | Age (day) | 24 |
| 13593066 | At_Drought_Soil_Dry | 20001555 | Organism | A. thaliana |
| 13593066 | At_Drought_Soil_Dry | 20001555 | Treatment | Drought vs. No Drought |
| 13593066 | At_Drought_Soil_Dry | 20001555 | Post Timepoint (hr) | None |
| 13593066 | At_Drought_Soil_Dry | 20001555 | Post-Treatment | None |
| 13593066 | At_Drought_Soil_Dry | 20001555 | Plant Line | WS |
| 13593066 | At_Drought_Soil_Dry | 20001556 | Timepoint (day) | 12 |
| 13593066 | At_Drought_Soil_Dry | 20001556 | Age (day) | 26 |
| 13593066 | At_Drought_Soil_Dry | 20001556 | Organism | A. thaliana |
| 13593066 | At_Drought_Soil_Dry | 20001556 | Treatment | Drought vs. No Drought |
| 13593066 | At_Drought_Soil_Dry | 20001556 | Post Timepoint (hr) | None |
| 13593066 | At_Drought_Soil_Dry | 20001556 | Post-Treatment | None |
| 13593066 | At_Drought_Soil_Dry | 20001556 | Plant Line | WS |
| 13593066 | At_Drought_Soil_Dry | 20001557 | Post Timepoint (hr) | 3 |
| 13593066 | At_Drought_Soil_Dry | 20001557 | Timepoint (day) | 13 |
| 13593066 | At_Drought_Soil_Dry | 20001557 | Age (day) | 27 |
| 13593066 | At_Drought_Soil_Dry | 20001557 | Organism | A. thaliana |
| 13593066 | At_Drought_Soil_Dry | 20001557 | Treatment | Drought vs. No Drought |
| 13593066 | At_Drought_Soil_Dry | 20001557 | Post-Treatment | Re-Water vs. No Drought |
| 13593066 | At_Drought_Soil_Dry | 20001557 | Plant Line | WS |
| 13593066 | At_Drought_Soil_Dry | 20001559 | Timepoint (day) | 14 |
| 13593066 | At_Drought_Soil_Dry | 20001559 | Age (day) | 28 |
| 13593066 | At_Drought_Soil_Dry | 20001559 | Post Timepoint (hr) | 29 |
| 13593066 | At_Drought_Soil_Dry | 20001559 | Organism | A. thaliana |
| 13593066 | At_Drought_Soil_Dry | 20001559 | Treatment | Drought vs. No Drought |
| 13593066 | At_Drought_Soil_Dry | 20001559 | Post-Treatment | Re-Water vs. No Drought |
| 13593066 | At_Drought_Soil_Dry | 20001559 | Plant Line | WS |
| 13593066 | At_Drought_Soil_Dry | 20001560 | Timepoint (day) | 14 |
| 13593066 | At_Drought_Soil_Dry | 20001560 | Age (day) | 28 |
| 13593066 | At_Drought_Soil_Dry | 20001560 | Organism | A. thaliana |
| 13593066 | At_Drought_Soil_Dry | 20001560 | Treatment | Drought vs. No Drought |
| 13593066 | At_Drought_Soil_Dry | 20001560 | Post Timepoint (hr) | None |
| 13593066 | At_Drought_Soil_Dry | 20001560 | Post-Treatment | None |
| 13593066 | At_Drought_Soil_Dry | 20001560 | Plant Line | WS |
| 13593066 | At_50mM_NH4NO3_L-to-H | 20001757 | Timepoint (hr) | 6 |
| 13593066 | At_50mM_NH4NO3_L-to-H | 20001757 | Treatment | 50 mM NH4NO3 vs 100 mM Mannitol |
| 13593066 | At_50mM_NH4NO3_L-to-H | 20001757 | Tissue | Leaf |
| 13593066 | At_Far-red-enriched-adult | 20001771 | Timepoint (hr) | 16 |
| 13593066 | At_Far-red-enriched-adult | 20001771 | Age (day) | 28 |
| 13593066 | At_Far-red-enriched-adult | 20001771 | Organism | A. thaliana |
| 13593066 | At_Far-red-enriched-adult | 20001771 | Tissue | Aerial |
| 13593066 | At_Far-red-enriched-adult | 20001771 | Plant Line | Columbia |
| 13593066 | At_Far-red-enriched-adult | 20001771 | Light | Far-red enriched vs. White |
| 13593066 | At_Drought_Reproduction | 20001904 | Timepoint (day) | 7 |
| 13593066 | At_Drought_Reproduction | 20001904 | Age (day) | 37 |
| 13593066 | At_Drought_Reproduction | 20001904 | Organism | A. thaliana |
| 13593066 | At_Drought_Reproduction | 20001904 | Treatment | Drought vs. No Drought |
| 13593066 | At_Drought_Reproduction | 20001904 | Tissue | Rosettes |
| 13593066 | At_Drought_Reproduction | 20001904 | Plant Line | WS |
| 13593066 | At_Drought_Reproduction | 20001905 | Timepoint (day) | 10 |
| 13593066 | At_Drought_Reproduction | 20001905 | Age (day) | 40 |
| 13593066 | At_Drought_Reproduction | 20001905 | Organism | A. thaliana |
| 13593066 | At_Drought_Reproduction | 20001905 | Treatment | Drought vs. No Drought |

TABLE 1-continued

Promoter Sequences and Related Information

| | | | | |
|---|---|---|---|---|
| 13593066 | At_Drought_Reproduction | 20001905 | Tissue | Rosettes |
| 13593066 | At_Drought_Reproduction | 20001905 | Plant Line | WS |
| 13593066 | At_Drought_Reproduction | 20001906 | Timepoint (day) | 5 |
| 13593066 | At_Drought_Reproduction | 20001906 | Age (day) | 35 |
| 13593066 | At_Drought_Reproduction | 20001906 | Organism | A. thaliana |
| 13593066 | At_Drought_Reproduction | 20001906 | Treatment | Drought vs. No Drought |
| 13593066 | At_Drought_Reproduction | 20001906 | Tissue | Siliques |
| 13593066 | At_Drought_Reproduction | 20001906 | Plant Line | WS |
| 13593066 | At_Drought_Reproduction | 20001907 | Timepoint (day) | 7 |
| 13593066 | At_Drought_Reproduction | 20001907 | Age (day) | 37 |
| 13593066 | At_Drought_Reproduction | 20001907 | Organism | A. thaliana |
| 13593066 | At_Drought_Reproduction | 20001907 | Treatment | Drought vs. No Drought |
| 13593066 | At_Drought_Reproduction | 20001907 | Tissue | Siliques |
| 13593066 | At_Drought_Reproduction | 20001907 | Plant Line | WS |
| 13593066 | At_Drought_Reproduction | 20001908 | Timepoint (day) | 10 |
| 13593066 | At_Drought_Reproduction | 20001908 | Age (day) | 40 |
| 13593066 | At_Drought_Reproduction | 20001908 | Organism | A. thaliana |
| 13593066 | At_Drought_Reproduction | 20001908 | Treatment | Drought vs. No Drought |
| 13593066 | At_Drought_Reproduction | 20001908 | Tissue | Siliques |
| 13593066 | At_Drought_Reproduction | 20001908 | Plant Line | WS |
| 13593066 | At_Drought_Reproduction | 20001911 | Timepoint (day) | 10 |
| 13593066 | At_Drought_Reproduction | 20001911 | Age (day) | 40 |
| 13593066 | At_Drought_Reproduction | 20001911 | Organism | A. thaliana |
| 13593066 | At_Drought_Reproduction | 20001911 | Treatment | Drought vs. No Drought |
| 13593066 | At_Drought_Reproduction | 20001911 | Tissue | Flowers |
| 13593066 | At_Drought_Reproduction | 20001911 | Plant Line | WS |
| 13593066 | At_8deg_Cold | 20002107 | Age (day) | 11 |
| 13593066 | At_8deg_Cold | 20002107 | Timepoint (hr) | 96 |
| 13593066 | At_8deg_Cold | 20002107 | Temperature (deg C.) | 8 vs. 22 |
| 13593066 | At_8deg_Cold | 20002107 | Organism | A. thaliana |
| 13593066 | At_8deg_Cold | 20002107 | Tissue | Whole Plant |
| 13593066 | At_8deg_Cold | 20002107 | Plant Line | WS |
| 13593066 | At_8deg_Cold | 20002108 | Age (day) | 14 |
| 13593066 | At_8deg_Cold | 20002108 | Timepoint (hr) | 168 |
| 13593066 | At_8deg_Cold | 20002108 | Temperature (deg C.) | 8 vs. 22 |
| 13593066 | At_8deg_Cold | 20002108 | Organism | A. thaliana |
| 13593066 | At_8deg_Cold | 20002108 | Tissue | Whole Plant |
| 13593066 | At_8deg_Cold | 20002108 | Plant Line | WS |
| 13593066 | At_8deg_Cold | 20002109 | Age (day) | 16 |
| 13593066 | At_8deg_Cold | 20002109 | Timepoint (hr) | 216 |
| 13593066 | At_8deg_Cold | 20002109 | Temperature (deg C.) | 8 vs. 22 |
| 13593066 | At_8deg_Cold | 20002109 | Organism | A. thaliana |
| 13593066 | At_8deg_Cold | 20002109 | Tissue | Whole Plant |
| 13593066 | At_8deg_Cold | 20002109 | Plant Line | WS |
| 13593066 | At_Drought-Air-Dry | 20002256 | Timepoint (hr) | 4 |
| 13593066 | At_Drought-Air-Dry | 20002256 | Age (day) | 35 |
| 13593066 | At_Drought-Air-Dry | 20002256 | Organism | A. thaliana |
| 13593066 | At_Drought-Air-Dry | 20002256 | Treatment | Drought vs. No Drought |
| 13593066 | At_Drought-Air-Dry | 20002256 | Tissue | Shoots |
| 13593066 | At_Drought-Air-Dry | 20002256 | Plant Line | WS |

Promoter YP0385

Modulates the gene: Neoxanthin cleavage enzyme.
The GenBank description of the gene: NM_112304 Arabidopsis thaliana 9-cis-epoxycarotenoid dioxygenase [neoxanthin cleavage enzyme](NC1)(NCED1), putative (At3g14440) mRNA, complete cds gi|30683162|ref|NM_112304.2|[30683162].
The promoter sequence:
5'aaaattccaattattgtgttactctattcttctaaatttgaacactaatagactatgacatatgagtat ataatgtgaagtcttaagatattttcatgtgggagatgaataggccaagttggagtctgcaaacaagaagc tcttgagccacgacataagccaagttgatgaccgtaattaatgaaactaaatgtgtgtggtatatattag ggacccatggccatatacacaattttttgtttctgtcgatagcatgcgtttatatatatttctaaaaaaact aacatatttactggatttgagttcgaatattgacactaatataaactacgtaccaaactacatatgtttat ctatatttgattgatcgaagaattctgaactgttttagaaaatttcaatacacttaacttcatcttacaac ggtaaaagaaatcaccactagacaaacaatgcctcataatgtctcgaaccctcaaactcaagagtatacat tttactagattagagaatttgatatcctcaagttgccaaagaattggaagcttttgttaccaaacttagaa acagaagaagccacaaaaaaagacaaagggagttaaagattgaagtgatgcatttgtctaagtgtgaaagg tctcaagtctcaactttgaaccataataacattactcacactccctttttttttcttttttttttcccaaag

TABLE 1-continued

Promoter Sequences and Related Information taccctttttaattccctctataacccactcactccattccctctttctgtcactgattcaacacgtggcc acactgatgggatccacctttcctcttacccacctcccggttTATAtaaaccctttcacaacacttcatcgc tctcaaaccaactctctcttctctcttctctcctctcttctacaagaagaaaaaaaacagagcctttacac atctcaaaatcgaacttactttaaccacc 3'-aATG
The promoter was cloned from the organism: *Arabidopsis thaliana*, Columbia ecotype

Alternative nucleotides:

| Predicted Position (bp) | Mismatch | Predicted/Experimental |
| --- | --- | --- |
| 7 | PCR error or ecotype variant SNP | g/— |
| 28 | Read error | a/a corrected |
| 29 | PCR error or ecotype variant SNP | a/— |

The promoter was cloned in the vector: pNewbin4-HAP1-GFP
When cloned into the vector the promoter was operably linked to a marker,
which was the type: GFP-ER
Promoter-marker vector was tested in: *Arabidopsis thaliana*, WS ecotype
Generation screened: XT1 Mature   XT2 Seedling   T2 Mature   T3 Seedling The spatial expression of the promoter-marker vector was found observed in and would be useful in expression in any or all of the following:

Flower                          L receptacle
Silique                         L abscission zone
Primary Root                    H epidermis
Observed expression pattern of the promoter-marker vector was in:
T1 mature: Expression specific to abscission zone of mature flowers.
T2 seedling: Expression in root epidermal cells. Expression rapidly decreases from
root transition zone to mid root.
Misc. promoter information: Bidirectionality: Pass  Exons: Pass   Repeats: No
Optional Promoter Fragments: 5' UTR region at base pairs 880-999.
The Ceres cDNA ID of the endogenous coding sequence to the promoter: 12658348
cDNA nucleotide sequence:
AAACCAACTCTCTCTTCTCTCTTCTCTCCTCTCTTCTACAAGAAGAAAAAAAACAGAGCCTTTA

CACATCTCAAAATCGAACTTACTTTAACCACCAAATACTGATTGAACACACTTGAAAAATGGC

TTCTTTCACGGCAACGGCTGCGGTTTCTGGGAGATGGCTTGGTGGCAATCATACTCAGCCGCC

ATTATCGTCTTCTCAAAGCTCCGACTTGAGTTATTGTAGCTCCTTACCTATGGCCAGTCGTGTC

ACACGTAAGCTCAATGTTTCATCTGCGCTTCACACTCCTCCAGCTCTTCATTTCCCTAAGCAAT

CATCAAACTCTCCCGCCATTGTTGTTAAGCCCAAAGCCAAAGAATCCAACACTAAACAGATGA

ATTTGTTCCAGAGAGCGGCGGCGGCAGCGTTGGACGCGGCGGAGGGTTTCCTTGTCAGCCACG

AGAAGCTACACCCGCTTCCTAAAACGGCTGATCCTAGTGTTCAGATCGCCGGAAATTTTGCTC

CGGTGAATGAACAGCCCGTCCGGCGTAATCTTCCGGTGGTCGGAAAACTTCCCGATTCCATCA

AAGGAGTGTATGTGCGCAACGGAGCTAACCCACTTCACGAGCCGGTGACAGGTCACCACTTCT

TCGACGGAGACGGTATGGTTCACGCCGTCAAATTCGAACACGGTTCAGCTAGCTACGCTTGCC

GGTTTACTCAGACTAACCGGTTTGTTCAGGAACGTCAATTGGGTCGACCGGTTTTCCCCAAAG

CCATCGGTGAGCTTCACGCCACACCGGTATTGCCCGACTCATGCTATTCTACGCCAGAGCTG

CAGCCGGTATAGTCGACCCGGCACACGGAACCGGTGTAGCTAACGCCGGTTTGGTCTATTTCA

ATGGCCGGTTATTGGCTATGTCGGAGGATGATTTACCTTACCAAGTTCAGATCACTCCCAATG

GAGATTTAAAAACCGTTGGTCGGTTCGATTTTGATGGACAATTAGAATCCACAATGATTGCCC

ACCCGAAAGTCGACCCGGAATCCGGTGAACTCTTCGCTTTAAGCTACGACGTCGTTTCAAAGC

CTTACCTAAAATACTTCCGATTCTCACCGGACGGAACTAAATCACCGGACGTCGAGATTCAGC

TTGATCAGCCAACGATGATGCACGATTTCGCGATTACAGAGAACTTCGTCGTCGTACCTGACC

AGCAAGTCGTTTTCAAGCTGCCGGAGATGATCCGCGGTGGGTCTCCGGTGGTTTACGACAAGA

ACAAGGTCGCAAGATTCGGGATTTTAGACAAATACGCCGAAGATTCATCGAACATTAAGTGGA

TABLE 1-continued

Promoter Sequences and Related Information

```
TTGATGCTCCAGATTGCTTCTGCTTCCATCTCTGGAACGCTTGGGAAGAGCCAGAAACAGATG

AAGTCGTCGTGATAGGGTCCTGTATGACTCCACCAGACTCAATTTTCAACGAGTCTGACAGAGA

ATCTCAAGAGTGTCCTGTCTGAAATCCGCCTGAATCTCAAAACCGGTGAATCAACTCGCCGTC

CGATCATCTCCAACGAAGATCAACAAGTCAACCTCGAAGCAGGGATGGTCAACAGAAACATG

CTCGGCCGTAAAACCAAATTCGCTTACTTGGCTTTAGCCGAGCCGTGGCCTAAAGTCTCAGGA

TTCGCTAAAGTTGATCTCACTACTGGAGAAGTTAAGAAACATCTTTACGGCGATAACCGTTAC

GGAGGAGAGCCTCTGTTTCTCCCCGGAGAAGGAGGAGAGGAAGACGAAGGATACATCCTCTG

TTTCGTTCACGACGAGAAGACATGGAAATCGGAGTTACAGATAGTTAACGCCGTTAGCTTAGA

GGTTGAAGCAACGGTTAAACTTCCGTCAAGGGTTCCGTACGGATTTCACGGTACATTCATCGG

AGCCGATGATTTGGCGAAGCAGGTCGTGTGAGTTCTTATGTGTAAATACGCACAAAATACATA

TACGTGATGAAGAAGCTTCTAGAAGGAAAAGAGAGAGCGAGATTTACCAGTGGGATGCTCTG

CATATACGTCCCCGGAATCTGCTCCTCTGTTTTTTTTTTTGCTCTGTTTCTTGTTTGTTGTTTC

TTTTGGGGTGCGGTTTGCTAGTTCCCTTTTTTTGGGGTCAATCTAGAAATCTGAAAGATTTTG

AGGGACCAGCTTGTAGCTTTTGGGCTGTAGGGTAGCCTAGCCGTTCGAGCTCAGCTGGTTTCT

GTTATTCTTTCACTTATTGTTCATCGTAATGAGAAGTATATAAAATATTAAACAACAAAGATAT

GTTTGTATATGTGCATGAATTAAGGAACATTTTTTTT

Coding sequence:
MASFTATAAVSGRWLGGNHTQPPLSSSQSSDLSYCSSLPMASRVTRKLNVSSALHTPPALHFPKQS

SNSPAIVVKPKAKESNTKQMNLFQRAAAAALDAAEGFLVSHEKLHPLPKTADPSVQIAGNFAPVN

EQPVRRNLPVVGKLPDSIKGVYVRNGANPLHEPVTGHHFFDGDGMVHAVKFEHGSASYACRFTQ

TNRFVQERQLGRPVFPKAIGELHGHTGIARLMLFYARAAAGIVDPAHGTGVANAGLVYFNGRLLA

MSEDDLPYQVQITPNGDLKTVGRFDFDGQLESTMIAHPKVDPESGELFALSYDVVSKPYLKYFRFS

PDGTKSPDVEIQLDQPTMMHDFAITENFVVVPDQQVVFKLPEMIRGGSPVVYDKNKVARFGILDK

YAEDSSNIKWIDAPDCFCFHLWNAWEEPETDEVVVIGSCMTPPDSIFNESDENLKSVLSEIRLNLKT

GESTRRPIISNEDQQVNLEAGMVNRNMLGRKTKFAYLALAEPWPKVSGFAKVDLTTGEVKKHLY

GDNRYGGEPLFLPGEGGEEDEGYILCFVHDEKTWKSELQIVNAVSLEVEATVKLPSRVPYGFHGTF

IGADDLAKQVV*
```

Microarray data shows that the coding sequence was expressed in the following experiments, which shows that the promoter would be useful to modulate expression in situations similar to the following:

| CDNA_ID | SHORT_NAME | EXPT_REP_ID | IS_UP |
|---|---|---|---|
| 12658348 | At_2mM_SA | 20000182 | + |
| 12658348 | At_Siliques | 20000235 | − |
| 12658348 | At_Siliques | 20000236 | − |
| 12658348 | At_Open_Flower | 20000264 | − |
| 12658348 | At_Open_Flower | 20000265 | − |
| 12658348 | At_Drought | 20000267 | + |
| 12658348 | At_100mM_NaCl | 20000268 | + |
| 12658348 | At_Open_Flower | 20000286 | − |
| 12658348 | At_Drought | 20000436 | + |
| 12658348 | At_Drought | 20000437 | + |
| 12658348 | At_100uM_ABA | 20000453 | + |
| 12658348 | At_Herbicide_Mutants | 20000640 | − |
| 12658348 | At_Line_Comparisons | 20001195 | − |
| 12658348 | At_Far-red-induction | 20001247 | + |
| 12658348 | At_Line_Comparisons | 20001309 | − |
| 12658348 | At_Line_Comparisons | 20001310 | − |
| 12658348 | At_Far-red-induction | 20001451 | + |
| 12658348 | At_Drought_Soil_Dry | 20001554 | + |

TABLE 1-continued

Promoter Sequences and Related Information

| 12658348 | At_Drought_Soil_Dry | 20001555 | + |
| --- | --- | --- | --- |
| 12658348 | At_Drought_Soil_Dry | 20001560 | − |
| 12658348 | At_50mM_NH4NO3_L-to-H | 20001762 | + |
| 12658348 | At_Drought_Reproduction | 20001904 | + |
| 12658348 | At_Drought_Reproduction | 20001905 | + |
| 12658348 | At_Drought_Reproduction | 20001906 | + |
| 12658348 | At_Drought_Reproduction | 20001907 | + |
| 12658348 | At_Drought_Reproduction | 20001908 | + |
| 12658348 | At_Drought_Reproduction | 20001910 | + |
| 12658348 | At_Drought_Reproduction | 20001911 | + |
| 12658348 | At_Line_Comparisons | 20002008 | + |
| 12658348 | At_Line_Comparisons | 20002010 | + |
| 12658348 | At_8deg_Cold | 20002105 | + |
| 12658348 | At_Drought-Air-Dry | 20002253 | + |
| 12658348 | At_Drought-Air-Dry | 20002255 | + |

The parameters for the microarray experiments listed above by Expt_Rep_ID and Short_Name are as follow below:

| CDNA_ID | SHORT_NAME | EXPT_REP_ID | PARAM_NAME | VALUE |
| --- | --- | --- | --- | --- |
| 12658348 | At_2mM_SA | 20000182 | Timepoint (hr) | 6 |
| 12658348 | At_2mM_SA | 20000182 | Age (day) | 14 |
| 12658348 | At_2mM_SA | 20000182 | Treatment | 2 mM SA vs. No Treatment |
| 12658348 | At_2mM_SA | 20000182 | Organism | A. thaliana |
| 12658348 | At_2mM_SA | 20000182 | Tissue | Aerial |
| 12658348 | At_2mM_SA | 20000182 | Plant Line | WS |
| 12658348 | At_Siliques | 20000235 | Age (day) | 21 |
| 12658348 | At_Siliques | 20000235 | Tissue | 5-10 mm Siliques vs. Whole Plant |
| 12658348 | At_Siliques | 20000235 | Organism | A. thaliana |
| 12658348 | At_Siliques | 20000235 | Plant Line | WS |
| 12658348 | At_Siliques | 20000236 | Age (day) | 21 |
| 12658348 | At_Siliques | 20000236 | Tissue | >10 mm Siliques vs. Whole Plant |
| 12658348 | At_Siliques | 20000236 | Organism | A. thaliana |
| 12658348 | At_Siliques | 20000236 | Plant Line | WS |
| 12658348 | At_Open_Flower | 20000264 | Age (day) | 21 |
| 12658348 | At_Open_Flower | 20000264 | Organism | A. thaliana |
| 12658348 | At_Open_Flower | 20000264 | Tissue | Open Flower vs. Whole Plant |
| 12658348 | At_Open_Flower | 20000264 | Plant Line | WS |
| 12658348 | At_Open_Flower | 20000265 | Age (day) | 21 |
| 12658348 | At_Open_Flower | 20000265 | Organism | A. thaliana |
| 12658348 | At_Open_Flower | 20000265 | Tissue | Closed Flower vs. Whole Plant |
| 12658348 | At_Open_Flower | 20000265 | Plant Line | WS |
| 12658348 | At_Drought | 20000267 | Timepoint (hr) | 6 |
| 12658348 | At_Drought | 20000267 | Age (day) | 7 |
| 12658348 | At_Drought | 20000267 | Organism | A. thaliana |
| 12658348 | At_Drought | 20000267 | Treatment | Drought vs. No Drought |
| 12658348 | At_Drought | 20000267 | Tissue | Whole Plant |
| 12658348 | At_Drought | 20000267 | Plant Line | WS |
| 12658348 | At_100mM_NaCl | 20000268 | Timepoint (hr) | 6 |
| 12658348 | At_100mM_NaCl | 20000268 | Age (day) | 14 |
| 12658348 | At_100mM_NaCl | 20000268 | Treatment | 100 mM NaCl vs. No Treatment |
| 12658348 | At_100mM_NaCl | 20000268 | Organism | A. thaliana |
| 12658348 | At_100mM_NaCl | 20000268 | Tissue | Whole Plant |
| 12658348 | At_100mM_NaCl | 20000268 | Plant Line | WS |
| 12658348 | At_Open_Flower | 20000286 | Age (day) | 21 |
| 12658348 | At_Open_Flower | 20000286 | Organism | A. thaliana |
| 12658348 | At_Open_Flower | 20000286 | Tissue | Half Open vs. Whole Plant |
| 12658348 | At_Open_Flower | 20000286 | Plant Line | WS |
| 12658348 | At_Drought | 20000436 | Age (day) | 7 |
| 12658348 | At_Drought | 20000436 | Timepoint (hr) | 12 |
| 12658348 | At_Drought | 20000436 | Organism | A. thaliana |
| 12658348 | At_Drought | 20000436 | Treatment | Drought vs. No Drought |
| 12658348 | At_Drought | 20000436 | Tissue | Whole Plant |
| 12658348 | At_Drought | 20000436 | Plant Line | WS |
| 12658348 | At_Drought | 20000437 | Age (day) | 8 |
| 12658348 | At_Drought | 20000437 | Timepoint (hr) | 24 |
| 12658348 | At_Drought | 20000437 | Organism | A. thaliana |
| 12658348 | At_Drought | 20000437 | Treatment | Drought vs. No Drought |
| 12658348 | At_Drought | 20000437 | Tissue | Whole Plant |
| 12658348 | At_Drought | 20000437 | Plant Line | WS |
| 12658348 | At_100uM_ABA | 20000453 | Age (day) | 15 |
| 12658348 | At_100uM_ABA | 20000453 | Timepoint (hr) | 24 |
| 12658348 | At_100uM_ABA | 20000453 | Treatment | 100 uM ABA vs. No Treatment |
| 12658348 | At_100uM_ABA | 20000453 | Organism | A. thaliana |
| 12658348 | At_100uM_ABA | 20000453 | Tissue | Aerial |

TABLE 1-continued

Promoter Sequences and Related Information

| 12658348 | At_100uM_ABA | 20000453 | Plant Line | WS |
|---|---|---|---|---|
| 12658348 | At_Herbicide_Mutants | 20000640 | Timepoint (hr) | 12 |
| 12658348 | At_Herbicide_Mutants | 20000640 | Plant Line | 05377RR/BR27173 |
| 12658348 | At_Herbicide_Mutants | 20000640 | Treatment | Roundup vs. No Treatment |
| 12658348 | At_Herbicide_Mutants | 20000640 | Tissue | Seedlings |
| 12658348 | At_Line_Comparisons | 20001195 | Plant Line | WBin4-WX14-B vs. WS |
| 12658348 | At_Far-red-induction | 20001247 | Timepoint (hr) | 1 |
| 12658348 | At_Far-red-induction | 20001247 | Age (day) | 7 |
| 12658348 | At_Far-red-induction | 20001247 | Organism | A. thaliana |
| 12658348 | At_Far-red-induction | 20001247 | Plant Line | Columbia |
| 12658348 | At_Far-red-induction | 20001247 | Light | Far-red vs. White |
| 12658348 | At_Far-red-induction | 20001247 | Tissue | Whole Plant |
| 12658348 | At_Line_Comparisons | 20001309 | Plant Line | WBin4-WX49R-A vs. WS |
| 12658348 | At_Line_Comparisons | 20001310 | Plant Line | WBin4-WX17-A vs. WS |
| 12658348 | At_Far-red-induction | 20001451 | Age (day) | 8 |
| 12658348 | At_Far-red-induction | 20001451 | Timepoint (hr) | 24 |
| 12658348 | At_Far-red-induction | 20001451 | Organism | A. thaliana |
| 12658348 | At_Far-red-induction | 20001451 | Plant Line | Columbia |
| 12658348 | At_Far-red-induction | 20001451 | Light | Far-red vs. White |
| 12658348 | At_Far-red-induction | 20001451 | Tissue | Whole Plant |
| 12658348 | At_Drought_Soil_Dry | 20001554 | Timepoint (day) | 7 |
| 12658348 | At_Drought_Soil_Dry | 20001554 | Age (day) | 21 |
| 12658348 | At_Drought_Soil_Dry | 20001554 | Organism | A. thaliana |
| 12658348 | At_Drought_Soil_Dry | 20001554 | Treatment | Drought vs. No Drought |
| 12658348 | At_Drought_Soil_Dry | 20001554 | Post Timepoint (hr) | None |
| 12658348 | At_Drought_Soil_Dry | 20001554 | Post-Treatment | None |
| 12658348 | At_Drought_Soil_Dry | 20001554 | Plant Line | WS |
| 12658348 | At_Drought_Soil_Dry | 20001555 | Timepoint (day) | 10 |
| 12658348 | At_Drought_Soil_Dry | 20001555 | Age (day) | 24 |
| 12658348 | At_Drought_Soil_Dry | 20001555 | Organism | A. thaliana |
| 12658348 | At_Drought_Soil_Dry | 20001555 | Treatment | Drought vs. No Drought |
| 12658348 | At_Drought_Soil_Dry | 20001555 | Post Timepoint (hr) | None |
| 12658348 | At_Drought_Soil_Dry | 20001555 | Post-Treatment | None |
| 12658348 | At_Drought_Soil_Dry | 20001555 | Plant Line | WS |
| 12658348 | At_Drought_Soil_Dry | 20001560 | Timepoint (day) | 14 |
| 12658348 | At_Drought_Soil_Dry | 20001560 | Age (day) | 28 |
| 12658348 | At_Drought_Soil_Dry | 20001560 | Organism | A. thaliana |
| 12658348 | At_Drought_Soil_Dry | 20001560 | Treatment | Drought vs. No Drought |
| 12658348 | At_Drought_Soil_Dry | 20001560 | Post Timepoint (hr) | None |
| 12658348 | At_Drought_Soil_Dry | 20001560 | Post-Treatment | None |
| 12658348 | At_Drought_Soil_Dry | 20001560 | Plant Line | WS |
| 12658348 | At_50mM_NH4NO3_L-to-H | 20001762 | Timepoint (hr) | 6 |
| 12658348 | At_50mM_NH4NO3_L-to-H | 20001762 | Treatment | 50 mM NH4NO3 vs 100 mM Mannitol |
| 12658348 | At_50mM_NH4NO3_L-to-H | 20001762 | Tissue | Siliques |
| 12658348 | At_Drought_Reproduction | 20001904 | Timepoint (day) | 7 |
| 12658348 | At_Drought_Reproduction | 20001904 | Age (day) | 37 |
| 12658348 | At_Drought_Reproduction | 20001904 | Organism | A. thaliana |
| 12658348 | At_Drought_Reproduction | 20001904 | Treatment | Drought vs. No Drought |
| 12658348 | At_Drought_Reproduction | 20001904 | Tissue | Rosettes |
| 12658348 | At_Drought_Reproduction | 20001904 | Plant Line | WS |
| 12658348 | At_Drought_Reproduction | 20001905 | Timepoint (day) | 10 |
| 12658348 | At_Drought_Reproduction | 20001905 | Age (day) | 40 |
| 12658348 | At_Drought_Reproduction | 20001905 | Organism | A. thaliana |
| 12658348 | At_Drought_Reproduction | 20001905 | Treatment | Drought vs. No Drought |
| 12658348 | At_Drought_Reproduction | 20001905 | Tissue | Rosettes |
| 12658348 | At_Drought_Reproduction | 20001905 | Plant Line | WS |
| 12658348 | At_Drought_Reproduction | 20001906 | Timepoint (day) | 5 |
| 12658348 | At_Drought_Reproduction | 20001906 | Age (day) | 35 |
| 12658348 | At_Drought_Reproduction | 20001906 | Organism | A. thaliana |
| 12658348 | At_Drought_Reproduction | 20001906 | Treatment | Drought vs. No Drought |
| 12658348 | At_Drought_Reproduction | 20001906 | Tissue | Siliques |
| 12658348 | At_Drought_Reproduction | 20001906 | Plant Line | WS |
| 12658348 | At_Drought_Reproduction | 20001907 | Timepoint (day) | 7 |
| 12658348 | At_Drought_Reproduction | 20001907 | Age (day) | 37 |
| 12658348 | At_Drought_Reproduction | 20001907 | Organism | A. thaliana |
| 12658348 | At_Drought_Reproduction | 20001907 | Treatment | Drought vs. No Drought |
| 12658348 | At_Drought_Reproduction | 20001907 | Tissue | Siliques |
| 12658348 | At_Drought_Reproduction | 20001907 | Plant Line | WS |
| 12658348 | At_Drought_Reproduction | 20001908 | Timepoint (day) | 10 |
| 12658348 | At_Drought_Reproduction | 20001908 | Age (day) | 40 |
| 12658348 | At_Drought_Reproduction | 20001908 | Organism | A. thaliana |
| 12658348 | At_Drought_Reproduction | 20001908 | Treatment | Drought vs. No Drought |
| 12658348 | At_Drought_Reproduction | 20001908 | Tissue | Siliques |
| 12658348 | At_Drought_Reproduction | 20001908 | Plant Line | WS |
| 12658348 | At_Drought_Reproduction | 20001910 | Timepoint (day) | 7 |
| 12658348 | At_Drought_Reproduction | 20001910 | Age (day) | 37 |
| 12658348 | At_Drought_Reproduction | 20001910 | Organism | A. thaliana |

TABLE 1-continued

Promoter Sequences and Related Information

| 12658348 | At_Drought_Reproduction | 20001910 | Treatment | Drought vs. No Drought |
|---|---|---|---|---|
| 12658348 | At_Drought_Reproduction | 20001910 | Tissue | Flowers |
| 12658348 | At_Drought_Reproduction | 20001910 | Plant Line | WS |
| 12658348 | At_Drought_Reproduction | 20001911 | Timepoint (day) | 10 |
| 12658348 | At_Drought_Reproduction | 20001911 | Age (day) | 40 |
| 12658348 | At_Drought_Reproduction | 20001911 | Organism | *A. thaliana* |
| 12658348 | At_Drought_Reproduction | 20001911 | Treatment | Drought vs. No Drought |
| 12658348 | At_Drought_Reproduction | 20001911 | Tissue | Flowers |
| 12658348 | At_Drought_Reproduction | 20001911 | Plant Line | WS |
| 12658348 | At_Line_Comparisons | 20002008 | Plant Line | ME03766 vs. WS |
| 12658348 | At_Line_Comparisons | 20002010 | Plant Line | ME02031 vs. WS |
| 12658348 | At_8deg_Cold | 20002105 | Age (day) | 7 |
| 12658348 | At_8deg_Cold | 20002105 | Timepoint (hr) | 8 |
| 12658348 | At_8deg_Cold | 20002105 | Temperature (deg C.) | 8 vs. 22 |
| 12658348 | At_8deg_Cold | 20002105 | Organism | *A. thaliana* |
| 12658348 | At_8deg_Cold | 20002105 | Tissue | Whole Plant |
| 12658348 | At_8deg_Cold | 20002105 | Plant Line | WS |
| 12658348 | At_Drought-Air-Dry | 20002253 | Timepoint (hr) | 1 |
| 12658348 | At_Drought-Air-Dry | 20002253 | Age (day) | 35 |
| 12658348 | At_Drought-Air-Dry | 20002253 | Organism | *A. thaliana* |
| 12658348 | At_Drought-Air-Dry | 20002253 | Treatment | Drought vs. No Drought |
| 12658348 | At_Drought-Air-Dry | 20002253 | Tissue | Roots |
| 12658348 | At_Drought-Air-Dry | 20002253 | Plant Line | WS |
| 12658348 | At_Drought-Air-Dry | 20002255 | Timepoint (hr) | 1 |
| 12658348 | At_Drought-Air-Dry | 20002255 | Age (day) | 35 |
| 12658348 | At_Drought-Air-Dry | 20002255 | Organism | *A. thaliana* |
| 12658348 | At_Drought-Air-Dry | 20002255 | Treatment | Drought vs. No Drought |
| 12658348 | At_Drought-Air-Dry | 20002255 | Tissue | Shoots |
| 12658348 | At_Drought-Air-Dry | 20002255 | Plant Line | WS |

Promoter YP0384

Modulates the gene: Heat shock transcription factor family.
The GenBank description of the gene: NM_113182 *Arabidopsis thaliana* heat shock transcription factor family (At3g22830) mRNA, complete cds gi|18403537|ref|NM_113182.1|[18403537]
The promoter sequence:
5'-ataaaaattcacatttgcaaattttattcagtcggaatatatatttgaaacaagttttgaaatccattg gacgattaaaattcattgttgagaggataaatatggatttgttcatctgaaccatgtcgttgattagtgat tgactaccatgaaaaatatgttatgaaaagtataacaacttttgataaatcacatttattaacaataaatc aagacaaaatatgtcaacaataatagtagtagaagatattaattcaaattcatccgtaacaacaaaaaatc ataccacaattaagtgtacagaaaaaccttttggatatatttattgtcgcttttcaatgattttcgtgaaa aggatatatttgtgtaaaataagaaggatcttgacgggtgtaaaaacatgcacaattcttaatttagacca atcagaagacaacacgaacacttctttattataagctattaaacaaaatcttgcctattttgcttagaata atatgaagagtgactcatcagggagtggaaaatatctcaggatttgcttttagctctaacatgtcaaacta tctagatgccaacaacacaaagtgcaaattctttaatatgaaaacaacaataatatttctaatagaaaat taaaagggaaataaaatatttttttaaaatatacaaaagaagaaggaatccatcatcaaagttttataaa attgtaatataatacaaacttgtttgcttccttgtctctccctctgtctctctcatctctcctatcttctc catatatacttcatcttcacacccaaaactccacacaaaatatctctccctctatctgcaaattttccaaa gttgcatcctttcaatttccactcctctctaaTATAattcacattttcccactattgctgattcatttttt tttgtgaattatttcaaacccacataaaa 3'-TG
The promoter was cloned from the organism: *Arabidopsis thaliana*, Columbia ecotype

Alternative nucleotides:

| Predicted Position (bp) | Mismatch | Predicted/Experimental |
|---|---|---|
| 18 | SNP | c/— |

The promoter was cloned in the vector: pNewbin4-HAP1-GFP
When cloned into the vector the promoter was operably linked to a marker, which was the type: GFP-ER
Promoter-marker vector was tested in: *Arabidopsis thaliana*, WS ecotype
Generation screened: XT1 Mature XT2 Seedling T2 Mature T3 Seedling TABLE 1-continued Promoter Sequences and Related Information The spatial expression of the promoter-marker vector was found observed in and would be useful in expression in any or all of the following:

Primary Root                        H epidermis H trichoblast H atrichoblast
Observed expression pattern of the promoter-marker vector was in:
T1 mature: No expression.
T2 seedling: High expression throughout root epidermal cells.
Misc. promoter information: Bidirectionality: Pass Exons: Pass    Repeats: No
Optional Promoter Fragments: 5' UTR region at base pairs 839-999.
The Ceres cDNA ID of the endogenous coding sequence to the promoter: 12730108
cDNA nucleotide sequence:
ACAAAATATCTCTCCCTCTATCTGCAAATTTTCCAAAGTTGCATCCTTTCAATTTCCACTCCTCT

CTAATATAATTCACATTTTCCCACTATTGCTGATTCATTTTTTTTGTGAATTATTTCAAACCCA

CATAAAAAAATCTTTGTTTAAATTTAAAACCATGGATCCTTCATTTAGGTTCATTAAAGAGGA

GTTTCCTGCTGGATTCAGTGATTCTCCATCACCACCATCTTCTTCTTCATACCTTTATTCATCTT

CCATGGCTGAAGCAGCCATAAATGATCCAACAACATTGAGCTATCCACAACCATTAGAAGGTC

TCCATGAATCAGGGCCACCTCCATTTTTGACAAAGACATATGACTTGGTGGAAGATTCAAGAA

CCAATCATGTCGTGTCTTGGAGCAAATCCAATAACAGCTTCATTGTCTGGGATCCACAGGCCT

TTTCTGTAACTCTCCTTCCCAGATTCTTCAAGCACAATAACTTCTCCAGTTTTGTCCGCCAGCTC

AACACATATGGTTTCAGAAAGGTGAATCCGGATCGGTGGGAGTTTGCAAACGAAGGGTTTCTT

AGAGGGCAAAAGCATCTCCTCAAGAACATAAGGAGAAGAAAAACAAGTAATAATAGTAATCA

AATGCAACAACCTCAAAGTTCTGAACAACAATCTCTAGACAATTTTTGCATAGAAGTGGGTAG

GTACGGTCTAGATGGAGAGATGGACAGCCTAAGGCGAGACAAGCAAGTGTTGATGATGGAGC

TAGTGAGACTAAGACAGCAACAACAAAGCACCAAAATGTATCTCACATTGATTGAAGAGAAG

CTCAAGAAGACCGAGTCAAAACAAAAACAAATGATGAGCTTCCTTGCCCGCGCAATGCAGAA

TCCAGATTTTATTCAGCAGCTAGTAGAGCAGAAGGAAAAGAGGAAAGAGATCGAAGAGGCGA

TCAGCAAGAAGAGACAAAGACCGATCGATCAAGGAAAAAGAAATGTGGAAGATTATGGTGAT

GAAAGTGGTTATGGGAATGATGTTGCAGCCTCATCCTCAGCATTGATTGGTATGAGTCAGGAA

TATACATATGGAAACATGTCTGAATTCGAGATGTCGGAGTTGGACAAACTTGCTATGCACATT

CAAGGACTTGGAGATAATTCCAGTGCTAGGGAAGAAGTCTTGAATGTGGAAAAAGGAAATGA

TGAGGAAGAAGTAGAAGATCAACAACAAGGGTACCATAAGGAGAACAATGAGATTTATGGTG

AAGGTTTTTGGGAAGATTTGTTAAATGAAGGTCAAAATTTTGATTTTGAAGGAGATCAAGAAA

ATGTTGATGTGTTAATTCAGCAACTTGGTTATTTGGGTTCTAGTTCACACACTAATTAAGAAGA

AATTGAAATGATGACTACTTTAAGCATTTGAATCAACTTGTTTCCTATTAGTAATTTGGCTTTG

TTTCAATCAAGTGAGTCGTGGACTAACTTATTGAATTTGGGGGTTAAATCCGTTTCTTATTTTT

GGAAATAAAATTGCTTTTTGTTT

Coding sequence:
MDPSFRFIKEEFPAGFSDSPSPPSSSSYLYSSSMAEAAINDPTTLSYPQPLEGLHESGPPPFLTKTYDL

VEDSRTNHVVSWSKSNNSFIVWDPQAFSVTLLPRFFKHNNFSSFVRQLNTYGFRKVNPDRWEFAN

EGFLRGQKHLLKNIRRRKTSNNSNQMQQPQSSEQQSLDNFCIEVGRYGLDGEMDSLRRDKQVLM

MELVRLRQQQQSTKMYLTLIEEKLKKTESKQKQMMSFLARAMQNPDFIQQLVEQKEKRKEIEEAI

SKKRQRPIDQGKRNVEDYGDESGYGNDVAASSSALIGMSQEYTYGNMSEFEMSELDKLAMHIQG

LGDNSSAREEVLNVEKGNDEEEVEDQQQGYHKENNEIYGEGFWEDLLNEGQNFDFEGDQENVDV

LIQQLGYLGSSSHTN*

TABLE 1-continued

Promoter Sequences and Related Information

Microarray data shows that the coding sequence was expressed in the following experiments, which shows that the promoter would be useful to modulate expression in situations similar to the following:

| CDNA_ID | SHORT_NAME | EXPT_REP_ID | IS_UP |
|---|---|---|---|
| 12730108 | At_Drought | 20000267 | + |
| 12730108 | At_100mM_NaCl | 20000268 | + |
| 12730108 | At_Drought | 20000288 | + |
| 12730108 | At_Drought | 20000436 | + |
| 12730108 | At_Drought | 20000437 | + |
| 12730108 | At_Guard_Cells | 20000495 | − |
| 12730108 | At_Herbicide_Mutants | 20000639 | − |
| 12730108 | At_Herbicide_Mutants | 20000641 | − |
| 12730108 | At_Drought_Reproduction | 20001904 | + |
| 12730108 | At_Drought_Reproduction | 20001905 | + |
| 12730108 | At_Drought_Reproduction | 20001911 | + |
| 12730108 | At_Drought-Air-Dry | 20002254 | + |

The parameters for the microarray experiments listed above by Expt_Rep_ID and Short_Name are as follow below:

| CDNA_ID | SHORT_NAME | EXPT_REP_ID | PARAM_NAME | VALUE |
|---|---|---|---|---|
| 12730108 | At_Drought | 20000267 | Timepoint (hr) | 6 |
| 12730108 | At_Drought | 20000267 | Age (day) | 7 |
| 12730108 | At_Drought | 20000267 | Organism | A. thaliana |
| 12730108 | At_Drought | 20000267 | Treatment | Drought vs. No Drought |
| 12730108 | At_Drought | 20000267 | Tissue | Whole Plant |
| 12730108 | At_Drought | 20000267 | Plant Line | WS |
| 12730108 | At_100mM_NaCl | 20000268 | Timepoint (hr) | 6 |
| 12730108 | At_100mM_NaCl | 20000268 | Age (day) | 14 |
| 12730108 | At_100mM_NaCl | 20000268 | Treatment | 100 mM NaCl vs. No Treatment |
| 12730108 | At_100mM_NaCl | 20000268 | Organism | A. thaliana |
| 12730108 | At_100mM_NaCl | 20000268 | Tissue | Whole Plant |
| 12730108 | At_100mM_NaCl | 20000268 | Plant Line | WS |
| 12730108 | At_Drought | 20000288 | Timepoint (hr) | 1 |
| 12730108 | At_Drought | 20000288 | Age (day) | 7 |
| 12730108 | At_Drought | 20000288 | Organism | A. thaliana |
| 12730108 | At_Drought | 20000288 | Treatment | Drought vs. No Drought |
| 12730108 | At_Drought | 20000288 | Tissue | Whole Plant |
| 12730108 | At_Drought | 20000288 | Plant Line | WS |
| 12730108 | At_Drought | 20000436 | Age (day) | 7 |
| 12730108 | At_Drought | 20000436 | Timepoint (hr) | 12 |
| 12730108 | At_Drought | 20000436 | Organism | A. thaliana |
| 12730108 | At_Drought | 20000436 | Treatment | Drought vs. No Drought |
| 12730108 | At_Drought | 20000436 | Tissue | Whole Plant |
| 12730108 | At_Drought | 20000436 | Plant Line | WS |
| 12730108 | At_Drought | 20000437 | Age (day) | 8 |
| 12730108 | At_Drought | 20000437 | Timepoint (hr) | 24 |
| 12730108 | At_Drought | 20000437 | Organism | A. thaliana |
| 12730108 | At_Drought | 20000437 | Treatment | Drought vs. No Drought |
| 12730108 | At_Drought | 20000437 | Tissue | Whole Plant |
| 12730108 | At_Drought | 20000437 | Plant Line | WS |
| 12730108 | At_Guard_Cells | 20000495 | Harvest Date | 08 Feb. 2002 |
| 12730108 | At_Guard_Cells | 20000495 | Organism | A. thaliana |
| 12730108 | At_Guard_Cells | 20000495 | Tissue | Guard Cells vs. Leaves |
| 12730108 | At_Herbicide_Mutants | 20000639 | Timepoint (hr) | 4 |
| 12730108 | At_Herbicide_Mutants | 20000639 | Plant Line | 05377RR/BR27173 |
| 12730108 | At_Herbicide_Mutants | 20000639 | Treatment | Roundup vs. No Treatment |
| 12730108 | At_Herbicide_Mutants | 20000639 | Tissue | Seedlings |
| 12730108 | At_Herbicide_Mutants | 20000641 | Timepoint (hr) | 4 |
| 12730108 | At_Herbicide_Mutants | 20000641 | Plant Line | 3950BR/PCJE10000 |
| 12730108 | At_Herbicide_Mutants | 20000641 | Treatment | Finale vs. No Treatment |
| 12730108 | At_Herbicide_Mutants | 20000641 | Tissue | Seedlings |
| 12730108 | At_Drought_Reproduction | 20001904 | Timepoint (day) | 7 |
| 12730108 | At_Drought_Reproduction | 20001904 | Age (day) | 37 |
| 12730108 | At_Drought_Reproduction | 20001904 | Organism | A. thaliana |
| 12730108 | At_Drought_Reproduction | 20001904 | Treatment | Drought vs. No Drought |
| 12730108 | At_Drought_Reproduction | 20001904 | Tissue | Rosettes |
| 12730108 | At_Drought_Reproduction | 20001904 | Plant Line | WS |
| 12730108 | At_Drought_Reproduction | 20001905 | Timepoint (day) | 10 |
| 12730108 | At_Drought_Reproduction | 20001905 | Age (day) | 40 |
| 12730108 | At_Drought_Reproduction | 20001905 | Organism | A. thaliana |
| 12730108 | At_Drought_Reproduction | 20001905 | Treatment | Drought vs. No Drought |
| 12730108 | At_Drought_Reproduction | 20001905 | Tissue | Rosettes |
| 12730108 | At_Drought_Reproduction | 20001905 | Plant Line | WS |
| 12730108 | At_Drought_Reproduction | 20001911 | Timepoint (day) | 10 |
| 12730108 | At_Drought_Reproduction | 20001911 | Age (day) | 40 |

TABLE 1-continued

Promoter Sequences and Related Information

| | | | | | |
|---|---|---|---|---|---|
| 12730108 | At_Drought_Reproduction | 20001911 | Organism | | *A. thaliana* |
| 12730108 | At_Drought_Reproduction | 20001911 | Treatment | | Drought vs. No Drought |
| 12730108 | At_Drought_Reproduction | 20001911 | Tissue | | Flowers |
| 12730108 | At_Drought_Reproduction | 20001911 | Plant Line | | WS |
| 12730108 | At_Drought-Air-Dry | 20002254 | Timepoint (hr) | | 4 |
| 12730108 | At_Drought-Air-Dry | 20002254 | Age (day) | | 35 |
| 12730108 | At_Drought-Air-Dry | 20002254 | Organism | | *A. thaliana* |
| 12730108 | At_Drought-Air-Dry | 20002254 | Treatment | | Drought vs. No Drought |
| 12730108 | At_Drought-Air-Dry | 20002254 | Tissue | | Roots |
| 12730108 | At_Drought-Air-Dry | 20002254 | Plant Line | | WS |

Promoter YP0382

Modulates the gene: product = "expressed protein"
The GenBank description of the gene: NM_129727 *Arabidopsis thaliana* expressed protein (At2g41640) mRNA, complete cds gi|30688728|ref|NM_129727.2|[30688728]
The promoter sequence:
5'tttttaaaattcgttggaacttggaagggatttaaatattattttgttttccttcattttataggt taataattgtcaaagatacaactcgatggaccaaaataaaataataaaattcgtcgaatttggtaaagcaa aacggtcgaggatagctaatatttatgcgaaacccgttgtcaaagcagatgttcagcgtcacgcacatgcc gcaaaaagaatatacatcaacctcttttgaacttcacgccgttttttaggcccacaataatgctacgtcgt cttctgggttcaccctcgtttttttttaaacttctaaccgataaaataaatggtccactatttcttttct tctctgtgtattgtcgtcagagatggtttaaaagttgaaccgaactataacgattctcttaaaatctgaaa accaaactgaccgattttcttaactgaaaaaaaaaaaaaaaaaactgaatttaggccaacttgttgtaat atcacaaagaaaattctacaatttaattcatttaaaaataaagaaaaatttaggtaacaatttaactaagt ggtctatctaaatcttgcaaattctttgactttgaccaaacacaacttaagttgacagccgtctcctctct gttgtttccgtgttattaccgaaatatcagaggaaagtccactaaaccccaaatattaaaaatagaaacat tactttctttacaaaaggaatctaaattgatcccttcattcgtttcactcgtttcatatagttgtatgta tatatgcgtatgcatcaaaaagtctcttTATAtcctcagagtcacccaatcttatctctctctccttcgtc ctcaagaaaagtaattctctgtttgtgtagttttcttaccggtgaattttctcttcgttttgtgcttcaa acgtcacccaaatcaccaagatcgatcaa 3'-TG
The promoter was cloned from the organism: *Arabidopsis thaliana*, Columbia ecotype

Alternative nucleotides:

| Predicted Position (bp) | Mismatch | Predicted/Experimental |
|---|---|---|
| 484 | Sequence resolution | a/— |

The promoter was cloned in the vector: pNewbin4-HAP1-GFP
When cloned into the vector the promoter was operably linked to a marker, which was the type: GFP-ER
Promoter-marker vector was tested in: *Arabidopsis thaliana*, WS ecotype
Generation screened: XT1 Mature XT2 Seedling T2 Mature T3 Seedling
The spatial expression of the promoter-marker vector was found observed in and would be useful in expression in any or all of the following:

Flower                                           H nectary M sepal M vascular
Primary Root                          H epidermis H root cap
Observed expression pattern:
T1 mature: Expressed in nectary glands of flowers and vasculature of sepals (see Report 129. Table 1.B.).
T2 seedling: High root epidermal expression through to root cap.
Misc. promoter information: Bidirectionality: Pass Exons: Pass    Repeats: No
Optional Promoter Fragments: 5' UTR region at base pairs 842-999.
The Ceres cDNA ID of the endogenous coding sequence to the promoter: 12735575
cDNA nucleotide sequence:
AGAGTCACCCAATCTTATCTCTCTCCTTCGTCCTCAAGAAAGTAATTCTCTGTTTGTGTAG

TTTTCTTTACCGGTGAATTTTCTCTTCGTTTTGTGCTTCAAACGTCACCCAAATCACCAAGATC

GATCAAAATCGAAACTTAACGTTTCAGAAGATGGTGCAGTACCAGAGATTAATCATCCACCAT

GGAAGAAAAGAAGATAAGTTTAGAGTTTCTTCAGCAGAGGAAAGTGGTGGAGGTGGTTGTTG

CTACTCCAAGAGAGCTAAACAAAAGTTTCGTTGTCTTCTCTTTCTCTCTATCCTCTCTTGCTGTT

TABLE 1-continued

Promoter Sequences and Related Information

```
TCGTCTTGTCTCCTTATTACCTCTTCGGCTTCTCTACTCTCTCCCTCCTAGATTCGTTTCGCAGA

GAAATCGAAGGTCTTAGCTCTTATGAGCCAGTTATTACCCCTCTGTGCTCAGAAATCTCCAATG

GAACCATTTGTTGTGACAGAACCGGTTTGAGATCTGATATTTGTGTAATGAAAGGTGATGTTC

GAACAAACTCTGCTTCTTCCTCAATCTTCCTCTTCACCTCCTCCACCAATAACAACACAAAACC

GGAAAAGATCAAACCTTACACTAGAAAATGGGAGACTAGTGTGATGGACACCGTTCAAGAAC

TCAACCTCATCACCAAAGATTCCAACAAATCTTCAGATCGTATGCGATGTGTACCATGATG

TTCCTGCTGTGTTCTTCTCCACTGGTGGATACACCGGTAACGTATACCACGAGTTTAACGACGG

GATTATCCCTTTGTTTATAACTTCACAGCATTACAACAAAAAGTTGTGTTTGTGATCGTCGAG

TATCATGACTGGTGGGAGATGAAGTATGGAGATGTCGTTTCGCAGCTCTCGGATTATCCTCTG

GTTGATTTCAATGGAGATACGAGAACACATTGTTTCAAAGAAGCAACCGTTGGATTACGTATT

CACGACGAGTTAACTGTGAATTCTTCTTTGGTCATTGGGAATCAAACCATTGTTGACTTCAGAA

ACGTTTTGGATAGGGGTTACTCGCATCGTATCCAAAGCTTGACTCAGGAGGAAACAGAGGCGA

ACGTGACCGCACTCGATTTCAAGAAGAAGCCAAAACTGGTGATTCTTTCAAGAAACGGGTCAT

CAAGGGCGATATTAAACGAGAATCTTCTCGTGGAGCTAGCAGAGAAAACAGGGTTCAATGTG

GAGGTTCTAAGACCACAAAAGACAACGGAAATGGCCAAGATTTATCGTTCGTTGAACACGAG

CGATGTAATGATCGGTGTACATGGAGCAGCAATGACTCATTTCCTTTTCTTGAAACCGAAAAC

CGTTTTCATTCAGATCATCCCATTAGGGACGGACTGGGCGGCAGAGACATATTATGGAGAACC

GGCGAAGAAGCTAGGATTGAAGTACGTTGGTTACAAGATTGCGCCGAAAGAGAGCTCTTTGT

ATGAAGAATATGGGAAAGATGACCCTGTAATCCGAGATCCGGATAGTCTAAACGACAAAGGA

TGGGAATATACGAAGAAAATCTATCTACAAGGACAGAACGTGAAGCTTGACTTGAGAAGATT

CAGAGAAACGTTAACTCGTTCGTATGATTTCTCCATTAGAAGGAGATTTAGAGAAGATTACTT

GTTACATAGAGAAGATTAAGAATCGTGTGATATTTTTTTGTAAAGTTTTGAATGACAATTAA

ATTTATTTATTTTAT
```

Coding sequence:
MVQYQRLIIHHGRKEDKFRVSSAEESGGGGCCYSKRAKQKFRCLLFLSILSCCFVLSPYYLFGFSTL

SLLDSFRREIEGLSSYEPVITPLCSEISNGTICCDRTGLRSDICVMKGDVRTNSASSSIFLFTSSTNNNT

KPEKIKPYTRKWETSVMDTVQELNLITKDSNKSSDRVCDVYHDVPAVFFSTGGYTGNVHEFND

GIIPLFITSQHYNKKVVFVIVEYHDWWEMKYGDVVSQLSDYPLVDFNGDTRTHCFKEATVGLRIH

DELTVNSSLVIGNQTIVDFRNVLDRGYSHRIQSLTQEETEANVTALDFKKKPKLVILSRNGSSRAIL

NENLLVELAEKTGFNVEVLRPQKTTEMAKIYRSLNTSDVMIGVHGAAMTHFLFLKPKTVFIQIIPLG

TDWAAETYYGEPAKKLGLKYVGYKIAPKESSLYEEYGKDDPVIRDPDSLNDKGWEYTKKIYLQG

QNVKLDLRRFRETLTRSYDFSIRRRFREDYLLHRED*

Microarray data shows that the coding sequence was expressed in the following experiments, which shows that the promoter would be useful to modulate expression in situations similar to the following:

| CDNA_ID | SHORT_NAME | EXPT_REP_ID | IS_UP |
| --- | --- | --- | --- |
| 12735575 | At_42deg_Heat | 20000171 | − |
| 12735575 | At_42deg_Heat | 20000173 | − |
| 12735575 | At_2mM_SA | 20000181 | + |
| 12735575 | At_2mM_SA | 20000182 | + |
| 12735575 | At_Shoots | 20000184 | − |
| 12735575 | At_Roots | 20000185 | − |
| 12735575 | At_Siliques | 20000234 | − |
| 12735575 | At_Siliques | 20000235 | − |
| 12735575 | At_Siliques | 20000236 | − |

TABLE 1-continued

Promoter Sequences and Related Information

| | | | |
|---|---|---|---|
| 12735575 | At_Open_Flower | 20000264 | − |
| 12735575 | At_Open_Flower | 20000265 | − |
| 12735575 | At_100mM_NaCl | 20000268 | − |
| 12735575 | At_Open_Flower | 20000286 | − |
| 12735575 | At_Pollen | 20000326 | − |
| 12735575 | At_Shoots | 20000438 | − |
| 12735575 | At_1uM_BR-BRZ | 20000441 | + |
| 12735575 | At_10percent_PEG | 20000460 | + |
| 12735575 | At_Guard_Cells | 20000495 | − |
| 12735575 | At_10percent_PEG | 20000527 | + |
| 12735575 | At_100uM_ABA_Mutants | 20000573 | − |
| 12735575 | At_100uM_ABA_Mutants | 20000574 | − |
| 12735575 | At_Herbicide_Mutants | 20000640 | − |
| 12735575 | At_15mM_NH4NO3_L-to-H | 20000709 | + |
| 12735575 | At_Line_Comparisons | 20001192 | − |
| 12735575 | At_Line_Comparisons | 20001195 | − |
| 12735575 | At_Far-red-induction | 20001247 | + |
| 12735575 | At_Far-red-induction | 20001248 | + |
| 12735575 | At_Line_Comparisons | 20001308 | + |
| 12735575 | At_Interploidy_Crosses | 20001316 | − |
| 12735575 | At_Line_Comparisons | 20001319 | − |
| 12735575 | At_Line_Comparisons | 20001347 | − |
| 12735575 | At_Far-red-induction | 20001450 | + |
| 12735575 | At_Drought_Soil_Dry | 20001557 | + |
| 12735575 | At_Interploidy_Crosses | 20001653 | + |
| 12735575 | At_Interploidy_Crosses | 20001654 | + |
| 12735575 | At_Interploidy_Crosses | 20001703 | − |
| 12735575 | At_Interploidy_Crosses | 20001704 | − |
| 12735575 | At_50mM_NH4NO3_L-to-H | 20001757 | − |
| 12735575 | At_Interploidy_Crosses | 20001853 | − |
| 12735575 | At_Drought_Reproduction | 20001905 | + |
| 12735575 | At_Drought_Reproduction | 20001911 | + |
| 12735575 | At_Line_Comparisons | 20002007 | + |
| 12735575 | At_Line_Comparisons | 20002008 | + |
| 12735575 | At_Line_Comparisons | 20002009 | + |
| 12735575 | At_Line_Comparisons | 20002010 | + |
| 12735575 | At_Line_Comparisons | 20002012 | + |
| 12735575 | At_8deg_Cold | 20002103 | − |
| 12735575 | At_8deg_Cold | 20002105 | − |
| 12735575 | At_8deg_Cold | 20002108 | − |
| 12735575 | At_8deg_Cold | 20002109 | − |

The parameters for the microarray experiments listed above by Expt_Rep_ID and Short_Name are as follow below:

| CDNA_ID | SHORT_NAME | EXPT_REP_ID | PARAM_NAME | VALUE |
|---|---|---|---|---|
| 12735575 | At_42deg_Heat | 20000171 | Timepoint (hr) | 1 |
| 12735575 | At_42deg_Heat | 20000171 | Age (day) | 14 |
| 12735575 | At_42deg_Heat | 20000171 | Temperature (deg C.) | 42 vs. 22 |
| 12735575 | At_42deg_Heat | 20000171 | Organism | *A. thaliana* |
| 12735575 | At_42deg_Heat | 20000171 | Tissue | Aerial |
| 12735575 | At_42deg_Heat | 20000171 | Plant Line | WS |
| 12735575 | At_42deg_Heat | 20000173 | Timepoint (hr) | 6 |
| 12735575 | At_42deg_Heat | 20000173 | Age (day) | 14 |
| 12735575 | At_42deg_Heat | 20000173 | Temperature (deg C.) | 42 vs. 22 |
| 12735575 | At_42deg_Heat | 20000173 | Organism | *A. thaliana* |
| 12735575 | At_42deg_Heat | 20000173 | Tissue | Aerial |
| 12735575 | At_42deg_Heat | 20000173 | Plant Line | WS |
| 12735575 | At_2mM_SA | 20000181 | Timepoint (hr) | 1 |
| 12735575 | At_2mM_SA | 20000181 | Age (day) | 14 |
| 12735575 | At_2mM_SA | 20000181 | Treatment | 2 mM SA vs. No Treatment |
| 12735575 | At_2mM_SA | 20000181 | Organism | *A. thaliana* |
| 12735575 | At_2mM_SA | 20000181 | Tissue | Aerial |
| 12735575 | At_2mM_SA | 20000181 | Plant Line | WS |
| 12735575 | At_2mM_SA | 20000182 | Timepoint (hr) | 6 |
| 12735575 | At_2mM_SA | 20000182 | Age (day) | 14 |
| 12735575 | At_2mM_SA | 20000182 | Treatment | 2 mM SA vs. No Treatment |
| 12735575 | At_2mM_SA | 20000182 | Organism | *A. thaliana* |
| 12735575 | At_2mM_SA | 20000182 | Tissue | Aerial |
| 12735575 | At_2mM_SA | 20000182 | Plant Line | WS |
| 12735575 | At_Shoots | 20000184 | Age (day) | 7 vs. 21 |
| 12735575 | At_Shoots | 20000184 | Organism | *A. thaliana* |
| 12735575 | At_Shoots | 20000184 | Tissue | Shoots vs. Whole Plant |
| 12735575 | At_Shoots | 20000184 | Plant Line | WS |
| 12735575 | At_Roots | 20000185 | Age (day) | 7 vs. 21 |
| 12735575 | At_Roots | 20000185 | Organism | *A. thaliana* |
| 12735575 | At_Roots | 20000185 | Tissue | Roots vs. Whole Plant |

TABLE 1-continued

Promoter Sequences and Related Information

| 12735575 | At_Roots | 20000185 | Plant Line | WS |
|---|---|---|---|---|
| 12735575 | At_Siliques | 20000234 | Age (day) | 21 |
| 12735575 | At_Siliques | 20000234 | Tissue | <5 mm Siliques vs. Whole Plant |
| 12735575 | At_Siliques | 20000234 | Organism | A. thaliana |
| 12735575 | At_Siliques | 20000234 | Plant Line | WS |
| 12735575 | At_Siliques | 20000235 | Age (day) | 21 |
| 12735575 | At_Siliques | 20000235 | Tissue | 5-10 mm Siliques vs. Whole Plant |
| 12735575 | At_Siliques | 20000235 | Organism | A. thaliana |
| 12735575 | At_Siliques | 20000235 | Plant Line | WS |
| 12735575 | At_Siliques | 20000236 | Age (day) | 21 |
| 12735575 | At_Siliques | 20000236 | Tissue | >10 mm Siliques vs. Whole Plant |
| 12735575 | At_Siliques | 20000236 | Organism | A. thaliana |
| 12735575 | At_Siliques | 20000236 | Plant Line | WS |
| 12735575 | At_Open_Flower | 20000264 | Age (day) | 21 |
| 12735575 | At_Open_Flower | 20000264 | Organism | A. thaliana |
| 12735575 | At_Open_Flower | 20000264 | Tissue | Open Flower vs. Whole Plant |
| 12735575 | At_Open_Flower | 20000264 | Plant Line | WS |
| 12735575 | At_Open_Flower | 20000265 | Age (day) | 21 |
| 12735575 | At_Open_Flower | 20000265 | Organism | A. thaliana |
| 12735575 | At_Open_Flower | 20000265 | Tissue | Closed Flower vs. Whole Plant |
| 12735575 | At_Open_Flower | 20000265 | Plant Line | WS |
| 12735575 | At_100mM_NaCl | 20000268 | Timepoint (hr) | 6 |
| 12735575 | At_100mM_NaCl | 20000268 | Age (day) | 14 |
| 12735575 | At_100mM_NaCl | 20000268 | Treatment | 100 mM NaCl vs. No Treatment |
| 12735575 | At_100mM_NaCl | 20000268 | Organism | A. thaliana |
| 12735575 | At_100mM_NaCl | 20000268 | Tissue | Whole Plant |
| 12735575 | At_100mM_NaCl | 20000268 | Plant Line | WS |
| 12735575 | At_Open_Flower | 20000286 | Age (day) | 21 |
| 12735575 | At_Open_Flower | 20000286 | Organism | A. thaliana |
| 12735575 | At_Open_Flower | 20000286 | Tissue | Half Open vs. Whole Plant |
| 12735575 | At_Open_Flower | 20000286 | Plant Line | WS |
| 12735575 | At_Pollen | 20000326 | Age (day) | 0 vs. 21 |
| 12735575 | At_Pollen | 20000326 | Organism | A. thaliana |
| 12735575 | At_Pollen | 20000326 | Tissue | Pollen vs. Whole Plant |
| 12735575 | At_Pollen | 20000326 | Plant Line | WS |
| 12735575 | At_Shoots | 20000438 | Age (day) | 14 vs. 21 |
| 12735575 | At_Shoots | 20000438 | Organism | A. thaliana |
| 12735575 | At_Shoots | 20000438 | Tissue | Shoots vs. Whole Plant |
| 12735575 | At_Shoots | 20000438 | Plant Line | WS |
| 12735575 | At_1uM_BR-BRZ | 20000441 | Treatment | 1uM BR vs. No Treatment |
| 12735575 | At_1uM_BR-BRZ | 20000441 | Tissue | Shoot Apices |
| 12735575 | At_10percent_PEG | 20000460 | Age (day) | 12 |
| 12735575 | At_10percent_PEG | 20000460 | Timepoint (day) | 12 |
| 12735575 | At_10percent_PEG | 20000460 | Treatment | 10 percent PEG vs. No Treatment |
| 12735575 | At_10percent_PEG | 20000460 | Organism | A. thaliana |
| 12735575 | At_10percent_PEG | 20000460 | Tissue | Whole Plant |
| 12735575 | At_10percent_PEG | 20000460 | Plant Line | WS |
| 12735575 | At_Guard_Cells | 20000495 | Harvest Date | 08 Feb. 2002 |
| 12735575 | At_Guard_Cells | 20000495 | Organism | A. thaliana |
| 12735575 | At_Guard_Cells | 20000495 | Tissue | Guard Cells vs. Leaves |
| 12735575 | At_10percent_PEG | 20000527 | Age (day) | 20 |
| 12735575 | At_10percent_PEG | 20000527 | Timepoint (day) | 20 |
| 12735575 | At_10percent_PEG | 20000527 | Treatment | 10 percent PEG vs. No Treatment |
| 12735575 | At_10percent_PEG | 20000527 | Organism | A. thaliana |
| 12735575 | At_10percent_PEG | 20000527 | Tissue | Whole Plant |
| 12735575 | At_10percent_PEG | 20000527 | Plant Line | WS |
| 12735575 | At_100uM_ABA_Mutants | 20000573 | Organism | A. thaliana |
| 12735575 | At_100uM_ABA_Mutants | 20000573 | Plant Line | CS22 vs. Ler wt |
| 12735575 | At_100uM_ABA_Mutants | 20000573 | Timepoint (hr) | N/A |
| 12735575 | At_100uM_ABA_Mutants | 20000573 | Treatment | None |
| 12735575 | At_100uM_ABA_Mutants | 20000573 | Tissue | Whole Plant |
| 12735575 | At_100uM_ABA_Mutants | 20000574 | Organism | A. thaliana |
| 12735575 | At_100uM_ABA_Mutants | 20000574 | Plant Line | CS23 vs. Ler wt |
| 12735575 | At_100uM_ABA_Mutants | 20000574 | Timepoint (hr) | N/A |
| 12735575 | At_100uM_ABA_Mutants | 20000574 | Treatment | None |
| 12735575 | At_100uM_ABA_Mutants | 20000574 | Tissue | Whole Plant |
| 12735575 | At_Herbicide_Mutants | 20000640 | Timepoint (hr) | 12 |
| 12735575 | At_Herbicide_Mutants | 20000640 | Plant Line | 05377RR/BR27173 |
| 12735575 | At_Herbicide_Mutants | 20000640 | Treatment | Roundup vs. No Treatment |
| 12735575 | At_Herbicide_Mutants | 20000640 | Tissue | Seedlings |
| 12735575 | At_15mM_NH4NO3_L-to-H | 20000709 | Timepoint (hr) | 4 |
| 12735575 | At_15mM_NH4NO3_L-to-H | 20000709 | Age (hr) | 14 |
| 12735575 | At_15mM_NH4NO3_L-to-H | 20000709 | Treatment | 15 mM NH4NO3 vs. 30 mM Mannitol |

TABLE 1-continued

Promoter Sequences and Related Information

| | | | | |
|---|---|---|---|---|
| 12735575 | At_15mM_NH4NO3_L-to-H | 20000709 | Organism | A. thaliana |
| 12735575 | At_15mM_NH4NO3_L-to-H | 20000709 | Tissue | Aerial |
| 12735575 | At_15mM_NH4NO3_L-to-H | 20000709 | Plant Line | WS |
| 12735575 | At_Line_Comparisons | 20001192 | Plant Line | WBin4-WX13R-A vs. WS |
| 12735575 | At_Line_Comparisons | 20001195 | Plant Line | WBin4-WX14-B vs. WS |
| 12735575 | At_Far-red-induction | 20001247 | Timepoint (hr) | 1 |
| 12735575 | At_Far-red-induction | 20001247 | Age (day) | 7 |
| 12735575 | At_Far-red-induction | 20001247 | Organism | A. thaliana |
| 12735575 | At_Far-red-induction | 20001247 | Plant Line | Columbia |
| 12735575 | At_Far-red-induction | 20001247 | Light | Far-red vs. White |
| 12735575 | At_Far-red-induction | 20001247 | Tissue | Whole Plant |
| 12735575 | At_Far-red-induction | 20001248 | Timepoint (hr) | 4 |
| 12735575 | At_Far-red-induction | 20001248 | Age (day) | 7 |
| 12735575 | At_Far-red-induction | 20001248 | Organism | A. thaliana |
| 12735575 | At_Far-red-induction | 20001248 | Plant Line | Columbia |
| 12735575 | At_Far-red-induction | 20001248 | Light | Far-red vs. White |
| 12735575 | At_Far-red-induction | 20001248 | Tissue | Whole Plant |
| 12735575 | At_Line_Comparisons | 20001308 | Plant Line | WBin4-WX49-C vs. WS |
| 12735575 | At_Interploidy_Crosses | 20001316 | Age (day) | 5 |
| 12735575 | At_Interploidy_Crosses | 20001316 | Organism | A. thaliana |
| 12735575 | At_Interploidy_Crosses | 20001316 | Plant Line | Columbia |
| 12735575 | At_Interploidy_Crosses | 20001316 | Cross | hemi x 2X vs. 2X x 2X |
| 12735575 | At_Interploidy_Crosses | 20001316 | Tissue | Siliques |
| 12735575 | At_Line_Comparisons | 20001319 | Plant Line | WBin4-WX24-A vs. WS |
| 12735575 | At_Line_Comparisons | 20001347 | Plant Line | ME01604-01 vs. WS |
| 12735575 | At_Far-red-induction | 20001450 | Age (day) | 7 |
| 12735575 | At_Far-red-induction | 20001450 | Timepoint (hr) | 8 |
| 12735575 | At_Far-red-induction | 20001450 | Organism | A. thaliana |
| 12735575 | At_Far-red-induction | 20001450 | Plant Line | Columbia |
| 12735575 | At_Far-red-induction | 20001450 | Light | Far-red vs. White |
| 12735575 | At_Far-red-induction | 20001450 | Tissue | Whole Plant |
| 12735575 | At_Drought_Soil_Dry | 20001557 | Post Timepoint (hr) | 3 |
| 12735575 | At_Drought_Soil_Dry | 20001557 | Timepoint (day) | 13 |
| 12735575 | At_Drought_Soil_Dry | 20001557 | Age (day) | 27 |
| 12735575 | At_Drought_Soil_Dry | 20001557 | Organism | A. thaliana |
| 12735575 | At_Drought_Soil_Dry | 20001557 | Treatment | Drought vs. No Drought |
| 12735575 | At_Drought_Soil_Dry | 20001557 | Post-Treatment | Re-Water vs. No Drought |
| 12735575 | At_Drought_Soil_Dry | 20001557 | Plant Line | WS |
| 12735575 | At_Interploidy_Crosses | 20001653 | Age (day) | 5 |
| 12735575 | At_Interploidy_Crosses | 20001653 | Cross | 2X x 6X vs. 2X x 2X |
| 12735575 | At_Interploidy_Crosses | 20001653 | Organism | A. thaliana |
| 12735575 | At_Interploidy_Crosses | 20001653 | Plant Line | Columbia |
| 12735575 | At_Interploidy_Crosses | 20001653 | Tissue | Siliques |
| 12735575 | At_Interploidy_Crosses | 20001654 | Age (day) | 5 |
| 12735575 | At_Interploidy_Crosses | 20001654 | Cross | 6X x 2X vs. 2X x 2X |
| 12735575 | At_Interploidy_Crosses | 20001654 | Organism | A. thaliana |
| 12735575 | At_Interploidy_Crosses | 20001654 | Plant Line | Columbia |
| 12735575 | At_Interploidy_Crosses | 20001654 | Tissue | Siliques |
| 12735575 | At_Interploidy_Crosses | 20001703 | Age (day) | 5 |
| 12735575 | At_Interploidy_Crosses | 20001703 | Cross | 2X x 4X vs. 2X x 2X |
| 12735575 | At_Interploidy_Crosses | 20001703 | Organism | A. thaliana |
| 12735575 | At_Interploidy_Crosses | 20001703 | Plant Line | Columbia |
| 12735575 | At_Interploidy_Crosses | 20001703 | Tissue | Siliques |
| 12735575 | At_Interploidy_Crosses | 20001704 | Age (day) | 5 |
| 12735575 | At_Interploidy_Crosses | 20001704 | Cross | 4X x 2X vs. 2X x 2X |
| 12735575 | At_Interploidy_Crosses | 20001704 | Organism | A. thaliana |
| 12735575 | At_Interploidy_Crosses | 20001704 | Plant Line | Columbia |
| 12735575 | At_Interploidy_Crosses | 20001704 | Tissue | Siliques |
| 12735575 | At_50mM_NH4NO3_L-to-H | 20001757 | Timepoint (hr) | 6 |
| 12735575 | At_50mM_NH4NO3_L-to-H | 20001757 | Treatment | 50 mM NH4NO3 vs 100 mM Mannitol |
| 12735575 | At_50mM_NH4NO3_L-to-H | 20001757 | Tissue | Leaf |
| 12735575 | At_Interploidy_Crosses | 20001853 | Age (day) | 5 |
| 12735575 | At_Interploidy_Crosses | 20001853 | Organism | A. thaliana |
| 12735575 | At_Interploidy_Crosses | 20001853 | Plant Line | Columbia |
| 12735575 | At_Interploidy_Crosses | 20001853 | Cross | Fis1 vs. 2X x 2X |
| 12735575 | At_Interploidy_Crosses | 20001853 | Tissue | Siliques |
| 12735575 | At_Drought_Reproduction | 20001905 | Timepoint (day) | 10 |
| 12735575 | At_Drought_Reproduction | 20001905 | Age (day) | 40 |
| 12735575 | At_Drought_Reproduction | 20001905 | Organism | A. thaliana |
| 12735575 | At_Drought_Reproduction | 20001905 | Treatment | Drought vs. No Drought |
| 12735575 | At_Drought_Reproduction | 20001905 | Tissue | Rosettes |
| 12735575 | At_Drought_Reproduction | 20001905 | Plant Line | WS |
| 12735575 | At_Drought_Reproduction | 20001911 | Timepoint (day) | 10 |
| 12735575 | At_Drought_Reproduction | 20001911 | Age (day) | 40 |
| 12735575 | At_Drought_Reproduction | 20001911 | Organism | A. thaliana |
| 12735575 | At_Drought_Reproduction | 20001911 | Treatment | Drought vs. No Drought |
| 12735575 | At_Drought_Reproduction | 20001911 | Tissue | Flowers |

TABLE 1-continued

Promoter Sequences and Related Information

| 12735575 | At_Drought_Reproduction | 20001911 | Plant Line | WS |
|---|---|---|---|---|
| 12735575 | At_Line_Comparisons | 20002007 | Plant Line | ME03793 vs. WS |
| 12735575 | At_Line_Comparisons | 20002008 | Plant Line | ME03766 vs. WS |
| 12735575 | At_Line_Comparisons | 20002009 | Plant Line | ME01642 vs. WS |
| 12735575 | At_Line_Comparisons | 20002010 | Plant Line | ME02031 vs. WS |
| 12735575 | At_Line_Comparisons | 20002012 | Plant Line | SALK_073455 vs. Columbia |
| 12735575 | At_8deg_Cold | 20002103 | Timepoint (hr) | 2 |
| 12735575 | At_8deg_Cold | 20002103 | Age (day) | 7 |
| 12735575 | At_8deg_Cold | 20002103 | Temperature (deg C.) | 8 vs. 22 |
| 12735575 | At_8deg_Cold | 20002103 | Organism | *A. thaliana* |
| 12735575 | At_8deg_Cold | 20002103 | Tissue | Whole Plant |
| 12735575 | At_8deg_Cold | 20002103 | Plant Line | WS |
| 12735575 | At_8deg_Cold | 20002105 | Age (day) | 7 |
| 12735575 | At_8deg_Cold | 20002105 | Timepoint (hr) | 8 |
| 12735575 | At_8deg_Cold | 20002105 | Temperature (deg C.) | 8 vs. 22 |
| 12735575 | At_8deg_Cold | 20002105 | Organism | *A. thaliana* |
| 12735575 | At_8deg_Cold | 20002105 | Tissue | Whole Plant |
| 12735575 | At_8deg_Cold | 20002105 | Plant Line | WS |
| 12735575 | At_8deg_Cold | 20002108 | Age (day) | 14 |
| 12735575 | At_8deg_Cold | 20002108 | Timepoint (hr) | 168 |
| 12735575 | At_8deg_Cold | 20002108 | Temperature (deg C.) | 8 vs. 22 |
| 12735575 | At_8deg_Cold | 20002108 | Organism | *A. thaliana* |
| 12735575 | At_8deg_Cold | 20002108 | Tissue | Whole Plant |
| 12735575 | At_8deg_Cold | 20002108 | Plant Line | WS |
| 12735575 | At_8deg_Cold | 20002109 | Age (day) | 16 |
| 12735575 | At_8deg_Cold | 20002109 | Timepoint (hr) | 216 |
| 12735575 | At_8deg_Cold | 20002109 | Temperature (deg C.) | 8 vs. 22 |
| 12735575 | At_8deg_Cold | 20002109 | Organism | *A. thaliana* |
| 12735575 | At_8deg_Cold | 20002109 | Tissue | Whole Plant |
| 12735575 | At_8deg_Cold | 20002109 | Plant Line | WS |

Promoter YP0381

Modulates the gene: Unknown expressed protein
The GenBank description of the gene: NM_113878 *Arabidopsis thaliana* expressed protein (At3g29575) mRNA, complete cds gi|30689672|ref|NM_113878.3|[30689672]
The promoter sequence:
5'tcattacattgaaaaagaaaattaattgtctttactcatgtttattctatacaaataaaatatta accaaccatcgcactaacaaaatagaaatcttattctaatcacttaattgttgacaattaaatcattg aaaaatacacttaaatgtcaaatattcgttttgcatacttttcaatttaaatacatttaaagttcgac aagttgcgtttactatcatagaaaactaaatctcctaccaaagcgaaatgaaactactaaagcgacag gcaggttacataacctaacaaatctccacgtgtcaattaccaagagaaaaaagagaagataagcgga acacgtggtagcacaaaaagataatgtgatttaaattaaaaaacaaaaacaaagacacgtgacgacc tgacgctgcaacatcccaccttacaacgtaataaccactgaacataagacacgtgtacgatcttgtct ttgttttctcgatgaaaaccacgtgggtgctcaaagtccttgggtcagagtcttccatgattccacgt gtcgttaatgcaccaaacaagggtactttcggtattttggcttccgcaaattagacaaaacagctttt tgtttgattgattttctcttctctttttccatctaaattctctttgggctcttaatttcttttgag tgttcgttcgagatttgtcggagatttttcggtaaatgttgaaattttgtgggattttttttttattt ctttattaaactttttttttattgaattTATAaaaagggaaggtcgtcattaatcgaagaaatggaatc ttccaaaatttgatattttgctgttttcttgggatttgaattgctctttatcatcaagaatctgttaa aatttctaatctaaaatctaagttgagaaaaagagagatctctaatttaaccggaattaatattctcc 3'-cATG
The promoter was cloned from the organism: *Arabidopsis thaliana*, Columbia ecotype

| Alternative nucleotides: Predicted (Columbia) Experimental (Columbia) | | |
|---|---|---|
| Predicted Position (bp) | Mismatch | Predicted/Experimental |
| 966 | Sequence read error | —/a |

TABLE 1-continued

Promoter Sequences and Related Information

The promoter was cloned in the vector: pNewbin4-HAP1-GFP
When cloned into the vector the promoter was operably linked to a marker, which was the type: GFP-ER
Promoter-marker vector was tested in: *Arabidopsis thaliana*, Columbia ecotype
Generation screened: XT1 Mature XT2 Seedling T2 Mature T3 Seedling
 The spatial expression of the promoter-marker vector was found observed in and would be useful in expression in any or all of the following:

Flower             L pedicel H nectary L epidermis
Hypocotyl          L vascular
Primary Root       H vascular
Observed expression pattern:
T1 mature: High expression in nectary glands of flowers. Low expression in epidermis of pedicles developing flowers.
T2 seedling: GFP expressed in root and hypocotyl vasculature.
Misc. promoter information: Bidirectionality: Pass Exons: Pass  Repeats: No
Optional Promoter Fragments: 5' UTR region at base pairs 671-975.
The Ceres cDNA ID of the endogenous coding sequence to the promoter: 12736859
cDNA nucleotide sequence:
AAATTCTCTTTGGGCTCTTAATTTCTTTTTGAGTGTTCGTTCGAGATTTGTCGGAGATTTTTTCG

GTAAATGTTGAAATTTTGTGGGATTTTTTTTATTTCTTTATTAAACTTTTTTTTATTGAATTTA

TAAAAGGGAAGGTCGTCATTAATCGAAGAAATGGAATCTTCCAAAATTTGATATTTTGCTGT

TTTCTTGGGATTTGAATTGCTCTTTATCATCAAGAATCTGTTAAAATTTCTAATCTAAAATCTA

AGTTGAGAAAAAGAGAGATCTCTAATTTAACCGGAATTAATATTCTCCGACCGAAGTTATTAT

GTTGCAGGCTCATGTCGAAGAAACAGAGATTGTCTGAAGAAGATGGAGAGGTAGAGATTGAG

TTAGACTTAGGTCTATCTCTAAATGGAAGATTTGGTGTTGACCCACTTGCGAAAACAAGGCTT

ATGAGGTCTACGTCGGTTCTTGATTTGGTGGTCAACGATAGGTCAGGGCTGAGTAGGACTTGT

TCGTTACCCGTGGAGACGGAGGAAGAGTGGAGGAAGAGGAAGGAGTTGCAGAGTTTGAGGAG

GCTTGAGGCTAAGAGAAAGAGATCAGAGAAGCAGAGGAAACATAAAGCTTGTGGTGGTGAAG

AGAAGGTTGTGGAAGAAGGATCTATTGGTTCTTCTGGTAGTGGTTCCTCTGGTTTGTCTGAAG

TTGATACTCTTCTTCCTCCTGTTCAAGCAACAACGAACAAGTCCGTGGAAACAAGCCCTTCAA

GTGCCCAATCTCAGCCCGAGAATTTGGGCAAAGAAGCGAGCCAAAACATTATAGAGGACATG

CCATTCGTGTCAACAACAGGCGATGGACCGAACGGGAAAAAGATTAATGGGTTTCTGTATCGG

TACCGCAAAGGTGAGGAGGTGAGGATTGTCTGTGTGTCATGGAAGCTTCCTCTCACCGGCA

GAATTCGTTAAGCATGCTGGTGGTGGTGACGTTGCACATCCCTTAAAGCACATCGTTGTAAAT

CCATCTCCCTTCTTGTGACCCTTTGGGTCTCTTTTGAGGGGTTTGTTGTATCGGAACCATGTTA

CAAATCCTCATTATCTCCGAGGTGTATAAACATAAATTTATCGAACTCGCAATTTTCAGATTTT

GTACTTAAAAGAATGGTTTCATTCGTTGAGATTAATTTTAGACCTTTTTCTTGTAC

Coding sequence:
MSKKQRLSEEDGEVEIELDLGLSLNGRFGVDPLAKTRLMRSTSVLDLVVNDRSGLSRTCSLPVETE

EEWRKRKELQSLRRLEAKRKRSEKQRKHKACGGEEKVVEEGSIGSSGSGSSGLSEVDTLLPPVQAT

TNKSVETSPSSAQSQPENLGKEASQNIIEDMPFVSTTGDGPNGKKINGFLYRYRKGEEVRIVCVCH

GSFLSPAEFVKHAGGGDVAHPLKHIVVNPSPFL*

Microarray data shows that the coding sequence was expressed in the following experiments, which shows that the promoter would be useful to modulate expression in situations similar to the following:

| CDNA_ID | SHORT_NAME | EXPT_REP_ID | IS_UP |
| --- | --- | --- | --- |
| 12736859 | At_100uM_ABA | 20000166 | + |
| 12736859 | At_100uM_ABA | 20000169 | + |
| 12736859 | At_Germinating_Seeds | 20000179 | + |
| 12736859 | At_Germinating_Seeds | 20000180 | + |
| 12736859 | At_2mM_SA | 20000182 | + |
| 12736859 | At_Root-Tips-vs-Tops | 20000227 | + |
| 12736859 | At_Siliques | 20000234 | − |

TABLE 1-continued

Promoter Sequences and Related Information

| 12736859 | At_Siliques | 20000236 | - |
|---|---|---|---|
| 12736859 | At_Open_Flower | 20000264 | - |
| 12736859 | At_Open_Flower | 20000265 | - |
| 12736859 | At_Drought | 20000267 | + |
| 12736859 | At_100mM_NaCl | 20000268 | + |
| 12736859 | At_Open_Flower | 20000286 | - |
| 12736859 | At_Drought | 20000436 | + |
| 12736859 | At_Drought | 20000437 | + |
| 12736859 | At_CS6879_Shoots-Roots | 20000451 | + |
| 12736859 | At_100uM_ABA | 20000453 | + |
| 12736859 | At_100uM_ABA | 20000455 | + |
| 12736859 | At_42deg_Heat | 20000458 | + |
| 12736859 | At_10percent_PEG | 20000460 | + |
| 12736859 | At_100uM_ABA_Mutants | 20000574 | - |
| 12736859 | At_CS8548_Mutant | 20000606 | - |
| 12736859 | At_Herbicide_Mutants | 20000639 | + |
| 12736859 | At_15mM_NH4NO3_L-to-H | 20000709 | - |
| 12736859 | At_Petals | 20000794 | - |
| 12736859 | At_Line_Comparisons | 20001151 | + |
| 12736859 | At_Line_Comparisons | 20001184 | + |
| 12736859 | At_Far-red-induction | 20001247 | + |
| 12736859 | At_Far-red-induction | 20001248 | + |
| 12736859 | At_Line_Comparisons | 20001307 | + |
| 12736859 | At_Line_Comparisons | 20001309 | - |
| 12736859 | At_Line_Comparisons | 20001310 | - |
| 12736859 | At_Line_Comparisons | 20001347 | + |
| 12736859 | At_Far-red-induction | 20001450 | + |
| 12736859 | At_Far-red-induction | 20001451 | + |
| 12736859 | At_Far-red-enriched | 20001504 | + |
| 12736859 | At_Drought_Soil_Dry | 20001553 | + |
| 12736859 | At_Drought_Soil_Dry | 20001554 | + |
| 12736859 | At_Drought_Soil_Dry | 20001556 | + |
| 12736859 | At_Drought_Soil_Dry | 20001559 | + |
| 12736859 | At_Interploidy_Crosses | 20001654 | + |
| 12736859 | At_Far-red-enriched-adult | 20001768 | + |
| 12736859 | At_Far-red-enriched-adult | 20001769 | + |
| 12736859 | At_Far-red-enriched-adult | 20001770 | + |
| 12736859 | At_Far-red-enriched-adult | 20001773 | + |
| 12736859 | At_Far-red-enriched-adult | 20001774 | + |
| 12736859 | At_Drought_Reproduction | 20001904 | + |
| 12736859 | At_Drought_Reproduction | 20001906 | + |
| 12736859 | At_Drought_Reproduction | 20001908 | + |
| 12736859 | At_Drought_Reproduction | 20001910 | + |
| 12736859 | At_8deg_Cold | 20002105 | + |
| 12736859 | At_8deg_Cold | 20002108 | - |
| 12736859 | At_Drought-Air-Dry | 20002254 | + |
| 12736859 | At_Drought-Air-Dry | 20002256 | + |

The parameters for the microarray experiments listed above by Expt_Rep_ID and Short_Name are as follow below:

| CDNA_ID | SHORT_NAME | EXPT_REP_ID | PARAM_NAME | VALUE |
|---|---|---|---|---|
| 12736859 | At_100uM_ABA | 20000166 | Timepoint (hr) | 1 |
| 12736859 | At_100uM_ABA | 20000166 | Age (day) | 14 |
| 12736859 | At_100uM_ABA | 20000166 | Treatment | 100 uM ABA vs. No Treatment |
| 12736859 | At_100uM_ABA | 20000166 | Organism | A. thaliana |
| 12736859 | At_100uM_ABA | 20000166 | Tissue | Aerial |
| 12736859 | At_100uM_ABA | 20000166 | Plant Line | WS |
| 12736859 | At_100uM_ABA | 20000169 | Timepoint (hr) | 6 |
| 12736859 | At_100uM_ABA | 20000169 | Age (day) | 14 |
| 12736859 | At_100uM_ABA | 20000169 | Treatment | 100 uM ABA vs. No Treatment |
| 12736859 | At_100uM_ABA | 20000169 | Organism | A. thaliana |
| 12736859 | At_100uM_ABA | 20000169 | Tissue | Aerial |
| 12736859 | At_100uM_ABA | 20000169 | Plant Line | WS |
| 12736859 | At_Germinating_Seeds | 20000179 | Age (hr) | 6 vs. 0 |
| 12736859 | At_Germinating_Seeds | 20000179 | Organism | A. thaliana |
| 12736859 | At_Germinating_Seeds | 20000179 | Tissue | Germinating Seeds |
| 12736859 | At_Germinating_Seeds | 20000179 | Plant Line | WS |
| 12736859 | At_Germinating_Seeds | 20000180 | Age (hr) | 24 vs. 0 |
| 12736859 | At_Germinating_Seeds | 20000180 | Organism | A. thaliana |
| 12736859 | At_Germinating_Seeds | 20000180 | Tissue | Germinating Seeds |
| 12736859 | At_Germinating_Seeds | 20000180 | Plant Line | WS |
| 12736859 | At_2mM_SA | 20000182 | Timepoint (hr) | 6 |
| 12736859 | At_2mM_SA | 20000182 | Age (day) | 14 |
| 12736859 | At_2mM_SA | 20000182 | Treatment | 2 mM SA vs. No Treatment |
| 12736859 | At_2mM_SA | 20000182 | Organism | A. thaliana |
| 12736859 | At_2mM_SA | 20000182 | Tissue | Aerial |

TABLE 1-continued

Promoter Sequences and Related Information

| 12736859 | At_2mM_SA | 20000182 | Plant Line | WS |
|---|---|---|---|---|
| 12736859 | At_Root-Tips-vs-Tops | 20000227 | Age (day) | 7, 10, 14 |
| 12736859 | At_Root-Tips-vs-Tops | 20000227 | Organism | A. thaliana |
| 12736859 | At_Root-Tips-vs-Tops | 20000227 | Tissue | Root Tips vs. Root Tops |
| 12736859 | At_Root-Tips-vs-Tops | 20000227 | Plant Line | WS |
| 12736859 | At_Siliques | 20000234 | Age (day) | 21 |
| 12736859 | At_Siliques | 20000234 | Tissue | <5 mm Siliques vs. Whole Plant |
| 12736859 | At_Siliques | 20000234 | Organism | A. thaliana |
| 12736859 | At_Siliques | 20000234 | Plant Line | WS |
| 12736859 | At_Siliques | 20000236 | Age (day) | 21 |
| 12736859 | At_Siliques | 20000236 | Tissue | >10 mm Siliques vs. Whole Plant |
| 12736859 | At_Siliques | 20000236 | Organism | A. thaliana |
| 12736859 | At_Siliques | 20000236 | Plant Line | WS |
| 12736859 | At_Open_Flower | 20000264 | Age (day) | 21 |
| 12736859 | At_Open_Flower | 20000264 | Organism | A. thaliana |
| 12736859 | At_Open_Flower | 20000264 | Tissue | Open Flower vs. Whole Plant |
| 12736859 | At_Open_Flower | 20000264 | Plant Line | WS |
| 12736859 | At_Open_Flower | 20000265 | Age (day) | 21 |
| 12736859 | At_Open_Flower | 20000265 | Organism | A. thaliana |
| 12736859 | At_Open_Flower | 20000265 | Tissue | Closed Flower vs. Whole Plant |
| 12736859 | At_Open_Flower | 20000265 | Plant Line | WS |
| 12736859 | At_Drought | 20000267 | Timepoint (hr) | 6 |
| 12736859 | At_Drought | 20000267 | Age (day) | 7 |
| 12736859 | At_Drought | 20000267 | Organism | A. thaliana |
| 12736859 | At_Drought | 20000267 | Treatment | Drought vs. No Drought |
| 12736859 | At_Drought | 20000267 | Tissue | Whole Plant |
| 12736859 | At_Drought | 20000267 | Plant Line | WS |
| 12736859 | At_100mM_NaCl | 20000268 | Timepoint (hr) | 6 |
| 12736859 | At_100mM_NaCl | 20000268 | Age (day) | 14 |
| 12736859 | At_100mM_NaCl | 20000268 | Treatment | 100 mM NaCl vs. No Treatment |
| 12736859 | At_100mM_NaCl | 20000268 | Organism | A. thaliana |
| 12736859 | At_100mM_NaCl | 20000268 | Tissue | Whole Plant |
| 12736859 | At_100mM_NaCl | 20000268 | Plant Line | WS |
| 12736859 | At_Open_Flower | 20000286 | Age (day) | 21 |
| 12736859 | At_Open_Flower | 20000286 | Organism | A. thaliana |
| 12736859 | At_Open_Flower | 20000286 | Tissue | Half Open vs. Whole Plant |
| 12736859 | At_Open_Flower | 20000286 | Plant Line | WS |
| 12736859 | At_Drought | 20000436 | Age (day) | 7 |
| 12736859 | At_Drought | 20000436 | Timepoint (hr) | 12 |
| 12736859 | At_Drought | 20000436 | Organism | A. thaliana |
| 12736859 | At_Drought | 20000436 | Treatment | Drought vs. No Drought |
| 12736859 | At_Drought | 20000436 | Tissue | Whole Plant |
| 12736859 | At_Drought | 20000436 | Plant Line | WS |
| 12736859 | At_Drought | 20000437 | Age (day) | 8 |
| 12736859 | At_Drought | 20000437 | Timepoint (hr) | 24 |
| 12736859 | At_Drought | 20000437 | Organism | A. thaliana |
| 12736859 | At_Drought | 20000437 | Treatment | Drought vs. No Drought |
| 12736859 | At_Drought | 20000437 | Tissue | Whole Plant |
| 12736859 | At_Drought | 20000437 | Plant Line | WS |
| 12736859 | At_CS6879_Shoots-Roots | 20000451 | Age (day) | 14 |
| 12736859 | At_CS6879_Shoots-Roots | 20000451 | Organism | A. thaliana |
| 12736859 | At_CS6879_Shoots-Roots | 20000451 | Plant Line | CS6879 vs. WS |
| 12736859 | At_CS6879_Shoots-Roots | 20000451 | Tissue | Roots |
| 12736859 | At_100uM_ABA | 20000453 | Age (day) | 15 |
| 12736859 | At_100uM_ABA | 20000453 | Timepoint (hr) | 24 |
| 12736859 | At_100uM_ABA | 20000453 | Treatment | 100 uM ABA vs. No Treatment |
| 12736859 | At_100uM_ABA | 20000453 | Organism | A. thaliana |
| 12736859 | At_100uM_ABA | 20000453 | Tissue | Aerial |
| 12736859 | At_100uM_ABA | 20000453 | Plant Line | WS |
| 12736859 | At_100uM_ABA | 20000455 | Age (day) | 16 |
| 12736859 | At_100uM_ABA | 20000455 | Timepoint (hr) | 48 |
| 12736859 | At_100uM_ABA | 20000455 | Treatment | 100 uM ABA vs. No Treatment |
| 12736859 | At_100uM_ABA | 20000455 | Organism | A. thaliana |
| 12736859 | At_100uM_ABA | 20000455 | Tissue | Aerial |
| 12736859 | At_100uM_ABA | 20000455 | Plant Line | WS |
| 12736859 | At_42deg_Heat | 20000458 | Timepoint (hr) | 8 |
| 12736859 | At_42deg_Heat | 20000458 | Age (day) | 14 |
| 12736859 | At_42deg_Heat | 20000458 | Temperature (deg C.) | 42 vs. 22 |
| 12736859 | At_42deg_Heat | 20000458 | Organism | A. thaliana |
| 12736859 | At_42deg_Heat | 20000458 | Tissue | Aerial |
| 12736859 | At_42deg_Heat | 20000458 | Plant Line | WS |
| 12736859 | At_10percent_PEG | 20000460 | Age (day) | 12 |
| 12736859 | At_10percent_PEG | 20000460 | Timepoint (day) | 12 |
| 12736859 | At_10percent_PEG | 20000460 | Treatment | 10 percent PEG vs. No Treatment |
| 12736859 | At_10percent_PEG | 20000460 | Organism | A. thaliana |

TABLE 1-continued

Promoter Sequences and Related Information

| 12736859 | At_10percent_PEG | 20000460 | Tissue | Whole Plant |
|---|---|---|---|---|
| 12736859 | At_10percent_PEG | 20000460 | Plant Line | WS |
| 12736859 | At_100uM_ABA_Mutants | 20000574 | Organism | *A. thaliana* |
| 12736859 | At_100uM_ABA_Mutants | 20000574 | Plant Line | CS23 vs. Ler wt |
| 12736859 | At_100uM_ABA_Mutants | 20000574 | Timepoint (hr) | N/A |
| 12736859 | At_100uM_ABA_Mutants | 20000574 | Treatment | None |
| 12736859 | At_100uM_ABA_Mutants | 20000574 | Tissue | Whole Plant |
| 12736859 | At_CS8548_Mutant | 20000606 | Age (day) | 14 |
| 12736859 | At_CS8548_Mutant | 20000606 | Plant Line | CS8548 vs. wt |
| 12736859 | At_CS8548_Mutant | 20000606 | Tissue | Whole Plant |
| 12736859 | At_Herbicide_Mutants | 20000639 | Timepoint (hr) | 4 |
| 12736859 | At_Herbicide_Mutants | 20000639 | Plant Line | 05377RR/BR27173 |
| 12736859 | At_Herbicide_Mutants | 20000639 | Treatment | Roundup vs. No Treatment |
| 12736859 | At_Herbicide_Mutants | 20000639 | Tissue | Seedlings |
| 12736859 | At_15mM_NH4NO3_L-to-H | 20000709 | Timepoint (hr) | 4 |
| 12736859 | At_15mM_NH4NO3_L-to-H | 20000709 | Age (hr) | 14 |
| 12736859 | At_15mM_NH4NO3_L-to-H | 20000709 | Treatment | 15 mM NH4NO3 vs. 30 mM Mannitol |
| 12736859 | At_15mM_NH4NO3_L-to-H | 20000709 | Organism | *A. thaliana* |
| 12736859 | At_15mM_NH4NO3_L-to-H | 20000709 | Tissue | Aerial |
| 12736859 | At_15mM_NH4NO3_L-to-H | 20000709 | Plant Line | WS |
| 12736859 | At_Petals | 20000794 | Age (day) | 23-25 days |
| 12736859 | At_Petals | 20000794 | Organism | *A. thaliana* |
| 12736859 | At_Petals | 20000794 | Tissue | Petals vs. Whole plant |
| 12736859 | At_Petals | 20000794 | Plant Line | WS |
| 12736859 | At_Line_Comparisons | 20001151 | Plant Line | ME01339-01 vs. WS |
| 12736859 | At_Line_Comparisons | 20001184 | Plant Line | ME01848-01 vs. WS |
| 12736859 | At_Far-red-induction | 20001247 | Timepoint (hr) | 1 |
| 12736859 | At_Far-red-induction | 20001247 | Age (day) | 7 |
| 12736859 | At_Far-red-induction | 20001247 | Organism | *A. thaliana* |
| 12736859 | At_Far-red-induction | 20001247 | Plant Line | Columbia |
| 12736859 | At_Far-red-induction | 20001247 | Light | Far-red vs. White |
| 12736859 | At_Far-red-induction | 20001247 | Tissue | Whole Plant |
| 12736859 | At_Far-red-induction | 20001248 | Timepoint (hr) | 4 |
| 12736859 | At_Far-red-induction | 20001248 | Age (day) | 7 |
| 12736859 | At_Far-red-induction | 20001248 | Organism | *A. thaliana* |
| 12736859 | At_Far-red-induction | 20001248 | Plant Line | Columbia |
| 12736859 | At_Far-red-induction | 20001248 | Light | Far-red vs. White |
| 12736859 | At_Far-red-induction | 20001248 | Tissue | Whole Plant |
| 12736859 | At_Line_Comparisons | 20001307 | Plant Line | WBin4-WX2-A vs. WS |
| 12736859 | At_Line_Comparisons | 20001309 | Plant Line | WBin4-WX49R-A vs. WS |
| 12736859 | At_Line_Comparisons | 20001310 | Plant Line | WBin4-WX17-A vs. WS |
| 12736859 | At_Line_Comparisons | 20001347 | Plant Line | ME01604-01 vs. WS |
| 12736859 | At_Far-red-induction | 20001450 | Age (day) | 7 |
| 12736859 | At_Far-red-induction | 20001450 | Timepoint (hr) | 8 |
| 12736859 | At_Far-red-induction | 20001450 | Organism | *A. thaliana* |
| 12736859 | At_Far-red-induction | 20001450 | Plant Line | Columbia |
| 12736859 | At_Far-red-induction | 20001450 | Light | Far-red vs. White |
| 12736859 | At_Far-red-induction | 20001450 | Tissue | Whole Plant |
| 12736859 | At_Far-red-induction | 20001451 | Age (day) | 8 |
| 12736859 | At_Far-red-induction | 20001451 | Timepoint (hr) | 24 |
| 12736859 | At_Far-red-induction | 20001451 | Organism | *A. thaliana* |
| 12736859 | At_Far-red-induction | 20001451 | Plant Line | Columbia |
| 12736859 | At_Far-red-induction | 20001451 | Light | Far-red vs. White |
| 12736859 | At_Far-red-induction | 20001451 | Tissue | Whole Plant |
| 12736859 | At_Far-red-enriched | 20001504 | Timepoint (day) | 6 |
| 12736859 | At_Far-red-enriched | 20001504 | Age (day) | 10 |
| 12736859 | At_Far-red-enriched | 20001504 | Organism | *A. thaliana* |
| 12736859 | At_Far-red-enriched | 20001504 | Plant Line | Columbia |
| 12736859 | At_Far-red-enriched | 20001504 | Light | Far-red enriched vs. White |
| 12736859 | At_Far-red-enriched | 20001504 | Tissue | Whole Plant |
| 12736859 | At_Drought_Soil_Dry | 20001553 | Timepoint (day) | 5 |
| 12736859 | At_Drought_Soil_Dry | 20001553 | Age (day) | 19 |
| 12736859 | At_Drought_Soil_Dry | 20001553 | Organism | *A. thaliana* |
| 12736859 | At_Drought_Soil_Dry | 20001553 | Treatment | Drought vs. No Drought |
| 12736859 | At_Drought_Soil_Dry | 20001553 | Post Timepoint (hr) | None |
| 12736859 | At_Drought_Soil_Dry | 20001553 | Post-Treatment | None |
| 12736859 | At_Drought_Soil_Dry | 20001553 | Plant Line | WS |
| 12736859 | At_Drought_Soil_Dry | 20001554 | Timepoint (day) | 7 |
| 12736859 | At_Drought_Soil_Dry | 20001554 | Age (day) | 21 |
| 12736859 | At_Drought_Soil_Dry | 20001554 | Organism | *A. thaliana* |
| 12736859 | At_Drought_Soil_Dry | 20001554 | Treatment | Drought vs. No Drought |
| 12736859 | At_Drought_Soil_Dry | 20001554 | Post Timepoint (hr) | None |
| 12736859 | At_Drought_Soil_Dry | 20001554 | Post-Treatment | None |
| 12736859 | At_Drought_Soil_Dry | 20001554 | Plant Line | WS |
| 12736859 | At_Drought_Soil_Dry | 20001556 | Timepoint (day) | 12 |
| 12736859 | At_Drought_Soil_Dry | 20001556 | Age (day) | 26 |
| 12736859 | At_Drought_Soil_Dry | 20001556 | Organism | *A. thaliana* |

TABLE 1-continued

Promoter Sequences and Related Information

| | | | | |
|---|---|---|---|---|
| 12736859 | At_Drought_Soil_Dry | 20001556 | Treatment | Drought vs. No Drought |
| 12736859 | At_Drought_Soil_Dry | 20001556 | Post Timepoint (hr) | None |
| 12736859 | At_Drought_Soil_Dry | 20001556 | Post-Treatment | None |
| 12736859 | At_Drought_Soil_Dry | 20001556 | Plant Line | WS |
| 12736859 | At_Drought_Soil_Dry | 20001559 | Timepoint (day) | 14 |
| 12736859 | At_Drought_Soil_Dry | 20001559 | Age (day) | 28 |
| 12736859 | At_Drought_Soil_Dry | 20001559 | Post Timepoint (hr) | 29 |
| 12736859 | At_Drought_Soil_Dry | 20001559 | Organism | A. thaliana |
| 12736859 | At_Drought_Soil_Dry | 20001559 | Treatment | Drought vs. No Drought |
| 12736859 | At_Drought_Soil_Dry | 20001559 | Post-Treatment | Re-Water vs. No Drought |
| 12736859 | At_Drought_Soil_Dry | 20001559 | Plant Line | WS |
| 12736859 | At_Interploidy_Crosses | 20001654 | Age (day) | 5 |
| 12736859 | At_Interploidy_Crosses | 20001654 | Cross | 6X × 2X vs. 2X × 2X |
| 12736859 | At_Interploidy_Crosses | 20001654 | Organism | A. thaliana |
| 12736859 | At_Interploidy_Crosses | 20001654 | Plant Line | Columbia |
| 12736859 | At_Interploidy_Crosses | 20001654 | Tissue | Siliques |
| 12736859 | At_Far-red-enriched-adult | 20001768 | Timepoint (hr) | 1 |
| 12736859 | At_Far-red-enriched-adult | 20001768 | Age (day) | 28 |
| 12736859 | At_Far-red-enriched-adult | 20001768 | Organism | A. thaliana |
| 12736859 | At_Far-red-enriched-adult | 20001768 | Tissue | Aerial |
| 12736859 | At_Far-red-enriched-adult | 20001768 | Plant Line | Columbia |
| 12736859 | At_Far-red-enriched-adult | 20001768 | Light | Far-red enriched vs. White |
| 12736859 | At_Far-red-enriched-adult | 20001769 | Timepoint (hr) | 4 |
| 12736859 | At_Far-red-enriched-adult | 20001769 | Age (day) | 28 |
| 12736859 | At_Far-red-enriched-adult | 20001769 | Organism | A. thaliana |
| 12736859 | At_Far-red-enriched-adult | 20001769 | Tissue | Aerial |
| 12736859 | At_Far-red-enriched-adult | 20001769 | Plant Line | Columbia |
| 12736859 | At_Far-red-enriched-adult | 20001769 | Light | Far-red enriched vs. White |
| 12736859 | At_Far-red-enriched-adult | 20001770 | Timepoint (hr) | 8 |
| 12736859 | At_Far-red-enriched-adult | 20001770 | Age (day) | 28 |
| 12736859 | At_Far-red-enriched-adult | 20001770 | Organism | A. thaliana |
| 12736859 | At_Far-red-enriched-adult | 20001770 | Tissue | Aerial |
| 12736859 | At_Far-red-enriched-adult | 20001770 | Plant Line | Columbia |
| 12736859 | At_Far-red-enriched-adult | 20001770 | Light | Far-red enriched vs. White |
| 12736859 | At_Far-red-enriched-adult | 20001773 | Age (day) | 30 |
| 12736859 | At_Far-red-enriched-adult | 20001773 | Timepoint (hr) | 48 |
| 12736859 | At_Far-red-enriched-adult | 20001773 | Organism | A. thaliana |
| 12736859 | At_Far-red-enriched-adult | 20001773 | Tissue | Aerial |
| 12736859 | At_Far-red-enriched-adult | 20001773 | Plant Line | Columbia |
| 12736859 | At_Far-red-enriched-adult | 20001773 | Light | Far-red enriched vs. White |
| 12736859 | At_Far-red-enriched-adult | 20001774 | Age (day) | 31 |
| 12736859 | At_Far-red-enriched-adult | 20001774 | Timepoint (hr) | 72 |
| 12736859 | At_Far-red-enriched-adult | 20001774 | Organism | A. thaliana |
| 12736859 | At_Far-red-enriched-adult | 20001774 | Tissue | Aerial |
| 12736859 | At_Far-red-enriched-adult | 20001774 | Plant Line | Columbia |
| 12736859 | At_Far-red-enriched-adult | 20001774 | Light | Far-red enriched vs. White |
| 12736859 | At_Drought_Reproduction | 20001904 | Timepoint (day) | 7 |
| 12736859 | At_Drought_Reproduction | 20001904 | Age (day) | 37 |
| 12736859 | At_Drought_Reproduction | 20001904 | Organism | A. thaliana |
| 12736859 | At_Drought_Reproduction | 20001904 | Treatment | Drought vs. No Drought |
| 12736859 | At_Drought_Reproduction | 20001904 | Tissue | Rosettes |
| 12736859 | At_Drought_Reproduction | 20001904 | Plant Line | WS |
| 12736859 | At_Drought_Reproduction | 20001906 | Timepoint (day) | 5 |
| 12736859 | At_Drought_Reproduction | 20001906 | Age (day) | 35 |
| 12736859 | At_Drought_Reproduction | 20001906 | Organism | A. thaliana |
| 12736859 | At_Drought_Reproduction | 20001906 | Treatment | Drought vs. No Drought |
| 12736859 | At_Drought_Reproduction | 20001906 | Tissue | Siliques |
| 12736859 | At_Drought_Reproduction | 20001906 | Plant Line | WS |
| 12736859 | At_Drought_Reproduction | 20001908 | Timepoint (day) | 10 |
| 12736859 | At_Drought_Reproduction | 20001908 | Age (day) | 40 |
| 12736859 | At_Drought_Reproduction | 20001908 | Organism | A. thaliana |
| 12736859 | At_Drought_Reproduction | 20001908 | Treatment | Drought vs. No Drought |
| 12736859 | At_Drought_Reproduction | 20001908 | Tissue | Siliques |
| 12736859 | At_Drought_Reproduction | 20001908 | Plant Line | WS |
| 12736859 | At_Drought_Reproduction | 20001910 | Timepoint (day) | 7 |
| 12736859 | At_Drought_Reproduction | 20001910 | Age (day) | 37 |
| 12736859 | At_Drought_Reproduction | 20001910 | Organism | A. thaliana |
| 12736859 | At_Drought_Reproduction | 20001910 | Treatment | Drought vs. No Drought |
| 12736859 | At_Drought_Reproduction | 20001910 | Tissue | Flowers |
| 12736859 | At_Drought_Reproduction | 20001910 | Plant Line | WS |
| 12736859 | At_8deg_Cold | 20002105 | Age (day) | 7 |
| 12736859 | At_8deg_Cold | 20002105 | Timepoint (hr) | 8 |
| 12736859 | At_8deg_Cold | 20002105 | Temperature (deg C.) | 8 vs. 22 |
| 12736859 | At_8deg_Cold | 20002105 | Organism | A. thaliana |
| 12736859 | At_8deg_Cold | 20002105 | Tissue | Whole Plant |
| 12736859 | At_8deg_Cold | 20002105 | Plant Line | WS |
| 12736859 | At_8deg_Cold | 20002108 | Age (day) | 14 |
| 12736859 | At_8deg_Cold | 20002108 | Timepoint (hr) | 168 |

TABLE 1-continued

Promoter Sequences and Related Information

| 12736859 | At_8deg_Cold | 20002108 | Temperature (deg C.) | 8 vs. 22 |
|---|---|---|---|---|
| 12736859 | At_8deg_Cold | 20002108 | Organism | *A. thaliana* |
| 12736859 | At_8deg_Cold | 20002108 | Tissue | Whole Plant |
| 12736859 | At_8deg_Cold | 20002108 | Plant Line | WS |
| 12736859 | At_Drought-Air-Dry | 20002254 | Timepoint (hr) | 4 |
| 12736859 | At_Drought-Air-Dry | 20002254 | Age (day) | 35 |
| 12736859 | At_Drought-Air-Dry | 20002254 | Organism | *A. thaliana* |
| 12736859 | At_Drought-Air-Dry | 20002254 | Treatment | Drought vs. No Drought |
| 12736859 | At_Drought-Air-Dry | 20002254 | Tissue | Roots |
| 12736859 | At_Drought-Air-Dry | 20002254 | Plant Line | WS |
| 12736859 | At_Drought-Air-Dry | 20002256 | Timepoint (hr) | 4 |
| 12736859 | At_Drought-Air-Dry | 20002256 | Age (day) | 35 |
| 12736859 | At_Drought-Air-Dry | 20002256 | Organism | *A. thaliana* |
| 12736859 | At_Drought-Air-Dry | 20002256 | Treatment | Drought vs. No Drought |
| 12736859 | At_Drought-Air-Dry | 20002256 | Tissue | Shoots |
| 12736859 | At_Drought-Air-Dry | 20002256 | Plant Line | WS |

Promoter YP0380

Modulates the gene: Responsive to Dehydration 20
The GenBank description of the gene:: NM_128898 *Arabidopsis thaliana* RD20 protein (At2g33380) mRNA, complete cds gi|30685670|ref|NM_128898.2|[30685670]
The promoter sequence:
5'tttcaatgtatacaatcatcatgtgataaaaaaaaaatgtaaccaatcaacacactgagatacggcca aaaaatggtaatacataaatgtttgtaggttttgtaatttaaatactttagttaagttatgattttattat ttttgcttatcacttatacgaaatcatcaatctattggtatctcttaatcccgcttttaatttccaccgc acacgcaaatcagcaaatggttccagccacgtgcatgtgaccacatattgtggtcacagtactcgtcctt tttttcttttgtaatcaataaatttcaatcctaaaacttcacacattgagcacgtcggcaacgttagctc ctaaatcataacgagcaaaaagttcaaattagggtatatgatcaattgatcatcactacatgtctacata attaatatgtattcaaccggtcggtttgttgatactcatagttaagtatatatgtgctaattagaattagg atgaatcagttcttgcaaacaactacggtttcatataatatgggagtgttatgtacaaaatgaaagaggat ggatcattctgagatgttatgggctcccagtcaatcatgttttgctcgcatatgctatcttttgagtctct tcctaaactcatagaataagcacgttggttttttccaccgtcctcctcgtgaacaaaagtacaattacatt ttagcaaattgaaaataaccacgtggatggaccatattatatgtgatcatattgcttgtcgtcttcgtttt cttttaaatgtttacaccactacttcctgacacgtgtccctattcacatcatccttgttatatcgttttac tTATAaaggatcacgaacaccaaaacatcaatgtgtacgtcttttgcataagaagaaacagagagcattat caattattaacaattacacaagacagcga 3'-aATG
The promoter was cloned from the organism: *Arabidopsis thaliana*, Columbia ecotype

Alternative nucleotides:

| Predicted Position (bp) | Mismatch | Predicted/Experimental |
|---|---|---|
| 5 | PCR error or ecotype variant SNP | g/— correct is —/— |
| 17 | PCR error or ecotype variant SNP | c/— correct is —/— |

The promoter was cloned in the vector: pNewbin4-HAP1-GFP
When cloned into the vector the promoter was operably linked to a marker, which was the type: GFP-ER
Promoter-marker vector was tested in: *Arabidopsis thaliana*, WS ecotype
Generation screened: XT1 Mature  XT2 Seedling  T2 Mature  T3 Seedling The spatial expression of the promoter-marker vector was found observed in and would be useful in expression in any or all of the following:

| | |
|---|---|
| Flower | H pedicel H receptacle H sepal H petal H filament H anther H carpel H stigma Hepidermis Hstomata H silique H style |
| Silique | H stigma H style H carpel H septum H placentae H epidermis |
| Stem | L epidermis L cortex H stomata |
| Leaf | H mesophyll H stomata |
| Hypocotyl | H epidermis H stomata |
| Cotyledon | H mesophyll H epidermis |
| Rosette Leaf | H mesophyll H epidermis |
| Primary Root | H epidermis |

TABLE 1-continued

Promoter Sequences and Related Information

Observed expression pattern:
T1 mature: High expression throughout floral organs. High expression in stem guard cells and cortex cells surrounding stomal chamber (see Table 1. FIG. P). Not expressed in shoot apical meristem, early flower primordia, pollen and ovules.
T2 seedling: Expressed in all tissues near seedling apex increasing toward root. High root epidermis expression.
Optional Promoter Fragments: 5' UTR region at base pairs 905-1000.
Misc. promoter information: Bidirectionality: Pass  Exons: Pass  Repeats: No
The Ceres cDNA ID of the endogenous coding sequence to the promoter: 12462179
cDNA nucleotide sequence:
AATGTGTACGTCTTTTGCATAAGAAGAAACAGAGAGCATTATCAATTATTAACAATTACACAA

GACAGCGAGATTGTAAAAGAGTAAGAGAGAGAGAATGGCAGGAGAGGCAGAGGCTTTGGCC

ACGACGGCACCGTTAGCTCCGGTCACCAGTCAGCGAAAAGTACGGAACGATTTGGAGGAAAC

ATTACCAAAACCATACATGGCAAGAGCATTAGCAGCTCCAGATACAGAGCATCCGAATGGAA

CAGAAGGTCACGATAGCAAAGGAATGAGTGTTATGCAACAACATGTTGCTTTCTTCGACCAAA

ACGACGATGGAATCGTCTATCCTTGGGAGACTTATAAGGGATTTCGTGACCTTGGTTTCAACC

CAATTTCCTCTATCTTTTGGACCTTACTCATAAACTTAGCGTTCAGCTACGTTACACTTCCGAG

TTGGGTGCCATCACCATTATTGCCGGTTTATATCGACAACATACACAAAGCCAAGCATGGGAG

TGATTCGAGCACCTATGACACCGAAGGAAGGTATGTCCCAGTTAACCTCGAGAACATATTTAG

CAAATACGCGCTAACGGTTAAAGATAAGTTATCATTTAAAGAGGTTTGGAATGTAACCGAGGG

AAATCGAATGGCAATCGATCCTTTTGGATGGCTTTCAAACAAAGTTGAATGGATACTACTCTA

TATTCTTGCTAAGGACGAAGATGGTTTCCTATCTAAAGAAGCTGTGAGAGGTTGCTTTGATGG

AAGTTTATTTGAACAAATTGCCAAAGAGAGGGCCAATTCTCGCAAACAAGACTAAGAATGTGT

GTGTTTGGTTAGCGAATAAAGCTTTTTGAAGAAAAGCATTGTGTAATTTAGCTTCTTTCGTCTT

GTTATTCAGTTTGGGGATTTGTATAATTAATGTGTTTGTAAACTATGTTTCAAAGTTATATAAA

TAAGAGAAGATGTTACAAAAAAAAAAAAAAGACTAATAAGAAGAATTTGGT

Coding sequence:
MAGEAEALATTAPLAPVTSQRKVRNDLEETLPKPYMARALAAPDTEHPNGTEGHDSKGMSVMQ

QHVAFFDQNDDGIVYPWETYKGFRDLGFNPISSIFWTLLINLAFSYVTLPSWVPSPLLPVYIDNIHK

AKHGSDSSTYDTEGRYVPVNLENIFSKYALTVKDKLSFKEVWNVTEGNRMAIDPFGWLSNKVEWI

LLYILAKDEDGFLSKEAVRGCFDGSLFEQIAKERANSRKQD*

Microarray data shows that the coding sequence was expressed in the following experiments, which shows that the promoter would be useful to modulate expression in situations similar to the following:

| CDNA_ID | SHORT_NAME | EXPT_REP_ID | IS_UP |
| --- | --- | --- | --- |
| 12462179 | At_100uM_ABA | 20000166 | + |
| 12462179 | At_100uM_ABA | 20000169 | + |
| 12462179 | At_2mM_SA | 20000182 | + |
| 12462179 | At_Shoots | 20000184 | − |
| 12462179 | At_Roots | 20000185 | − |
| 12462179 | At_0.001percent_MeJA | 20000211 | + |
| 12462179 | At_Open_Flower | 20000264 | + |
| 12462179 | At_Open_Flower | 20000265 | + |
| 12462179 | At_100mM_NaCl | 20000268 | + |
| 12462179 | At_100mM_NaCl | 20000308 | + |
| 12462179 | At_Pollen | 20000326 | − |
| 12462179 | At_Drought | 20000436 | + |
| 12462179 | At_Drought | 20000437 | + |
| 12462179 | At_Shoots | 20000438 | − |
| 12462179 | At_Roots | 20000439 | − |
| 12462179 | At_100uM_NAA | 20000445 | + |
| 12462179 | At_100uM_ABA | 20000453 | + |
| 12462179 | At_100uM_ABA | 20000455 | + |
| 12462179 | At_42deg_Heat | 20000458 | + |
| 12462179 | At_Wounding | 20000506 | + |

TABLE 1-continued

Promoter Sequences and Related Information

| | | | |
|---|---|---|---|
| 12462179 | At_100uM_ABA_Mutants | 20000575 | + |
| 12462179 | At_100uM_ABA_Mutants | 20000576 | + |
| 12462179 | At_Herbicide_Mutants | 20000640 | − |
| 12462179 | At_Herbicide_Mutants | 20000642 | − |
| 12462179 | At_15mM_NH4NO3_L-to-H | 20000709 | − |
| 12462179 | At_Petals | 20000794 | + |
| 12462179 | At_Line_Comparisons | 20001151 | + |
| 12462179 | At_Line_Comparisons | 20001184 | + |
| 12462179 | At_Far-red-induction | 20001248 | − |
| 12462179 | At_Line_Comparisons | 20001307 | + |
| 12462179 | At_Line_Comparisons | 20001310 | − |
| 12462179 | At_Interploidy_Crosses | 20001316 | − |
| 12462179 | At_Line_Comparisons | 20001319 | + |
| 12462179 | At_Line_Comparisons | 20001347 | + |
| 12462179 | At_Far-red-induction | 20001451 | + |
| 12462179 | At_Far-red-enriched | 20001504 | + |
| 12462179 | At_Drought_Soil_Dry | 20001553 | + |
| 12462179 | At_Drought_Soil_Dry | 20001554 | + |
| 12462179 | At_Drought_Soil_Dry | 20001555 | + |
| 12462179 | At_Drought_Soil_Dry | 20001556 | + |
| 12462179 | At_Drought_Soil_Dry | 20001559 | + |
| 12462179 | At_Interploidy_Crosses | 20001654 | + |
| 12462179 | At_50mM_NH4NO3_L-to-H | 20001757 | − |
| 12462179 | At_Far-red-enriched-adult | 20001768 | + |
| 12462179 | At_Far-red-enriched-adult | 20001770 | + |
| 12462179 | At_Far-red-enriched-adult | 20001771 | + |
| 12462179 | At_Far-red-enriched-adult | 20001774 | + |
| 12462179 | At_Drought_Reproduction | 20001904 | + |
| 12462179 | At_Drought_Reproduction | 20001905 | + |
| 12462179 | At_Drought_Reproduction | 20001906 | + |
| 12462179 | At_Drought_Reproduction | 20001908 | + |
| 12462179 | At_Drought_Reproduction | 20001910 | + |
| 12462179 | At_Drought_Reproduction | 20001911 | + |
| 12462179 | At_8deg_Cold | 20002107 | − |
| 12462179 | At_8deg_Cold | 20002108 | − |
| 12462179 | At_8deg_Cold | 20002109 | − |

The parameters for the microarray experiments listed above by Expt_Rep_ID and Short_Name are as follow below:

| CDNA_ID | SHORT_NAME | EXPT_REP_ID | PARAM_NAME | VALUE |
|---|---|---|---|---|
| 12462179 | At_100uM_ABA | 20000166 | Timepoint (hr) | 1 |
| 12462179 | At_100uM_ABA | 20000166 | Age (day) | 14 |
| 12462179 | At_100uM_ABA | 20000166 | Treatment | 100 uM ABA vs. No Treatment |
| 12462179 | At_100uM_ABA | 20000166 | Organism | *A. thaliana* |
| 12462179 | At_100uM_ABA | 20000166 | Tissue | Aerial |
| 12462179 | At_100uM_ABA | 20000166 | Plant Line | WS |
| 12462179 | At_100uM_ABA | 20000169 | Timepoint (hr) | 6 |
| 12462179 | At_100uM_ABA | 20000169 | Age (day) | 14 |
| 12462179 | At_100uM_ABA | 20000169 | Treatment | 100 uM ABA vs. No Treatment |
| 12462179 | At_100uM_ABA | 20000169 | Organism | *A. thaliana* |
| 12462179 | At_100uM_ABA | 20000169 | Tissue | Aerial |
| 12462179 | At_100uM_ABA | 20000169 | Plant Line | WS |
| 12462179 | At_2mM_SA | 20000182 | Timepoint (hr) | 6 |
| 12462179 | At_2mM_SA | 20000182 | Age (day) | 14 |
| 12462179 | At_2mM_SA | 20000182 | Treatment | 2 mM SA vs. No Treatment |
| 12462179 | At_2mM_SA | 20000182 | Organism | *A. thaliana* |
| 12462179 | At_2mM_SA | 20000182 | Tissue | Aerial |
| 12462179 | At_2mM_SA | 20000182 | Plant Line | WS |
| 12462179 | At_Shoots | 20000184 | Age (day) | 7 vs. 21 |
| 12462179 | At_Shoots | 20000184 | Organism | *A. thaliana* |
| 12462179 | At_Shoots | 20000184 | Tissue | Shoots vs. Whole Plant |
| 12462179 | At_Shoots | 20000184 | Plant Line | WS |
| 12462179 | At_Roots | 20000185 | Age (day) | 7 vs. 21 |
| 12462179 | At_Roots | 20000185 | Organism | *A. thaliana* |
| 12462179 | At_Roots | 20000185 | Tissue | Roots vs. Whole Plant |
| 12462179 | At_Roots | 20000185 | Plant Line | WS |
| 12462179 | At_0.001percent_MeJA | 20000211 | Timepoint (hr) | 1 |
| 12462179 | At_0.001percent_MeJA | 20000211 | Age (day) | 14 |
| 12462179 | At_0.001percent_MeJA | 20000211 | Treatment | 0.001 percent MeJA vs. No Treatment |
| 12462179 | At_0.001percent_MeJA | 20000211 | Organism | *A. thaliana* |
| 12462179 | At_0.001percent_MeJA | 20000211 | Tissue | Aerial |
| 12462179 | At_0.001percent_MeJA | 20000211 | Plant Line | WS |
| 12462179 | At_Open_Flower | 20000264 | Age (day) | 21 |
| 12462179 | At_Open_Flower | 20000264 | Organism | *A. thaliana* |
| 12462179 | At_Open_Flower | 20000264 | Tissue | Open Flower vs. Whole Plant |

TABLE 1-continued

Promoter Sequences and Related Information

| | | | | |
|---|---|---|---|---|
| 12462179 | At_Open_Flower | 20000264 | Plant Line | WS |
| 12462179 | At_Open_Flower | 20000265 | Age (day) | 21 |
| 12462179 | At_Open_Flower | 20000265 | Organism | A. thaliana |
| 12462179 | At_Open_Flower | 20000265 | Tissue | Closed Flower vs. Whole Plant |
| 12462179 | At_Open_Flower | 20000265 | Plant Line | WS |
| 12462179 | At_100mM_NaCl | 20000268 | Timepoint (hr) | 6 |
| 12462179 | At_100mM_NaCl | 20000268 | Age (day) | 14 |
| 12462179 | At_100mM_NaCl | 20000268 | Treatment | 100 mM NaCl vs. No Treatment |
| 12462179 | At_100mM_NaCl | 20000268 | Organism | A. thaliana |
| 12462179 | At_100mM_NaCl | 20000268 | Tissue | Whole Plant |
| 12462179 | At_100mM_NaCl | 20000268 | Plant Line | WS |
| 12462179 | At_100mM_NaCl | 20000308 | Age (day) | 17 |
| 12462179 | At_100mM_NaCl | 20000308 | Timepoint (hr) | 72 |
| 12462179 | At_100mM_NaCl | 20000308 | Treatment | 100 mM NaCl vs. No Treatment |
| 12462179 | At_100mM_NaCl | 20000308 | Organism | A. thaliana |
| 12462179 | At_100mM_NaCl | 20000308 | Tissue | Whole Plant |
| 12462179 | At_100mM_NaCl | 20000308 | Plant Line | WS |
| 12462179 | At_Pollen | 20000326 | Age (day) | 0 vs. 21 |
| 12462179 | At_Pollen | 20000326 | Organism | A. thaliana |
| 12462179 | At_Pollen | 20000326 | Tissue | Pollen vs. Whole Plant |
| 12462179 | At_Pollen | 20000326 | Plant Line | WS |
| 12462179 | At_Drought | 20000436 | Age (day) | 7 |
| 12462179 | At_Drought | 20000436 | Timepoint (hr) | 12 |
| 12462179 | At_Drought | 20000436 | Organism | A. thaliana |
| 12462179 | At_Drought | 20000436 | Treatment | Drought vs. No Drought |
| 12462179 | At_Drought | 20000436 | Tissue | Whole Plant |
| 12462179 | At_Drought | 20000436 | Plant Line | WS |
| 12462179 | At_Drought | 20000437 | Age (day) | 8 |
| 12462179 | At_Drought | 20000437 | Timepoint (hr) | 24 |
| 12462179 | At_Drought | 20000437 | Organism | A. thaliana |
| 12462179 | At_Drought | 20000437 | Treatment | Drought vs. No Drought |
| 12462179 | At_Drought | 20000437 | Tissue | Whole Plant |
| 12462179 | At_Drought | 20000437 | Plant Line | WS |
| 12462179 | At_Shoots | 20000438 | Age (day) | 14 vs. 21 |
| 12462179 | At_Shoots | 20000438 | Organism | A. thaliana |
| 12462179 | At_Shoots | 20000438 | Tissue | Shoots vs. Whole Plant |
| 12462179 | At_Shoots | 20000438 | Plant Line | WS |
| 12462179 | At_Roots | 20000439 | Age (day) | 14 vs. 21 |
| 12462179 | At_Roots | 20000439 | Organism | A. thaliana |
| 12462179 | At_Roots | 20000439 | Tissue | Roots vs. Whole Plant |
| 12462179 | At_Roots | 20000439 | Plant Line | WS |
| 12462179 | At_100uM_NAA | 20000445 | Timepoint (hr) | 6 |
| 12462179 | At_100uM_NAA | 20000445 | Age (day) | 14 |
| 12462179 | At_100uM_NAA | 20000445 | Treatment | 100 uM NAA vs. No Treatment |
| 12462179 | At_100uM_NAA | 20000445 | Organism | A. thaliana |
| 12462179 | At_100uM_NAA | 20000445 | Tissue | Aerial |
| 12462179 | At_100uM_NAA | 20000445 | Plant Line | WS |
| 12462179 | At_100uM_ABA | 20000453 | Age (day) | 15 |
| 12462179 | At_100uM_ABA | 20000453 | Timepoint (hr) | 24 |
| 12462179 | At_100uM_ABA | 20000453 | Treatment | 100 uM ABA vs. No Treatment |
| 12462179 | At_100uM_ABA | 20000453 | Organism | A. thaliana |
| 12462179 | At_100uM_ABA | 20000453 | Tissue | Aerial |
| 12462179 | At_100uM_ABA | 20000453 | Plant Line | WS |
| 12462179 | At_100uM_ABA | 20000455 | Age (day) | 16 |
| 12462179 | At_100uM_ABA | 20000455 | Timepoint (hr) | 48 |
| 12462179 | At_100uM_ABA | 20000455 | Treatment | 100 uM ABA vs. No Treatment |
| 12462179 | At_100uM_ABA | 20000455 | Organism | A. thaliana |
| 12462179 | At_100uM_ABA | 20000455 | Tissue | Aerial |
| 12462179 | At_100uM_ABA | 20000455 | Plant Line | WS |
| 12462179 | At_42deg_Heat | 20000458 | Timepoint (hr) | 8 |
| 12462179 | At_42deg_Heat | 20000458 | Age (day) | 14 |
| 12462179 | At_42deg_Heat | 20000458 | Temperature (deg C.) | 42 vs. 22 |
| 12462179 | At_42deg_Heat | 20000458 | Organism | A. thaliana |
| 12462179 | At_42deg_Heat | 20000458 | Tissue | Aerial |
| 12462179 | At_42deg_Heat | 20000458 | Plant Line | WS |
| 12462179 | At_Wounding | 20000506 | Timepoint (hr) | 6 |
| 12462179 | At_Wounding | 20000506 | Age (day) | 14 |
| 12462179 | At_Wounding | 20000506 | Organism | A. thaliana |
| 12462179 | At_Wounding | 20000506 | Tissue | Aerial |
| 12462179 | At_Wounding | 20000506 | Treatment | Wounding vs. No Wounding |
| 12462179 | At_Wounding | 20000506 | Plant Line | WS |
| 12462179 | At_100uM_ABA_Mutants | 20000575 | Timepoint (hr) | 6 |
| 12462179 | At_100uM_ABA_Mutants | 20000575 | Treatment | 1 uM ABA vs. No Treatment |
| 12462179 | At_100uM_ABA_Mutants | 20000575 | Organism | A. thaliana |
| 12462179 | At_100uM_ABA_Mutants | 20000575 | Plant Line | CS22 |
| 12462179 | At_100uM_ABA_Mutants | 20000575 | Tissue | Whole Plant |
| 12462179 | At_100uM_ABA_Mutants | 20000576 | Timepoint (hr) | 6 |
| 12462179 | At_100uM_ABA_Mutants | 20000576 | Treatment | 1 uM ABA vs. No Treatment |

TABLE 1-continued

Promoter Sequences and Related Information

| | | | | |
|---|---|---|---|---|
| 12462179 | At_100uM_ABA_Mutants | 20000576 | Organism | A. thaliana |
| 12462179 | At_100uM_ABA_Mutants | 20000576 | Plant Line | CS23 |
| 12462179 | At_100uM_ABA_Mutants | 20000576 | Tissue | Whole Plant |
| 12462179 | At_Herbicide_Mutants | 20000640 | Timepoint (hr) | 12 |
| 12462179 | At_Herbicide_Mutants | 20000640 | Plant Line | 05377RR/BR27173 |
| 12462179 | At_Herbicide_Mutants | 20000640 | Treatment | Roundup vs. No Treatment |
| 12462179 | At_Herbicide_Mutants | 20000640 | Tissue | Seedlings |
| 12462179 | At_Herbicide_Mutants | 20000642 | Timepoint (hr) | 12 |
| 12462179 | At_Herbicide_Mutants | 20000642 | Plant Line | 3950BR/PCJE10000 |
| 12462179 | At_Herbicide_Mutants | 20000642 | Treatment | Finale vs. No Treatment |
| 12462179 | At_Herbicide_Mutants | 20000642 | Tissue | Seedlings |
| 12462179 | At_15mM_NH4NO3_L-to-H | 20000709 | Timepoint (hr) | 4 |
| 12462179 | At_15mM_NH4NO3_L-to-H | 20000709 | Age (hr) | 14 |
| 12462179 | At_15mM_NH4NO3_L-to-H | 20000709 | Treatment | 15 mM NH4NO3 vs. 30 mM Mannitol |
| 12462179 | At_15mM_NH4NO3_L-to-H | 20000709 | Organism | A. thaliana |
| 12462179 | At_15mM_NH4NO3_L-to-H | 20000709 | Tissue | Aerial |
| 12462179 | At_15mM_NH4NO3_L-to-H | 20000709 | Plant Line | WS |
| 12462179 | At_Petals | 20000794 | Age (day) | 23-25 days |
| 12462179 | At_Petals | 20000794 | Organism | A. thaliana |
| 12462179 | At_Petals | 20000794 | Tissue | Petals vs. Whole plant |
| 12462179 | At_Petals | 20000794 | Plant Line | WS |
| 12462179 | At_Line_Comparisons | 20001151 | Plant Line | ME01339-01 vs. WS |
| 12462179 | At_Line_Comparisons | 20001184 | Plant Line | ME01848-01 vs. WS |
| 12462179 | At_Far-red-induction | 20001248 | Timepoint (hr) | 4 |
| 12462179 | At_Far-red-induction | 20001248 | Age (day) | 7 |
| 12462179 | At_Far-red-induction | 20001248 | Organism | A. thaliana |
| 12462179 | At_Far-red-induction | 20001248 | Plant Line | Columbia |
| 12462179 | At_Far-red-induction | 20001248 | Light | Far-red vs. White |
| 12462179 | At_Far-red-induction | 20001248 | Tissue | Whole Plant |
| 12462179 | At_Line_Comparisons | 20001307 | Plant Line | WBin4-WX2-A vs. WS |
| 12462179 | At_Line_Comparisons | 20001310 | Plant Line | WBin4-WX17-A vs. WS |
| 12462179 | At_Interploidy_Crosses | 20001316 | Age (day) | 5 |
| 12462179 | At_Interploidy_Crosses | 20001316 | Organism | A. thaliana |
| 12462179 | At_Interploidy_Crosses | 20001316 | Plant Line | Columbia |
| 12462179 | At_Interploidy_Crosses | 20001316 | Cross | hemi x 2X vs. 2X x 2X |
| 12462179 | At_Interploidy_Crosses | 20001316 | Tissue | Siliques |
| 12462179 | At_Line_Comparisons | 20001319 | Plant Line | WBin4-WX24-A vs. WS |
| 12462179 | At_Line_Comparisons | 20001347 | Plant Line | ME01604-01 vs. WS |
| 12462179 | At_Far-red-induction | 20001451 | Age (day) | 8 |
| 12462179 | At_Far-red-induction | 20001451 | Timepoint (hr) | 24 |
| 12462179 | At_Far-red-induction | 20001451 | Organism | A. thaliana |
| 12462179 | At_Far-red-induction | 20001451 | Plant Line | Columbia |
| 12462179 | At_Far-red-induction | 20001451 | Light | Far-red vs. White |
| 12462179 | At_Far-red-induction | 20001451 | Tissue | Whole Plant |
| 12462179 | At_Far-red-enriched | 20001504 | Timepoint (day) | 6 |
| 12462179 | At_Far-red-enriched | 20001504 | Age (day) | 10 |
| 12462179 | At_Far-red-enriched | 20001504 | Organism | A. thaliana |
| 12462179 | At_Far-red-enriched | 20001504 | Plant Line | Columbia |
| 12462179 | At_Far-red-enriched | 20001504 | Light | Far-red enriched vs. White |
| 12462179 | At_Far-red-enriched | 20001504 | Tissue | Whole Plant |
| 12462179 | At_Drought_Soil_Dry | 20001553 | Timepoint (day) | 5 |
| 12462179 | At_Drought_Soil_Dry | 20001553 | Age (day) | 19 |
| 12462179 | At_Drought_Soil_Dry | 20001553 | Organism | A. thaliana |
| 12462179 | At_Drought_Soil_Dry | 20001553 | Treatment | Drought vs. No Drought |
| 12462179 | At_Drought_Soil_Dry | 20001553 | Post Timepoint (hr) | None |
| 12462179 | At_Drought_Soil_Dry | 20001553 | Post-Treatment | None |
| 12462179 | At_Drought_Soil_Dry | 20001553 | Plant Line | WS |
| 12462179 | At_Drought_Soil_Dry | 20001554 | Timepoint (day) | 7 |
| 12462179 | At_Drought_Soil_Dry | 20001554 | Age (day) | 21 |
| 12462179 | At_Drought_Soil_Dry | 20001554 | Organism | A. thaliana |
| 12462179 | At_Drought_Soil_Dry | 20001554 | Treatment | Drought vs. No Drought |
| 12462179 | At_Drought_Soil_Dry | 20001554 | Post Timepoint (hr) | None |
| 12462179 | At_Drought_Soil_Dry | 20001554 | Post-Treatment | None |
| 12462179 | At_Drought_Soil_Dry | 20001554 | Plant Line | WS |
| 12462179 | At_Drought_Soil_Dry | 20001555 | Timepoint (day) | 10 |
| 12462179 | At_Drought_Soil_Dry | 20001555 | Age (day) | 24 |
| 12462179 | At_Drought_Soil_Dry | 20001555 | Organism | A. thaliana |
| 12462179 | At_Drought_Soil_Dry | 20001555 | Treatment | Drought vs. No Drought |
| 12462179 | At_Drought_Soil_Dry | 20001555 | Post Timepoint (hr) | None |
| 12462179 | At_Drought_Soil_Dry | 20001555 | Post-Treatment | None |
| 12462179 | At_Drought_Soil_Dry | 20001555 | Plant Line | WS |
| 12462179 | At_Drought_Soil_Dry | 20001556 | Timepoint (day) | 12 |
| 12462179 | At_Drought_Soil_Dry | 20001556 | Age (day) | 26 |
| 12462179 | At_Drought_Soil_Dry | 20001556 | Organism | A. thaliana |
| 12462179 | At_Drought_Soil_Dry | 20001556 | Treatment | Drought vs. No Drought |
| 12462179 | At_Drought_Soil_Dry | 20001556 | Post Timepoint (hr) | None |
| 12462179 | At_Drought_Soil_Dry | 20001556 | Post-Treatment | None |

TABLE 1-continued

Promoter Sequences and Related Information

| | | | | |
|---|---|---|---|---|
| 12462179 | At_Drought_Soil_Dry | 20001556 | Plant Line | WS |
| 12462179 | At_Drought_Soil_Dry | 20001559 | Timepoint (day) | 14 |
| 12462179 | At_Drought_Soil_Dry | 20001559 | Age (day) | 28 |
| 12462179 | At_Drought_Soil_Dry | 20001559 | Post Timepoint (hr) | 29 |
| 12462179 | At_Drought_Soil_Dry | 20001559 | Organism | A. thaliana |
| 12462179 | At_Drought_Soil_Dry | 20001559 | Treatment | Drought vs. No Drought |
| 12462179 | At_Drought_Soil_Dry | 20001559 | Post-Treatment | Re-Water vs. No Drought |
| 12462179 | At_Drought_Soil_Dry | 20001559 | Plant Line | WS |
| 12462179 | At_Interploidy_Crosses | 20001654 | Age (day) | 5 |
| 12462179 | At_Interploidy_Crosses | 20001654 | Cross | 6X × 2X vs. 2X × 2X |
| 12462179 | At_Interploidy_Crosses | 20001654 | Organism | A. thaliana |
| 12462179 | At_Interploidy_Crosses | 20001654 | Plant Line | Columbia |
| 12462179 | At_Interploidy_Crosses | 20001654 | Tissue | Siliques |
| 12462179 | At_50mM_NH4NO3_L-to-H | 20001757 | Timepoint (hr) | 6 |
| 12462179 | At_50mM_NH4NO3_L-to-H | 20001757 | Treatment | 50 mM NH4NO3 vs 100 mM Mannitol |
| 12462179 | At_50mM_NH4NO3_L-to-H | 20001757 | Tissue | Leaf |
| 12462179 | At_Far-red-enriched-adult | 20001768 | Timepoint (hr) | 1 |
| 12462179 | At_Far-red-enriched-adult | 20001768 | Age (day) | 28 |
| 12462179 | At_Far-red-enriched-adult | 20001768 | Organism | A. thaliana |
| 12462179 | At_Far-red-enriched-adult | 20001768 | Tissue | Aerial |
| 12462179 | At_Far-red-enriched-adult | 20001768 | Plant Line | Columbia |
| 12462179 | At_Far-red-enriched-adult | 20001768 | Light | Far-red enriched vs. White |
| 12462179 | At_Far-red-enriched-adult | 20001770 | Timepoint (hr) | 8 |
| 12462179 | At_Far-red-enriched-adult | 20001770 | Age (day) | 28 |
| 12462179 | At_Far-red-enriched-adult | 20001770 | Organism | A. thaliana |
| 12462179 | At_Far-red-enriched-adult | 20001770 | Tissue | Aerial |
| 12462179 | At_Far-red-enriched-adult | 20001770 | Plant Line | Columbia |
| 12462179 | At_Far-red-enriched-adult | 20001770 | Light | Far-red enriched vs. White |
| 12462179 | At_Far-red-enriched-adult | 20001771 | Timepoint (hr) | 16 |
| 12462179 | At_Far-red-enriched-adult | 20001771 | Age (day) | 28 |
| 12462179 | At_Far-red-enriched-adult | 20001771 | Organism | A. thaliana |
| 12462179 | At_Far-red-enriched-adult | 20001771 | Tissue | Aerial |
| 12462179 | At_Far-red-enriched-adult | 20001771 | Plant Line | Columbia |
| 12462179 | At_Far-red-enriched-adult | 20001771 | Light | Far-red enriched vs. White |
| 12462179 | At_Far-red-enriched-adult | 20001774 | Age (day) | 31 |
| 12462179 | At_Far-red-enriched-adult | 20001774 | Timepoint (hr) | 72 |
| 12462179 | At_Far-red-enriched-adult | 20001774 | Organism | A. thaliana |
| 12462179 | At_Far-red-enriched-adult | 20001774 | Tissue | Aerial |
| 12462179 | At_Far-red-enriched-adult | 20001774 | Plant Line | Columbia |
| 12462179 | At_Far-red-enriched-adult | 20001774 | Light | Far-red enriched vs. White |
| 12462179 | At_Drought_Reproduction | 20001904 | Timepoint (day) | 7 |
| 12462179 | At_Drought_Reproduction | 20001904 | Age (day) | 37 |
| 12462179 | At_Drought_Reproduction | 20001904 | Organism | A. thaliana |
| 12462179 | At_Drought_Reproduction | 20001904 | Treatment | Drought vs. No Drought |
| 12462179 | At_Drought_Reproduction | 20001904 | Tissue | Rosettes |
| 12462179 | At_Drought_Reproduction | 20001904 | Plant Line | WS |
| 12462179 | At_Drought_Reproduction | 20001905 | Timepoint (day) | 10 |
| 12462179 | At_Drought_Reproduction | 20001905 | Age (day) | 40 |
| 12462179 | At_Drought_Reproduction | 20001905 | Organism | A. thaliana |
| 12462179 | At_Drought_Reproduction | 20001905 | Treatment | Drought vs. No Drought |
| 12462179 | At_Drought_Reproduction | 20001905 | Tissue | Rosettes |
| 12462179 | At_Drought_Reproduction | 20001905 | Plant Line | WS |
| 12462179 | At_Drought_Reproduction | 20001906 | Timepoint (day) | 5 |
| 12462179 | At_Drought_Reproduction | 20001906 | Age (day) | 35 |
| 12462179 | At_Drought_Reproduction | 20001906 | Organism | A. thaliana |
| 12462179 | At_Drought_Reproduction | 20001906 | Treatment | Drought vs. No Drought |
| 12462179 | At_Drought_Reproduction | 20001906 | Tissue | Siliques |
| 12462179 | At_Drought_Reproduction | 20001906 | Plant Line | WS |
| 12462179 | At_Drought_Reproduction | 20001908 | Timepoint (day) | 10 |
| 12462179 | At_Drought_Reproduction | 20001908 | Age (day) | 40 |
| 12462179 | At_Drought_Reproduction | 20001908 | Organism | A. thaliana |
| 12462179 | At_Drought_Reproduction | 20001908 | Treatment | Drought vs. No Drought |
| 12462179 | At_Drought_Reproduction | 20001908 | Tissue | Siliques |
| 12462179 | At_Drought_Reproduction | 20001908 | Plant Line | WS |
| 12462179 | At_Drought_Reproduction | 20001910 | Timepoint (day) | 7 |
| 12462179 | At_Drought_Reproduction | 20001910 | Age (day) | 37 |
| 12462179 | At_Drought_Reproduction | 20001910 | Organism | A. thaliana |
| 12462179 | At_Drought_Reproduction | 20001910 | Treatment | Drought vs. No Drought |
| 12462179 | At_Drought_Reproduction | 20001910 | Tissue | Flowers |
| 12462179 | At_Drought_Reproduction | 20001910 | Plant Line | WS |
| 12462179 | At_Drought_Reproduction | 20001911 | Timepoint (day) | 10 |
| 12462179 | At_Drought_Reproduction | 20001911 | Age (day) | 40 |
| 12462179 | At_Drought_Reproduction | 20001911 | Organism | A. thaliana |
| 12462179 | At_Drought_Reproduction | 20001911 | Treatment | Drought vs. No Drought |
| 12462179 | At_Drought_Reproduction | 20001911 | Tissue | Flowers |
| 12462179 | At_Drought_Reproduction | 20001911 | Plant Line | WS |
| 12462179 | At_8deg_Cold | 20002107 | Age (day) | 11 |

TABLE 1-continued

Promoter Sequences and Related Information

| | | | | |
|---|---|---|---|---|
| 12462179 | At_8deg_Cold | 20002107 | Timepoint (hr) | 96 |
| 12462179 | At_8deg_Cold | 20002107 | Temperature (deg C.) | 8 vs. 22 |
| 12462179 | At_8deg_Cold | 20002107 | Organism | A. thaliana |
| 12462179 | At_8deg_Cold | 20002107 | Tissue | Whole Plant |
| 12462179 | At_8deg_Cold | 20002107 | Plant Line | WS |
| 12462179 | At_8deg_Cold | 20002108 | Age (day) | 14 |
| 12462179 | At_8deg_Cold | 20002108 | Timepoint (hr) | 168 |
| 12462179 | At_8deg_Cold | 20002108 | Temperature (deg C.) | 8 vs. 22 |
| 12462179 | At_8deg_Cold | 20002108 | Organism | A. thaliana |
| 12462179 | At_8deg_Cold | 20002108 | Tissue | Whole Plant |
| 12462179 | At_8deg_Cold | 20002108 | Plant Line | WS |
| 12462179 | At_8deg_Cold | 20002109 | Age (day) | 16 |
| 12462179 | At_8deg_Cold | 20002109 | Timepoint (hr) | 216 |
| 12462179 | At_8deg_Cold | 20002109 | Temperature (deg C.) | 8 vs. 22 |
| 12462179 | At_8deg_Cold | 20002109 | Organism | A. thaliana |
| 12462179 | At_8deg_Cold | 20002109 | Tissue | Whole Plant |
| 12462179 | At_8deg_Cold | 20002109 | Plant Line | WS |
| 13613778 | At_Root_Tips | 108434 | Tissue | Root Tips |
| 13613778 | At_20uM_KNO3_H-to-L | 108455 | Timepoint (hr) | 1 |
| 13613778 | At_20uM_KNO3_H-to-L | 108455 | Treatment | 20 uM KNO3 vs. 50 mM KNO3 |
| 13613778 | At_5-1-F2-137 | 108460 | Plant Line | 5-1-F2-137(mutant) |
| 13613778 | At_5-1-F2-137 | 108460 | Probe Method | Amplified |
| 13613778 | At_5-1-F2-137 | 108460 | Tissue | Inflorescences |
| 13613778 | At_Germinating_Seeds | 108464 | Age (day) | 4 vs. 0 |
| 13613778 | At_Germinating_Seeds | 108464 | Tissue | Germinating Seeds |
| 13613778 | At_Shoot_Apices | 108480 | Treatment | 1uM BR vs. No Treatment |
| 13613778 | At_Shoot_Apices | 108480 | Plant Line | Ws-2 |
| 13613778 | At_Shoot_Apices | 108481 | Treatment | 1uM BRZ vs. No Treatment |
| 13613778 | At_Shoot_Apices | 108481 | Plant Line | Ws-2 |
| 13613778 | At_15mM_NH4NO3_L-to-H_Rosette | 108487 | Timepoint (hr) | 0.5 |
| 13613778 | At_15mM_NH4NO3_L-to-H_Rosette | 108487 | Treatment | 15 mM NH4NO3 vs. 30 mM Mannitol |
| 13613778 | At_15mM_NH4NO3_L-to-H_Rosette | 108487 | Tissue | Rosette |
| 13613778 | At_15mM_NH4NO3_L-to-H_Rosette | 108488 | Timepoint (hr) | 2 |
| 13613778 | At_15mM_NH4NO3_L-to-H_Rosette | 108488 | Treatment | 15 mM NH4NO3 vs. 30 mM Mannitol |
| 13613778 | At_15mM_NH4NO3_L-to-H_Rosette | 108488 | Tissue | Rosette |
| 13613778 | At_ap2_floral_buds | 108501 | Plant Line | ap2 (Ler.) |
| 13613778 | At_ap2_floral_buds | 108501 | Tissue | Closed Flower |
| 13613778 | At_42deg_Heat | 108577 | Timepoint (hr) | 6 |
| 13613778 | At_42deg_Heat | 108577 | Temperature (deg C.) | 42 vs. 22 |
| 13613778 | At_42deg_Heat | 108577 | Tissue | Aerial |
| 13613778 | At_4deg_Cold | 108578 | Timepoint (hr) | 1 |
| 13613778 | At_4deg_Cold | 108578 | Temperature (deg C.) | 4 vs. 22 |
| 13613778 | At_4deg_Cold | 108578 | Tissue | Aerial |
| 13613778 | At_4deg_Cold | 108579 | Timepoint (hr) | 6 |
| 13613778 | At_4deg_Cold | 108579 | Temperature (deg C.) | 4 vs. 22 |
| 13613778 | At_4deg_Cold | 108579 | Tissue | Aerial |
| 13613778 | At_5mM_NaNP | 108584 | Timepoint (hr) | 1 |
| 13613778 | At_5mM_NaNP | 108584 | Treatment | 5 mM sodium nitroprusside vs. No Treatment |
| 13613778 | At_5mM_NaNP | 108584 | Tissue | Aerial |
| 13613778 | At_5mM_NaNP | 108585 | Timepoint (hr) | 6 |
| 13613778 | At_5mM_NaNP | 108585 | Treatment | 5 mM sodium nitroprusside vs. No Treatment |
| 13613778 | At_5mM_NaNP | 108585 | Tissue | Aerial |
| 13613778 | At_2mM_SA | 108586 | Timepoint (hr) | 1 |
| 13613778 | At_2mM_SA | 108586 | Treatment | 2 mM SA vs. No Treatment |
| 13613778 | At_2mM_SA | 108586 | Tissue | Aerial |
| 13613778 | At_2mM_SA | 108587 | Timepoint (hr) | 6 |
| 13613778 | At_2mM_SA | 108587 | Treatment | 2 mM SA vs. No Treatment |
| 13613778 | At_2mM_SA | 108587 | Tissue | Aerial |
| 13613778 | At_15mM_NH4NO3_L-to-H | 108588 | Timepoint (hr) | 2 |
| 13613778 | At_15mM_NH4NO3_L-to-H | 108588 | Treatment | 15 mM NH4NO3 vs. 30 mM Mannitol |
| 13613778 | At_15mM_NH4NO3_L-to-H | 108588 | Tissue | Aerial |
| 13613778 | At_Ler-pi_Ovule | 108595 | Plant Line | Ler_pi |
| 13613778 | At_Ler-pi_Ovule | 108595 | Tissue | Ovules |
| 13613778 | At_100uM_ABA | 108606 | Timepoint (hr) | 2 |
| 13613778 | At_100uM_ABA | 108606 | Treatment | 100 uM ABA vs. No Treatment |
| 13613778 | At_100uM_ABA | 108606 | Tissue | Aerial |
| 13613778 | At_2mM_SA | 108667 | Timepoint (hr) | 1 |

TABLE 1-continued

Promoter Sequences and Related Information

| | | | | |
|---|---|---|---|---|
| 13613778 | At_2mM_SA | 108667 | Treatment | 2 mM SA vs. No Treatment |
| 13613778 | At_2mM_SA | 108667 | Plant Line | WS |
| 13613778 | At_100uM_ABA_Mutants | 20000069 | Timepoint (hr) | 6 |
| 13613778 | At_100uM_ABA_Mutants | 20000069 | Treatment | 100 uM ABA vs. No Treatment |
| 13613778 | At_100uM_ABA_Mutants | 20000069 | Tissue | Aerial |
| 13613778 | At_100uM_ABA_Mutants | 20000069 | Plant Line | CS23 |
| 13613778 | At_100uM_ABA_Mutants | 20000071 | Timepoint (hr) | 6 |
| 13613778 | At_100uM_ABA_Mutants | 20000071 | Treatment | 100 uM ABA vs. No Treatment |
| 13613778 | At_100uM_ABA_Mutants | 20000071 | Tissue | Aerial |
| 13613778 | At_100uM_ABA_Mutants | 20000071 | Plant Line | CS8104 |
| 13613778 | At_100uM_ABA_Mutants | 20000086 | Timepoint (hr) | 6 |
| 13613778 | At_100uM_ABA_Mutants | 20000086 | Treatment | 100 uM ABA vs. No Treatment |
| 13613778 | At_100uM_ABA_Mutants | 20000086 | Tissue | Aerial |
| 13613778 | At_100uM_ABA_Mutants | 20000086 | Plant Line | CS22 |
| 13613778 | At_100uM_ABA_Mutants | 20000087 | Timepoint (hr) | 6 |
| 13613778 | At_100uM_ABA_Mutants | 20000087 | Treatment | 100 uM ABA vs. No Treatment |
| 13613778 | At_100uM_ABA_Mutants | 20000087 | Tissue | Aerial |
| 13613778 | At_100uM_ABA_Mutants | 20000087 | Plant Line | WS |
| 13613778 | At_2mM_SA_CS3726-Columbia | 20000091 | Timepoint (hr) | 0 |
| 13613778 | At_2mM_SA_CS3726-Columbia | 20000091 | Tissue | Aerial |
| 13613778 | At_2mM_SA_CS3726-Columbia | 20000091 | Plant Line | CS3726 vs. Columbia |
| 13613778 | At_2mM_SA_CS3726-Columbia | 20000091 | Treatment | None |
| 13613778 | At_100uM_ABA_Mutants | 20000117 | Timepoint (hr) | 6 |
| 13613778 | At_100uM_ABA_Mutants | 20000117 | Treatment | 100 uM ABA vs. No Treatment |
| 13613778 | At_100uM_ABA_Mutants | 20000117 | Tissue | Aerial |
| 13613778 | At_100uM_ABA_Mutants | 20000117 | Plant Line | Columbia |
| 13613778 | At_42deg_Heat | 20000144 | Timepoint (hr) | 1 |
| 13613778 | At_42deg_Heat | 20000144 | Temperature (deg C.) | 42 vs. 22 |
| 13613778 | At_42deg_Heat | 20000144 | Tissue | Aerial |
| 13613778 | At_42deg_Heat | 20000171 | Timepoint (hr) | 1 |
| 13613778 | At_42deg_Heat | 20000171 | Age (day) | 14 |
| 13613778 | At_42deg_Heat | 20000171 | Temperature (deg C.) | 42 vs. 22 |
| 13613778 | At_42deg_Heat | 20000171 | Organism | A. thaliana |
| 13613778 | At_42deg_Heat | 20000171 | Tissue | Aerial |
| 13613778 | At_42deg_Heat | 20000171 | Plant Line | WS |
| 13613778 | At_42deg_Heat | 20000173 | Timepoint (hr) | 6 |
| 13613778 | At_42deg_Heat | 20000173 | Age (day) | 14 |
| 13613778 | At_42deg_Heat | 20000173 | Temperature (deg C.) | 42 vs. 22 |
| 13613778 | At_42deg_Heat | 20000173 | Organism | A. thaliana |
| 13613778 | At_42deg_Heat | 20000173 | Tissue | Aerial |
| 13613778 | At_42deg_Heat | 20000173 | Plant Line | WS |
| 13613778 | At_2mM_SA | 20000181 | Timepoint (hr) | 1 |
| 13613778 | At_2mM_SA | 20000181 | Age (day) | 14 |
| 13613778 | At_2mM_SA | 20000181 | Treatment | 2 mM SA vs. No Treatment |
| 13613778 | At_2mM_SA | 20000181 | Organism | A. thaliana |
| 13613778 | At_2mM_SA | 20000181 | Tissue | Aerial |
| 13613778 | At_2mM_SA | 20000181 | Plant Line | WS |
| 13613778 | At_Shoots | 20000184 | Age (day) | 7 vs. 21 |
| 13613778 | At_Shoots | 20000184 | Organism | A. thaliana |
| 13613778 | At_Shoots | 20000184 | Tissue | Shoots vs. Whole Plant |
| 13613778 | At_Shoots | 20000184 | Plant Line | WS |
| 13613778 | At_Roots | 20000185 | Age (day) | 7 vs. 21 |
| 13613778 | At_Roots | 20000185 | Organism | A. thaliana |
| 13613778 | At_Roots | 20000185 | Tissue | Roots vs. Whole Plant |
| 13613778 | At_Roots | 20000185 | Plant Line | WS |
| 13613778 | At_4deg_Cold | 20000213 | Timepoint (hr) | 2 |
| 13613778 | At_Siliques | 20000234 | Age (day) | 21 |
| 13613778 | At_Siliques | 20000234 | Tissue | <5 mm Siliques vs. Whole Plant |
| 13613778 | At_Siliques | 20000234 | Organism | A. thaliana |
| 13613778 | At_Siliques | 20000234 | Plant Line | WS |
| 13613778 | At_Siliques | 20000236 | Age (day) | 21 |
| 13613778 | At_Siliques | 20000236 | Tissue | >10 mm Siliques vs. Whole Plant |
| 13613778 | At_Siliques | 20000236 | Organism | A. thaliana |
| 13613778 | At_Siliques | 20000236 | Plant Line | WS |
| 13613778 | At_Open_Flower | 20000264 | Age (day) | 21 |
| 13613778 | At_Open_Flower | 20000264 | Organism | A. thaliana |
| 13613778 | At_Open_Flower | 20000264 | Tissue | Open Flower vs. Whole Plant |
| 13613778 | At_Open_Flower | 20000264 | Plant Line | WS |
| 13613778 | At_100mM_NaCl | 20000268 | Timepoint (hr) | 6 |
| 13613778 | At_100mM_NaCl | 20000268 | Age (day) | 14 |
| 13613778 | At_100mM_NaCl | 20000268 | Treatment | 100 mM NaCl vs. No Treatment |

TABLE 1-continued

Promoter Sequences and Related Information

| 13613778 | At_100mM_NaCl | 20000268 | Organism | *A. thaliana* |
|---|---|---|---|---|
| 13613778 | At_100mM_NaCl | 20000268 | Tissue | Whole Plant |
| 13613778 | At_100mM_NaCl | 20000268 | Plant Line | WS |
| 13613778 | At_Open_Flower | 20000286 | Age (day) | 21 |
| 13613778 | At_Open_Flower | 20000286 | Organism | *A. thaliana* |
| 13613778 | At_Open_Flower | 20000286 | Tissue | Half Open vs. Whole Plant |
| 13613778 | At_Open_Flower | 20000286 | Plant Line | WS |
| 13613778 | At_Pollen | 20000326 | Age (day) | 0 vs. 21 |
| 13613778 | At_Pollen | 20000326 | Organism | *A. thaliana* |
| 13613778 | At_Pollen | 20000326 | Tissue | Pollen vs. Whole Plant |
| 13613778 | At_Pollen | 20000326 | Plant Line | WS |
| 13613778 | At_Shoots | 20000438 | Age (day) | 14 vs. 21 |
| 13613778 | At_Shoots | 20000438 | Organism | *A. thaliana* |
| 13613778 | At_Shoots | 20000438 | Tissue | Shoots vs. Whole Plant |
| 13613778 | At_Shoots | 20000438 | Plant Line | WS |
| 13613778 | At_Roots | 20000439 | Age (day) | 14 vs. 21 |
| 13613778 | At_Roots | 20000439 | Organism | *A. thaliana* |
| 13613778 | At_Roots | 20000439 | Tissue | Roots vs. Whole Plant |
| 13613778 | At_Roots | 20000439 | Plant Line | WS |
| 13613778 | At_1uM_BR-BRZ | 20000441 | Treatment | 1 uM BR vs. No Treatment |
| 13613778 | At_1uM_BR-BRZ | 20000441 | Tissue | Shoot Apices |
| 13613778 | At_1uM_BR-BRZ | 20000443 | Treatment | 1 uM BRZ vs. No Treatment |
| 13613778 | At_1uM_BR-BRZ | 20000443 | Tissue | Shoot Apices |
| 13613778 | At_42deg_Heat | 20000458 | Timepoint (hr) | 8 |
| 13613778 | At_42deg_Heat | 20000458 | Age (day) | 14 |
| 13613778 | At_42deg_Heat | 20000458 | Temperature (deg C.) | 42 vs. 22 |
| 13613778 | At_42deg_Heat | 20000458 | Organism | *A. thaliana* |
| 13613778 | At_42deg_Heat | 20000458 | Tissue | Aerial |
| 13613778 | At_42deg_Heat | 20000458 | Plant Line | WS |
| 13613778 | At_10percent_PEG | 20000460 | Age (day) | 12 |
| 13613778 | At_10percent_PEG | 20000460 | Timepoint (day) | 12 |
| 13613778 | At_10percent_PEG | 20000460 | Treatment | 10 percent PEG vs. No Treatment |
| 13613778 | At_10percent_PEG | 20000460 | Organism | *A. thaliana* |
| 13613778 | At_10percent_PEG | 20000460 | Tissue | Whole Plant |
| 13613778 | At_10percent_PEG | 20000460 | Plant Line | WS |
| 13613778 | At_Guard_Cells | 20000495 | Harvest Date | Aug. 02, 2002 |
| 13613778 | At_Guard_Cells | 20000495 | Organism | *A. thaliana* |
| 13613778 | At_Guard_Cells | 20000495 | Tissue | Guard Cells vs. Leaves |
| 13613778 | At_10percent_PEG | 20000527 | Age (day) | 20 |
| 13613778 | At_10percent_PEG | 20000527 | Timepoint (day) | 20 |
| 13613778 | At_10percent_PEG | 20000527 | Treatment | 10 percent PEG vs. No Treatment |
| 13613778 | At_10percent_PEG | 20000527 | Organism | *A. thaliana* |
| 13613778 | At_10percent_PEG | 20000527 | Tissue | Whole Plant |
| 13613778 | At_10percent_PEG | 20000527 | Plant Line | WS |
| 13613778 | At_100uM_ABA_Mutants | 20000573 | Organism | *A. thaliana* |
| 13613778 | At_100uM_ABA_Mutants | 20000573 | Plant Line | CS22 vs. Ler wt |
| 13613778 | At_100uM_ABA_Mutants | 20000573 | Timepoint (hr) | N/A |
| 13613778 | At_100uM_ABA_Mutants | 20000573 | Treatment | None |
| 13613778 | At_100uM_ABA_Mutants | 20000573 | Tissue | Whole Plant |
| 13613778 | At_100uM_ABA_Mutants | 20000574 | Organism | *A. thaliana* |
| 13613778 | At_100uM_ABA_Mutants | 20000574 | Plant Line | CS23 vs. Ler wt |
| 13613778 | At_100uM_ABA_Mutants | 20000574 | Timepoint (hr) | N/A |
| 13613778 | At_100uM_ABA_Mutants | 20000574 | Treatment | None |
| 13613778 | At_100uM_ABA_Mutants | 20000574 | Tissue | Whole Plant |
| 13613778 | At_Herbicide_Mutants | 20000640 | Timepoint (hr) | 12 |
| 13613778 | At_Herbicide_Mutants | 20000640 | Plant Line | 05377RR/BR27173 |
| 13613778 | At_Herbicide_Mutants | 20000640 | Treatment | Roundup vs. No Treatment |
| 13613778 | At_Herbicide_Mutants | 20000640 | Tissue | Seedlings |
| 13613778 | At_15mM_NH4NO3_L-to-H | 20000709 | Timepoint (hr) | 4 |
| 13613778 | At_15mM_NH4NO3_L-to-H | 20000709 | Age (hr) | 14 |
| 13613778 | At_15mM_NH4NO3_L-to-H | 20000709 | Treatment | 15 mM NH4NO3 vs. 30 mM Mannitol |
| 13613778 | At_15mM_NH4NO3_L-to-H | 20000709 | Organism | *A. thaliana* |
| 13613778 | At_15mM_NH4NO3_L-to-H | 20000709 | Tissue | Aerial |
| 13613778 | At_15mM_NH4NO3_L-to-H | 20000709 | Plant Line | WS |
| 13613778 | At_Petals | 20000794 | Age (day) | 23-25 days |
| 13613778 | At_Petals | 20000794 | Organism | *A. thaliana* |
| 13613778 | At_Petals | 20000794 | Tissue | Petals vs. Whole plant |
| 13613778 | At_Petals | 20000794 | Plant Line | WS |
| 13613778 | At_Line_Comparisons | 20001151 | Plant Line | ME01339-01 vs. WS |
| 13613778 | At_Line_Comparisons | 20001184 | Plant Line | ME01848-01 vs. WS |
| 13613778 | At_Line_Comparisons | 20001192 | Plant Line | WBin4-WX13R-A vs. WS |
| 13613778 | At_Line_Comparisons | 20001195 | Plant Line | WBin4-WX14-B vs. WS |
| 13613778 | At_Far-red-induction | 20001247 | Timepoint (hr) | 1 |
| 13613778 | At_Far-red-induction | 20001247 | Age (day) | 7 |
| 13613778 | At_Far-red-induction | 20001247 | Organism | *A. thaliana* |
| 13613778 | At_Far-red-induction | 20001247 | Plant Line | Columbia |
| 13613778 | At_Far-red-induction | 20001247 | Light | Far-red vs. White |

TABLE 1-continued

Promoter Sequences and Related Information

| | | | | |
|---|---|---|---|---|
| 13613778 | At_Far-red-induction | 20001247 | Tissue | Whole Plant |
| 13613778 | At_Far-red-induction | 20001248 | Timepoint (hr) | 4 |
| 13613778 | At_Far-red-induction | 20001248 | Age (day) | 7 |
| 13613778 | At_Far-red-induction | 20001248 | Organism | A. thaliana |
| 13613778 | At_Far-red-induction | 20001248 | Plant Line | Columbia |
| 13613778 | At_Far-red-induction | 20001248 | Light | Far-red vs. White |
| 13613778 | At_Far-red-induction | 20001248 | Tissue | Whole Plant |
| 13613778 | At_Line_Comparisons | 20001300 | Plant Line | ME01338-05 vs. WS |
| 13613778 | At_Line_Comparisons | 20001307 | Plant Line | WBin4-WX2-A vs. WS |
| 13613778 | At_Line_Comparisons | 20001308 | Plant Line | WBin4-WX49-C vs. WS |
| 13613778 | At_Line_Comparisons | 20001309 | Plant Line | WBin4-WX49R-A vs. WS |
| 13613778 | At_Line_Comparisons | 20001310 | Plant Line | WBin4-WX17-A vs. WS |
| 13613778 | At_Line_Comparisons | 20001318 | Plant Line | WBin4-WX14R-A vs. WS |
| 13613778 | At_Line_Comparisons | 20001319 | Plant Line | WBin4-WX24-A vs. WS |
| 13613778 | At_Line_Comparisons | 20001347 | Plant Line | ME01604-01 vs. WS |
| 13613778 | At_Line_Comparisons | 20001448 | Plant Line | ME01323-01 vs. WS |
| 13613778 | At_50mM_NH4NO3_L-to-H | 20001458 | Timepoint (hr) | 2 |
| 13613778 | At_50mM_NH4NO3_L-to-H | 20001458 | Treatment | 50 mM NH4NO3 vs. 100 mM Manitol |
| 13613778 | At_50mM_NH4NO3_L-to-H | 20001458 | Organism | A. thaliana |
| 13613778 | At_50mM_NH4NO3_L-to-H | 20001458 | Tissue | Siliques |
| 13613778 | At_50mM_NH4NO3_L-to-H | 20001458 | Age (day) | Undefined |
| 13613778 | At_50mM_NH4NO3_L-to-H | 20001458 | Plant Line | WS |
| 13613778 | At_Drought_Soil_Dry | 20001554 | Timepoint (day) | 7 |
| 13613778 | At_Drought_Soil_Dry | 20001554 | Age (day) | 21 |
| 13613778 | At_Drought_Soil_Dry | 20001554 | Organism | A. thaliana |
| 13613778 | At_Drought_Soil_Dry | 20001554 | Treatment | Drought vs. No Drought |
| 13613778 | At_Drought_Soil_Dry | 20001554 | Post Timepoint (hr) | None |
| 13613778 | At_Drought_Soil_Dry | 20001554 | Post-Treatment | None |
| 13613778 | At_Drought_Soil_Dry | 20001554 | Plant Line | WS |
| 13613778 | At_Drought_Soil_Dry | 20001555 | Timepoint (day) | 10 |
| 13613778 | At_Drought_Soil_Dry | 20001555 | Age (day) | 24 |
| 13613778 | At_Drought_Soil_Dry | 20001555 | Organism | A. thaliana |
| 13613778 | At_Drought_Soil_Dry | 20001555 | Treatment | Drought vs. No Drought |
| 13613778 | At_Drought_Soil_Dry | 20001555 | Post Timepoint (hr) | None |
| 13613778 | At_Drought_Soil_Dry | 20001555 | Post-Treatment | None |
| 13613778 | At_Drought_Soil_Dry | 20001555 | Plant Line | WS |
| 13613778 | At_Drought_Soil_Dry | 20001556 | Timepoint (day) | 12 |
| 13613778 | At_Drought_Soil_Dry | 20001556 | Age (day) | 26 |
| 13613778 | At_Drought_Soil_Dry | 20001556 | Organism | A. thaliana |
| 13613778 | At_Drought_Soil_Dry | 20001556 | Treatment | Drought vs. No Drought |
| 13613778 | At_Drought_Soil_Dry | 20001556 | Post Timepoint (hr) | None |
| 13613778 | At_Drought_Soil_Dry | 20001556 | Post-Treatment | None |
| 13613778 | At_Drought_Soil_Dry | 20001556 | Plant Line | WS |
| 13613778 | At_Drought_Soil_Dry | 20001557 | Post Timepoint (hr) | 3 |
| 13613778 | At_Drought_Soil_Dry | 20001557 | Timepoint (day) | 13 |
| 13613778 | At_Drought_Soil_Dry | 20001557 | Age (day) | 27 |
| 13613778 | At_Drought_Soil_Dry | 20001557 | Organism | A. thaliana |
| 13613778 | At_Drought_Soil_Dry | 20001557 | Treatment | Drought vs. No Drought |
| 13613778 | At_Drought_Soil_Dry | 20001557 | Post-Treatment | Re-Water vs. No Drought |
| 13613778 | At_Drought_Soil_Dry | 20001557 | Plant Line | WS |
| 13613778 | At_Interploidy_Crosses | 20001703 | Age (day) | 5 |
| 13613778 | At_Interploidy_Crosses | 20001703 | Cross | 2X × 4X vs. 2X × 2X |
| 13613778 | At_Interploidy_Crosses | 20001703 | Organism | A. thaliana |
| 13613778 | At_Interploidy_Crosses | 20001703 | Plant Line | Columbia |
| 13613778 | At_Interploidy_Crosses | 20001703 | Tissue | Siliques |
| 13613778 | At_50mM_NH4NO3_L-to-H | 20001757 | Timepoint (hr) | 6 |
| 13613778 | At_50mM_NH4NO3_L-to-H | 20001757 | Treatment | 50 mM NH4NO3 vs 100 mM Mannitol |
| 13613778 | At_50mM_NH4NO3_L-to-H | 20001757 | Tissue | Leaf |
| 13613778 | At_Far-red-enriched-adult | 20001773 | Age (day) | 30 |
| 13613778 | At_Far-red-enriched-adult | 20001773 | Timepoint (hr) | 48 |
| 13613778 | At_Far-red-enriched-adult | 20001773 | Organism | A. thaliana |
| 13613778 | At_Far-red-enriched-adult | 20001773 | Tissue | Aerial |
| 13613778 | At_Far-red-enriched-adult | 20001773 | Plant Line | Columbia |
| 13613778 | At_Far-red-enriched-adult | 20001773 | Light | Far-red enriched vs. White |
| 13613778 | At_Far-red-enriched-adult | 20001774 | Age (day) | 31 |
| 13613778 | At_Far-red-enriched-adult | 20001774 | Timepoint (hr) | 72 |
| 13613778 | At_Far-red-enriched-adult | 20001774 | Organism | A. thaliana |
| 13613778 | At_Far-red-enriched-adult | 20001774 | Tissue | Aerial |
| 13613778 | At_Far-red-enriched-adult | 20001774 | Plant Line | Columbia |
| 13613778 | At_Far-red-enriched-adult | 20001774 | Light | Far-red enriched vs. White |
| 13613778 | At_Drought_Reproduction | 20001904 | Timepoint (day) | 7 |
| 13613778 | At_Drought_Reproduction | 20001904 | Age (day) | 37 |
| 13613778 | At_Drought_Reproduction | 20001904 | Organism | A. thaliana |
| 13613778 | At_Drought_Reproduction | 20001904 | Treatment | Drought vs. No Drought |

TABLE 1-continued

Promoter Sequences and Related Information

| 13613778 | At_Drought_Reproduction | 20001904 | Tissue | Rosettes |
|---|---|---|---|---|
| 13613778 | At_Drought_Reproduction | 20001904 | Plant Line | WS |
| 13613778 | At_Drought_Reproduction | 20001907 | Timepoint (day) | 7 |
| 13613778 | At_Drought_Reproduction | 20001907 | Age (day) | 37 |
| 13613778 | At_Drought_Reproduction | 20001907 | Organism | *A. thaliana* |
| 13613778 | At_Drought_Reproduction | 20001907 | Treatment | Drought vs. No Drought |
| 13613778 | At_Drought_Reproduction | 20001907 | Tissue | Siliques |
| 13613778 | At_Drought_Reproduction | 20001907 | Plant Line | WS |
| 13613778 | At_Line_Comparisons | 20002012 | Plant Line | SALK_073455 vs. Columbia |
| 13613778 | At_8deg_Cold | 20002108 | Age (day) | 14 |
| 13613778 | At_8deg_Cold | 20002108 | Timepoint (hr) | 168 |
| 13613778 | At_8deg_Cold | 20002108 | Temperature (deg C.) | 8 vs. 22 |
| 13613778 | At_8deg_Cold | 20002108 | Organism | *A. thaliana* |
| 13613778 | At_8deg_Cold | 20002108 | Tissue | Whole Plant |
| 13613778 | At_8deg_Cold | 20002108 | Plant Line | WS |
| 13613778 | At_8deg_Cold | 20002109 | Age (day) | 16 |
| 13613778 | At_8deg_Cold | 20002109 | Timepoint (hr) | 216 |
| 13613778 | At_8deg_Cold | 20002109 | Temperature (deg C.) | 8 vs. 22 |
| 13613778 | At_8deg_Cold | 20002109 | Organism | *A. thaliana* |
| 13613778 | At_8deg_Cold | 20002109 | Tissue | Whole Plant |
| 13613778 | At_8deg_Cold | 20002109 | Plant Line | WS |

Promoter YP00374

Modulates the gene: Putative cytochrome P450
The GenBank description of the gene: NM_112814 *Arabidopsis thaliana* cytochrome P450, putative (At3g19270) mRNA, complete cds gi|18402178|ref|NM_112814.1|[18402178]
The promoter sequence:

5'agaagaaactagaaacgttaaacgcatcaaatcaagaaattaaattgaaggtaattttaacgccgcct ttcaaatattcttcctaggagaggctacaagacgcgtatttctttcgaattctccaaaccattaccatttt gatatataataccgacatgccgttgataaagtttgtatgcaaatcgttcattgggtatgagcaaatgccat ccattggttcttgtaattaaatggtccaaaaatagtttgttcccactactagttactaatttgtatcactc tgcaaaataatcatgatataaacgtatgtgctatttctaattaaaactcaaaagtaatcaatgtacaatgc agagatgaccataaaagaacattaaaacactacttccactaaatctatggggtgccttggcaaggcaattg aataaggagaatgcatcaagatgatatagaaaatgctattcagtttataacattaatgttttggcggaaaa ttttctatatattagacctttctgtaaaaaaaaaaaatgatgtagaaaatgctattatgtttcaaaaatt tcgcactagtataatacggaacattgtagtttacactgctcattaccatgaaaaccaaggcagtatatacc aacattaataaactaaatcgcgatttctagcaccccccattaattaattttactattatacattctctttgc ttctcgaaataataaacttctctatatcattctacataataaataagaaagaaatcgacaagatctaaatt tagatctattcagcttttttcgcctgagaagccaaaattgtgaatagaagaaagcagtcgtcatcttcccac gtttggacgaaataaaacataacaataataaaataataaatcaaatatataaatccctaatttgtctttat tactccacaattttctatgtgtatataTA 3'- tgtatgttttgttccctattatatcttctagcttctttcttcctcttcttccttaaaaattcatcctcca aaaca ttctatcatcaacgaaacatttcatattaaattaaataataatcgATG

The promoter was cloned from the organism: *Arabidopsis thaliana*

Alternative nucleotides:
Query = Predicted
Subject = Experimental

| Predicted Position (bp) | Mismatch | Predicted/Experimental |
|---|---|---|
| 1-1000 | None | Identities = 1000/1000 (100%) |

The promoter was cloned in the vector: pNewbin4-HAP1-GFP
When cloned into the vector the promoter was operably linked to a marker, which was the type: GFP-ER
Promoter-marker vector was tested in:
Generation screened:   XT1 Mature   XT2 Seedling   T2 Mature   T3 Seedling

TABLE 1-continued

Promoter Sequences and Related Information

The spatial expression of the promoter-marker vector was found observed in and would be useful in expression in any or all of the following:

| | |
|---|---|
| Flower | M vascular |
| Silique | M placenta, M vascular |
| Hypocotyl | H vascular |
| Cotyledon | H vascular, H petiole |
| Primary Root | H vascular |

Observed expression pattern of the promoter-marker vector was in:
T1 mature: GFP expressed in outer integument of developing ovule primordium. Higher integument expression at chalazal pole observed through maturity.
T2 seedling: Medium to low expression in root vascular bundles weakening toward hypocotyl. Weak expression in epidermal cells at root transition zone..
Misc. promoter information:   Bidirectionality: Pass  Exons: Pass    Repeats: No
The Ceres cDNA ID of the endogenous coding sequence to the promoter:: 12370888
cDNA nucleotide sequence:
GTATGTTTTGTTCCCTATTATATCTTCTAGCTTCTTTCTTCCTCTTCTTCCTTAAAAATTCATCC

TCCAAAACATTCTATCATCAACGAAACATTTCATATTAAATTAAATAATAATCGATGGCTGAA

ATTTGGTTCTTGGTTGTACCAATCCTCATCTTATGCTTGCTTTTGGTAAGAGTGATTGTTTCAA

AGAAGAAAAGAACAGTAGAGGTAAGCTTCCTCCTGGTTCCATGGGATGGCCTTACTTAGGAG

AGACTCTACAACTCTATTCACAAAACCCCAATGTTTTCTTCACCTCCAAGCAAAAGAGATATG

GAGAGATATTCAAAACCCGAATCCTCGGCTATCCATGCGTGATGTTGGCTAGCCCTGAGGCTG

CGAGGTTTGTACTTGTGACTCATGCCCATATGTTCAAACCAACTTATCCGAGAAGCAAAGAGA

AGCTGATAGGACCCTCTGCACTCTTTTTCCACCAAGGAGATTATCATTCCCATATAAGGAAACT

TGTTCAATCCTCTTTCTACCCTGAAACCATCCGTAAACTCATCCCTGATATCGAGCACATTGCC

CTTTCTTCCTTACAATCTTGGGCCAATATGCCGATTGTCTCCACCTACCAGGAGATGAAGAAGT

TCGCCTTTGATGTGGGTATTCTAGCCATATTTGGACATTTGGAGAGTTCTTACAAAGAGATCTT

GAAACATAACTACAATATTGTGGACAAAGGCTACAACTCTTTCCCCATGAGTCTCCCCGGAAC

ATCTTATCACAAAGCTCTCATGGCGAGAAAGCAGCTAAAGACGATAGTAAGCGAGATTATATG

CGAAAGAAGAGAGAAAAGGGCCTTGCAAACGGACTTTCTTGGTCATCTACTCAACTTCAAGAA

CGAAAAAGGTCGTGTGCTAACCCAAGAACAGATTGCAGACAACATCATCGGAGTCCTTTTCGC

CGCACAGGACACGACAGCTAGTTGCTTAACTTGGATTCTTAAGTACTTACATGATGATCAGAA

ACTTCTAGAAGCTGTTAAGGCTGAGCAAAAGGCTATATATGAAGAAAACAGTAGAGAGAAGA

AACCTTTAACATGGAGACAAACGAGGAATATGCCACTGACACATAAGGTTATAGTTGAAAGCT

TGAGGATGGCAAGCATCATATCCTTCACATTCAGAGAAGCAGTGGTTGATGTTGAATATAAGG

GATATTTGATACCTAAGGGATGGAAAGTGATGCCACTGTTTCGGAATATTCATCACAATCCGA

AATATTTTTCAAACCCTGAGGTTTTCGACCCATCTAGATTCGAGGTAAATCCGAAGCCGAATA

CATTCATGCCTTTTGGAAGTGGAGTTCATGCTTGTCCCGGGAACGAACTCGCCAAGTTACAAA

TTCTTATATTTCTCCACCATTTAGTTTCCAATTTCCGATGGGAAGTGAAGGGAGGAGAGAAAG

GAATACAGTACAGTCCATTTCCAATACCTCAAAACGGTCTTCCCGCTACATTTCGTCGACATTC

TCTTTAGTTCCTTAAACCTTTGTAGTAATCTTTGTTGTAGTTAGCCAAATCTAATCCAAATTCG

ATATAAAAAATCCCCTTTCTATTTTTTTTAAAATCATTGTTGTAGTCTTGAGGGGGTTTAACA

TGTAACAACTATGATGAAGTAAAATGTCGATTCCGGT

Coding sequence:
MAEIWFLVVPILILCLLLVRVIVSKKKKNSRGKLPPGSMGWPYLGETLQLYSQNPNVFFTSKQKRY

GEIFKTRILGYPCVMLASPEARFVLVTHAHMFKPTYPRSKEKLIGPSALFFHQGDYHSHIRKLVQS

SFYPETIRKLIPDIEHIALSSLQSWANMPIVSTYQEMKKFAFDVGILAIFGHLESSYKEILKHNYNIVD

KGYNSFPMSLPGTSYHKALMARKQLKTIVSEIICERREKRALQTDFLGHLLNEKNEKGRVLTQEQI

TABLE 1-continued

Promoter Sequences and Related Information

ADNIIGVLFAAQDTTASCLTWILKYLHDDQKLLEAVKAEQKAIYEENSREKKPLTWRQTRNMPLT

HKVIVESLRMASIISFTFREAVVDVEYKGYLIPKGWKVMPLFRNIHHNPKYFSNPEVFDPSRFEVNP

KPNTFMPFGSGVHACPGNELAKLQILIFLHHLVSNFRWEVKGGEKGIQYSPFPIPQNGLPATFRRHS

L*

Microarray data shows that the coding sequence was expressed in the following experiments, which shows that the promoter would be useful to modulate expression in situations similar to the following:

| CDNA_ID | SHORT_NAME | EXPT_REP_ID | IS_UP |
|---|---|---|---|
| 12370888 | At_100uM_ABA | 20000166 | + |
| 12370888 | At_100uM_ABA | 20000169 | + |
| 12370888 | At_42deg_Heat | 20000171 | + |
| 12370888 | At_42deg_Heat | 20000173 | + |
| 12370888 | At_2mM_SA | 20000182 | + |
| 12370888 | At_Open_Flower | 20000264 | + |
| 12370888 | At_Shoots | 20000438 | + |
| 12370888 | At_100uM_ABA | 20000453 | + |
| 12370888 | At_42deg_Heat | 20000457 | − |
| 12370888 | At_42deg_Heat | 20000458 | + |
| 12370888 | At_Guard_Cells | 20000495 | + |
| 12370888 | At_10percent_PEG | 20000527 | + |
| 12370888 | At_Petals | 20000794 | + |
| 12370888 | At_Far-red-induction | 20001248 | − |
| 12370888 | At_Far-red-enriched | 20001504 | + |
| 12370888 | At_Far-red-enriched-adult | 20001771 | + |
| 12370888 | At_Drought_Reproduction | 20001906 | + |
| 12370888 | At_Drought_Reproduction | 20001907 | + |
| 12370888 | At_8deg_Cold | 20002107 | − |
| 12370888 | At_8deg_Cold | 20002108 | − |
| 12370888 | At_8deg_Cold | 20002109 | − |

The parameters for the microarray experiments listed above by Expt_Rep_ID and Short_Name are as follow below:

| CDNA_ID | SHORT_NAME | EXPT_REP_ID | PARAM_NAME | VALUE |
|---|---|---|---|---|
| 12370888 | At_100uM_ABA | 20000166 | Timepoint (hr) | 1 |
| 12370888 | At_100uM_ABA | 20000166 | Age (day) | 14 |
| 12370888 | At_100uM_ABA | 20000166 | Treatment | 100 uM ABA vs. No Treatment |
| 12370888 | At_100uM_ABA | 20000166 | Organism | A. thaliana |
| 12370888 | At_100uM_ABA | 20000166 | Tissue | Aerial |
| 12370888 | At_100uM_ABA | 20000166 | Plant Line | WS |
| 12370888 | At_100uM_ABA | 20000169 | Timepoint (hr) | 6 |
| 12370888 | At_100uM_ABA | 20000169 | Age (day) | 14 |
| 12370888 | At_100uM_ABA | 20000169 | Treatment | 100 uM ABA vs. No Treatment |
| 12370888 | At_100uM_ABA | 20000169 | Organism | A. thaliana |
| 12370888 | At_100uM_ABA | 20000169 | Tissue | Aerial |
| 12370888 | At_100uM_ABA | 20000169 | Plant Line | WS |
| 12370888 | At_42deg_Heat | 20000171 | Timepoint (hr) | 1 |
| 12370888 | At_42deg_Heat | 20000171 | Age (day) | 14 |
| 12370888 | At_42deg_Heat | 20000171 | Temperature (deg C.) | 42 vs. 22 |
| 12370888 | At_42deg_Heat | 20000171 | Organism | A. thaliana |
| 12370888 | At_42deg_Heat | 20000171 | Tissue | Aerial |
| 12370888 | At_42deg_Heat | 20000171 | Plant Line | WS |
| 12370888 | At_42deg_Heat | 20000173 | Timepoint (hr) | 6 |
| 12370888 | At_42deg_Heat | 20000173 | Age (day) | 14 |
| 12370888 | At_42deg_Heat | 20000173 | Temperature (deg C.) | 42 vs. 22 |
| 12370888 | At_42deg_Heat | 20000173 | Organism | A. thaliana |
| 12370888 | At_42deg_Heat | 20000173 | Tissue | Aerial |
| 12370888 | At_42deg_Heat | 20000173 | Plant Line | WS |
| 12370888 | At_2mM_SA | 20000182 | Timepoint (hr) | 6 |
| 12370888 | At_2mM_SA | 20000182 | Age (day) | 14 |
| 12370888 | At_2mM_SA | 20000182 | Treatment | 2 mM SA vs. No Treatment |
| 12370888 | At_2mM_SA | 20000182 | Organism | A. thaliana |
| 12370888 | At_2mM_SA | 20000182 | Tissue | Aerial |
| 12370888 | At_2mM_SA | 20000182 | Plant Line | WS |
| 12370888 | At_Open_Flower | 20000264 | Age (day) | 21 |
| 12370888 | At_Open_Flower | 20000264 | Organism | A. thaliana |
| 12370888 | At_Open_Flower | 20000264 | Tissue | Open Flower vs. Whole Plant |
| 12370888 | At_Open_Flower | 20000264 | Plant Line | WS |
| 12370888 | At_Shoots | 20000438 | Age (day) | 14 vs. 21 |
| 12370888 | At_Shoots | 20000438 | Organism | A. thaliana |

TABLE 1-continued

Promoter Sequences and Related Information

| | | | | |
|---|---|---|---|---|
| 12370888 | At_Shoots | 20000438 | Tissue | Shoots vs. Whole Plant |
| 12370888 | At_Shoots | 20000438 | Plant Line | WS |
| 12370888 | At_100uM_ABA | 20000453 | Age (day) | 15 |
| 12370888 | At_100uM_ABA | 20000453 | Timepoint (hr) | 24 |
| 12370888 | At_100uM_ABA | 20000453 | Treatment | 100 uM ABA vs. No Treatment |
| 12370888 | At_100uM_ABA | 20000453 | Organism | *A. thaliana* |
| 12370888 | At_100uM_ABA | 20000453 | Tissue | Aerial |
| 12370888 | At_100uM_ABA | 20000453 | Plant Line | WS |
| 12370888 | At_42deg_Heat | 20000457 | Timepoint (hr) | 0.166 |
| 12370888 | At_42deg_Heat | 20000457 | Age (day) | 14 |
| 12370888 | At_42deg_Heat | 20000457 | Temperature (deg C.) | 42 vs. 22 |
| 12370888 | At_42deg_Heat | 20000457 | Organism | *A. thaliana* |
| 12370888 | At_42deg_Heat | 20000457 | Tissue | Aerial |
| 12370888 | At_42deg_Heat | 20000457 | Plant Line | WS |
| 12370888 | At_42deg_Heat | 20000458 | Timepoint (hr) | 8 |
| 12370888 | At_42deg_Heat | 20000458 | Age (day) | 14 |
| 12370888 | At_42deg_Heat | 20000458 | Temperature (deg C.) | 42 vs. 22 |
| 12370888 | At_42deg_Heat | 20000458 | Organism | *A. thaliana* |
| 12370888 | At_42deg_Heat | 20000458 | Tissue | Aerial |
| 12370888 | At_42deg_Heat | 20000458 | Plant Line | WS |
| 12370888 | At_Guard_Cells | 20000495 | Harvest Date | Aug. 02, 2002 |
| 12370888 | At_Guard_Cells | 20000495 | Organism | *A. thaliana* |
| 12370888 | At_Guard_Cells | 20000495 | Tissue | Guard Cells vs. Leaves |
| 12370888 | At_10percent_PEG | 20000527 | Age (day) | 20 |
| 12370888 | At_10percent_PEG | 20000527 | Timepoint (day) | 20 |
| 12370888 | At_10percent_PEG | 20000527 | Treatment | 10 percent PEG vs. No Treatment |
| 12370888 | At_10percent_PEG | 20000527 | Organism | *A. thaliana* |
| 12370888 | At_10percent_PEG | 20000527 | Tissue | Whole Plant |
| 12370888 | At_10percent_PEG | 20000527 | Plant Line | WS |
| 12370888 | At_Petals | 20000794 | Age (day) | 23-25 days |
| 12370888 | At_Petals | 20000794 | Organism | *A. thaliana* |
| 12370888 | At_Petals | 20000794 | Tissue | Petals vs. Whole plant |
| 12370888 | At_Petals | 20000794 | Plant Line | WS |
| 12370888 | At_Far-red-induction | 20001248 | Timepoint (hr) | 4 |
| 12370888 | At_Far-red-induction | 20001248 | Age (day) | 7 |
| 12370888 | At_Far-red-induction | 20001248 | Organism | *A. thaliana* |
| 12370888 | At_Far-red-induction | 20001248 | Plant Line | Columbia |
| 12370888 | At_Far-red-induction | 20001248 | Light | Far-red vs. White |
| 12370888 | At_Far-red-induction | 20001248 | Tissue | Whole Plant |
| 12370888 | At_Far-red-enriched | 20001504 | Timepoint (day) | 6 |
| 12370888 | At_Far-red-enriched | 20001504 | Age (day) | 10 |
| 12370888 | At_Far-red-enriched | 20001504 | Organism | *A. thaliana* |
| 12370888 | At_Far-red-enriched | 20001504 | Plant Line | Columbia |
| 12370888 | At_Far-red-enriched | 20001504 | Light | Far-red enriched vs. White |
| 12370888 | At_Far-red-enriched | 20001504 | Tissue | Whole Plant |
| 12370888 | At_Far-red-enriched-adult | 20001771 | Timepoint (hr) | 16 |
| 12370888 | At_Far-red-enriched-adult | 20001771 | Age (day) | 28 |
| 12370888 | At_Far-red-enriched-adult | 20001771 | Organism | *A. thaliana* |
| 12370888 | At_Far-red-enriched-adult | 20001771 | Tissue | Aerial |
| 12370888 | At_Far-red-enriched-adult | 20001771 | Plant Line | Columbia |
| 12370888 | At_Far-red-enriched-adult | 20001771 | Light | Far-red enriched vs. White |
| 12370888 | At_Drought_Reproduction | 20001906 | Timepoint (day) | 5 |
| 12370888 | At_Drought_Reproduction | 20001906 | Age (day) | 35 |
| 12370888 | At_Drought_Reproduction | 20001906 | Organism | *A. thaliana* |
| 12370888 | At_Drought_Reproduction | 20001906 | Treatment | Drought vs. No Drought |
| 12370888 | At_Drought_Reproduction | 20001906 | Tissue | Siliques |
| 12370888 | At_Drought_Reproduction | 20001906 | Plant Line | WS |
| 12370888 | At_Drought_Reproduction | 20001907 | Timepoint (day) | 7 |
| 12370888 | At_Drought_Reproduction | 20001907 | Age (day) | 37 |
| 12370888 | At_Drought_Reproduction | 20001907 | Organism | *A. thaliana* |
| 12370888 | At_Drought_Reproduction | 20001907 | Treatment | Drought vs. No Drought |
| 12370888 | At_Drought_Reproduction | 20001907 | Tissue | Siliques |
| 12370888 | At_Drought_Reproduction | 20001907 | Plant Line | WS |
| 12370888 | At_Drought_Reproduction | 20001910 | Timepoint (day) | 7 |
| 12370888 | At_Drought_Reproduction | 20001910 | Age (day) | 37 |
| 12370888 | At_Drought_Reproduction | 20001910 | Organism | *A. thaliana* |
| 12370888 | At_Drought_Reproduction | 20001910 | Treatment | Drought vs. No Drought |
| 12370888 | At_Drought_Reproduction | 20001910 | Tissue | Flowers |
| 12370888 | At_Drought_Reproduction | 20001910 | Plant Line | WS |
| 12370888 | At_8deg_Cold | 20002107 | Age (day) | 11 |
| 12370888 | At_8deg_Cold | 20002107 | Timepoint (hr) | 96 |
| 12370888 | At_8deg_Cold | 20002107 | Temperature (deg C.) | 8 vs. 22 |
| 12370888 | At_8deg_Cold | 20002107 | Organism | *A. thaliana* |
| 12370888 | At_8deg_Cold | 20002107 | Tissue | Whole Plant |
| 12370888 | At_8deg_Cold | 20002107 | Plant Line | WS |
| 12370888 | At_8deg_Cold | 20002108 | Age (day) | 14 |
| 12370888 | At_8deg_Cold | 20002108 | Timepoint (hr) | 168 |

TABLE 1-continued

Promoter Sequences and Related Information

| 12370888 | At_8deg_Cold | 20002108 | Temperature (deg C.) | 8 vs. 22 |
|---|---|---|---|---|
| 12370888 | At_8deg_Cold | 20002108 | Organism | A. thaliana |
| 12370888 | At_8deg_Cold | 20002108 | Tissue | Whole Plant |
| 12370888 | At_8deg_Cold | 20002108 | Plant Line | WS |
| 12370888 | At_8deg_Cold | 20002109 | Age (day) | 16 |
| 12370888 | At_8deg_Cold | 20002109 | Timepoint (hr) | 216 |
| 12370888 | At_8deg_Cold | 20002109 | Temperature (deg C.) | 8 vs. 22 |
| 12370888 | At_8deg_Cold | 20002109 | Organism | A. thaliana |
| 12370888 | At_8deg_Cold | 20002109 | Tissue | Whole Plant |
| 12370888 | At_8deg_Cold | 20002109 | Plant Line | WS |

Promoter YP0371

Modulates the gene: Unknown protein. Contains putative conserved domains: [ATPase family associated with various cellular activities (AAA). AAA family proteins often perform chaperone-like functions that assist in the assembly, operation, or disassembly of protein complexes]
The GenBank description of the gene: NM_179511 *Arabidopsis thaliana* AAA-type ATPase family protein (At1g64110) mRNA, complete cds gi|30696967|ref|NM_179511.1|[30696967].
The promoter sequence:
5'gattctgcgaagacaggagaagccatacctttcaatctaagccgtcaacttgttcccttacgtgggatc ctattatacaatccaacggttctaaatgagccacgccttccagatctaacacagtcatgctttctacagtc tgcaccccttttttttttagtgttttatctacatttttctttgtgtttaattttgtgccaacatctata acttacccctataaaatattcaattatcacagaatacccacaatcgaaaacaaaatttaccggaataatt taattaaagctggactataatgacaattccgaaactatcaaggaataaattaaagaaactaaaaaactaaa gggcattagagtaaagaagcggcaacatcagaattaaaaaactgccgaaaaaccaacctagtagccgttta tatgacaacacgtacgcaaagtctcggtaatgactcatcagttttcatgtgcaaacatattaccccatga aataaaaaagcagagaagcgatcaaaaaaatcttcattaaaagaaccctaaatctctcatatccgccgccg tctttgcctcattttcaacaccggtgatgacgtgtaaatagatctggttttcacggttctcactactctct gtgattttcagactattgaatcgttaggaccaaaacaagtacaaagaaactgcagaagaaaagatttgag agagatatcttacgaaacaaggtatatatttctcttgttaaatctttgaaaatactttcaaagtttcggtt ggattctcgaataagttaggttaaatagtcaatatagaattatagataaatcgatacctttgtttgttat cattcaatttttattgttgttacgattagtaacaacgttttagatcttgatctaTATAttaataatactaa tactttgtttttttttgtttttttttttaa 3'-aATG
The promoter was cloned from the organism: *Arabidopsis thaliana*, Columbia ecotype

Alternative nucleotides:

| Predicted Position (bp) | Mismatch | Predicted/Experimental |
|---|---|---|
| 155 | PCR error or ecotype variant SNP | t/c |

The promoter was cloned in the vector: pNewbin4-HAP1-GFP
When cloned into the vector the promoter was operably linked to a marker, which was the type: GFP-ER
Promoter-marker vector was tested in: *Arabidopsis thaliana*, WS ecotype
Generation screened:   XT1 Mature XT2 Seedling   T2 Mature   T3 Seedling The spatial expression of the promoter-marker vector was found observed in and would be useful in expression in any or all of the following:

Flower                                  M pedicel M stomata
Primary Root                            L epidermis
Observed expression pattern of the promoter-marker vector was in:
T1 mature: Weak guard cell expression in pedicles.
T2 seedling: Weak root epidermal expression.
Misc. promoter information:   Bidirectionality: Pass  Exons: Pass    Repeats: No
An overlap in an exon with the endogenous coding sequence to the promoter occurs at base pairs 537-754
The Ceres cDNA ID of the endogenous coding sequence to the promoter: 12657397
cDNA nucleotide sequence:
AGCGATCAAAAAAATCTTCATTAAAAGAACCCTAAATCTCTCATATCCGCCGCCGTCTTTGCCT

CATTTTCAACACCGGTGATGACGTGTAAATAGATCTGGTTTTCACGGTTCTCACTACTCTCTGT

GATTTTCAGACTATTGAATCGTTAGGACCAAAACAAGTACAAAGAAACTGCAGAAGAAAG

TABLE 1-continued

Promoter Sequences and Related Information

ATTTGAGAGAGATATCTTACGAAACAAGCAAACAGATGTTGTTGTCGGCGCTTGGCGTCGGAG

TTGGAGTAGGTGTGGGTTTAGGCTTGGCTTCTGGTCAAGCCGTCGGAAAATGGGCCGGCGGGA

ACTCGTCGTCAAATAACGCCGTCACGGCGGATAAGATGGAGAAGGAGATACTCCGTCAAGTT

GTTGACGGCAGAGAGAGTAAAATTACTTTCGATGAGTTTCCTTATTATCTCAGTGAACAAACA

CGAGTGCTTCTAACAAGTGCAGCTTATGTCCATTTGAAGCACTTCGATGCTTCAAAATATACG

AGAAACTTGTCTCCAGCTAGCCGAGCCATTCTCTTGTCCGGCCCTGCCGAGCTTTACCAACAA

ATGCTAGCCAAAGCCCTAGCTCATTTCTTCGATGCCAAGTTACTTCTTCTAGACGTCAACGATT

TTGCACTCAAGATACAGAGCAAATACGGCAGTGGAAATACAGAATCATCGTCATTCAAGAGAT

CTCCCTCAGAATCTGCTTTAGAGCAACTATCAGGACTGTTTAGTTCCTTCTCCATCCTTCCTCA

GAGAGAAGAGTCAAAAGCTGGTGGTACCTTGAGGAGGCAAAGCAGTGGTGTGGATATCAAAT

CAAGCTCAATGGAAGGCTCTAGTAATCCTCCAAAGCTTCGTCGAAACTCTTCAGCAGCAGCTA

ATATTAGCAACCTTGCATCTTCCTCAAATCAAGTTTCAGCGCCTTTGAAACGAAGTAGCAGTTG

GTCATTCGATGAAAAGCTTCTCGTCCAATCTTTATATAAGGTCTTGGCCTATGTCTCCAAGGCG

AATCCGATTGTGTTATATCTTCGAGACGTCGAGAACTTTCTGTTCCGCTCACAGAGAACTTACA

ACTTGTTCCAGAAGCTTCTCCAGAAACTCAGTGGACCGGTCCTCATTCTCGGTTCAAGAATTGT

GGACTTGTCAAGCGAAGACGCTCAAGAAATTGATGAGAAGCTCTCTGCTGTTTTCCCTTATAA

TATCGACATAAGACCTCCTGAGGATGAGACTCATCTAGTGAGCTGGAAATCGCAGCTTGAACG

CGACATGAACATGATCCAAACTCAGGACAATAGGAACCATATCATGGAAGTTTTGTCGGAGAA

TGATCTTATATGCGATGACCTTGAATCCATCTCTTTTGAGGACACGAAGGTTTTAAGCAATTAC

ATTGAAGAGATCGTTGTCTCTGCTCTTTCCTATCATCTGATGAACAACAAAGATCCTGAGTACA

GAAACGGAAAACTGGTGATATCTTCTATAAGTTTGTCGCATGGATTCAGTCTCTTCAGAGAAG

GCAAAGCTGGCGGTCGTGAGAAGCTGAAGCAAAAAACTAAGGAGGAATCATCCAAGGAAGTA

AAAGCTGAATCAATCAAGCCGGAGACAAAAACAGAGAGTGTCACCACCGTAAGCAGCAAGGA

AGAACCAGAGAAAGAAGCTAAAGCTGAGAAAGTTACCCCAAAAGCTCCGGAAGTTGCACCGG

ATAACGAGTTTGAGAAACGGATAAGACCGGAAGTAATCCCAGCAGAAGAAATTAACGTCACA

TTCAAAGACATTGGTGCACTTGACGAGATAAAAGAGTCACTACAAGAACTTGTAATGCTTCCT

CTCCGTAGGCCAGACCTCTTCACAGGAGGTCTCTTGAAGCCCTGCAGAGGAATCTTACTCTTC

GGTCCACCGGGTACAGGTAAAACAATGCTAGCTAAAGCCATTGCCAAAGAGGCAGGAGCGAG

TTTCATAAACGTTTCGATGTCAACAATAACTTCGAAATGGTTTGGAGAAGACGAGAAGAATGT

TAGGGCTTTGTTTACTCTAGCTTCGAAGGTGTCACCAACCATAATATTTGTGGATGAAGTTGAT

AGTATGTTGGGACAGAGAACAAGAGTTGGAGAACATGAAGCTATGAGAAAGATCAAGAATGA

GTTTATGAGTCATTGGGATGGGTTAATGACTAAACCTGGTGAACGTATCTTAGTCCTTGCTGCT

ACTAATCGGCCTTTCGATCTTGATGAAGCCATTATCAGACGATTCGAACGAAGGATCATGGTG

GGACTACCGGCTGTAGAGAACAGAGAAAAGATTCTAAGAACATTGTTGGCGAAGGAGAAAGT

AGATGAAAACTTGGATTACAAGGAACTAGCAATGATGACAGAAGGATACACAGGAAGTGATC

TTAAGAATCTGTGCACAACCGCTGCGTATAGGCCGGTGAGAGAACTTATACAGCAAGAGAGG

ATCAAAGACACAGAGAAGAAGAAGCAGAGAGAGCCTACAAAAGCAGGTGAAGAAGATGAAG

GAAAAGAAGAGAGAGTTATAACACTTCGTCCGTTGAACAGACAAGACTTTAAAGAAGCCAAG

AATCAGGTGGCGGCGAGTTTTGCGGCTGAGGGAGCGGGAATGGGAGAGTTGAAGCAGTGGAA

TABLE 1-continued

Promoter Sequences and Related Information

TGAATTGTATGGAGAAGGAGGATCGAGGAAGAAAGAACAACTCACTTACTTCTTGTAATGATG

ATGATGAATCATGATGCTGGTAATGGATTATGAAATTTGGTAATGTAATAGTATGGTGAATTT

TTGTTTCCATGGTTAATAAGAGAATAAGAATATGATGATATTGCTAAAAGTTTGACCCGT

Coding sequence:
MLLSALGVGVGVGLGLASGQAVGKWAGGNSSSNNAVTADKMEKEILRQVVDGRESKITFDEF

PYYLSEQTRVLLTSAAYVHLKHFDASKYTRNLSPASRAILLSGPAELYQQMLAKALAHFFDAKLLL

LDVNDFALKIQSKYGSGNTESSSFKRSPSESALEQLSGLFSSFSILPQREESKAGGTLRRQSSGVDIKS

SSMEGSSNPPKLRRNSSAAANISNLASSSNQVSAPLKRSSSWSFDEKLLVQSLYKVLAYVSKANPIV

LYLRDVENFLFRSQRTYNLFQKLLQKLSGPVLILGSRIVDLSSEDAQEIDEKLSAVFPYNIDIRPPEDE

THLVSWKSQLERDMNMIQTQDNRNHIMEVLSENDLICDDLESISFEDTKVLSNYIEEIVVSALSYHL

MNNKDPEYRNGKLVISSISLSHGFSLFREGKAGGREKLKQKTKEESSKEVKAESIKPETKTESVTTV

SSKEEPEKEAKAEKVTPKAPEVAPDNEFEKRIRPEVIPAEEINVTFKDIGALDEIKESLQELVMLPLR

RPDLFTGGLLKPCRGILLFGPPGTGKTMLAKAIAKEAGASFINVSMSTITSKWFGEDEKNVRALFTL

ASKVSPTIIFVDEVDSMLGQRTRVGEHEAMRKIKNEFMSHWDGLMTKPGERILVLAATNRPFDLD

EAIIRRFERRIMVGLPAVENREKILRTLLAKEKVDENLDYKELAMMTEGYTGSDLKNLCTTAAYRP

VRELIQQERIKDTEKKQREPTKAGEEDEGKEERVITLRPLNRQDFKEAKNQVAASFAAEGAGMG

ELKQWNELYGEGGSRKKEQLTYFL*

Microarray data shows that the coding sequence was expressed in the following experiments,
which shows that the promoter would be useful to modulate expression in situations similar
to the following:

| CDNA_ID | SHORT_NAME | EXPT_REP_ID | IS_UP |
| --- | --- | --- | --- |
| 12657397 | At_100uM_ABA | 20000169 | + |
| 12657397 | At_Germinating_Seeds | 20000180 | − |
| 12657397 | At_Roots | 20000185 | + |
| 12657397 | At_Siliques | 20000234 | − |
| 12657397 | At_Siliques | 20000235 | − |
| 12657397 | At_Siliques | 20000236 | − |
| 12657397 | At_Drought | 20000267 | + |
| 12657397 | At_100mM_NaCl | 20000268 | + |
| 12657397 | At_100mM_NaCl | 20000308 | + |
| 12657397 | At_Pollen | 20000326 | + |
| 12657397 | At_Drought | 20000436 | + |
| 12657397 | At_Drought | 20000437 | + |
| 12657397 | At_Roots | 20000439 | + |
| 12657397 | At_10percent_PEG | 20000460 | + |
| 12657397 | At_10percent_PEG | 20000527 | + |
| 12657397 | At_100uM_ABA_Mutants | 20000575 | + |
| 12657397 | At_100uM_ABA_Mutants | 20000576 | + |
| 12657397 | At_Herbicide_Mutants | 20000639 | + |
| 12657397 | At_Herbicide_Mutants | 20000642 | + |
| 12657397 | At_Line_Comparisons | 20001300 | − |
| 12657397 | At_Line_Comparisons | 20001307 | + |
| 12657397 | At_Line_Comparisons | 20001309 | − |
| 12657397 | At_Line_Comparisons | 20001310 | − |
| 12657397 | At_Line_Comparisons | 20001319 | + |
| 12657397 | At_Far-red-induction | 20001451 | + |
| 12657397 | At_Far-red-enriched | 20001504 | + |
| 12657397 | At_Drought_Soil_Dry | 20001554 | + |
| 12657397 | At_Drought_Soil_Dry | 20001555 | + |
| 12657397 | At_Drought_Soil_Dry | 20001556 | + |
| 12657397 | At_Drought_Soil_Dry | 20001557 | + |
| 12657397 | At_Drought_Soil_Dry | 20001559 | + |
| 12657397 | At_Drought_Soil_Dry | 20001560 | + |
| 12657397 | At_Drought_Reproduction | 20001904 | + |
| 12657397 | At_Drought_Reproduction | 20001906 | + |
| 12657397 | At_Drought_Reproduction | 20001907 | + |
| 12657397 | At_Drought_Reproduction | 20001909 | + |

TABLE 1-continued

Promoter Sequences and Related Information

| | | | |
|---|---|---|---|
| 12657397 | At_Line_Comparisons | 20002009 | + |
| 12657397 | At_Drought-Air-Dry | 20002256 | + |

The parameters for the microarray experiments listed above by Expt_Rep_ID and Short_Name are as follow below:

| CDNA_ID | SHORT_NAME | EXPT_REP_ID | PARAM_NAME | VALUE |
|---|---|---|---|---|
| 12657397 | At_100uM_ABA | 20000169 | Timepoint (hr) | 6 |
| 12657397 | At_100uM_ABA | 20000169 | Age (day) | 14 |
| 12657397 | At_100uM_ABA | 20000169 | Treatment | 100 uM ABA vs. No Treatment |
| 12657397 | At_100uM_ABA | 20000169 | Organism | A. thaliana |
| 12657397 | At_100uM_ABA | 20000169 | Tissue | Aerial |
| 12657397 | At_100uM_ABA | 20000169 | Plant Line | WS |
| 12657397 | At_Germinating_Seeds | 20000180 | Age (hr) | 24 vs. 0 |
| 12657397 | At_Germinating_Seeds | 20000180 | Organism | A. thaliana |
| 12657397 | At_Germinating_Seeds | 20000180 | Tissue | Germinating Seeds |
| 12657397 | At_Germinating_Seeds | 20000180 | Plant Line | WS |
| 12657397 | At_Roots | 20000185 | Age (day) | 7 vs. 21 |
| 12657397 | At_Roots | 20000185 | Organism | A. thaliana |
| 12657397 | At_Roots | 20000185 | Tissue | Roots vs. Whole Plant |
| 12657397 | At_Roots | 20000185 | Plant Line | WS |
| 12657397 | At_Siliques | 20000234 | Age (day) | 21 |
| 12657397 | At_Siliques | 20000234 | Tissue | <5 mm Siliques vs. Whole Plant |
| 12657397 | At_Siliques | 20000234 | Organism | A. thaliana |
| 12657397 | At_Siliques | 20000234 | Plant Line | WS |
| 12657397 | At_Siliques | 20000235 | Age (day) | 21 |
| 12657397 | At_Siliques | 20000235 | Tissue | 5-10 mm Siliques vs. Whole Plant |
| 12657397 | At_Siliques | 20000235 | Organism | A. thaliana |
| 12657397 | At_Siliques | 20000235 | Plant Line | WS |
| 12657397 | At_Siliques | 20000236 | Age (day) | 21 |
| 12657397 | At_Siliques | 20000236 | Tissue | >10 mm Siliques vs. Whole Plant |
| 12657397 | At_Siliques | 20000236 | Organism | A. thaliana |
| 12657397 | At_Siliques | 20000236 | Plant Line | WS |
| 12657397 | At_Drought | 20000267 | Timepoint (hr) | 6 |
| 12657397 | At_Drought | 20000267 | Age (day) | 7 |
| 12657397 | At_Drought | 20000267 | Organism | A. thaliana |
| 12657397 | At_Drought | 20000267 | Treatment | Drought vs. No Drought |
| 12657397 | At_Drought | 20000267 | Tissue | Whole Plant |
| 12657397 | At_Drought | 20000267 | Plant Line | WS |
| 12657397 | At_100mM_NaCl | 20000268 | Timepoint (hr) | 6 |
| 12657397 | At_100mM_NaCl | 20000268 | Age (day) | 14 |
| 12657397 | At_100mM_NaCl | 20000268 | Treatment | 100 mM NaCl vs. No Treatment |
| 12657397 | At_100mM_NaCl | 20000268 | Organism | A. thaliana |
| 12657397 | At_100mM_NaCl | 20000268 | Tissue | Whole Plant |
| 12657397 | At_100mM_NaCl | 20000268 | Plant Line | WS |
| 12657397 | At_100mM_NaCl | 20000308 | Age (day) | 17 |
| 12657397 | At_100mM_NaCl | 20000308 | Timepoint (hr) | 72 |
| 12657397 | At_100mM_NaCl | 20000308 | Treatment | 100 mM NaCl vs. No Treatment |
| 12657397 | At_100mM_NaCl | 20000308 | Organism | A. thaliana |
| 12657397 | At_100mM_NaCl | 20000308 | Tissue | Whole Plant |
| 12657397 | At_100mM_NaCl | 20000308 | Plant Line | WS |
| 12657397 | At_Pollen | 20000326 | Age (day) | 0 vs. 21 |
| 12657397 | At_Pollen | 20000326 | Organism | A. thaliana |
| 12657397 | At_Pollen | 20000326 | Tissue | Pollen vs. Whole Plant |
| 12657397 | At_Pollen | 20000326 | Plant Line | WS |
| 12657397 | At_Drought | 20000436 | Age (day) | 7 |
| 12657397 | At_Drought | 20000436 | Timepoint (hr) | 12 |
| 12657397 | At_Drought | 20000436 | Organism | A. thaliana |
| 12657397 | At_Drought | 20000436 | Treatment | Drought vs. No Drought |
| 12657397 | At_Drought | 20000436 | Tissue | Whole Plant |
| 12657397 | At_Drought | 20000436 | Plant Line | WS |
| 12657397 | At_Drought | 20000437 | Age (day) | 8 |
| 12657397 | At_Drought | 20000437 | Timepoint (hr) | 24 |
| 12657397 | At_Drought | 20000437 | Organism | A. thaliana |
| 12657397 | At_Drought | 20000437 | Treatment | Drought vs. No Drought |
| 12657397 | At_Drought | 20000437 | Tissue | Whole Plant |
| 12657397 | At_Drought | 20000437 | Plant Line | WS |
| 12657397 | At_Roots | 20000439 | Age (day) | 14 vs. 21 |
| 12657397 | At_Roots | 20000439 | Organism | A. thaliana |
| 12657397 | At_Roots | 20000439 | Tissue | Roots vs. Whole Plant |
| 12657397 | At_Roots | 20000439 | Plant Line | WS |
| 12657397 | At_10percent_PEG | 20000460 | Age (day) | 12 |
| 12657397 | At_10percent_PEG | 20000460 | Timepoint (day) | 12 |
| 12657397 | At_10percent_PEG | 20000460 | Treatment | 10 percent PEG vs. No Treatment |

TABLE 1-continued

Promoter Sequences and Related Information

| | | | | |
|---|---|---|---|---|
| 12657397 | At_10percent_PEG | 20000460 | Organism | A. thaliana |
| 12657397 | At_10percent_PEG | 20000460 | Tissue | Whole Plant |
| 12657397 | At_10percent_PEG | 20000460 | Plant Line | WS |
| 12657397 | At_10percent_PEG | 20000527 | Age (day) | 20 |
| 12657397 | At_10percent_PEG | 20000527 | Timepoint (day) | 20 |
| 12657397 | At_10percent_PEG | 20000527 | Treatment | 10 percent PEG vs. No Treatment |
| 12657397 | At_10percent_PEG | 20000527 | Organism | A. thaliana |
| 12657397 | At_10percent_PEG | 20000527 | Tissue | Whole Plant |
| 12657397 | At_10percent_PEG | 20000527 | Plant Line | WS |
| 12657397 | At_100uM_ABA_Mutants | 20000575 | Timepoint (hr) | 6 |
| 12657397 | At_100uM_ABA_Mutants | 20000575 | Treatment | 1 uM ABA vs. No Treatment |
| 12657397 | At_100uM_ABA_Mutants | 20000575 | Organism | A. thaliana |
| 12657397 | At_100uM_ABA_Mutants | 20000575 | Plant Line | CS22 |
| 12657397 | At_100uM_ABA_Mutants | 20000575 | Tissue | Whole Plant |
| 12657397 | At_100uM_ABA_Mutants | 20000576 | Timepoint (hr) | 6 |
| 12657397 | At_100uM_ABA_Mutants | 20000576 | Treatment | 1 uM ABA vs. No Treatment |
| 12657397 | At_100uM_ABA_Mutants | 20000576 | Organism | A. thaliana |
| 12657397 | At_100uM_ABA_Mutants | 20000576 | Plant Line | CS23 |
| 12657397 | At_100uM_ABA_Mutants | 20000576 | Tissue | Whole Plant |
| 12657397 | At_Herbicide_Mutants | 20000639 | Timepoint (hr) | 4 |
| 12657397 | At_Herbicide_Mutants | 20000639 | Plant Line | 05377RR/BR27173 |
| 12657397 | At_Herbicide_Mutants | 20000639 | Treatment | Roundup vs. No Treatment |
| 12657397 | At_Herbicide_Mutants | 20000639 | Tissue | Seedlings |
| 12657397 | At_Herbicide_Mutants | 20000642 | Timepoint (hr) | 12 |
| 12657397 | At_Herbicide_Mutants | 20000642 | Plant Line | 3950BR/PCJE10000 |
| 12657397 | At_Herbicide_Mutants | 20000642 | Treatment | Finale vs. No Treatment |
| 12657397 | At_Herbicide_Mutants | 20000642 | Tissue | Seedlings |
| 12657397 | At_Line_Comparisons | 20001300 | Plant Line | ME01338-05 vs. WS |
| 12657397 | At_Line_Comparisons | 20001307 | Plant Line | WBin4-WX2-A vs. WS |
| 12657397 | At_Line_Comparisons | 20001309 | Plant Line | WBin4-WX49R-A vs. WS |
| 12657397 | At_Line_Comparisons | 20001310 | Plant Line | WBin4-WX17-A vs. WS |
| 12657397 | At_Line_Comparisons | 20001319 | Plant Line | WBin4-WX24-A vs. WS |
| 12657397 | At_Far-red-induction | 20001451 | Age (day) | 8 |
| 12657397 | At_Far-red-induction | 20001451 | Timepoint (hr) | 24 |
| 12657397 | At_Far-red-induction | 20001451 | Organism | A. thaliana |
| 12657397 | At_Far-red-induction | 20001451 | Plant Line | Columbia |
| 12657397 | At_Far-red-induction | 20001451 | Light | Far-red vs. White |
| 12657397 | At_Far-red-induction | 20001451 | Tissue | Whole Plant |
| 12657397 | At_Far-red-enriched | 20001504 | Timepoint (day) | 6 |
| 12657397 | At_Far-red-enriched | 20001504 | Age (day) | 10 |
| 12657397 | At_Far-red-enriched | 20001504 | Organism | A. thaliana |
| 12657397 | At_Far-red-enriched | 20001504 | Plant Line | Columbia |
| 12657397 | At_Far-red-enriched | 20001504 | Light | Far-red enriched vs. White |
| 12657397 | At_Far-red-enriched | 20001504 | Tissue | Whole Plant |
| 12657397 | At_Drought_Soil_Dry | 20001554 | Timepoint (day) | 7 |
| 12657397 | At_Drought_Soil_Dry | 20001554 | Age (day) | 21 |
| 12657397 | At_Drought_Soil_Dry | 20001554 | Organism | A. thaliana |
| 12657397 | At_Drought_Soil_Dry | 20001554 | Treatment | Drought vs. No Drought |
| 12657397 | At_Drought_Soil_Dry | 20001554 | Post Timepoint (hr) | None |
| 12657397 | At_Drought_Soil_Dry | 20001554 | Post-Treatment | None |
| 12657397 | At_Drought_Soil_Dry | 20001554 | Plant Line | WS |
| 12657397 | At_Drought_Soil_Dry | 20001555 | Timepoint (day) | 10 |
| 12657397 | At_Drought_Soil_Dry | 20001555 | Age (day) | 24 |
| 12657397 | At_Drought_Soil_Dry | 20001555 | Organism | A. thaliana |
| 12657397 | At_Drought_Soil_Dry | 20001555 | Treatment | Drought vs. No Drought |
| 12657397 | At_Drought_Soil_Dry | 20001555 | Post Timepoint (hr) | None |
| 12657397 | At_Drought_Soil_Dry | 20001555 | Post-Treatment | None |
| 12657397 | At_Drought_Soil_Dry | 20001555 | Plant Line | WS |
| 12657397 | At_Drought_Soil_Dry | 20001556 | Timepoint (day) | 12 |
| 12657397 | At_Drought_Soil_Dry | 20001556 | Age (day) | 26 |
| 12657397 | At_Drought_Soil_Dry | 20001556 | Organism | A. thaliana |
| 12657397 | At_Drought_Soil_Dry | 20001556 | Treatment | Drought vs. No Drought |
| 12657397 | At_Drought_Soil_Dry | 20001556 | Post Timepoint (hr) | None |
| 12657397 | At_Drought_Soil_Dry | 20001556 | Post-Treatment | None |
| 12657397 | At_Drought_Soil_Dry | 20001556 | Plant Line | WS |
| 12657397 | At_Drought_Soil_Dry | 20001557 | Post Timepoint (hr) | 3 |
| 12657397 | At_Drought_Soil_Dry | 20001557 | Timepoint (day) | 13 |
| 12657397 | At_Drought_Soil_Dry | 20001557 | Age (day) | 27 |
| 12657397 | At_Drought_Soil_Dry | 20001557 | Organism | A. thaliana |
| 12657397 | At_Drought_Soil_Dry | 20001557 | Treatment | Drought vs. No Drought |
| 12657397 | At_Drought_Soil_Dry | 20001557 | Post-Treatment | Re-Water vs. No Drought |
| 12657397 | At_Drought_Soil_Dry | 20001557 | Plant Line | WS |
| 12657397 | At_Drought_Soil_Dry | 20001559 | Timepoint (day) | 14 |
| 12657397 | At_Drought_Soil_Dry | 20001559 | Age (day) | 28 |
| 12657397 | At_Drought_Soil_Dry | 20001559 | Post Timepoint (hr) | 29 |
| 12657397 | At_Drought_Soil_Dry | 20001559 | Organism | A. thaliana |
| 12657397 | At_Drought_Soil_Dry | 20001559 | Treatment | Drought vs. No Drought |

TABLE 1-continued

Promoter Sequences and Related Information

| 12657397 | At_Drought_Soil_Dry | 20001559 | Post-Treatment | Re-Water vs. No Drought |
| --- | --- | --- | --- | --- |
| 12657397 | At_Drought_Soil_Dry | 20001559 | Plant Line | WS |
| 12657397 | At_Drought_Soil_Dry | 20001560 | Timepoint (day) | 14 |
| 12657397 | At_Drought_Soil_Dry | 20001560 | Age (day) | 28 |
| 12657397 | At_Drought_Soil_Dry | 20001560 | Organism | A. thaliana |
| 12657397 | At_Drought_Soil_Dry | 20001560 | Treatment | Drought vs. No Drought |
| 12657397 | At_Drought_Soil_Dry | 20001560 | Post Timepoint (hr) | None |
| 12657397 | At_Drought_Soil_Dry | 20001560 | Post-Treatment | None |
| 12657397 | At_Drought_Soil_Dry | 20001560 | Plant Line | WS |
| 12657397 | At_Drought_Reproduction | 20001904 | Timepoint (day) | 7 |
| 12657397 | At_Drought_Reproduction | 20001904 | Age (day) | 37 |
| 12657397 | At_Drought_Reproduction | 20001904 | Organism | A. thaliana |
| 12657397 | At_Drought_Reproduction | 20001904 | Treatment | Drought vs. No Drought |
| 12657397 | At_Drought_Reproduction | 20001904 | Tissue | Rosettes |
| 12657397 | At_Drought_Reproduction | 20001904 | Plant Line | WS |
| 12657397 | At_Drought_Reproduction | 20001906 | Timepoint (day) | 5 |
| 12657397 | At_Drought_Reproduction | 20001906 | Age (day) | 35 |
| 12657397 | At_Drought_Reproduction | 20001906 | Organism | A. thaliana |
| 12657397 | At_Drought_Reproduction | 20001906 | Treatment | Drought vs. No Drought |
| 12657397 | At_Drought_Reproduction | 20001906 | Tissue | Siliques |
| 12657397 | At_Drought_Reproduction | 20001906 | Plant Line | WS |
| 12657397 | At_Drought_Reproduction | 20001907 | Timepoint (day) | 7 |
| 12657397 | At_Drought_Reproduction | 20001907 | Age (day) | 37 |
| 12657397 | At_Drought_Reproduction | 20001907 | Organism | A. thaliana |
| 12657397 | At_Drought_Reproduction | 20001907 | Treatment | Drought vs. No Drought |
| 12657397 | At_Drought_Reproduction | 20001907 | Tissue | Siliques |
| 12657397 | At_Drought_Reproduction | 20001907 | Plant Line | WS |
| 12657397 | At_Drought_Reproduction | 20001909 | Timepoint (day) | 5 |
| 12657397 | At_Drought_Reproduction | 20001909 | Age (day) | 35 |
| 12657397 | At_Drought_Reproduction | 20001909 | Organism | A. thaliana |
| 12657397 | At_Drought_Reproduction | 20001909 | Treatment | Drought vs. No Drought |
| 12657397 | At_Drought_Reproduction | 20001909 | Tissue | Flowers |
| 12657397 | At_Drought_Reproduction | 20001909 | Plant Line | WS |
| 12657397 | At_Line_Comparisons | 20002009 | Plant Line | ME01642 vs. WS |
| 12657397 | At_Drought-Air-Dry | 20002256 | Timepoint (hr) | 4 |
| 12657397 | At_Drought-Air-Dry | 20002256 | Age (day) | 35 |
| 12657397 | At_Drought-Air-Dry | 20002256 | Organism | A. thaliana |
| 12657397 | At_Drought-Air-Dry | 20002256 | Treatment | Drought vs. No Drought |
| 12657397 | At_Drought-Air-Dry | 20002256 | Tissue | Shoots |
| 12657397 | At_Drought-Air-Dry | 20002256 | Plant Line | WS |

Promoter YP0356

Modulates the gene: Dehydration-induced protein RD22
The GenBank description of the geneNM_122472 Arabidopsis thaliana dehydration-induced protein
RD22 (At5g25610) mRNA, complete cds gi|30689960|ref|NM_122472.2|[30689960]
The promoter sequence:
5'tacttgcaaccactttgtaggaccattaactgcaaaataagaattctctaagcttcacaaggggttcgt ttggtgctataaaaacattgttttaagaactggtttactggttctataaatctataaatccaaatatgaag tatggcaataataataacatgttagcacaaaaaatactcattaaattcctacccaaaaaaaatctttatat gaaactaaaacttatatacacaataatagtgatacaaagtaggtcttgatattcaactattcgggattttc tggtttcgagtaattcgtataaaaggtttaagatctattatgttcactgaaatcttaactttgttttgttt ccagttttaactagtagaaattgaaagttttaaaaattgttacttacaataaaatttgaatcaatatccatt aatcaaaggatcttaagactagcacaattaaaacatataacgtagaatatctgaaataactcgaaaatatc tgaactaagttagtagttttaaaatataatcccggtttggaccgggcagtatgtacttcaatacttgtggg ttttgacgattttggatcggattgggcgggccagccagattgatctattacaaatttcacctgtcaacgct aactccgaacttaatcaaagattttgagctaaggaaaactaatcagtgatcacccaaagaaaacattcgtg aataattgtttgctttccatggcagcaaaacaaataggacccaaataggaatgtcaaaaaaaagaaagaca cgaaacgaagtagtataacgtaacacacaaaaataaactagagatattaaaaacacatgtccacacatgga tacaagagcatttaaggagcagaaggcacgtagtggttagaaggtatgtgatataattaatcggcccaaat agattggtaagtagtagccgtcTATAtca 3'- cagctccttctactaaaaacccttttactataaattctacgtacacgtaccacttcttctcctcaaattca
The promoter was cloned from the organism: Arabidopsis thaliana, WS ecotype

TABLE 1-continued

Promoter Sequences and Related Information

Alternative nucleotides:
Predicted (Columbia)
Experimental (Wassilewskija)

| Predicted Position (bp) | Mismatch | Columbia/Wassilewskija |
|---|---|---|
| 405 | SNP | g/t |

The promoter was cloned in the vector: pNewbin4-HAP1-GFP
When cloned into the vector the promoter was operably linked to a marker, which was the type: GFP-ER
Promoter-marker vector was tested in: *Arabidopsis thaliana*, WS ecotype
Generation screened: XT1 Mature XT2 Seedling T2 Mature T3 Seedling The spatial expression of the promoter-marker vector was found observed in and would be useful in expression in any or all of the following:

Flower              H pedicel H petal H epidermis
Silique             H stigma L style L carpel L septum Lepidermis
Ovule               H outer integument
Stem                H epidermis H stomata
Hypocotyl           H epidermis
Cotyledon           H epidermis
Rosette Leaf        H epidermis H trichome Observed expression pattern of the promoter-marker vector was in:
T1 mature: GFP expression specific to epidermal call types. High GFP expression in epidermis of stem decreasing toward pedicles and inflorescence apex. In the flower, high expression observed in epidermal cells of petals and stigma, and lower expression in carpels. High expression in outer integuments of matureing ovules. High expression throughout epidermal cells of mature lower stem.
T2 seedling: GFP expression specific to epidermal cell types. High expression in epidermis of hypocotyl, cotyledon, and trichomes of rosette leaves. Not detected in root.
Misc. promoter information: Bidirectionality: Pass Exons: Pass Repeats: None:
The Ceres cDNA ID of the endogenous coding sequence to the promoter: 12394809
cDNA nucleotide sequence:
agCTCCTTTCTACTAAAACCCTTTTACTATAAATTCTACGTACACGTACCACTTCTTCTCCTCAA

ATTCATCAAACCCATTTCTATTCCAACTCCCAAAAATGGCGATTCGTCTTCCTCTGATCTGTCT

TCTTGGTTCATTCATGGTAGTGGCGATTGCGGCTGATTTAACACCGGAGCGTTATTGGAGCAC

TGCTTTACCAAACACTCCCATTCCCAACTCTCTCCATAATCTTTTGACTTTCGATTTTACCGACG

AGAAAAGTACCAACGTCCAAGTAGGTAAAGGCGGAGTAAACGTTAACACCCATAAAGGTAAA

ACCGGTAGCGGAACCGCCGTGAACGTTGGAAAGGGAGGTGTACGCGTGGACACAGGCAAGGG

CAAGCCCGGAGGAGGGACACACGTGAGCGTTGGCAGCGGAAAAGGTCACGGAGGTGGCGTCG

CAGTCCACACGGGTAAACCCGGTAAAAGAACCGACGTAGGAGTCGGTAAAGGCGGTGTGACG

GTGCACACGCGCCACAAGGGAAGACCGATTTACGTTGGTGTGAAACCAGGAGCAAACCCTTTC

GTGTATAACTATGCAGCGAAGGAGACTCAGCTCCACGACGATCCTAACGCGGCTCTCTTCTTC

TTGGAGAAGGACTTGGTTCGCGGGAAAGAAATGAATGTCCGGTTTAACGCTGAGGATGGTTA

CGGAGGCAAAACTGCGTTCTTGCCACGTGGAGAGGCTGAAACGGTGCCTTTTGGATCGGAGA

AGTTTTCGGAGACGTTGAAACGTTTCTCGGTGGAAGCTGGTTCGGAAGAAGCGGAGATGATG

AAGAAGACCATTGAGGAGTGTGAAGCCAGAAAAGTTAGTGGAGAGGAGAAGTATTGTGCGAC

GTCTTTGGAGTCGATGGTCGACTTTAGTGTTTCGAAACTTGGTAAATATCACGTCAGGGCTGTT

TCCACTGAGGTGGCTAAGAAGAACGCACCGATGCAGAAGTACAAAATCGCGGCGGCTGGGGT

AAAGAAGTTGTCTGACGATAAATCTGTGGTGTGTCACAAACAGAAGTACCCATTCGCGGTGTT

CTACTGCCACAAGGCGATGATGACGACCGTCTACGCGGTTCCGCTCGAGGGAGAGAACGGGA

TGCGAGCTAAAGCAGTTGCGGTATGCCACAAGAACACCTCAGCTTGGAACCCAAACCACTTGG

CCTTCAAAGTCTTAAAGGTGAAGCCAGGGACCGTTCCGGTCTGCCACTTCCTCCCGGAGACTC

ATGTTGTGTGGTTCAGCTACTAGATAGATCTGTTTTCTATCTTATTGTGGGTTATGTATAATTA

CGTTTCAGATAATCTATCTTTTGGGATGTTTTGGTTATGAATATACATACATATACATATAGTA

TABLE 1-continued

Promoter Sequences and Related Information

```
ATGCGTGGTTTCCATATAAGAGTGAAGGCATCTATATGTTTTTTTTTTATTAACCTACGTAGC

TGTCTTTTGTGGTCTGTATCTTGTGGTTTTGCAAAAACCTATAATAAAATTAGAGCTGAAATGT

TACCATTTC
Coding sequence:
<MAIRLPLICLLGSFMVVAIA>
ADLTPERYWSTALPNTPIPNSLHNLLTFDFTDEKSTNVQVGKGGVNVNTHKGKTGSGTAVNVGK

GGVRVDTGKGKPGGGTHVSVGSGKGHGGGVAVHTGKPGKRTDVGVGKGGVTVHTRHKGRPIY

VGVKPGANPFVYNYAAKETQLHDDPNAALFFLEKDLVRGKEMNVRFNAEDGYGGKTAFLPRGE

AETVPFGSEKFSETLKRFSVEAGSEEAEMMKKTIEECEARKVSGEEKYCATSLESMVDFSVSKLGK

YHVRAVSTEVAKKNAPMQKYKIAAAGVKKLSDDKSVVCHKQKYPFAVFYCHKAMMTTVYAVP

LEGENGMRAKAVAVCHKNTSAWNPNHLAFKVLKVKPGTVPVCHFLPETHVVWFSY*
```

Microarray data shows that the coding sequence was expressed in the following experiments, which shows that the promoter would be useful to modulate expression in situations similar to the following:

| CDNA_ID | SHORT_NAME | EXPT_REP_ID | IS_UP |
|---|---|---|---|
| 12394809 | At_100 uM_ABA_Mutants | 20000071 | + |
| 12394809 | At_100 uM_ABA | 20000169 | + |
| 12394809 | At_Roots | 20000185 | - |
| 12394809 | At_Drought | 20000267 | + |
| 12394809 | At_100mM_NaCl | 20000268 | + |
| 12394809 | At_Pollen | 20000326 | - |
| 12394809 | At_Drought | 20000436 | + |
| 12394809 | At_Drought | 20000437 | + |
| 12394809 | At_Roots | 20000439 | - |
| 12394809 | At_100 uM_ABA | 20000453 | + |
| 12394809 | At_100 uM_ABA_Mutants | 20000573 | - |
| 12394809 | At_100 uM_ABA_Mutants | 20000574 | - |
| 12394809 | At_Far-red-induction | 20001247 | + |
| 12394809 | At_Far-red-induction | 20001248 | - |
| 12394809 | At_Line_Comparisons | 20001310 | - |
| 12394809 | At_Interploidy_Crosses | 20001316 | - |
| 12394809 | At_Far-red-induction | 20001450 | - |
| 12394809 | At_Far-red-induction | 20001451 | - |
| 12394809 | At_Drought_Soil_Dry | 20001554 | + |
| 12394809 | At_Drought_Soil_Dry | 20001555 | + |
| 12394809 | At_Drought_Soil_Dry | 20001556 | + |
| 12394809 | At_Drought_Soil_Dry | 20001559 | + |
| 12394809 | At_Interploidy_Crosses | 20001853 | + |
| 12394809 | At_Drought_Reproduction | 20001904 | + |
| 12394809 | At_Drought_Reproduction | 20001911 | + |
| 12394809 | At_8deg_Cold | 20002107 | + |

The parameters for the microarray experiments listed above by Expt_Rep_ID and Short_Name are as follow below:

| CDNA_ID | SHORT_NAME | EXPT_REP_ID | PARAM_NAME | VALUE |
|---|---|---|---|---|
| 12394809 | At_100 uM_ABA_Mutants | 20000071 | Timepoint (hr) | 6 |
| 12394809 | At_100 uM_ABA_Mutants | 20000071 | Treatment | 100 uM ABA vs. No Treatment |
| 12394809 | At_100 uM_ABA_Mutants | 20000071 | Tissue | Aerial |
| 12394809 | At_100 uM_ABA_Mutants | 20000071 | Plant Line | CS8104 |
| 12394809 | At_100 uM_ABA | 20000169 | Timepoint (hr) | 6 |
| 12394809 | At_100 uM_ABA | 20000169 | Age (day) | 14 |
| 12394809 | At_100 uM_ABA | 20000169 | Treatment | 100 uM ABA vs. No Treatment |
| 12394809 | At_100 uM_ABA | 20000169 | Organism | A. thaliana |
| 12394809 | At_100 uM_ABA | 20000169 | Tissue | Aerial |
| 12394809 | At_100 uM_ABA | 20000169 | Plant Line | WS |
| 12394809 | At_Roots | 20000185 | Age (day) | 7 vs. 21 |
| 12394809 | At_Roots | 20000185 | Organism | A. thaliana |
| 12394809 | At_Roots | 20000185 | Tissue | Roots vs. Whole Plant |
| 12394809 | At_Roots | 20000185 | Plant Line | WS |
| 12394809 | At_Drought | 20000267 | Timepoint (hr) | 6 |
| 12394809 | At_Drought | 20000267 | Age (day) | 7 |
| 12394809 | At_Drought | 20000267 | Organism | A. thaliana |
| 12394809 | At_Drought | 20000267 | Treatment | Drought vs. No Drought |
| 12394809 | At_Drought | 20000267 | Tissue | Whole Plant |
| 12394809 | At_Drought | 20000267 | Plant Line | WS |
| 12394809 | At_100mM_NaCl | 20000268 | Timepoint (hr) | 6 |
| 12394809 | At_100mM_NaCl | 20000268 | Age (day) | 14 |

TABLE 1-continued

Promoter Sequences and Related Information

| | | | | |
|---|---|---|---|---|
| 12394809 | At_100mM_NaCl | 20000268 | Treatment | 100 mM NaCl vs. No Treatment |
| 12394809 | At_100mM_NaCl | 20000268 | Organism | A. thaliana |
| 12394809 | At_100mM_NaCl | 20000268 | Tissue | Whole Plant |
| 12394809 | At_100mM_NaCl | 20000268 | Plant Line | WS |
| 12394809 | At_Pollen | 20000326 | Age (day) | 0 vs. 21 |
| 12394809 | At_Pollen | 20000326 | Organism | A. thaliana |
| 12394809 | At_Pollen | 20000326 | Tissue | Pollen vs. Whole Plant |
| 12394809 | At_Pollen | 20000326 | Plant Line | WS |
| 12394809 | At_Drought | 20000436 | Age (day) | 7 |
| 12394809 | At_Drought | 20000436 | Timepoint (hr) | 12 |
| 12394809 | At_Drought | 20000436 | Organism | A. thaliana |
| 12394809 | At_Drought | 20000436 | Treatment | Drought vs. No Drought |
| 12394809 | At_Drought | 20000436 | Tissue | Whole Plant |
| 12394809 | At_Drought | 20000436 | Plant Line | WS |
| 12394809 | At_Drought | 20000437 | Age (day) | 8 |
| 12394809 | At_Drought | 20000437 | Timepoint (hr) | 24 |
| 12394809 | At_Drought | 20000437 | Organism | A. thaliana |
| 12394809 | At_Drought | 20000437 | Treatment | Drought vs. No Drought |
| 12394809 | At_Drought | 20000437 | Tissue | Whole Plant |
| 12394809 | At_Drought | 20000437 | Plant Line | WS |
| 12394809 | At_Roots | 20000439 | Age (day) | 14 vs. 21 |
| 12394809 | At_Roots | 20000439 | Organism | A. thaliana |
| 12394809 | At_Roots | 20000439 | Tissue | Roots vs. Whole Plant |
| 12394809 | At_Roots | 20000439 | Plant Line | WS |
| 12394809 | At_100 uM_ABA | 20000453 | Age (day) | 15 |
| 12394809 | At_100 uM_ABA | 20000453 | Timepoint (hr) | 24 |
| 12394809 | At_100 uM_ABA | 20000453 | Treatment | 100 uM ABA vs. No Treatment |
| 12394809 | At_100 uM_ABA | 20000453 | Organism | A. thaliana |
| 12394809 | At_100 uM_ABA | 20000453 | Tissue | Aerial |
| 12394809 | At_100 uM_ABA | 20000453 | Plant Line | WS |
| 12394809 | At_100 uM_ABA_Mutants | 20000573 | Organism | A. thaliana |
| 12394809 | At_100 uM_ABA_Mutants | 20000573 | Plant Line | CS22 vs. Ler wt |
| 12394809 | At_100 uM_ABA_Mutants | 20000573 | Timepoint (hr) | N/A |
| 12394809 | At_100 uM_ABA_Mutants | 20000573 | Treatment | None |
| 12394809 | At_100 uM_ABA_Mutants | 20000573 | Tissue | Whole Plant |
| 12394809 | At_100 uM_ABA_Mutants | 20000574 | Organism | A. thaliana |
| 12394809 | At_100 uM_ABA_Mutants | 20000574 | Plant Line | CS23 vs. Ler wt |
| 12394809 | At_100 uM_ABA_Mutants | 20000574 | Timepoint (hr) | N/A |
| 12394809 | At_100 uM_ABA_Mutants | 20000574 | Treatment | None |
| 12394809 | At_100 uM_ABA_Mutants | 20000574 | Tissue | Whole Plant |
| 12394809 | At_Far-red-induction | 20001247 | Timepoint (hr) | 1 |
| 12394809 | At_Far-red-induction | 20001247 | Age (day) | 7 |
| 12394809 | At_Far-red-induction | 20001247 | Organism | A. thaliana |
| 12394809 | At_Far-red-induction | 20001247 | Plant Line | Columbia |
| 12394809 | At_Far-red-induction | 20001247 | Light | Far-red vs. White |
| 12394809 | At_Far-red-induction | 20001247 | Tissue | Whole Plant |
| 12394809 | At_Far-red-induction | 20001248 | Timepoint (hr) | 4 |
| 12394809 | At_Far-red-induction | 20001248 | Age (day) | 7 |
| 12394809 | At_Far-red-induction | 20001248 | Organism | A. thaliana |
| 12394809 | At_Far-red-induction | 20001248 | Plant Line | Columbia |
| 12394809 | At_Far-red-induction | 20001248 | Light | Far-red vs. White |
| 12394809 | At_Far-red-induction | 20001248 | Tissue | Whole Plant |
| 12394809 | At_Line_Comparisons | 20001310 | Plant Line | WBin4-WX17-A vs. WS |
| 12394809 | At_Interploidy_Crosses | 20001316 | Age (day) | 5 |
| 12394809 | At_Interploidy_Crosses | 20001316 | Organism | A. thaliana |
| 12394809 | At_Interploidy_Crosses | 20001316 | Plant Line | Columbia |
| 12394809 | At_Interploidy_Crosses | 20001316 | Cross | hemi x 2X vs. 2X x 2X |
| 12394809 | At_Interploidy_Crosses | 20001316 | Tissue | Siliques |
| 12394809 | At_Far-red-induction | 20001450 | Age (day) | 7 |
| 12394809 | At_Far-red-induction | 20001450 | Timepoint (hr) | 8 |
| 12394809 | At_Far-red-induction | 20001450 | Organism | A. thaliana |
| 12394809 | At_Far-red-induction | 20001450 | Plant Line | Columbia |
| 12394809 | At_Far-red-induction | 20001450 | Light | Far-red vs. White |
| 12394809 | At_Far-red-induction | 20001450 | Tissue | Whole Plant |
| 12394809 | At_Far-red-induction | 20001451 | Age (day) | 8 |
| 12394809 | At_Far-red-induction | 20001451 | Timepoint (hr) | 24 |
| 12394809 | At_Far-red-induction | 20001451 | Organism | A. thaliana |
| 12394809 | At_Far-red-induction | 20001451 | Plant Line | Columbia |
| 12394809 | At_Far-red-induction | 20001451 | Light | Far-red vs. White |
| 12394809 | At_Far-red-induction | 20001451 | Tissue | Whole Plant |
| 12394809 | At_Drought_Soil_Dry | 20001554 | Timepoint (day) | 7 |
| 12394809 | At_Drought_Soil_Dry | 20001554 | Age (day) | 21 |
| 12394809 | At_Drought_Soil_Dry | 20001554 | Organism | A. thaliana |
| 12394809 | At_Drought_Soil_Dry | 20001554 | Treatment | Drought vs. No Drought |
| 12394809 | At_Drought_Soil_Dry | 20001554 | Post Timepoint (hr) | None |
| 12394809 | At_Drought_Soil_Dry | 20001554 | Post-Treatment | None |
| 12394809 | At_Drought_Soil_Dry | 20001554 | Plant Line | WS |

TABLE 1-continued

Promoter Sequences and Related Information

| 12394809 | At_Drought_Soil_Dry | 20001555 | Timepoint (day) | 10 |
|---|---|---|---|---|
| 12394809 | At_Drought_Soil_Dry | 20001555 | Age (day) | 24 |
| 12394809 | At_Drought_Soil_Dry | 20001555 | Organism | A. thaliana |
| 12394809 | At_Drought_Soil_Dry | 20001555 | Treatment | Drought vs. No Drought |
| 12394809 | At_Drought_Soil_Dry | 20001555 | Post Timepoint (hr) | None |
| 12394809 | At_Drought_Soil_Dry | 20001555 | Post-Treatment | None |
| 12394809 | At_Drought_Soil_Dry | 20001555 | Plant Line | WS |
| 12394809 | At_Drought_Soil_Dry | 20001556 | Timepoint (day) | 12 |
| 12394809 | At_Drought_Soil_Dry | 20001556 | Age (day) | 26 |
| 12394809 | At_Drought_Soil_Dry | 20001556 | Organism | A. thaliana |
| 12394809 | At_Drought_Soil_Dry | 20001556 | Treatment | Drought vs. No Drought |
| 12394809 | At_Drought_Soil_Dry | 20001556 | Post Timepoint (hr) | None |
| 12394809 | At_Drought_Soil_Dry | 20001556 | Post-Treatment | None |
| 12394809 | At_Drought_Soil_Dry | 20001556 | Plant Line | WS |
| 12394809 | At_Drought_Soil_Dry | 20001559 | Timepoint (day) | 14 |
| 12394809 | At_Drought_Soil_Dry | 20001559 | Age (day) | 28 |
| 12394809 | At_Drought_Soil_Dry | 20001559 | Post Timepoint (hr) | 29 |
| 12394809 | At_Drought_Soil_Dry | 20001559 | Organism | A. thaliana |
| 12394809 | At_Drought_Soil_Dry | 20001559 | Treatment | Drought vs. No Drought |
| 12394809 | At_Drought_Soil_Dry | 20001559 | Post-Treatment | Re-Water vs. No Drought |
| 12394809 | At_Drought_Soil_Dry | 20001559 | Plant Line | WS |
| 12394809 | At_Interploidy_Crosses | 20001853 | Age (day) | 5 |
| 12394809 | At_Interploidy_Crosses | 20001853 | Organism | A. thaliana |
| 12394809 | At_Interploidy_Crosses | 20001853 | Plant Line | Columbia |
| 12394809 | At_Interploidy_Crosses | 20001853 | Cross | Fis1 vs. 2X x 2X |
| 12394809 | At_Interploidy_Crosses | 20001853 | Tissue | Siliques |
| 12394809 | At_Drought_Reproduction | 20001904 | Timepoint (day) | 7 |
| 12394809 | At_Drought_Reproduction | 20001904 | Age (day) | 37 |
| 12394809 | At_Drought_Reproduction | 20001904 | Organism | A. thaliana |
| 12394809 | At_Drought_Reproduction | 20001904 | Treatment | Drought vs. No Drought |
| 12394809 | At_Drought_Reproduction | 20001904 | Tissue | Rosettes |
| 12394809 | At_Drought_Reproduction | 20001904 | Plant Line | WS |
| 12394809 | At_Drought_Reproduction | 20001911 | Timepoint (day) | 10 |
| 12394809 | At_Drought_Reproduction | 20001911 | Age (day) | 40 |
| 12394809 | At_Drought_Reproduction | 20001911 | Organism | A. thaliana |
| 12394809 | At_Drought_Reproduction | 20001911 | Treatment | Drought vs. No Drought |
| 12394809 | At_Drought_Reproduction | 20001911 | Tissue | Flowers |
| 12394809 | At_Drought_Reproduction | 20001911 | Plant Line | WS |
| 12394809 | At_8deg_Cold | 20002107 | Age (day) | 11 |
| 12394809 | At_8deg_Cold | 20002107 | Timepoint (hr) | 96 |
| 12394809 | At_8deg_Cold | 20002107 | Temperature (deg C.) | 8 vs. 22 |
| 12394809 | At_8deg_Cold | 20002107 | Organism | A. thaliana |
| 12394809 | At_8deg_Cold | 20002107 | Tissue | Whole Plant |
| 12394809 | At_8deg_Cold | 20002107 | Plant Line | WS |

Promoter YP0337

Modulates the gene: Unknown protein.
The GenBank description of the gene: NM_101546 *Arabidopsis thaliana* expressed protein (At1g16850) mRNA, complete cds gi|18394408|ref|NM_101546.1|[18394408]
The promoter sequence:
5'-acttattagtttaggtttccatcacctatttaattcgtaattcttatacatgcatataatagagataca tatatacaaatttatgatcattttttgcacaacatgtgatctcattcattagtatgcattatgcgaaaacct cgacgcgcaaaagacacgtaatagctaataatgttactcatttataatgattgaagcaagacgaaaacaac aacatatatatcaaattgtaaactagatatttcttaaaagtgaaaaaaaacaaagaaatataaaggacaat tttgagtcagtctcttaatattaaaacatatatacataaataagcacaaacgtggttacctgtcttcatgc aatgtggactttagtttatctaatcaaatcaaaataaaaggtgtaatagttctcgtcatttttcaaattt taaaaatcagaaccaagtgattttttgtttgagtattgatccattgtttaaacaatttaacacagtatatac gtctcttgagatgttgacatgatgataaaatacgagatcgtctcttggttttcgaattttgaactttaata gtttttttttagggaaactttaatagttgtttatcataagattagtcacctaatggttacgttgcagta ccgaaccaattttttacccttttttctaaatgtggtcgtggcataatttccaaaagagatccaaacccgg tttgctcaactgataagccggtcggttctggtttgaaaaacaagaaataatctgaaagtgtgaaacagcaa cgtgtctcggtgtttcatgagccacctgccacctcattcacgtcggtcattttgtcgtttcacggttcacg ctctagacacgtgctctgtccccaccatgactttcgctgccgactcgcttcgctttgcaaactcaaacatg tgtgTATAtgtaagtttcatcctaataag 3'-caaagaaaacatcaaaATG

TABLE 1-continued

Promoter Sequences and Related Information

The promoter was cloned from the organism: *Arabidopsis thaliana*, WS ecotype

Alternative nucleotides:
Predicted (Columbia)
Experimental (Wassilewskija)

| Sequence (bp) | Mismatch | Columbia/Wassilewskija |
|---|---|---|
| 597 | SNP | t/c |
| 996 | SNP | t/a |

The promoter was cloned in the vector: pNewbin4-HAP1-GFP
When cloned into the vector the promoter was operably linked to a marker, which was the type: GFP-ER
Promoter-marker vector was tested in: *Arabidopsis thaliana*, WS ecotype
Generation screened: XT1 Mature XT2 Seedling T2 Mature T3 Seedling
The spatial expression of the promoter-marker vector was found observed in and would be useful in expression in any or all of the following:
Primary Root    L epidermis L trichoblast L atrichoblast L root hair
Observed expression pattern of the promoter-marker vector was in:
T1 mature: No expression.
T2 seedling: Low expression in root epidermal cells at transition zone decreasing to expression in single cells at mid root
Misc. promoter information: Bidirectionality: Pass Exons: Pass  Repeats: No
The Ceres cDNA ID of the endogenous coding sequence to the promoter: 12326510
cDNA nucleotide sequence:
ACCACATTAATTTAAAACAAAGAAAACATCAAAATGGCTGAAAAAGTAAAGTCTGGTCAAGTT

TTTAACCTATTATGCATATTCTCGATCTTTTTCTTCCTCTTTGTGTTATCAGTGAATGTTTCGGC

TGATGTCGATTCTGAGAGAGCGGTGCCATCTGAAGATAAAACGACGACTGTTTGGCTAACTAA

AATCAAACGGTCCGGTAAAAATTATTGGGCTAAAGTTAGAGAGACTTTGGATCGTGGACAGTC

CCACTTCTTTCCTCCGAACACATATTTTACCGGAAAGAATGATGCGCCGATGGGAGCCGGTGA

AAATATGAAAGAGGCGGCGACGAGGAGCTTTGAGCATAGCAAAGCGACGGTGGAGGAAGCTG

CTAGATCAGCGGCAGAAGTGGTGAGTGATACGGCGGAAGCTGTGAAAGAAAAGGTGAAGAGG

AGCGTTTCCGGTGGAGTGACGCAGCCGTCGGAGGGATCTGAGGAGCTATAAATACGCAGTTGT

TCTAAGCTTATGGGTTTTAATTATTTAAATAATTAGTGTGTGTTTGAGATCAAAATGACACAGT

TTTGGGGGAGTATATCTCCACATCATATGTTGTTTGCATCACATGGTTTCTCTGTATACAACGA

CCAGATCCACATCACTCATTCTCGTCCTTCTTTTTGTCATGAATACAGAATAATATTTTAGATT

CTAC
Coding sequence:
MAEKVKSGQVFNLLCIFSIFFFLFVLSVNVSADVDSERAVPSEDKTTTVWLTKIKRSGKNYWAKVR

ETLDRGQSHFFPPNTYFTGKNDAPMGAGENMKEAATRSFEHSKATVEEAARSAAEVVSDTAEAV

KEKVKRSVSGGVTQPSEGSEEL*

Microarray data shows that the coding sequence was expressed in the following experiments, which shows that the promoter would be useful to modulate expression in situations similar to the following:

| CDNA_ID | SHORT_NAME | EXPT_REP_ID | IS_UP |
|---|---|---|---|
| 12326510 | At_Germinating_Seeds | 108461 | − |
| 12326510 | At_Germinating_Seeds | 108462 | − |
| 12326510 | At_Germinating_Seeds | 108464 | − |
| 12326510 | At_Drought_Flowers | 108473 | + |
| 12326510 | At_ap2_floral_buds | 108501 | − |
| 12326510 | At_100 uM_ABA | 108560 | + |
| 12326510 | At_100 uM_ABA | 108561 | + |
| 12326510 | At_Drought | 108572 | + |
| 12326510 | At_Drought | 108573 | + |
| 12326510 | At_Wounding | 108574 | + |
| 12326510 | At_4deg_Cold | 108579 | + |
| 12326510 | At_15 mM_NH4NO3_L-to-H | 108588 | − |
| 12326510 | At_15 mM_NH4NO3_L-to-H | 108589 | − |
| 12326510 | At_15 mM_NH4NO3_L-to-H | 108590 | − |
| 12326510 | At_15 mM_NH4NO3_L-to-H | 108591 | − |
| 12326510 | At_Ler-rhl_Root | 108594 | + |
| 12326510 | At_Ler-pi_Ovule | 108595 | + |

TABLE 1-continued

Promoter Sequences and Related Information

| | | | |
|---|---|---|---|
| 12326510 | At_100 uM_ABA | 108605 | + |
| 12326510 | At_100 uM_ABA | 108606 | + |
| 12326510 | At_100 uM_ABA | 108607 | + |
| 12326510 | At_100 uM_ABA | 108608 | + |
| 12326510 | At_100 uM_ABA | 108609 | + |
| 12326510 | At_100 uM_ABA_Mutants | 108624 | − |
| 12326510 | At_100 uM_ABA_Mutants | 20000069 | + |
| 12326510 | At_100 uM_ABA_Mutants | 20000070 | + |
| 12326510 | At_100 uM_ABA_Mutants | 20000071 | + |
| 12326510 | At_100 uM_ABA_Mutants | 20000072 | + |
| 12326510 | At_100 uM_ABA_Mutants | 20000086 | + |
| 12326510 | At_100 uM_ABA_Mutants | 20000087 | + |
| 12326510 | At_100 uM_ABA_Mutants | 20000088 | + |
| 12326510 | At_2 mM_SA_CS3726-Columbia | 20000089 | + |
| 12326510 | At_2 mM_SA_CS3726-Columbia | 20000090 | + |
| 12326510 | At_100 uM_ABA_Mutants | 20000117 | + |
| 12326510 | At_100 uM_ABA | 20000166 | + |
| 12326510 | At_100 uM_ABA | 20000169 | + |
| 12326510 | At_Germinating_Seeds | 20000179 | − |
| 12326510 | At_Germinating_Seeds | 20000180 | − |
| 12326510 | At_Shoots | 20000184 | − |
| 12326510 | At_Root-Tips-vs-Tops | 20000227 | + |
| 12326510 | At_Drought | 20000267 | + |
| 12326510 | At_100 mM_NaCl | 20000268 | + |
| 12326510 | At_100 mM_NaCl | 20000308 | + |
| 12326510 | At_Drought | 20000436 | + |
| 12326510 | At_Drought | 20000437 | + |
| 12326510 | At_1 uM_BR-BRZ | 20000441 | − |
| 12326510 | At_1 uM_BR-BRZ | 20000443 | − |
| 12326510 | At_100 uM_ABA | 20000453 | + |
| 12326510 | At_Guard_Cells | 20000495 | − |
| 12326510 | At_100 uM_ABA_Mutants | 20000573 | − |
| 12326510 | At_100 uM_ABA_Mutants | 20000574 | − |
| 12326510 | At_100 uM_ABA_Mutants | 20000575 | + |
| 12326510 | At_100 uM_ABA_Mutants | 20000576 | + |
| 12326510 | At_15 mM_NH4NO3_L-to-H | 20000709 | − |
| 12326510 | At_Far-red-induction | 20001248 | + |
| 12326510 | At_Line_Comparisons | 20001309 | − |
| 12326510 | At_Line_Comparisons | 20001310 | − |
| 12326510 | At_Far-red-induction | 20001450 | + |
| 12326510 | At_Far-red-induction | 20001451 | + |
| 12326510 | At_Drought_Soil_Dry | 20001553 | + |
| 12326510 | At_Drought_Soil_Dry | 20001554 | + |
| 12326510 | At_Drought_Soil_Dry | 20001555 | + |
| 12326510 | At_Drought_Soil_Dry | 20001556 | + |
| 12326510 | At_Drought_Soil_Dry | 20001557 | + |
| 12326510 | At_Drought_Soil_Dry | 20001559 | + |
| 12326510 | At_Far-red-enriched-adult | 20001770 | + |
| 12326510 | At_Interploidy_Crosses | 20001853 | + |
| 12326510 | At_Drought_Reproduction | 20001904 | + |
| 12326510 | At_Drought_Reproduction | 20001905 | + |
| 12326510 | At_Drought_Reproduction | 20001906 | + |
| 12326510 | At_Drought_Reproduction | 20001907 | + |
| 12326510 | At_Drought_Reproduction | 20001908 | + |
| 12326510 | At_Drought_Reproduction | 20001911 | + |
| 12326510 | At_Line_Comparisons | 20002009 | + |
| 12326510 | At_8deg_Cold | 20002105 | + |
| 12326510 | At_8deg_Cold | 20002107 | + |
| 12326510 | At_8deg_Cold | 20002108 | + |
| 12326510 | At_8deg_Cold | 20002109 | + |

The parameters for the microarray experiments listed above by Expt_Rep_ID and Short_Name are as follow below:

| CDNA_ID | SHORT_NAME | EXPT_REP_ID | PARAM_NAME | VALUE |
|---|---|---|---|---|
| 12326510 | At_Germinating_Seeds | 108461 | Age (day) | 1 vs. 0 |
| 12326510 | At_Germinating_Seeds | 108461 | Tissue | Germinating Seeds |
| 12326510 | At_Germinating_Seeds | 108462 | Age (day) | 2 vs. 0 |
| 12326510 | At_Germinating_Seeds | 108462 | Tissue | Germinating Seeds |
| 12326510 | At_Germinating_Seeds | 108464 | Age (day) | 4 vs. 0 |
| 12326510 | At_Germinating_Seeds | 108464 | Tissue | Germinating Seeds |
| 12326510 | At_Drought_Flowers | 108473 | Timepoint (hr) | 7 d |
| 12326510 | At_Drought_Flowers | 108473 | Treatment | Drought vs. No Drought |

TABLE 1-continued

Promoter Sequences and Related Information

| | | | | |
|---|---|---|---|---|
| 12326510 | At_Drought_Flowers | 108473 | Tissue | Flower |
| 12326510 | At_ap2_floral_buds | 108501 | Plant Line | ap2 (Ler.) |
| 12326510 | At_ap2_floral_buds | 108501 | Tissue | Closed Flower |
| 12326510 | At_100 uM_ABA | 108560 | Timepoint (hr) | 1 |
| 12326510 | At_100 uM_ABA | 108560 | Treatment | 100 uM ABA vs. No Treatment |
| 12326510 | At_100 uM_ABA | 108560 | Tissue | Aerial |
| 12326510 | At_100 uM_ABA | 108561 | Timepoint (hr) | 6 |
| 12326510 | At_100 uM_ABA | 108561 | Treatment | 100 uM ABA vs. No Treatment |
| 12326510 | At_100 uM_ABA | 108561 | Tissue | Aerial |
| 12326510 | At_Drought | 108572 | Timepoint (hr) | 1 |
| 12326510 | At_Drought | 108572 | Tissue | Aerial |
| 12326510 | At_Drought | 108572 | Treatment | Drought vs. No Drought |
| 12326510 | At_Drought | 108573 | Timepoint (hr) | 6 |
| 12326510 | At_Drought | 108573 | Tissue | Aerial |
| 12326510 | At_Drought | 108573 | Treatment | Drought vs. No Drought |
| 12326510 | At_Wounding | 108574 | Timepoint (hr) | 1 |
| 12326510 | At_Wounding | 108574 | Tissue | Aerial |
| 12326510 | At_Wounding | 108574 | Treatment | Wounding vs. No Wounding |
| 12326510 | At_4deg_Cold | 108579 | Timepoint (hr) | 6 |
| 12326510 | At_4deg_Cold | 108579 | Temperature (deg C.) | 4 vs. 22 |
| 12326510 | At_4deg_Cold | 108579 | Tissue | Aerial |
| 12326510 | At_15mM_NH4NO3_L-to-H | 108588 | Timepoint (hr) | 2 |
| 12326510 | At_15mM_NH4NO3_L-to-H | 108588 | Treatment | 15 mM NH4NO3 vs. 30 mM Mannitol |
| 12326510 | At_15mM_NH4NO3_L-to-H | 108588 | Tissue | Aerial |
| 12326510 | At_15mM_NH4NO3_L-to-H | 108589 | Timepoint (hr) | 6 |
| 12326510 | At_15mM_NH4NO3_L-to-H | 108589 | Treatment | 15 mM NH4NO3 vs. 30 mM Mannitol |
| 12326510 | At_15mM_NH4NO3_L-to-H | 108589 | Tissue | Aerial |
| 12326510 | At_15mM_NH4NO3_L-to-H | 108590 | Timepoint (hr) | 9 |
| 12326510 | At_15mM_NH4NO3_L-to-H | 108590 | Treatment | 15 mM NH4NO3 vs. 30 mM Mannitol |
| 12326510 | At_15mM_NH4NO3_L-to-H | 108590 | Tissue | Aerial |
| 12326510 | At_15mM_NH4NO3_L-to-H | 108591 | Timepoint (hr) | 12 |
| 12326510 | At_15mM_NH4NO3_L-to-H | 108591 | Treatment | 15 mM NH4NO3 vs. 30 mM Mannitol |
| 12326510 | At_15mM_NH4NO3_L-to-H | 108591 | Tissue | Aerial |
| 12326510 | At_Ler-rhl_Root | 108594 | Plant Line | Ler_rhl |
| 12326510 | At_Ler-rhl_Root | 108594 | Tissue | Roots |
| 12326510 | At_Ler-pi_Ovule | 108595 | Plant Line | Ler_pi |
| 12326510 | At_Ler-pi_Ovule | 108595 | Tissue | Ovules |
| 12326510 | At_100 uM_ABA | 108605 | Timepoint (hr) | 6 |
| 12326510 | At_100 uM_ABA | 108605 | Treatment | 100 uM ABA vs. No Treatment |
| 12326510 | At_100 uM_ABA | 108605 | Tissue | Aerial |
| 12326510 | At_100 uM_ABA | 108606 | Timepoint (hr) | 2 |
| 12326510 | At_100 uM_ABA | 108606 | Treatment | 100 uM ABA vs. No Treatment |
| 12326510 | At_100 uM_ABA | 108606 | Tissue | Aerial |
| 12326510 | At_100 uM_ABA | 108607 | Timepoint (hr) | 4 |
| 12326510 | At_100 uM_ABA | 108607 | Treatment | 100 uM ABA vs. No Treatment |
| 12326510 | At_100 uM_ABA | 108607 | Tissue | Aerial |
| 12326510 | At_100 uM_ABA | 108608 | Timepoint (hr) | 1 |
| 12326510 | At_100 uM_ABA | 108608 | Treatment | 100 uM ABA vs. No Treatment |
| 12326510 | At_100 uM_ABA | 108608 | Tissue | Aerial |
| 12326510 | At_100 uM_ABA | 108609 | Timepoint (hr) | 24 |

TABLE 1-continued

Promoter Sequences and Related Information

| | | | | |
|---|---|---|---|---|
| 12326510 | At_100 uM_ABA | 108609 | Treatment | 100 uM ABA vs. No Treatment |
| 12326510 | At_100 uM_ABA | 108609 | Tissue | Aerial |
| 12326510 | At_100 uM_ABA_Mutants | 108624 | Timepoint (hr) | 6 |
| 12326510 | At_100 uM_ABA_Mutants | 108624 | Treatment | 100 uM ABA vs. No Treatment |
| 12326510 | At_100 uM_ABA_Mutants | 108624 | Tissue | Aerial |
| 12326510 | At_100 uM_ABA_Mutants | 108624 | Plant Line | CS8105 |
| 12326510 | At_100 uM_ABA_Mutants | 20000069 | Timepoint (hr) | 6 |
| 12326510 | At_100 uM_ABA_Mutants | 20000069 | Treatment | 100 uM ABA vs. No Treatment |
| 12326510 | At_100 uM_ABA_Mutants | 20000069 | Tissue | Aerial |
| 12326510 | At_100 uM_ABA_Mutants | 20000069 | Plant Line | CS23 |
| 12326510 | At_100 uM_ABA_Mutants | 20000070 | Timepoint (hr) | 6 |
| 12326510 | At_100 uM_ABA_Mutants | 20000070 | Treatment | 100 uM ABA vs. No Treatment |
| 12326510 | At_100 uM_ABA_Mutants | 20000070 | Tissue | Aerial |
| 12326510 | At_100 uM_ABA_Mutants | 20000070 | Plant Line | CS24 |
| 12326510 | At_100 uM_ABA_Mutants | 20000071 | Timepoint (hr) | 6 |
| 12326510 | At_100 uM_ABA_Mutants | 20000071 | Treatment | 100 uM ABA vs. No Treatment |
| 12326510 | At_100 uM_ABA_Mutants | 20000071 | Tissue | Aerial |
| 12326510 | At_100 uM_ABA_Mutants | 20000071 | Plant Line | CS8104 |
| 12326510 | At_100 uM_ABA_Mutants | 20000072 | Timepoint (hr) | 6 |
| 12326510 | At_100 uM_ABA_Mutants | 20000072 | Treatment | 100 uM ABA vs. No Treatment |
| 12326510 | At_100 uM_ABA_Mutants | 20000072 | Tissue | Aerial |
| 12326510 | At_100 uM_ABA_Mutants | 20000072 | Plant Line | CS8105 |
| 12326510 | At_100 uM_ABA_Mutants | 20000086 | Timepoint (hr) | 6 |
| 12326510 | At_100 uM_ABA_Mutants | 20000086 | Treatment | 100 uM ABA vs. No Treatment |
| 12326510 | At_100 uM_ABA_Mutants | 20000086 | Tissue | Aerial |
| 12326510 | At_100 uM_ABA_Mutants | 20000086 | Plant Line | CS22 |
| 12326510 | At_100 uM_ABA_Mutants | 20000087 | Timepoint (hr) | 6 |
| 12326510 | At_100 uM_ABA_Mutants | 20000087 | Treatment | 100 uM ABA vs. No Treatment |
| 12326510 | At_100 uM_ABA_Mutants | 20000087 | Tissue | Aerial |
| 12326510 | At_100 uM_ABA_Mutants | 20000087 | Plant Line | WS |
| 12326510 | At_100 uM_ABA_Mutants | 20000088 | Timepoint (hr) | 6 |
| 12326510 | At_100 uM_ABA_Mutants | 20000088 | Treatment | 100 uM ABA vs. No Treatment |
| 12326510 | At_100 uM_ABA_Mutants | 20000088 | Tissue | Aerial |
| 12326510 | At_100 uM_ABA_Mutants | 20000088 | Plant Line | Landsberg |
| 12326510 | At_2mM_SA_CS3726-Columbia | 20000089 | Timepoint (hr) | 6 |
| 12326510 | At_2mM_SA_CS3726-Columbia | 20000089 | Treatment | 2 mM SA vs. No Treatment |
| 12326510 | At_2mM_SA_CS3726-Columbia | 20000089 | Tissue | Aerial |
| 12326510 | At_2mM_SA_CS3726-Columbia | 20000089 | Plant Line | CS3726 |
| 12326510 | At_2mM_SA_CS3726-Columbia | 20000090 | Timepoint (hr) | 6 |
| 12326510 | At_2mM_SA_CS3726-Columbia | 20000090 | Treatment | 2 mM SA vs. No Treatment |
| 12326510 | At_2mM_SA_CS3726-Columbia | 20000090 | Tissue | Aerial |
| 12326510 | At_2mM_SA_CS3726-Columbia | 20000090 | Plant Line | Columbia |
| 12326510 | At_100 uM_ABA_Mutants | 20000117 | Timepoint (hr) | 6 |
| 12326510 | At_100 uM_ABA_Mutants | 20000117 | Treatment | 100 uM ABA vs. No Treatment |
| 12326510 | At_100 uM_ABA_Mutants | 20000117 | Tissue | Aerial |
| 12326510 | At_100 uM_ABA_Mutants | 20000117 | Plant Line | Columbia |
| 12326510 | At_100 uM_ABA | 20000166 | Timepoint (hr) | 1 |
| 12326510 | At_100 uM_ABA | 20000166 | Age (day) | 14 |

TABLE 1-continued

Promoter Sequences and Related Information

| | | | | |
|---|---|---|---|---|
| 12326510 | At_100 uM_ABA | 20000166 | Treatment | 100 uM ABA vs. No Treatment |
| 12326510 | At_100 uM_ABA | 20000166 | Organism | A. thaliana |
| 12326510 | At_100 uM_ABA | 20000166 | Tissue | Aerial |
| 12326510 | At_100 uM_ABA | 20000166 | Plant Line | WS |
| 12326510 | At_100 uM_ABA | 20000169 | Timepoint (hr) | 6 |
| 12326510 | At_100 uM_ABA | 20000169 | Age (day) | 14 |
| 12326510 | At_100 uM_ABA | 20000169 | Treatment | 100 uM ABA vs. No Treatment |
| 12326510 | At_100 uM_ABA | 20000169 | Organism | A. thaliana |
| 12326510 | At_100 uM_ABA | 20000169 | Tissue | Aerial |
| 12326510 | At_100 uM_ABA | 20000169 | Plant Line | WS |
| 12326510 | At_Germinating_Seeds | 20000179 | Age (hr) | 6 vs. 0 |
| 12326510 | At_Germinating_Seeds | 20000179 | Organism | A. thaliana |
| 12326510 | At_Germinating_Seeds | 20000179 | Tissue | Germinating Seeds |
| 12326510 | At_Germinating_Seeds | 20000179 | Plant Line | WS |
| 12326510 | At_Germinating_Seeds | 20000180 | Age (hr) | 24 vs. 0 |
| 12326510 | At_Germinating_Seeds | 20000180 | Organism | A. thaliana |
| 12326510 | At_Germinating_Seeds | 20000180 | Tissue | Germinating Seeds |
| 12326510 | At_Germinating_Seeds | 20000180 | Plant Line | WS |
| 12326510 | At_Shoots | 20000184 | Age (day) | 7 vs. 21 |
| 12326510 | At_Shoots | 20000184 | Organism | A. thaliana |
| 12326510 | At_Shoots | 20000184 | Tissue | Shoots vs. Whole Plant |
| 12326510 | At_Shoots | 20000184 | Plant Line | WS |
| 12326510 | At_Root-Tips-vs-Tops | 20000227 | Age (day) | 7, 10, 14 |
| 12326510 | At_Root-Tips-vs-Tops | 20000227 | Organism | A. thaliana |
| 12326510 | At_Root-Tips-vs-Tops | 20000227 | Tissue | Root Tips vs. Root Tops |
| 12326510 | At_Root-Tips-vs-Tops | 20000227 | Plant Line | WS |
| 12326510 | At_Drought | 20000267 | Timepoint (hr) | 6 |
| 12326510 | At_Drought | 20000267 | Age (day) | 7 |
| 12326510 | At_Drought | 20000267 | Organism | A. thaliana |
| 12326510 | At_Drought | 20000267 | Treatment | Drought vs. No Drought |
| 12326510 | At_Drought | 20000267 | Tissue | Whole Plant |
| 12326510 | At_Drought | 20000267 | Plant Line | WS |
| 12326510 | At_100mM_NaCl | 20000268 | Timepoint (hr) | 6 |
| 12326510 | At_100mM_NaCl | 20000268 | Age (day) | 14 |
| 12326510 | At_100mM_NaCl | 20000268 | Treatment | 100 mM NaCl vs. No Treatment |
| 12326510 | At_100mM_NaCl | 20000268 | Organism | A. thaliana |
| 12326510 | At_100mM_NaCl | 20000268 | Tissue | Whole Plant |
| 12326510 | At_100mM_NaCl | 20000268 | Plant Line | WS |
| 12326510 | At_100mM_NaCl | 20000308 | Age (day) | 17 |
| 12326510 | At_100mM_NaCl | 20000308 | Timepoint (hr) | 72 |
| 12326510 | At_100mM_NaCl | 20000308 | Treatment | 100 mM NaCl vs. No Treatment |
| 12326510 | At_100mM_NaCl | 20000308 | Organism | A. thaliana |
| 12326510 | At_100mM_NaCl | 20000308 | Tissue | Whole Plant |
| 12326510 | At_100mM_NaCl | 20000308 | Plant Line | WS |
| 12326510 | At_Drought | 20000436 | Age (day) | 7 |
| 12326510 | At_Drought | 20000436 | Timepoint (hr) | 12 |
| 12326510 | At_Drought | 20000436 | Organism | A. thaliana |
| 12326510 | At_Drought | 20000436 | Treatment | Drought vs. No Drought |
| 12326510 | At_Drought | 20000436 | Tissue | Whole Plant |
| 12326510 | At_Drought | 20000436 | Plant Line | WS |
| 12326510 | At_Drought | 20000437 | Age (day) | 8 |
| 12326510 | At_Drought | 20000437 | Timepoint (hr) | 24 |
| 12326510 | At_Drought | 20000437 | Organism | A. thaliana |
| 12326510 | At_Drought | 20000437 | Treatment | Drought vs. No Drought |
| 12326510 | At_Drought | 20000437 | Tissue | Whole Plant |
| 12326510 | At_Drought | 20000437 | Plant Line | WS |
| 12326510 | At_1 uM_BR-BRZ | 20000441 | Treatment | 1 uM BR vs. No Treatment |
| 12326510 | At_1 uM_BR-BRZ | 20000441 | Tissue | Shoot Apices |
| 12326510 | At_1 uM_BR-BRZ | 20000443 | Treatment | 1 uM BRZ vs. No Treatment |
| 12326510 | At_1 uM_BR-BRZ | 20000443 | Tissue | Shoot Apices |
| 12326510 | At_100 uM_ABA | 20000453 | Age (day) | 15 |

TABLE 1-continued

Promoter Sequences and Related Information

| 12326510 | At_100 uM_ABA | 20000453 | Timepoint (hr) | 24 |
|---|---|---|---|---|
| 12326510 | At_100 uM_ABA | 20000453 | Treatment | 100 uM ABA vs. No Treatment |
| 12326510 | At_100 uM_ABA | 20000453 | Organism | A. thaliana |
| 12326510 | At_100 uM_ABA | 20000453 | Tissue | Aerial |
| 12326510 | At_100 uM_ABA | 20000453 | Plant Line | WS |
| 12326510 | At_Guard_Cells | 20000495 | Harvest Date | Aug. 2, 2002 |
| 12326510 | At_Guard_Cells | 20000495 | Organism | A. thaliana |
| 12326510 | At_Guard_Cells | 20000495 | Tissue | Guard Cells vs. Leaves |
| 12326510 | At_100 uM_ABA_Mutants | 20000573 | Organism | A. thaliana |
| 12326510 | At_100 uM_ABA_Mutants | 20000573 | Plant Line | CS22 vs. Ler wt |
| 12326510 | At_100 uM_ABA_Mutants | 20000573 | Timepoint (hr) | N/A |
| 12326510 | At_100 uM_ABA_Mutants | 20000573 | Treatment | None |
| 12326510 | At_100 uM_ABA_Mutants | 20000573 | Tissue | Whole Plant |
| 12326510 | At_100 uM_ABA_Mutants | 20000574 | Organism | A. thaliana |
| 12326510 | At_100 uM_ABA_Mutants | 20000574 | Plant Line | CS23 vs. Ler wt |
| 12326510 | At_100 uM_ABA_Mutants | 20000574 | Timepoint (hr) | N/A |
| 12326510 | At_100 uM_ABA_Mutants | 20000574 | Treatment | None |
| 12326510 | At_100 uM_ABA_Mutants | 20000574 | Tissue | Whole Plant |
| 12326510 | At_100 uM_ABA_Mutants | 20000575 | Timepoint (hr) | 6 |
| 12326510 | At_100 uM_ABA_Mutants | 20000575 | Treatment | 1 uM ABA vs. No Treatment |
| 12326510 | At_100 uM_ABA_Mutants | 20000575 | Organism | A. thaliana |
| 12326510 | At_100 uM_ABA_Mutants | 20000575 | Plant Line | CS22 |
| 12326510 | At_100 uM_ABA_Mutants | 20000575 | Tissue | Whole Plant |
| 12326510 | At_100 uM_ABA_Mutants | 20000576 | Timepoint (hr) | 6 |
| 12326510 | At_100 uM_ABA_Mutants | 20000576 | Treatment | 1 uM ABA vs. No Treatment |
| 12326510 | At_100 uM_ABA_Mutants | 20000576 | Organism | A. thaliana |
| 12326510 | At_100 uM_ABA_Mutants | 20000576 | Plant Line | CS23 |
| 12326510 | At_100 uM_ABA_Mutants | 20000576 | Tissue | Whole Plant |
| 12326510 | At_15mM_NH4NO3_L-to-H | 20000709 | Timepoint (hr) | 4 |
| 12326510 | At_15mM_NH4NO3_L-to-H | 20000709 | Age (hr) | 14 |
| 12326510 | At_15mM_NH4NO3_L-to-H | 20000709 | Treatment | 15 mM NH4NO3 vs. 30 mM Mannitol |
| 12326510 | At_15mM_NH4NO3_L-to-H | 20000709 | Organism | A. thaliana |
| 12326510 | At_15mM_NH4NO3_L-to-H | 20000709 | Tissue | Aerial |
| 12326510 | At_15mM_NH4NO3_L-to-H | 20000709 | Plant Line | WS |
| 12326510 | At_Far-red-induction | 20001248 | Timepoint (hr) | 4 |
| 12326510 | At_Far-red-induction | 20001248 | Age (day) | 7 |
| 12326510 | At_Far-red-induction | 20001248 | Organism | A. thaliana |
| 12326510 | At_Far-red-induction | 20001248 | Plant Line | Columbia |
| 12326510 | At_Far-red-induction | 20001248 | Light | Far-red vs. White |
| 12326510 | At_Far-red-induction | 20001248 | Tissue | Whole Plant |
| 12326510 | At_Line_Comparisons | 20001309 | Plant Line | WBin4-WX49R-A vs. WS |
| 12326510 | At_Line_Comparisons | 20001310 | Plant Line | WBin4-WX17-A vs. WS |
| 12326510 | At_Far-red-induction | 20001450 | Age (day) | 7 |
| 12326510 | At_Far-red-induction | 20001450 | Timepoint (hr) | 8 |
| 12326510 | At_Far-red-induction | 20001450 | Organism | A. thaliana |
| 12326510 | At_Far-red-induction | 20001450 | Plant Line | Columbia |
| 12326510 | At_Far-red-induction | 20001450 | Light | Far-red vs. White |
| 12326510 | At_Far-red-induction | 20001450 | Tissue | Whole Plant |
| 12326510 | At_Far-red-induction | 20001451 | Age (day) | 8 |
| 12326510 | At_Far-red-induction | 20001451 | Timepoint (hr) | 24 |
| 12326510 | At_Far-red-induction | 20001451 | Organism | A. thaliana |
| 12326510 | At_Far-red-induction | 20001451 | Plant Line | Columbia |
| 12326510 | At_Far-red-induction | 20001451 | Light | Far-red vs. White |
| 12326510 | At_Far-red-induction | 20001451 | Tissue | Whole Plant |
| 12326510 | At_Drought_Soil_Dry | 20001553 | Timepoint (day) | 5 |
| 12326510 | At_Drought_Soil_Dry | 20001553 | Age (day) | 19 |
| 12326510 | At_Drought_Soil_Dry | 20001553 | Organism | A. thaliana |
| 12326510 | At_Drought_Soil_Dry | 20001553 | Treatment | Drought vs. No Drought |
| 12326510 | At_Drought_Soil_Dry | 20001553 | Post Timepoint (hr) | None |
| 12326510 | At_Drought_Soil_Dry | 20001553 | Post-Treatment | None |

TABLE 1-continued

Promoter Sequences and Related Information

| | | | | |
|---|---|---|---|---|
| 12326510 | At_Drought_Soil_Dry | 20001553 | Plant Line | WS |
| 12326510 | At_Drought_Soil_Dry | 20001554 | Timepoint (day) | 7 |
| 12326510 | At_Drought_Soil_Dry | 20001554 | Age (day) | 21 |
| 12326510 | At_Drought_Soil_Dry | 20001554 | Organism | A. thaliana |
| 12326510 | At_Drought_Soil_Dry | 20001554 | Treatment | Drought vs. No Drought |
| 12326510 | At_Drought_Soil_Dry | 20001554 | Post Timepoint (hr) | None |
| 12326510 | At_Drought_Soil_Dry | 20001554 | Post-Treatment | None |
| 12326510 | At_Drought_Soil_Dry | 20001554 | Plant Line | WS |
| 12326510 | At_Drought_Soil_Dry | 20001555 | Timepoint (day) | 10 |
| 12326510 | At_Drought_Soil_Dry | 20001555 | Age (day) | 24 |
| 12326510 | At_Drought_Soil_Dry | 20001555 | Organism | A. thaliana |
| 12326510 | At_Drought_Soil_Dry | 20001555 | Treatment | Drought vs. No Drought |
| 12326510 | At_Drought_Soil_Dry | 20001555 | Post Timepoint (hr) | None |
| 12326510 | At_Drought_Soil_Dry | 20001555 | Post-Treatment | None |
| 12326510 | At_Drought_Soil_Dry | 20001555 | Plant Line | WS |
| 12326510 | At_Drought_Soil_Dry | 20001556 | Timepoint (day) | 12 |
| 12326510 | At_Drought_Soil_Dry | 20001556 | Age (day) | 26 |
| 12326510 | At_Drought_Soil_Dry | 20001556 | Organism | A. thaliana |
| 12326510 | At_Drought_Soil_Dry | 20001556 | Treatment | Drought vs. No Drought |
| 12326510 | At_Drought_Soil_Dry | 20001556 | Post Timepoint (hr) | None |
| 12326510 | At_Drought_Soil_Dry | 20001556 | Post-Treatment | None |
| 12326510 | At_Drought_Soil_Dry | 20001556 | Plant Line | WS |
| 12326510 | At_Drought_Soil_Dry | 20001557 | Post Timepoint (hr) | 3 |
| 12326510 | At_Drought_Soil_Dry | 20001557 | Timepoint (day) | 13 |
| 12326510 | At_Drought_Soil_Dry | 20001557 | Age (day) | 27 |
| 12326510 | At_Drought_Soil_Dry | 20001557 | Organism | A. thaliana |
| 12326510 | At_Drought_Soil_Dry | 20001557 | Treatment | Drought vs. No Drought |
| 12326510 | At_Drought_Soil_Dry | 20001557 | Post-Treatment | Re-Water vs. No Drought |
| 12326510 | At_Drought_Soil_Dry | 20001557 | Plant Line | WS |
| 12326510 | At_Drought_Soil_Dry | 20001559 | Timepoint (day) | 14 |
| 12326510 | At_Drought_Soil_Dry | 20001559 | Age (day) | 28 |
| 12326510 | At_Drought_Soil_Dry | 20001559 | Post Timepoint (hr) | 29 |
| 12326510 | At_Drought_Soil_Dry | 20001559 | Organism | A. thaliana |
| 12326510 | At_Drought_Soil_Dry | 20001559 | Treatment | Drought vs. No Drought |
| 12326510 | At_Drought_Soil_Dry | 20001559 | Post-Treatment | Re-Water vs. No Drought |
| 12326510 | At_Drought_Soil_Dry | 20001559 | Plant Line | WS |
| 12326510 | At_Far-red-enriched-adult | 20001770 | Timepoint (hr) | 8 |
| 12326510 | At_Far-red-enriched-adult | 20001770 | Age (day) | 28 |
| 12326510 | At_Far-red-enriched-adult | 20001770 | Organism | A. thaliana |
| 12326510 | At_Far-red-enriched-adult | 20001770 | Tissue | Aerial |
| 12326510 | At_Far-red-enriched-adult | 20001770 | Plant Line | Columbia |
| 12326510 | At_Far-red-enriched-adult | 20001770 | Light | Far-red enriched vs. White |
| 12326510 | At_Interploidy_Crosses | 20001853 | Age (day) | 5 |
| 12326510 | At_Interploidy_Crosses | 20001853 | Organism | A. thaliana |
| 12326510 | At_Interploidy_Crosses | 20001853 | Plant Line | Columbia |
| 12326510 | At_Interploidy_Crosses | 20001853 | Cross | Fis1 vs. 2X x 2X |
| 12326510 | At_Interploidy_Crosses | 20001853 | Tissue | Siliques |
| 12326510 | At_Drought_Reproduction | 20001904 | Timepoint (day) | 7 |
| 12326510 | At_Drought_Reproduction | 20001904 | Age (day) | 37 |
| 12326510 | At_Drought_Reproduction | 20001904 | Organism | A. thaliana |
| 12326510 | At_Drought_Reproduction | 20001904 | Treatment | Drought vs. No Drought |
| 12326510 | At_Drought_Reproduction | 20001904 | Tissue | Rosettes |

TABLE 1-continued

Promoter Sequences and Related Information

| | | | | |
|---|---|---|---|---|
| 12326510 | At_Drought_Reproduction | 20001904 | Plant Line | WS |
| 12326510 | At_Drought_Reproduction | 20001905 | Timepoint (day) | 10 |
| 12326510 | At_Drought_Reproduction | 20001905 | Age (day) | 40 |
| 12326510 | At_Drought_Reproduction | 20001905 | Organism | *A. thaliana* |
| 12326510 | At_Drought_Reproduction | 20001905 | Treatment | Drought vs. No Drought |
| 12326510 | At_Drought_Reproduction | 20001905 | Tissue | Rosettes |
| 12326510 | At_Drought_Reproduction | 20001905 | Plant Line | WS |
| 12326510 | At_Drought_Reproduction | 20001906 | Timepoint (day) | 5 |
| 12326510 | At_Drought_Reproduction | 20001906 | Age (day) | 35 |
| 12326510 | At_Drought_Reproduction | 20001906 | Organism | *A. thaliana* |
| 12326510 | At_Drought_Reproduction | 20001906 | Treatment | Drought vs. No Drought |
| 12326510 | At_Drought_Reproduction | 20001906 | Tissue | Siliques |
| 12326510 | At_Drought_Reproduction | 20001906 | Plant Line | WS |
| 12326510 | At_Drought_Reproduction | 20001907 | Timepoint (day) | 7 |
| 12326510 | At_Drought_Reproduction | 20001907 | Age (day) | 37 |
| 12326510 | At_Drought_Reproduction | 20001907 | Organism | *A. thaliana* |
| 12326510 | At_Drought_Reproduction | 20001907 | Treatment | Drought vs. No Drought |
| 12326510 | At_Drought_Reproduction | 20001907 | Plant Line | WS |
| 12326510 | At_Drought_Reproduction | 20001908 | Timepoint (day) | 10 |
| 12326510 | At_Drought_Reproduction | 20001908 | Age (day) | 40 |
| 12326510 | At_Drought_Reproduction | 20001908 | Organism | *A. thaliana* |
| 12326510 | At_Drought_Reproduction | 20001908 | Treatment | Drought vs. No Drought |
| 12326510 | At_Drought_Reproduction | 20001908 | Tissue | Siliques |
| 12326510 | At_Drought_Reproduction | 20001908 | Plant Line | WS |
| 12326510 | At_Drought_Reproduction | 20001911 | Timepoint (day) | 10 |
| 12326510 | At_Drought_Reproduction | 20001911 | Age (day) | 40 |
| 12326510 | At_Drought_Reproduction | 20001911 | Organism | *A. thaliana* |
| 12326510 | At_Drought_Reproduction | 20001911 | Treatment | Drought vs. No Drought |
| 12326510 | At_Drought_Reproduction | 20001911 | Tissue | Flowers |
| 12326510 | At_Drought_Reproduction | 20001911 | Plant Line | WS |
| 12326510 | At_Line_Comparisons | 20002009 | Plant Line | ME01642 vs. WS |
| 12326510 | At_8deg_Cold | 20002105 | Age (day) | 7 |
| 12326510 | At_8deg_Cold | 20002105 | Timepoint (hr) | 8 |
| 12326510 | At_8deg_Cold | 20002105 | Temperature (deg C.) | 8 vs. 22 |
| 12326510 | At_8deg_Cold | 20002105 | Organism | *A. thaliana* |
| 12326510 | At_8deg_Cold | 20002105 | Tissue | Whole Plant |
| 12326510 | At_8deg_Cold | 20002105 | Plant Line | WS |
| 12326510 | At_8deg_Cold | 20002107 | Age (day) | 11 |
| 12326510 | At_8deg_Cold | 20002107 | Timepoint (hr) | 96 |
| 12326510 | At_8deg_Cold | 20002107 | Temperature (deg C.) | 8 vs. 22 |
| 12326510 | At_8deg_Cold | 20002107 | Organism | *A. thaliana* |
| 12326510 | At_8deg_Cold | 20002107 | Tissue | Whole Plant |
| 12326510 | At_8deg_Cold | 20002107 | Plant Line | WS |
| 12326510 | At_8deg_Cold | 20002108 | Age (day) | 14 |

TABLE 1-continued

Promoter Sequences and Related Information

| 12326510 | At_8deg_Cold | 20002108 | Timepoint (hr) | 168 |
|---|---|---|---|---|
| 12326510 | At_8deg_Cold | 20002108 | Temperature (deg C.) | 8 vs. 22 |
| 12326510 | At_8deg_Cold | 20002108 | Organism | *A. thaliana* |
| 12326510 | At_8deg_Cold | 20002108 | Tissue | Whole Plant |
| 12326510 | At_8deg_Cold | 20002108 | Plant Line | WS |
| 12326510 | At_8deg_Cold | 20002108 | Age (day) | 16 |
| 12326510 | At_8deg_Cold | 20002109 | Timepoint (hr) | 216 |
| 12326510 | At_8deg_Cold | 20002109 | Temperature (deg C.) | 8 vs. 22 |
| 12326510 | At_8deg_Cold | 20002109 | Organism | *A. thaliana* |
| 12326510 | At_8deg_Cold | 20002109 | Tissue | Whole Plant |
| 12326510 | At_8deg_Cold | 20002109 | Plant Line | WS |

Promoter YP0289

Modulates the gene: phi-1-related protein
The GenBank description of the gene: NM_125822 *Arabidopsis thaliana* phi-1-related protein
(At5g64260) mRNA, complete cds gi|30697983|ref|NM_125822.2|[30697983]
The promoter sequence:
5' caaacaattactgctcaatgtatttgcgtatagagcatgtccaataccatgcctcatgatgtgagattg cgaggcggagtcagagaacgagttaaagtgacgacgttttttttgtttttttgggcatagtgtaaagtga tattaaatttcatggttggcaggtgactgaaaataaaaatgtgtataggatgtgtttatatgctgacgga aaaatagttactcaactaatacagatctttataaagagtatataagtctatggttaatcatgaatggcaat atataagagtagatgagatttatgtttatattgaaacaagggaaagatatgtgtaattgaaacaatggcaa aatataagtcaaatcaaactggtttctgataatatatgtgtttgaatcaatgtatatcttggtattcaaaac caaaacaactacaccaatttctttaaaaaaccagttgatctaataactacattttaatactagtagctatt agctgaatttcataatcaatttcttgcattaaaatttaaagtgggttttgcatttaaacttactcggtttg tattaatagactttcaaagattaaagaaaactactgcattcagagaataaagctatcttactaaacacta cttttaaagtttctttttcacttattaatcttcttttacaaatggatctgtctctctgcatggcaaaata tcttacactaattttatttcttgtttgataacaaatttatcggctaagcatcacttaaatttaatacac gttatgaagacttaaaccacgtcacacTATAagaaccttacaggctgtcaaacacccttccctacccactc acatctctccacgtggcaatctttgatattgacaccttagccactacagctgtcacactcctctctcggtt tcaaaacaacatctctggtataaata 3'- aatcaaaacctctcctatatctcttcaatctgatataactacccttctcaATG
The promoter was cloned from the organism: *Arabidopsis thaliana*, WS ecotype Alternative nucleotides:
Predicted (Columbia)
Experimental (Wassilewskija)

| Predicted Position (bp) | Mismatch | Columbia/Wassilewskija |
|---|---|---|
| 138 | SNP | t/— |
| 529 | SNP | a/t |
| 561 | SNP | a/g |
| 666 | Read Error | c/c |
| 702 | SNP | t/a |
| 820 | SNP | t/a |

The promoter was cloned in the vector: pNewbin4-HAP1-GFP
When cloned into the vector the promoter was operably linked to a marker, which was the type: GFP-ER
Promoter-marker vector was tested in: *Arabidopsis thaliana*, WS ecotype
Generation screened: XT1 Mature  XT2 Seedling  T2 Mature  T3 Seedling The spatial expression of the promoter-marker vector was found observed in and would be useful in expression in any or all of the following:

| | |
|---|---|
| Flower | L anther |
| Ovule | Post-fertilization: L endothelium |
| Cotyledon | H epidermis H petiole |
| Rosette Leaf | H trichome |
| Primary Root | H epidermis H root hairs |

TABLE 1-continued

Promoter Sequences and Related Information

Observed expression pattern of the promoter-marker vector was in:
Expression very weak and may not have been detected by standard screen. Only tissue with visible GFP
expression is analyzed by confocal microscopy. This may account for the expressing/screened ratio.
T1 mature: Low GFP expression in endothelium cells of mature ovules and tapetum cell layer of anthers.
Not expressed in pollen. T2 seedling: High GFP expression specific to epidermal tissues of cotyledons,
root and trichomes of rosette leaves.
Misc. promoter information: Bidirectionality: Exons:    Repeats:
The Ceres cDNA ID of the endogenous coding sequence to the promoter: 12326995
cDNA nucleotide sequence:
aaatcaaaacctctcctatatctcttcaatctgatataactacccttctcaatggcttctaattaccgttt tgccatcttcctcactctcttttttcgccaccgctggtttctccgccgccgcgttggtcgaggagcagccgc ttgttatgaaataccacaacggagttctgttgaaaggtaacatcacagtcaatctcgtatggtacgggaaa ttcacaccgatccaacggtccgtaatcgtcgatttcatccactcgctaaactccaaagacgttgcatcttc cgccgcagttccttccgttgcttcgtggtggaagacgacggagaaatacaaaggtggctcttcaacactcg tcgtcgggaaacagcttctactcgagaactatcctctcggaaaatctctcaaaaatccttacctccgtgct ttatccaccaaacttaacggcggtctccgttccataaccgtcgttctaacggcgaaagatgttaccgtcga aagattctgtatgagccggtgcgggactcacggatcctccggttcgaatcccgtcgcgcagctaacggcg cggcttacgtatgggtcgggaactccgagacgcagtgccctggatattgcgcgtggccgtttcaccagccg atttacggaccacaaacgccgccgttagtagcgcctaacggtgacgttggagttgacggaatgattataaa ccttgccacacttctagctaacaccgtgacgaatccgtttaataacggatattaccaaggcccaccaactg caccgcttgaagctgtgtctgcttgtcctggtatattcgggtcaggttcttatccgggttacgcgggtcgg gtacttgttgacaaaacaacccgggtctagttacaacgctcgtggactcgccggtaggaaatatctattgcc ggcgatgtgggatccgcagagttcgacgtgcaagactctggtttgatccaagggatgtgagtaagacacgt ggcatagtagtgagagcgatgacgagatctagacggcatgtgtagtcaaaatcaagttgcacgcgagcgtg tgtataaaaaaatctttcgggtttgggtctcgggtttggattgtggataggggctctctctttgcttttttgt cgttttgtaatgacgtgtaaaaactgtactcggaaatgtgaagaatgcatataaaataataaaaaatcatt ttgtttctact
Coding sequence:
MASNYRFAIFLTLFFATAGFSAAALVEEQPLVMKYHNGVLLKGNITVNLVWYGKFTPIQRSVIVDF

IHSLNSKDVASSAAVPSVASWWKTTEKYKGGSSTLVVGKQLLLENYPLGKSLKNPYLRALSTKLN

GGLRSITVVLTAKDVTVERFCMSRCGTHGSSGSNPRRAANGAAYVWVGNSETQCPGYCAWPFHQ

PIYGPQTPPLVAPNGDVGVDGMIINLATLLANTVTNPFNNGYYQGPPTAPLEAVSACPGIFGSGSYP

GYAGRVLVDKTTGSSYNARGLAGRKYLLPAMWDPQSSTCKTLV*

Microarray data shows that the coding sequence was expressed in the following experiments, which
shows that the promoter would be useful to modulate expression in situations similar to the following:

| CDNA_ID | SHORT_NAME | EXPT_REP_ID | IS_UP |
| --- | --- | --- | --- |
| 12326995 | At_Root_Tips | 108434 | − |
| 12326995 | At_Germinating_Seeds | 108462 | + |
| 12326995 | At_Germinating_Seeds | 108463 | + |
| 12326995 | At_42deg_Heat | 108576 | + |
| 12326995 | At_100 uM_ABA_Mutants | 20000072 | + |
| 12326995 | At_42deg_Heat | 20000111 | + |
| 12326995 | At_42deg_Heat | 20000144 | + |
| 12326995 | At_100 uM_ABA | 20000166 | + |
| 12326995 | At_100 uM_ABA | 20000169 | + |
| 12326995 | At_2mM_SA | 20000181 | + |
| 12326995 | At_Siliques | 20000234 | − |
| 12326995 | At_Siliques | 20000235 | − |
| 12326995 | At_Siliques | 20000236 | − |
| 12326995 | At_Open_Flower | 20000265 | − |
| 12326995 | At_Open_Flower | 20000286 | − |
| 12326995 | At_Pollen | 20000326 | − |
| 12326995 | At_100 uM_ABA | 20000453 | + |
| 12326995 | At_Far-red-induction | 20001247 | + |

TABLE 1-continued

Promoter Sequences and Related Information

| | | | |
|---|---|---|---|
| 12326995 | At_Far-red-induction | 20001248 | + |
| 12326995 | At_Far-red-induction | 20001450 | + |
| 12326995 | At_Far-red-induction | 20001451 | + |
| 12326995 | At_Drought_Soil_Dry | 20001556 | − |
| 12326995 | At_Drought_Soil_Dry | 20001557 | − |
| 12326995 | At_Drought_Soil_Dry | 20001558 | − |
| 12326995 | At_Interploidy_Crosses | 20001654 | + |
| 12326995 | At_Drought_Reproduction | 20001904 | − |
| 12326995 | At_8deg_Cold | 20002103 | − |
| 12326995 | At_8deg_Cold | 20002105 | − |

Microarray data shows that the coding sequence was expressed in the following experiments, which shows that the promoter would be useful to modulate expression in situations similar to the following:

| CDNA_ID | SHORT_NAME | EXPT_REP_ID | PARAM_NAME | VALUE |
|---|---|---|---|---|
| 12326995 | At_Root_Tips | 108434 | Tissue | Root Tips |
| 12326995 | At_Germinating_Seeds | 108462 | Age (day) | 2 vs. 0 |
| 12326995 | At_Germinating_Seeds | 108462 | Tissue | Germinating Seeds |
| 12326995 | At_Germinating_Seeds | 108463 | Age (day) | 3 vs. 0 |
| 12326995 | At_Germinating_Seeds | 108463 | Tissue | Germinating Seeds |
| 12326995 | At_42deg_Heat | 108576 | Timepoint (hr) | 1 |
| 12326995 | At_42deg_Heat | 108576 | Temperature (deg C.) | 42 vs. 22 |
| 12326995 | At_42deg_Heat | 108576 | Tissue | Aerial |
| 12326995 | At_100 uM_ABA_Mutants | 20000072 | Timepoint (hr) | 6 |
| 12326995 | At_100 uM_ABA_Mutants | 20000072 | Treatment | 100 uM ABA vs. No Treatment |
| 12326995 | At_100 uM_ABA_Mutants | 20000072 | Tissue | Aerial |
| 12326995 | At_100 uM_ABA_Mutants | 20000072 | Plant Line | CS8105 |
| 12326995 | At_42deg_Heat | 20000111 | Timepoint (hr) | 6 |
| 12326995 | At_42deg_Heat | 20000111 | Temperature (deg C.) | 42 vs. 22 |
| 12326995 | At_42deg_Heat | 20000111 | Tissue | Aerial |
| 12326995 | At_42deg_Heat | 20000144 | Timepoint (hr) | 1 |
| 12326995 | At_42deg_Heat | 20000144 | Temperature (deg C.) | 42 vs. 22 |
| 12326995 | At_42deg_Heat | 20000144 | Tissue | Aerial |
| 12326995 | At_100 uM_ABA | 20000166 | Timepoint (hr) | 1 |
| 12326995 | At_100 uM_ABA | 20000166 | Age (day) | 14 |
| 12326995 | At_100 uM_ABA | 20000166 | Treatment | 100 uM ABA vs. No Treatment |
| 12326995 | At_100 uM_ABA | 20000166 | Organism | A. thaliana |
| 12326995 | At_100 uM_ABA | 20000166 | Tissue | Aerial |
| 12326995 | At_100 uM_ABA | 20000166 | Plant Line | WS |
| 12326995 | At_100 uM_ABA | 20000169 | Timepoint (hr) | 6 |
| 12326995 | At_100 uM_ABA | 20000169 | Age (day) | 14 |
| 12326995 | At_100 uM_ABA | 20000169 | Treatment | 100 uM ABA vs. No Treatment |
| 12326995 | At_100 uM_ABA | 20000169 | Organism | A. thaliana |
| 12326995 | At_100 uM_ABA | 20000169 | Tissue | Aerial |
| 12326995 | At_100 uM_ABA | 20000169 | Plant Line | WS |
| 12326995 | At_2mM_SA | 20000181 | Timepoint (hr) | 1 |
| 12326995 | At_2mM_SA | 20000181 | Age (day) | 14 |
| 12326995 | At_2mM_SA | 20000181 | Treatment | 2 mM SA vs. No Treatment |
| 12326995 | At_2mM_SA | 20000181 | Organism | A. thaliana |
| 12326995 | At_2mM_SA | 20000181 | Tissue | Aerial |
| 12326995 | At_2mM_SA | 20000181 | Plant Line | WS |
| 12326995 | At_Siliques | 20000234 | Age (day) | 21 |
| 12326995 | At_Siliques | 20000234 | Tissue | <5 mm Siliques vs. Whole Plant |
| 12326995 | At_Siliques | 20000234 | Organism | A. thaliana |
| 12326995 | At_Siliques | 20000234 | Plant Line | WS |
| 12326995 | At_Siliques | 20000235 | Age (day) | 21 |
| 12326995 | At_Siliques | 20000235 | Tissue | 5-10 mm Siliques vs. Whole Plant |
| 12326995 | At_Siliques | 20000235 | Organism | A. thaliana |
| 12326995 | At_Siliques | 20000235 | Plant Line | WS |
| 12326995 | At_Siliques | 20000236 | Age (day) | 21 |
| 12326995 | At_Siliques | 20000236 | Tissue | >10 mm Siliques vs. Whole Plant |
| 12326995 | At_Siliques | 20000236 | Organism | A. thaliana |
| 12326995 | At_Siliques | 20000236 | Plant Line | WS |
| 12326995 | At_Open_Flower | 20000265 | Age (day) | 21 |
| 12326995 | At_Open_Flower | 20000265 | Organism | A. thaliana |
| 12326995 | At_Open_Flower | 20000265 | Tissue | Closed Flower vs. Whole Plant |
| 12326995 | At_Open_Flower | 20000265 | Plant Line | WS |
| 12326995 | At_Open_Flower | 20000286 | Age (day) | 21 |
| 12326995 | At_Open_Flower | 20000286 | Organism | A. thaliana |
| 12326995 | At_Open_Flower | 20000286 | Tissue | Half Open vs. Whole Plant |
| 12326995 | At_Open_Flower | 20000286 | Plant Line | WS |
| 12326995 | At_Pollen | 20000326 | Age (day) | 0 vs. 21 |
| 12326995 | At_Pollen | 20000326 | Organism | A. thaliana |
| 12326995 | At_Pollen | 20000326 | Tissue | Pollen vs. Whole Plant |
| 12326995 | At_Pollen | 20000326 | Plant Line | WS |
| 12326995 | At_100 uM_ABA | 20000453 | Age (day) | 15 |

TABLE 1-continued

Promoter Sequences and Related Information

| 12326995 | At_100 uM_ABA | 20000453 | Timepoint (hr) | 24 |
| --- | --- | --- | --- | --- |
| 12326995 | At_100 uM_ABA | 20000453 | Treatment | 100 uM ABA vs. No Treatment |
| 12326995 | At_100 uM_ABA | 20000453 | Organism | A. thaliana |
| 12326995 | At_100 uM_ABA | 20000453 | Tissue | Aerial |
| 12326995 | At_100 uM_ABA | 20000453 | Plant Line | WS |
| 12326995 | At_Far-red-induction | 20001247 | Timepoint (hr) | 1 |
| 12326995 | At_Far-red-induction | 20001247 | Age (day) | 7 |
| 12326995 | At_Far-red-induction | 20001247 | Organism | A. thaliana |
| 12326995 | At_Far-red-induction | 20001247 | Plant Line | Columbia |
| 12326995 | At_Far-red-induction | 20001247 | Light | Far-red vs. White |
| 12326995 | At_Far-red-induction | 20001247 | Tissue | Whole Plant |
| 12326995 | At_Far-red-induction | 20001248 | Timepoint (hr) | 4 |
| 12326995 | At_Far-red-induction | 20001248 | Age (day) | 7 |
| 12326995 | At_Far-red-induction | 20001248 | Organism | A. thaliana |
| 12326995 | At_Far-red-induction | 20001248 | Plant Line | Columbia |
| 12326995 | At_Far-red-induction | 20001248 | Light | Far-red vs. White |
| 12326995 | At_Far-red-induction | 20001248 | Tissue | Whole Plant |
| 12326995 | At_Far-red-induction | 20001450 | Age (day) | 7 |
| 12326995 | At_Far-red-induction | 20001450 | Timepoint (hr) | 8 |
| 12326995 | At_Far-red-induction | 20001450 | Organism | A. thaliana |
| 12326995 | At_Far-red-induction | 20001450 | Plant Line | Columbia |
| 12326995 | At_Far-red-induction | 20001450 | Light | Far-red vs. White |
| 12326995 | At_Far-red-induction | 20001450 | Tissue | Whole Plant |
| 12326995 | At_Far-red-induction | 20001451 | Age (day) | 8 |
| 12326995 | At_Far-red-induction | 20001451 | Timepoint (hr) | 24 |
| 12326995 | At_Far-red-induction | 20001451 | Organism | A. thaliana |
| 12326995 | At_Far-red-induction | 20001451 | Plant Line | Columbia |
| 12326995 | At_Far-red-induction | 20001451 | Light | Far-red vs. White |
| 12326995 | At_Far-red-induction | 20001451 | Tissue | Whole Plant |
| 12326995 | At_Drought_Soil_Dry | 20001556 | Timepoint (day) | 12 |
| 12326995 | At_Drought_Soil_Dry | 20001556 | Age (day) | 26 |
| 12326995 | At_Drought_Soil_Dry | 20001556 | Organism | A. thaliana |
| 12326995 | At_Drought_Soil_Dry | 20001556 | Treatment | Drought vs. No Drought |
| 12326995 | At_Drought_Soil_Dry | 20001556 | Post Timepoint (hr) | None |
| 12326995 | At_Drought_Soil_Dry | 20001556 | Post-Treatment | None |
| 12326995 | At_Drought_Soil_Dry | 20001556 | Plant Line | WS |
| 12326995 | At_Drought_Soil_Dry | 20001557 | Post Timepoint (hr) | 3 |
| 12326995 | At_Drought_Soil_Dry | 20001557 | Timepoint (day) | 13 |
| 12326995 | At_Drought_Soil_Dry | 20001557 | Age (day) | 27 |
| 12326995 | At_Drought_Soil_Dry | 20001557 | Organism | A. thaliana |
| 12326995 | At_Drought_Soil_Dry | 20001557 | Treatment | Drought vs. No Drought |
| 12326995 | At_Drought_Soil_Dry | 20001557 | Post-Treatment | Re-Water vs. No Drought |
| 12326995 | At_Drought_Soil_Dry | 20001557 | Plant Line | WS |
| 12326995 | At_Drought_Soil_Dry | 20001558 | Post Timepoint (hr) | 6 |
| 12326995 | At_Drought_Soil_Dry | 20001558 | Timepoint (day) | 13 |
| 12326995 | At_Drought_Soil_Dry | 20001558 | Age (day) | 27 |
| 12326995 | At_Drought_Soil_Dry | 20001558 | Organism | A. thaliana |
| 12326995 | At_Drought_Soil_Dry | 20001558 | Treatment | Drought vs. No Drought |
| 12326995 | At_Drought_Soil_Dry | 20001558 | Post-Treatment | Re-Water vs. No Drought |
| 12326995 | At_Drought_Soil_Dry | 20001558 | Plant Line | WS |
| 12326995 | At_Interploidy_Crosses | 20001654 | Age (day) | 5 |
| 12326995 | At_Interploidy_Crosses | 20001654 | Cross | 6X × 2X vs. 2X × 2X |
| 12326995 | At_Interploidy_Crosses | 20001654 | Organism | A. thaliana |
| 12326995 | At_Interploidy_Crosses | 20001654 | Plant Line | Columbia |
| 12326995 | At_Interploidy_Crosses | 20001654 | Tissue | Siliques |
| 12326995 | At_Drought_Reproduction | 20001904 | Timepoint (day) | 7 |
| 12326995 | At_Drought_Reproduction | 20001904 | Age (day) | 37 |
| 12326995 | At_Drought_Reproduction | 20001904 | Organism | A. thaliana |
| 12326995 | At_Drought_Reproduction | 20001904 | Treatment | Drought vs. No Drought |
| 12326995 | At_Drought_Reproduction | 20001904 | Tissue | Rosettes |
| 12326995 | At_Drought_Reproduction | 20001904 | Plant Line | WS |
| 12326995 | At_8deg_Cold | 20002103 | Timepoint (hr) | 2 |
| 12326995 | At_8deg_Cold | 20002103 | Age (day) | 7 |
| 12326995 | At_8deg_Cold | 20002103 | Temperature (deg C.) | 8 vs. 22 |
| 12326995 | At_8deg_Cold | 20002103 | Organism | A. thaliana |
| 12326995 | At_8deg_Cold | 20002103 | Tissue | Whole Plant |
| 12326995 | At_8deg_Cold | 20002103 | Plant Line | WS |
| 12326995 | At_8deg_Cold | 20002105 | Age (day) | 7 |
| 12326995 | At_8deg_Cold | 20002105 | Timepoint (hr) | 8 |
| 12326995 | At_8deg_Cold | 20002105 | Temperature (deg C.) | 8 vs. 22 |
| 12326995 | At_8deg_Cold | 20002105 | Organism | A. thaliana |
| 12326995 | At_8deg_Cold | 20002105 | Tissue | Whole Plant |
| 12326995 | At_8deg_Cold | 20002105 | Plant Line | WS |

Promoter YP0286

Modulates the gene: Hypothetical protein
The GenBank description of the gene: NM_102758 *Arabidopsis thaliana* hypothetical protein TABLE 1-continued Promoter Sequences and Related Information (At1g30190) mRNA, complete cds gi|18397396|ref|NM_102758.1|[18397396]
The promoter sequence:
5'atcatcgaaaggtatgtgatgcatattcccattgaaccagatttccatatattttatttgtaaagtgat aatgaatcacaagatgattcaatattaaaaatgggtaactcactttgacgtgtagtacgtggaagaatagt tagctatcacgcatatatatatctatgattaagtgtgtatgacataagaaactaaaatatttacctaaagt ccagttactcatactgattttatgcatatatgtattatttatttatttttaataaagaagcgattggtgtt ttcatagaaatcatgatagattgataggtatttcagttccacaaatctagatctgtgtgctatacatgcat gtattaattttttccccttaaatcatttcagttgataatattgctctttgttccaactttagaaaaggtat gaaccaacctgacgattaacaagtaaacattaattaatctttatatatatgagataaaaccgaggatatat atgattgtgttgctgtctattgatgatgtgtcgatattatgcttgttgtaccaatgctcgagccgagcgtg atcgatgccttgacaaactatatatgtttcccgaattaattaagttttgtatcttaattagaataacattt ttatacaatgtaatttctcaagcagacaagatatgtatcctatattaattactatatatgaattgccgggc acctaccaggatgtttcaaatacgagagcccattagtttccacgtaaatcacaatgacgcgacaaaatcta gaatcgtgtcaaaactctatcaatacaataatatatatttcaagggcaatttcgacttctcctcaactcaa tgattcaacgccatgaatctctaTATAaaggctacaacaccacaaggatcatcagtcatcacaaccacat taactcttcaccactatctctcaatctct 3'-ATG
The promoter was cloned from the organism: *Arabidopsis thaliana*, WS ecotype

| | Alternative nucleotides:<br>Predicred (Columbia)<br>Experimental (Wassilewskija) | |
|---|---|---|
| Predicted Position (bp) | Mismatch | Columbia/Wassilewskija |
| 194 | SNP | t/a |
| 257 | SNP | t/c |
| 491-494 | SSLP | tata/- - - - |
| 527 | No g in Ws | -/- |

The promoter was cloned in the vector: pNewbin4-HAP1-GFP
When cloned into the vector the promoter was operably linked to a marker, which was the type: GFP-ER
Promoter-marker vector was tested in: *Arabidopsis thaliana*, WS ecotype
Generation screened: XT1 Mature   XT2 Seedling   T2 Mature   T3 Seedling The spatial expression of the promoter-marker vector was found observed in and would be useful in expression in any or all of the following:

| | |
|---|---|
| Flower | L pedicel L epidermis |
| Stem | L epidermis |
| Hypocotyl | H epidermis |
| Cotyledon | H mesophyll H vascular H epidermis H petiole |
| Rosette Leaf | H epidermis H petiole |
| Primary Root | H epidermis |
| Lateral root | H lateral root cap |

Observed expression pattern of the promoter-marker vector was in:
T1 mature: GFP expressed in vasculature of silique and pedicles of flowers.
T2 seedling: High GFP expression throughout vasculature of root, hypocotyl, and petioles.
Misc. promoter information: Bidirectionality: Pass  Exons: Pass   Repeats: No
The Ceres cDNA ID of the endogenous coding sequence to the promoter: 12669548
cDNA nucleotide sequence:
ATGACAGAAATGCCCTCGTACATGATCGAGAACCCAAAGTTCGAGCCAAAGAAACGACGTTAT

TACTCTTCTTCGATGCTTACCATCTTCTTACCGATCTTCACATACATTATGATCTTTCACGTTTT

CGAAGTATCACTATCTTCGGTCTTTAAAGACACAAAGGTCTTGTTCTTCATCTCCAATACTCTC

ATCCTCATAATAGCCGCCGATTATGGTTCCTTCTCTGATAAAGAGAGTCAAGACTTTTACGGTG

AATACACTGTCGCAGCGGCAACGATGCGAAACCGAGCTGATAACTACTCTCCGATTCCCGTCT

TGACATACCGAGAAAACACTAAAGATGGAGAAATCAAGAACCCTAAAGATGTCGAATTCAGG

AACCCTGAAGAAGAAGACGAACCGATGGTGAAAGATATCATTTGCGTTTCTCCTCCCGAGAAA

TABLE 1-continued

Promoter Sequences and Related Information

ATAGTACGAGTGGTGAGTGAGAAGAAACAGAGAGATGATGTAGCTATGGAAGAATACAAACC

AGTTACAGAACAAACTCTTGCTAGCGAAGAAGCTTGCAACACAAGAAACCATGTGAACCCTAA

TAAACCGTACGGGCGAAGTAAATCAGATAAGCCACGGAGAAAGAGGCTCAGCGTAGATACAG

AGACGACCAAACGTAAAAGTTATGGTCGAAAGAAATCAGATTGCTCGAGATGGATGGTTATTC

CGGAGAAGTGGGAATATGTTAAAGAAGAATCTGAAGAGTTTTCAAAGTTGTCCAACGAGGAG

TTGAACAAACGAGTCGAAGAATTCATCCAACGGTTCAATAGACAGATCAGATCACAATCACCG

CGAGTTTCGTCTACTTGA

Coding sequence:
MTEMPSYMIENPKFEPKKRRYYSSSMLTIFLPIFTYIMIFHVFEVSLSSVFKDTKVLFFI

SNTLILIIAADYGSFSDKESQDFYGEYTVAAATMRNRADNYSPIPVLTYRENTKDGEIKN

PKDVEFRNPEEEDEPMVKDIICVSPPEKIVRVVSEKKQRDDVAMEEYKPVTEQTLASEEA

CNTRNHVNPNKPYGRSKSDKPRRKRLSVDTETTKRKSYGRKKSDCSRWMVIPEKWEYVKE

ESEEFSKLSNEELNKRVEEFIQRFNRQIRSQSPRVSST*

Microarray data shows that the coding sequence was expressed in the following experiments, which shows that the promoter would be useful to modulate expression in situations similar to the following:

| CDNA_ID | SHORT_NAME | EXPT_REP_ID | IS_UP |
|---|---|---|---|
| 12669548 | At_100uM_ABA | 20000169 | + |
| 12669548 | At_42deg_Heat | 20000171 | + |
| 12669548 | At_42deg_Heat | 20000173 | + |
| 12669548 | At_2mM_SA | 20000182 | + |
| 12669548 | At_0.001_percent_MeJA | 20000211 | − |
| 12669548 | At_Open_Flower | 20000264 | − |
| 12669548 | At_Open_Flower | 20000265 | − |
| 12669548 | At_Drought | 20000267 | + |
| 12669548 | At_100mM_NaCl | 20000268 | + |
| 12669548 | At_Open_Flower | 20000286 | − |
| 12669548 | At_Drought | 20000436 | + |
| 12669548 | At_Drought | 20000437 | + |
| 12669548 | At_100uM_NAA | 20000444 | + |
| 12669548 | At_100uM_NAA | 20000445 | + |
| 12669548 | At_100uM_ABA | 20000453 | + |
| 12669548 | At_42deg_Heat | 20000457 | − |
| 12669548 | At_10percent_PEG | 20000527 | + |
| 12669548 | At_Line_Comparisons | 20001192 | − |
| 12669548 | At_Line_Comparisons | 20001307 | + |
| 12669548 | At_Line_Comparisons | 20001309 | − |
| 12669548 | At_Line_Comparisons | 20001310 | − |
| 12669548 | At_Drought_Soil_Dry | 20001554 | + |
| 12669548 | At_Drought_Soil_Dry | 20001555 | + |
| 12669548 | At_Drought_Soil_Dry | 20001556 | + |
| 12669548 | At_Drought_Soil_Dry | 20001559 | + |
| 12669548 | At_50mM_NH4NO3_L-to-H | 20001757 | − |
| 12669548 | At_Drought_Reproduction | 20001904 | + |
| 12669548 | At_Drought_Reproduction | 20001905 | + |
| 12669548 | At_Drought_Reproduction | 20001910 | + |
| 12669548 | At_Drought_Reproduction | 20001911 | + |
| 12669548 | At_Line_Comparisons | 20002009 | + |
| 12669548 | At_Line_Comparisons | 20002010 | + |
| 12669548 | At_Drought-Air-Dry | 20002253 | − |
| 12669548 | At_Drought-Air-Dry | 20002256 | + |

The parameters for the microarray experiments listed above by Expt_Rep_ID and Short_Name are as follow below:

| CDNA_ID | SHORT_NAME | EXPT_REP_ID | PARAM_NAME | VALUE |
|---|---|---|---|---|
| 12669548 | At_100uM_ABA | 20000169 | Timepoint (hr) | 6 |
| 12669548 | At_100uM_ABA | 20000169 | Age (day) | 14 |
| 12669548 | At_100uM_ABA | 20000169 | Treatment | 100 uM ABA vs. No Treatment |
| 12669548 | At_100uM_ABA | 20000169 | Organism | A. thaliana |
| 12669548 | At_100uM_ABA | 20000169 | Tissue | Aerial |
| 12669548 | At_100uM_ABA | 20000169 | Plant Line | WS |
| 12669548 | At_42deg_Heat | 20000171 | Timepoint (hr) | 1 |

TABLE 1-continued

Promoter Sequences and Related Information

| 12669548 | At_42deg_Heat | 20000171 | Age (day) | 14 |
|---|---|---|---|---|
| 12669548 | At_42deg_Heat | 20000171 | Temperature (deg C.) | 42 vs. 22 |
| 12669548 | At_42deg_Heat | 20000171 | Organism | A. thaliana |
| 12669548 | At_42deg_Heat | 20000171 | Tissue | Aerial |
| 12669548 | At_42deg_Heat | 20000171 | Plant Line | WS |
| 12669548 | At_42deg_Heat | 20000173 | Timepoint (hr) | 6 |
| 12669548 | At_42deg_Heat | 20000173 | Age (day) | 14 |
| 12669548 | At_42deg_Heat | 20000173 | Temperature (deg C.) | 42 vs. 22 |
| 12669548 | At_42deg_Heat | 20000173 | Organism | A. thaliana |
| 12669548 | At_42deg_Heat | 20000173 | Tissue | Aerial |
| 12669548 | At_42deg_Heat | 20000173 | Plant Line | WS |
| 12669548 | At_2mM_SA | 20000182 | Timepoint (hr) | 6 |
| 12669548 | At_2mM_SA | 20000182 | Age (day) | 14 |
| 12669548 | At_2mM_SA | 20000182 | Treatment | 2 mM SA vs. No Treatment |
| 12669548 | At_2mM_SA | 20000182 | Organism | A. thaliana |
| 12669548 | At_2mM_SA | 20000182 | Tissue | Aerial |
| 12669548 | At_2mM_SA | 20000182 | Plant Line | WS |
| 12669548 | At_0.001percent_MeJA | 20000211 | Timepoint (hr) | 1 |
| 12669548 | At_0.001percent_MeJA | 20000211 | Age (day) | 14 |
| 12669548 | At_0.001percent_MeJA | 20000211 | Treatment | 0.001 percent MeJA vs. No Treatment |
| 12669548 | At_0.001percent_MeJA | 20000211 | Organism | A. thaliana |
| 12669548 | At_0.001percent_MeJA | 20000211 | Tissue | Aerial |
| 12669548 | At_0.001percent_MeJA | 20000211 | Plant Line | WS |
| 12669548 | At_Open_Flower | 20000264 | Age (day) | 21 |
| 12669548 | At_Open_Flower | 20000264 | Organism | A. thaliana |
| 12669548 | At_Open_Flower | 20000264 | Tissue | Open Flower vs. Whole Plant |
| 12669548 | At_Open_Flower | 20000264 | Plant Line | WS |
| 12669548 | At_Open_Flower | 20000265 | Age (day) | 21 |
| 12669548 | At_Open_Flower | 20000265 | Organism | A. thaliana |
| 12669548 | At_Open_Flower | 20000265 | Tissue | Closed Flower vs. Whole Plant |
| 12669548 | At_Open_Flower | 20000265 | Plant Line | WS |
| 12669548 | At_Drought | 20000267 | Timepoint (hr) | 6 |
| 12669548 | At_Drought | 20000267 | Age (day) | 7 |
| 12669548 | At_Drought | 20000267 | Organism | A. thaliana |
| 12669548 | At_Drought | 20000267 | Treatment | Drought vs. No Drought |
| 12669548 | At_Drought | 20000267 | Tissue | Whole Plant |
| 12669548 | At_Drought | 20000267 | Plant Line | WS |
| 12669548 | At_100mM_NaCl | 20000268 | Timepoint (hr) | 6 |
| 12669548 | At_100mM_NaCl | 20000268 | Age (day) | 14 |
| 12669548 | At_100mM_NaCl | 20000268 | Treatment | 100 mM NaCl vs. No Treatment |
| 12669548 | At_100mM_NaCl | 20000268 | Organism | A. thaliana |
| 12669548 | At_100mM_NaCl | 20000268 | Tissue | Whole Plant |
| 12669548 | At_100mM_NaCl | 20000268 | Plant Line | WS |
| 12669548 | At_Open_Flower | 20000286 | Age (day) | 21 |
| 12669548 | At_Open_Flower | 20000286 | Organism | A. thaliana |
| 12669548 | At_Open_Flower | 20000286 | Tissue | Half Open vs. Whole Plant |
| 12669548 | At_Open_Flower | 20000286 | Plant Line | WS |
| 12669548 | At_Drought | 20000436 | Age (day) | 7 |
| 12669548 | At_Drought | 20000436 | Timepoint (hr) | 12 |
| 12669548 | At_Drought | 20000436 | Organism | A. thaliana |
| 12669548 | At_Drought | 20000436 | Treatment | Drought vs. No Drought |
| 12669548 | At_Drought | 20000436 | Tissue | Whole Plant |
| 12669548 | At_Drought | 20000436 | Plant Line | WS |
| 12669548 | At_Drought | 20000437 | Age (day) | 8 |
| 12669548 | At_Drought | 20000437 | Timepoint (hr) | 24 |
| 12669548 | At_Drought | 20000437 | Organism | A. thaliana |
| 12669548 | At_Drought | 20000437 | Treatment | Drought vs. No Drought |
| 12669548 | At_Drought | 20000437 | Tissue | Whole Plant |
| 12669548 | At_Drought | 20000437 | Plant Line | WS |
| 12669548 | At_100uM_NAA | 20000444 | Timepoint (hr) | 1 |
| 12669548 | At_100uM_NAA | 20000444 | Age (day) | 14 |
| 12669548 | At_100uM_NAA | 20000444 | Treatment | 100 uM NAA vs. No Treatment |
| 12669548 | At_100uM_NAA | 20000444 | Organism | A. thaliana |
| 12669548 | At_100uM_NAA | 20000444 | Tissue | Aerial |
| 12669548 | At_100uM_NAA | 20000444 | Plant Line | WS |
| 12669548 | At_100uM_NAA | 20000445 | Timepoint (hr) | 6 |
| 12669548 | At_100uM_NAA | 20000445 | Age (day) | 14 |
| 12669548 | At_100uM_NAA | 20000445 | Treatment | 100 uM NAA vs. No Treatment |
| 12669548 | At_100uM_NAA | 20000445 | Organism | A. thaliana |
| 12669548 | At_100uM_NAA | 20000445 | Tissue | Aerial |
| 12669548 | At_100uM_NAA | 20000445 | Plant Line | WS |
| 12669548 | At_100uM_ABA | 20000453 | Age (day) | 15 |
| 12669548 | At 100uM_ABA | 20000453 | Timepoint (hr) | 24 |
| 12669548 | At_100uM_ABA | 20000453 | Treatment | 100 uM ABA vs. No Treatment |
| 12669548 | At_100uM_ABA | 20000453 | Organism | A. thaliana |
| 12669548 | At_100uM_ABA | 20000453 | Tissue | Aerial |
| 12669548 | At_100uM_ABA | 20000453 | Plant Line | WS |

TABLE 1-continued

Promoter Sequences and Related Information

| | | | | |
|---|---|---|---|---|
| 12669548 | At_42deg_Heat | 20000457 | Timepoint (hr) | 0.166 |
| 12669548 | At_42deg_Heat | 20000457 | Age (day) | 14 |
| 12669548 | At_42deg_Heat | 20000457 | Temperature (deg C.) | 42 vs. 22 |
| 12669548 | At_42deg_Heat | 20000457 | Organism | A. thaliana |
| 12669548 | At_42deg_Heat | 20000457 | Tissue | Aerial |
| 12669548 | At_42deg_Heat | 20000457 | Plant Line | WS |
| 12669548 | At_10percent_PEG | 20000527 | Age (day) | 20 |
| 12669548 | At_10percent_PEG | 20000527 | Timepoint (day) | 20 |
| 12669548 | At_10percent_PEG | 20000527 | Treatment | 10 percent PEG vs. No Treatment |
| 12669548 | At_10percent_PEG | 20000527 | Organism | A. thaliana |
| 12669548 | At_10percent_PEG | 20000527 | Tissue | Whole Plant |
| 12669548 | At_10percent_PEG | 20000527 | Plant Line | WS |
| 12669548 | At_Line_Comparisons | 20001192 | Plant Line | WBin4-WX13R-A vs. WS |
| 12669548 | At_Line_Comparisons | 20001307 | Plant Line | WBin4-WX2-A vs. WS |
| 12669548 | At_Line_Comparisons | 20001309 | Plant Line | WBin4-WX49R-A vs. WS |
| 12669548 | At_Line_Comparisons | 20001310 | Plant Line | WBin4-WX17-A vs. WS |
| 12669548 | At_Drought_Soil_Dry | 20001554 | Timepoint (day) | 7 |
| 12669548 | At_Drought_Soil_Dry | 20001554 | Age (day) | 21 |
| 12669548 | At_Drought_Soil_Dry | 20001554 | Organism | A. thaliana |
| 12669548 | At_Drought_Soil_Dry | 20001554 | Treatment | Drought vs. No Drought |
| 12669548 | At_Drought_Soil_Dry | 20001554 | Post Timepoint (hr) | None |
| 12669548 | At_Drought_Soil_Dry | 20001554 | Post-Treatment | None |
| 12669548 | At_Drought_Soil_Dry | 20001554 | Plant Line | WS |
| 12669548 | At_Drought_Soil_Dry | 20001555 | Timepoint (day) | 10 |
| 12669548 | At_Drought_Soil_Dry | 20001555 | Age (day) | 24 |
| 12669548 | At_Drought_Soil_Dry | 20001555 | Organism | A. thaliana |
| 12669548 | At_Drought_Soil_Dry | 20001555 | Treatment | Drought vs. No Drought |
| 12669548 | At_Drought_Soil_Dry | 20001555 | Post Timepoint (hr) | None |
| 12669548 | At_Drought_Soil_Dry | 20001555 | Post-Treatment | None |
| 12669548 | At_Drought_Soil_Dry | 20001555 | Plant Line | WS |
| 12669548 | At_Drought_Soil_Dry | 20001556 | Timepoint (day) | 12 |
| 12669548 | At_Drought_Soil_Dry | 20001556 | Age (day) | 26 |
| 12669548 | At_Drought_Soil_Dry | 20001556 | Organism | A. thaliana |
| 12669548 | At_Drought_Soil_Dry | 20001556 | Treatment | Drought vs. No Drought |
| 12669548 | At_Drought_Soil_Dry | 20001556 | Post Timepoint (hr) | None |
| 12669548 | At_Drought_Soil_Dry | 20001556 | Post-Treatment | None |
| 12669548 | At_Drought_Soil_Dry | 20001556 | Plant Line | WS |
| 12669548 | At_Drought_Soil_Dry | 20001559 | Timepoint (day) | 14 |
| 12669548 | At_Drought_Soil_Dry | 20001559 | Age (day) | 28 |
| 12669548 | At_Drought_Soil_Dry | 20001559 | Post Timepoint (hr) | 29 |
| 12669548 | At_Drought_Soil_Dry | 20001559 | Organism | A. thaliana |
| 12669548 | At_Drought_Soil_Dry | 20001559 | Treatment | Drought vs. No Drought |
| 12669548 | At_Drought_Soil_Dry | 20001559 | Post-Treatment | Re-Water vs. No Drought |
| 12669548 | At_Drought_Soil_Dry | 20001559 | Plant Line | WS |
| 12669548 | At_50mM_NH4NO3_L-to-H | 20001757 | Timepoint (hr) | 6 |
| 12669548 | At_50mM_NH4NO3_L-to-H | 20001757 | Treatment | 50 mM NH4NO3 vs 100 mM Mannitol |
| 12669548 | At_50mM_NH4NO3_L-to-H | 20001757 | Tissue | Leaf |
| 12669548 | At_Drought_Reproduction | 20001904 | Timepoint (day) | 7 |
| 12669548 | At_Drought_Reproduction | 20001904 | Age (day) | 37 |
| 12669548 | At_Drought_Reproduction | 20001904 | Organism | A. thaliana |
| 12669548 | At_Drought_Reproduction | 20001904 | Treatment | Drought vs. No Drought |
| 12669548 | At_Drought_Reproduction | 20001904 | Tissue | Rosettes |
| 12669548 | At_Drought_Reproduction | 20001904 | Plant Line | WS |
| 12669548 | At_Drought_Reproduction | 20001905 | Timepoint (day) | 10 |
| 12669548 | At_Drought_Reproduction | 20001905 | Age (day) | 40 |
| 12669548 | At_Drought_Reproduction | 20001905 | Organism | A. thaliana |
| 12669548 | At_Drought_Reproduction | 20001905 | Treatment | Drought vs. No Drought |
| 12669548 | At_Drought_Reproduction | 20001905 | Tissue | Rosettes |
| 12669548 | At_Drought_Reproduction | 20001905 | Plant Line | WS |
| 12669548 | At_Drought_Reproduction | 20001910 | Timepoint (day) | 7 |
| 12669548 | At_Drought_Reproduction | 20001910 | Age (day) | 37 |
| 12669548 | At_Drought_Reproduction | 20001910 | Organism | A. thaliana |
| 12669548 | At_Drought_Reproduction | 20001910 | Treatment | Drought vs. No Drought |
| 12669548 | At_Drought_Reproduction | 20001910 | Tissue | Flowers |
| 12669548 | At_Drought_Reproduction | 20001910 | Plant Line | WS |
| 12669548 | At_Drought_Reproduction | 20001911 | Timepoint (day) | 10 |
| 12669548 | At_Drought_Reproduction | 20001911 | Age (day) | 40 |
| 12669548 | At_Drought_Reproduction | 20001911 | Organism | A. thaliana |
| 12669548 | At_Drought_Reproduction | 20001911 | Treatment | Drought vs. No Drought |
| 12669548 | At_Drought_Reproduction | 20001911 | Tissue | Flowers |
| 12669548 | At_Drought_Reproduction | 20001911 | Plant Line | WS |
| 12669548 | At_Line_Comparisons | 20002009 | Plant Line | ME01642 vs. WS |
| 12669548 | At_Line_Comparisons | 20002010 | Plant Line | ME02031 vs. WS |
| 12669548 | At_Drought-Air-Dry | 20002253 | Timepoint (hr) | 1 |
| 12669548 | At_Drought-Air-Dry | 20002253 | Age (day) | 35 |
| 12669548 | At_Drought-Air-Dry | 20002253 | Organism | A. thaliana |

TABLE 1-continued

Promoter Sequences and Related Information

| 12669548 | At_Drought-Air-Dry | 20002253 | Treatment | Drought vs. No Drought |
|---|---|---|---|---|
| 12669548 | At_Drought-Air-Dry | 20002253 | Tissue | Roots |
| 12669548 | At_Drought-Air-Dry | 20002253 | Plant Line | WS |
| 12669548 | At_Drought-Air-Dry | 20002256 | Timepoint (hr) | 4 |
| 12669548 | At_Drought-Air-Dry | 20002256 | Age (day) | 35 |
| 12669548 | At_Drought-Air-Dry | 20002256 | Organism | *A. thaliana* |
| 12669548 | At_Drought-Air-Dry | 20002256 | Treatment | Drought vs. No Drought |
| 12669548 | At_Drought-Air-Dry | 20002256 | Tissue | Shoots |
| 12669548 | At_Drought-Air-Dry | 20002256 | Plant Line | WS |

Promoter YP0275

Modulates the gene: Glycosyl hydrolase family.
The GenBank description of the gene: NM_115876 *Arabidopsis thaliana* glycosyl hydrolase family 1 (At3g60130) mRNA, complete cds gi|30695130|ref|NM_115876.2|[30695130]
The promoter sequence:
5'gcgtatgctttactttttaaaatgggcctatgctataattgaatgacaaggattaaacaactaataaaa gtgtagatgggttaagatgacttatttttttacttaccaatttataaatgggcttcgatgtactgaaatat atcgcgcctattaacgaggccattcaacgaatgttttaagggccctatttcgacatttttaaagaacaccta ggtcatcattccagaaatggatattataggatttagataaatttcccacgtttggtttatttatctattttt tgacgttgaccaacataatcgtgcccaaccgtttcacgcaacgaatttatatacgaaatatatatattttt caaattaagataccacaatcaaaacagctgttgattaacaaagagatttttttttttttggttttgagttac aataacgttagaggataaggtttcttgcaacgattaggaaatcgtataaaataaaatatgttataattaag tgttttatttttataatgagtattaatataaataaaacctgcaaaaggatagggatattgaataataaagag aaacgaaagagcaattttacttctttataattgaaattatgtgaatgttatgtttacaatgaatgattcat cgttctatatattgaagtaaagaatgagtttattgtgcttgcataatgacgttaacttcacatatacactt attacataacatttatcacatgtgcgtctttttttttttttactttgtaaaatttcctcactttaaagact tttataacaattactagtaaaataaagttgcttggggctacacccttctccctccaacaactctatttat agataacattatatcaaaatcaaaacatagtcccttttcttctataaaggtttttttcacaaccaaatttcca rTATAaatcaaaaaataaaaacttaatta 3'-aATG
The promoter was cloned from the organism: *Arabidopsis thaliana*, WS ecotype Alternative nucleotides:
Predicted (Columbia)
Experimenral (Wassilewskija)

| Sequence (bp) | Mismatch | Columbia/Wassilewskija |
|---|---|---|
| 95 | SNP | g/t |
| 798 | SNP | a/t |

The promoter was cloned in the vector: pNewbin4-HAP1-GFP
When cloned into the vector the promoter was operably linked to a marker, which was the type: GFP-ER
Promoter-marker vector was tested in: *Arabidopsis thaliana*, WS ecotype
Generation screened: XT1 Mature   XT2 Seedling   T2 Mature   T3 Seedling The spatial expression of the promoter-marker vector was found observed in and would be useful in expression in any or all of the following:

Primary Root        H epidermis H trichoblast H atrichoblast L root cap H root hairs
Observed expression pattern of the promoter-marker vector was in:
T1 mature: No expression.
T2 seedling: High expression in root epidermal at transition zone decreasing toward root tip.
Misc. promoter information: Bidirectionality: Pass  Exons: Pass   Repeats: No
The Ceres cDNA ID of the endogenous coding sequence to the promoter: 12668112
cDNA nucleotide sequence:
ATAAAAACTTAATTAGTTTTTACAGAAGAAAAGAAAACAATGAGAGGTAAATTTCTAAGTTTA

CTGTTGCTCATTACTTTGGCCTGCATTGGAGTTTCCGCCAAGAAGCATTCCACAAGGCCTAGAT

TAAGAAGAAATGATTTCCCACAAGATTTCGTTTTTGGATCTGCTACTTCTGCTTATCAGTGTGA

AGGAGCTGCACATGAAGATGGTAGAGGTCCAAGTATCTGGGACTCCTTCTCTGAAAAATTCCC

TABLE 1-continued

Promoter Sequences and Related Information

AGAAAAGATAATGGATGGTAGTAATGGGTCCATTGCAGATGATTCTTACAATCTTTACAAGGA

AGATGTGAATTTGCTGCATCAAATTGGCTTCGATGCTTACCGATTTTCGATCTCATGGTCACGG

ATTTTGCCTCGTGGGACTCTAAAGGGAGGAATCAACCAGGCTGGAATTGAATATTATAACAAC

TTGATTAATCAACTTATATCTAAAGGAGTGAAGCCATTTGTCACACTCTTTCACTGGGACTTAC

CAGATGCACTCGAAAATGCTTACGGTGGCCTCCTTGGAGATGAATTTGTGAACGATTTCCGAG

ACTATGCAGAACTTTGTTTCCAGAAGTTTGGAGATAGAGTGAAGCAGTGGACGACACTAAACG

AGCCATATACAATGGTACATGAAGGTTATATAACAGGTCAAAAGGCACCTGGAAGATGTTCCA

ATTTCTATAAACCTGATTGCTTAGGTGGCGATGCAGCCACGGAGCCTTACATCGTCGGCCATA

ACCTCCTCCTTGCTCATGGAGTTGCCGTAAAAGTATATAGAGAAAAGTACCAGGCAACTCAGA

AAGGTGAAATTGGTATTGCCTTAAACACAGCATGGCACTACCCTTATTCAGATTCATATGCTG

ACCGGTTAGCTGCGACTCGAGCGACTGCCTTCACCTTCGACTACTTCATGGAGCCAATCGTGT

ACGGTAGATATCCAATTGAAATGGTCAGCCACGTTAAAGACGGTCGTCTTCCTACCTTCACAC

CAGAAGAGTCCGAAATGCTCAAAGGATCATATGATTTCATAGGCGTTAACTATTACTCATCTC

TTTACGCAAAAGACGTGCCGTGTGCAACTGAAAACATCACCATGACCACCGATTCTTGCGTCA

GCCTCGTAGGTGAACGAAATGGAGTGCCTATCGGTCCAGCGGCTGGATCGGATTGGCTTTTGA

TATATCCCAAGGGTATTCGTGATCTCCTACTACATGCAAAATTCAGATACAATGATCCCGTCTT

GTACATTACAGAGAATGGAGTGGATGAAGCAAATATTGGCAAAATATTTCTTAACGACGATTT

GAGAATTGATTACTATGCTCATCACCTCAAGATGGTTAGCGATGCTATCTCGATCGGGGTGAA

TGTGAAGGGATATTTCGCGTGGTCATTGATGGATAATTTCGAGTGGTCGGAAGGATACACGGT

CCGGTTCGGGCTAGTGTTTGTGGACTTTGAAGATGGACGTAAGAGGTATCTGAAGAAATCAGC

TAAGTGGTTTAGGAGATTGTTGAAGGGAGCGCATGGTGGGACGAATGAGCAGGTGGCTGTTA

TTTAATAAACCACGAGTCATTGGTCAATTTAGTCTACTGTTTCTTTTGCTCTATGTACAGAAAG

AAAATAAACTTTCCAAAATAAGAGGTGGCTTTGTTTGGACTTTGGATGTTACTATATATATTG

GTAATTCTTGGCGTTTGTTAGTTTCCAAACCAAACATTAAT

Coding sequence:
MRGKFLSLLLLITLACIGVSAKKHSTRPRLRRNDFPQDFVFGSATSAYQCEGAAHEDGRGPSIWDSF

SEKFPEKIMDGSNGSIADDSYNLYKEDVNLLHQIGFDAYRFSISWSRILPRGTLKGGINQAGIEYYN

NLINQLISKGVKPFVTLFHWDLPDALENAYGGLLGDEFVNDFRDYAELCFQKFGDRVKQWTTLNE

PYTMVHEGYITGQKAPGRCSNFYKPDCLGGDAATEPYIVGHNLLAHGVAVKVYREKYQATQKG

EIGIALNTAWHYPYSDSYADRLAATRATAFTFDYFMEPIVYGRYPIEMVSHVKDGRLPTFTPEESE

MLKGSYDFIGVNYYSSLYAKDVPCATENITMTTDSCVSLVGERNGVPIGPAAGSDWLLIYPKGIRD

LLLHAKFRYNDPVLYITENGVDEANIGKIFLNDDLRIDYYAHHLKMVSDAISIGVNVKGYFAWSL

MDNFEWSEGYTVRFGLVFVDFEDGRKRYLKKSAKWFRRLLKGAHGGTNEQVAVI*

Microarray data shows that the coding sequence was expressed in the following experiments, which shows that the promoter would be useful to modulate expression in situations similar to the following:

| CDNA_ID | SHORT_NAME | EXPT_REP_ID | IS_UP |
|---|---|---|---|
| 12668112 | At_4deg_Cold | 20000214 | - |
| 12668112 | At_10percent_PEG | 20000527 | - |
| 12668112 | At_Drought_Soil_Dry | 20001554 | - |
| 12668112 | At_Drought_Soil_Dry | 20001555 | - |
| 12668112 | At_Interploidy_Crosses | 20001853 | - |
| 12668112 | At_8deg_Cold | 20002105 | - |

TABLE 1-continued

Promoter Sequences and Related Information

The parameters for the microarray experiments listed above by Expt_Rep_ID and Short_Name are as follow below:

| CDNA_ID | SHORT_NAME | EXPT_REP_ID | PARAM_NAME | VALUE |
|---|---|---|---|---|
| 12668112 | At_4deg_Cold | 20000214 | Timepoint (hr) | 6 |
| 12668112 | At_10percent_PEG | 20000527 | Age (day) | 20 |
| 12668112 | At_10percent_PEG | 20000527 | Timepoint (day) | 20 |
| 12668112 | At_10percent_PEG | 20000527 | Treatment | 10 percent PEG vs. No Treatment |
| 12668112 | At_10percent_PEG | 20000527 | Organism | A. thaliana |
| 12668112 | At_10percent_PEG | 20000527 | Tissue | Whole Plant |
| 12668112 | At_10percent_PEG | 20000527 | Plant Line | WS |
| 12668112 | At_Drought_Soil_Dry | 20001554 | Timepoint (day) | 7 |
| 12668112 | At_Drought_Soil_Dry | 20001554 | Age (day) | 21 |
| 12668112 | At_Drought_Soil_Dry | 20001554 | Organism | A. thaliana |
| 12668112 | At_Drought_Soil_Dry | 20001554 | Treatment | Drought vs. No Drought |
| 12668112 | At_Drought_Soil_Dry | 20001554 | Post Timepoint (hr) | None |
| 12668112 | At_Drought_Soil_Dry | 20001554 | Post-Treatment | None |
| 12668112 | At_Drought_Soil_Dry | 20001554 | Plant Line | WS |
| 12668112 | At_Drought_Soil_Dry | 20001555 | Timepoint (day) | 10 |
| 12668112 | At_Drought_Soil_Dry | 20001555 | Age (day) | 24 |
| 12668112 | At_Drought_Soil_Dry | 20001555 | Organism | A. thaliana |
| 12668112 | At_Drought_Soil_Dry | 20001555 | Treatment | Drought vs. No Drought |
| 12668112 | At_Drought_Soil_Dry | 20001555 | Post Timepoint (hr) | None |
| 12668112 | At_Drought_Soil_Dry | 20001555 | Post-Treatment | None |
| 12668112 | At_Drought_Soil_Dry | 20001555 | Plant Line | WS |
| 12668112 | At_Interploidy_Crosses | 20001853 | Age (day) | 5 |
| 12668112 | At_Interploidy_Crosses | 20001853 | Organism | A. thaliana |
| 12668112 | At_Interploidy_Crosses | 20001853 | Plant Line | Columbia |
| 12668112 | At_Interploidy_Crosses | 20001853 | Cross | Fis1 vs. 2X x 2X |
| 12668112 | At_Interploidy_Crosses | 20001853 | Tissue | Siliques |
| 12668112 | At_8deg_Cold | 20002105 | Age (day) | 7 |
| 12668112 | At_8deg_Cold | 20002105 | Timepoint (hr) | 8 |
| 12668112 | At_8deg_Cold | 20002105 | Temperature (deg C.) | 8 vs. 22 |
| 12668112 | At_8deg_Cold | 20002105 | Organism | A. thaliana |
| 12668112 | At_8deg_Cold | 20002105 | Tissue | Whole Plant |
| 12668112 | At_8deg_Cold | 20002105 | Plant Line | WS |

Promoter YP0244

Modulates the gene: Ca2+-ATPase 7
The GenBank description of the gene: NM_127860 Arabidopsis thaliana potential calcium-transporting ATPase 7, plasma membrane-type (Ca2+-ATPase, isoform 7) (At2g22950) mRNA, complete cds gi|18400128|ref|NM_127860.1|[18400128]
The promoter sequence:
5'aaagtcttatttgtgaaattttacaaatgttggaaaaaagcattttatggtgctatatttgtcaatttc ccttgattatatatccttttgaaaagtaatgttttttttatgtgtgtgtattcatgaaccttggaaaaact acaaatcagatcatggtttgttttaggtgaaaaatttagaacacagttacgcaagaaagatatcggtaaat ttttgtttctttgaatcgaaattaatcaaaaagtattttccattatataacaacaactaatctctgtttttt ttttttttttttttaacaactaatctcttatcaaaatgacactacagaatcacgattgtaaatctttaaaag gcagtctgaaaaatattcatgaggatgagattttattcattcatggttgtaagtaatcattatgtaaagtt taggataaggacgttcaaaatcatataaaaaaactctacgaataaagtttatagtctatcatattgattca tatttcatagaaagttactggaaaacattacacaagtattctcgattttttacgagtttgtttagtagtcgc aaaattttatttttactttttgagtatacgaacccataagctgattttcttccaagttccaataatgatatc atagtgtactcttcatgaatgtttcaagcatataattataacgttcataagtaatattctactgcatgttt gttatTATAaattaactaataatcgaacgtatgagttttgattgagattgttgtgctcacgaaatgaagga ctcggtcaattctaaagcttaaaataagaagctcagatcttaaaactcgctttcgtcttcgtcctccatt aagtttgcgattcttttgctcttctttctctctcacatttttgtcccaaaacaataaaaagaaacaataat agaaagtgttacagaaaaagaaagaaaac 3'-ATG
The promoter was cloned from the organism: Arabidopsis thaliana, WS ecotype TABLE 1-continued Promoter Sequences and Related Information Alternative nucleotides:
Predicted (Columbia)
Experimental (Wassilewskija)

| Sequence Position (bp) | Mismatch | Columbia/Wassilewskija |
|---|---|---|
| 90 | SNP | a/g |
| 183 | SNP | t/c |
| 373 | SNP | t/c |
| 380 | No g in Ws | —/— |
| 393 | No a in Ws | —/— |
| 717 | SNP | t/c |
| 774 | SNP | a/g |

The promoter was cloned in the vector: pNewbin4-HAP1-GFP
When cloned into the vector the promoter was operably linked to a marker, which was the type: GFP-ER
Promoter-marker vector was tested in: *Arabidopsis thaliana*, WS ecotype
Generation screened: XT1 Mature   XT2 Seedling   T2 Mature   T3 Seedling The spatial expression of the promoter-marker vector was found observed in and would be useful in expression in any or all of the following:

Flower                                          H pollen
Observed expression pattern of the promoter-marker vector was in:
T1 mature: Pollen specific expression in mature plants.
T2 seedling: No GFP expression observed.

The promoter can be of use in the following trait and sub-trait areas: (search for the trait and sub-trait table)

| Trait Area: | Paternal inheritance trait where 50% is desired |
|---|---|
| Sub-trait Area: | Yield |

The promoter has utility in:
Utility: Modulation of pollen tube growth, incompatibility.
Misc. promoter information: Bidirectionality: Pass Exons: Pass Repeats: No
The Ceres cDNA ID of the endogenous coding sequence to the promoter: 12736016
cDNA nucleotide sequence:

atggagagttacctcaactcgaatttcgacgttaaggcgaagcattcgtcggaggaagtgctagaaaaatg gcggaatctttgcagtgtcgtcaagaacccgaaacgtcggtttcgattcactgccaatctctccaaacgtt acgaagctgctgccatgcgccgcaccaaccaggagaaattaaggattgcagttctcgtgtcaaaagccgca tttcaatttatctctggtgtttctccaagtgactacaaggtgcctgaggaagttaaagcagcaggctttga catttgtgcagacgagttaggatcaatagtggaaggtcatgatgtgaagaagctcaagttccatggtggtg ttgatggtctttcaggtaagctcaaggcatgtcccaatgctggtctctcaacaggtgaacctgagcagtta agcaaacgacaagagcttttcggaatcaataagtttgcagagagtgaattacgaagtttctgggtgtttgt ttgggaagcacttcaagatatgactcttatgattcttggtgtttgtgctttcgtctctttgattgttggga ttgcaactgaaggatggcctcaaggatcgcatgatggtcttggcattgttgctagtattcttttagttgtg tttgtgacagcaactagtgactatagacaatctttgcagttccgggatttggataaagagaagaagaagat cacggttcaagttacgcgaaacgggtttagacaaaagatgtctatatatgatttgctccctggagatgttg ttcatcttgctatcggagatcaagtccctgcagatggtcttttcctctcgggattctctgttgttatcgat gaatcgagtttaactggagagagtgagcctgtgatggtgactgcacagaaccctttccttctctctggaac caaagttcaagatgggtcatgtaagatgttggttacaacagttgggatgagaactcaatggggaaagttaa tggcaacacttagtgaaggaggagatgacgaaactccgttgcaggtgaaacttaatggagttgcaaccatc attgggaaaattggtctttccttcgctattgttacctttgcggttttggtacaaggaatgtttatgaggaa gctttcattaggccctcattggtggtggtccggagatgatgcattagagcttttggagtattttgctattg ctgtcacaattgttgttgttgcggttcctgaaggtttaccattagctgtcacacttagtctcgcgtttgcg atgaagaagatgatgaacgataaagcgcttgttcgccatttagcagcttgtgagacaatgggatctgcaac taccatttgtagtgacaagactggtacattaacaacaaatcacatgactgttgtgaaatcttgcatttgta TABLE 1-continued Promoter Sequences and Related Information

```
tgaatgttcaagatgtagctagcaaaagttctagtttacaatctgatatccctgaagctgccttgaaacta
cttctccagttgattttaataataccggtggagaagttgttgtgaacgaacgtggcaagactgagatatt
ggggacaccaacagagactgctatattggagttaggactatctcttggaggtaagtttcaagaagagagac
aatctaacaaagttattaaagttgagccttttaactcaacaaagaaaagaatgggagtagtcattgagctg
cctgaaggaggacgcattcgcgctcacacgaaaggagcttcagagatagttttagcggcttgtgataaagt
catcaactcaagtggtgaagttgttccgcttgatgatgaatccatcaagttcttgaatgttacaatcgatg
agtttgcaaatgaagctcttcgtactctttgccttgcttatatggatatcgaaagcgggttttcggctgat
gaaggtattccggaaaagggtttacatgcatagggattgttggtatcaaagaccctgttcgtcctggagt
tcgggagtccgtggaactttgtcgccgtgcgggtattatggtgagaatggttacaggagataacattaaca
ccgcaaaggctattgctagagaatgtggaattctcactgatgatggtatagcaattgaaggtcctgtgttt
agagagaagaaccaagaagagatgcttgaactcattcccaagattcaggtcatggctcgttcttcccaat
ggacaagcatacactggtgaagcagttgaggactacttttgatgaagttgttgctgtgactggcgacggga
caaacgatgcaccagcgctccacgaggctgacataggattagcaatgggcattgccgggactgaagtagct
aaagagattgcggatgtcatcattctcgacgataacttcagcacaatcgtcaccgtagcgaaatggggacg
ttctgtttacattaacattcagaaatttgtgcagtttcaactaacagtcaatgttgttgcccttattgtta
acttctcttcagcttgcttgactggaagtgctcctctaactgctgttcaactgctttgggttaacatgatc
atggacacacttggagctcttgctctagctacagaacctccgaacaacgagctgatgaaacgtatgcctgt
tggaagaagagggaatttcattaccaatgcgatgtggagaaacatcttaggacaagctgtgtatcaattta
ttatcatatggattctacaggccaaagggaagtccatgtttggtcttgttggttctgactctactctcgta
ttgaacacacttatcttcaactgctttgtattctgccaggttttcaatgaagtaagctcgcgggagatgga
agagatcgatgttttcaaaggcatactcgacaactatgttttcgtggttgttattggtgcaacagttttct
ttcagatcataatcattgagttcttgggcacatttgcaagcaccacacctcttacaatagttcaatggttc
ttcagcattttcgttggcttcttgggtatgccgatcgctgctggcttgaagaaaatacccgtgtga
Coding sequence:
MESYLNSNFDVKAKHSSEEVLEKWRNLCSVVKNPKRRFRFTANLSKRYEAAAMRRTNQEKLRTA
VLVSKAAFQFISGVSPSDYKVPEEVKAAGFDICADELGSIVEGHDVKKLKFHGGVDGLSGKLKACP
NAGLSTGEPEQLSKRQELFGINKFAESELRSFWVFVWEALQDMTLMILGVCAFVSLIVGIATEGWP
QGSHDGLGIVASILLVVFVTATSDYRQSLQFRDLDKEKKKITVQVTRNGFRQKMSIYDLLPGDVVH
LAIGDQVPADGLFLSGFSVVIDESSLTGESEPVMVTAQNPFLLSGTKVQDGSCKMLVTTVGMRTQ
WGKLMATLSEGGDDETPLQVKLNGVATIIGKIGLSFAIVTFAVLVQGMFMRKLSLGPHWWWSGD
DALELLEYFAIAVTIVVVAVPEGLPLAVTLSLAFAMKKMMNDKALVRHLAACETMGSATTICSDK
TGTLTTNHMTVVKSCICMNVQDVASKSSSLQSDIPEAALKLLLQLIFNNTGGEVVVNERGKTEILG
TPTETAILELGLSLGGKFQEERQSNKVIKVEPFNSTKKRMGVVIELPEGGRIRAHTKGASEIVLAAC
DKVINSSGEVVPLDDESIKFLNVTIDEFANEALRTLCLAYMDIESGFSADEGIPEKGFTCIGIVGIKDP
VRPGVRESVELCRRAGIMVRMVTGDNINTAKAIARECGILTDDGIAIEGPVFREKNQEEMLELIPKI
QVMARSSPMDKHTLVKQLRTTFDEVVAVTGDGTNDAPALHEADIGLAMGIAGTEVAKEIADVIIL
DDNFSTIVTVAKWGRSVYINIQKFVQFQLTVNVVALIVNFSSACLTGSAPLTAVQLLWVNMIMDTL
GALALATEPPNNELMKRMPVGRRGNFITNAMWRNILGQAVYQFIIIWILQAKGKSMFGLVGSDST
```

TABLE 1-continued

Promoter Sequences and Related Information

LVLNTLIFNCFVFCQVFNEVSSREMEEIDVFKGILDNYVFVVVIGATVFFQIIIIEFLGTFASTTPLTIV

QWFFSIFVGFLGMPIAAGLKKIPV*

Microarray data shows that the coding sequence was expressed in the following experiments, which shows that the promoter would be useful to modulate expression in situations similar to the following:

Promoter YP0226

Modulates the gene: Indoleacetic acid-induced protein 12
The GenBank description of the gene: NM_100334 *Arabidopsis thaliana* auxin-responsive protein IAA12 (Indoleacetic acid-induced protein 12) (At1g04550) mRNA, complete cds gi|30678909|ref|NM_100334.2
The promoter sequence:
5'tcaaaagtgtaatttccacaaaccaattgcgcctgcaaaagttttcaaaggatcatcaaacataatgat gaatatctcatcaccacgattttataataatgcatcttttcccaccattttttttccctcacttttctttta taatcttgttcgacaacaatcatggtctaaggaaaaagttgaaaatatatattatcttagttattagaaaa gaaagataatcaaatggtcaatatgcaaatggcatatgaccataaacgagtttgctagtataaagaatgat ggccaacctgttaaagagagactaaaattaggtctaaaatctaggagcaatgtaaccaatacatagtatat gaaatataaaagttaatttagatttttttgattagcccaaattaaagaaaaatggtatttaaaacagagact cttcatcctaaaggctaaagcaatacaattttttggttaagaaaagaaaaaaaccacaagcggaaaagaaaa caaaaaagaactatattatgatgcaacagcaacacaaagcaaaaccttgcacacacacatacaactgtaaa caagtttcttgggactctctattttctcttgctgcttgaaccaaacacaacaacgatatcccaacgagagc acaacaggtttgattatgtcggaagacaagttttgagagaaaacaaacaatatttTATAacaaaggagaag acttttggttagaaaaaattggtatggccattacaagacatatgggtcccaattctcatcactctctccac caccaaaatcctcctctctctctctctttactctgttttcatcatctctttctctcgtctctctcaaa ccctaaatacactcttttctcttcttgttgtctccattctctctgtgtcatcaagcttcttttttgtgtggg ttatttgaaagacactttctctgctggtatcattggagt 3'-ATG
The promoter was cloned from the organism: *Arabidopsis thaliana*, WS ecotype Alternative nucleotides:

| Sequence (bp) | Mismatch | Columbia/Wassilewskija |
|---|---|---|
| 523 | SNP | g/— |
| 558 | SNP | a/c |
| 741 | SNP | a/g |

The promoter was cloned in the vector: pNewbin4-HAP1-GFP
When cloned into the vector the promoter was operably linked to a marker, which was the type: GFP-ER
Promoter-marker vector was tested in: *Arabidopsis thaliana*, WS ecotype
Generation screened: XT1 Mature   XT2 Seedling   T2 Mature   T3 Seedling The spatial expression of the promoter-marker vector was found observed in and would be useful in expression in any or all of the following:

Flower                           M vascular
Silique                          M placenta, M vascular
Hypocotyl                        H vascular
Cotyledon                        H vascular, H petiole
Primary Root                     H vascular
Observed expression pattern of the promoter-marker vector was in:
T1 mature: GFP expressed in vasculature of silique and pedicles of flowers.
T2 seedling: High GFP expression throughout vasculature of root, hypocotyl, and petioles.
Misc. promoter information:   Bidirectionality: Pass   Exons: Pass   Repeats: No
Optional Promoter Fragments: 5' UTR region at base pairs 832-1000
The Ceres cDNA ID of the endogenous coding sequence to the promoter: 12327003
cDNA nucleotide sequence:
ACTCTGTTTTCATCATCTCTTTCTCTCGTCTCTCTCAAACCCTAAATACACTCTTTCTCTTCTTG

TTGTCTCCATTCTCTCTGTGTCATCAAGCTTCTTTTTTGTGTGGGTTATTTGAAAGACACTTTCT

CTGCTGGTATCATTGGAGTCTAGGGTTTTGTTATTGACATGCGTGGTGTGTCAGAATTGGAGG

TABLE 1-continued

Promoter Sequences and Related Information

```
TGGGGAAGAGTAATCTTCCGGCGGAGAGTGAGCTGGAATTGGGATTAGGGCTCAGCCTCGGT

GGTGGCGCGTGGAAAGAGCGTGGGAGGATTCTTACTGCTAAGGATTTTCCTTCCGTTGGGTCT

AAACGCTCTGCTGAATCTTCCTCTCACCAAGGAGCTTCTCCTCCTCGTTCAAGTCAAGTGGTAG

GATGGCCACCAATTGGGTTACACAGGATGAACAGTTTGGTTAATAACCAAGCTATGAAGGCAG

CAAGAGCGGAAGAAGGAGACGGGGAGAAGAAAGTTGTGAAGAATGATGAGCTCAAAGATGT

GTCAATGAAGGTGAATCCGAAAGTTCAGGGCTTAGGGTTTGTTAAGGTGAATATGGATGGAGT

TGGTATAGGCAGAAAAGTGGATATGAGAGCTCATTCGTCTTACGAAAACTTGGCTCAGACGCT

TGAGGAAATGTTCTTTGGAATGACAGGTACTACTTGTCGAGAAAAGGTTAAACCTTTAAGGCT

TTTAGATGGATCATCAGACTTTGTACTCACTTATGAAGATAAGGAAGGGGATTGGATGCTTGT

TGGAGATGTTCCATGGAGAATGTTTATCAACTCGGTGAAAAGGCTTCGGATCATGGGAACCTC

AGAAGCTAGTGGACTAGCTCCAAGACGTCAAGAGCAGAAGGATAGACAAAGAAACAACCCTG

TTTAGCTTCCCTTCCAAAGCTGGCATTGTTTATGTATTGTTTGAGGTTTGCAATTTACTCGATA

CTTTTTGAAGAAAGTATTTTGGAGAATATGGATAAAAGCATGCAGAAGCTTAGATATGATTTG

AATCCGGTTTTCGGATATGGTTTTGCTTAGGTCATTCAATTCGTAGTTTTCCAGTTTGTTTCTTC

TTTGGCTGTGTACCAATTATCTATGTTCTGTGAGAGAAAGCTCTTGTTTATTTGTTCTCTCAGA

TTGTAAATAGTTGAAGTTATCTAATTAATGTGATAAGAGTTATGTTTATGATTCC

Coding sequence:
MRGVSELEVGKSNLPAESELELGLGLSLGGGAWKERGRILTAKDFPSVGSKRSAESSSHQGASPPR

SSQVVGWPPIGLHRMNSLVNNQAMKAARAEEGDGEKKVVKNDELKDVSMKVNPKVQGLGFVK

VNMDGVGIGRKVDMRAHSSYENLAQTLEEMFFGMTGTTCREKVKPLRLLDGSSDFVLTYEDKEG

DWMLVGDVPWRMFINSVKRLRIMGTSEASGLAPRRQEQKDRQRNNPV*
```

Microarray data shows that the coding sequence was expressed in the following experiments, which shows that the promoter would be useful to modulate expression in situations similar to the following:

| CDNA_ID | SHORT_NAME | EXPT_REP_ID | IS_UP |
|---|---|---|---|
| 12327003 | At_Diversity_Expt | 108457 | − |
| 12327003 | At_100uM_ABA | 108561 | − |
| 12327003 | At_100uM_ABA_Mutants | 20000069 | − |
| 12327003 | At_100uM_ABA_Mutants | 20000070 | − |
| 12327003 | At_100uM_ABA_Mutants | 20000072 | − |
| 12327003 | At_100uM_ABA_Mutants | 20000086 | − |
| 12327003 | At_100uM_ABA_Mutants | 20000087 | − |
| 12327003 | At_100uM_ABA_Mutants | 20000088 | − |
| 12327003 | At_2mM_SA_CS3726-Columbia | 20000089 | − |
| 12327003 | At_100uM_ABA_Mutants | 20000117 | − |
| 12327003 | At_Far-red-induction | 20001248 | − |
| 12327003 | At_8deg_Cold | 20002105 | + |

The parameters for the microarray experiments listed above by Expt_Rep_ID and Short_Name are as follow below:

| CDNA_ID | SHORT_NAME | EXPT_REP_ID | PARAM_NAME | VALUE |
|---|---|---|---|---|
| 12327003 | At_Diversity_Expt | 108457 | Plant Line | Canola vs. WS |
| 12327003 | At_Diversity_Expt | 108457 | Tissue | Hypocotyl |
| 12327003 | At_100uM_ABA | 108561 | Timepoint (hr) | 6 |
| 12327003 | At_100uM_ABA | 108561 | Treatment | 100 uM ABA vs. No Treatment |
| 12327003 | At_100uM_ABA | 108561 | Tissue | Aerial |
| 12327003 | At_100uM_ABA_Mutants | 20000069 | Timepoint (hr) | 6 |
| 12327003 | At_100uM_ABA_Mutants | 20000069 | Treatment | 100 uM ABA vs. No Treatment |
| 12327003 | At_100uM_ABA_Mutants | 20000069 | Tissue | Aerial |
| 12327003 | At_100uM_ABA_Mutants | 20000069 | Plant Line | CS23 |
| 12327003 | At_100uM_ABA_Mutants | 20000070 | Timepoint (hr) | 6 |

TABLE 1-continued

Promoter Sequences and Related Information

| 12327003 | At_100uM_ABA_Mutants | 20000070 | Treatment | 100 uM ABA vs. No Treatment |
|---|---|---|---|---|
| 12327003 | At_100uM_ABA_Mutants | 20000070 | Tissue | Aerial |
| 12327003 | At_100uM_ABA_Mutants | 20000070 | Plant Line | CS24 |
| 12327003 | At_100uM_ABA_Mutants | 20000072 | Timepoint (hr) | 6 |
| 12327003 | At_100uM_ABA_Mutants | 20000072 | Treatment | 100 uM ABA vs. No Treatment |
| 12327003 | At_100uM_ABA_Mutants | 20000072 | Tissue | Aerial |
| 12327003 | At_100uM_ABA_Mutants | 20000072 | Plant Line | CS8105 |
| 12327003 | At_100uM_ABA_Mutants | 20000086 | Timepoint (hr) | 6 |
| 12327003 | At_100uM_ABA_Mutants | 20000086 | Treatment | 100 uM ABA vs. No Treatment |
| 12327003 | At_100uM_ABA_Mutants | 20000086 | Tissue | Aerial |
| 12327003 | At_100uM_ABA_Mutants | 20000086 | Plant Line | CS22 |
| 12327003 | At_100uM_ABA_Mutants | 20000087 | Timepoint (hr) | 6 |
| 12327003 | At_100uM_ABA_Mutants | 20000087 | Treatment | 100 uM ABA vs. No Treatment |
| 12327003 | At_100uM_ABA_Mutants | 20000087 | Tissue | Aerial |
| 12327003 | At_100uM_ABA_Mutants | 20000087 | Plant Line | WS |
| 12327003 | At_100uM_ABA_Mutants | 20000088 | Timepoint (hr) | 6 |
| 12327003 | At_100uM_ABA_Mutants | 20000088 | Treatment | 100 uM ABA vs. No Treatment |
| 12327003 | At_100 uM_ABA_Mutants | 20000088 | Tissue | Aerial |
| 12327003 | At_100uM_ABA_Mutants | 20000088 | Plant Line | Landsberg |
| 12327003 | At_2mM_SA_CS3726-Columbia | 20000089 | Timepoint (hr) | 6 |
| 12327003 | At_2mM_SA_CS3726-Columbia | 20000089 | Treatment | 2 mM SA vs. No Treatment |
| 12327003 | At_2mM_SA_CS3726-Columbia | 20000089 | Tissue | Aerial |
| 12327003 | At_2mM_SA_CS3726-Columbia | 20000089 | Plant Line | CS3726 |
| 12327003 | At_100uM_ABA_Mutants | 20000117 | Timepoint (hr) | 6 |
| 12327003 | At_100uM_ABA_Mutants | 20000117 | Treatment | 100 uM ABA vs. No Treatment |
| 12327003 | At_100uM_ABA_Mutants | 20000117 | Tissue | Aerial |
| 12327003 | At_100uM_ABA_Mutants | 20000117 | Plant Line | Columbia |
| 12327003 | At_Far-red-induction | 20001248 | Timepoint (hr) | 4 |
| 12327003 | At_Far-red-induction | 20001248 | Age (day) | 7 |
| 12327003 | At_Far-red-induction | 20001248 | Organism | A. thaliana |
| 12327003 | At_Far-red-induction | 20001248 | Plant Line | Columbia |
| 12327003 | At_Far-red-induction | 20001248 | Light | Far-red vs. White |
| 12327003 | At_Far-red-induction | 20001248 | Tissue | Whole Plant |
| 12327003 | At_8deg_Cold | 20002105 | Age (day) | 7 |
| 12327003 | At_8deg_Cold | 20002105 | Timepoint (hr) | 8 |
| 12327003 | At_8deg_Cold | 20002105 | Temperature (deg C.) | 8 vs. 22 |
| 12327003 | At_8deg_Cold | 20002105 | Organism | A. thaliana |
| 12327003 | At_8deg_Cold | 20002105 | Tissue | Whole Plant |
| 12327003 | At_8deg_Cold | 20002105 | Plant Line | WS |

Promoter PT0511

Modulates the gene: Major intrinsic protein (MIP)
The GenBank description of the gene:: NM_106724 *Arabidopsis thaliana* major intrinsic protein (MIP) family (At1g80760) mRNA, complete cds gi|30699534|ref|NM_106724.2|[30699534].
The promoter sequence:

5'gacgggtcatcacagattcttcgttttttttatagatagaaaaggaataacgttaaaagtatacaaatta tatgcaagagtcattcgaaagaattaaataaagagatgaactcaaaagtgatttttaaattttaatgataag aatatacatctcacagaaatctttttatttgacatgtaaaatcttgttttcacctatcttttgttagtaaac aagaatatttaatttgagcctcacttggaacgtgataataatatacatcttatcataattgcatattttgc ggatagttttttgcatggggagattaaaggcttaataaagccttgaatttccgagggaggaatcatgttttt atacttgcaaactatacaaccatctgcatcgataattggtgttaatacatgcaaggattatacactaaaac aaatcatttatttccttacaaaaagagagtcgactgtgagtcacattctgtgacaaggaaaggtcaagaac catcgcttttatcatcattctctttgctaacaacttacaaccacacaaacgcaagagttccattctcatgg agaagaacatattatgcaaaataatgtatgtcgatcgatagagaaaaggatccacaattattgctccatct caaaagcttctttagtacacgatacatgtatcatgtaaatagaaatatgaaagatacaatacacgacccat tctcataaagatagcaacatttcatgttatgtaaagagtcttccttaggacacatgcattaaaactaagga

TABLE 1-continued

Promoter Sequences and Related Information ttaccaacccacttactcctcactccaaccaaatatcaatcatctattttgggtccttcactcataagtca actctcatgccttcctctataaataccgtaccctacgcatcccttagttctacatcacataaaaacaatca tagcaaaaacaTATAtcctcaaattaatt 3'-cATG
The promoter was cloned from the organism: *Arabidopsis thaliana*, Columbia ecotype

Alternative nucleotides:

| Predicted Position (bp) | Mismatch | Predicted/Experimental |
| --- | --- | --- |
| 1-1000 | None | Identities = 1000/1000 (100%) |

The promoter was cloned in the vector: pNewbin4-HAP1-GFP
When cloned into the vector the promoter was operably linked to a marker, which was the type: GFP-ER
Promoter-marker vector was tested in: *Arabidopsis thaliana*, WS ecotype
Generation screened: XT1 Mature  XT2 Seedling  T2 Mature  T3 Seedling The spatial expression of the promoter-marker vector was found observed in and would be useful in expression in any or all of the following:

Flower                           H filament H anther L vascular
Cotyledon                        L vascular L petiole
Primary Root                     L epidermis
Observed expression pattern of the promoter-marker vector was in:
T1 mature: High expression at vascular connective tissue between locules of anther.
T2 seedling: Low expression in root epidermal cells and vasculature of petioles.
Misc. promoter information:  Bidirectionality: Pass  Exons: Pass  Repeats: No
Optional Promoter Fragments: 5' UTR region at base pairs 927-1000.
The Ceres cDNA ID of the endogenous coding sequence to the promoter: 12711931
cDNA nucleotide sequence:
ATGGATCATGAGGAAATTCCATCCACGCCCTCAACGCCGGCGACAACCCCGGGGACTCCAGGA

GCGCCGCTCTTTGGAGGATTCGAAGGGAAGAGGAATGGACACAATGGTAGATACACACCAAA

GTCACTTCTCAAAAGCTGCAAATGTTTCAGTGTTGACAATGAATGGGCTCTTGAAGATGGAAG

ACTCCCTCCGGTCACTTGCTCTCTCCCTCCCCCTAACGTTTCCCTCTACCGCAAGTTGGGAGCA

GAGTTTGTTGGGACATTGATCCTGATATTCGCCGGAACAGCGACGGCGATCGTGAACCAGAAG

ACAGATGGAGCTGAGACGCTTATTGGTTGCGCCGCCTCGGCTGGTTTGGCGGTTATGATCGTT

ATATTATCGACCGGTCACATCTCCGGGGCACATCTCAATCCGGCTGTAACCATTGCCTTTGCTG

CTCTCAAACACTTCCCTTGGAAACACGTGCCGGTGTATATCGGAGCTCAGGTGATGGCCTCCG

TGAGTGCGGCGTTTGCACTGAAAGCAGTGTTTGAACCAACGATGAGCGGTGGCGTGACGGTG

CCGACGGTGGGTCTCAGCCAAGCTTTCGCCTTGGAATTCATTATCAGCTTCAACCTCATGTTCG

TTGTCACAGCCGTAGCCACCGACACGAGAGCTGTGGGAGAGTTGGCGGGAATTGCCGTAGGA

GCAACGGTCATGCTTAACATACTTATAGCTGGACCTGCAACTTCTGCTTCGATGAACCCTGTAA

GAACACTGGGTCCAGCCATTGCAGCAAACAATTACAGAGCTATTTGGGTTTACCTCACTGCCC

CCATTCTTGGAGCGTTAATCGGAGCAGGTACATACACAATTGTCAAGTTGCCAGAGGAAGATG

AAGCACCCAAAGAGAGGAGGAGCTTCAGAAGATGA

Coding sequence:
MDHEEIPSTPSTPATTPGTPGAPLFGGFEGKRNGHNGRYTPKSLLKSCKCFSVDNEWALEDGRLPP

VTCSLPPPNVSLYRKLGAEFVGTLILIFAGTATAIVNQKTDGAETLIGCAASAGLAVMIVILSTGHIS

GAHLNPAVTIAFAALKHFPWKHVPVYIGAQVMASVSAAFALKAVFEPTMSGGVTVPTVGLSQAF

ALEFIISFNLMFVVTAVATDTRAVGELAGIAVGATVMLNILIAGPATSASMNPVRTLGPAIAANNYR

AIWVYLTAPILGALIGAGTYTIVKLPEEDEAPKERRSFRR*

TABLE 1-continued

Promoter Sequences and Related Information

Microarray data shows that the coding sequence was expressed in the following experiments, which shows that the promoter would be useful to modulate expression in situations similar to the following:

| CDNA_ID | SHORT_NAME | EXPT_REP_ID | IS_UP |
|---|---|---|---|
| 12711931 | At_Root_Tips | 108434 | − |
| 12711931 | At_stm_Mutants | 108435 | + |
| 12711931 | At_Diversity_Expt | 108457 | + |
| 12711931 | At_Diversity_Expt | 108458 | + |
| 12711931 | At_Germinating_Seeds | 108464 | + |
| 12711931 | At_ap2_floral_buds | 108501 | + |
| 12711931 | At_4deg_Cold | 108579 | + |
| 12711931 | At_Ler-pi_Ovule | 108595 | + |
| 12711931 | At_100uM_ABA_Mutants | 20000069 | − |
| 12711931 | At_100uM_ABA_Mutants | 20000070 | − |
| 12711931 | At_100uM_ABA_Mutants | 20000071 | − |
| 12711931 | At_100uM_ABA_Mutants | 20000086 | − |
| 12711931 | At_100uM_ABA_Mutants | 20000087 | − |
| 12711931 | At_100uM_ABA_Mutants | 20000088 | − |
| 12711931 | At_2mM_SA_CS3726-Columbia | 20000089 | − |
| 12711931 | At_2mM_SA_CS3726-Columbia | 20000090 | − |
| 12711931 | At_100uM_ABA_Mutants | 20000117 | − |
| 12711931 | At_CS6632_Shoots-Roots | 20000224 | + |
| 12711931 | At_Root-Tips-vs-Tops | 20000227 | + |
| 12711931 | At_Siliques | 20000234 | + |
| 12711931 | At_Siliques | 20000236 | + |
| 12711931 | At_Caf_Knockout | 20000244 | − |
| 12711931 | At_Open_Flower | 20000264 | + |
| 12711931 | At_Open_Flower | 20000286 | + |
| 12711931 | At_Drought | 20000437 | − |
| 12711931 | At_Shoots | 20000438 | + |
| 12711931 | At_CS6879_Shoots-Roots | 20000451 | − |
| 12711931 | At_42deg_Heat | 20000458 | − |
| 12711931 | At_Guard_Cells | 20000495 | + |
| 12711931 | At_100uM_ABA_Mutants | 20000576 | + |
| 12711931 | At_Herbicide_Mutants | 20000640 | − |
| 12711931 | At_Herbicide_Mutants | 20000642 | − |
| 12711931 | At_Petals | 20000794 | + |
| 12711931 | At_Line_Comparisons | 20001151 | + |
| 12711931 | At_Line_Comparisons | 20001184 | + |
| 12711931 | At_Far-red-induction | 20001248 | − |
| 12711931 | At_Line_Comparisons | 20001307 | + |
| 12711931 | At_Line_Comparisons | 20001318 | + |
| 12711931 | At_Line_Comparisons | 20001319 | + |
| 12711931 | At_Line_Comparisons | 20001347 | + |
| 12711931 | At_50mM_NH4NO3_L-to-H | 20001458 | − |
| 12711931 | At_Drought_Soil_Dry | 20001556 | − |
| 12711931 | At_Drought_Soil_Dry | 20001557 | − |
| 12711931 | At_Drought_Soil_Dry | 20001558 | − |
| 12711931 | At_Drought_Reproduction | 20001905 | − |
| 12711931 | At_Drought_Reproduction | 20001906 | − |
| 12711931 | At_Drought_Reproduction | 20001907 | − |
| 12711931 | At_8deg_Cold | 20002105 | + |

The parameters for the microarray experiments listed above by Expt_Rep_ID and Short_Name are as follow below:

| CDNA_ID | SHORT_NAME | EXPT_REP_ID | PARAM_NAME | VALUE |
|---|---|---|---|---|
| 12711931 | At_Root_Tips | 108434 | Tissue | Root Tips |
| 12711931 | At_stm_Mutants | 108435 | Tissue | Shoot Apical Meristem Region |
| 12711931 | At_stm_Mutants | 108435 | Plant Line | wt Landsburg vs stm |
| 12711931 | At_Diversity_Expt | 108457 | Plant Line | Canola vs. WS |
| 12711931 | At_Diversity_Expt | 108457 | Tissue | Hypocotyl |
| 12711931 | At_Diversity_Expt | 108458 | Plant Line | Holbolliie vs. WS |
| 12711931 | At_Diversity_Expt | 108458 | Tissue | Hypocotyl |
| 12711931 | At_Germinating_Seeds | 108464 | Age (day) | 4 vs. 0 |
| 12711931 | At_Germinating_Seeds | 108464 | Tissue | Germinating Seeds |
| 12711931 | At_ap2_floral_buds | 108501 | Plant Line | ap2 (Ler.) |
| 12711931 | At_ap2_floral_buds | 108501 | Tissue | Closed Flower |
| 12711931 | At_4deg_Cold | 108579 | Timepoint (hr) | 6 |
| 12711931 | At_4deg_Cold | 108579 | Temperature (deg C.) | 4 vs. 22 |
| 12711931 | At_4deg_Cold | 108579 | Tissue | Aerial |
| 12711931 | At_Ler-pi_Ovule | 108595 | Plant Line | Ler_pi |
| 12711931 | At_Ler-pi_Ovule | 108595 | Tissue | Ovules |
| 12711931 | At_100uM_ABA_Mutants | 20000069 | Timepoint (hr) | 6 |
| 12711931 | At_100uM_ABA_Mutants | 20000069 | Treatment | 100 uM ABA vs. No Treatment |
| 12711931 | At_100uM_ABA_Mutants | 20000069 | Tissue | Aerial |

TABLE 1-continued

Promoter Sequences and Related Information

| | | | | |
|---|---|---|---|---|
| 12711931 | At_100uM_ABA_Mutants | 20000069 | Plant Line | CS23 |
| 12711931 | At_100uM_ABA_Mutants | 20000070 | Timepoint (hr) | 6 |
| 12711931 | At_100uM_ABA_Mutants | 20000070 | Treatment | 100 uM ABA vs. No Treatment |
| 12711931 | At_100uM_ABA_Mutants | 20000070 | Tissue | Aerial |
| 12711931 | At_100uM_ABA_Mutants | 20000070 | Plant Line | CS24 |
| 12711931 | At_100uM_ABA_Mutants | 20000071 | Timepoint (hr) | 6 |
| 12711931 | At_100uM_ABA_Mutants | 20000071 | Treatment | 100 uM ABA vs. No Treatment |
| 12711931 | At_100uM_ABA_Mutants | 20000071 | Tissue | Aerial |
| 12711931 | At_100uM_ABA_Mutants | 20000071 | Plant Line | CS8104 |
| 12711931 | At_100uM_ABA_Mutants | 20000086 | Timepoint (hr) | 6 |
| 12711931 | At_100uM_ABA_Mutants | 20000086 | Treatment | 100 uM ABA vs. No Treatment |
| 12711931 | At_100uM_ABA_Mutants | 20000086 | Tissue | Aerial |
| 12711931 | At_100uM_ABA_Mutants | 20000086 | Plant Line | CS22 |
| 12711931 | At_100uM_ABA_Mutants | 20000087 | Timepoint (hr) | 6 |
| 12711931 | At_100uM_ABA_Mutants | 20000087 | Treatment | 100 uM ABA vs. No Treatment |
| 12711931 | At_100uM_ABA_Mutants | 20000087 | Tissue | Aerial |
| 12711931 | At_100uM_ABA_Mutants | 20000087 | Plant Line | WS |
| 12711931 | At_100uM_ABA_Mutants | 20000088 | Timepoint (hr) | 6 |
| 12711931 | At_100uM_ABA_Mutants | 20000088 | Treatment | 100 uM ABA vs. No Treatment |
| 12711931 | At_100uM_ABA_Mutants | 20000088 | Tissue | Aerial |
| 12711931 | At_100uM_ABA_Mutants | 20000088 | Plant Line | Landsberg |
| 12711931 | At_2mM_SA_CS3726-Columbia | 20000089 | Timepoint (hr) | 6 |
| 12711931 | At_2mM_SA_CS3726-Columbia | 20000089 | Treatment | 2 mM SA vs. No Treatment |
| 12711931 | At_2mM_SA_CS3726-Columbia | 20000089 | Tissue | Aerial |
| 12711931 | At_2mM_SA_CS3726-Columbia | 20000089 | Plant Line | CS3726 |
| 12711931 | At_2mM_SA_CS3726-Columbia | 20000090 | Timepoint (hr) | 6 |
| 12711931 | At_2mM_SA_CS3726-Columbia | 20000090 | Treatment | 2 mM SA vs. No Treatment |
| 12711931 | At_2mM_SA_CS3726-Columbia | 20000090 | Tissue | Aerial |
| 12711931 | At_2mM_SA_CS3726-Columbia | 20000090 | Plant Line | Columbia |
| 12711931 | At_100uM_ABA_Mutants | 20000117 | Timepoint (hr) | 6 |
| 12711931 | At_100uM_ABA_Mutants | 20000117 | Treatment | 100 uM ABA vs. No Treatment |
| 12711931 | At_100uM_ABA_Mutants | 20000117 | Tissue | Aerial |
| 12711931 | At_100uM_ABA_Mutants | 20000117 | Plant Line | Columbia |
| 12711931 | At_CS6632_Shoots-Roots | 20000224 | Age (day) | 14 |
| 12711931 | At_CS6632_Shoots-Roots | 20000224 | Organism | *A. thaliana* |
| 12711931 | At_CS6632_Shoots-Roots | 20000224 | Plant Line | CS6632 vs. WS |
| 12711931 | At_CS6632_Shoots-Roots | 20000224 | Tissue | Shoots |
| 12711931 | At_Root-Tips-vs-Tops | 20000227 | Age (day) | 7, 10, 14 |
| 12711931 | At_Root-Tips-vs-Tops | 20000227 | Organism | *A. thaliana* |
| 12711931 | At_Root-Tips-vs-Tops | 20000227 | Tissue | Root Tips vs. Root Tops |
| 12711931 | At_Root-Tips-vs-Tops | 20000227 | Plant Line | WS |
| 12711931 | At_Siliques | 20000234 | Age (day) | 21 |
| 12711931 | At_Siliques | 20000234 | Tissue | <5 mm Siliques vs. Whole Plant |
| 12711931 | At_Siliques | 20000234 | Organism | *A. thaliana* |
| 12711931 | At_Siliques | 20000234 | Plant Line | WS |
| 12711931 | At_Siliques | 20000236 | Age (day) | 21 |
| 12711931 | At_Siliques | 20000236 | Tissue | >10 mm Siliques vs. Whole Plant |
| 12711931 | At_Siliques | 20000236 | Organism | *A. thaliana* |
| 12711931 | At_Siliques | 20000236 | Plant Line | WS |
| 12711931 | At_Caf_Knockout | 20000244 | Plant Line | caf Knockout vs. wt |
| 12711931 | At_Caf_Knockout | 20000244 | Tissue | Rosette |
| 12711931 | At_Open_Flower | 20000264 | Age (day) | 21 |
| 12711931 | At_Open_Flower | 20000264 | Organism | *A. thaliana* |
| 12711931 | At_Open_Flower | 20000264 | Tissue | Open Flower vs. Whole Plant |
| 12711931 | At_Open_Flower | 20000264 | Plant Line | WS |
| 12711931 | At_Open_Flower | 20000286 | Age (day) | 21 |
| 12711931 | At_Open_Flower | 20000286 | Organism | *A. thaliana* |
| 12711931 | At_Open_Flower | 20000286 | Tissue | Half Open vs. Whole Plant |
| 12711931 | At_Open_Flower | 20000286 | Plant Line | WS |
| 12711931 | At_Drought | 20000437 | Age (day) | 8 |
| 12711931 | At_Drought | 20000437 | Timepoint (hr) | 24 |
| 12711931 | At_Drought | 20000437 | Organism | *A. thaliana* |
| 12711931 | At_Drought | 20000437 | Treatment | Drought vs. No Drought |
| 12711931 | At_Drought | 20000437 | Tissue | Whole Plant |
| 12711931 | At_Drought | 20000437 | Plant Line | WS |
| 12711931 | At_Shoots | 20000438 | Age (day) | 14 vs. 21 |
| 12711931 | At_Shoots | 20000438 | Organism | *A. thaliana* |
| 12711931 | At_Shoots | 20000438 | Tissue | Shoots vs. Whole Plant |

TABLE 1-continued

Promoter Sequences and Related Information

| 12711931 | At_Shoots | 20000438 | Plant Line | WS |
|---|---|---|---|---|
| 12711931 | At_CS6879_Shoots-Roots | 20000451 | Age (day) | 14 |
| 12711931 | At_CS6879_Shoots-Roots | 20000451 | Organism | A. thaliana |
| 12711931 | At_CS6879_Shoots-Roots | 20000451 | Plant Line | CS6879 vs. WS |
| 12711931 | At_CS6879_Shoots-Roots | 20000451 | Tissue | Roots |
| 12711931 | At_42deg_Heat | 20000458 | Timepoint (hr) | 8 |
| 12711931 | At_42deg_Heat | 20000458 | Age (day) | 14 |
| 12711931 | At_42deg_Heat | 20000458 | Temperature (deg C.) | 42 vs. 22 |
| 12711931 | At_42deg_Heat | 20000458 | Organism | A. thaliana |
| 12711931 | At_42deg_Heat | 20000458 | Tissue | Aerial |
| 12711931 | At_42deg_Heat | 20000458 | Plant Line | WS |
| 12711931 | At_Guard_Cells | 20000495 | Harvest Date | 08 Feb. 2002 |
| 12711931 | At_Guard_Cells | 20000495 | Organism | A. thaliana |
| 12711931 | At_Guard_Cells | 20000495 | Tissue | Guard Cells vs. Leaves |
| 12711931 | At_100uM_ABA_Mutants | 20000576 | Timepoint (hr) | 6 |
| 12711931 | At_100uM_ABA_Mutants | 20000576 | Treatment | 1 uM ABA vs. No Treatment |
| 12711931 | At_100uM_ABA_Mutants | 20000576 | Organism | A. thaliana |
| 12711931 | At_100uM_ABA_Mutants | 20000576 | Plant Line | CS23 |
| 12711931 | At_100uM_ABA_Mutants | 20000576 | Tissue | Whole Plant |
| 12711931 | At_Herbicide_Mutants | 20000640 | Timepoint (hr) | 12 |
| 12711931 | At_Herbicide_Mutants | 20000640 | Plant Line | 05377RR/BR27173 |
| 12711931 | At_Herbicide_Mutants | 20000640 | Treatment | Roundup vs. No Treatment |
| 12711931 | At_Herbicide_Mutants | 20000640 | Tissue | Seedlings |
| 12711931 | At_Herbicide_Mutants | 20000642 | Timepoint (hr) | 12 |
| 12711931 | At_Herbicide_Mutants | 20000642 | Plant Line | 3950BR/PCJE10000 |
| 12711931 | At_Herbicide_Mutants | 20000642 | Treatment | Finale vs. No Treatment |
| 12711931 | At_Herbicide_Mutants | 20000642 | Tissue | Seedlings |
| 12711931 | At_Petals | 20000794 | Age (day) | 23-25 days |
| 12711931 | At_Petals | 20000794 | Organism | A. thaliana |
| 12711931 | At_Petals | 20000794 | Tissue | Petals vs. Whole plant |
| 12711931 | At_Petals | 20000794 | Plant Line | WS |
| 12711931 | At_Line_Comparisons | 20001151 | Plant Line | ME01339-01 vs. WS |
| 12711931 | At_Line_Comparisons | 20001184 | Plant Line | ME01848-01 vs. WS |
| 12711931 | At_Far-red-induction | 20001248 | Timepoint (hr) | 4 |
| 12711931 | At_Far-red-induction | 20001248 | Age (day) | 7 |
| 12711931 | At_Far-red-induction | 20001248 | Organism | A. thaliana |
| 12711931 | At_Far-red-induction | 20001248 | Plant Line | Columbia |
| 12711931 | At_Far-red-induction | 20001248 | Light | Far-red vs. White |
| 12711931 | At_Far-red-induction | 20001248 | Tissue | Whole Plant |
| 12711931 | At_Line_Comparisons | 20001307 | Plant Line | WBin4-WX2-A vs. WS |
| 12711931 | At_Line_Comparisons | 20001318 | Plant Line | WBin4-WX14R-A vs. WS |
| 12711931 | At_Line_Comparisons | 20001319 | Plant Line | WBin4-WX24-A vs. WS |
| 12711931 | At_Line_Comparisons | 20001347 | Plant Line | ME01604-01 vs. WS |
| 12711931 | At_50mM_NH4NO3_L-to-H | 20001458 | Timepoint (hr) | 2 |
| 12711931 | At_50mM_NH4NO3_L-to-H | 20001458 | Treatment | 50 mM NH4NO3 vs. 100 mM Manitol |
| 12711931 | At_50mM_NH4NO3_L-to-H | 20001458 | Organism | A. thaliana |
| 12711931 | At_50mM_NH4NO3_L-to-H | 20001458 | Tissue | Siliques |
| 12711931 | At_50mM_NH4NO3_L-to-H | 20001458 | Age (day) | Undefined |
| 12711931 | At_50mM_NH4NO3_L-to-H | 20001458 | Plant Line | WS |
| 12711931 | At_Drought_Soil_Dry | 20001556 | Timepoint (day) | 12 |
| 12711931 | At_Drought_Soil_Dry | 20001556 | Age (day) | 26 |
| 12711931 | At_Drought_Soil_Dry | 20001556 | Organism | A. thaliana |
| 12711931 | At_Drought_Soil_Dry | 20001556 | Treatment | Drought vs. No Drought |
| 12711931 | At_Drought_Soil_Dry | 20001556 | Post Timepoint (hr) | None |
| 12711931 | At_Drought_Soil_Dry | 20001556 | Post-Treatment | None |
| 12711931 | At_Drought_Soil_Dry | 20001556 | Plant Line | WS |
| 12711931 | At_Drought_Soil_Dry | 20001557 | Post Timepoint (hr) | 3 |
| 12711931 | At_Drought_Soil_Dry | 20001557 | Timepoint (day) | 13 |
| 12711931 | At_Drought_Soil_Dry | 20001557 | Age (day) | 27 |
| 12711931 | At_Drought_Soil_Dry | 20001557 | Organism | A. thaliana |
| 12711931 | At_Drought_Soil_Dry | 20001557 | Treatment | Drought vs. No Drought |
| 12711931 | At_Drought_Soil_Dry | 20001557 | Post-Treatment | Re-Water vs. No Drought |
| 12711931 | At_Drought_Soil_Dry | 20001557 | Plant Line | WS |
| 12711931 | At_Drought_Soil_Dry | 20001558 | Post Timepoint (hr) | 6 |
| 12711931 | At_Drought_Soil_Dry | 20001558 | Timepoint (day) | 13 |
| 12711931 | At_Drought_Soil_Dry | 20001558 | Age (day) | 27 |
| 12711931 | At_Drought_Soil_Dry | 20001558 | Organism | A. thaliana |
| 12711931 | At_Drought_Soil_Dry | 20001558 | Treatment | Drought vs. No Drought |
| 12711931 | At_Drought_Soil_Dry | 20001558 | Post-Treatment | Re-Water vs. No Drought |
| 12711931 | At_Drought_Soil_Dry | 20001558 | Plant Line | WS |
| 12711931 | At_Drought_Reproduction | 20001905 | Timepoint (day) | 10 |
| 12711931 | At_Drought_Reproduction | 20001905 | Age (day) | 40 |
| 12711931 | At_Drought_Reproduction | 20001905 | Organism | A. thaliana |
| 12711931 | At_Drought_Reproduction | 20001905 | Treatment | Drought vs. No Drought |
| 12711931 | At_Drought_Reproduction | 20001905 | Tissue | Rosettes |
| 12711931 | At_Drought_Reproduction | 20001905 | Plant Line | WS |
| 12711931 | At_Drought_Reproduction | 20001906 | Timepoint (day) | 5 |

TABLE 1-continued

Promoter Sequences and Related Information

| | | | | |
|---|---|---|---|---|
| 12711931 | At_Drought_Reproduction | 20001906 | Age (day) | 35 |
| 12711931 | At_Drought_Reproduction | 20001906 | Organism | A. thaliana |
| 12711931 | At_Drought_Reproduction | 20001906 | Treatment | Drought vs. No Drought |
| 12711931 | At_Drought_Reproduction | 20001906 | Tissue | Siliques |
| 12711931 | At_Drought_Reproduction | 20001906 | Plant Line | WS |
| 12711931 | At_Drought_Reproduction | 20001907 | Timepoint (day) | 7 |
| 12711931 | At_Drought_Reproduction | 20001907 | Age (day) | 37 |
| 12711931 | At_Drought_Reproduction | 20001907 | Organism | A. thaliana |
| 12711931 | At_Drought_Reproduction | 20001907 | Treatment | Drought vs. No Drought |
| 12711931 | At_Drought_Reproduction | 20001907 | Tissue | Siliques |
| 12711931 | At_Drought_Reproduction | 20001907 | Plant Line | WS |
| 12711931 | At_8deg_Cold | 20002105 | Age (day) | 7 |
| 12711931 | At_8deg_Cold | 20002105 | Timepoint (hr) | 8 |
| 12711931 | At_8deg_Cold | 20002105 | Temperature (deg C.) | 8 vs. 22 |
| 12711931 | At_8deg_Cold | 20002105 | Organism | A. thaliana |
| 12711931 | At_8deg_Cold | 20002105 | Tissue | Whole Plant |
| 12711931 | At_8deg_Cold | 20002105 | Plant Line | WS |

Promoter PT0506

Modulates the gene: CYCD1
The GenBank description of the gene: NM_105689 *Arabidopsis thaliana* cyclin delta-1 (CYCD1) (At1g70210) mRNA, complete cds gi|30698007|ref|NM_105689.2|[30698007]. Go function: cyclin-dependent protein kinase regulator.
The promoter sequence:
5'cgctccagaccactgtttgctttcctctgattaaccaatctcaattaaactactaatttataattcaag ataattagataaccaatcttaaaatttggaatcttcttccctcacttgatattacaaaaaaaaactgatt tatcatacggttaattcaagaaaacagcaaaaaaattgcactataatgcaaaacatcaattaattacattc gattaaaaaatcatcattgaatctaaaatggcctcaaatctattgagcatttgtcatgtgcctaaaatggt tcaggagttttacatctaatcacataaaaagcaaacaataaccaaaaaaattgcattttagcaaatcaaat acttatatatatacgtatgattaagcgtcatgactttaaaacctctgtaaaattttgatttattttcgat gcttttattttttaaccaatagtaataaagtccaaatcttaaatacgaaaaaatgtttctttctaagcgac caacaaaatggtccaaatcacagaaaatgttccataatccaggcccattaagctaatcaccaagtaataca ttacacgtcaccaattaatacattacacgtacggccttctctcttcacgagtaatatgcaaacaaacgtac attagctgtaatgtactcactcatgcaacgtcttaacctgccacgtattacgtaattacaccactccttgt tcctaacctacgcatttcactttagcgcatgttagtcaaaaaacacaaacataaactacaaataaaaaaac tcaaaacaaaacccaatgaacgaacggaccagccccgtctcgattgatggaacagtgacaacagtcccgtt ttctcgggcataacggaaacggtaaccgtctctctgtttcatttgcaacaacaccattttTATAaataaaa acacatttaaataaaaaattattaaaacc 3'- tatatccaaacaaatgaatgtgttaaaccttcactcttctctccacacaaaattcaaaaacctcacatttc acttctctcttctcgcttcttctagatctcaccggtttatctagctccggtttgattcatctccggttatg gggagagaATG
The promoter was cloned from the organism: *Arabidopsis thaliana*, Columbia ecotype Alternative nucleotides:

| Predicted Position (bp) | Mismatch | Predicted/Experimental |
|---|---|---|
| 1-1000 | None | Identities = 1000/1000 (100%) |

The promoter was cloned in the vector: pNewbin4-HAP1-GFP
When cloned into the vector the promoter was operably linked to a marker, which was the type: GFP-ER
Promoter-marker vector was tested in: *Arabidopsis thaliana*, WS ecotype
Generation screened: XT1 Mature   XT2 Seedling   T2 Mature   T3 Seedling The spatial expression of the promoter-marker vector was found observed in and would be useful in expression in any or all of the following:

Flower                                              L anther
Observed expression pattern of the promoter-marker vector was in:
T1 mature: Low expression in anther walls early in stamen development through pre-dehiscence stage. Not in pollen TABLE 1-continued Promoter Sequences and Related Information

```
T2 seedling: No expression observed.
Misc. promoter information:  Bidirectionality: Pass   Exons: Pass    Repeats: No
The Ceres cDNA ID of the endogenous coding sequence to the promoter: 13497447
cDNA nucleotide sequence:
ATATATCCAAACAAATGAATGTGTTAAACCTTCACTCTTCTCTCCACACAAAATTCAAAACCT

CACATTTCACTTCTCTCTTCTCGCTTCTTCTAGATCTCACCGGTTTATCTAGCTCCGGTTTGATT

CATCTCCGGTTATGGGGAGAGAATGAGGAGTTACCGTTTTAGTGATTATCTACACATGTCTGT

TTCATTCTCTAACGATATGGATTTGTTTTGTGGAGAAGACTCCGGTGTGTTTTCCGGTGAGTCA

ACGGTTGATTTCTCGTCTTCCGAGGTTGATTCATGGCCTGGTGATTCTATCGCTTGTTTTATCG

AAGACGAGCGTCACTTCGTTCCTGGACATGATTATCTCTCTAGATTTCAAACTCGATCTCTCGA

TGCTTCCGCTAGAGAAGATTCCGTCGCATGGATTCTCAAGGTACAAGCGTATTATAACTTTCA

GCCTTTAACGGCGTACCTCGCCGTTAACTATATGGATCGGTTTCTTTACGCTCGTCGATTACCG

GAAACGAGTGGTTGGCCAATGCAACTTTTAGCAGTGGCATGCTTGTCTTTAGCTGCAAAGATG

GAGGAAATTCTCGTTCCTTCTCTTTTTGATTTTCAGGTTGCAGGAGTGAAGTATTTATTTGAAG

CAAAAACTATAAAAAGAATGGAACTTCTTGTTCTAAGTGTGTTAGATTGGAGACTAAGATCGG

TTACACCGTTTGATTTCATTAGCTTCTTTGCTTACAAGATCGATCCTTCGGGTACCTTTCTCGG

GTTCTTTATCTCCCATGCTACAGAGATTATACTCTCCAACATAAAAGAAGCGAGCTTTCTTGAG

TACTGGCCATCGAGTATAGCTGCAGCCGCGATTCTCTGTGTAGCGAACGAGTTACCTTCTCTAT

CCTCTGTTGTCAATCCCCACGAGAGCCCTGAGACTTGGTGTGACGGATTGAGCAAAGAGAAGA

TAGTGAGATGCTATAGACTGATGAAAGCGATGGCCATCGAGAATAACCGGTTAAATACACCA

AAAGTGATAGCAAAGCTTCGAGTGAGTGTAAGGGCATCATCGACGTTAACAAGGCCAAGTGA

TGAATCCTCTTTCTCATCCTCTTCTCCTTGTAAAAGGAGAAAATTAAGTGGCTATTCATGGGTA

GGTGATGAAACATCTACCTCTAATTAAAATTTGGGGAGTGAAAGTAGAGGACCAAGGAAACA

AAACCTAGAAGAAAAAAAACCCTCTTCTGTTTAAGTAGAGTATATTTTTTAACAAGTACATAG

TAATAAGGGAGTGATGAAGAAAAGTAAAAGTGTTTATTGGCTGAGTTAAAGTAATTAAGAGT

TTTCCAACCAAGGGGAAGGAATAAGAGTTTTGGTTACAATTTCTTTTATGGAAAGGGTAAAAA

TTGGGTTTTGGGGTTGGTTGGTTGGTGGGAGAGACGAAGCTCATCATTAATGGCTTTGCAGA

TTCCCAAGAAAGCAAAATGAGTAAGTGAGTGTAACACACACGTGTTAGAGAAAAGATATGAT

CATGTGAGTGTGTGTGTGAGAGAGAGAGAGAAGAGTATTTGCATTAGAGTCCTCATCACAC

AGGTACTGATGGATAAGACAGGGGAGCGTTTGCAAAAGATTTGTGAGTGGAGATTTTTCTGAG

CTCTTTGTCTTAATGGATCGCAGCAGTTCATGGGACCCTTCCTCAGCTTCATCATCAAACAAA

AAAAAATCAAGTTGCGAAGTATATATAATTTGTTTTTTTGTTTGGATTTTTAAGATTTTTGATT

CCTTGTGTGTGACTTCACGTGACGGAGGCGTGTGTCTCACGTGTTTGTTTTCTCTTCAAATCTT

TTATTTTGGCGGGAAATTTTGTGTTTTTGATTTCTACGTATTCGTGGACTCCAAATGAGTTTTG

TCACGGTGCGTTTTAGTAGCGTTTGCATGCGTGTAAGGTGTCACGTATGTGTATATATATGATT

TTTTTTTGGTTTCTTGAAAGGTTGAATTTTATAAATAAAACGTTTCTATTAT

Coding sequence:
MRSYRFSDYLHMSVSFSNDMDLFCGEDSGVFSGESTVDFSSSEVDSWPGDSIACFIEDERHFVPGH

DYLSRFQTRSLDASAREDSVAWILKVQAYYNFQPLTAYLAVNYMDRFLYARRLPETSGWPMQLL

AVACLSLAAKMEEILVPSLFDFQVAGVKYLFEAKTIKRMELLVLSVLDWRLSVTPFDFISFFAYKI

DPSGTFLGFFISHATEIILSNIKEASFLEYWPSSIAAAAILCVANELPSLSSVVNPHESPETWCDGLSK
```

TABLE 1-continued

Promoter Sequences and Related Information

EKIVRCYRLMKAMAIENNRLNTPKVIAKLRVSVRASSTLTRPSDESSFSSSSPCKRRKLSGYSWVG

DETSTSN*

Microarray data shows that the coding sequence was expressed in the following experiments, which shows that the promoter would be useful to modulate expression in situations similar to the following:

| CDNA_ID | SHORT_NAME | EXPT_REP_ID | IS_UP |
|---|---|---|---|
| 13497447 | At_Diversity_Expt | 108457 | − |
| 13497447 | At_Diversity_Expt | 108458 | − |
| 13497447 | At_5-1-F2-137 | 108460 | − |
| 13497447 | At_Germinating_Seeds | 108463 | + |
| 13497447 | At_Germinating_Seeds | 108464 | + |
| 13497447 | At_100uM_ABA_Mutants | 20000069 | − |
| 13497447 | At_42deg_Heat | 20000173 | − |
| 13497447 | At_Open_Flower | 20000286 | + |
| 13497447 | At_100uM_ABA_Mutants | 20000573 | − |
| 13497447 | At_100uM_ABA_Mutants | 20000574 | − |
| 13497447 | At_Drought_Reproduction | 20001906 | − |
| 13497447 | At_Drought_Reproduction | 20001911 | − |
| 13497447 | At_8deg_Cold | 20002108 | − |

The parameters for the microarray experiments listed above by Expt_Rep_ID and Short_Name are as follow below:

| CDNA_ID | SHORT_NAME | EXPT_REP_ID | PARAM_NAME | VALUE |
|---|---|---|---|---|
| 13497447 | At_Diversity_Expt | 108457 | Plant Line | Canola vs. WS |
| 13497447 | At_Diversity_Expt | 108457 | Tissue | Hypocotyl |
| 13497447 | At_Diversity_Expt | 108458 | Plant Line | Holbolliie vs. WS |
| 13497447 | At_Diversity_Expt | 108458 | Tissue | Hypocotyl |
| 13497447 | At_5-1-F2-137 | 108460 | Plant Line | 5-1-F2-137 (mutant) |
| 13497447 | At_5-1-F2-137 | 108460 | Probe Method | Amplified |
| 13497447 | At_5-1-F2-137 | 108460 | Tissue | Inflorescences |
| 13497447 | At_Germinating_Seeds | 108463 | Age (day) | 3 vs. 0 |
| 13497447 | At_Germinating_Seeds | 108463 | Tissue | Germinating Seeds |
| 13497447 | At_Germinating_Seeds | 108464 | Age (day) | 4 vs. 0 |
| 13497447 | At_Germinating_Seeds | 108464 | Tissue | Germinating Seeds |
| 13497447 | At_100uM_ABA_Mutants | 20000069 | Timepoint (hr) | 6 |
| 13497447 | At_100uM_ABA_Mutants | 20000069 | Treatment | 100 uM ABA vs. No Treatment |
| 13497447 | At_100uM_ABA_Mutants | 20000069 | Tissue | Aerial |
| 13497447 | At_100uM_ABA_Mutants | 20000069 | Plant Line | CS23 |
| 13497447 | At_42deg_Heat | 20000173 | Timepoint (hr) | 6 |
| 13497447 | At_42deg_Heat | 20000173 | Age (day) | 14 |
| 13497447 | At_42deg_Heat | 20000173 | Temperature (deg C.) | 42 vs. 22 |
| 13497447 | At_42deg_Heat | 20000173 | Organism | A. thaliana |
| 13497447 | At_42deg_Heat | 20000173 | Tissue | Aerial |
| 13497447 | At_42deg_Heat | 20000173 | Plant Line | WS |
| 13497447 | At_Open_Flower | 20000286 | Age (day) | 21 |
| 13497447 | At_Open_Flower | 20000286 | Organism | A. thaliana |
| 13497447 | At_Open_Flower | 20000286 | Tissue | Half Open vs. Whole Plant |
| 13497447 | At_Open_Flower | 20000286 | Plant Line | WS |
| 13497447 | At_100uM_ABA_Mutants | 20000573 | Organism | A. thaliana |
| 13497447 | At_100uM_ABA_Mutants | 20000573 | Plant Line | CS22 vs. Ler wt |
| 13497447 | At_100uM_ABA_Mutants | 20000573 | Timepoint (hr) | N/A |
| 13497447 | At_100uM_ABA_Mutants | 20000573 | Treatment | None |
| 13497447 | At_100uM_ABA_Mutants | 20000573 | Tissue | Whole Plant |
| 13497447 | At_100uM_ABA_Mutants | 20000574 | Organism | A. thaliana |
| 13497447 | At_100uM_ABA_Mutants | 20000574 | Plant Line | CS23 vs. Ler wt |
| 13497447 | At_100uM_ABA_Mutants | 20000574 | Timepoint (hr) | N/A |
| 13497447 | At_100uM_ABA_Mutants | 20000574 | Treatment | None |
| 13497447 | At_100uM_ABA_Mutants | 20000574 | Tissue | Whole Plant |
| 13497447 | At_Drought_Reproduction | 20001906 | Timepoint (day) | 5 |
| 13497447 | At_Drought_Reproduction | 20001906 | Age (day) | 35 |
| 13497447 | At_Drought_Reproduction | 20001906 | Organism | A. thaliana |
| 13497447 | At_Drought_Reproduction | 20001906 | Treatment | Drought vs. No Drought |
| 13497447 | At_Drought_Reproduction | 20001906 | Tissue | Siliques |
| 13497447 | At_Drought_Reproduction | 20001906 | Plant Line | WS |
| 13497447 | At_Drought_Reproduction | 20001911 | Timepoint (day) | 10 |
| 13497447 | At_Drought_Reproduction | 20001911 | Age (day) | 40 |
| 13497447 | At_Drought_Reproduction | 20001911 | Organism | A. thaliana |
| 13497447 | At_Drought_Reproduction | 20001911 | Treatment | Drought vs. No Drought |
| 13497447 | At_Drought_Reproduction | 20001911 | Tissue | Flowers |
| 13497447 | At_Drought_Reproduction | 20001911 | Plant Line | WS |
| 13497447 | At_8deg_Cold | 20002108 | Age (day) | 14 |
| 13497447 | At_8deg_Cold | 20002108 | Timepoint (hr) | 168 |

TABLE 1-continued

Promoter Sequences and Related Information

| 13497447 | At_8deg_Cold | 20002108 | Temperature (deg C.) | 8 vs. 22 |
| 13497447 | At_8deg_Cold | 20002108 | Organism | A. thaliana |
| 13497447 | At_8deg_Cold | 20002108 | Tissue | Whole Plant |
| 13497447 | At_8deg_Cold | 20002108 | Plant Line | WS |

Promoter YP0377

Modulates the gene: product = "glycine-rich protein", note: unknown protein
The GenBank description of the gene::NM_100587 Arabidopsis thaliana glycine-rich protein
(At1g07135) mRNA, complete cds gi|22329385|ref|NM_100587.2|[22329385]
The promoter sequence:
5'tttaaacataacaatgaattgcttggatttcaaactttattaaatttggatttttaaattttaatttgat tgaattatacccccttaattggataaaattcaaatatgtcaactttttttttttgtaagatttttttatgga aaaaaaaattgattattcactaaaaagatgacaggttacttataatttaatatatgtaaaccctaaaaaga agaaaatagtttctgttttcactttaggtcttattatctaaacttctttaagaaaatcgcaataaattggt ttgagttctaactttaaacacattaatatttgtgtgctatttaaaaaataatttacaaaaaaaaaaacaaa ttgacagaaaatatcaggttttgtaataagatatttcctgataaatatttagggaatataacatatcaaa gattcaaattctgaaaatcaagaatggtagacatgtgaaagttgtcatcaatatggtccacttttctttgc tctataacccaaaattgaccctgacagtcaacttgtacacgcggccaaacctttttataatcatgctattt atttccttcattttattctatttgctatctaactgattttttcattaacatgataccagaaatgaatttag atggattaattcttttccatccacgacatctggaaacacttatctcctaattaaccttacttttttttag tttgtgtgctccttcataaaatctatattgtttaaaacaaaggtcaataaatataaatatggataagtata ataaatcttattggatattcttttttttaaaaaagaaataaatctttttggatattttcgtggcagcat cataatgagagactacgtcgaaactgctggcaaccacttttgccgcgtttaatttctttctgaggcttata taaatagatcaaaggggaaagtgagaTAT 3'
The promoter was cloned from the organism: Arabidopsis thaliana, Columbia ecotype

Alternative nucleotides:

| Predicted Position (bp) | Mismatch | Predicted/Experimental |
|---|---|---|
| 145 | Sequence or PCR error | ctttttttttttg/<br>cttttttt-ttg Exp. 1<br>cttttttt--tg Exp. 2 |

The promoter was cloned in the vector: pNewbin4-HAP1-GFP
When cloned into the vector the promoter was operably linked to a marker, which was the type:
GFP-ER
Promoter-marker vector was tested in: Arabidopsis thaliana, WS ecotype
Generation screened: XT1 Mature   XT2 Seedling   T2 Mature   T3 Seedling The spatial expression of the promoter-marker vector was found observed in and would be useful in
expression in any or all of the following:

Flower                                       M sepal M petal M epidermis
Hypocotyl                                    L epidermis L vascular H stomata
Cotyledon                                    M vascular L epidermis
Primary Root                                 M epidermis M vascular M root hairs
Observed expression pattern of the promoter-marker vector was in:
T1 mature: Expressed in epidermal cells of sepals and petals in developing flowers.
T2 seedling: Medium to low expression in epidermal and vascular cells of hypocotyls and cotyledons.
Epidermal and vascular expression at root transition zone decreasing toward root tip.
Misc. promoter information:   Bidirectionality: Pass   Exons: Pass    Repeats: No
The Ceres cDNA ID of the endogenous coding sequence to the promoter: 13613778
cDNA nucleotide sequence:
AAAGAAAATGGGTTTGAGAAGAACATGGTTGGTTTTGTACATTCTCTTCATCTTTCATCTTCAG

CACAATCTTCCTTCCGTGAGCTCACGACCTTCCTCAGTCGATACAAACCACGAGACTCTCCCTT

TTAGTGTTTCAAAGCCAGACGTTGTTGTGTTTGAAGGAAAGGCTCGGGAATTAGCTGTCGTTA

TCAAAAAAGGAGGAGGTGGAGGAGGTGGAGGACGCGGAGGCGGTGGAGCACGAAGCGGCGG

TAGGAGCAGGGGAGGAGGAGGTGGCAGCAGTAGTAGCCGCAGCCGTGACTGGAAACGCGGC

TABLE 1-continued

Promoter Sequences and Related Information

GGAGGGGTGGTTCCGATTCATACGGGTGGTGGTAATGGCAGTCTGGGTGGTGGATCGGCAGG

ATCACATAGATCAAGCGGCAGCATGAATCTTCGAGGAACAATGTGTGCGGTCTGTTGGTTGGC

TTTATCGGTTTTAGCCGGTTTAGTCTTGGTTCAGTAGGGTTCAGAGTAATTATTGGCCATTTAT

TTATTGGTTTTGTAACGTTTATGTTTGTGGTCCGGTCTGATATTTATTTGGGCAAACGGTACAT

TAAGGTGTAGACTGTTAATATTATATGTAGAAAGAGATTCTTAGCAGGATTCTACTGGTAGTA

TTAAGAGTGAGTTATCTTTAGTATGCCATTTGTAAATGGAAATTTAATGAAATAAGAAATTGT

GAAATTTAAAC

Coding sequence:
KKMGLRRTWLVLYILFIFHLQHNLPSVSSRPSSVDTNHETLPFSVSKPDVVVFEGKARELAVVI

KKGGGGGGGGRGGGGARSGGRSRGGGGGSSSSRSRDWKRGGGVVPIHTGGGNGSLGGGS

AGSHRSSGSMNLRGTMCAVCWLALSVLAGLVLVQ*

Microarray data shows that the coding sequence was expressed in the following experiments, which shows that the promoter would be useful to modulate expression in situations similar to the following:

| CDNA_ID | SHORT_NAME | EXPT_REP_ID | IS_UP |
| --- | --- | --- | --- |
| 13613778 | At_Root_Tips | 108434 | - |
| 13613778 | At_20uM_KNO3_H-to-L | 108455 | + |
| 13613778 | At_5-1-F2-137 | 108460 | + |
| 13613778 | At_Germinating_Seeds | 108464 | + |
| 13613778 | At_Shoot_Apices | 108480 | + |
| 13613778 | At_Shoot_Apices | 108481 | + |
| 13613778 | At_15mM_NH4NO3_L-to-H_Rosette | 108487 | - |
| 13613778 | At_15mM_NH4NO3_L-to-H_Rosette | 108488 | - |
| 13613778 | At_ap2_floral_buds | 108501 | - |
| 13613778 | At_42deg_Heat | 108577 | - |
| 13613778 | At_4deg_Cold | 108578 | + |
| 13613778 | At_4deg_Cold | 108579 | + |
| 13613778 | At_5mM_NaNP | 108584 | + |
| 13613778 | At_5mM_NaNP | 108585 | + |
| 13613778 | At_2mM_SA | 108586 | - |
| 13613778 | At_2mM_SA | 108587 | - |
| 13613778 | At_15mM_NH4NO3_L-to-H | 108588 | + |
| 13613778 | At_Ler-pi_Ovule | 108595 | + |
| 13613778 | At_100uM_ABA | 108606 | - |
| 13613778 | At_2mM_SA | 108667 | + |
| 13613778 | At_100uM_ABA_Mutants | 20000069 | + |
| 13613778 | At_100uM_ABA_Mutants | 20000071 | + |
| 13613778 | At_100uM_ABA_Mutants | 20000086 | + |
| 13613778 | At_100uM_ABA_Mutants | 20000087 | + |
| 13613778 | At_2mM_SA_CS3726-Columbia | 20000091 | + |
| 13613778 | At_100uM_ABA_Mutants | 20000117 | + |
| 13613778 | At_42deg_Heat | 20000144 | - |
| 13613778 | At_42deg_Heat | 20000171 | - |
| 13613778 | At_42deg_Heat | 20000173 | - |
| 13613778 | At_2mM_SA | 20000181 | + |
| 13613778 | At_Shoots | 20000184 | - |
| 13613778 | At_Roots | 20000185 | - |
| 13613778 | At_4deg_Cold | 20000213 | + |
| 13613778 | At_Siliques | 20000234 | - |
| 13613778 | At_Siliques | 20000236 | - |
| 13613778 | At_Open_Flower | 20000264 | - |
| 13613778 | At_100mM_NaCl | 20000268 | - |
| 13613778 | At_Open_Flower | 20000286 | - |
| 13613778 | At_Pollen | 20000326 | - |
| 13613778 | At_Shoots | 20000438 | - |
| 13613778 | At_Roots | 20000439 | - |
| 13613778 | At_1uM_BR-BRZ | 20000441 | + |
| 13613778 | At_1uM_BR-BRZ | 20000443 | + |
| 13613778 | At_42deg_Heat | 20000458 | - |
| 13613778 | At_10percent_PEG | 20000460 | + |
| 13613778 | At_Guard_Cells | 20000495 | - |
| 13613778 | At_10percent_PEG | 20000527 | + |
| 13613778 | At_100uM_ABA_Mutants | 20000573 | - |
| 13613778 | At_100uM_ABA_Mutants | 20000574 | - |
| 13613778 | At_Herbicide_Mutants | 20000640 | - |
| 13613778 | At_15mM_NH4NO3_L-to-H | 20000709 | + |
| 13613778 | At_Petals | 20000794 | - |

TABLE 1-continued

Promoter Sequences and Related Information

| | | | |
|---|---|---|---|
| 13613778 | At_Line_Comparisons | 20001151 | − |
| 13613778 | At_Line_Comparisons | 20001184 | − |
| 13613778 | At_Line_Comparisons | 20001192 | − |
| 13613778 | At_Line_Comparisons | 20001195 | − |
| 13613778 | At_Far-red-induction | 20001247 | + |
| 13613778 | At_Far-red-induction | 20001248 | + |
| 13613778 | At_Line_Comparisons | 20001300 | − |
| 13613778 | At_Line_Comparisons | 20001307 | − |
| 13613778 | At_Line_Comparisons | 20001308 | + |
| 13613778 | At_Line_Comparisons | 20001309 | + |
| 13613778 | At_Line_Comparisons | 20001310 | + |
| 13613778 | At_Line_Comparisons | 20001318 | − |
| 13613778 | At_Line_Comparisons | 20001319 | − |
| 13613778 | At_Line_Comparisons | 20001347 | − |
| 13613778 | At_Line_Comparisons | 20001448 | − |
| 13613778 | At_50mM_NH4NO3_L-to-H | 20001458 | + |
| 13613778 | At_Drought_Soil_Dry | 20001554 | − |
| 13613778 | At_Drought_Soil_Dry | 20001555 | − |
| 13613778 | At_Drought_Soil_Dry | 20001556 | − |
| 13613778 | At_Drought_Soil_Dry | 20001557 | + |
| 13613778 | At_Interploidy_Crosses | 20001703 | − |
| 13613778 | At_50mM_NH4NO3_L-to-H | 20001757 | − |
| 13613778 | At_Far-red-enriched-adult | 20001773 | − |
| 13613778 | At_Far-red-enriched-adult | 20001774 | − |
| 13613778 | At_Drought_Reproduction | 20001904 | − |
| 13613778 | At_Drought_Reproduction | 20001907 | − |
| 13613778 | At_Line_Comparisons | 20002012 | + |
| 13613778 | At_8deg_Cold | 20002108 | − |
| 13613778 | At_8deg_Cold | 20002109 | − |

The parameters for the microarray experiments listed above by Expt_Rep_ID and Short_Name are as follow below:

| CDNA_ID | SHORT_NAME | EXPT_REP_ID | PARAM_NAME | VALUE |
|---|---|---|---|---|
| 13613778 | At_Root_Tips | 108434 | Tissue | Root Tips |
| 13613778 | At_20uM_KNO3_H-to-L | 108455 | Timepoint (hr) | 1 |
| 13613778 | At_20uM_KNO3_H-to-L | 108455 | Treatment | 20 uM KNO3 vs. 50 mM KNO3 |
| 13613778 | At_5-1-F2-137 | 108460 | Plant Line | 5-1-F2-137 (mutant) |
| 13613778 | At_5-1-F2-137 | 108460 | Probe Method | Amplified |
| 13613778 | At_5-1-F2-137 | 108460 | Tissue | Inflorescences |
| 13613778 | At_Germinating_Seeds | 108464 | Age (day) | 4 vs. 0 |
| 13613778 | At_Germinating_Seeds | 108464 | Tissue | Germinating Seeds |
| 13613778 | At_Shoot_Apices | 108480 | Treatment | 1 uM BR vs. No Treatment |
| 13613778 | At_Shoot_Apices | 108480 | Plant Line | Ws-2 |
| 13613778 | At_Shoot_Apices | 108481 | Treatment | 1 uM BRZ vs. No Treatment |
| 13613778 | At_Shoot_Apices | 108481 | Plant Line | Ws-2 |
| 13613778 | At_15mM_NH4NO3_L-to-H_Rosette | 108487 | Timepoint (hr) | 0.5 |
| 13613778 | At_15mM_NH4NO3_L-to-H_Rosette | 108487 | Treatment | 15 mM NH4NO3 vs. 30 mM Mannitol |
| 13613778 | At_15mM_NH4NO3_L-to-H_Rosette | 108487 | Tissue | Rosette |
| 13613778 | At_15mM_NH4NO3_L-to-H_Rosette | 108488 | Timepoint (hr) | 2 |
| 13613778 | At_15mM_NH4NO3_L-to-H_Rosette | 108488 | Treatment | 15 mM NH4NO3 vs. 30 mM Mannitol |
| 13613778 | At_15mM_NH4NO3_L-to-H_Rosette | 108488 | Tissue | Rosette |
| 13613778 | At_ap2_floral_buds | 108501 | Plant Line | ap2 (Ler.) |
| 13613778 | At_ap2_floral_buds | 108501 | Tissue | Closed Flower |
| 13613778 | At_42deg_Heat | 108577 | Timepoint (hr) | 6 |
| 13613778 | At_42deg_Heat | 108577 | Temperature (deg C.) | 42 vs. 22 |
| 13613778 | At_42deg_Heat | 108577 | Tissue | Aerial |
| 13613778 | At_4deg_Cold | 108578 | Timepoint (hr) | 1 |
| 13613778 | At_4deg_Cold | 108578 | Temperature (deg C.) | 4 vs. 22 |
| 13613778 | At_4deg_Cold | 108578 | Tissue | Aerial |
| 13613778 | At_4deg_Cold | 108579 | Timepoint (hr) | 6 |
| 13613778 | At_4deg_Cold | 108579 | Temperature (deg C.) | 4 vs. 22 |
| 13613778 | At_4deg_Cold | 108579 | Tissue | Aerial |
| 13613778 | At_5mM_NaNP | 108584 | Timepoint (hr) | 1 |
| 13613778 | At_5mM_NaNP | 108584 | Treatment | 5 mM sodium nitroprusside vs. No Treatment |
| 13613778 | At_5mM_NaNP | 108584 | Tissue | Aerial |
| 13613778 | At_5mM_NaNP | 108585 | Timepoint (hr) | 6 |

TABLE 1-continued

Promoter Sequences and Related Information

| | | | | |
|---|---|---|---|---|
| 13613778 | At_5mM_NaNP | 108585 | Treatment | 5 mM sodium nitroprusside vs. No Treatment |
| 13613778 | At_5mM_NaNP | 108585 | Tissue | Aerial |
| 13613778 | At_2mM_SA | 108586 | Timepoint (hr) | 1 |
| 13613778 | At_2mM_SA | 108586 | Treatment | 2 mM SA vs. No Treatment |
| 13613778 | At_2mM_SA | 108586 | Tissue | Aerial |
| 13613778 | At_2mM_SA | 108587 | Timepoint (hr) | 6 |
| 13613778 | At_2mM_SA | 108587 | Treatment | 2 mM SA vs. No Treatment |
| 13613778 | At_2mM_SA | 108587 | Tissue | Aerial |
| 13613778 | At_15mM_NH4NO3_L-to-H | 108588 | Timepoint (hr) | 2 |
| 13613778 | At_15mM_NH4NO3_L-to-H | 108588 | Treatment | 15 mM NH4NO3 vs. 30 mM Mannitol |
| 13613778 | At_15mM_NH4NO3_L-to-H | 108588 | Tissue | Aerial |
| 13613778 | At_Ler-pi_Ovule | 108595 | Plant Line | Ler_pi |
| 13613778 | At_Ler-pi_Ovule | 108595 | Tissue | Ovules |
| 13613778 | At_100uM_ABA | 108606 | Timepoint (hr) | 2 |
| 13613778 | At_100uM_ABA | 108606 | Treatment | 100 uM ABA vs. No Treatment |
| 13613778 | At_100uM_ABA | 108606 | Tissue | Aerial |
| 13613778 | At_2mM_SA | 108667 | Timepoint (hr) | 1 |
| 13613778 | At_2mM_SA | 108667 | Treatment | 2 mM SA vs. No Treatment |
| 13613778 | At_2mM_SA | 108667 | Plant Line | WS |
| 13613778 | At_100uM_ABA_Mutants | 20000069 | Timepoint (hr) | 6 |
| 13613778 | At_100uM_ABA_Mutants | 20000069 | Treatment | 100 uM ABA vs. No Treatment |
| 13613778 | At_100uM_ABA_Mutants | 20000069 | Tissue | Aerial |
| 13613778 | At_100uM_ABA_Mutants | 20000069 | Plant Line | CS23 |
| 13613778 | At_100uM_ABA_Mutants | 20000071 | Timepoint (hr) | 6 |
| 13613778 | At_100uM_ABA_Mutants | 20000071 | Treatment | 100 uM ABA vs. No Treatment |
| 13613778 | At_100uM_ABA_Mutants | 20000071 | Tissue | Aerial |
| 13613778 | At_100uM_ABA_Mutants | 20000071 | Plant Line | CS8104 |
| 13613778 | At_100uM_ABA_Mutants | 20000086 | Timepoint (hr) | 6 |
| 13613778 | At_100uM_ABA_Mutants | 20000086 | Treatment | 100 uM ABA vs. No Treatment |
| 13613778 | At_100uM_ABA_Mutants | 20000086 | Tissue | Aerial |
| 13613778 | At_100uM_ABA_Mutants | 20000086 | Plant Line | CS22 |
| 13613778 | At_100uM_ABA_Mutants | 20000087 | Timepoint (hr) | 6 |
| 13613778 | At_100uM_ABA_Mutants | 20000087 | Treatment | 100 uM ABA vs. No Treatment |
| 13613778 | At_100uM_ABA_Mutants | 20000087 | Tissue | Aerial |
| 13613778 | At_100uM_ABA_Mutants | 20000087 | Plant Line | WS |
| 13613778 | At_2mM_SA_CS3726-Columbia | 20000091 | Timepoint (hr) | 0 |
| 13613778 | At_2mM_SA_CS3726-Columbia | 20000091 | Tissue | Aerial |
| 13613778 | At_2mM_SA_CS3726-Columbia | 20000091 | Plant Line | CS3726 vs. Columbia |
| 13613778 | At_2mM_SA_CS3726-Columbia | 20000091 | Treatment | None |
| 13613778 | At_100uM_ABA_Mutants | 20000117 | Timepoint (hr) | 6 |
| 13613778 | At_100uM_ABA_Mutants | 20000117 | Treatment | 100 uM ABA vs. No Treatment |
| 13613778 | At_100uM_ABA_Mutants | 20000117 | Tissue | Aerial |
| 13613778 | At_100uM_ABA_Mutants | 20000117 | Plant Line | Columbia |
| 13613778 | At_42deg_Heat | 20000144 | Timepoint (hr) | 1 |
| 13613778 | At_42deg_Heat | 20000144 | Temperature (deg C.) | 42 vs. 22 |
| 13613778 | At_42deg_Heat | 20000144 | Tissue | Aerial |
| 13613778 | At_42deg_Heat | 20000171 | Timepoint (hr) | 1 |
| 13613778 | At_42deg_Heat | 20000171 | Age (day) | 14 |
| 13613778 | At_42deg_Heat | 20000171 | Temperature (deg C.) | 42 vs. 22 |
| 13613778 | At_42deg_Heat | 20000171 | Organism | A. thaliana |
| 13613778 | At_42deg_Heat | 20000171 | Tissue | Aerial |
| 13613778 | At_42deg_Heat | 20000171 | Plant Line | WS |
| 13613778 | At_42deg_Heat | 20000173 | Timepoint (hr) | 6 |
| 13613778 | At_42deg_Heat | 20000173 | Age (day) | 14 |
| 13613778 | At_42deg_Heat | 20000173 | Temperature (deg C.) | 42 vs. 22 |
| 13613778 | At_42deg_Heat | 20000173 | Organism | A. thaliana |
| 13613778 | At_42deg_Heat | 20000173 | Tissue | Aerial |
| 13613778 | At_42deg_Heat | 20000173 | Plant Line | WS |
| 13613778 | At_2mM_SA | 20000181 | Timepoint (hr) | 1 |
| 13613778 | At_2mM_SA | 20000181 | Age (day) | 14 |
| 13613778 | At_2mM_SA | 20000181 | Treatment | 2 mM SA vs. No Treatment |
| 13613778 | At_2mM_SA | 20000181 | Organism | A. thaliana |
| 13613778 | At_2mM_SA | 20000181 | Tissue | Aerial |
| 13613778 | At_2mM_SA | 20000181 | Plant Line | WS |
| 13613778 | At_Shoots | 20000184 | Age (day) | 7 vs. 21 |
| 13613778 | At_Shoots | 20000184 | Organism | A. thaliana |
| 13613778 | At_Shoots | 20000184 | Tissue | Shoots vs. Whole Plant |
| 13613778 | At_Shoots | 20000184 | Plant Line | WS |
| 13613778 | At_Roots | 20000185 | Age (day) | 7 vs. 21 |
| 13613778 | At_Roots | 20000185 | Organism | A. thaliana |

TABLE 1-continued

Promoter Sequences and Related Information

| | | | | |
|---|---|---|---|---|
| 13613778 | At_Roots | 20000185 | Tissue | Roots vs. Whole Plant |
| 13613778 | At_Roots | 20000185 | Plant Line | WS |
| 13613778 | At_4deg_Cold | 20000213 | Timepoint (hr) | 2 |
| 13613778 | At_Siliques | 20000234 | Age (day) | 21 |
| 13613778 | At_Siliques | 20000234 | Tissue | <5 mm Siliques vs. Whole Plant |
| 13613778 | At_Siliques | 20000234 | Organism | *A. thaliana* |
| 13613778 | At_Siliques | 20000234 | Plant Line | WS |
| 13613778 | At_Siliques | 20000236 | Age (day) | 21 |
| 13613778 | At_Siliques | 20000236 | Tissue | >10 mm Siliques vs. Whole Plant |
| 13613778 | At_Siliques | 20000236 | Organism | *A. thaliana* |
| 13613778 | At_Siliques | 20000236 | Plant Line | WS |
| 13613778 | At_Open_Flower | 20000264 | Age (day) | 21 |
| 13613778 | At_Open_Flower | 20000264 | Organism | *A. thaliana* |
| 13613778 | At_Open_Flower | 20000264 | Tissue | Open Flower vs. Whole Plant |
| 13613778 | At_Open_Flower | 20000264 | Plant Line | WS |
| 13613778 | At_100mM_NaCl | 20000268 | Timepoint (hr) | 6 |
| 13613778 | At_100mM_NaCl | 20000268 | Age (day) | 14 |
| 13613778 | At_100mM_NaCl | 20000268 | Treatment | 100 mM NaCl vs. No Treatment |
| 13613778 | At_100mM_NaCl | 20000268 | Organism | *A. thaliana* |
| 13613778 | At_100mM_NaCl | 20000268 | Tissue | Whole Plant |
| 13613778 | At_100mM_NaCl | 20000268 | Plant Line | WS |
| 13613778 | At_Open_Flower | 20000286 | Age (day) | 21 |
| 13613778 | At_Open_Flower | 20000286 | Organism | *A. thaliana* |
| 13613778 | At_Open_Flower | 20000286 | Tissue | Half Open vs. Whole Plant |
| 13613778 | At_Open_Flower | 20000286 | Plant Line | WS |
| 13613778 | At_Pollen | 20000326 | Age (day) | 0 vs. 21 |
| 13613778 | At_Pollen | 20000326 | Organism | *A. thaliana* |
| 13613778 | At_Pollen | 20000326 | Tissue | Pollen vs. Whole Plant |
| 13613778 | At_Pollen | 20000326 | Plant Line | WS |
| 13613778 | At_Shoots | 20000438 | Age (day) | 14 vs. 21 |
| 13613778 | At_Shoots | 20000438 | Organism | *A. thaliana* |
| 13613778 | At_Shoots | 20000438 | Tissue | Shoots vs. Whole Plant |
| 13613778 | At_Shoots | 20000438 | Plant Line | WS |
| 13613778 | At_Roots | 20000439 | Age (day) | 14 vs. 21 |
| 13613778 | At_Roots | 20000439 | Organism | *A. thaliana* |
| 13613778 | At_Roots | 20000439 | Tissue | Roots vs. Whole Plant |
| 13613778 | At_Roots | 20000439 | Plant Line | WS |
| 13613778 | At_1uM_BR-BRZ | 20000441 | Treatment | 1 uM BR vs. No Treatment |
| 13613778 | At_1uM_BR-BRZ | 20000441 | Tissue | Shoot Apices |
| 13613778 | At_1uM_BR-BRZ | 20000443 | Treatment | 1 uM BRZ vs. No Treatment |
| 13613778 | At_1uM_BR-BRZ | 20000443 | Tissue | Shoot Apices |
| 13613778 | At_42deg_Heat | 20000458 | Timepoint (hr) | 8 |
| 13613778 | At_42deg_Heat | 20000458 | Age (day) | 14 |
| 13613778 | At_42deg_Heat | 20000458 | Temperature (deg C.) | 42 vs. 22 |
| 13613778 | At_42deg_Heat | 20000458 | Organism | *A. thaliana* |
| 13613778 | At_42deg_Heat | 20000458 | Tissue | Aerial |
| 13613778 | At_42deg_Heat | 20000458 | Plant Line | WS |
| 13613778 | At_10percent_PEG | 20000460 | Age (day) | 12 |
| 13613778 | At_10percent_PEG | 20000460 | Timepoint (day) | 12 |
| 13613778 | At_10percent_PEG | 20000460 | Treatment | 10 percent PEG vs. No Treatment |
| 13613778 | At_10percent_PEG | 20000460 | Organism | *A. thaliana* |
| 13613778 | At_10percent_PEG | 20000460 | Tissue | Whole Plant |
| 13613778 | At_10percent_PEG | 20000460 | Plant Line | WS |
| 13613778 | At_Guard_Cells | 20000495 | Harvest Date | 08 Feb. 2002 |
| 13613778 | At_Guard_Cells | 20000495 | Organism | *A. thaliana* |
| 13613778 | At_Guard_Cells | 20000495 | Tissue | Guard Cells vs. Leaves |
| 13613778 | At_10percent_PEG | 20000527 | Age (day) | 20 |
| 13613778 | At_10percent_PEG | 20000527 | Timepoint (day) | 20 |
| 13613778 | At_10percent_PEG | 20000527 | Treatment | 10 percent PEG vs. No Treatment |
| 13613778 | At_10percent_PEG | 20000527 | Organism | *A. thaliana* |
| 13613778 | At_10percent_PEG | 20000527 | Tissue | Whole Plant |
| 13613778 | At_10percent_PEG | 20000527 | Plant Line | WS |
| 13613778 | At_100uM_ABA_Mutants | 20000573 | Organism | *A. thaliana* |
| 13613778 | At_100uM_ABA_Mutants | 20000573 | Plant Line | CS22 vs. Ler wt |
| 13613778 | At_100uM_ABA_Mutants | 20000573 | Timepoint (hr) | N/A |
| 13613778 | At_100uM_ABA_Mutants | 20000573 | Treatment | None |
| 13613778 | At_100uM_ABA_Mutants | 20000573 | Tissue | Whole Plant |
| 13613778 | At_100uM_ABA_Mutants | 20000574 | Organism | *A. thaliana* |
| 13613778 | At_100uM_ABA_Mutants | 20000574 | Plant Line | CS23 vs. Ler wt |
| 13613778 | At_100uM_ABA_Mutants | 20000574 | Timepoint (hr) | N/A |
| 13613778 | At_100uM_ABA_Mutants | 20000574 | Treatment | None |
| 13613778 | At_100uM_ABA_Mutants | 20000574 | Tissue | Whole Plant |
| 13613778 | At_Herbicide_Mutants | 20000640 | Timepoint (hr) | 12 |
| 13613778 | At_Herbicide_Mutants | 20000640 | Plant Line | 05377RR/BR27173 |
| 13613778 | At_Herbicide_Mutants | 20000640 | Treatment | Roundup vs. No Treatment |
| 13613778 | At_Herbicide_Mutants | 20000640 | Tissue | Seedlings |
| 13613778 | At_15mM_NH4NO3_L-to-H | 20000709 | Timepoint (hr) | 4 |

TABLE 1-continued

Promoter Sequences and Related Information

| 13613778 | At_15mM_NH4NO3_L-to-H | 20000709 | Age (hr) | 14 |
|---|---|---|---|---|
| 13613778 | At_15mM_NH4NO3_L-to-H | 20000709 | Treatment | 15 mM NH4NO3 vs. 30 mM Mannitol |
| 13613778 | At_15mM_NH4NO3_L-to-H | 20000709 | Organism | A. thaliana |
| 13613778 | At_15mM_NH4NO3_L-to-H | 20000709 | Tissue | Aerial |
| 13613778 | At_15mM_NH4NO3_L-to-H | 20000709 | Plant Line | WS |
| 13613778 | At_Petals | 20000794 | Age (day) | 23-25 days |
| 13613778 | At_Petals | 20000794 | Organism | A. thaliana |
| 13613778 | At_Petals | 20000794 | Tissue | Petals vs. Whole plant |
| 13613778 | At_Petals | 20000794 | Plant Line | WS |
| 13613778 | At_Line_Comparisons | 20001151 | Plant Line | ME01339-01 vs. WS |
| 13613778 | At_Line_Comparisons | 20001184 | Plant Line | ME01848-01 vs. WS |
| 13613778 | At_Line_Comparisons | 20001192 | Plant Line | WBin4-WX13R-A vs. WS |
| 13613778 | At_Line_Comparisons | 20001195 | Plant Line | WBin4-WX14-B vs. WS |
| 13613778 | At_Far-red-induction | 20001247 | Timepoint (hr) | 1 |
| 13613778 | At_Far-red-induction | 20001247 | Age (day) | 7 |
| 13613778 | At_Far-red-induction | 20001247 | Organism | A. thaliana |
| 13613778 | At_Far-red-induction | 20001247 | Plant Line | Columbia |
| 13613778 | At_Far-red-induction | 20001247 | Light | Far-red vs. White |
| 13613778 | At_Far-red-induction | 20001247 | Tissue | Whole Plant |
| 13613778 | At_Far-red-induction | 20001248 | Timepoint (hr) | 4 |
| 13613778 | At_Far-red-induction | 20001248 | Age (day) | 7 |
| 13613778 | At_Far-red-induction | 20001248 | Organism | A. thaliana |
| 13613778 | At_Far-red-induction | 20001248 | Plant Line | Columbia |
| 13613778 | At_Far-red-induction | 20001248 | Light | Far-red vs. White |
| 13613778 | At_Far-red-induction | 20001248 | Tissue | Whole Plant |
| 13613778 | At_Line_Comparisons | 20001300 | Plant Line | ME01338-05 vs. WS |
| 13613778 | At_Line_Comparisons | 20001307 | Plant Line | WBin4-WX2-A vs. WS |
| 13613778 | At_Line_Comparisons | 20001308 | Plant Line | WBin4-WX49-C vs. WS |
| 13613778 | At_Line_Comparisons | 20001309 | Plant Line | WBin4-WX49R-A vs. WS |
| 13613778 | At_Line_Comparisons | 20001310 | Plant Line | WBin4-WX17-A vs. WS |
| 13613778 | At_Line_Comparisons | 20001318 | Plant Line | WBin4-WX14R-A vs. WS |
| 13613778 | At_Line_Comparisons | 20001319 | Plant Line | WBin4-WX24-A vs. WS |
| 13613778 | At_Line_Comparisons | 20001347 | Plant Line | ME01604-01 vs. WS |
| 13613778 | At_Line_Comparisons | 20001448 | Plant Line | ME01323-01 vs. WS |
| 13613778 | At_50mM_NH4NO3_L-to-H | 20001458 | Timepoint (hr) | 2 |
| 13613778 | At_50mM_NH4NO3_L-to-H | 20001458 | Treatment | 50 mM NH4NO3 vs. 100 mM Manitol |
| 13613778 | At_50mM_NH4NO3_L-to-H | 20001458 | Organism | A. thaliana |
| 13613778 | At_50mM_NH4NO3_L-to-H | 20001458 | Tissue | Siliques |
| 13613778 | At_50mM_NH4NO3_L-to-H | 20001458 | Age (day) | Undefined |
| 13613778 | At_50mM_NH4NO3_L-to-H | 20001458 | Plant Line | WS |
| 13613778 | At_Drought_Soil_Dry | 20001554 | Timepoint (day) | 7 |
| 13613778 | At_Drought_Soil_Dry | 20001554 | Age (day) | 21 |
| 13613778 | At_Drought_Soil_Dry | 20001554 | Organism | A. thaliana |
| 13613778 | At_Drought_Soil_Dry | 20001554 | Treatment | Drought vs. No Drought |
| 13613778 | At_Drought_Soil_Dry | 20001554 | Post Timepoint (hr) | None |
| 13613778 | At_Drought_Soil_Dry | 20001554 | Post-Treatment | None |
| 13613778 | At_Drought_Soil_Dry | 20001554 | Plant Line | WS |
| 13613778 | At_Drought_Soil_Dry | 20001555 | Timepoint (day) | 10 |
| 13613778 | At_Drought_Soil_Dry | 20001555 | Age (day) | 24 |
| 13613778 | At_Drought_Soil_Dry | 20001555 | Organism | A. thaliana |
| 13613778 | At_Drought_Soil_Dry | 20001555 | Treatment | Drought vs. No Drought |
| 13613778 | At_Drought_Soil_Dry | 20001555 | Post Timepoint (hr) | None |
| 13613778 | At_Drought_Soil_Dry | 20001555 | Post-Treatment | None |
| 13613778 | At_Drought_Soil_Dry | 20001555 | Plant Line | WS |
| 13613778 | At_Drought_Soil_Dry | 20001556 | Timepoint (day) | 12 |
| 13613778 | At_Drought_Soil_Dry | 20001556 | Age (day) | 26 |
| 13613778 | At_Drought_Soil_Dry | 20001556 | Organism | A. thaliana |
| 13613778 | At_Drought_Soil_Dry | 20001556 | Treatment | Drought vs. No Drought |
| 13613778 | At_Drought_Soil_Dry | 20001556 | Post Timepoint (hr) | None |
| 13613778 | At_Drought_Soil_Dry | 20001556 | Post-Treatment | None |
| 13613778 | At_Drought_Soil_Dry | 20001556 | Plant Line | WS |
| 13613778 | At_Drought_Soil_Dry | 20001557 | Post Timepoint (hr) | 3 |
| 13613778 | At_Drought_Soil_Dry | 20001557 | Timepoint (day) | 13 |
| 13613778 | At_Drought_Soil_Dry | 20001557 | Age (day) | 27 |
| 13613778 | At_Drought_Soil_Dry | 20001557 | Organism | A. thaliana |
| 13613778 | At_Drought_Soil_Dry | 20001557 | Treatment | Drought vs. No Drought |
| 13613778 | At_Drought_Soil_Dry | 20001557 | Post-Treatment | Re-Water vs. No Drought |
| 13613778 | At_Drought_Soil_Dry | 20001557 | Plant Line | WS |
| 13613778 | At_Interploidy_Crosses | 20001703 | Age (day) | 5 |
| 13613778 | At_Interploidy_Crosses | 20001703 | Cross | 2X x 4X vs. 2X x 2X |
| 13613778 | At_Interploidy_Crosses | 20001703 | Organism | A. thaliana |
| 13613778 | At_Interploidy_Crosses | 20001703 | Plant Line | Columbia |
| 13613778 | At_Interploidy_Crosses | 20001703 | Tissue | Siliques |
| 13613778 | At_50mM_NH4NO3_L-to-H | 20001757 | Timepoint (hr) | 6 |

TABLE 1-continued

Promoter Sequences and Related Information

| 13613778 | At_50mM_NH4NO3_L-to-H | 20001757 | Treatment | 50 mM NH4NO3 vs 100 mM Mannitol |
|---|---|---|---|---|
| 13613778 | At_50mM_NH4NO3_L-to-H | 20001757 | Tissue | Leaf |
| 13613778 | At_Far-red-enriched-adult | 20001773 | Age (day) | 30 |
| 13613778 | At_Far-red-enriched-adult | 20001773 | Timepoint (hr) | 48 |
| 13613778 | At_Far-red-enriched-adult | 20001773 | Organism | A. thaliana |
| 13613778 | At_Far-red-enriched-adult | 20001773 | Tissue | Aerial |
| 13613778 | At_Far-red-enriched-adult | 20001773 | Plant Line | Columbia |
| 13613778 | At_Far-red-enriched-adult | 20001773 | Light | Far-red enriched vs. White |
| 13613778 | At_Far-red-enriched-adult | 20001774 | Age (day) | 31 |
| 13613778 | At_Far-red-enriched-adult | 20001774 | Timepoint (hr) | 72 |
| 13613778 | At_Far-red-enriched-adult | 20001774 | Organism | A. thaliana |
| 13613778 | At_Far-red-enriched-adult | 20001774 | Tissue | Aerial |
| 13613778 | At_Far-red-enriched-adult | 20001774 | Plant Line | Columbia |
| 13613778 | At_Far-red-enriched-adult | 20001774 | Light | Far-red enriched vs. White |
| 13613778 | At_Drought_Reproduction | 20001904 | Timepoint (day) | 7 |
| 13613778 | At_Drought_Reproduction | 20001904 | Age (day) | 37 |
| 13613778 | At_Drought_Reproduction | 20001904 | Organism | A. thaliana |
| 13613778 | At_Drought_Reproduction | 20001904 | Treatment | Drought vs. No Drought |
| 13613778 | At_Drought_Reproduction | 20001904 | Tissue | Rosettes |
| 13613778 | At_Drought_Reproduction | 20001904 | Plant Line | WS |
| 13613778 | At_Drought_Reproduction | 20001907 | Timepoint (day) | 7 |
| 13613778 | At_Drought_Reproduction | 20001907 | Age (day) | 37 |
| 13613778 | At_Drought_Reproduction | 20001907 | Organism | A. thaliana |
| 13613778 | At_Drought_Reproduction | 20001907 | Treatment | Drought vs. No Drought |
| 13613778 | At_Drought_Reproduction | 20001907 | Tissue | Siliques |
| 13613778 | At_Drought_Reproduction | 20001907 | Plant Line | WS |
| 13613778 | At_Line_Comparisons | 20002012 | Plant Line | SALK_073455 vs. Columbia |
| 13613778 | At_8deg_Cold | 20002108 | Age (day) | 14 |
| 13613778 | At_8deg_Cold | 20002108 | Timepoint (hr) | 168 |
| 13613778 | At_8deg_Cold | 20002108 | Temperature (deg C.) | 8 vs. 22 |
| 13613778 | At_8deg_Cold | 20002108 | Organism | A. thaliana |
| 13613778 | At_8deg_Cold | 20002108 | Tissue | Whole Plant |
| 13613778 | At_8deg_Cold | 20002108 | Plant Line | WS |
| 13613778 | At_8deg_Cold | 20002109 | Age (day) | 16 |
| 13613778 | At_8deg_Cold | 20002109 | Timepoint (hr) | 216 |
| 13613778 | At_8deg_Cold | 20002109 | Temperature (deg C.) | 8 vs. 22 |
| 13613778 | At_8deg_Cold | 20002109 | Organism | A. thaliana |
| 13613778 | At_8deg_Cold | 20002109 | Tissue | Whole Plant |
| 13613778 | At_8deg_Cold | 20002109 | Plant Line | WS |

TABLE 2

Promoter Utilities Based on Differential Expression Experiments

| EXPT_REP_ID | SHORT_NAME | UTILITY |
|---|---|---|
| 20000166 | At_100uM_ABA | Promoters and cDNAs corresponding to endogenous cDNAs which were differentially expressed in this experiment would be useful in modulating ABA, stress, and drought induced and/or regulated responses |
| 20000169 | At_100uM_ABA | Promoters and cDNAs corresponding to endogenous cDNAs which were differentially expressed in this experiment would be useful in modulating ABA, stress, and drought induced and/or regulated responses |
| 20000171 | At_42deg_Heat | Promoters and cDNAs corresponding to endogenous cDNAs which were differentially expressed in this experiment would be useful in modulating stress, heat and cold induced and/or regulated responses |
| 20000173 | At_42deg_Heat | Promoters and cDNAs corresponding to endogenous cDNAs which were differentially expressed in this experiment would be useful in modulating stress, heat and cold induced and/or regulated responses |
| 20000179 | At_Germinating_Seeds | Promoters and cDNAs corresponding to endogenous cDNAs which were differentially expressed in this experiment would be useful for modulating growth, yield and plant development |
| 20000180 | At_Germinating_Seeds | Promoters and cDNAs corresponding to endogenous cDNAs which were differentially |

TABLE 2-continued

Promoter Utilities Based on Differential Expression Experiments

| EXPT_REP_ID | SHORT_NAME | UTILITY |
|---|---|---|
| | | expressed in this experiment would be useful for modulating growth, yield and plant development |
| 20000182 | At_2mM_SA | Promoters and cDNAs corresponding to endogenous cDNAs which were differentially expressed in this experiment would be useful in modulating stress and SA induced and/or regulated responses |
| 20000184 | At_Shoots | Promoters and cDNAs corresponding to endogenous cDNAs which were differentially expressed in this experiment would be useful for modulating growth, yield, and plant development for instance in roots and/or shoots |
| 20000185 | At_Roots | Promoters and cDNAs corresponding to endogenous cDNAs which were differentially expressed in this experiment would be useful for modulating growth, yield, and plant development for instance in roots and/or shoots |
| 20000227 | At_Root-Tips-vs-Tops | Promoters and cDNAs corresponding to endogenous cDNAs which were differentially expressed in this experiment would be useful for modulating growth, yield, and plant development for instance in roots and/or shoots |
| 20000234 | At_Siliques | Promoters and cDNAs corresponding to endogenous cDNAs which were differentially expressed in this experiment would be useful for modulating fertility, fruit and seed size, number and/or yield |
| 20000235 | At_Siliques | Promoters and cDNAs corresponding to endogenous cDNAs which were differentially expressed in this experiment would be useful for modulating fertility, fruit and seed size, number and/or yield |
| 20000264 | At_Open_Flower | Promoters and cDNAs corresponding to endogenous cDNAs which were differentially expressed in this experiment would be useful for modulating fertility, fruit and seed size, number and/or yield, including flowers development and number |
| 20000265 | At_Open_Flower | Promoters and cDNAs corresponding to endogenous cDNAs which were differentially expressed in this experiment would be useful for modulating fertility, fruit and seed size, number and/or yield, including flowers development and number |
| 20000267 | At_Drought | Promoters and cDNAs corresponding to endogenous cDNAs which were differentially expressed in this experiment would be useful for modulating stress and drought tolerance |
| 20000286 | At_Open_Flower | Promoters and cDNAs corresponding to endogenous cDNAs which were differentially expressed in this experiment would be useful for modulating fertility, fruit and seed size, number and/or yield, including flowers development and number |
| 20000436 | At_Drought | Promoters and cDNAs corresponding to endogenous cDNAs which were differentially expressed in this experiment would be useful for modulating stress and drought tolerance |
| 20000437 | At_Drought | Promoters and cDNAs corresponding to endogenous cDNAs which were differentially expressed in this experiment would be useful for modulating stress and drought tolerance |
| 20000438 | At_Shoots | Promoters and cDNAs corresponding to endogenous cDNAs which were differentially expressed in this experiment would be useful for modulating growth, yield, and plant development for instance in roots and/or shoots |
| 20000439 | At_Roots | Promoters and cDNAs corresponding to endogenous cDNAs which were differentially expressed in this experiment would be useful for modulating growth, yield, and plant |

TABLE 2-continued

Promoter Utilities Based on Differential Expression Experiments

| EXPT_REP_ID | SHORT_NAME | UTILITY |
|---|---|---|
| | | development for instance in roots and/or shoots |
| 20000441 | At_1uM_BR-BRZ | Promoters and cDNAs corresponding to endogenous cDNAs which were differentially expressed in this experiment would be useful for modulating growth, yield and BR induced and/regulated responses |
| 20000443 | At_1uM_BR-BRZ | Promoters and cDNAs corresponding to endogenous cDNAs which were differentially expressed in this experiment would be useful for modulating growth, yield and BR induced and/regulated responses |
| 20000451 | At_CS6879_Shoots-Roots | Promoters and cDNAs corresponding to endogenous cDNAs which were differentially expressed in this experiment would be useful for modulating growth, yield, and plant development for instance in roots and/or shoots |
| 20000453 | At_100uM_ABA | Promoters and cDNAs corresponding to endogenous cDNAs which were differentially expressed in this experiment would be useful in modulating ABA, stress, and drought induced and/or regulated responses |
| 20000457 | At_42deg_Heat | Promoters and cDNAs corresponding to endogenous cDNAs which were differentially expressed in this experiment would be useful in modulating stress, heat and cold induced and/or regulated responses |
| 20000458 | At_42deg_Heat | Promoters and cDNAs corresponding to endogenous cDNAs which were differentially expressed in this experiment would be useful in modulating stress, heat and cold induced and/or regulated responses |
| 20000460 | At_10percent_PEG | Promoters and cDNAs corresponding to endogenous cDNAs which were differentially expressed in this experiment would be useful for modulating stress, drought tolerance, and osmotic stress |
| 20000495 | At_Guard_Cells | Promoters and cDNAs corresponding to endogenous cDNAs which were differentially expressed in this experiment would be useful for modulating guard cells, drought and stress tolerance |
| 20000527 | At_10percent_PEG | Promoters and cDNAs corresponding to endogenous cDNAs which were differentially expressed in this experiment would be useful for modulating stress, drought tolerance, and osmotic stress |
| 20000573 | At_100uM_ABA_Mutants | Promoters and cDNAs corresponding to endogenous cDNAs which were differentially expressed in this experiment would be useful in modulating ABA, stress, and drought induced and/or regulated responses |
| 20000574 | At_100uM_ABA_Mutants | Promoters and cDNAs corresponding to endogenous cDNAs which were differentially expressed in this experiment would be useful in modulating ABA, stress, and drought induced and/or regulated responses |
| 20000709 | At_15mM_NH4NO3_L-to-H | Promoters and cDNAs corresponding to endogenous cDNAs which were differentially expressed in this experiment would be useful for modulating growth, yield and nitrogen induced and/regulated responses |
| 20000794 | At_Petals | Promoters and cDNAs corresponding to endogenous cDNAs which were differentially expressed in this experiment would be useful for modulating fertility, fruit and seed size, number and/or yield, including flowers development and number |
| 20001151 | At_Line_Comparisons | Promoters and cDNAs corresponding to endogenous cDNAs which were differentially expressed in this experiment would be useful for modulating alkaloid biosynthesis and alkaloid induced and/or regulated responses |
| 20001184 | At_Line_Comparisons | Promoters and cDNAs corresponding to endogenous cDNAs which were differentially |

TABLE 2-continued

Promoter Utilities Based on Differential Expression Experiments

| EXPT_REP_ID | SHORT_NAME | UTILITY |
|---|---|---|
| | | expressed in this experiment would be useful for modulating methyl jasmonate induced and/or regulated responses including biosynthesis. They are useful also to modulate stress responses. |
| 20001195 | At_Line_Comparisons | Promoters and cDNAs corresponding to endogenous cDNAs which were differentially expressed in this experiment would be useful for modulating alkaloid biosynthesis and alkaloid induced and/or regulated responses |
| 20001247 | At_Far-red-induction | Promoters and cDNAs corresponding to endogenous cDNAs which were differentially expressed in this experiment would be useful for modulating shade avoidance |
| 20001248 | At_Far-red-induction | Promoters and cDNAs corresponding to endogenous cDNAs which were differentially expressed in this experiment would be useful for modulating shade avoidance |
| 20001307 | At_Line_Comparisons | Promoters and cDNAs corresponding to endogenous cDNAs which were differentially expressed in this experiment would be useful for modulating alkaloid biosynthesis and alkaloid induced and/or regulated responses |
| 20001308 | At_Line_Comparisons | Promoters and cDNAs corresponding to endogenous cDNAs which were differentially expressed in this experiment would be useful for modulating alkaloid biosynthesis and alkaloid induced and/or regulated responses |
| 20001309 | At_Line_Comparisons | Promoters and cDNAs corresponding to endogenous cDNAs which were differentially expressed in this experiment would be useful for modulating alkaloid biosynthesis and alkaloid induced and/or regulated responses |
| 20001310 | At_Line_Comparisons | Promoters and cDNAs corresponding to endogenous cDNAs which were differentially expressed in this experiment would be useful for modulating alkaloid biosynthesis and alkaloid induced and/or regulated responses |
| 20001318 | At_Line_Comparisons | Promoters and cDNAs corresponding to endogenous cDNAs which were differentially expressed in this experiment would be useful for modulating alkaloid biosynthesis and alkaloid induced and/or regulated responses |
| 20001319 | At_Line_Comparisons | Promoters and cDNAs corresponding to endogenous cDNAs which were differentially expressed in this experiment would be useful for modulating alkaloid biosynthesis and alkaloid induced and/or regulated responses |
| 20001347 | At_Line_Comparisons | Promoters and cDNAs corresponding to endogenous cDNAs which were differentially expressed in this experiment would be useful for modulating methyl jasmonate induced and/or regulated responses including biosynthesis. They are useful also to modulate stress responses. |
| 20001450 | At_Far-red-induction | Promoters and cDNAs corresponding to endogenous cDNAs which were differentially expressed in this experiment would be useful for modulating shade avoidance |
| 20001451 | At_Far-red-induction | Promoters and cDNAs corresponding to endogenous cDNAs which were differentially expressed in this experiment would be useful for modulating shade avoidance |
| 20001458 | At_50mM_NH4NO3_L-to-H | Promoters and cDNAs corresponding to endogenous cDNAs which were differentially expressed in this experiment would be useful for modulating growth, yield and nitrogen induced and/regulated responses |
| 20001504 | At_Far-red-enriched | Promoters and cDNAs corresponding to endogenous cDNAs which were differentially expressed in this experiment would be useful for modulating shade avoidance |
| 20001554 | At_Drought_Soil_Dry | Promoters and cDNAs corresponding to endogenous cDNAs which were differentially expressed in this experiment would be useful for modulating stress and drought tolerance |

TABLE 2-continued

Promoter Utilities Based on Differential Expression Experiments

| EXPT_REP_ID | SHORT_NAME | UTILITY |
|---|---|---|
| 20001555 | At_Drought_Soil_Dry | Promoters and cDNAs corresponding to endogenous cDNAs which were differentially expressed in this experiment would be useful for modulating stress and drought tolerance |
| 20001556 | At_Drought_Soil_Dry | Promoters and cDNAs corresponding to endogenous cDNAs which were differentially expressed in this experiment would be useful for modulating stress and drought tolerance |
| 20001557 | At_Drought_Soil_Dry | Promoters and cDNAs corresponding to endogenous cDNAs which were differentially expressed in this experiment would be useful for modulating stress and drought tolerance |
| 20001558 | At_Drought_Soil_Dry | Promoters and cDNAs corresponding to endogenous cDNAs which were differentially expressed in this experiment would be useful for modulating stress and drought tolerance |
| 20001559 | At_Drought_Soil_Dry | Promoters and cDNAs corresponding to endogenous cDNAs which were differentially expressed in this experiment would be useful for modulating stress and drought tolerance |
| 20001560 | At_Drought_Soil_Dry | Promoters and cDNAs corresponding to endogenous cDNAs which were differentially expressed in this experiment would be useful for modulating stress and drought tolerance |
| 20001653 | At_Interploidy_Crosses | Promoters and cDNAs corresponding to endogenous cDNAs which were differentially expressed in this experiment would be useful for modulating fertility, fruit and seed size, number and/or yield, including endosperm size and seed abortion |
| 20001654 | At_Interploidy_Crosses | Promoters and cDNAs corresponding to endogenous cDNAs which were differentially expressed in this experiment would be useful for modulating fertility, fruit and seed size, number and/or yield, including endosperm size and seed abortion |
| 20001704 | At_Interploidy_Crosses | Promoters and cDNAs corresponding to endogenous cDNAs which were differentially expressed in this experiment would be useful for modulating fertility, fruit and seed size, number and/or yield, including endosperm size and seed abortion |
| 20001757 | At_50mM_NH4NO3_L-to-H | Promoters and cDNAs corresponding to endogenous cDNAs which were differentially expressed in this experiment would be useful for modulating growth, yield and nitrogen induced and/regulated responses |
| 20001768 | At_Far-red-enriched-adult | Promoters and cDNAs corresponding to endogenous cDNAs which were differentially expressed in this experiment would be useful for modulating shade avoidance |
| 20001770 | At_Far-red-enriched-adult | Promoters and cDNAs corresponding to endogenous cDNAs which were differentially expressed in this experiment would be useful for modulating shade avoidance |
| 20001771 | At_Far-red-enriched-adult | Promoters and cDNAs corresponding to endogenous cDNAs which were differentially expressed in this experiment would be useful for modulating shade avoidance |
| 20001773 | At_Far-red-enriched-adult | Promoters and cDNAs corresponding to endogenous cDNAs which were differentially expressed in this experiment would be useful for modulating shade avoidance |
| 20001853 | At_Interploidy_Crosses | Promoters and cDNAs corresponding to endogenous cDNAs which were differentially expressed in this experiment would be useful for modulating fertility, fruit and seed size, number and/or yield, including endosperm size and seed abortion |
| 20001904 | At_Drought_Reproduction | Promoters and cDNAs corresponding to endogenous cDNAs which were differentially expressed in this experiment would be useful for modulating stress and drought tolerance |
| 20001905 | At_Drought_Reproduction | Promoters and cDNAs corresponding to endogenous cDNAs which were differentially |

TABLE 2-continued

Promoter Utilities Based on Differential Expression Experiments

| EXPT_REP_ID | SHORT_NAME | UTILITY |
|---|---|---|
| 20001906 | At_Drought_Reproduction | Promoters and cDNAs corresponding to endogenous cDNAs which were differentially expressed in this experiment would be useful for modulating stress and drought tolerance |
| 20001907 | At_Drought_Reproduction | Promoters and cDNAs corresponding to endogenous cDNAs which were differentially expressed in this experiment would be useful for modulating stress and drought tolerance |
| 20001908 | At_Drought_Reproduction | Promoters and cDNAs corresponding to endogenous cDNAs which were differentially expressed in this experiment would be useful for modulating stress and drought tolerance |
| 20001909 | At_Drought_Reproduction | Promoters and cDNAs corresponding to endogenous cDNAs which were differentially expressed in this experiment would be useful for modulating stress and drought tolerance |
| 20001910 | At_Drought_Reproduction | Promoters and cDNAs corresponding to endogenous cDNAs which were differentially expressed in this experiment would be useful for modulating stress and drought tolerance |
| 20001911 | At_Drought_Reproduction | Promoters and cDNAs corresponding to endogenous cDNAs which were differentially expressed in this experiment would be useful for modulating stress and drought tolerance |
| 20002007 | At_Line_Comparisons | Promoters and cDNAs corresponding to endogenous cDNAs which were differentially expressed in this experiment would be useful for modulating sterol biosynthesis and sterol induced and/or regulated responses. |
| 20002008 | At_Line_Comparisons | Promoters and cDNAs corresponding to endogenous cDNAs which were differentially expressed in this experiment would be useful for modulating sterol biosynthesis and sterol induced and/or regulated responses. |
| 20002009 | At_Line_Comparisons | Promoters and cDNAs corresponding to endogenous cDNAs which were differentially expressed in this experiment would be useful for modulating sterol biosynthesis and sterol induced and/or regulated responses. |
| 20002010 | At_Line_Comparisons | Promoters and cDNAs corresponding to endogenous cDNAs which were differentially expressed in this experiment would be useful for modulating sterol biosynthesis and sterol induced and/or regulated responses. |
| 20002012 | At_Line_Comparisons | Promoters and cDNAs corresponding to endogenous cDNAs which were differentially expressed in this experiment would be useful for modulating triterpene biosynthesis and triterpene induced and/or regulated responses. |
| 20002103 | At_8deg_Cold | Promoters and cDNAs corresponding to endogenous cDNAs which were differentially expressed in this experiment would be useful in modulating stress, heat and cold induced and/or regulated responses |
| 20002107 | At_8deg_Cold | Promoters and cDNAs corresponding to endogenous cDNAs which were differentially expressed in this experiment would be useful in modulating stress, heat and cold induced and/or regulated responses |

TABLE 3

| Promoter Name | Fl | Si | Lf | St | Em | Ov | Hy | Co | Rt |
|---|---|---|---|---|---|---|---|---|---|
| YP0226 | Y | Y | | | | | Y | Y | Y |
| YP0244 | Y | | | | | | | | |
| YP0286 | Y | | | Y | | | Y | Y | Y |
| YP0289 | Y | | | | | Y | | Y | Y |
| YP0356 | Y | Y | Y | | Y | Y | Y | | |
| YP0374 | | | | | | | Y | Y | Y |
| YP0377 | Y | | | | | | Y | Y | Y |
| YP0380 | Y | Y | Y | Y | | | Y | Y | Y |
| YP0381 | Y | | | | | | | Y | Y |
| YP0382 | Y | | | | | | | | Y |
| YP0388 | Y | Y | Y | | | | Y | | Y |
| YP0396 | Y | Y | Y | | | | Y | | Y |
| PT0506 | Y | | | | | | | | |

TABLE 3-continued

| | | | | | |
|---|---|---|---|---|---|
| PT0511 | Y | | | Y | Y |
| YP0275 | | | | | Y |
| YP0337 | | | | | Y |
| YP0384 | | | | | Y |
| YP0385 | Y | Y | | | Y |
| YP0371 | Y | | | | Y |

Legend for Table 3
Fl  Flower
Si  Silique
Lf  Leaf
St  Stem
Em  Embryo
Ov  Ovule

TABLE 3-continued

Hy  Hypocotyl
Co  Cotyledon
Rt  Rosette
    Leaf

The invention being thus described, it will be apparent to one of ordinary skill in the art that various modifications of the materials and methods for practicing the invention can be made. Such modifications are to be considered within the scope of the invention as defined by the following claims.

Each of the references from the patent and periodical literature cited herein is hereby expressly incorporated in its entirety by such citation.

What is claimed is:

1. An isolated nucleic acid molecule having promoter activity consisting of a nucleotide sequence selected from the group consisting of:
   (a) a nucleotide sequence according to SEQ ID NO:19;
   (b) a nucleotide sequence consisting of a functional fragment of (a), wherein said fragment has promoter activity; and
   (c) a nucleotide sequence having at least 99% sequence identity to one of (a) or (b).

2. A vector construct comprising:
   a. a first nucleic acid selected from the group consisting of
      i. a nucleotide sequence according to SEQ ID NO:19,
      ii. a nucleotide sequence comprising a functional fragment of (i), wherein said fragment has promoter activity; and
      iii. a nucleotide sequence having at least 99% sequence identity to one of (i) or (ii); and
   b. a second nucleic acid to be transcribed,
wherein said first and second nucleic acid molecules are heterologous to each other and are operably linked together.

3. A host cell comprising an isolated nucleic acid molecule selected from the group consisting of
   (a) a nucleotide sequence according to SEQ ID NO:19;
   (b) a nucleotide sequence comprising a functional fragment of (a), wherein said fragment has promoter activity; and
   (c) a nucleotide sequence having at least 99% sequence identity to one of (a) or (b),
wherein said nucleic acid molecule is flanked by exogenous sequence.

4. A host cell comprising a vector construct of claim 2.

5. A method of directing transcription in an environment suitable for transcription comprising:
   a. introducing a first nucleic acid molecule selected from the group consisting of
      i. a nucleotide sequence according to SEQ ID NO: 19,
      ii. a nucleotide sequence comprising a functional fragment of (i), wherein said fragment has promoter activity; and
      iii. a nucleotide sequence having at least 99% sequence identity to one of (i) or (ii) according to claim 1; and
   b. introducing a second nucleic acid molecule to be transcribed;
wherein the first and second nucleic acid molecules are heterologous to each other and operably linked together, and wherein the second nucleic acid sequence is transcribed.

6. A plant comprising a vector construct according to claim 2.

7. The isolated nucleic acid of claim 1, wherein the promoter activity occurs in response to drought.

8. The isolated nucleic acid of claim 1, wherein said nucleotide sequence is SEQ ID NO:19 or a functional fragment thereof.

9. The vector construct of claim 6, wherein said nucleotide sequence is SEQ ID NO:19 or a functional fragment thereof.

10. The method of claim 5, wherein said nucleotide sequence is SEQ ID NO:19 or a functional fragment thereof.

11. The plant of claim 6, wherein said nucleotide sequence is SEQ ID NO:19 or a functional fragment thereof.

12. The isolated nucleic acid of claim 1, wherein said nucleotide sequence is a functional fragment of SEQ ID NO:19.

* * * * *